(12) United States Patent
Rousso et al.

(10) Patent No.: US 8,644,910 B2
(45) Date of Patent: Feb. 4, 2014

(54) IMAGING PROTOCOLS

(75) Inventors: Benny Rousso, Rishon-LeZion (IL);
Dalia Dickman, Doar-Na Misgav (IL);
Yael Nir, Caesarea (IL); Michael Nagler, Tel-Aviv (IL); Zohar Bronshtine, Talmey ElAzar (IL);
Shankar Vallabhajosula, Larchmont, NY (US); Shlomo Ben-Haim, London (GB); Simona Ben-Haim, London (GB)

(73) Assignee: Biosensors International Group, Ltd., HaMilton (BM)

( * ) Notice: Subject to any disclaimer, the term of this patent is extended or adjusted under 35 U.S.C. 154(b) by 579 days.

(21) Appl. No.: 11/989,223

(22) PCT Filed: Jul. 19, 2006

(86) PCT No.: PCT/IL2006/000834
§ 371 (c)(1),
(2), (4) Date: Aug. 5, 2009

(87) PCT Pub. No.: WO2007/010534
PCT Pub. Date: Jan. 25, 2007

(65) Prior Publication Data
US 2009/0304582 A1   Dec. 10, 2009

Related U.S. Application Data

(63) Continuation-in-part of application No. PCT/IL2006/000562, filed on May 11, 2006, and a continuation-in-part of application No. PCT/IL2006/000059, filed on Jan. 15, 2006, and a continuation-in-part of application No. PCT/IL2005/001215, filed on Nov. 16, 2005, and a continuation-in-part of application No. PCT/IL2005/001173, filed on Nov. 9, 2005.

(60) Provisional application No. 60/700,299, filed on Jul. 19, 2005, provisional application No. 60/700,318, filed on Jul. 19, 2005, provisional application No. 60/700,317, filed on Jul. 19, 2005, provisional application No. 60/700,752, filed on Jul. 20, 2005, provisional application No. 60/700,753, filed on Jul. 20, 2005, provisional application No. 60/702,979, filed on Jul. 28, 2005, provisional application No. 60/720,034, filed on Sep. 26, 2005, provisional application No. 60/720,541, filed on Sep. 27, 2005, provisional application No. 60/720,652, filed on Sep. 27, 2005, provisional application No. 60/741,440, filed on Dec. 2, 2005, provisional application No. 60/750,287, filed on Dec. 13, 2005, provisional application No. 60/750,597, filed on Dec. 15, 2005, provisional application No. 60/750,334, filed on Dec. 15, 2005, provisional application No. 60/763,458, filed on Jan. 31, 2006, provisional application No. 60/799,688, filed on May 11, 2006, provisional application No. 60/800,845, filed on May 17, 2006, provisional application No. 60/800,846, filed on May 17, 2006, provisional application No. 60/816,970, filed on Jun. 28, 2006.

(30) Foreign Application Priority Data

Oct. 10, 2005  (IL) .......................................... 171346
Nov. 27, 2005  (IL) .......................................... 172349

(51) Int. Cl.
*A61B 5/05*   (2006.01)

(52) U.S. Cl.
USPC ..................................... 600/436; 250/370.09

(58) Field of Classification Search
USPC ..................................... 600/436; 250/370.09
See application file for complete search history.

(56) References Cited

U.S. PATENT DOCUMENTS

| | | |
|---|---|---|
| 630,611 A | 8/1899 | Knapp et al. |
| 2,776,377 A | 1/1957 | Anger |
| 3,340,866 A | 9/1967 | Nöller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluzhnikov et al. |

| | | | | | | |
|---|---|---|---|---|---|---|
| 3,719,183 A | 3/1973 | Schwartz | | 5,263,077 A | 11/1993 | Cowan et al. |
| 3,739,279 A | 6/1973 | Hollis | | 5,279,607 A | 1/1994 | Schentag et al. |
| 3,971,362 A | 7/1976 | Pope et al. | | 5,284,147 A | 2/1994 | Hanaoka et al. |
| 3,978,337 A | 8/1976 | Nickles et al. | | 5,299,253 A | 3/1994 | Wessels |
| 3,988,585 A | 10/1976 | O'Neill et al. | | 5,304,165 A | 4/1994 | Haber et al. |
| 4,000,502 A | 12/1976 | Butler et al. | | 5,307,808 A | 5/1994 | Dumoulin et al. |
| 4,015,592 A | 4/1977 | Bradley-Moore | | 5,307,814 A | 5/1994 | Kressel et al. |
| 4,055,765 A | 10/1977 | Gerber et al. | | 5,309,959 A | 5/1994 | Shaw et al. |
| 4,061,919 A | 12/1977 | Miller et al. | | 5,317,506 A | 5/1994 | Coutre et al. |
| 4,095,107 A | 6/1978 | Genna et al. | | 5,317,619 A | 5/1994 | Hellmick et al. |
| 4,165,462 A | 8/1979 | Macovski et al. | | 5,323,006 A | 6/1994 | Thompson et al. |
| 4,181,856 A | 1/1980 | Bone | | 5,329,976 A | 7/1994 | Haber et al. |
| 4,278,077 A | 7/1981 | Mizumoto | | 5,334,141 A | 8/1994 | Carr et al. |
| 4,289,969 A | 9/1981 | Cooperstein et al. | | 5,349,190 A | 9/1994 | Hines et al. |
| 4,291,708 A | 9/1981 | Frei et al. | | 5,355,087 A | 10/1994 | Claiborne et al. |
| 4,296,785 A | 10/1981 | Vitello et al. | | 5,365,069 A | 11/1994 | Eisen et al. |
| 4,302,675 A | 11/1981 | Wake et al. | | 5,365,928 A | 11/1994 | Rhinehart et al. |
| 4,364,377 A | 12/1982 | Smith | | 5,367,552 A | 11/1994 | Peschmann |
| 4,383,327 A | 5/1983 | Kruger | | 5,377,681 A | 1/1995 | Drane |
| 4,476,381 A | 10/1984 | Rubin | | 5,381,791 A | 1/1995 | Qian |
| 4,503,331 A | 3/1985 | Kovacs, Jr. et al. | | 5,383,456 A | 1/1995 | Arnold et al. |
| 4,521,688 A | 6/1985 | Yin | | 5,383,858 A | 1/1995 | Reilly et al. |
| H12 H | 1/1986 | Bennett et al. | | 5,386,446 A | 1/1995 | Fujimoto et al. |
| 4,580,054 A | 4/1986 | Shimoni | | 5,387,409 A | 2/1995 | Nunn et al. |
| 4,595,014 A | 6/1986 | Barrett et al. | | 5,391,877 A | 2/1995 | Marks |
| 4,674,107 A | 6/1987 | Urban et al. | | 5,395,366 A | 3/1995 | D'Andrea |
| 4,679,142 A | 7/1987 | Lee | | 5,399,868 A | 3/1995 | Jones et al. |
| 4,689,041 A | 8/1987 | Corday et al. | | 5,404,293 A | 4/1995 | Weng et al. |
| 4,689,621 A | 8/1987 | Kleinberg | | 5,415,181 A | 5/1995 | Hofgrefe et al. |
| 4,709,382 A | 11/1987 | Sones | | 5,431,161 A | 7/1995 | Ryals et al. |
| 4,710,624 A | 12/1987 | Alvarez et al. | | 5,435,302 A | 7/1995 | Lenkinski et al. |
| 4,731,536 A | 3/1988 | Rische et al. | | 5,436,458 A | 7/1995 | Tran et al. |
| 4,773,430 A | 9/1988 | Porath | | 5,441,050 A | 8/1995 | Thurston et al. |
| 4,782,840 A | 11/1988 | Martin, Jr. et al. | | 5,448,073 A | 9/1995 | Jeanguillaume |
| 4,791,934 A | 12/1988 | Brunnett | | 5,451,232 A | 9/1995 | Rhinehart et al. |
| 4,801,803 A | 1/1989 | Denen et al. | | 5,472,403 A | 12/1995 | Cornacchia et al. |
| 4,828,841 A | 5/1989 | Porter et al. | | 5,475,219 A | 12/1995 | Olson |
| 4,834,112 A | 5/1989 | Machek et al. | | 5,475,232 A | 12/1995 | Powers et al. |
| 4,844,067 A | 7/1989 | Ikada et al. | | 5,476,095 A | 12/1995 | Schnall et al. |
| 4,844,076 A | 7/1989 | Lesho et al. | | 5,479,969 A | 1/1996 | Hardie et al. |
| 4,853,546 A | 8/1989 | Abe et al. | | 5,481,115 A | 1/1996 | Hsieh et al. |
| 4,854,324 A | 8/1989 | Hirschman et al. | | 5,484,384 A | 1/1996 | Fearnot |
| 4,854,330 A | 8/1989 | Evans, III et al. | | 5,489,782 A | 2/1996 | Wernikoff |
| 4,867,962 A | 9/1989 | Abrams | | 5,493,595 A | 2/1996 | Schoolman |
| 4,893,013 A | 1/1990 | Denen et al. | | 5,493,805 A | 2/1996 | Penuela et al. |
| 4,893,322 A | 1/1990 | Hellmick et al. | | 5,494,036 A | 2/1996 | Uber, III et al. |
| 4,919,146 A | 4/1990 | Rhinehart et al. | | 5,501,674 A | 3/1996 | Trombley, III et al. |
| 4,924,486 A | 5/1990 | Weber et al. | | 5,517,120 A | 5/1996 | Misic et al. |
| 4,928,250 A | 5/1990 | Greenberg et al. | | 5,519,221 A | 5/1996 | Weinberg |
| 4,929,832 A | 5/1990 | Ledley | | 5,519,222 A | 5/1996 | Besett |
| 4,938,230 A | 7/1990 | Machek et al. | | 5,519,931 A | 5/1996 | Reich |
| 4,951,653 A | 8/1990 | Fry et al. | | 5,520,182 A | 5/1996 | Leighton et al. |
| 4,959,547 A | 9/1990 | Carroll et al. | | 5,520,653 A | 5/1996 | Reilly et al. |
| 4,970,391 A | 11/1990 | Uber, III | | 5,521,506 A | 5/1996 | Misic et al. |
| 4,995,396 A | 2/1991 | Inaba et al. | | 5,536,945 A | 7/1996 | Reich |
| 5,014,708 A | 5/1991 | Hayashi et al. | | 5,545,899 A | 8/1996 | Tran et al. |
| 5,018,182 A | 5/1991 | Cowan et al. | | 5,559,335 A | 9/1996 | Zeng et al. |
| 5,032,729 A | 7/1991 | Charpak | | 5,565,684 A | 10/1996 | Gullberg et al. |
| 5,033,998 A | 7/1991 | Corday et al. | | 5,569,181 A | 10/1996 | Heilman et al. |
| 5,039,863 A | 8/1991 | Matsuno et al. | | 5,572,132 A | 11/1996 | Pulyer et al. |
| 5,042,056 A | 8/1991 | Hellmick et al. | | 5,572,999 A | 11/1996 | Funda et al. |
| 5,070,878 A | 12/1991 | Denen | | 5,579,766 A | 12/1996 | Gray |
| 5,088,492 A | 2/1992 | Takayama et al. | | 5,580,541 A | 12/1996 | Wells et al. |
| 5,115,137 A | 5/1992 | Andersson-Engels et al. | | 5,585,637 A | 12/1996 | Bertelsen et al. |
| 5,119,818 A | 6/1992 | Carroll et al. | | 5,587,585 A | 12/1996 | Eisen et al. |
| 5,132,542 A | 7/1992 | Bassalleck et al. | | 5,591,143 A | 1/1997 | Trombley, III et al. |
| 5,145,163 A | 9/1992 | Cowan et al. | | 5,600,145 A | 2/1997 | Plummer |
| 5,151,598 A | 9/1992 | Denen | | 5,604,531 A | 2/1997 | Iddan et al. |
| 5,170,055 A | 12/1992 | Carroll et al. | | 5,610,520 A | 3/1997 | Misic |
| 5,170,439 A | 12/1992 | Zeng et al. | | 5,617,858 A | 4/1997 | Taverna et al. |
| 5,170,789 A | 12/1992 | Narayan et al. | | 5,629,524 A | 5/1997 | Stettner et al. |
| 5,196,796 A | 3/1993 | Misic et al. | | 5,635,717 A | 6/1997 | Popescu |
| 5,210,421 A | 5/1993 | Gullberg et al. | | 5,657,759 A | 8/1997 | Essen-Moller |
| 5,243,988 A | 9/1993 | Sieben et al. | | 5,672,877 A | 9/1997 | Liebig et al. |
| 5,246,005 A | 9/1993 | Carroll et al. | | 5,677,539 A | 10/1997 | Apotovsky et al. |
| 5,249,124 A | 9/1993 | DeVito | | 5,682,888 A | 11/1997 | Olson et al. |
| 5,252,830 A | 10/1993 | Weinberg | | 5,687,542 A | 11/1997 | Lawecki et al. |
| 5,254,101 A | 10/1993 | Trombley, III | | 5,690,691 A | 11/1997 | Chen et al. |
| 5,258,717 A | 11/1993 | Misic et al. | | 5,692,640 A | 12/1997 | Caulfield et al. |

| | | | | | | |
|---|---|---|---|---|---|---|
| 5,694,933 | A | 12/1997 | Madden et al. | 6,040,697 | A | 3/2000 | Misic |
| 5,695,500 | A | 12/1997 | Taylor et al. | 6,042,565 | A | 3/2000 | Hirschman et al. |
| 5,716,595 | A | 2/1998 | Goldenberg | RE36,648 | E | 4/2000 | Uber, III et al. |
| 5,727,554 | A | 3/1998 | Kalend et al. | 6,046,454 | A | 4/2000 | Lingren et al. |
| 5,729,129 | A | 3/1998 | Acker | 6,048,334 | A | 4/2000 | Hirschman et al. |
| 5,732,704 | A | 3/1998 | Thurston et al. | 6,052,618 | A | 4/2000 | Dahlke et al. |
| 5,739,508 | A | 4/1998 | Uber, III | 6,055,450 | A | 4/2000 | Ashburn |
| 5,741,232 | A | 4/1998 | Reilly et al. | 6,055,452 | A | 4/2000 | Pearlman |
| 5,742,060 | A | 4/1998 | Ashburn | RE36,693 | E | 5/2000 | Reich |
| 5,744,805 | A | 4/1998 | Raylman et al. | 6,063,052 | A | 5/2000 | Uber et al. |
| 5,757,006 | A | 5/1998 | De Vito et al. | D426,891 | S | 6/2000 | Beale et al. |
| 5,779,675 | A | 7/1998 | Reilly et al. | D426,892 | S | 6/2000 | Beale et al. |
| 5,780,855 | A | 7/1998 | Pare et al. | 6,072,177 | A | 6/2000 | McCroskey et al. |
| 5,781,442 | A | 7/1998 | Engleson et al. | 6,076,009 | A | 6/2000 | Raylman et al. |
| 5,784,432 | A | 7/1998 | Kurtz et al. | 6,080,984 | A | 6/2000 | Friesenhahn |
| 5,786,597 | A | 7/1998 | Lingren et al. | D428,491 | S | 7/2000 | Beale et al. |
| 5,795,333 | A | 8/1998 | Reilly et al. | 6,082,366 | A | 7/2000 | Andra et al. |
| 5,800,355 | A | 9/1998 | Hasegawa | 6,090,064 | A | 7/2000 | Reilly et al. |
| 5,803,914 | A | 9/1998 | Ryals et al. | 6,091,070 | A | 7/2000 | Lingren et al. |
| 5,806,519 | A | 9/1998 | Evans, III et al. | 6,096,011 | A | 8/2000 | Trombley, III et al. |
| 5,808,203 | A | 9/1998 | Nolan, Jr. et al. | 6,107,102 | A | 8/2000 | Ferrari |
| 5,810,742 | A | 9/1998 | Pearlman | 6,115,635 | A | 9/2000 | Bourgeois |
| 5,811,814 | A | 9/1998 | Leone et al. | 6,129,670 | A | 10/2000 | Burdette et al. |
| 5,813,985 | A | 9/1998 | Carroll | 6,132,372 | A | 10/2000 | Essen-Moller |
| 5,818,050 | A | 10/1998 | Dilmanian et al. | 6,135,955 | A | 10/2000 | Madden et al. |
| 5,821,541 | A | 10/1998 | Tümer | 6,135,968 | A | 10/2000 | Brounstein |
| 5,825,031 | A | 10/1998 | Wong et al. | 6,137,109 | A | 10/2000 | Hayes |
| 5,827,219 | A | 10/1998 | Uber, III et al. | 6,145,277 | A | 11/2000 | Lawecki et al. |
| 5,828,073 | A | 10/1998 | Zhu et al. | 6,147,352 | A | 11/2000 | Ashburn |
| 5,833,603 | A | 11/1998 | Kovacs et al. | 6,147,353 | A | 11/2000 | Gagnon et al. |
| 5,838,009 | A | 11/1998 | Plummer et al. | 6,148,229 | A | 11/2000 | Morris, Sr. et al. |
| 5,840,026 | A | 11/1998 | Uber, III et al. | 6,149,627 | A | 11/2000 | Uber, III |
| 5,841,141 | A | 11/1998 | Gullberg et al. | 6,155,485 | A | 12/2000 | Coughlin et al. |
| 5,842,977 | A | 12/1998 | Lesho et al. | 6,160,398 | A | 12/2000 | Walsh |
| 5,843,037 | A | 12/1998 | Uber, III | 6,162,198 | A | 12/2000 | Coffey et al. |
| 5,846,513 | A | 12/1998 | Carroll et al. | 6,172,362 | B1 | 1/2001 | Lingren et al. |
| 5,847,396 | A | 12/1998 | Lingren et al. | 6,173,201 | B1 | 1/2001 | Front |
| 5,857,463 | A | 1/1999 | Thurston et al. | 6,184,530 | B1 | 2/2001 | Hines et al. |
| 5,871,013 | A | 2/1999 | Wainer et al. | 6,189,195 | B1 | 2/2001 | Reilly et al. |
| 5,873,861 | A | 2/1999 | Hitchins et al. | 6,194,715 | B1 | 2/2001 | Lingren et al. |
| 5,880,475 | A | 3/1999 | Oka et al. | 6,194,725 | B1 | 2/2001 | Colsher et al. |
| 5,882,338 | A | 3/1999 | Gray | 6,194,726 | B1 | 2/2001 | Pi et al. |
| 5,884,457 | A | 3/1999 | Ortiz et al. | 6,197,000 | B1 | 3/2001 | Reilly et al. |
| 5,885,216 | A | 3/1999 | Evans, III et al. | 6,202,923 | B1 | 3/2001 | Boyer et al. |
| 5,891,030 | A | 4/1999 | Johnson et al. | 6,203,775 | B1 | 3/2001 | Torchilin et al. |
| 5,893,397 | A | 4/1999 | Peterson et al. | 6,205,347 | B1 | 3/2001 | Morgan et al. |
| 5,899,885 | A | 5/1999 | Reilly et al. | 6,212,423 | B1 | 4/2001 | Krakovitz |
| 5,900,533 | A | 5/1999 | Chou | 6,223,065 | B1 | 4/2001 | Misic et al. |
| 5,903,008 | A | 5/1999 | Li | 6,224,577 | B1 | 5/2001 | Dedola et al. |
| 5,910,112 | A | 6/1999 | Judd et al. | 6,226,350 | B1 | 5/2001 | Hsieh |
| 5,911,252 | A | 6/1999 | Cassel | 6,229,145 | B1 | 5/2001 | Weinberg |
| 5,916,167 | A | 6/1999 | Kramer et al. | 6,232,605 | B1 | 5/2001 | Soluri et al. |
| 5,916,197 | A | 6/1999 | Reilly et al. | 6,233,304 | B1 | 5/2001 | Hu et al. |
| 5,920,054 | A | 7/1999 | Uber, III | 6,236,050 | B1 | 5/2001 | Tumer |
| 5,927,351 | A | 7/1999 | Zhu et al. | 6,236,878 | B1 | 5/2001 | Taylor et al. |
| 5,928,150 | A | 7/1999 | Call | 6,236,880 | B1 | 5/2001 | Raylman et al. |
| 5,932,879 | A | 8/1999 | Raylman et al. | 6,239,438 | B1 | 5/2001 | Schubert |
| 5,938,639 | A | 8/1999 | Reilly et al. | 6,240,312 | B1 | 5/2001 | Alfano et al. |
| 5,939,724 | A | 8/1999 | Eisen et al. | 6,241,708 | B1 | 6/2001 | Reilly et al. |
| 5,944,190 | A | 8/1999 | Edelen | 6,242,743 | B1 * | 6/2001 | DeVito et al. ............ 250/363.05 |
| 5,944,694 | A | 8/1999 | Hitchins et al. | 6,242,744 | B1 | 6/2001 | Soluri et al. |
| 5,947,935 | A | 9/1999 | Rhinehart et al. | 6,242,745 | B1 | 6/2001 | Berlad et al. |
| 5,953,884 | A | 9/1999 | Lawecki et al. | 6,246,901 | B1 | 6/2001 | Benaron |
| 5,954,668 | A | 9/1999 | Uber, III et al. | 6,252,924 | B1 | 6/2001 | Davantes et al. |
| 5,961,457 | A | 10/1999 | Raylman et al. | 6,258,576 | B1 | 7/2001 | Richards-Kortum et al. |
| 5,967,983 | A | 10/1999 | Ashburn | 6,259,095 | B1 | 7/2001 | Bouton et al. |
| 5,973,598 | A | 10/1999 | Beigel | 6,261,562 | B1 | 7/2001 | Xu et al. |
| 5,974,165 | A | 10/1999 | Giger et al. | 6,263,229 | B1 | 7/2001 | Atalar et al. |
| 5,984,860 | A | 11/1999 | Shan | 6,269,340 | B1 | 7/2001 | Ford et al. |
| 5,987,350 | A | 11/1999 | Thurston | 6,270,463 | B1 | 8/2001 | Morris, Sr. et al. |
| 5,993,378 | A | 11/1999 | Lemelson | 6,271,524 | B1 | 8/2001 | Wainer et al. |
| 5,997,502 | A | 12/1999 | Reilly et al. | 6,271,525 | B1 | 8/2001 | Majewski et al. |
| 6,002,134 | A | 12/1999 | Lingren | 6,280,704 | B1 | 8/2001 | Schutt et al. |
| 6,002,480 | A | 12/1999 | Izatt et al. | 6,281,505 | B1 | 8/2001 | Hines et al. |
| 6,017,330 | A | 1/2000 | Hitchins et al. | 6,308,097 | B1 | 10/2001 | Pearlman |
| 6,019,745 | A | 2/2000 | Gray | 6,310,968 | B1 | 10/2001 | Hawkins et al. |
| 6,021,341 | A | 2/2000 | Scibilia et al. | 6,315,981 | B1 | 11/2001 | Unger |
| 6,026,317 | A | 2/2000 | Verani | 6,317,623 | B1 | 11/2001 | Griffiths et al. |
| 6,037,595 | A | 3/2000 | Lingren | 6,317,648 | B1 | 11/2001 | Sleep et al. |

| | | |
|---|---|---|
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tuemer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engleson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |

| | | | | | | |
|---|---|---|---|---|---|---|
| 6,906,330 B2 | 6/2005 | Blevis et al. | | 2001/0035902 A1 | 11/2001 | Iddan et al. |
| D507,832 S | 7/2005 | Yanniello et al. | | 2001/0049608 A1 | 12/2001 | Hochman |
| 6,915,170 B2 | 7/2005 | Engleson et al. | | 2002/0068864 A1* | 6/2002 | Bishop et al. .................. 600/407 |
| 6,915,823 B2 | 7/2005 | Osborne et al. | | 2002/0072784 A1 | 6/2002 | Sheppard, Jr. et al. |
| 6,917,828 B2 | 7/2005 | Fukuda | | 2002/0085748 A1 | 7/2002 | Baumberg |
| 6,921,384 B2 | 7/2005 | Reilly et al. | | 2002/0087101 A1 | 7/2002 | Barrick et al. |
| 6,928,142 B2* | 8/2005 | Shao et al. ....................... 378/63 | | 2002/0099295 A1 | 7/2002 | Gil et al. |
| 6,935,560 B2 | 8/2005 | Andreasson et al. | | 2002/0099310 A1 | 7/2002 | Kimchy et al. |
| 6,936,030 B1 | 8/2005 | Pavlik et al. | | 2002/0099334 A1 | 7/2002 | Hanson et al. |
| 6,937,750 B2 | 8/2005 | Natanzon et al. | | 2002/0103429 A1 | 8/2002 | DeCharms |
| 6,939,302 B2 | 9/2005 | Griffiths et al. | | 2002/0103431 A1 | 8/2002 | Toker et al. |
| 6,940,070 B2 | 9/2005 | Tumer | | 2002/0145114 A1 | 10/2002 | Inoue et al. |
| 6,943,355 B2 | 9/2005 | Shwartz et al. | | 2002/0148970 A1 | 10/2002 | Wong et al. |
| 6,957,522 B2 | 10/2005 | Baldwin et al. | | 2002/0165491 A1 | 11/2002 | Reilly |
| 6,958,053 B1 | 10/2005 | Reilly | | 2002/0168094 A1 | 11/2002 | Kaushikkar et al. |
| 6,963,770 B2 | 11/2005 | Scarantino et al. | | 2002/0168317 A1 | 11/2002 | Daighighian et al. |
| 6,970,735 B2 | 11/2005 | Uber, III et al. | | 2002/0172405 A1 | 11/2002 | Schultz |
| 6,972,001 B2 | 12/2005 | Emig et al. | | 2002/0179843 A1 | 12/2002 | Tanaka et al. |
| 6,974,443 B2 | 12/2005 | Reilly et al. | | 2002/0183645 A1 | 12/2002 | Nachaliel |
| 6,976,349 B2 | 12/2005 | Baldwin et al. | | 2002/0188197 A1 | 12/2002 | Bishop et al. |
| 6,984,222 B1 | 1/2006 | Hitchins et al. | | 2002/0198738 A1 | 12/2002 | Osborne |
| 6,985,870 B2 | 1/2006 | Martucci et al. | | 2003/0001098 A1 | 1/2003 | Stoddart et al. |
| 6,988,981 B2 | 1/2006 | Hamazaki | | 2003/0001837 A1 | 1/2003 | Baumberg |
| 6,994,249 B2 | 2/2006 | Peterka et al. | | 2003/0006376 A1 | 1/2003 | Tumer |
| 7,009,183 B2 | 3/2006 | Wainer et al. | | 2003/0013950 A1 | 1/2003 | Rollo et al. |
| 7,011,814 B2 | 3/2006 | Suddarth et al. | | 2003/0013966 A1 | 1/2003 | Barnes et al. |
| 7,012,430 B2 | 3/2006 | Misic | | 2003/0038240 A1 | 2/2003 | Weinberg |
| 7,017,622 B2 | 3/2006 | Osborne et al. | | 2003/0055685 A1 | 3/2003 | Cobb et al. |
| 7,018,363 B2 | 3/2006 | Cowan et al. | | 2003/0063787 A1 | 4/2003 | Natanzon et al. |
| 7,019,783 B2 | 3/2006 | Kindem et al. | | 2003/0071219 A1 | 4/2003 | Motomura et al. |
| 7,025,757 B2 | 4/2006 | Reilly et al. | | 2003/0081716 A1 | 5/2003 | Tumer |
| 7,026,623 B2 | 4/2006 | Oaknin et al. | | 2003/0135388 A1 | 7/2003 | Martucci et al. |
| 7,043,063 B1 | 5/2006 | Noble et al. | | 2003/0136912 A1 | 7/2003 | Juni |
| 7,102,138 B2 | 9/2006 | Belvis et al. | | 2003/0144322 A1 | 7/2003 | Kozikowski et al. |
| 7,103,204 B1 | 9/2006 | Celler et al. | | 2003/0147887 A1 | 8/2003 | Wang et al. |
| 7,127,026 B2 | 10/2006 | Amemiya et al. | | 2003/0158481 A1 | 8/2003 | Stotzka et al. |
| 7,142,634 B2 | 11/2006 | Engler et al. | | 2003/0183226 A1 | 10/2003 | Brand et al. |
| 7,145,986 B2 | 12/2006 | Wear et al. | | 2003/0189174 A1 | 10/2003 | Tanaka et al. |
| 7,147,372 B2 | 12/2006 | Nelson et al. | | 2003/0191430 A1 | 10/2003 | D'Andrea et al. |
| 7,164,130 B2 | 1/2007 | Welsh et al. | | 2003/0202629 A1 | 10/2003 | Dunham et al. |
| 7,176,466 B2 | 2/2007 | Rousso et al. | | 2003/0208117 A1* | 11/2003 | Shwartz et al. ................ 600/407 |
| 7,187,790 B2 | 3/2007 | Sabol et al. | | 2003/0215122 A1 | 11/2003 | Tanaka |
| 7,217,953 B2 | 5/2007 | Carlson | | 2003/0215124 A1 | 11/2003 | Li |
| 7,256,386 B2 | 8/2007 | Carlson et al. | | 2003/0216631 A1 | 11/2003 | Bloch et al. |
| 7,327,822 B2 | 2/2008 | Sauer et al. | | 2003/0219149 A1 | 11/2003 | Vailaya et al. |
| 7,359,535 B2 | 4/2008 | Salla et al. | | 2004/0003001 A1 | 1/2004 | Shimura |
| 7,373,197 B2 | 5/2008 | Daighighian et al. | | 2004/0010397 A1 | 1/2004 | Barbour et al. |
| 7,394,923 B2 | 7/2008 | Zou et al. | | 2004/0015075 A1 | 1/2004 | Kimchy et al. |
| 7,444,010 B2 | 10/2008 | De Man | | 2004/0021065 A1 | 2/2004 | Weber |
| 7,468,513 B2 | 12/2008 | Charron et al. | | 2004/0044282 A1 | 3/2004 | Mixon et al. |
| 7,470,896 B2 | 12/2008 | Pawlak et al. | | 2004/0051368 A1 | 3/2004 | Caputo et al. |
| 7,490,085 B2 | 2/2009 | Walker et al. | | 2004/0054248 A1 | 3/2004 | Kimchy et al. |
| 7,495,225 B2 | 2/2009 | Hefetz et al. | | 2004/0054278 A1 | 3/2004 | Kimchy et al. |
| 7,502,499 B2 | 3/2009 | Grady | | 2004/0065838 A1 | 4/2004 | Tumer |
| 7,570,732 B2 | 8/2009 | Stanton et al. | | 2004/0075058 A1 | 4/2004 | Blevis et al. |
| 7,592,597 B2 | 9/2009 | Hefetz et al. | | 2004/0081623 A1 | 4/2004 | Eriksen et al. |
| 7,620,444 B2 | 11/2009 | Le et al. | | 2004/0082918 A1 | 4/2004 | Evans et al. |
| 7,627,084 B2 | 12/2009 | Jabri et al. | | 2004/0084340 A1 | 5/2004 | Morelle et al. |
| 7,652,259 B2 | 1/2010 | Kimchy et al. | | 2004/0086437 A1 | 5/2004 | Jackson et al. |
| 7,671,331 B2 | 3/2010 | Hefetz | | 2004/0101176 A1 | 5/2004 | Mendonca et al. |
| 7,671,340 B2 | 3/2010 | Uribe et al. | | 2004/0101177 A1 | 5/2004 | Zahlmann et al. |
| 7,672,491 B2 | 3/2010 | Krishnan et al. | | 2004/0116807 A1 | 6/2004 | Amrami et al. |
| 7,680,240 B2 | 3/2010 | Manjeshwar et al. | | 2004/0120557 A1 | 6/2004 | Sabol |
| 7,705,316 B2 | 4/2010 | Rousso et al. | | 2004/0122311 A1 | 6/2004 | Cosman |
| 7,734,331 B2 | 6/2010 | Dhawale et al. | | 2004/0125918 A1 | 7/2004 | Shanmugaval et al. |
| 7,826,889 B2 | 11/2010 | David et al. | | 2004/0138557 A1 | 7/2004 | Le et al. |
| 7,831,024 B2 | 11/2010 | Metzler et al. | | 2004/0143449 A1 | 7/2004 | Behrenbruch et al. |
| 7,835,927 B2 | 11/2010 | Schlotterbeck et al. | | 2004/0144925 A1* | 7/2004 | Stoddart et al. .......... 250/363.04 |
| 7,872,235 B2 | 1/2011 | Rousso et al. | | 2004/0153128 A1 | 8/2004 | Suresh et al. |
| 7,894,650 B2 | 2/2011 | Weng et al. | | 2004/0162492 A1 | 8/2004 | Kobayashi |
| 7,968,851 B2 | 6/2011 | Rousso et al. | | 2004/0171924 A1 | 9/2004 | Mire et al. |
| 8,013,308 B2 | 9/2011 | Guerin et al. | | 2004/0183022 A1 | 9/2004 | Weinberg |
| 8,055,329 B2 | 11/2011 | Kimchy et al. | | 2004/0184644 A1 | 9/2004 | Leichter et al. |
| 8,111,886 B2 | 2/2012 | Rousso et al. | | 2004/0193453 A1 | 9/2004 | Butterfield et al. |
| 8,158,951 B2 | 4/2012 | Bal et al. | | 2004/0195512 A1 | 10/2004 | Crosetto |
| 8,204,500 B2 | 6/2012 | Weintraub et al. | | 2004/0204646 A1 | 10/2004 | Nagler et al. |
| 8,338,788 B2 | 12/2012 | Zilberstein et al. | | 2004/0205343 A1 | 10/2004 | Forth et al. |
| 2001/0016029 A1 | 8/2001 | Tumer | | 2004/0210126 A1 | 10/2004 | Hajaj et al. |
| 2001/0020131 A1 | 9/2001 | Kawagishi et al. | | 2004/0238743 A1 | 12/2004 | Gravrand et al. |

| | | |
|---|---|---|
| 2004/0251419 A1 | 12/2004 | Nelson et al. |
| 2004/0253177 A1 | 12/2004 | Elmaleh et al. |
| 2004/0263865 A1 | 12/2004 | Pawlak et al. |
| 2005/0001170 A1 | 1/2005 | Juni |
| 2005/0006589 A1 | 1/2005 | Young et al. |
| 2005/0020898 A1 | 1/2005 | Vosniak et al. |
| 2005/0020915 A1 | 1/2005 | Bellardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1 | 4/2005 | Cagnolini et al. |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0121505 A1 | 6/2005 | Metz et al. |
| 2005/0131270 A1 | 6/2005 | Weil et al. |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0173643 A1 | 8/2005 | Tumer |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0207526 A1 | 9/2005 | Altman |
| 2005/0211909 A1 | 9/2005 | Smith |
| 2005/0215889 A1 | 9/2005 | Patterson, II |
| 2005/0234424 A1 | 10/2005 | Besing et al. |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1 | 1/2006 | Charron et al. |
| 2006/0033028 A1 | 2/2006 | Juni |
| 2006/0036157 A1 | 2/2006 | Tumer |
| 2006/0072799 A1 | 4/2006 | McLain |
| 2006/0074290 A1 | 4/2006 | Chen et al. |
| 2006/0104519 A1 | 5/2006 | Stoeckel et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0188136 A1 | 8/2006 | Ritt et al. |
| 2006/0214097 A1 | 9/2006 | Wang et al. |
| 2006/0237652 A1 | 10/2006 | Kimchy et al. |
| 2006/0257012 A1 | 11/2006 | Kaufman et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0001090 A1 | 1/2008 | Ben-Haim et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0128626 A1 | 6/2008 | Rousso et al. |
| 2008/0137938 A1 | 6/2008 | Zahniser |
| 2008/0230702 A1 | 9/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260580 A1 | 10/2008 | Helle et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2009/0304582 A1 | 12/2009 | Rousso et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0140483 A1 | 6/2010 | Rousso et al. |
| 2010/0202664 A1 | 8/2010 | Busch et al. |
| 2010/0245354 A1 | 9/2010 | Rousso et al. |
| 2012/0106820 A1 | 5/2012 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |
| 2013/0114792 A1 | 5/2013 | Zilberstein et al. |

FOREIGN PATENT DOCUMENTS

| | | |
|---|---|---|
| DE | 1516429 | 12/1969 |
| DE | 19814199 | 10/1999 |
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 6-109848 | 4/1994 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/25268 | 5/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |

| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.
Official Action Dated Dec. 15, 2011 From the US Patent and Trademark Office Re.: U.S. Appl. No. 10/343,792.
Response Dated Nov. 13, 2011 to Official Action of Sep. 12, 2011 From the US Patent and Trademark Office Re. U.S. Appl. No. 11/980,653.
Response Dated Dec. 29, 2011 to Office Action of Jul. 17, 2007 From the Israeli Patent Office Re.: Application No. 154323.
Berman et al. "Dual-Isotope Myocardial Perfusion SPECT With Rest Thallium-201 and Stress Tc-99m Sestamibi", Cardiology Clinics, 12(2): 261-270, May 1994.
DeGrado et al. "Topics in Integrated Systems Physiology. Tracer Kinetic Modeling in Nuclear Cardiology", Journal of Nuclear Cardiology, 7: 686-700, 2000.
Links "Advances in SPECT and PET Imaging", Annals in Nuclear Medical Science, 13(2): 107-120, Jun. 2000.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Bromiley et al. "Attenuation Correction in PET Using Consistency Conditions and a Three-Dimensional Template", IEEE Transactions on Nuclear Science, 48(4): 1371-1377, 2001. p. 1376, col. 2, § 2.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Hassan et al. "A Radiotelemetry Pill for the Measurement of Ionising Radiation Using a Mercuric Iodide Detector", Phys. Med. Biol., 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry 89(3-4): 349-352, 2000.
Jessup "Tumor Markers—Prognostic and Therapeutic Implications for Colorectal Carcinoma", Surgical Oncology, 7: 139-151, 1998.

Kojima et al. "Quantitative Planar Imaging Method for Measurement of Renal Activity by Using a Conjugate-Emission Image and Transmission Data", Medical Physics, 27(3): 608-615, 2000. p. 608.
Lavallée et al. "Building a Hybrid Patient's Model for Augmented Reality in Surgery: A Registration Problem", Computing in Biological Medicine, 25(2): 149-164, 1995. p. 149-150.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Mori et al. "Overexpression of Matrix Metalloproteinase-7mRNA in Human Colon Carcinomas", Cancer, 75: 1516-1519, 1995.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Piperno et al. "Breast Cancer Screening by Impedance Measurements", Frontiers Med. Biol. Engng., 2(2): 11-17, 1990.
Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedence Monitoring During CT-Guided Stereotactic Surgery: Relative Value in Cystic and Solid Lesions", British Journal of Neurosurgery, 6: 439-444, 1992.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Zhang et al. "An Innovative High Efficiency and High Resolution Probe for Prostate Imaging", The Journal of Nuclear Medicine, 68: 18, 2000. Abstract.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.
Official Action Dated Oct. 7, 2011 From the US Patent and Trademark Office Re. U.S. Appl. No. 11/750,057.
Official Action Dated Oct. 7, 2011 From the US Patent and Trademark Office Re. U.S. Appl. No. 11/932,872.
Official Action Dated Jan. 19, 2012 From the US Patent and Trademark Office Re. U.S. Appl. No. 11/667,793.
Official Action Dated Jan. 23, 2012 From the US Patent and Trademark Office Re. U.S. Appl. No. 12/087,150.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Toennies et al. "Scatter Segmentation in Dynamic SPECT Images Using Principal Component Analysis", Progress in Biomedical Optics and Imaging, 4(23): 507-516, 2003.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Sep. 2, 2009 From the US Patent and Trademark Office Re.: U.S. Appl. No. 10/343,792.
Official Action Dated Aug. 11, 2009 From the US Patent and Trademark Office Re.: U.S. Appl. No. 09/641,973.
Official Action Dated Sep. 15, 2009 From the US Patent and Trademark Office Re.: U.S. Appl. No. 10/616,307.
Official Action Dated Sep. 16, 2009 From the US Patent and Trademark Office Re.: U.S. Appl. No. 09/727,464.

Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Response Dated Nov. 16, 2009 to Official Action of Jul. 15, 2009 From the US Patent and Trademark Office Re.: U.S. Appl. No. 10/616,301.
Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Communication Pursuant to Article 94(3) EPC Dated Sep. 23, 2011 From the European Patent Office Re.: Application No. 06832278.3.
Written Opinion Dated Nov. 1, 2007 from the International Searching Authority of the Patent Cooperation Treaty Re.: Application No. PCT/IL06/00840.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Notice of Allowance Dated Feb. 2, 2012 From the US Patent and Trademark Office Re. U.S. Appl. No. 11/628,074.
Communication Pursuant to Article 94(3) EPC Dated Mar. 2, 2011 From the European Patent Office Re.: Application No. 06756259.5.
Notice of Allowance Dated Nov. 15, 2010 From the US Patent and Trademark Office Re. U.S. Appl. No. 10/616,301.
Notice of Non-Compliant Amendment Dated Feb. 14, 2011 From the US Patent and Trademark Office Re.: U.S. Appl. No. 10/616,307.
Response Dated Feb. 10, 2011 to Notice of Allowance of Nov. 15, 2010 From the US Patent and Trademark Office Re. U.S. Appl. No. 10/616,301.
Mettler et al. "Legal Requirements and Radiation Safety", Essentials of Nuclear Medicine Imaging, 2nd Ed., Chap.13: 323-331, 1985.
Notice of Panel Decision From Pre-Appeal Brief Review Dated Feb. 29, 2012 From the US Patent and Trademark Office Re.: U.S. Appl. No. 10/836,223.
Official Action Dated Mar. 1, 2012 From the US Patent and Trademark Office Re.: U.S. Appl. No. 10/616,307.
Official Action Dated Dec. 22, 2011 From the US Patent and Trademark Office Re. U.S. Appl. No. 12/514,785.
Official Action Dated Feb. 28, 2012 From the US Patent and Trademark Office Re.: U.S. Appl. No. 09/641,973.
International Search Report Dated Aug. 3, 2006 From the International Searching Authority of the Patent Cooperation Treaty Re.: Application No. PCT/IL05/001173.

Official Action Dated Jan. 31, 2011 From the US Patent and Trademark Office Re. U.S. Appl. No. 11/667,793.
Response Dated Mar. 8, 2011 to Official Action of Dec. 8, 2010 From the US Patent and Trademark Office Re.: U.S. Appl. No. 11/980,690.
Written Opinion Dated Mar. 23, 2006 From the International Searching Authority of the Patent Cooperation Treaty Re.: Application No. PCT/IL05/00572.
Lavall?e et al. "Building a Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Response Dated Mar. 24, 2011 to Official Action of Dec. 8, 2010 From the US Patent and Trademark Office Re.: U.S. Appl. No. 09/641,973.
Official Action Dated Mar. 6, 2012 From the US Patent and Trademark Office Re. U.S. Appl. No. 12/792,856.
Restriction Official Action Dated Mar. 9, 2012 From the US Patent and Trademark Office Re. U.S. Appl. No. 11/976,852.
Office Action Dated Jul. 17, 2007 From the Israeli Patent Office Re.: Application No. 154323 and Its Translation Into English.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Response Dated Mar. 3, 2011 to Notice of Non-Compliant Amendment of Feb. 14, 2011 From the US Patent and Trademark Office Re.: U.S. Appl. No. 10/616,307.
Official Action Dated Apr. 16, 2012 From the US Patent and Trademark Office Re.: U.S. Appl. No. 10/836,223.
Notice of Allowance Dated May 5, 2011 From the US Patent and Trademark Office Re.: U.S. Appl. No. 10/240,239.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.

Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated May 3, 2007 From the US Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Oct. 7, 2008 From the US Patent and Trademark Office Re.: U.S. Appl. No. 10/616,301.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Aug. 10, 2007 From the US Patent and Trademark Office Re.: U.S. Appl. No. 10/836,223.
Official Action Dated Mar. 11, 2010 From the US Patent and Trademark Office Re.: U.S. Appl. No. 11/607,075.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/725,316.
Official Action Dated Sep. 15, 2009 From the US Patent and Trademark Office Re.: U.S. Appl. No. 10/836,223.
Official Action Dated Jan. 17, 2006 From the United States Patent and Trademark Office Re.: U.S. Appl. No. 11/034,007.
Official Action Dated Mar. 19, 2010 From the US Patent and Trademark Office Re.: U.S. Appl. No. 10/240,239.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Feb. 23, 2010 From the US Patent and Trademark Office Re.: U.S. Appl. No. 09/641,973.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.

Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Jul. 2, 2007 From the International Searching Authority of the Patent Cooperation Treaty Re.: Application No. PCT/IL2006/001291.
Written Opinion Dated Oct. 10, 2006 From the International Searching Authority of the Patent Cooperation Treaty Re.: Application No. PCT/IL06/00059.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Communication Pursuant to Article 93(3) EPC Dated Mar. 8, 2010 From the European Patent Office Re.: Application No. 06832278.3.
International Search Report Dated Oct. 10, 2006 From the International Searching Authority of the Patent Cooperation Treaty Re.: Application No. PCT/IL06/00059.
Written Opinion Dated Aug. 3, 2006 From the International Searching Authority of the Patent Cooperation Treaty Re.: Application No. PCT/IL05/001173.
Official Action Dated Apr. 9, 2010 From the US Patent and Trademark Office Re.: U.S. Appl. No. 11/798,017.
Official Action Dated May 23, 2011 From the US Patent and Trademark Office Re. U.S. Appl. No. 11/667,793.

Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
McJilton et al. "Protein Kinase Cε Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Interview Summary Dated May 31, 2011 From the US Patent and Trademark Office Re. U.S. Appl. No. 10/616,301.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Response Dated Jan. 27, 2011 to Official Action of Nov. 1, 2010 From the US Patent and Trademark Office Re.: U.S. Appl. No. 12/728,383.
McJilton et al. "Protein Kinase C? Interacts With Bax and Promotes Survival of Human Prostate Cancer Cells", Oncogene, 22; 7958-7968, 2003.
Notice of Allowance Dated Jun. 23, 2011 From the US Patent and Trademark Office Re.: U.S. Appl. No. 10/616,301.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Official Action Dated Jun. 28, 2011 From the US Patent and Trademark Office Re. U.S. Appl. No. 11/628,074.
Response Dated Jul. 8, 2010 to Communication Pursuant to Article 94(3) EPC of Mar. 8, 2010 From the European Patent Office Re.: Application No. 06832278.3.
Official Action Dated Jan. 7, 2009 From the US Patent and Trademark Office Re.: U.S. Appl. No. 10/616,307.
Summons to Attend Oral Proceedings Pursuant to Rule 115(1) EPC Dated Jan. 16, 2009 From the European Patent Office Re.: Application No. 03810570.6.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Kinahan et al. "Attenuation Correction for a Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magnetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Examination Report Dated Jun. 22, 2011 From the Government of India, Patent Office, Intellectual Property Building Re. Application No. 2963/CHENP/2006.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.

Response Dated Jun. 28, 2011 to Official Action of Dec. 28, 2010 From the US Patent and Trademark Office Re.: U.S. Appl. No. 11/607,075.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office Re.: U.S. Appl. No. 09/641,973.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Official Action Dated Jul. 12, 2011 From the US Patent and Trademark Office Re.: U.S. Appl. No. 09/641,973.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Notice of Allowance Dated Jul. 22, 2010 From the US Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Response Dated Aug. 25, 2010 to Official Action of Jul. 27, 2010 From the US Patent and Trademark Office Re.: U.S. Appl. No. 10/616,307.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.
Response Dated Sep. 12, 2011 to Official Action of Jul. 11, 2011 From the US Patent and Trademark Office Re.: U.S. Appl. No. 11/980,683.
Response Dated Sep. 20, 2011 to Official Action of Apr. 20, 2011 From the US Patent and Trademark Office Re.: U.S. Appl. No. 11/798,017.
Communication Pursuant to Article 94(3) EPC Dated Sep. 22, 2011 From the European Patent Office Re. Application No. 06756258.7.

Notice of Allowance Dated Sep. 16, 2011 From the US Patent and Trademark Office Re.: U.S. Appl. No. 11/607,075.
Official Action Dated Sep. 13, 2011 From the US Patent and Trademark Office Re. U.S. Appl. No. 11/976,852.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With a Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
Communication Pursuant to Article 94(3) EPC Dated Jul. 22, 2009 From the European Patent Office Re.: Application No. 06809851.6.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Jul. 15, 2009 From the US Patent and Trademark Office Re.: U.S. Appl. No. 10/616,301.
Official Action Dated Dec. 16, 2008 From the US Patent and Trademark Office Re.: U.S. Appl. No. 10/343,792.
Official Action Dated Jul. 20, 2009 From the US Patent and Trademark Office Re.: U.S. Appl. No. 11/980,617.
Official Action Dated Dec. 23, 2008 From the US Patent and Trademark Office Re.: U.S. Appl. No. 09/727,464.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.

Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Oct. 31, 2007 to Official Action of Jul. 12, 2007 From the US Patent and Trademark Office Re.: U.S. Appl. No. 10/616,301.
Response to the International Search Report and the Written Opinion of Oct. 10, 2006 From the International Searching Authority Re.: Application No. PCT/IL06/00059.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Zaidi et al. "Magenetic Resonance Imaging-Guided Attenuation and Scatter Corrections in Three-Dimensional Brain Positron Emission Tomography", Medical Physics, 30(5): 937-948, May 2003.
Response dated Sep. 1, 2010 to Official Action of Aug. 3, 2010 From the US Patent and Trademark Office Re.: U.S. Appl. No. 11/980,690.
Response Dated Oct. 14, 2011 to Supplementary European Search Report and the European Search Opinion of Mar. 16, 2011 From the European Patent Office Re. Application No. 05803689.8.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Supplemental Notice of Allowability Dated Oct. 24, 2011 From the US Patent and Trademark Office Re.: U.S. Appl. No. 11/607,075.
Notice of Allowance Dated Oct. 11, 2011 From the US Patent and Trademark Office Re. U.S. Appl. No. 11/988,926.

Response Dated Oct. 14, 2011 to Communication Pursuant to Rules 70(2) and 70a(2) EPC of Apr. 4, 2011 From the European Patent Office Re. Application No. 05803689.8.
International Preliminary Report on Patentability Dated Apr. 16, 2009 From the International Bureau of WIPO Re.: Applicaiton No. PCT/IL2007/000918.
Official Action Dated Mar. 15, 2004 From the US Patent and Trademark Office Re.: U.S. Appl. No. 09/765,316.
Response to the International Search Report and the Written Opinion of Oct. 10, 2006 From the International Searching Authority Re.: Appliction No. PCT/IL06/00059.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Hassan et al. "A Radiotelemetry Pill for the Measurement of Ionising Radiation Using a Mercuric Iodide Detector", Physics in Medicine and Biology, 23(2): 302-308, 1978.
Lavallée et al. "Building a Hybrid Patient's Model for Augmented Reality in Surgery: A Registration Problem", Computing in Biological Medicine, 25(2): 149-164, 1995.
Restriction Official Action Dated Nov. 8, 2011 From the US Patent and Trademark Office Re. U.S. Appl. No. 12/309,479.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Restriction Official Action Dated Nov. 15, 2011 From the US Patent and Trademark Office Re. U.S. Appl. No. 11/980,683.
Communication Pursuant to Article 94(3) EPC Dated Nov. 18, 2011 From the European Patent Office Re. Application No. 05803689.8.
Response Dated Nov. 14, 2011 to Official Action of Jul. 12, 2011 From the US Patent and Trademark Office Re.: U.S. Appl. No. 09/641,973.
Response Dated Nov. 23, 2011 to Official Action of May 23, 2011 From the US Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.
Response Dated Nov. 28, 2011 to Official Action of Jun. 28, 2011 From the US Patent and Trademark Office Re. U.S. Appl. No. 11/628,074.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Response Dated Dec. 8, 2011 to Restriction Official Action of Nov. 8, 2011 From the US Patent and Trademark Office Re. U.S. Appl. No. 12/309,479.
Restriction Official Action Dated Aug. 16, 2012 From the US Patent and Trademark Office Re. U.S. Appl. No. 12/448,473.
Communication Pursuant to Article 94(3) EPC Dated Oct. 26, 2012 From the European Patent Office Re. Application No. 05803689.8.
Official Action Dated Aug. 2, 2012 From the US Patent and Trademark Office Re. U.S. Appl. No. 12/087,150.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Communication Pursuant to Article 94(3) EPC Dated Jun. 11, 2012 From the European Patent Office Re.: Application No. 06756259.5.

Communication Pursuant to Article 94(3) EPC Dated May 12, 2010 From the European Patent Office Re. Application No. 06809851.6.
Communication Pursuant to Article 94(3) EPC Dated May 29, 2012 From the European Patent Office Re. Application No. 05803689.8.
Communication Under Rule 71(3) EPC Dated May 30, 2012 From the European Patent Office Re.: Application No. 02716285.8.
International Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Search Report Dated Jul. 1, 2008 From the International Searching Authority Re. Application No. PCT/IL2006/000834.
International Search Report Dated Jul. 2, 2007 From the International Searching Authority Re. Application No. PCT/IL2006/001291.
International Search Report Dated Aug. 3, 2006 From the International Searching Authority Re. Application No. PCT/IL2005/001173.
International Search Report Dated Oct. 15, 2008 From the International Searching Authority Re. Application No. PCT/2007/000918.
Official Action Dated Nov. 1, 2010 From the US Patent and Trademark Office Re. U.S. Appl. No. 12/728,383.
Official Action Dated Mar. 2, 2010 From the US Patent and Trademark Office Re. U.S. Appl. No. 11/980,617.
Official Action Dated Dec. 8, 2010 From the US Patent and Trademark Office Re. U.S. Appl. No. 11/980,690.
Official Action Dated Apr. 9, 2010 From the US Patent and Trademark Office Re. U.S. Appl. No. 11/798,017.
Official Action Dated Aug. 13, 2008 From the US Patent and Trademark Office Re. U.S. Appl. No. 11/769,826.
Official Action Dated Feb. 16, 2012 From the US Patent and Trademark Office Re. U.S. Appl. No. 11/747,378.
Official Action Dated Apr. 20, 2011 From the US Patent and Trademark Office Re. U.S. Appl. No. 11/798,017.
Official Action Dated Dec. 20, 2011 From the US Patent and Trademark Office Re. U.S. Appl. No. 12/309,479.
Official Action Dated Sep. 21, 2009 From the US Patent and Trademark Office Re. U.S. Appl. No. 11/798,017.
Official Action Dated May 23, 2011 From the US Patent and Trademark Office Re. U.S. Appl. No. 11/980,690.
Official Action Dated Sep. 30, 2010 From the US Patent and Trademark Office Re. U.S. Appl. No. 11/798,017.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dillman "Radiolabeled Anti-CD20 Monoclonal Antibodies for the Treatment of B-Cell Lymphoma", Journal of Clinical Oncology, 20(16): 3545-3557, Aug. 15, 2002.
Mallinckrodt "Kit for the Preparation of Technetium Tc 99m Sestamibi Injection", Mallinckrodt Inc., Product Sheet, 2 P., Sep. 8, 2008.
Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.
Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Sands et al. "Methods for the Study of the Metabolism of Radiolabeled Monoclonal Antibodies by Liver and Tumor", The Journal of Nuclear Medicine, 28: 390-398, 1987.

Trikha et al. "Monoclonal Antibodies as Therapeutics in Oncology", Current Opinion in Biotechnology, 13: 609-614, 2002.
Volkow et al "Imaging the Living Human Brain: Magnetic Resonance Imaging and Positron Emission Tomography", Proc. Natl. Acad. Sci. USA, 94: 2787-2788, Apr. 1997.
Official Action Dated Aug. 31, 2012 From the US Patent and Trademark Office Re. U.S. Appl. No. 11/980,653.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Lange et al. "EM Reconstruction Algorithms for Emission and Transmission Tomography", Journal of Computer Assisted Tomography, 8(2): 306-316, Apr. 1984.
Öhrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.
Rockmore et al. "A Maximum Likelihood Approach to Emission Image Reconstruction From Projections", IEEE Transactions on Nuclear Science, 23(4): 1428-1432, Aug. 1976.
Shepp et al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Solanki "The Use of Automation in Radiopharmacy", Hospital Pharmacist, 7(4): 94-98, Apr. 2000.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Official Action Dated Oct. 11, 2012 From the US Patent and Trademark Office Re. U.S. Appl. No. 11/976,852.
Official Action Dated Oct. 10, 2012 From the US Patent and Trademark Office Re. U.S. Appl. No. 11/798,017.
Official Action Dated Jul. 30, 2012 From the US Patent and Trademark Office Re.: U.S. Appl. No. 11/980,683.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Advisory Action Before the Filing of an Appeal Brief Dated Jul. 12, 2012 From the US Patent and Trademark Office Re. U.S. Appl. No. 11/667,793.
Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Apr. 23, 2012 From the US Patent and Trademark Office Re. U.S. Appl. No. 11/932,987.
Official Action Dated Jun. 21, 2012 From the US Patent and Trademark Office Re. U.S. Appl. No. 12/309,479.
Applicant-Initiated Interview Summary Dated Jan. 28, 2013 From the US Patent and Trademark Office Re.: U.S. Appl. No. 11/798,017.
Communication Pursuant to Article 94(3) EPC Dated Nov. 12, 2012 From the European Patent Office Re. Application No. 06756258.7.
Communication Under Rule 71(3) EPC Dated Feb. 26, 2013 From the European Patent Office Re. Application No. 06756259.5.
Notice of Allowance Dated Mar. 7, 2013 From the US Patent and Trademark Office Re. U.S. Appl. No. 13/726,316.
Notice of Allowance Dated Mar. 14, 2013 From the US Patent and Trademark Office Re.: U.S. Appl. No. 11/798,017.
Notice of Allowance Dated Nov. 15, 2012 From the US Patent and Trademark Office Re.: U.S. Appl. No. 11/980,683.
Notice of Allowance Dated Feb. 25, 2013 From the US Patent and Trademark Office Re.: U.S. Appl. No. 09/641,973.
Notice of Allowance Dated Dec. 26, 2012 From the US Patent and Trademark Office Re.: U.S. Appl. No. 11/980,690.
Notice of Allowance Dated Feb. 27, 2013 From the US Patent and Trademark Office Re. U.S. Appl. No. 12/514,785.
Official Action Dated Feb. 7, 2013 From the US Patent and Trademark Office Re. U.S. Appl. No. 11/980,653.

Official Action Dated Dec. 19, 2012 From the US Patent and Trademark Office Re. U.S. Appl. No. 12/448,473.
Official Action Dated Feb. 22, 2013 From the US Patent and Trademark Office Re.: U.S. Appl. No. 10/616,307.
Official Action Dated Dec. 28, 2012 From the US Patent and Trademark Office Re.: U.S. Appl. No. 10/343,792.
Summons to Attend Oral Proceedings Pursuant to Rule 115(1) EPC Dated Nov. 29, 2012 From the European Patent Office Re. Application No. 06756259.5.
Supplementary European Search Report and the European Search Opinion Dated Nov. 13, 2012 From the European Patent Office Re. Application No. 06728347.3.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Charland et al. "The Use of Deconvolution and Total Least Squares in Recovering a Radiation Detector Line Spread Function", Medical Physics, 25(2): 152-160, Feb. 1998. Abstract Only!
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniformity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Studen "Compton Camera With Position-Sensitive Silicon Detectors", Doctoral Thesis, University of Ljubljana, Faculty of Mathematics and Physics, 36 P.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Advisory Action before the Filing of an Appeal Brief Dated May 21, 2013 From the US Patent and Trademark Office Re. U.S. Appl. No. 11/980,653.
Applicant-Initiated Interview Summary Dated May 9, 2013 From the US Patent and Trademark Office Re. U.S. Appl. No. 12/448,473.
Notice of Allowance Dated Feb. 23, 2011 From the US Patent and Trademark Office Re.: U.S. Appl. No. 12/728,383.
Notice of Allowance Dated Oct. 26, 2012 From the US Patent and Trademark Office Re. U.S. Appl. No. 12/514,785.
Notice of Allowance Dated Sep. 28, 2012 From the US Patent and Trademark Office Re. U.S. Appl. No. 12/792,856.
Official Action Dated Mar. 11, 2013 From the US Patent and Trademark Office Re. U.S. Appl. No. 13/345,719.
Response Dated Apr. 7, 2009 to Official Action of Oct. 7, 2008 From the US Patent and Trademark Office Re.: U.S. Appl. No. 10/616,301.
Written Opinion Dated Jul. 11, 2008 from the International Searching Authority of the Patent Cooperation Treaty Re.: Application No. PCT/IL06/01511.
Berman et al. "Dual-Isotope Myocardial Perfusion SPECT With Rest Thallium-201 and Stress Tc-99m Sestamibi", Nuclear Cardiology, 12(2): 261-270, May 1994.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Chengazi et al. "Imaging Prostate Cancer With Technetium-99m-7E11-C5.3 (CYT-351)", Journal of Nuclear Medicine, 38: 675-682, 1997.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.
Applicant-Initiated Interview Summary Dated May 1, 2013 From the US Patent and Trademark Office Re. U.S. Appl. No. 10/343,792.
Applicant-Initiated Interview Summary Dated May 1, 2013 From the US Patent and Trademark Office Re. U.S. Appl. No. 11/980,653.
Notice of Allowance Dated Jul. 15, 2013 From the US Patent and Trademark Office U.S. Appl. No. 11/932,987.
Notice of Allowance Dated Jul. 25, 2013 From the US Patent and Trademark Office U.S. Appl. No. 13/345,719.
Official Action Dated Aug. 5, 2013 From the US Patent and Trademark Office U.S. Appl. No. 12/309,479.
Official Action Dated Jul. 5, 2013 From the US Patent and Trademark Office U.S. Appl. No. 11/656,548.
Official Action Dated Aug. 14, 2013 From the US Patent and Trademark Office U.S. Appl. No. 12/448,473.
Official Action Dated Jul. 30, 2013 From the US Patent and Trademark Office U.S. Appl. No. 10/343,792.
Official Action Dated Jul. 31, 2013 From the US Patent and Trademark Office U.S. Appl. No. 11/667,793.
Supplemental Notice of Allowability Dated Aug. 20, 2013 From the US Patent and Trademark Office U.S. Appl. No. 11/980,653.
Berman et al. "D-SPECT: A Novel Camera for High Speed Quantitative Molecular Imaging: Initial Clinical Results", The Journal of Nuclear Medicine, 47(Suppl.1): 131P, 2006.
Berman et al. "Myocardial Perfusion Imaging With Technetium-99m-Sestamibi: Comparative Analysis of Available Imaging Protocols", The Journal of Nuclear Medicine, 35: 681-688, 1994.
Borges-Neto et al. "Perfusion and Function at Rest and Treadmill Exercise Using Technetium-99m-Sestamibi: Comparison of One- and Two-Day Protocols in Normal Volunteers", The Journal of Nuclear Medicine, 31(7): 1128-1132, Jul. 1990.
Kwok et al. "Feasability of Simultaneous Dual-Isotope Myocardial Perfusion Acquisition Using A Lower Dose of Sestamibi", European Journal of Nuclear Medicine, 24(3): 281-285, Mar. 1997.
Patton et al. "D-SPECT: A New Solid State Camera for High Speed Molecular Imaging", The Journal of Nuclear Medicine, 47(Suppl.1): 189P, 2006.
Notice of Allowance Dated Jun. 21, 2013 From the US Patent and Trademark Office U.S. Appl. No. 11/980,653.
Notice of Allowance Dated Jun. 14, 2013 From the US Patent and Trademark Office U.S. Appl. No. 10/616,307.
Official Action Dated Jun. 12, 2013 From the US Patent and Trademark Office U.S. Appl. No. 12/087,150.
Bacharach et al. "Attenuation Correction in Cardiac Positron Emission Tomography and Single-Photon Emission Computed Tomography", Journal of Nucelar Cardiology, 2(3): 246-255, 1995.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.
Communication Pursuant to Article 94(3) EPC Dated Sep. 16, 2013 From the European Patent Office U.S. Appl. No. 06832278.3.
Notice of Allowance Dated Aug. 20, 2013 From the US Patent and Trademark Office U.S. Appl. No. 11/932,872.
Official Action Dated Sep.5, 2013 From the US Patent and Trademark Office U.S. Appl. No. 13/947,198.

* cited by examiner

*Primary Examiner* — Jonathan Cwern

(57) ABSTRACT

Protocols for radioimaging an event or disorder are provided. An exemplary protocol comprises a method of radioimaging a myocardial perfusion, the method comprising in sequence:

(a) administering to a subject about 3 mCi Tl201 thallous chloride;
(b) allowing said subject to rest;
(c) radioimaging a heart of said subject;
(d) subjecting said subject to a physical stress;
(e) administering to said subject at a peak of said physical stress about 20-30 mCi Tc99m sestamibi; and
(f) radioimaging said heart of said subject, thereby radioimaging a myocardial perfusion.

41 Claims, 160 Drawing Sheets

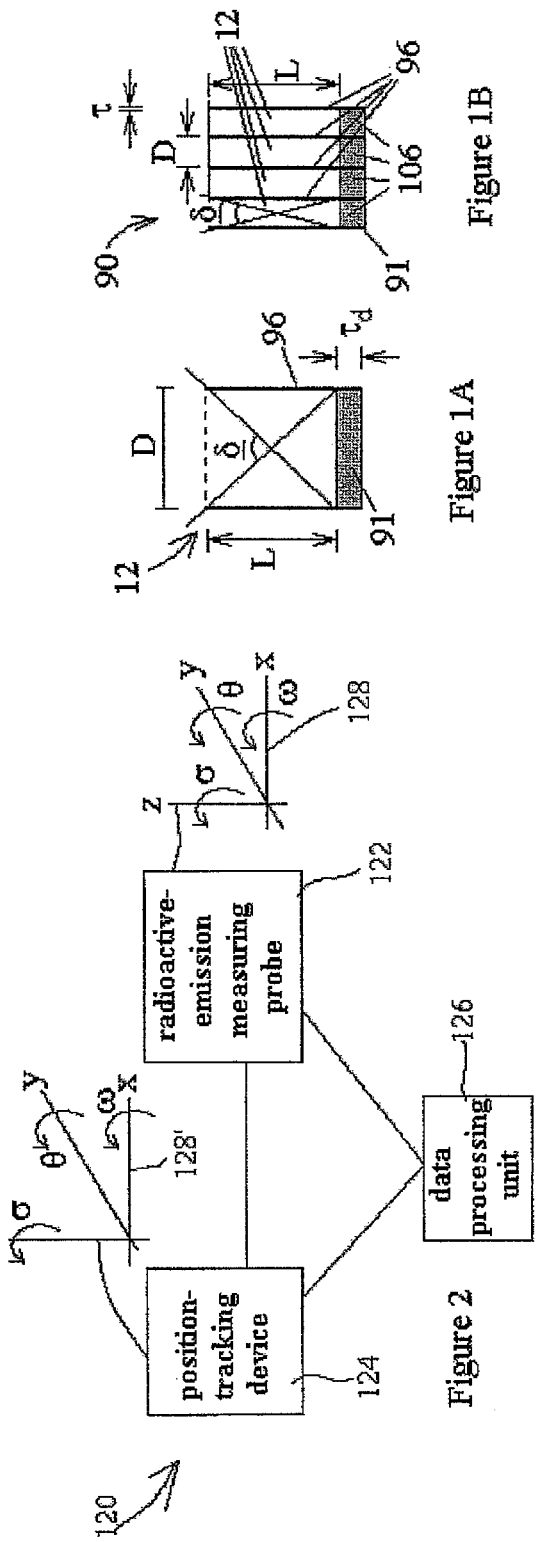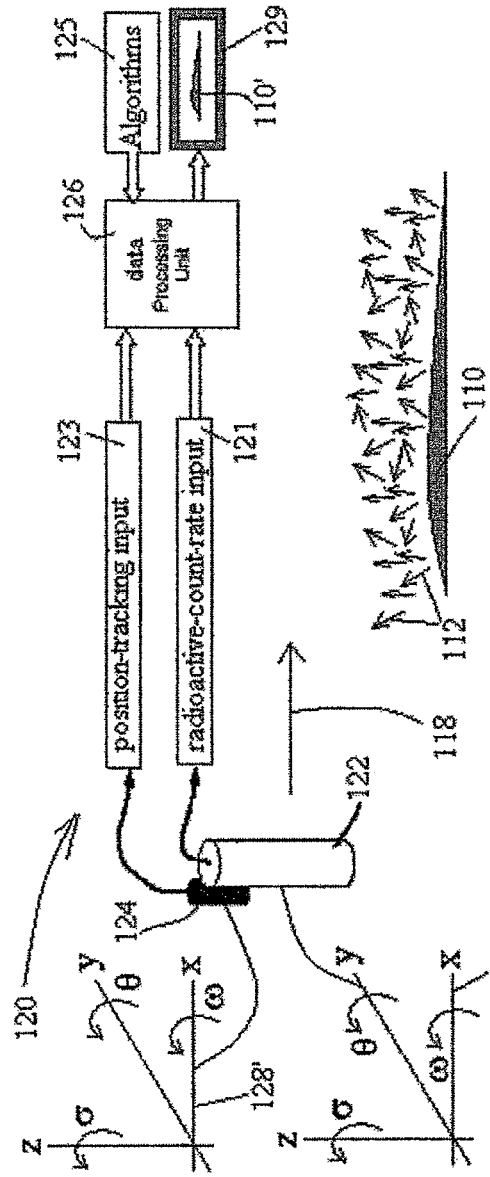

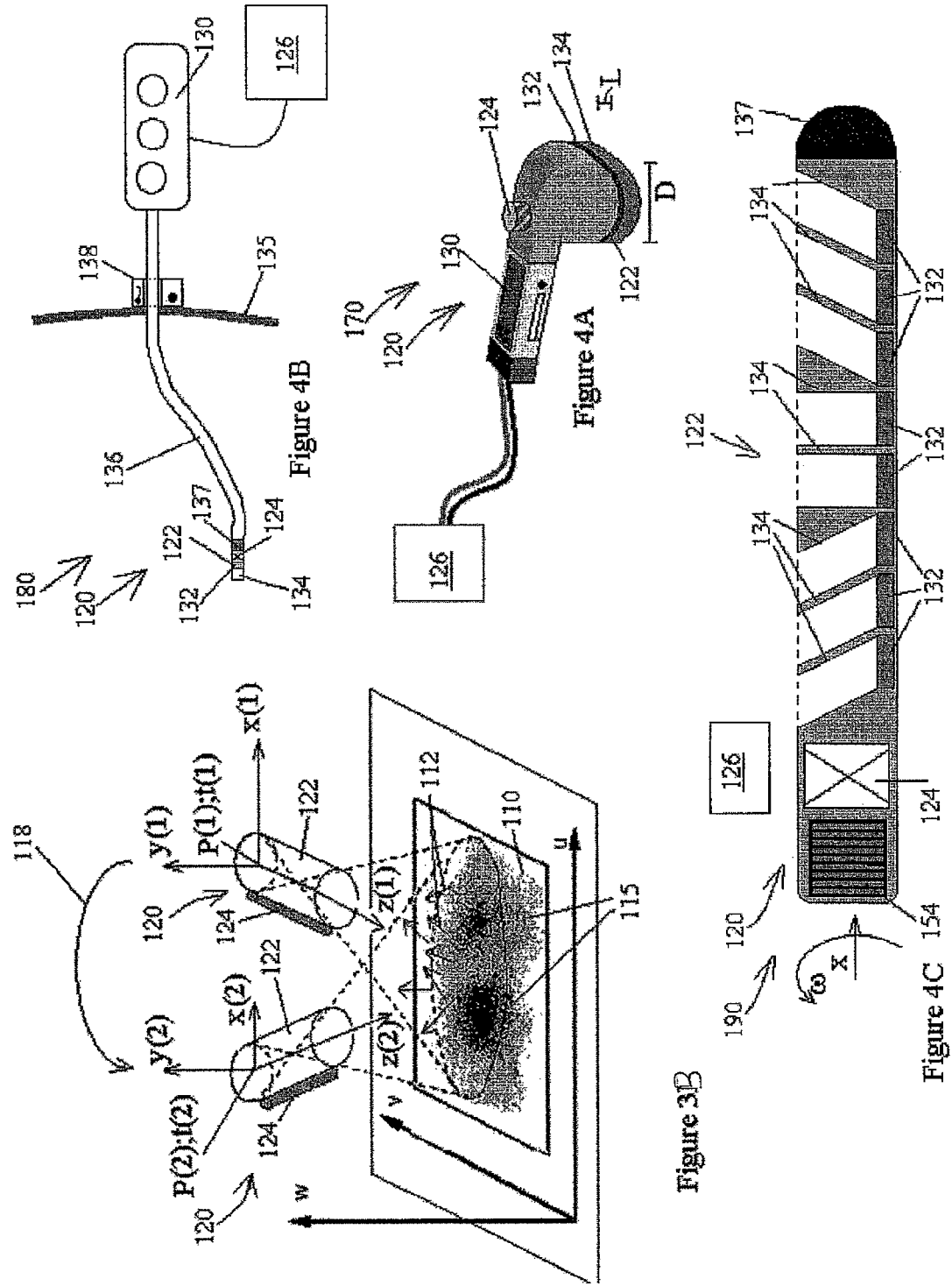

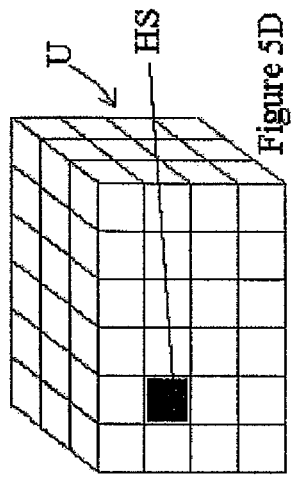
Figure 5D
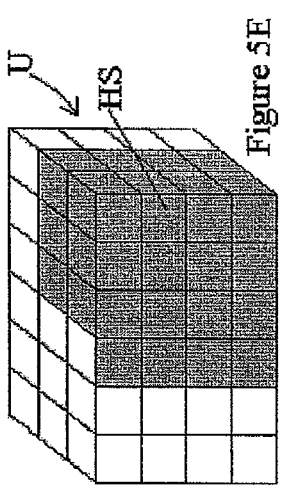
Figure 5E
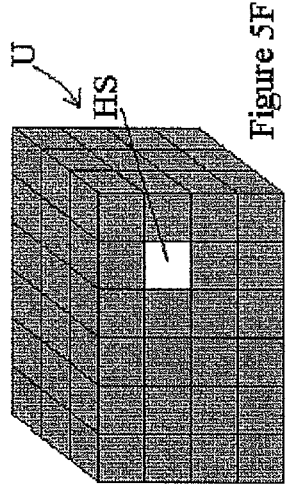
Figure 5F
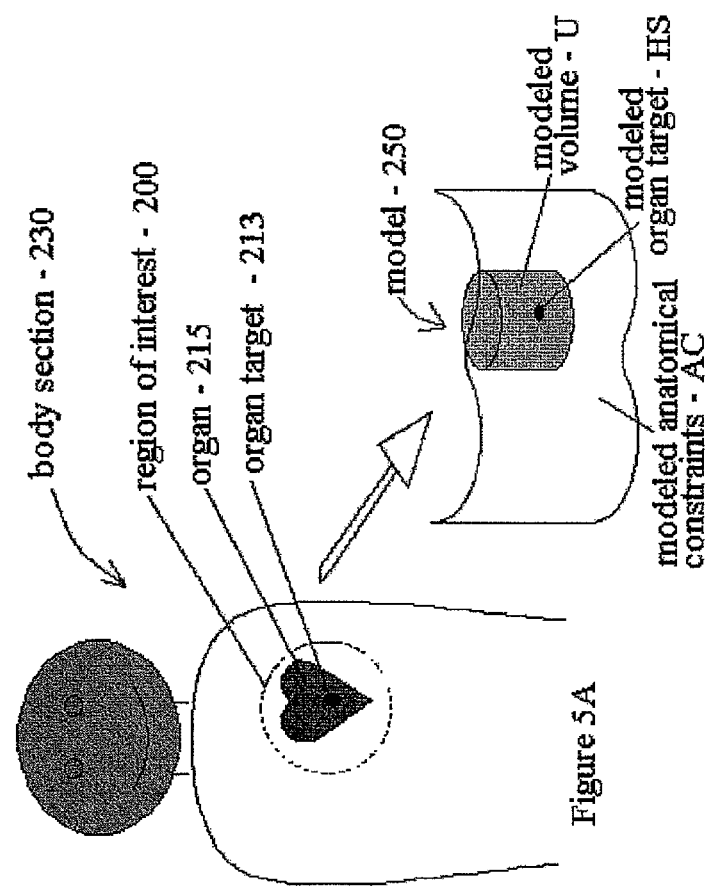
Figure 5A
Figure 5B

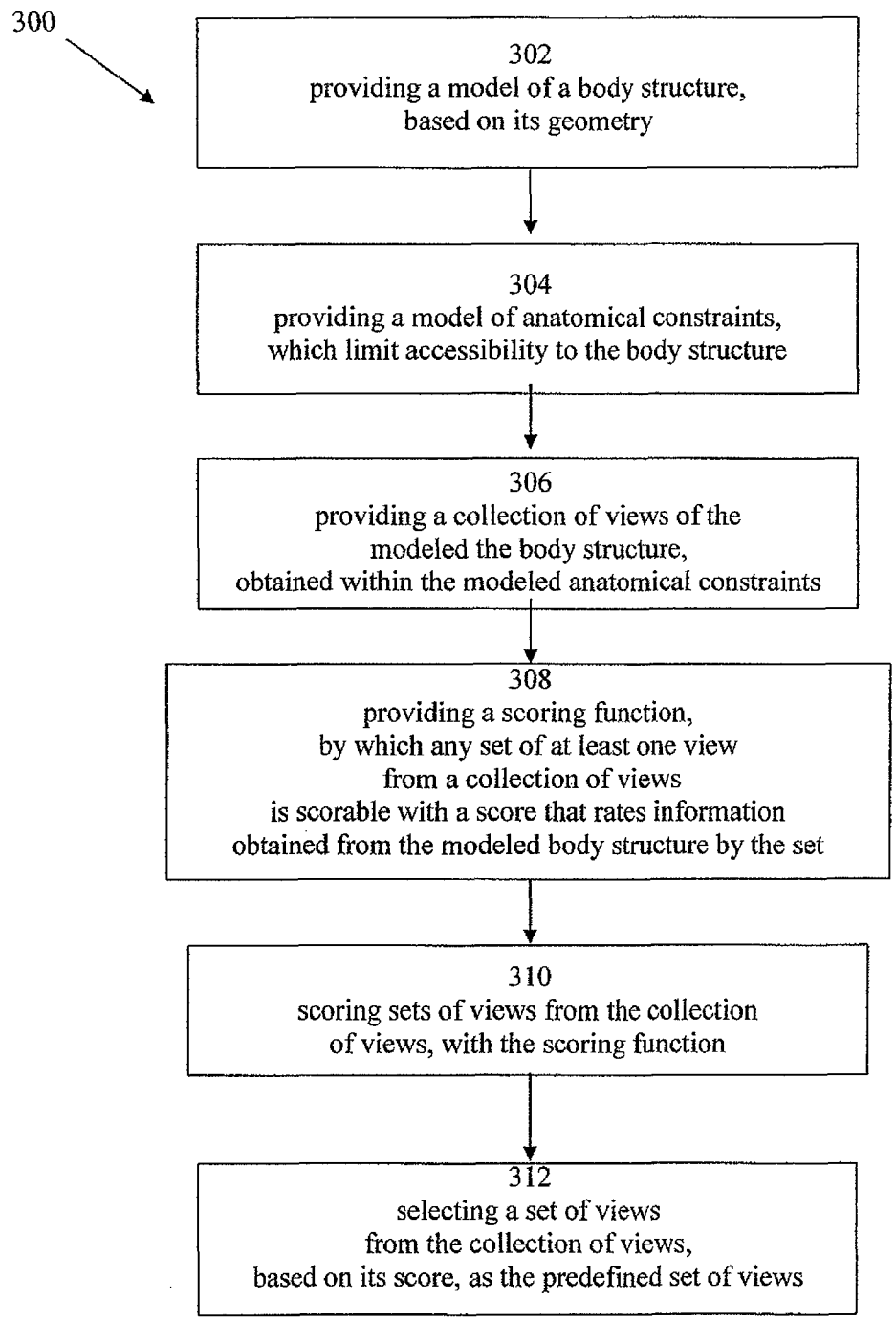

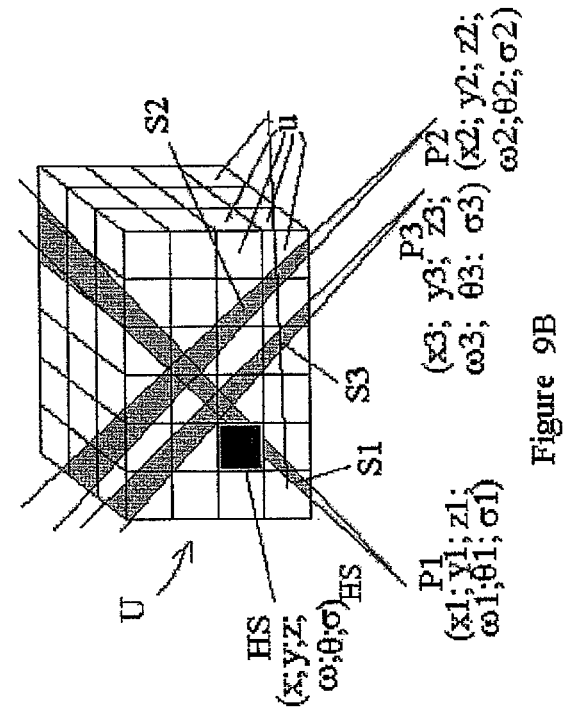
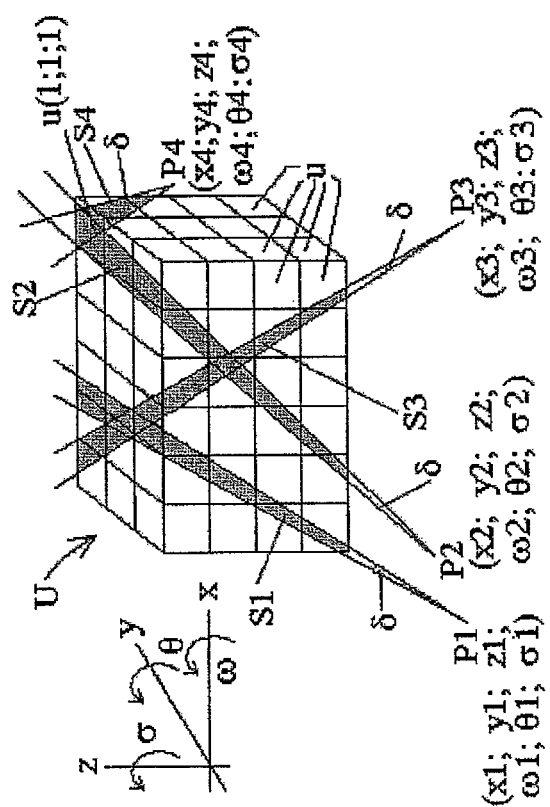

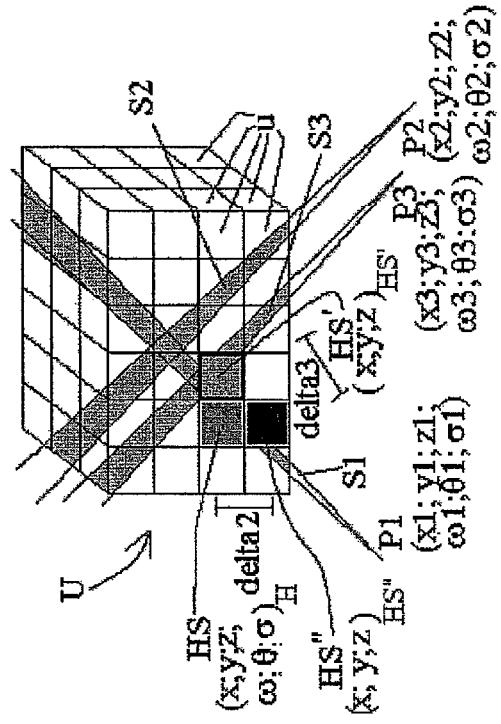
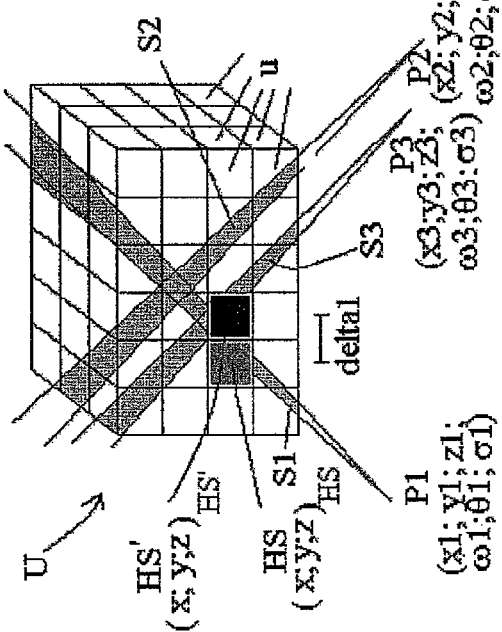
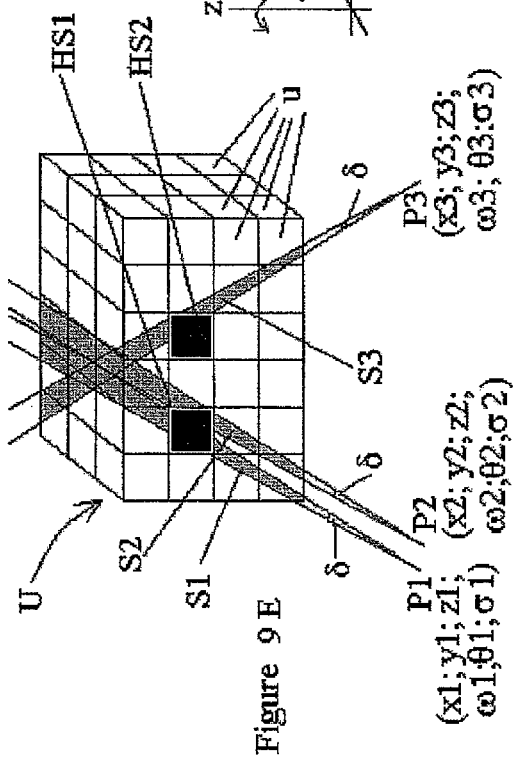
Figure 9C
Figure 9D
Figure 9E

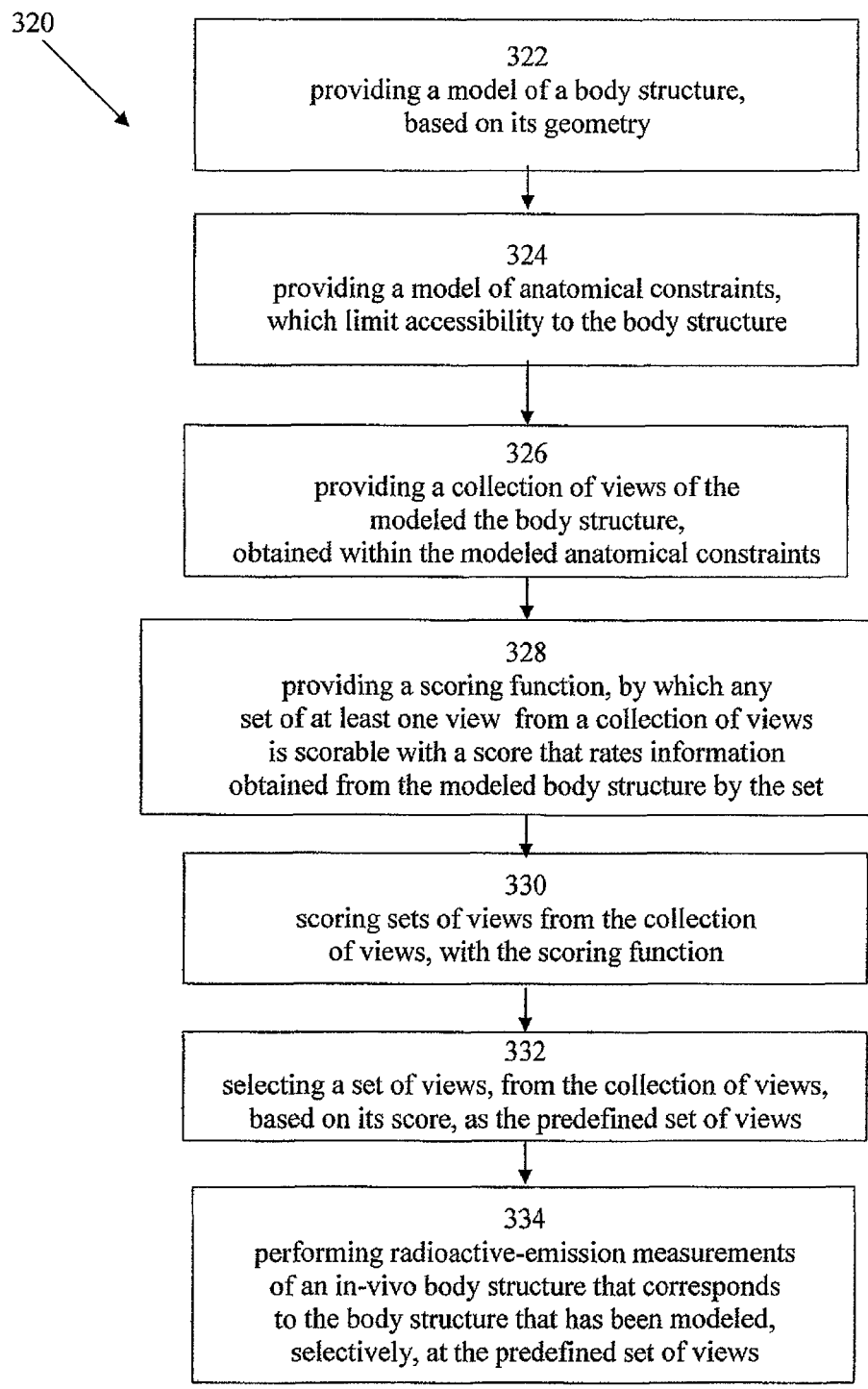

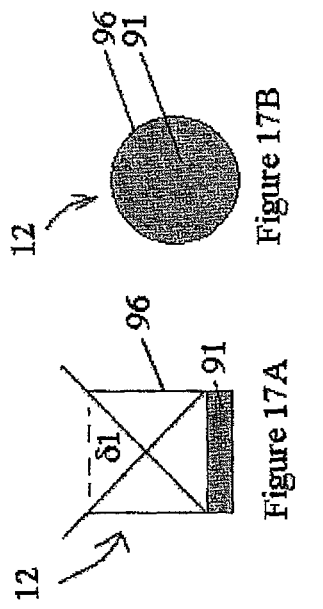
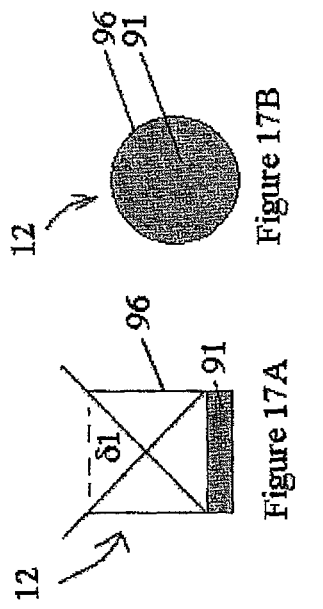
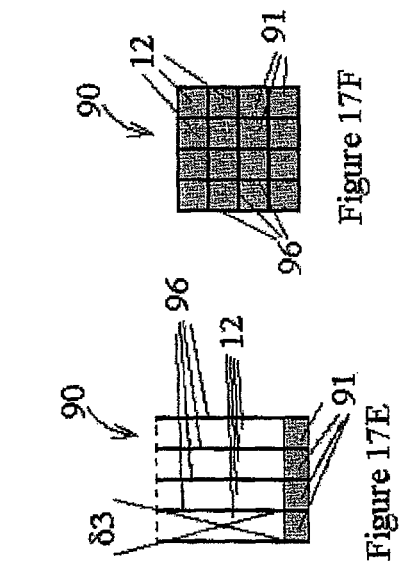
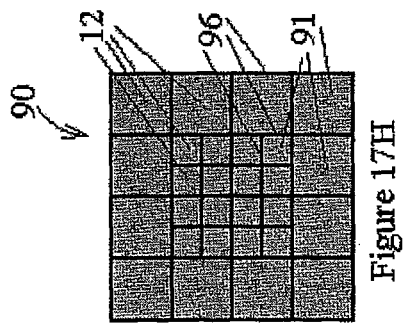
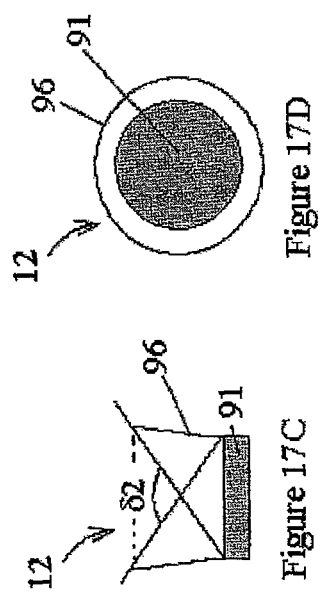
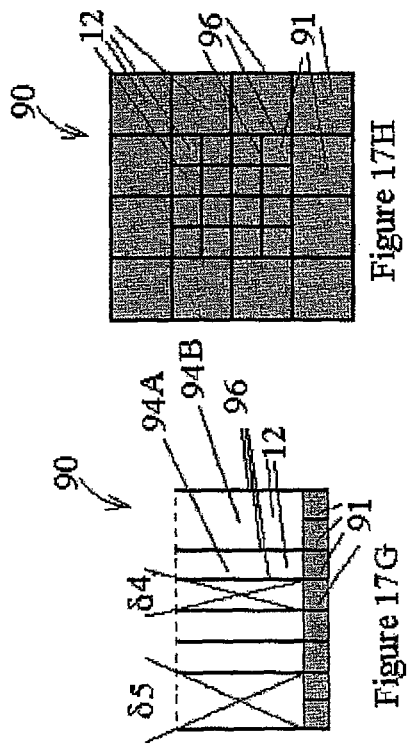

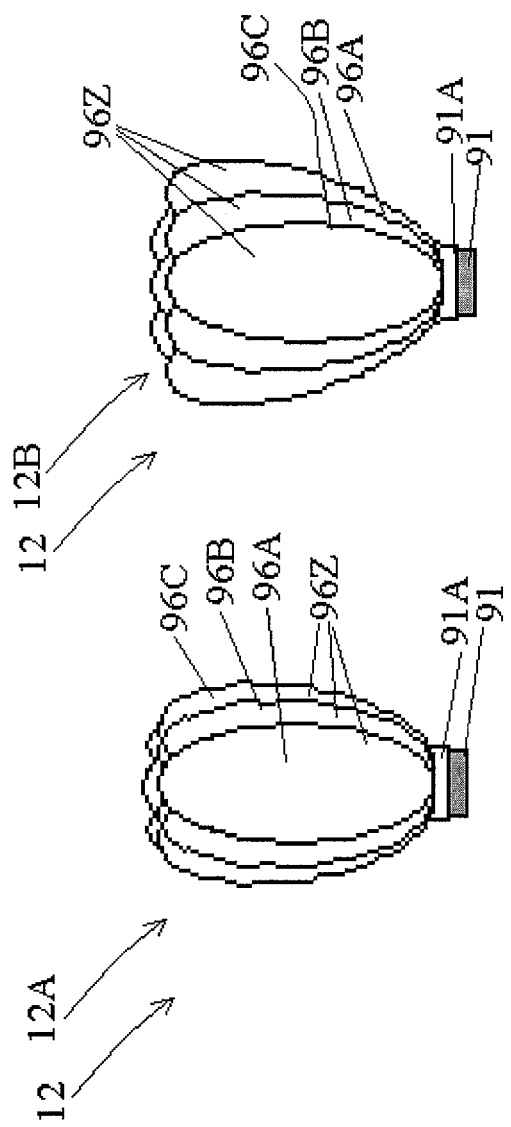

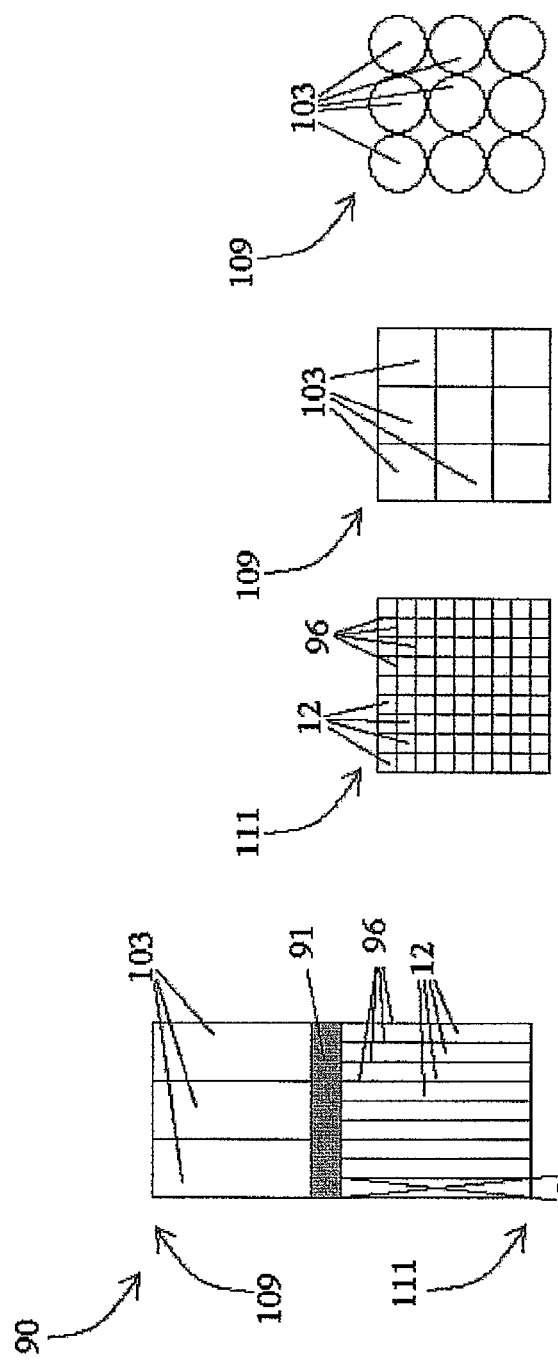

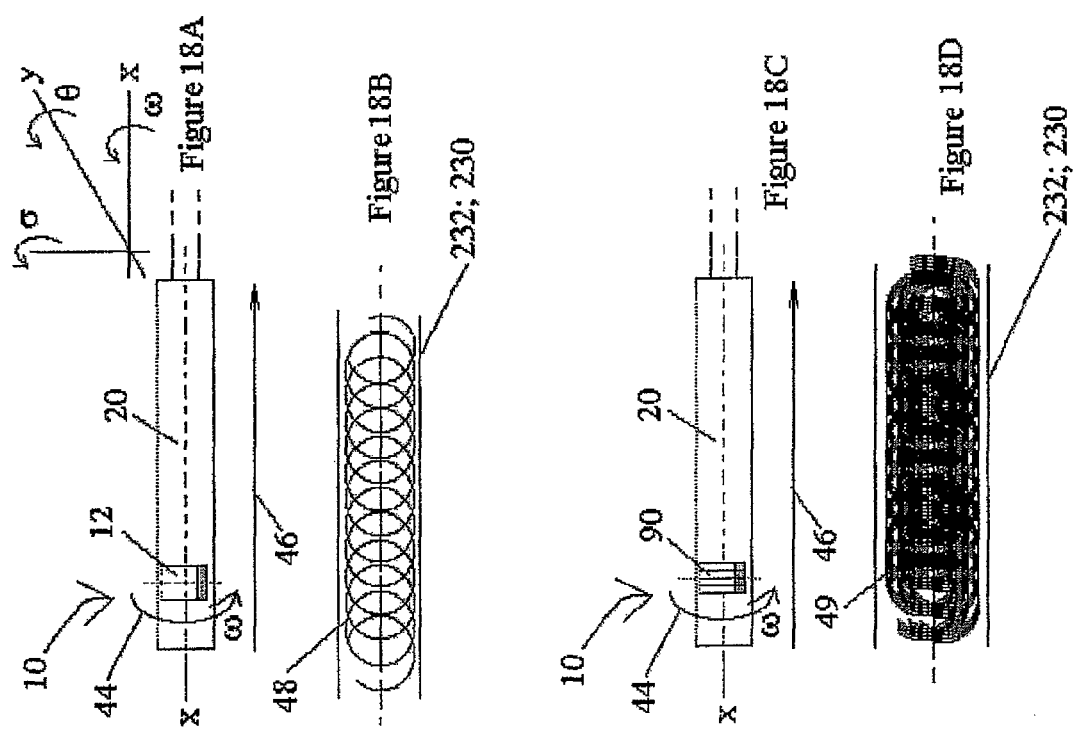

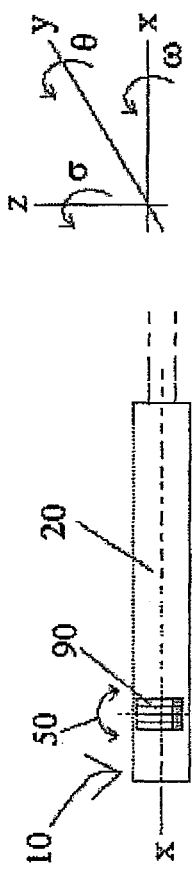
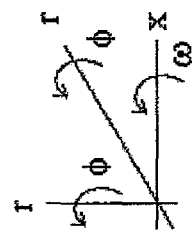
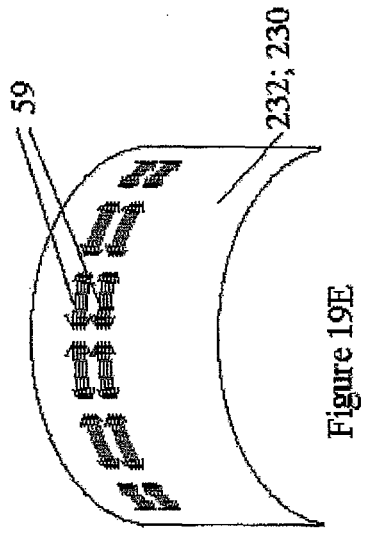
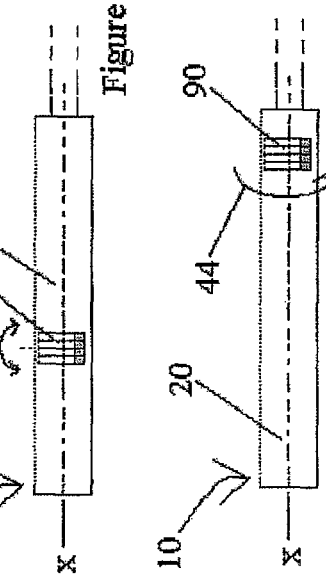
Figure 19A
Figure 19B
Figure 19C
Figure 19D
Figure 19E

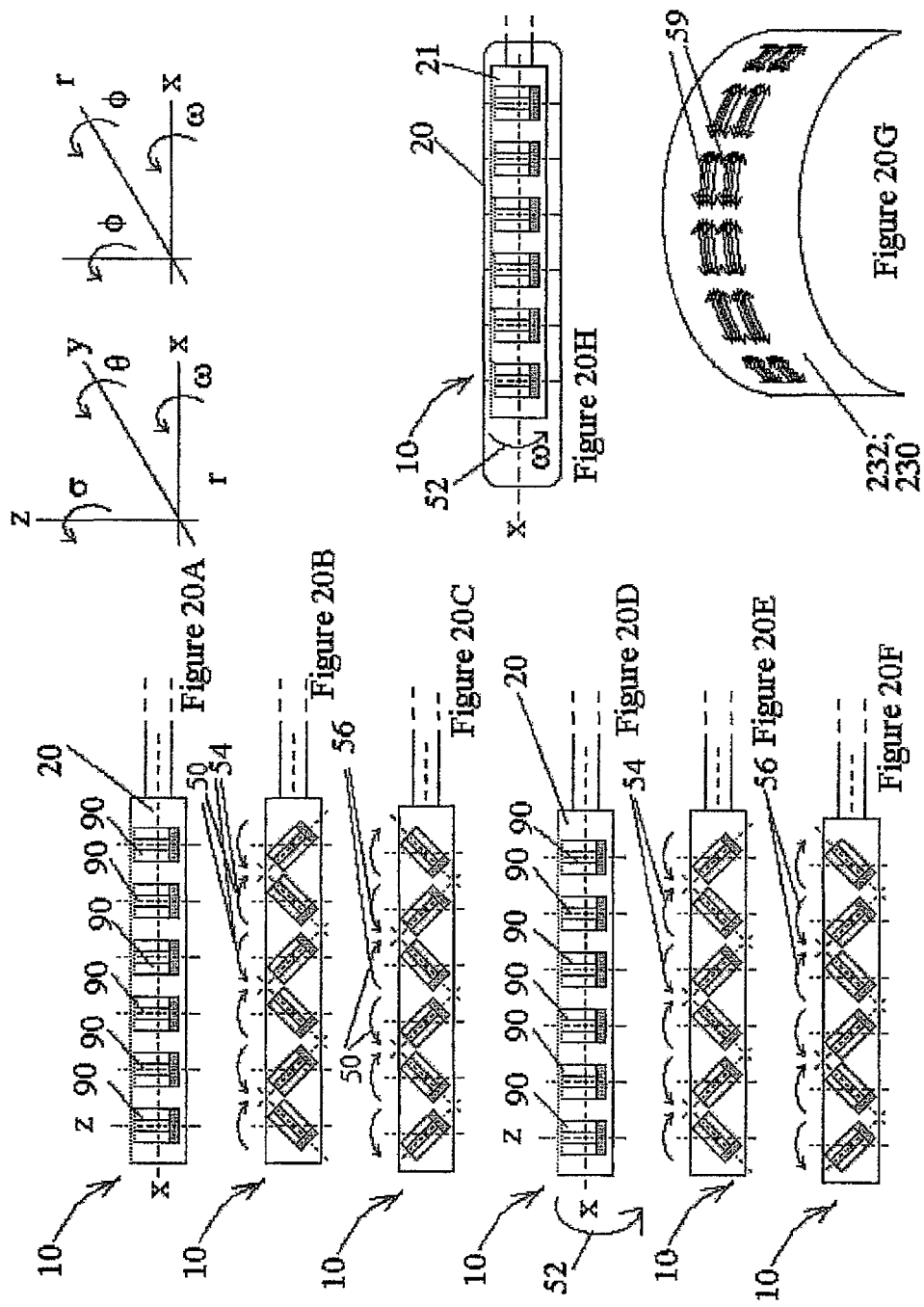

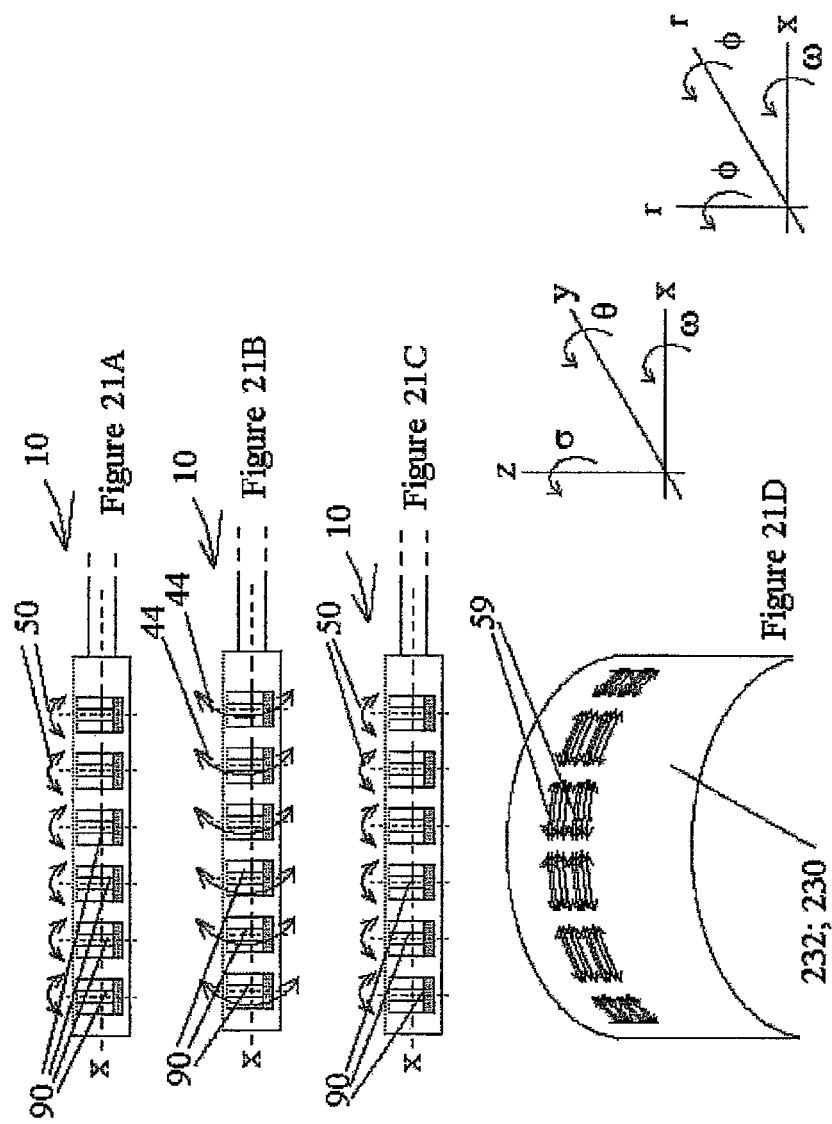

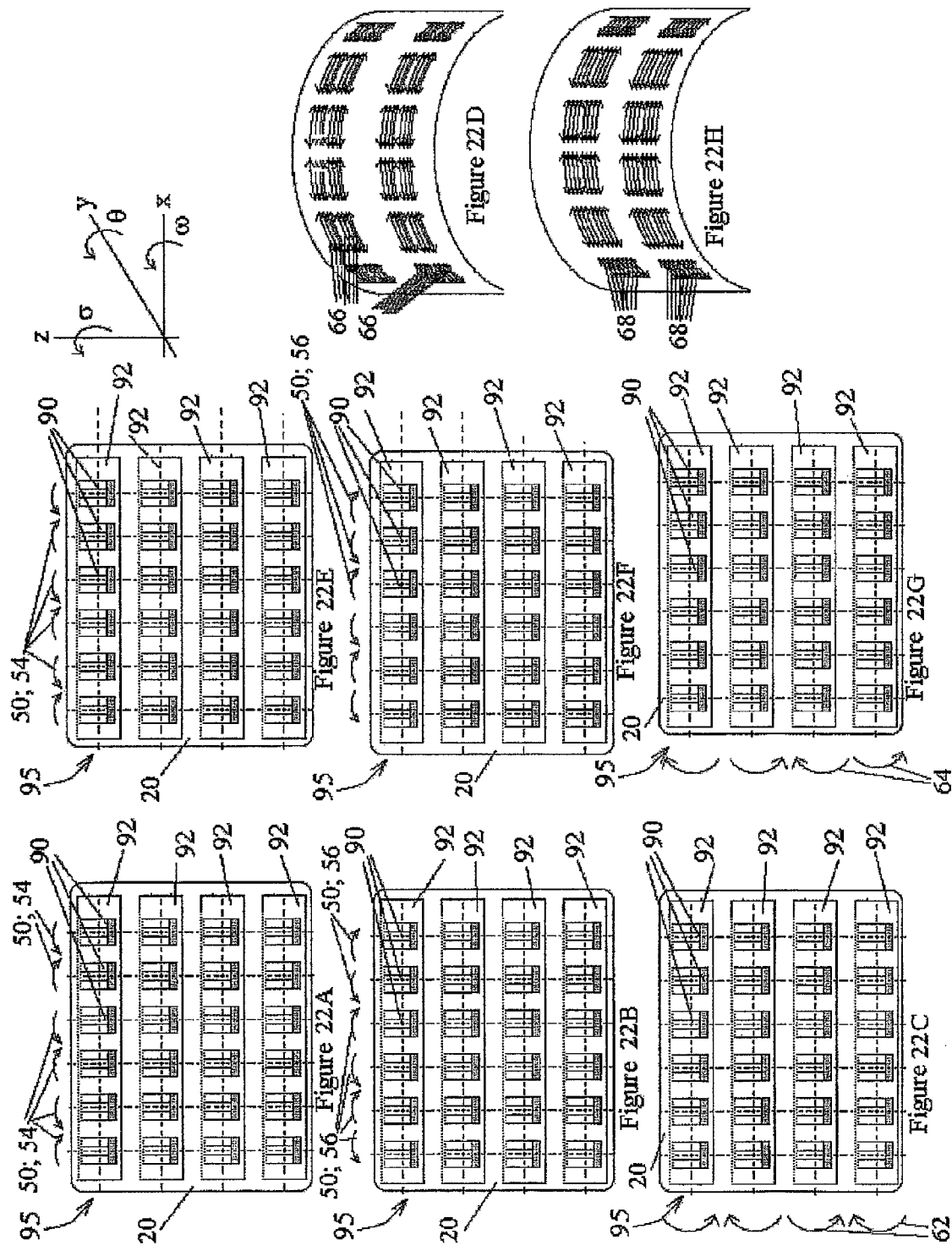

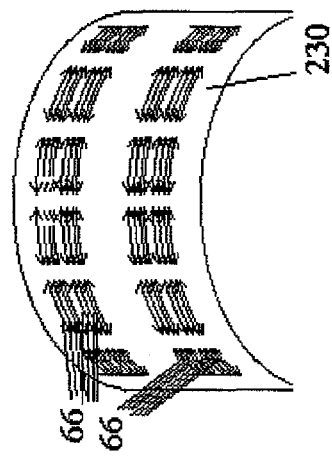
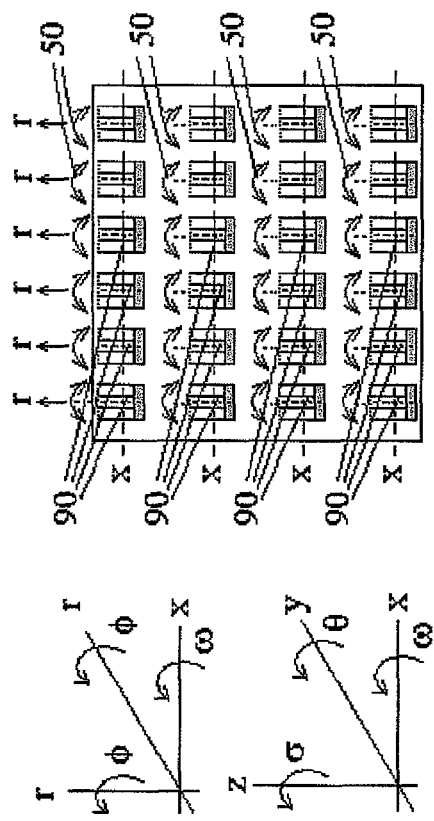
Figure 22J
Figure 22I

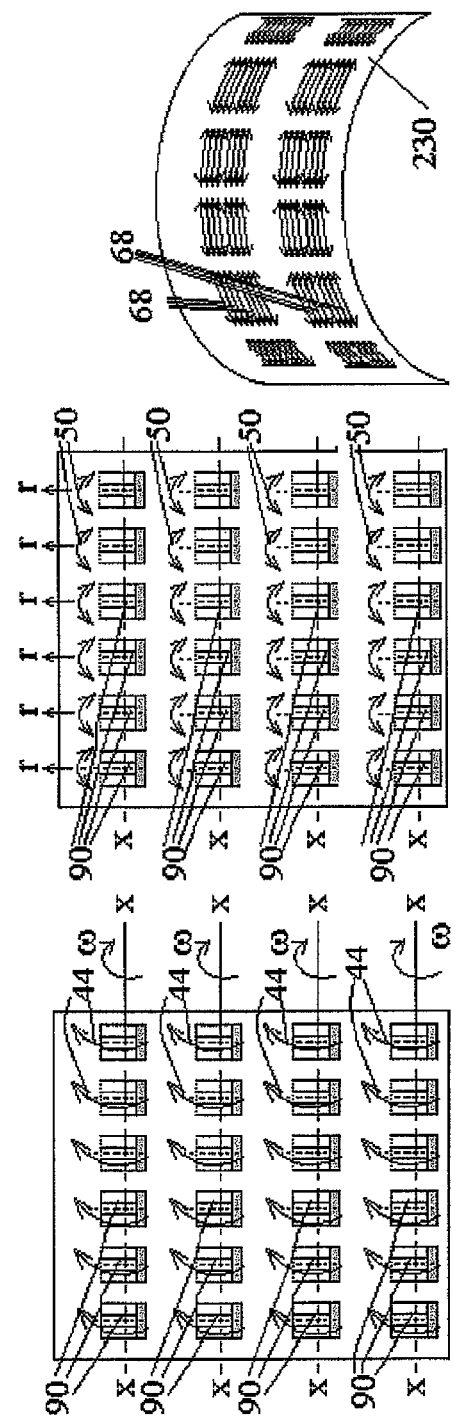

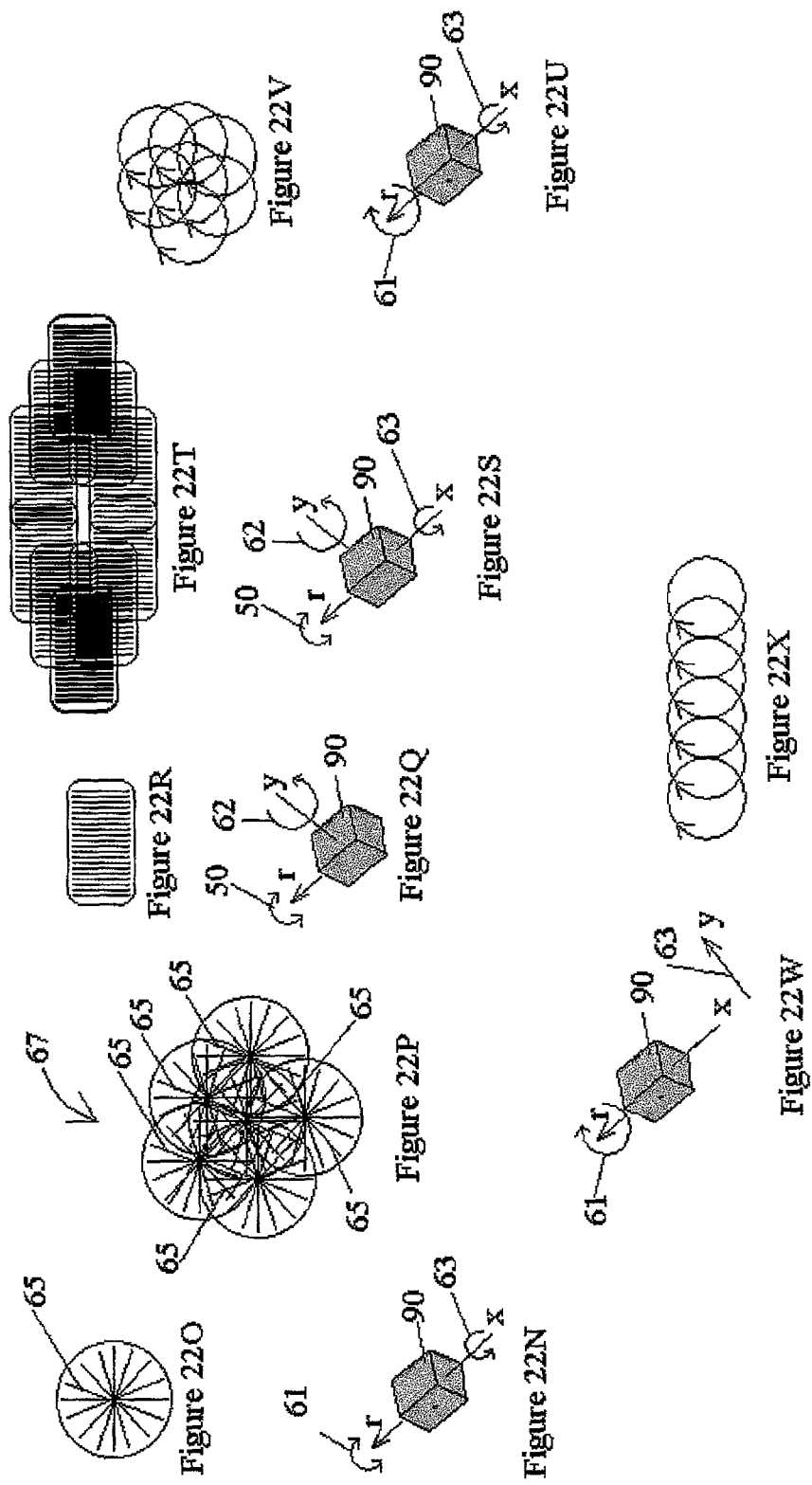

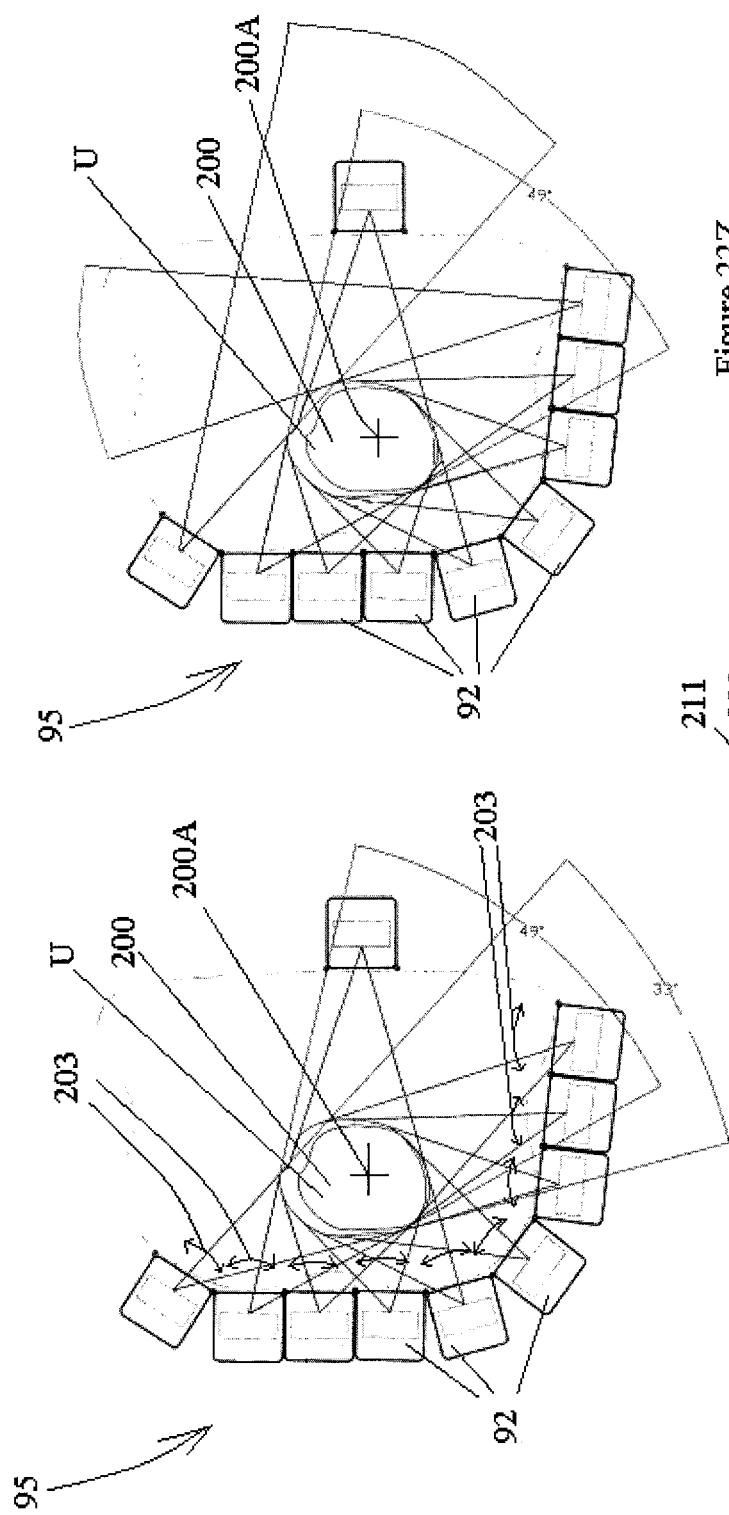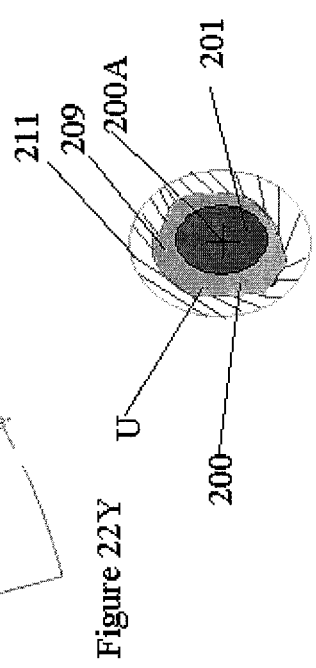

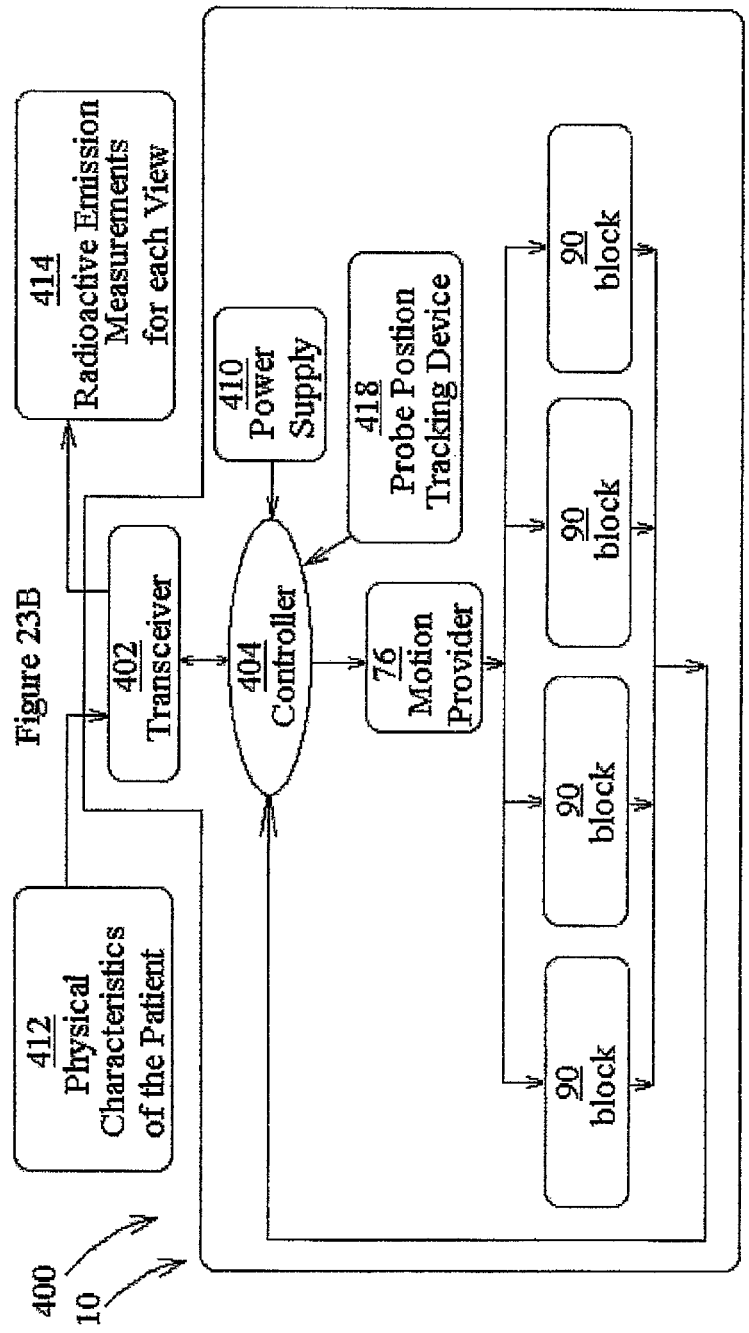

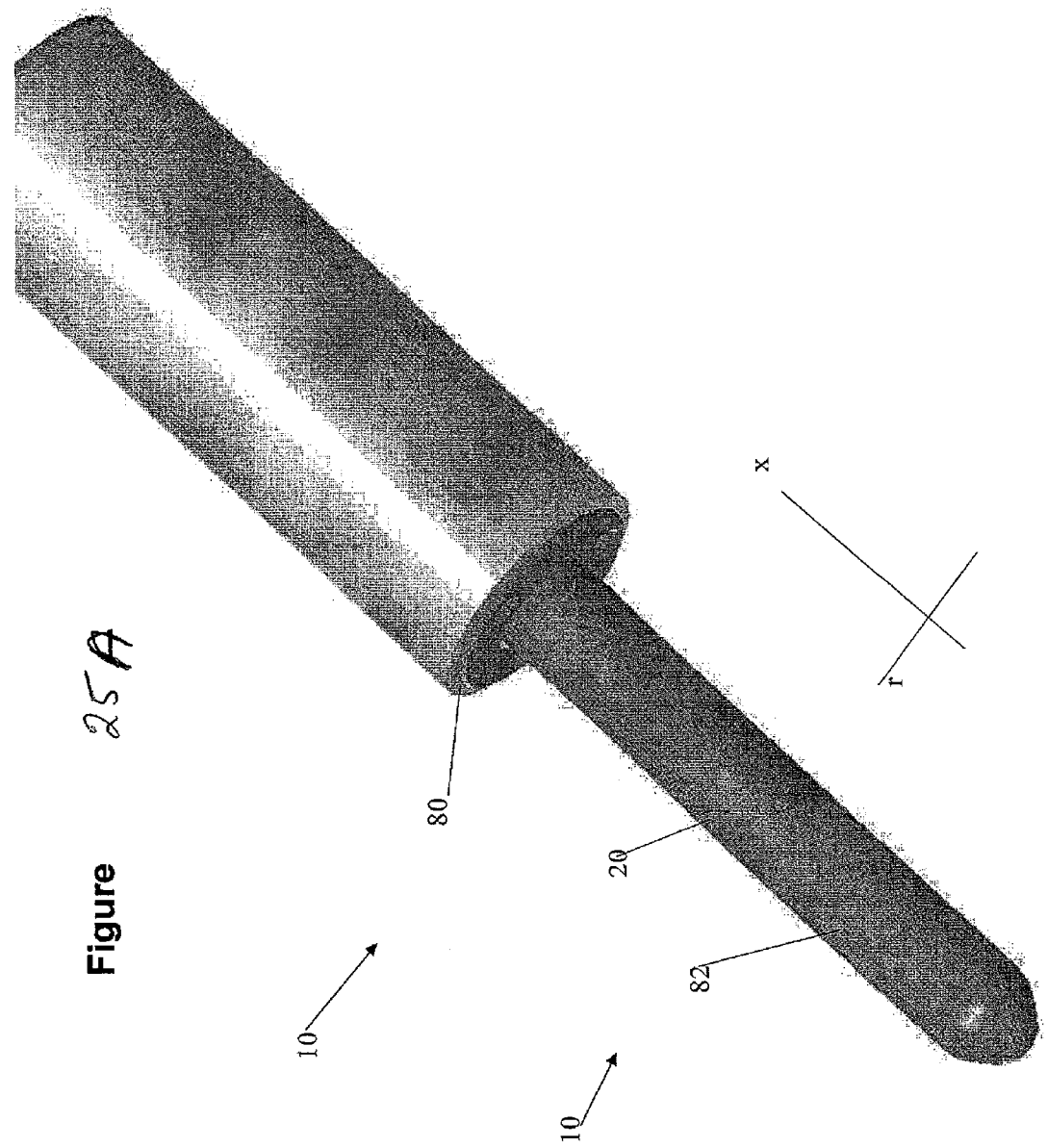

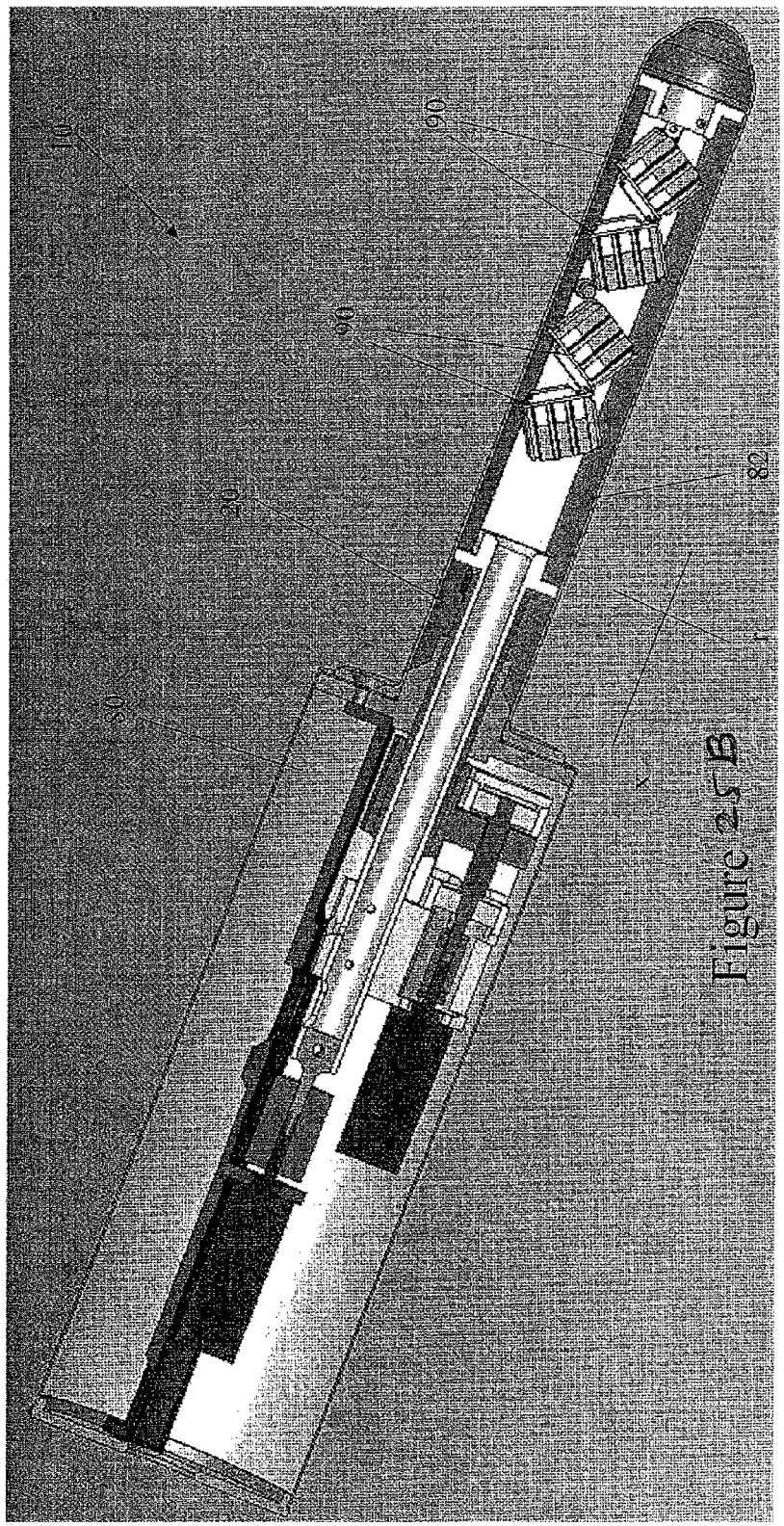

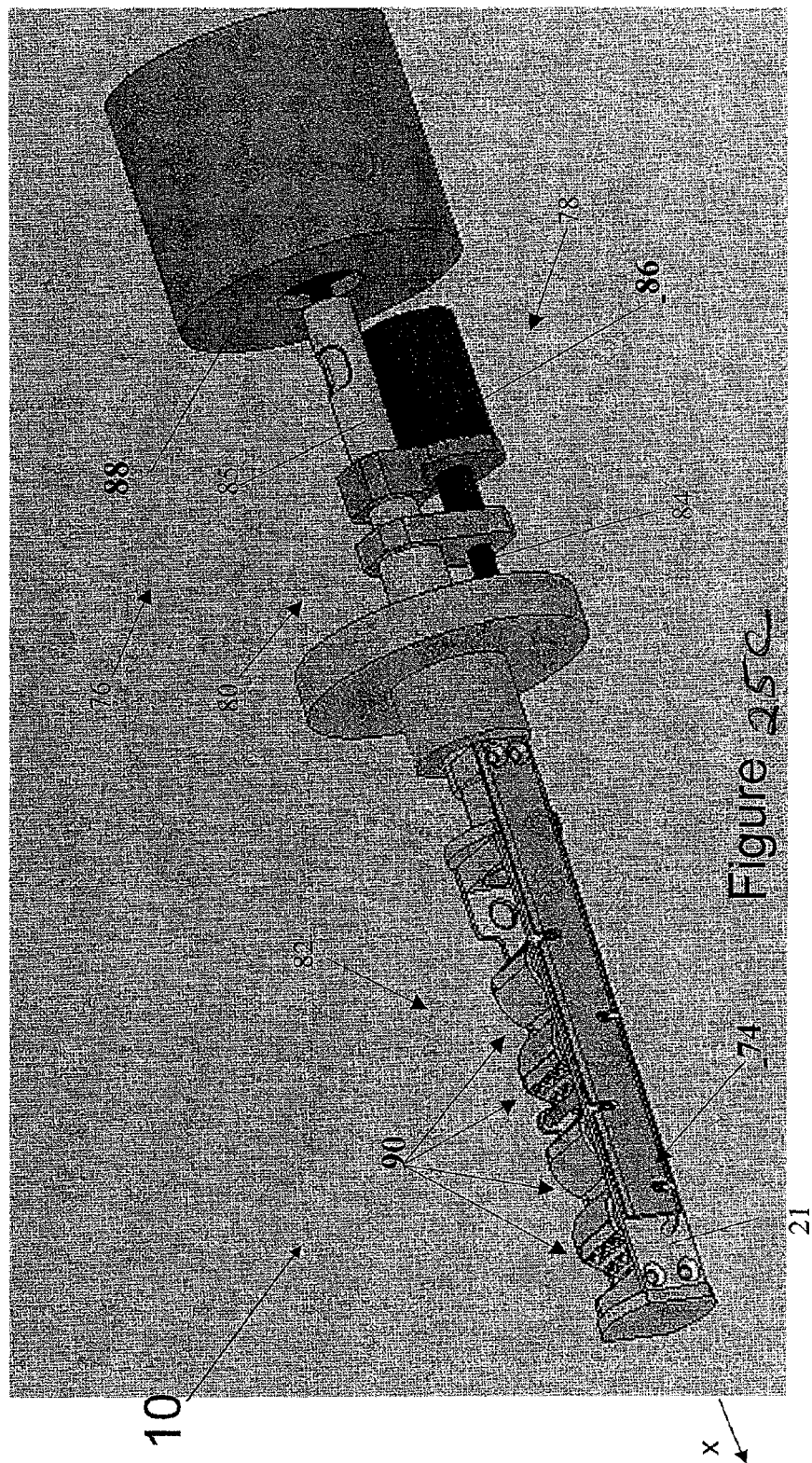

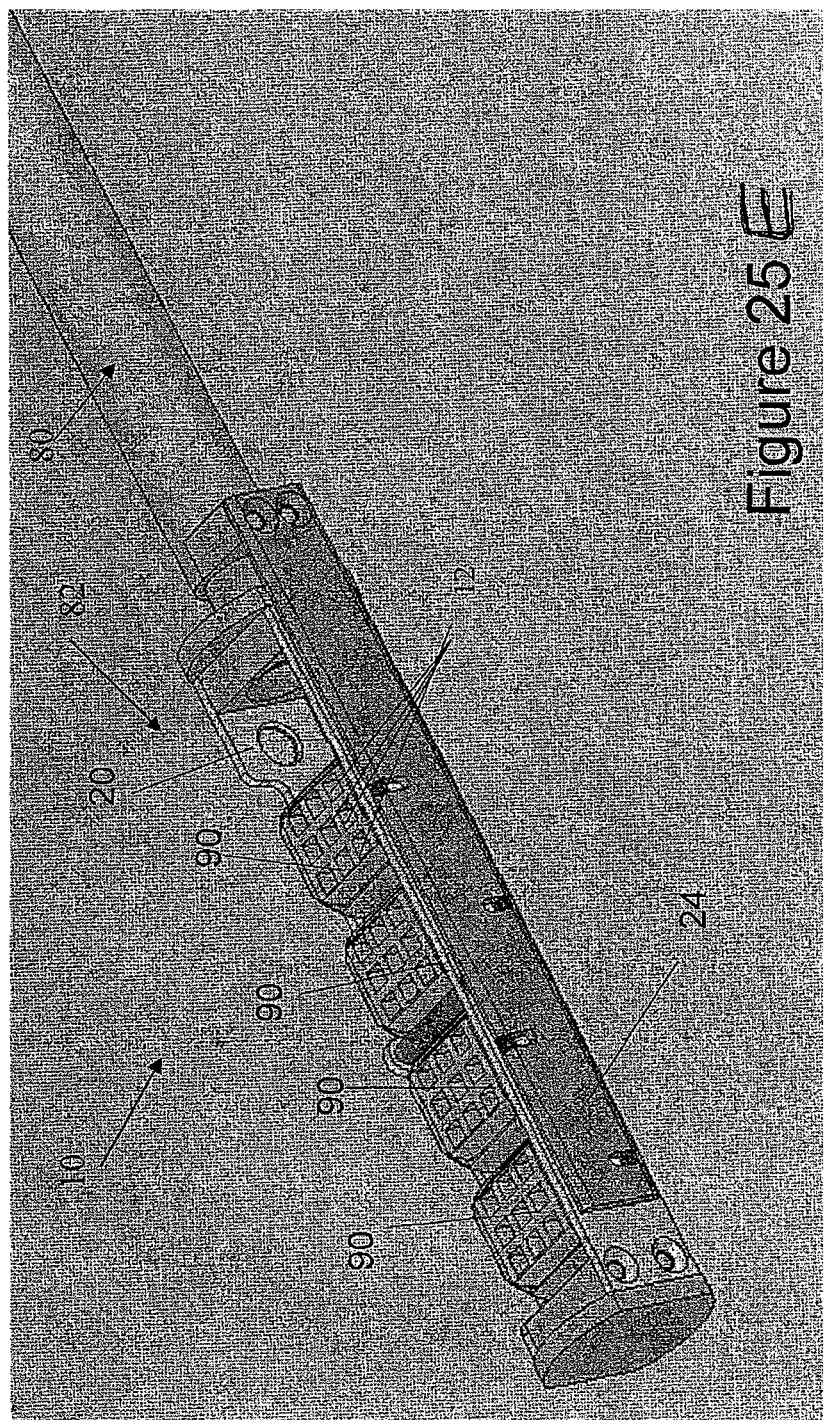

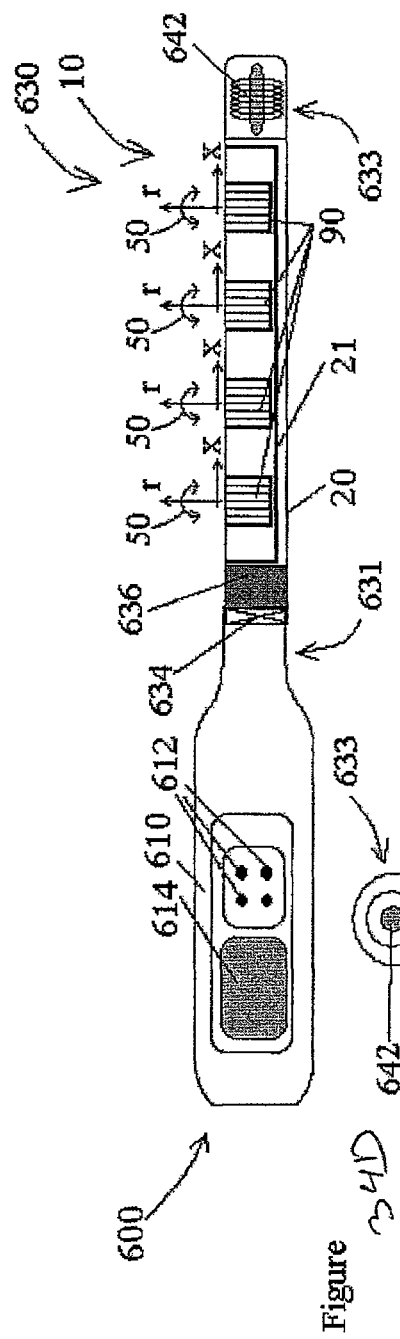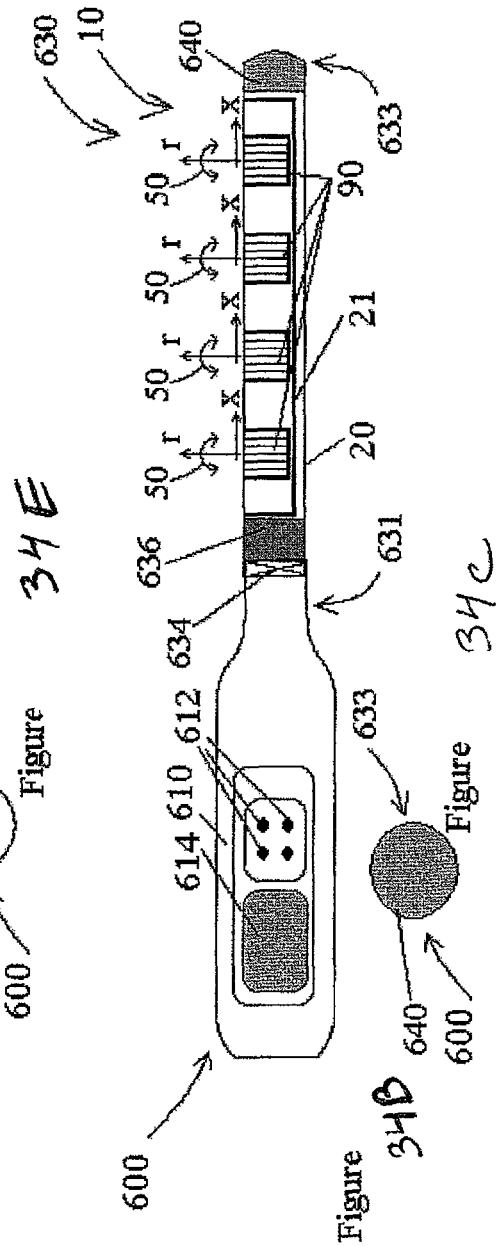

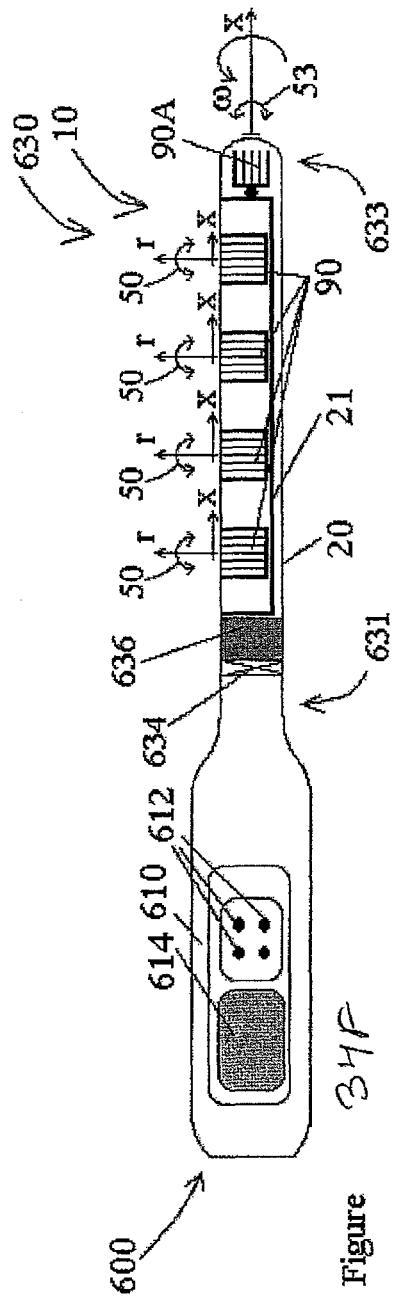
Figure 34F
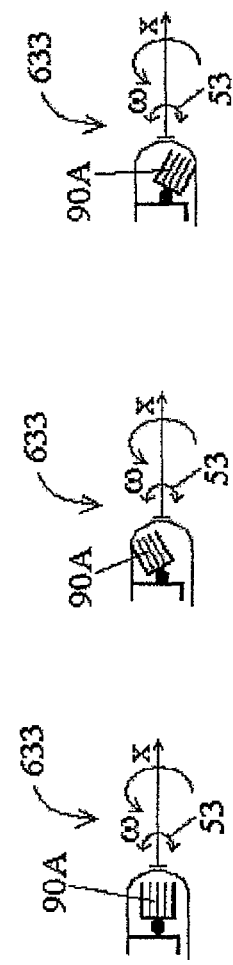
Figure 34H
Figure 34I
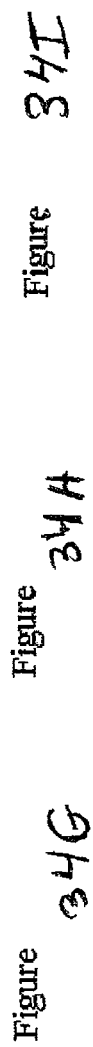
Figure 34G

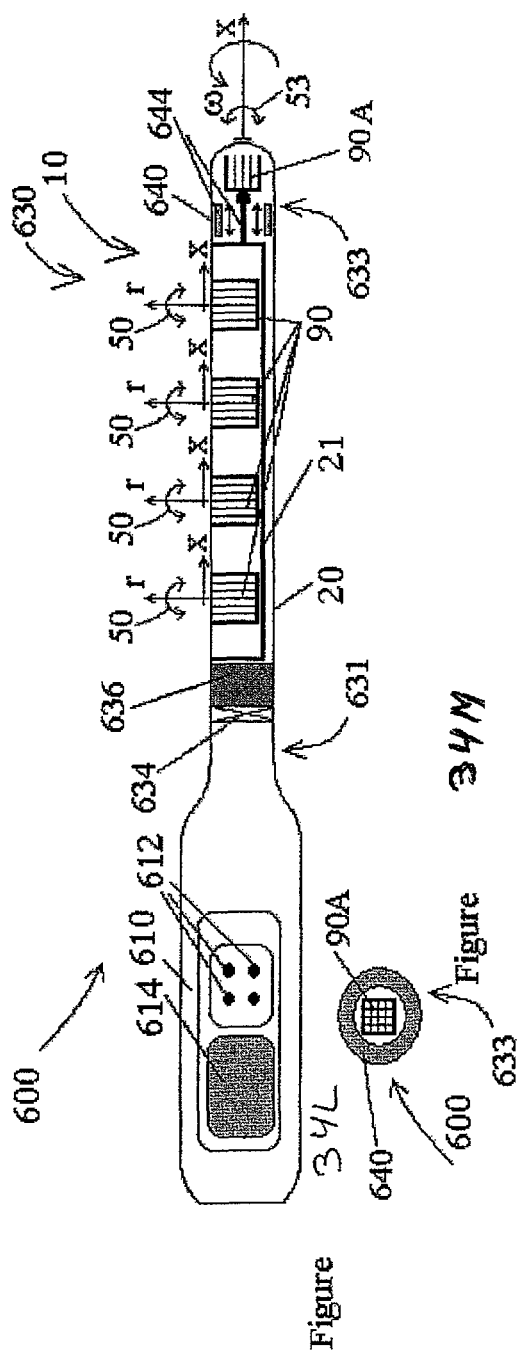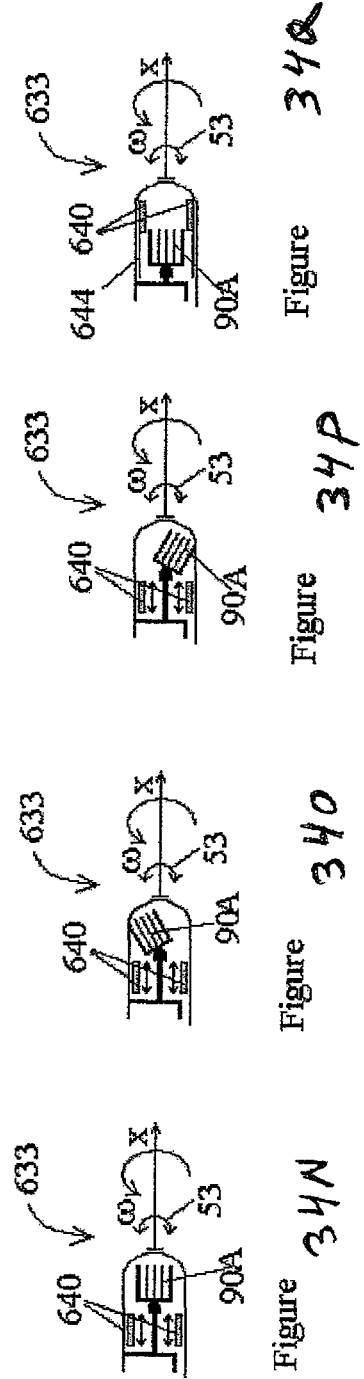

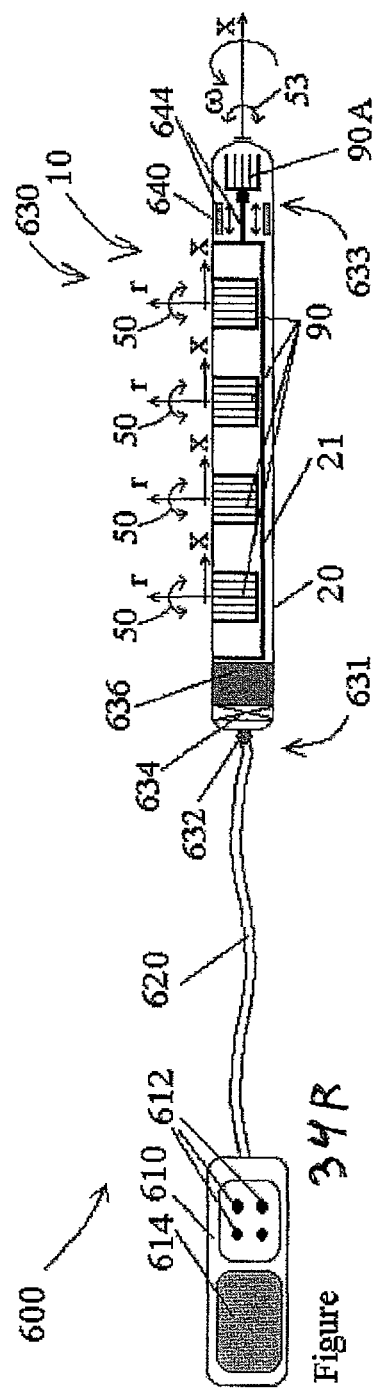

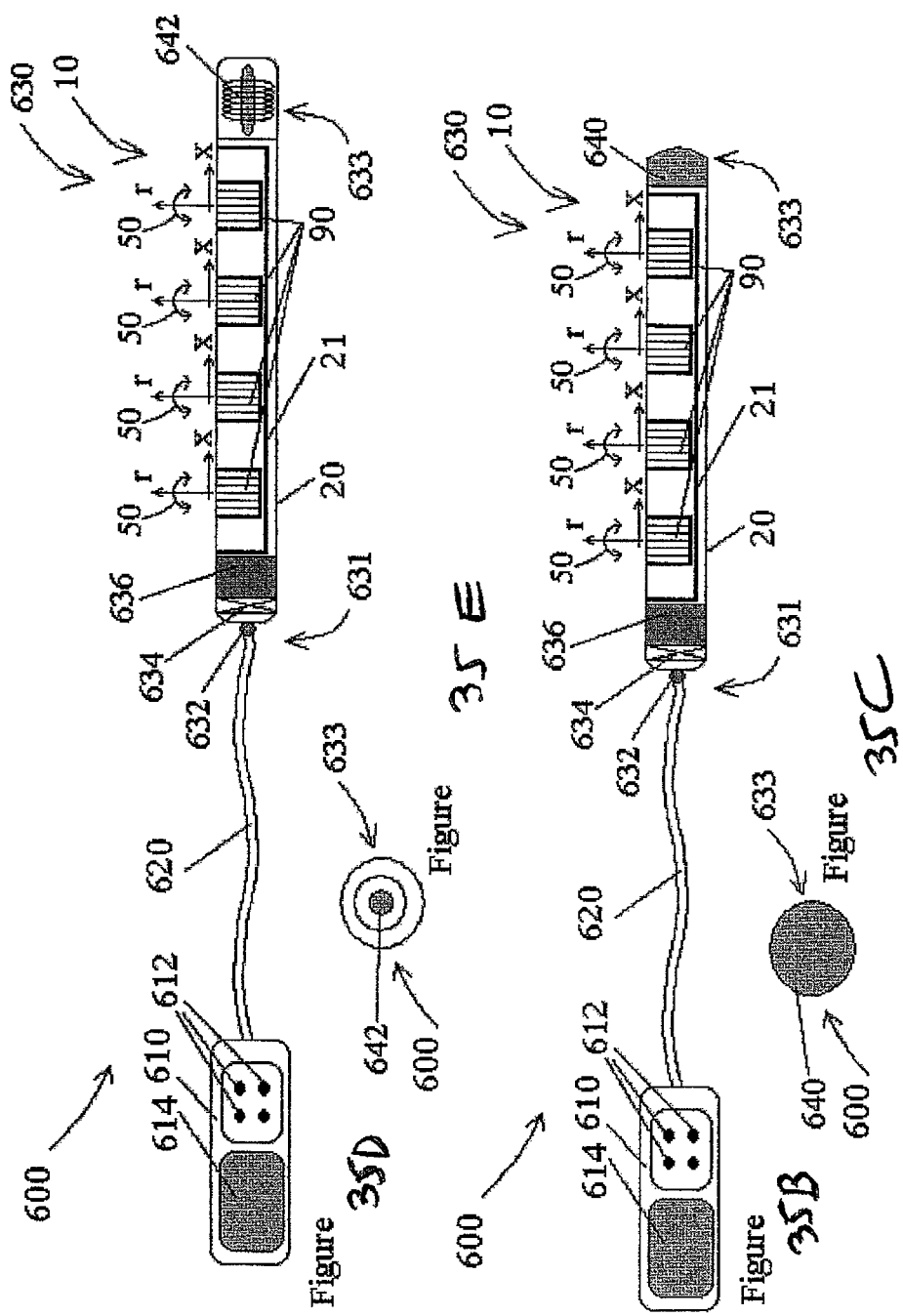

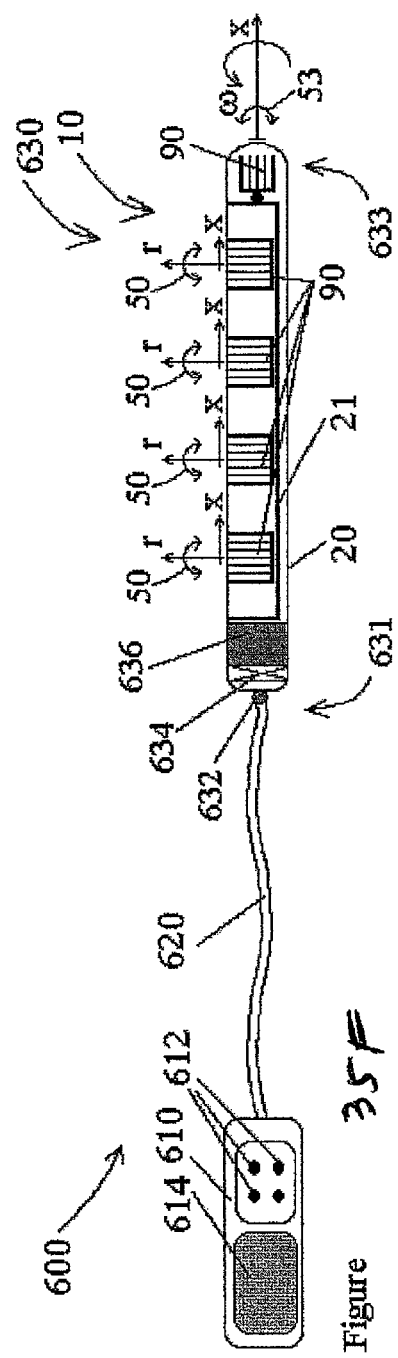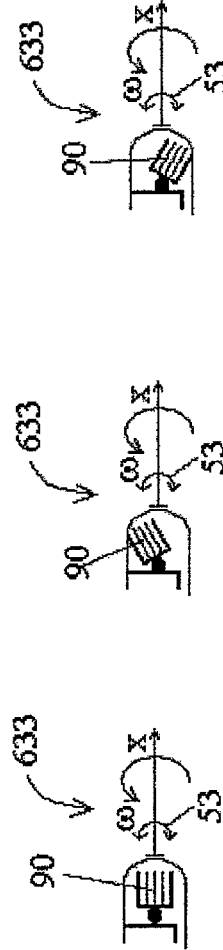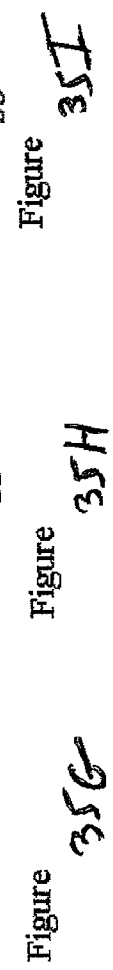
Figure 35F  Figure 35G  Figure 35H  Figure 35I

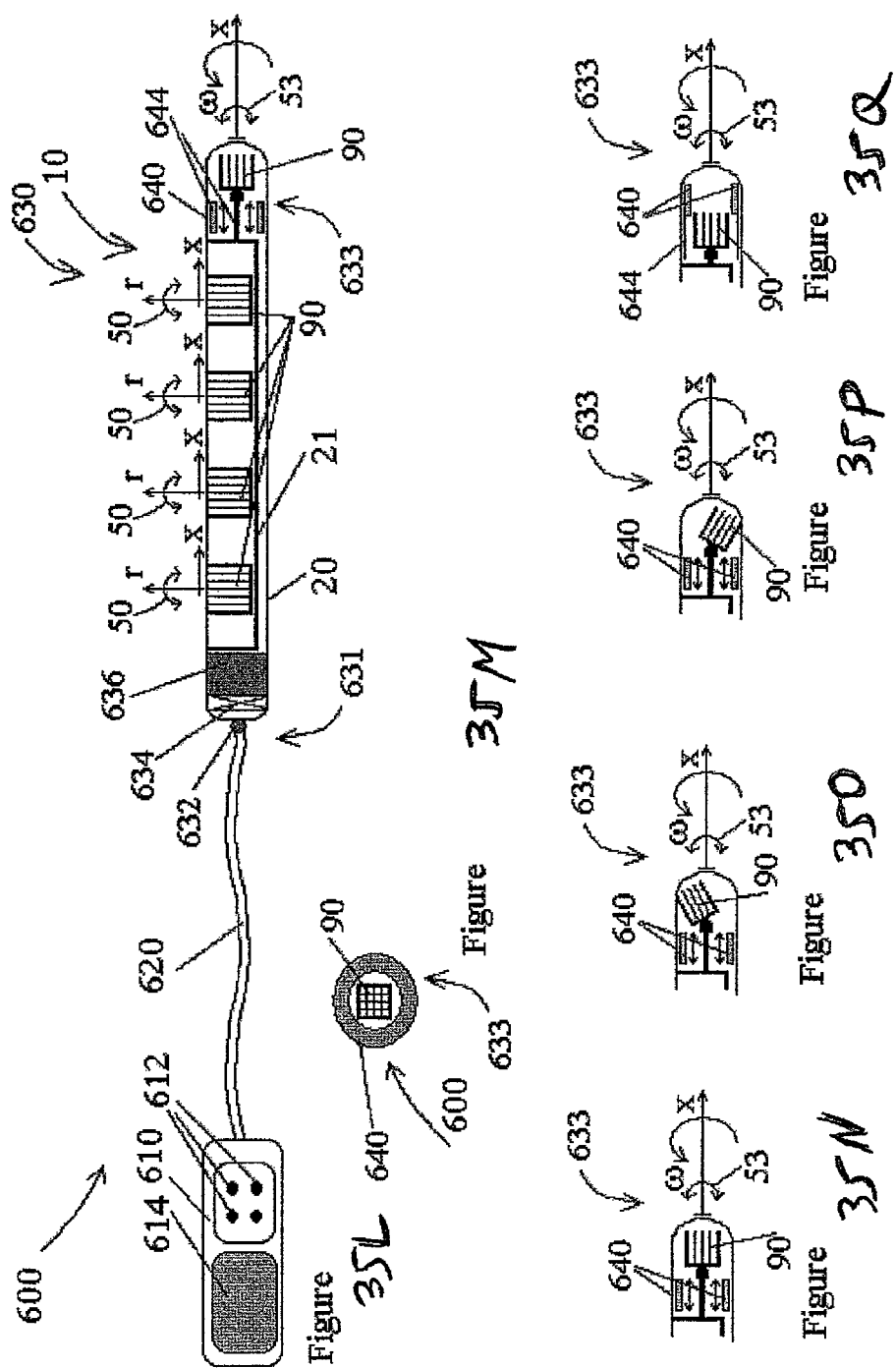

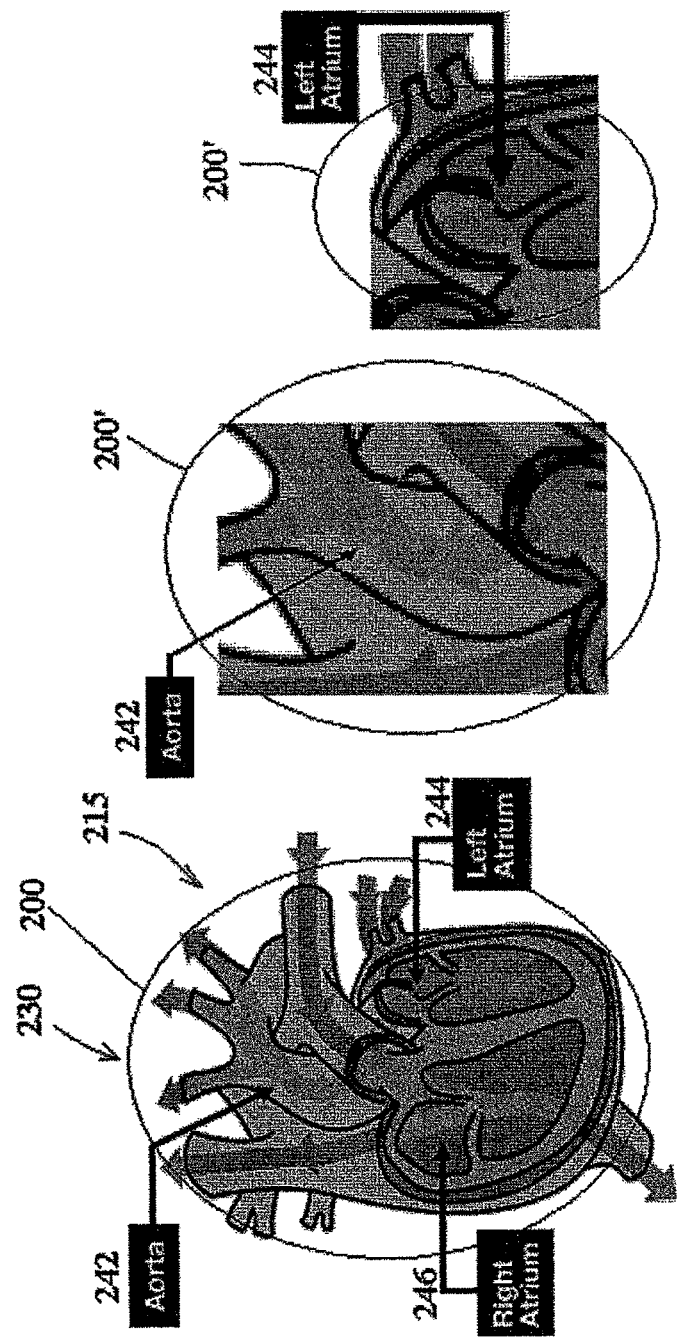

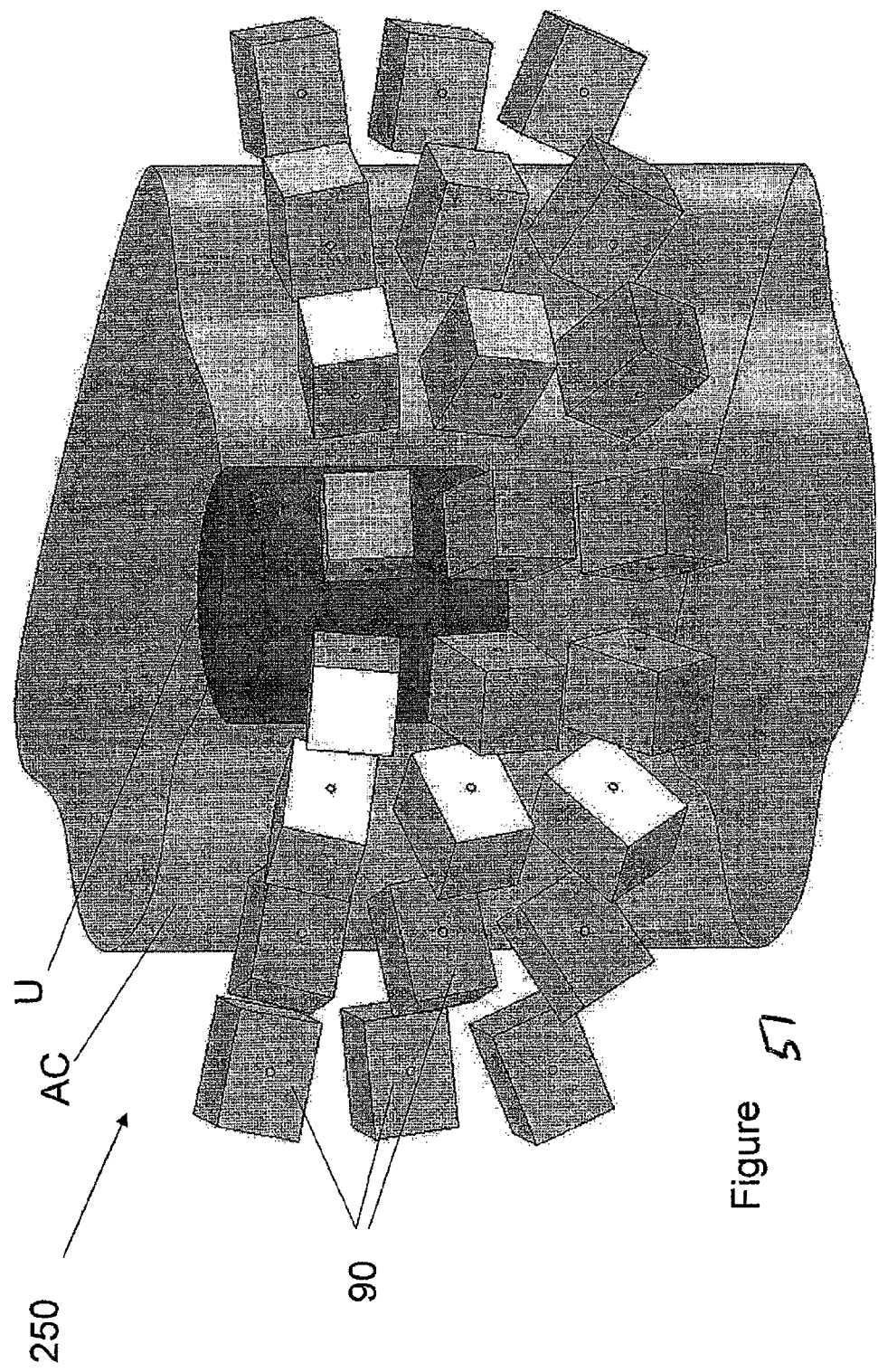

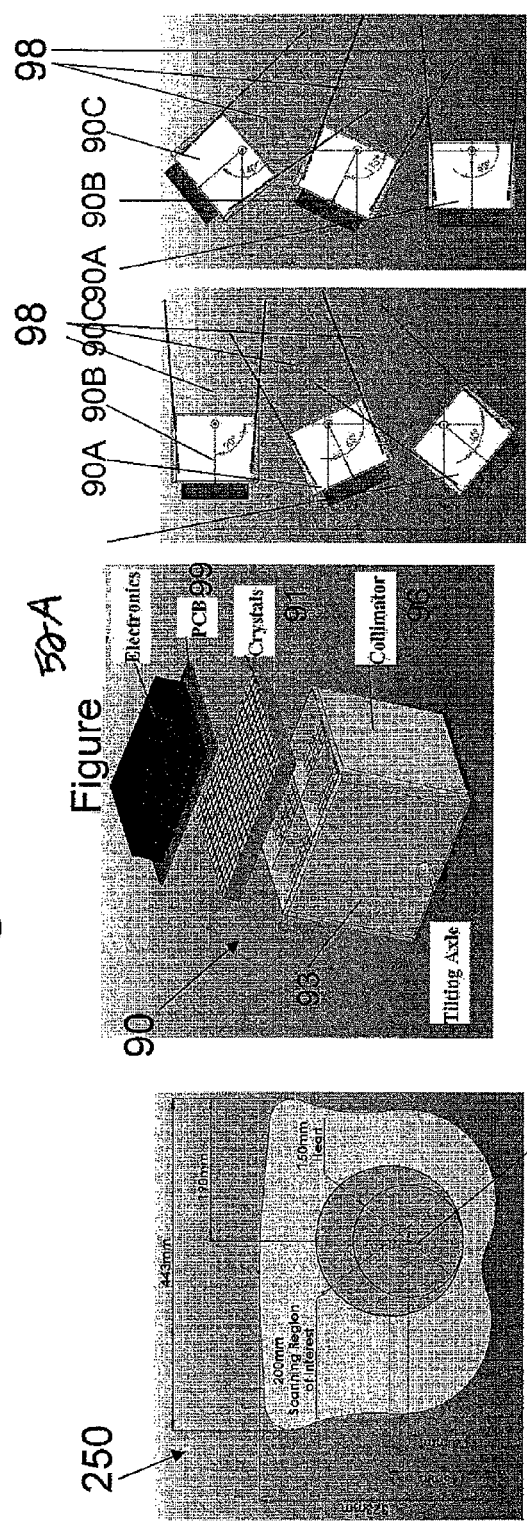
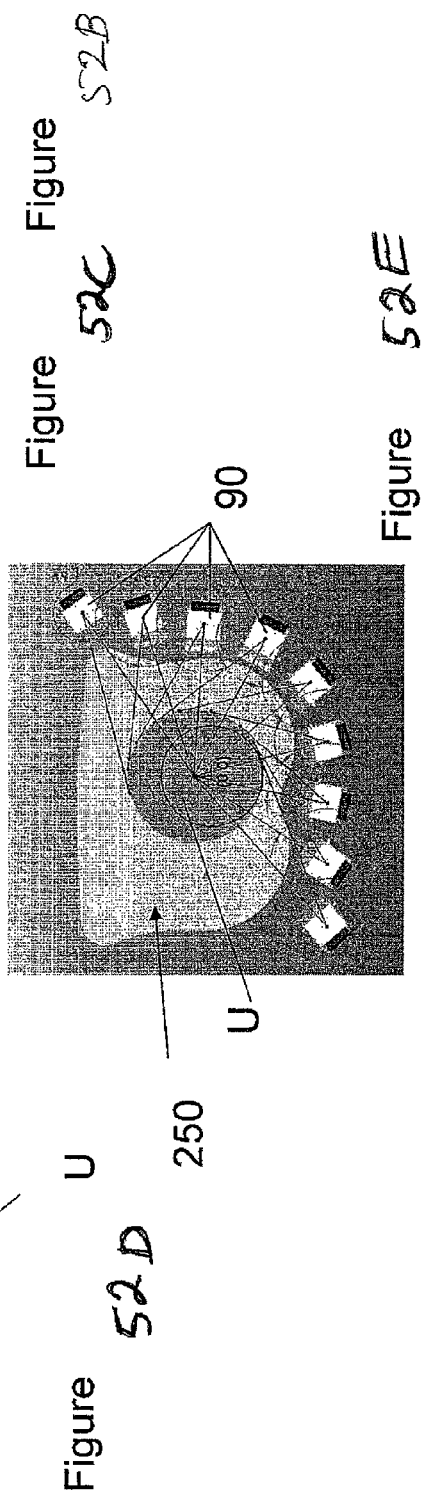

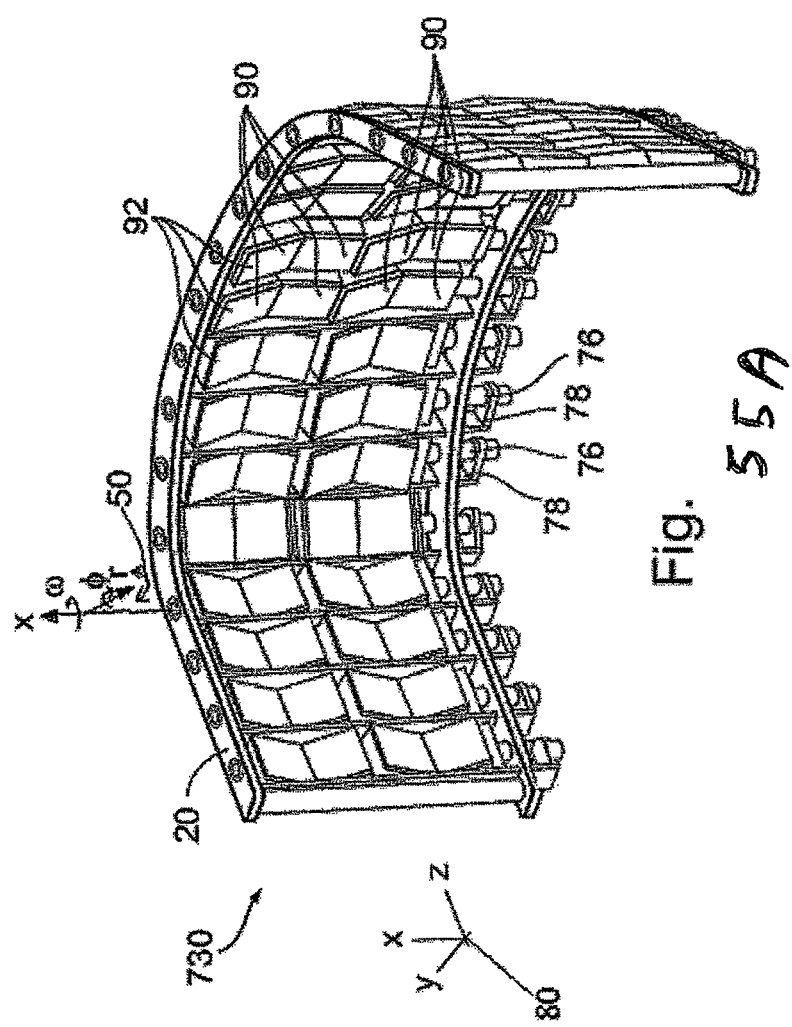

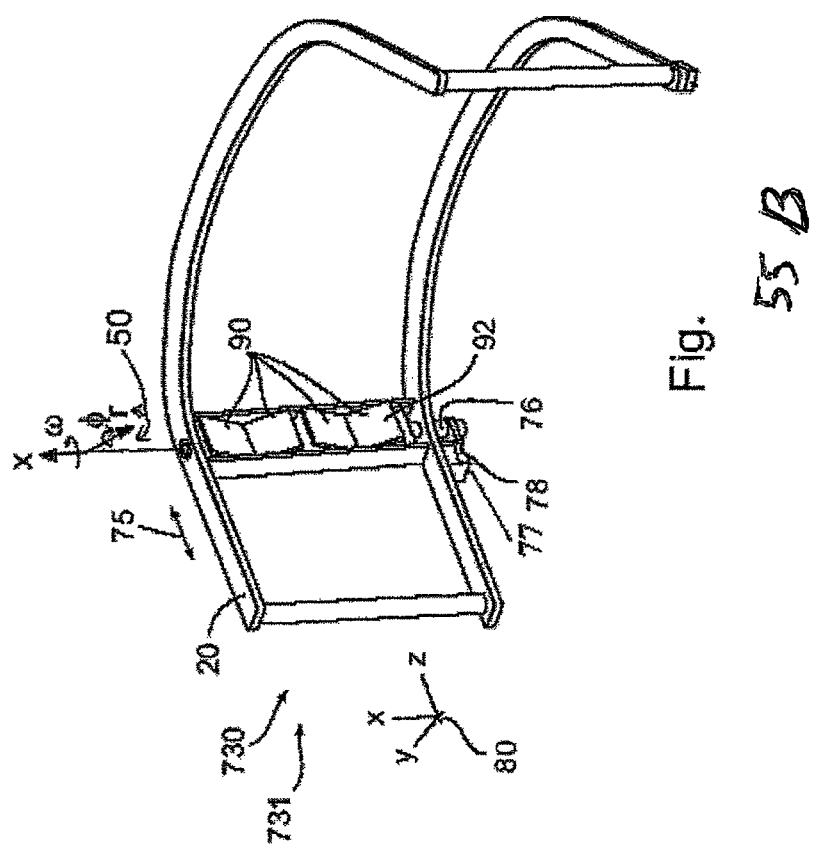

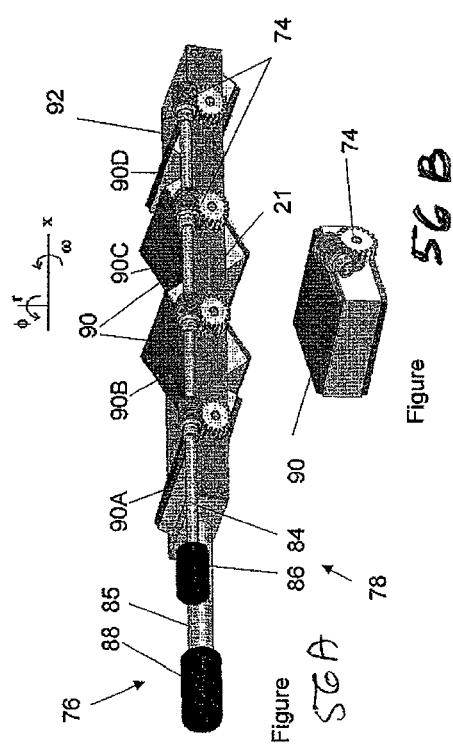

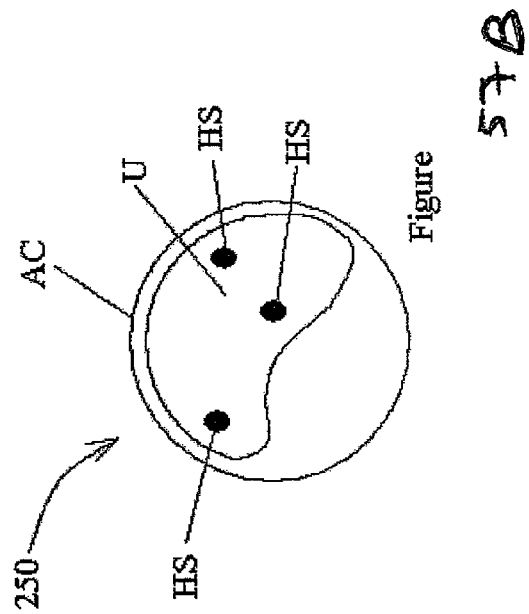
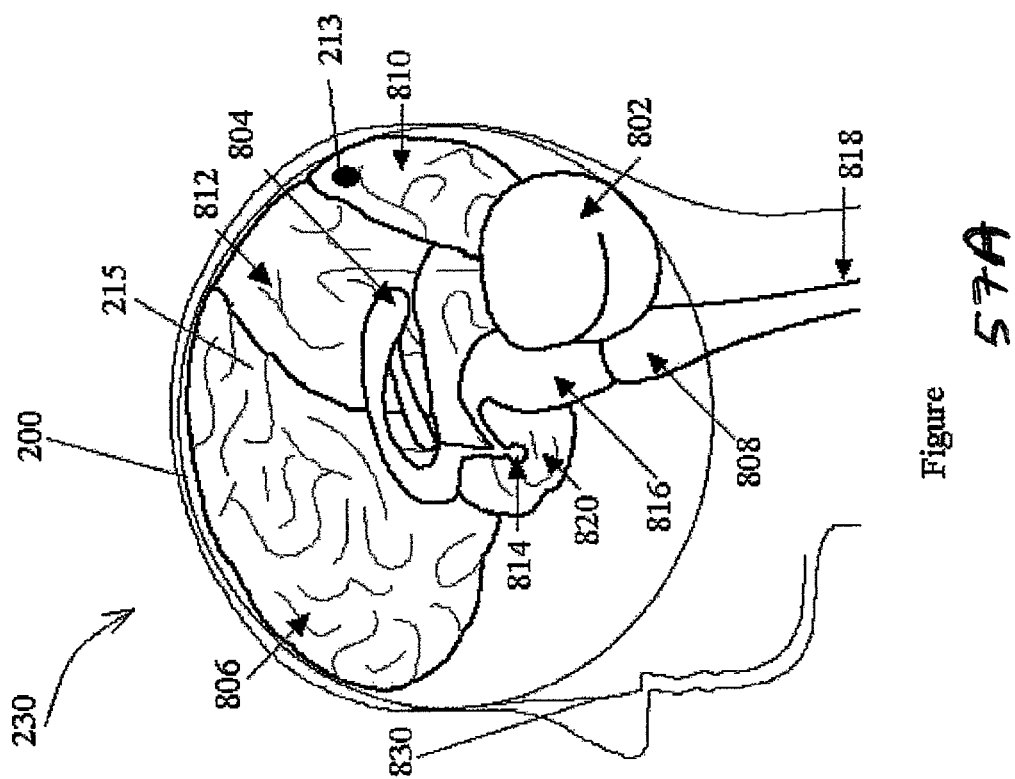

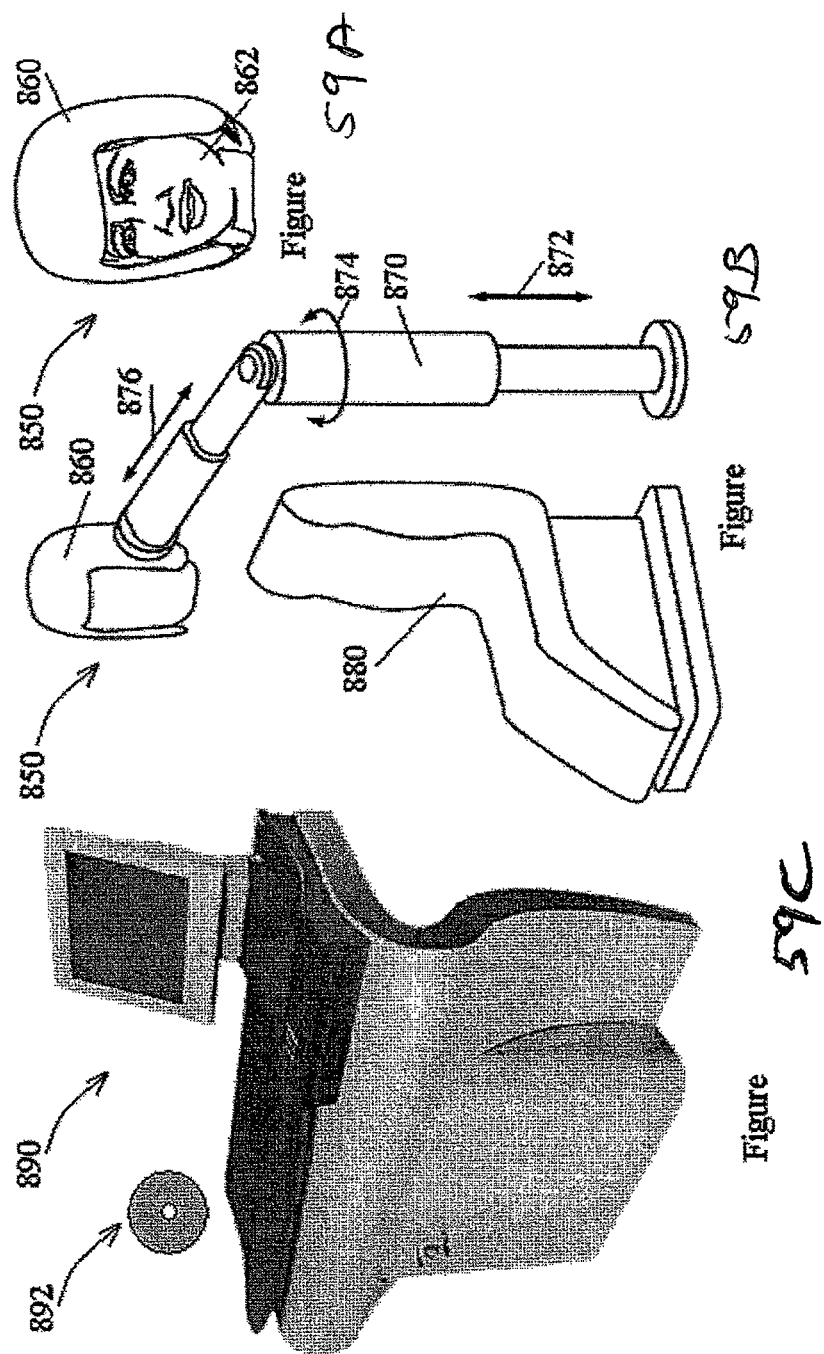

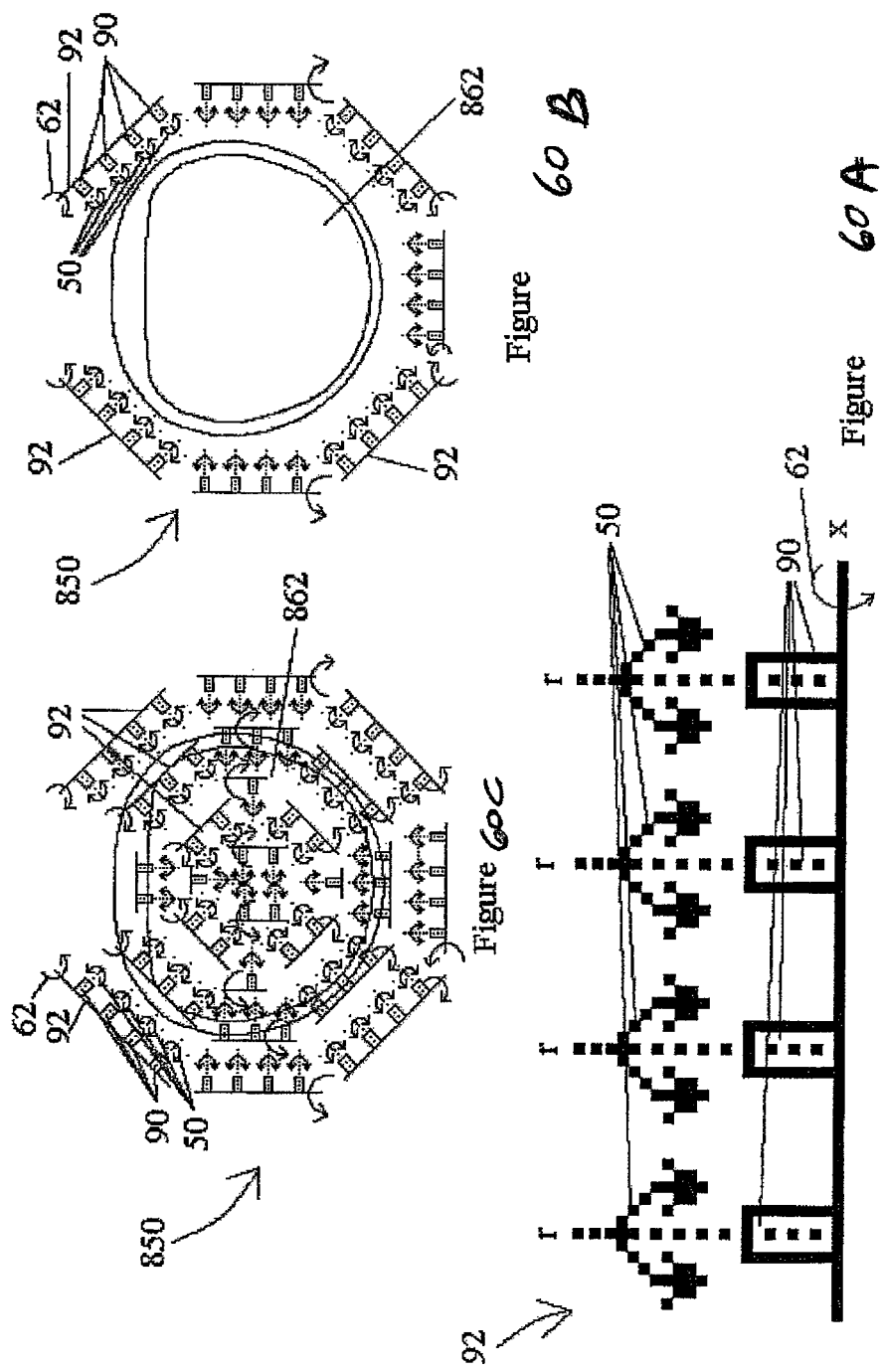

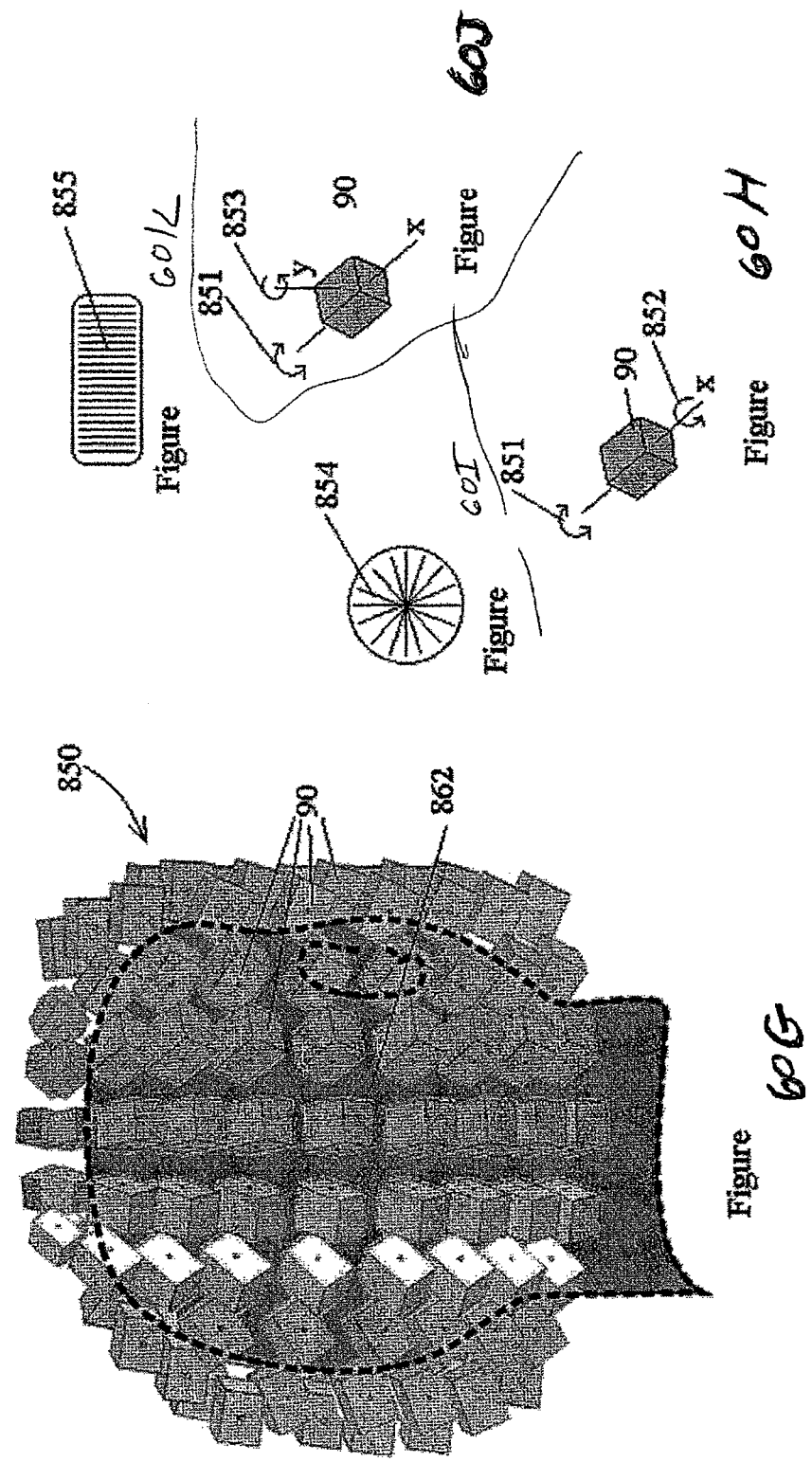

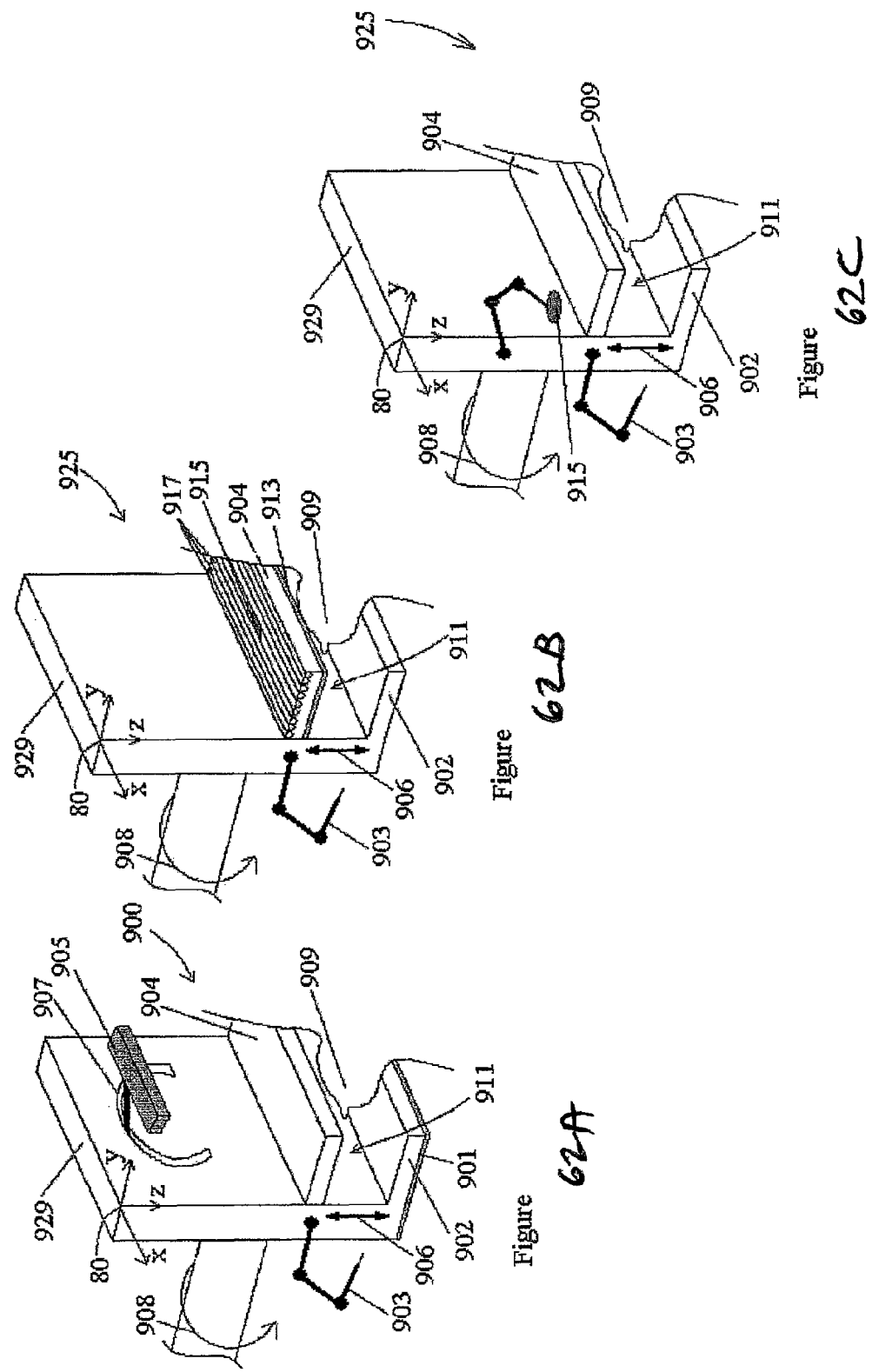

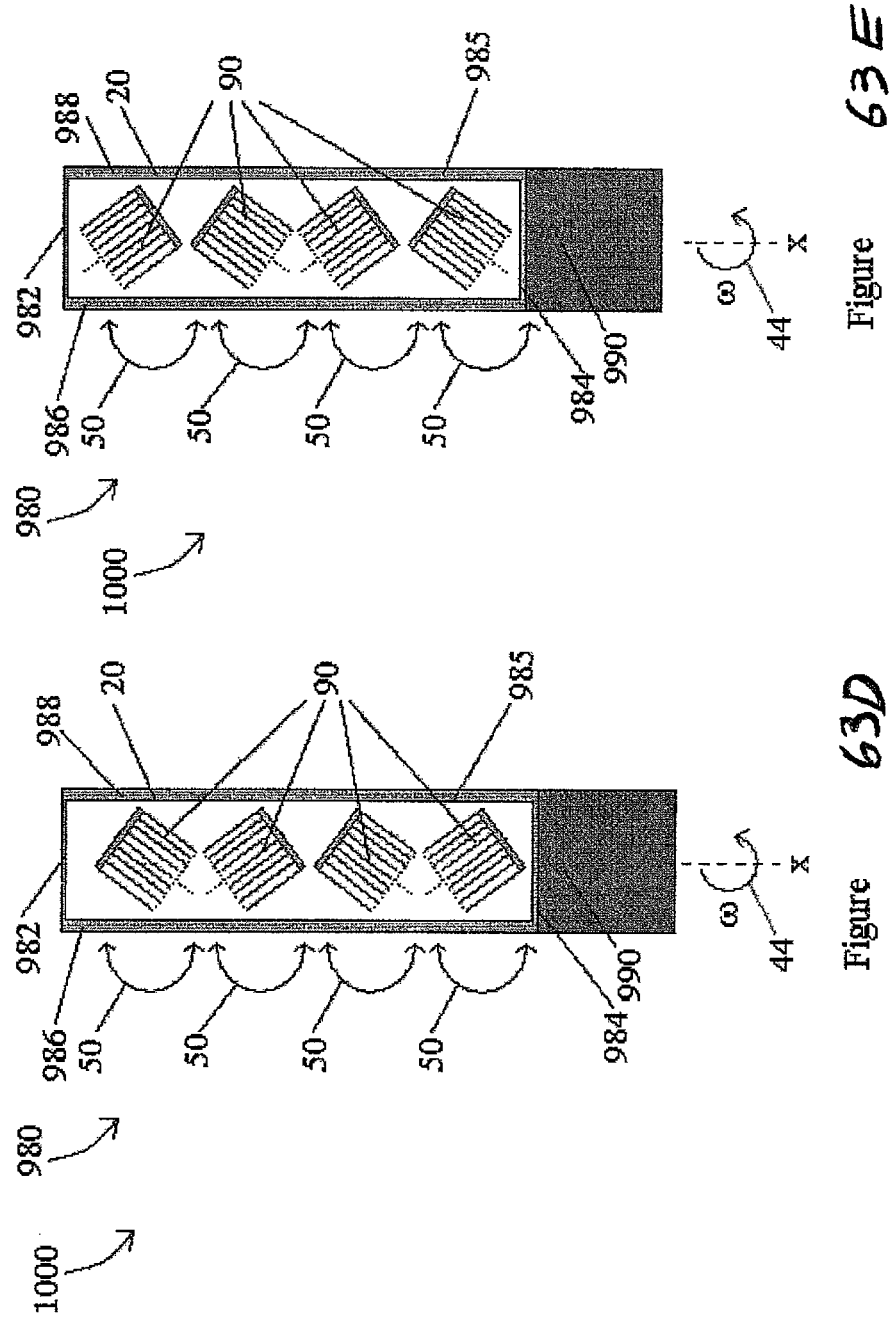

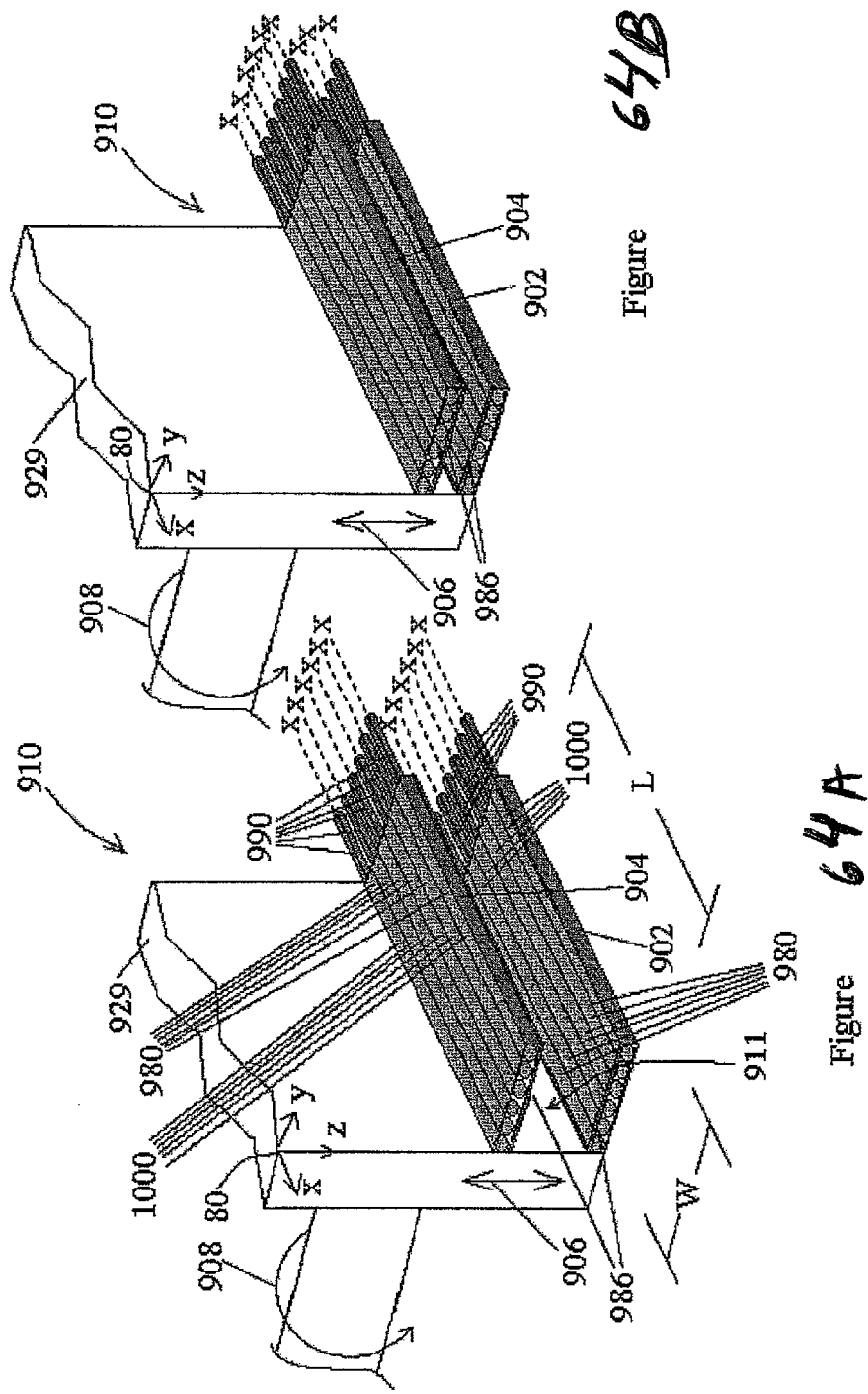

Figure 64L

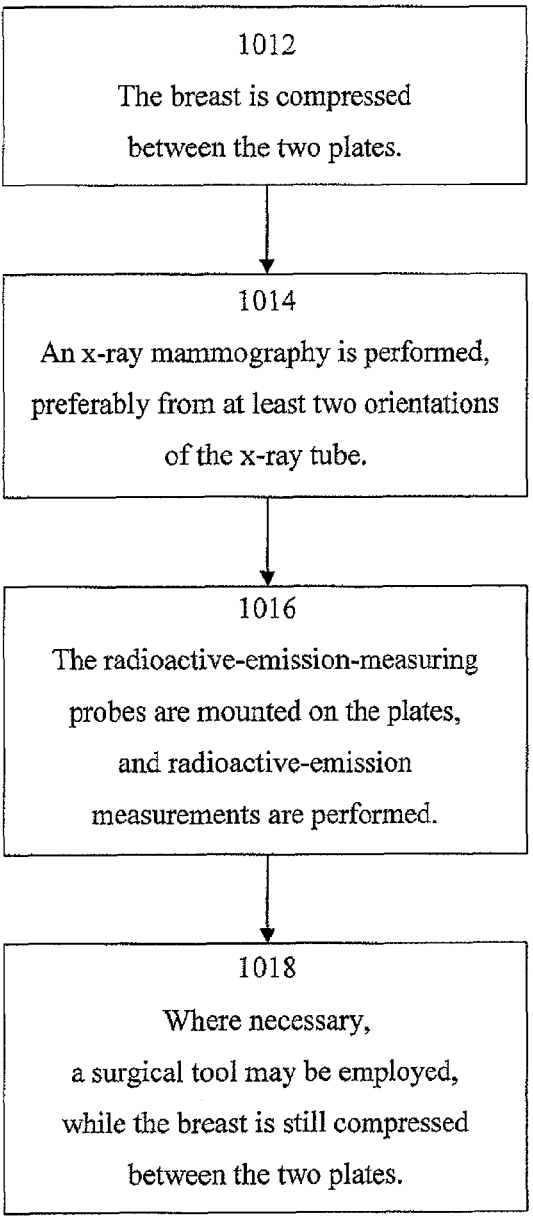
1010

```
┌─────────────────────────────┐
│            1012             │
│   The breast is compressed  │
│   between the two plates.   │
└─────────────────────────────┘
              │
              ▼
┌─────────────────────────────────┐
│              1014               │
│ An x-ray mammography is performed,│
│ preferably from at least two orientations│
│        of the x-ray tube.       │
└─────────────────────────────────┘
              │
              ▼
┌─────────────────────────────────┐
│              1016               │
│ The radioactive-emission-measuring│
│   probes are mounted on the plates,│
│     and radioactive-emission    │
│    measurements are performed.  │
└─────────────────────────────────┘
              │
              ▼
┌─────────────────────────────────┐
│              1018               │
│        Where necessary,         │
│  a surgical tool may be employed,│
│ while the breast is still compressed│
│     between the two plates.     │
└─────────────────────────────────┘
```

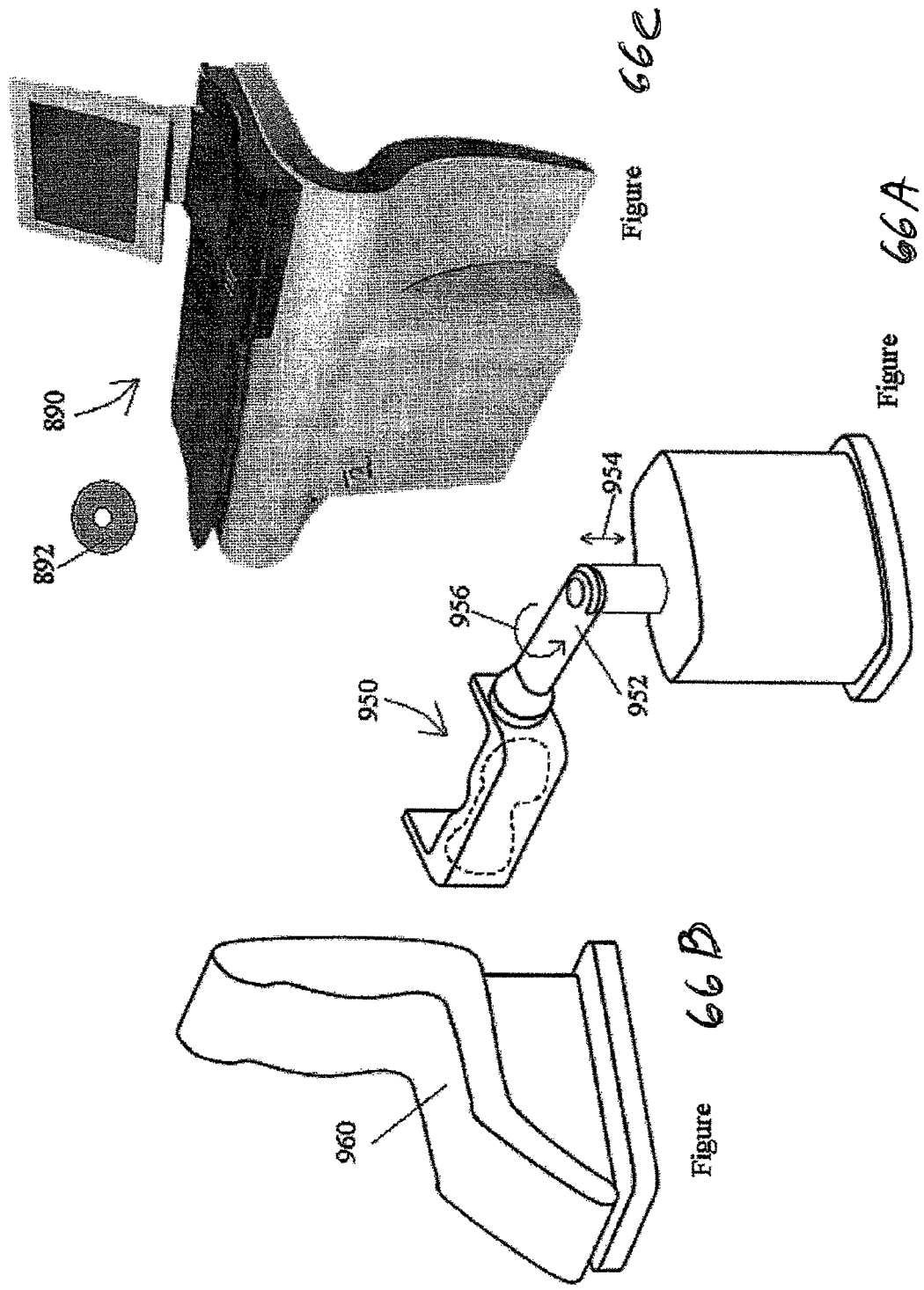

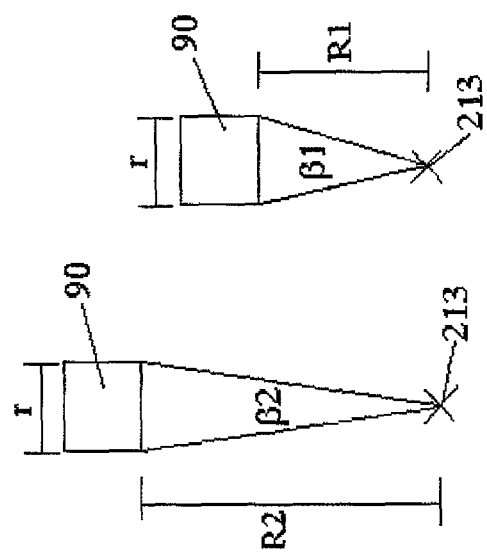

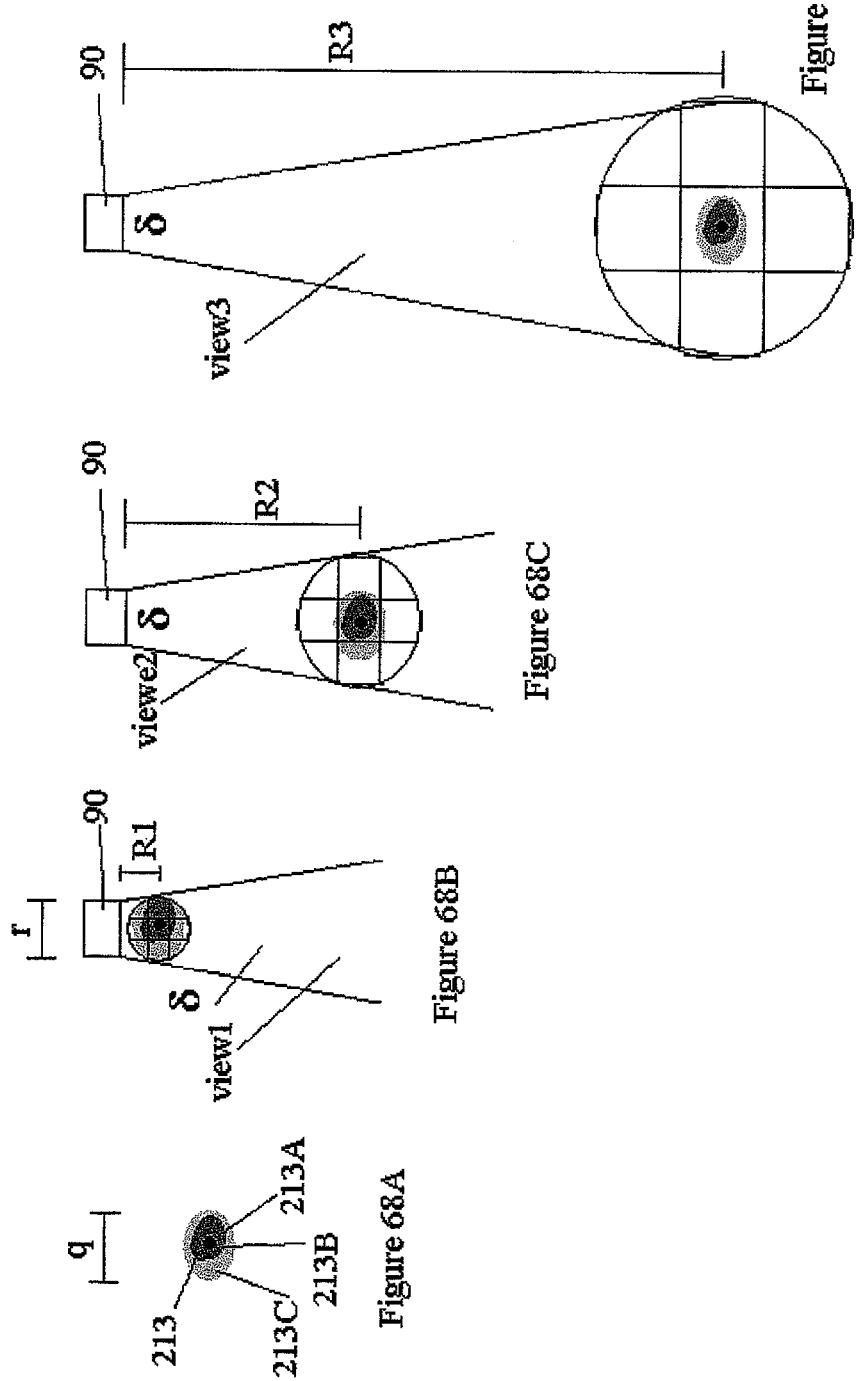

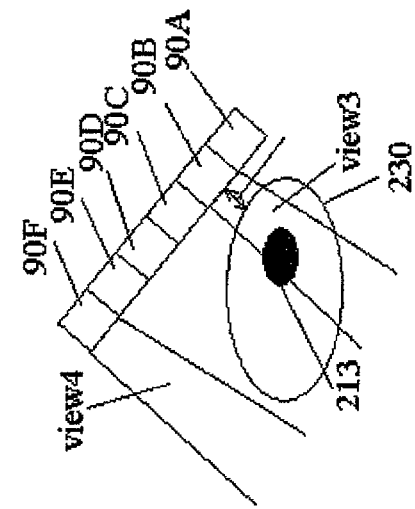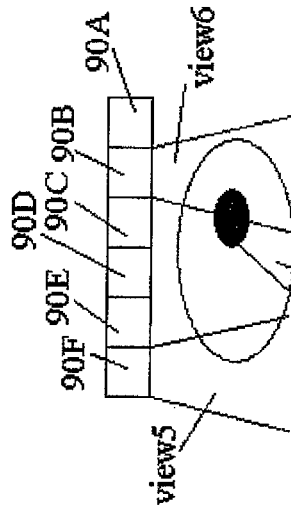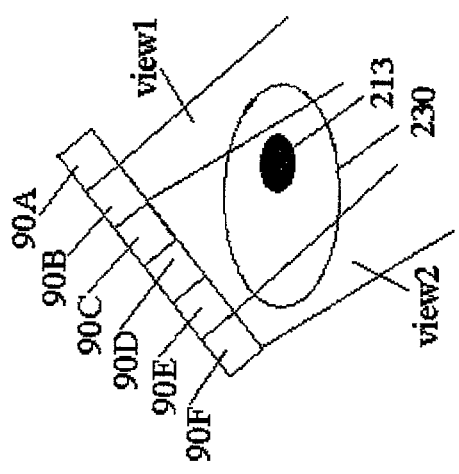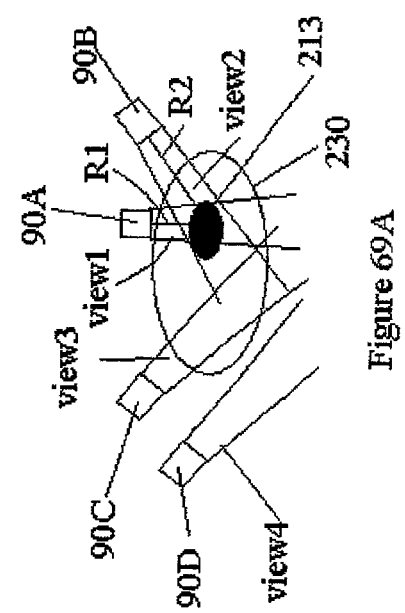
Figure 69B
Figure 69D
Figure 69C
Figure 69A Fig. 70A
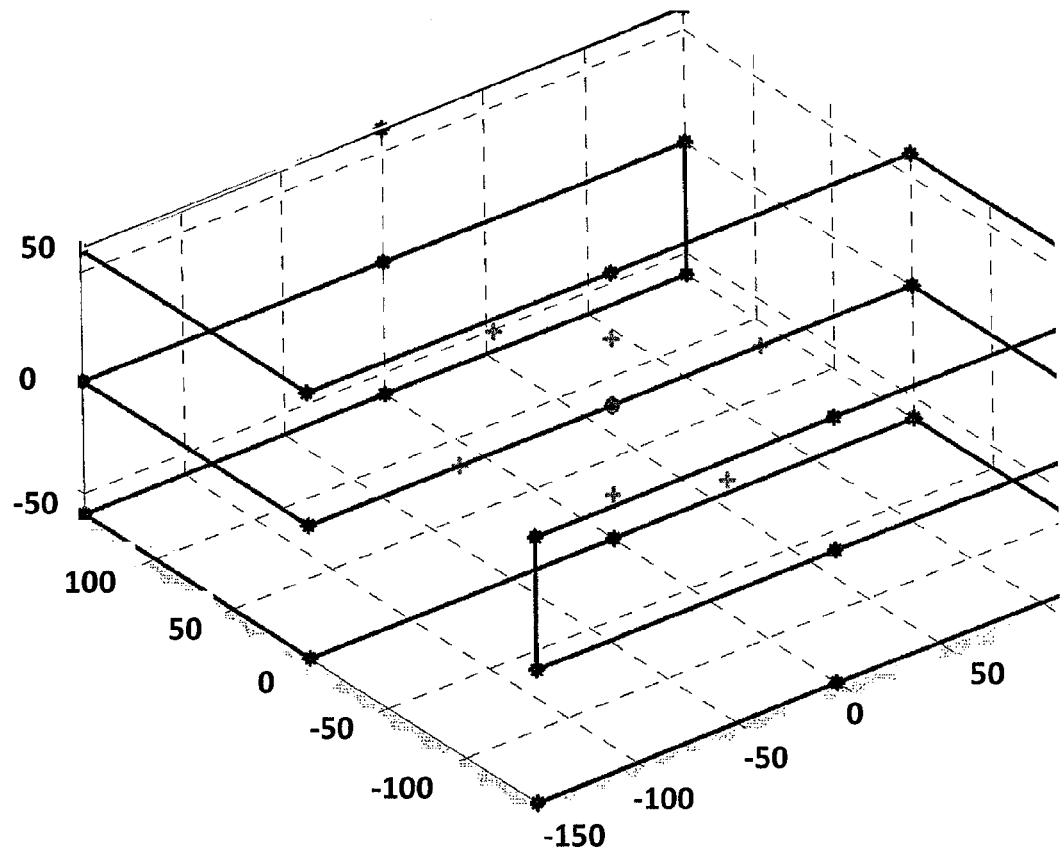
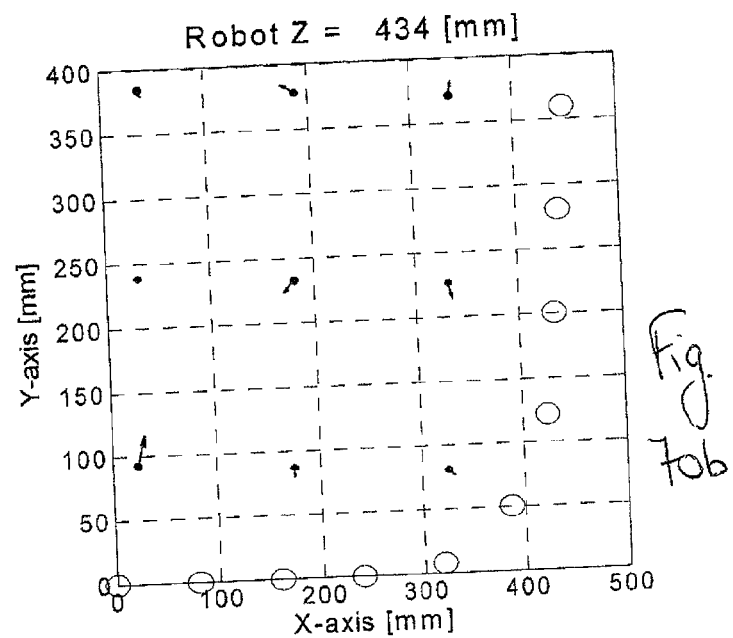
Fig. 70b

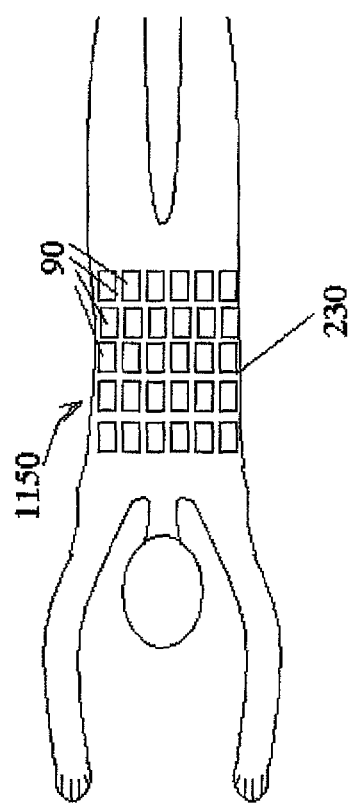

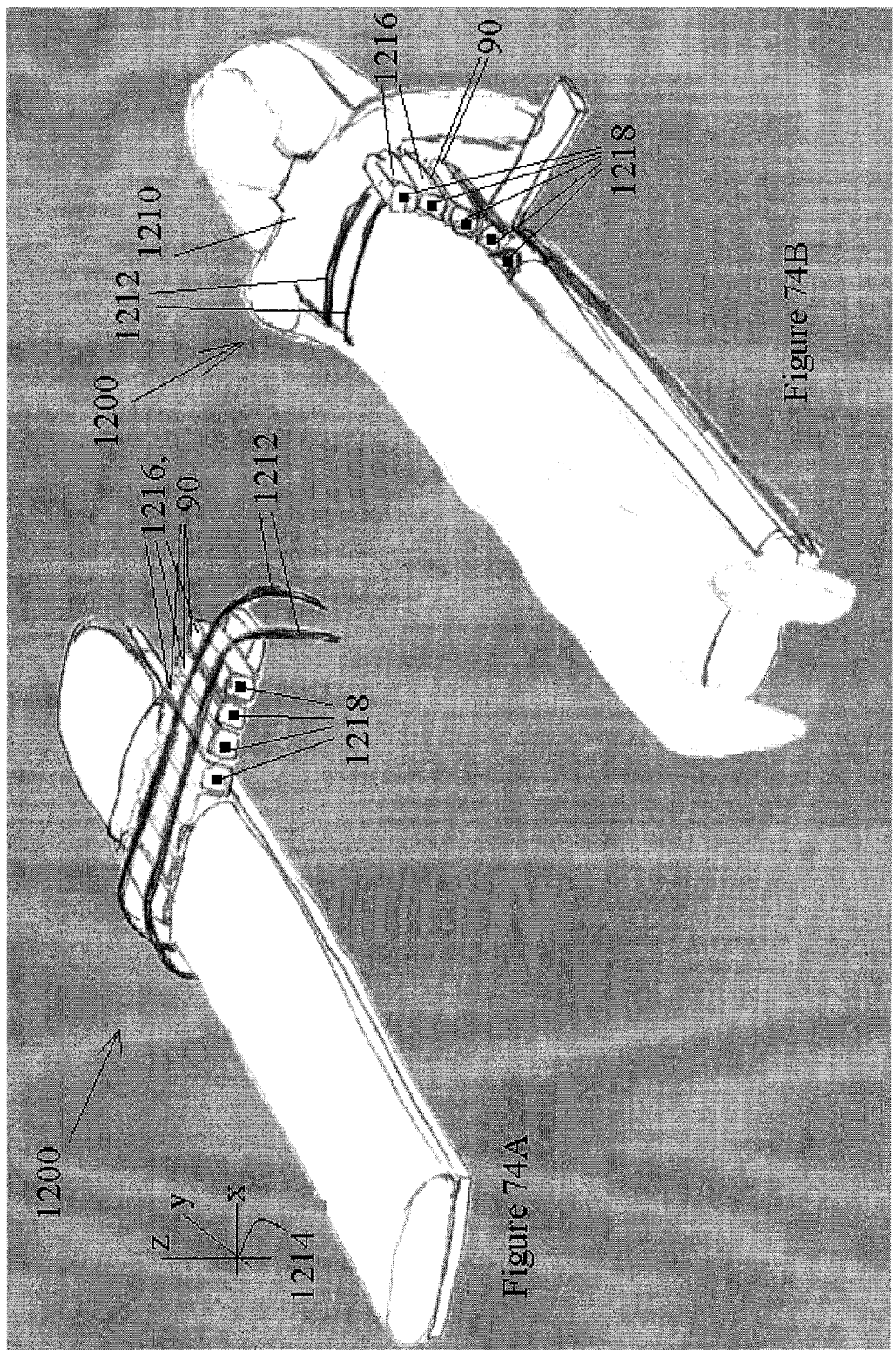

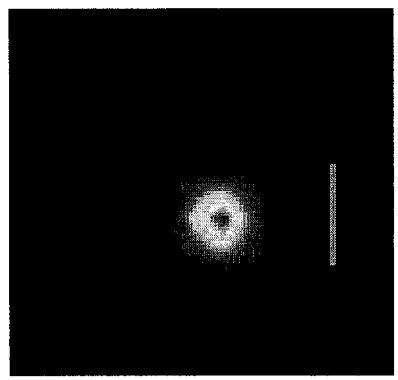 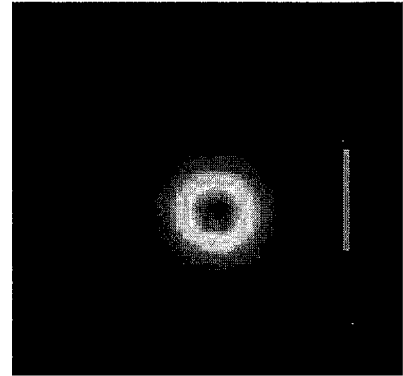
Figure 76A
Figure 76B
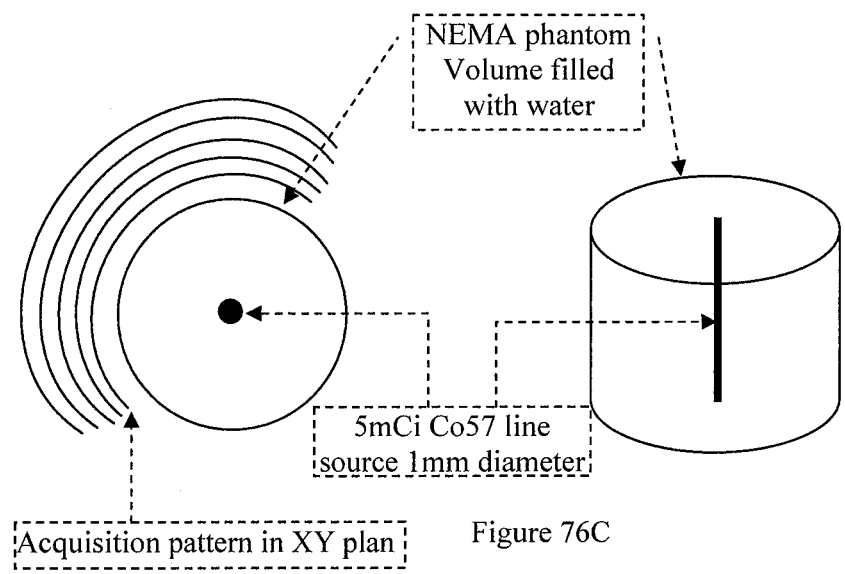
Figure 76C

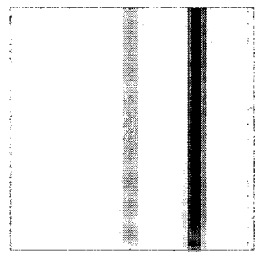
Figure 77B
x-z plane
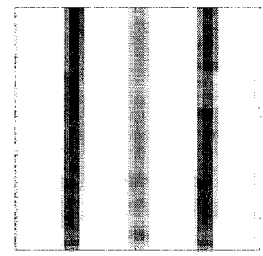
Figure 77C
y-z plane
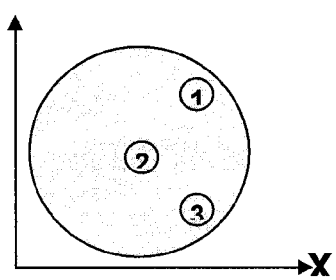
Figure 77A
Geometry
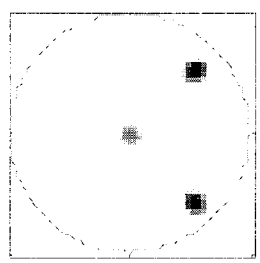
Figure 77D
x-y plane
reconstruction, without attenuation correction or smoothing.
Figure 77E of x-z plane
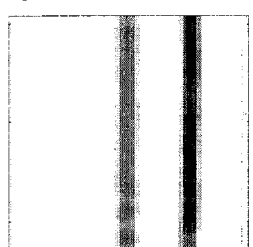
Figure 77F of y-z plane
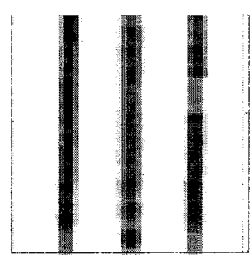
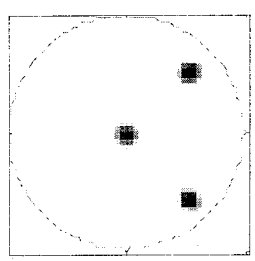
Figure 77G of x-y plane A,B: Ø10 h=15
Target volume: 1.17cc
Background volume: 158cc Figure 79A of x-z plane
Figure 79B of y-z plane
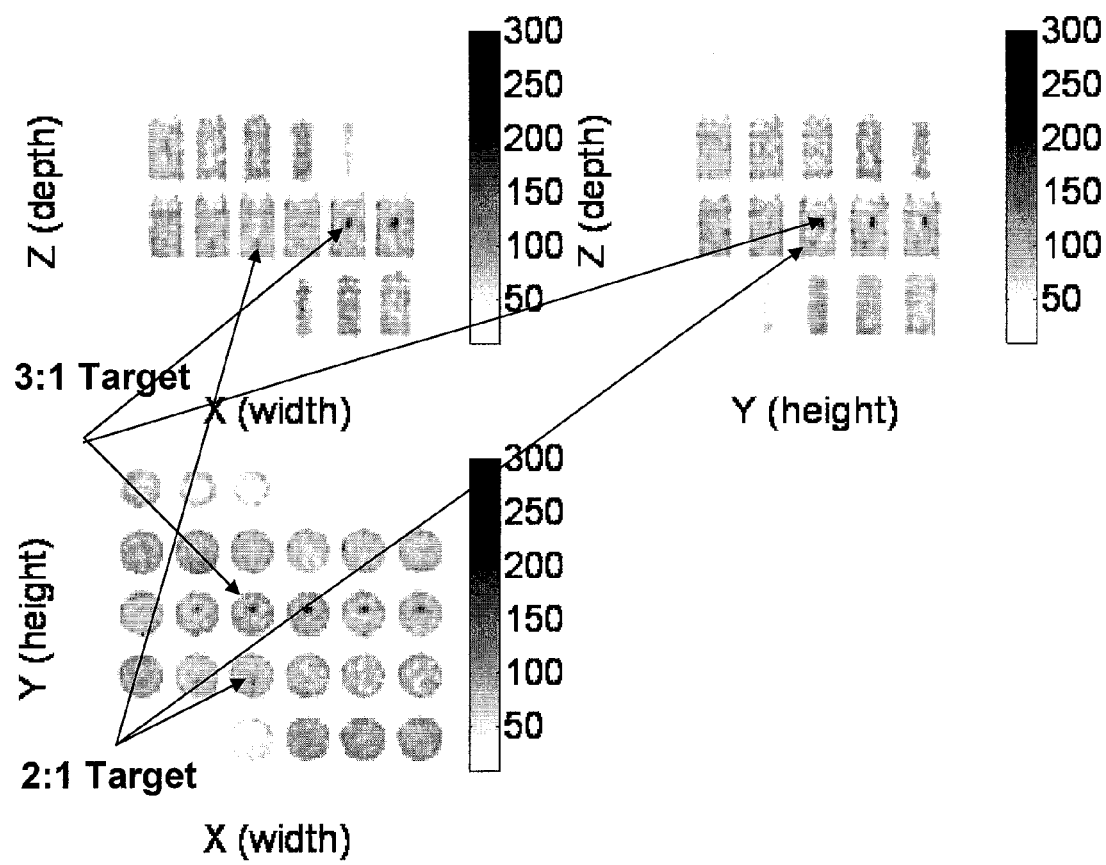
Figure 79C of x-y plane Anthropomorphic Torso Phantom
Model ECT/TOR/P
Produced by Data Spectrum
Corporation, USA The resulting reconstructions as compared to that performed by the conventional camera are shown below (keeping the same brightness and spatial scale):

probe of the present invention
Net Acquisition time = 1.25min

Conventional Camera
Net Acquisition time= 12.5min

FIG. 98

| Time (sec) | No. of events | Average rate (MHz) |
|---|---|---|
| 0.001 | 56 | 0.056 |
| 0.002 | 369 | 0.369 |
| 0.003 | 379 | 0.379 |
| 0.004 | 378 | 0.378 |
| 0.005 | 382 | 0.382 |
| 0.006 | 376 | 0.376 |
| 0.007 | 366 | 0.366 |
| 0.008 | 372 | 0.372 |
| 0.009 | 374 | 0.374 |
| 0.010 | 372 | 0.372 |
| 0.011 | 370 | 0.370 |
| 0.012 | 371 | 0.371 |
| 0.013 | 364 | 0.364 |
| 0.014 | 372 | 0.372 |
| 0.015 | 374 | 0.374 |
| 0.016 | 372 | 0.372 |
| 0.017 | 364 | 0.364 |
| 0.018 | 368 | 0.368 |
| 0.019 | 364 | 0.364 |
| 0.020 | 373 | 0.373 |
| 0.021 | 362 | 0.362 |
| 0.022 | 374 | 0.374 |
| 0.023 | 372 | 0.372 |
| 0.024 | 377 | 0.377 |
| 0.025 | 367 | 0.367 |
| 0.026 | 377 | 0.377 |
| 0.027 | 373 | 0.373 |
| 0.028 | 363 | 0.363 |
| 0.029 | 373 | 0.373 |
| 0.030 | 370 | 0.370 |
| 0.031 | 370 | 0.370 |
| 0.032 | 370 | 0.370 |
| 0.033 | 378 | 0.378 |
| 0.034 | 372 | 0.372 |
| 0.035 | 380 | 0.380 |
| 0.036 | 372 | 0.372 |
| 0.037 | 373 | 0.373 |
| 0.038 | 373 | 0.373 |
| 0.039 | 375 | 0.375 |
| 0.040 | 372 | 0.372 |
| 0.041 | 379 | 0.379 |
| 0.042 | 373 | 0.373 |
| 0.043 | 374 | 0.374 |
| 0.044 | 368 | 0.368 |
| 0.045 | 370 | 0.370 |
| 0.046 | 373 | 0.373 |
| 0.047 | 369 | 0.369 |
| 0.048 | 372 | 0.372 |
| 0.049 | 372 | 0.372 |

| | | |
|---|---|---|
| 0.050 | 372 | 0.372 |
| 0.051 | 365 | 0.365 |
| 0.052 | 370 | 0.370 |
| 0.053 | 364 | 0.364 |
| 0.054 | 377 | 0.377 |
| 0.055 | 372 | 0.372 |
| 0.056 | 374 | 0.374 |
| 0.057 | 371 | 0.371 |
| 0.058 | 368 | 0.368 |
| 0.059 | 373 | 0.373 |
| 0.060 | 370 | 0.370 |
| 0.061 | 375 | 0.375 |
| 0.062 | 368 | 0.368 |
| 0.063 | 370 | 0.370 |
| 0.064 | 372 | 0.372 |
| 0.065 | 372 | 0.372 |
| 0.066 | 370 | 0.370 |
| 0.067 | 370 | 0.370 |
| 0.068 | 365 | 0.365 |
| 0.069 | 367 | 0.367 |
| 0.070 | 376 | 0.376 |

| | REST PHASE | | | STRESS PHASE | | | |
|---|---|---|---|---|---|---|---|
| | INJECTION | | ACQUISITION DURATION [MIN] | STRESS | INJECTION | | GATED ACQUISITION DURATION [MIN] |
| | RP | DOSE [mCi] | | | RP | DOSE [mCi] | WAITING TIME [MIN] | |
| | RP | DOSE [mCi] | WAITING TIME [MIN] | ACQUISITION DURATION [MIN] | STRESS | RP | DOSE [mCi] | WAITING TIME [MIN] | GATED ACQUISITION DURATION [MIN] |
| SINGLE ISOTOPE/ LOW DOSE/FAST IMAGING | TL | <0.3 | 2 | 15 | EXERCISE | TL | <3 | 10-15 | 1.5 |
| DUAL ISOTOPE/ LOW DOSE/FAST IMAGING | TL | <0.3 | 2 | 15 | EXERCISE | Tc-MIBI | 30 | 30-60 | 1.5 |
| GATED REST THALLIUM (STUNNING) | TL | 1.5 | 2 | 5 (GATED) | EXERCISE | Tc-MIBI | 30 | 30-60 | 1.5 |
| THALLIUM STRESS PERFUSION | Tc-MIBI | 3 | 30 | 1.5 | PHARMA | TL | 3 | 0 | 10 (DYNAMIC) |
| SIMULTANEOUS DUAL ISOTOPE STRESS PERFUSION | Tc-MIBI | 3 | 20 | | EXERCISE/PHARMA | TL | 3 | | 10 (DYNAMIC) |
| DYNAMIC IMAGING | TL | 0.3 | | | PHARMA (ADENOSINE) | TL | 3 | | 10 (DYNAMIC) |

FIG. 99B

| NO. | PROTOCOL NAME | KEY FEATURES AND PROPERTIES | ADMINISTRATION PARAMETERS | | | DETECTOR PARAMETERS |
|---|---|---|---|---|---|---|
| | | | DOSE (mCi) | INJECTION PROFILE | INJECT TO ACQUISITION TIME | DETECTED PHOTON ENERGY / RESOLUTION |
| A | CARDIAC MAPPING | MIBI-TC, FAST, BEFORE LIVER UPTAKE | 20-40 | BOLUS | 2 MIN, OR ADMIN UNDER THE CAMERA | 140 KeV / 15% |
| B | CARDIAC MAPPING | MIBI-TC AFTER LIVER UPTAKE | 20-40 | BOLUS | 30+ MIN | 140 KeV / 15% |
| C | CARDIAC MAPPING | SIMULTANEOUS FAST DUAL-ISOTOPE TL-201+ LOW DOSE MIBI-TC | TL-201: 3.5-5; MIBI-Tc-99m: 4-8 | 2 BOLUS (BEFORE AND AT PEAK STRESS) | TL INJECTED PREVIOUSLY AT REST, TC UNDER CAMERA OR 2 MIN | Tc-140 KeV, Tl-72 KeV / 15% |
| D | CARDIAC MAPPING | SIMULTANEOUS DUAL-ISOTOPE TL-201+ LOW DOSE MIBI-TC | TL-201: 3.5-5; MIBI-Tc-99m: 4-8 | 2 BOLUS (BEFORE AND AT PEAK STRESS) | SAME AS ONE OF FIRST 2 CARDIAC MAPPING PROTOCOLS | Tc-140 KeV, Tl-72 KeV / 15% |
| E | CARDIAC MAPPING | SIMULTANEOUS DUAL-ISOTOPE FULL TL-201+ FULL DOSE MIBI-TC | TL-201: 3.5-5; MIBI-Tc-99m: 20-40 | 2 BOLUS (BEFORE AND AT PEAK STRESS) | SAME AS ONE OF PROTOCOLS A OR B | Tc-140 KeV, Tl-167 KeV / 10% |
| F | CARDIAC MAPPING - UNDERWEIGHT (BMI<18.5) | MIBI-TC-99M AFTER LIVER UPTAKE | 15-20 | BOLUS | 30+ MIN | 140 KeV / 15% |
| G1 | CARDIAC MAPPING - NORMAL (18.6<BMI<24.9) | MIBI-TC-99M AFTER LIVER UPTAKE | 20-30 | BOLUS | 30+ MIN | 140 KeV / 10% |
| G2 | CARDIAC MAPPING - OVERWEIGHT (25<BMI<29.9) | MIBI-TC-99M AFTER LIVER UPTAKE | 30-35 | BOLUS | 30+ MIN | 140 KeV / 10% |

FIG. 99C

| NO. | SCANNING PARAMETERS ||||||| ANALYSIS PARAMETERS |||
|---|---|---|---|---|---|---|---|---|---|
| | TOTAL SCAN TIME | COLUMNS DIFFERENCES / UNIFORM SCAN | ANGULAR RANGE | TOTAL # ANGULAR ORIENT- TATIONS | ANGULAR STEP / INTERLACE | DWELL TIME | GATED ANALYSIS OF VOLUMES | ANALYSIS ALGORITHM / PARAMETERS |
| A | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| B | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| C | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| D | 120 SEC | a) 4 X OUTER b) 6 X INNER | a) 40-60 DEG b) 90-120 DEG | 120X10 | a) 0.3-0.5 DEG b) 0.75-1 DEG | 1 SEC | YES, 16-32 FRAMES | INTENSITY IMAGE, EJECTION FRACTION |
| E | UP TO 1200 SEC | a) 4 X OUTER b) 6 X INNER | a) 40-60 DEG b) 90-120 DEG | 240X10 | a) 0.15-0.25 DEG b) 0.375-0.5 DEG | 5 SEC | YES, 16-32 FRAMES | INTENSITY IMAGE, EJECTION FRACTION |
| F | 90 SEC | a) 4 X OUTER b) 6 X INNER | a) 20-35 DEG b) 45-60 DEG | 60X10 | a) .3-.75 DEG b) 0.75-1DEG | 1 SEC | YES, 16-32 FRAMES | INTENSITY IMAGE, EJECTION FRACTION |
| G1 | 120 SEC | a) 4 X OUTER b) 6 X INNER | a) 30-45 DEG b) 75-90 DEG | 120X10 | a) 0.5-0.75 DEG b) 0.625-1 DEG | 1.5 SEC | YES, 16-32 FRAMES | INTENSITY IMAGE, EJECTION FRACTION |
| G2 | 120 SEC | a) 4 X OUTER b) 6 X INNER | a) 40-60 DEG b) 90-120 DEG | 120X10 | a) 0.3-0.5 DEG b) 0.75-1 DEG | 2 SEC | YES, 16-32 FRAMES | INTENSITY IMAGE, EJECTION FRACTION |

FIG. 99D

| NO. | PROTOCOL NAME | KEY FEATURES AND PROPERTIES | ADMINISTRATION PARAMETERS | | | DETECTOR PARAMETERS |
|---|---|---|---|---|---|---|
| | | | DOSE (mCi) | INJECTION PROFILE | INJECT TO ACQUISITION TIME | DETECTED PHOTON ENERGY / RESOLUTION |
| H | CARDIAC MAPPING - OBESE (BMI>30) | MIBI-TC AFTER LIVER UPTAKE | 35-40 | BOLUS | 30+ MIN | 140 KeV / 6% |
| I | CARDIAC DYNAMIC MAPPING | TEBOROXIME-TC | 20-40 | BOLUS | ~1 MIN (IMAGE BEFORE INJECT), OR SIMULTANEOUSLY WITH INJECT | 140 KeV / 15% |
| J | CARDIAC DYNAMIC MAPPING (2-STEP) | TEBOROXIME-TC | 20-40 | (i) INITIAL SMALL BOLUS FOR IDENTIFYING ROI, (ii) FULL BOLUS FOR DYNAMIC STUDY | (i) 5+ MIN (ii) ~1 MIN (IMAGE BEFORE INJECT) | 140 KeV / 15% |
| K | TUMOR SCAN (MULTIPLE BODY SEGMENTS - HEAD TO LEGS) | MDP-TC-99M AFTER LIVER UPTAKE | 20-40 | BOLUS | 30+ MIN | 140 KeV / 15% |
| L | TUMOR SCAN (MULTIPLE BODY SEGMENTS - HEAD TO LEGS), FOCUSED SCAN | MDP-TC-99M AFTER LIVER UPTAKE | 20-40 | BOLUS | 30+ MIN | 140 KeV / 15% |
| M | TUMOR SCAN WITH COCKTAIL (MULTIPLE BODY SEGMENTS - HEAD TO LEGS), FOCUSED SCAN | FDG (METABOLISM), MIBI-TC-99M AND TL (PERFUSION) | TL-201: 3.5-5; MIBI-TC-99M: 20-40; 18-F FDG 10-30 | BOLUS | 30+ MIN | Tc-140 KeV, Tl-72 KeV, FDG 511 KeV / 10% |

FIG. 99E

| | SCANNING PARAMETERS | | | | | | ANALYSIS PARAMETERS | |
|---|---|---|---|---|---|---|---|---|
| NO. | TOTAL SCAN TIME | COLUMNS DIFFERENCES / UNIFORM SCAN | ANGULAR RANGE | TOTAL # ANGULAR ORIENT-TATIONS | ANGULAR STEP / INTERLACE | DWELL TIME | GATED ANALYSIS OF VOLUMES | ANALYSIS ALGORITHM / PARAMETERS |
| H | 180 SEC | a) 4 X OUTER b) 6 X INNER | a) 40-60 DEG b) 90-120 DEG | 160X10 | a) 0.25-0.375 DEG b) 0.6-0.75 DEG | 1.2 SEC | YES, 8-16 FRAMES | INTENSITY IMAGE, EJECTION FRACTION |
| I | <= 600 SEC | a) 2 X OUTER b) 8 X INNER | a) 40-60 DEG b) 90-120 DEG | 600X10 | a) continuous b) continuous INTERLACED SCAN | 1 SEC | YES, 8 FRAMES | KINETIC PARAMETES, PREDEFINED PATHOLOGICAL VALUES |
| J | (i) 60 SEC FOR IDENTIFYING ROI (ii) 600 SEC DYNAMIC STUDY | a) 2 X OUTER b) 8 X INNER | a) 40-60 DEG b) 90-120 DEG | (i) 60X10 (ii) 600X10 | (i) a) 0.75-1 DEG b) 0.75-0.75-1 DEG (ii) a) continuous b) continuous INTERLACED SCAN | 1 SEC | YES, 8 FRAMES | KINETIC PARAMETES, PREDEFINED PATHOLOGICAL VALUES |
| K | 240 SEC PER BODY SEGMENT | 16 | 40-60 DEG | 120X16 | 0.3-0.5 DEG | 2 SEC | NO | INTENSITY IMAGE, PREDEFINED PATHOLOGICAL VALUES |
| L | (i) 120 SEC PER BODY SEGMENT (ii) 60 SEC PER ROI | 16 | (i) 45-60 DEG (ii) 15-20 DEG | (i) 120X16 (ii) 60x16 | (i) 0.375-0.5 DEG (ii) 0.25-0.3 | 1 SEC | NO | INTENSITY IMAGE, PREDEFINED PATHOLOGICAL VALUES |
| M | (i) 120 SEC PER BODY SEGMENT (ii) 60 SEC PER ROI | 16 | (i) 45-60 DEG (ii) 15-20 DEG | (i) 120X16 (ii) 60x16 | (i) 0.375-0.5 DEG (ii) 0.25-0.4 | 1 SEC | NO | INTENSITY IMAGE, PREDEFINED PATHOLOGICAL VALUES |

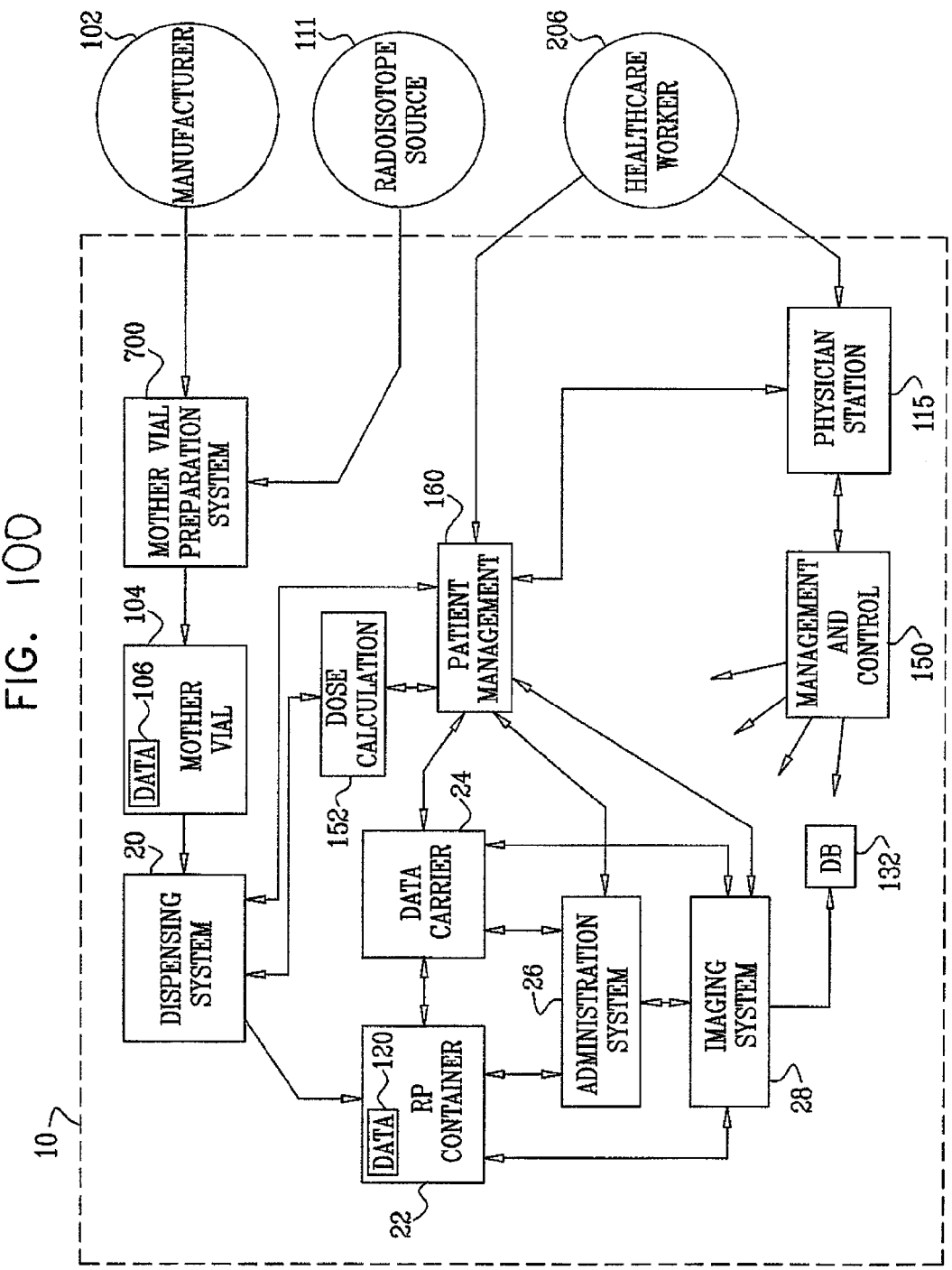

Real patient study-Time slices

2 Minutes Gated study
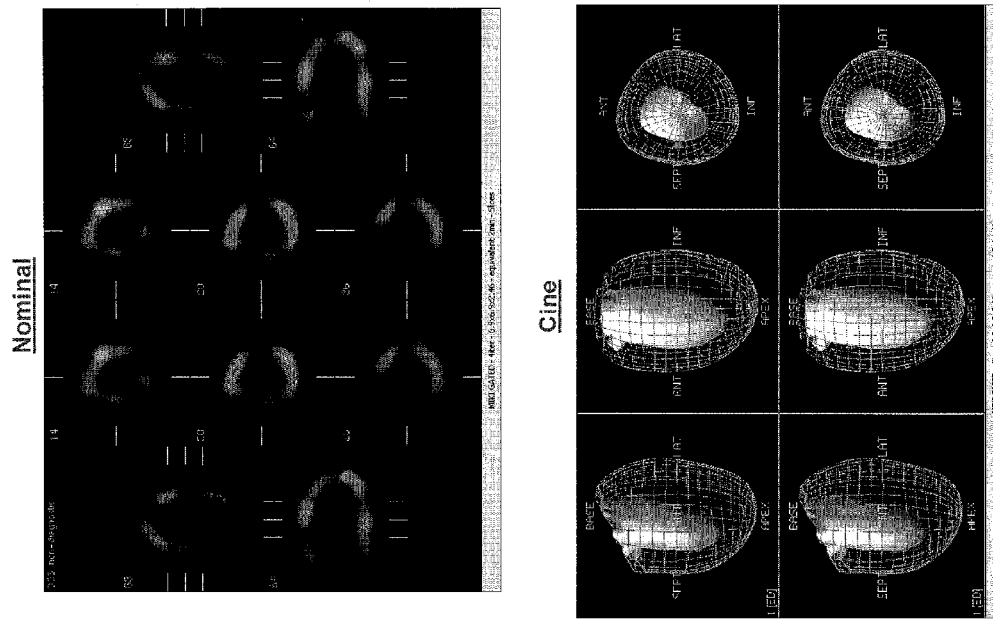
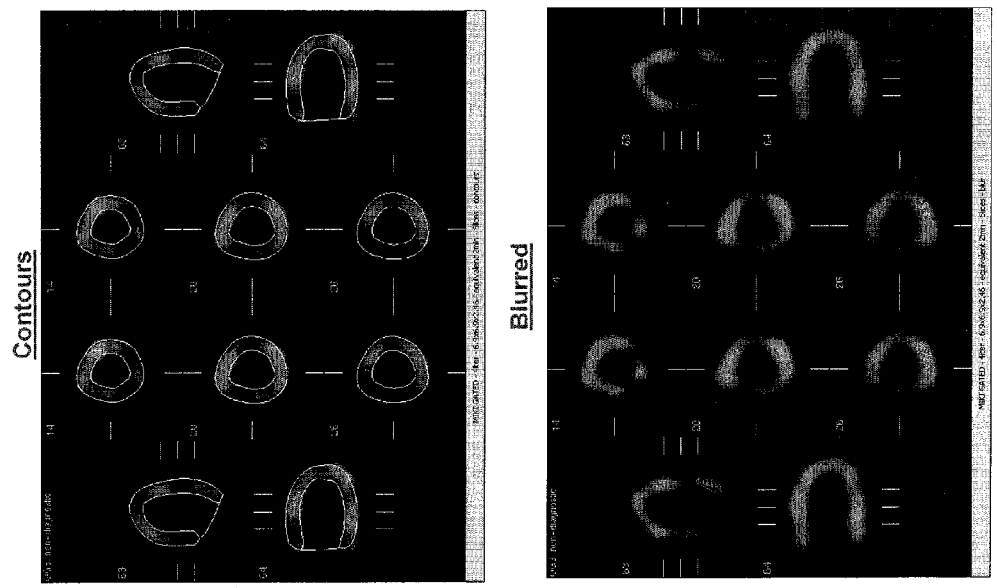
Fig. 101B

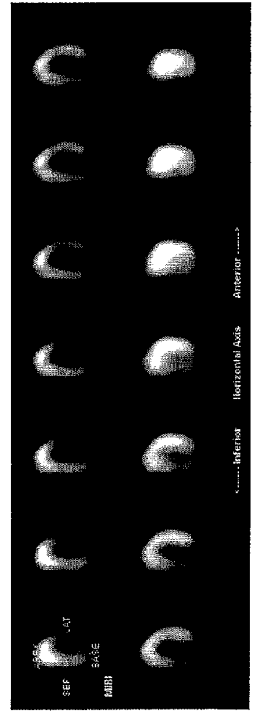

Dual Isotope- no defect, Tl window

Fig. 101C

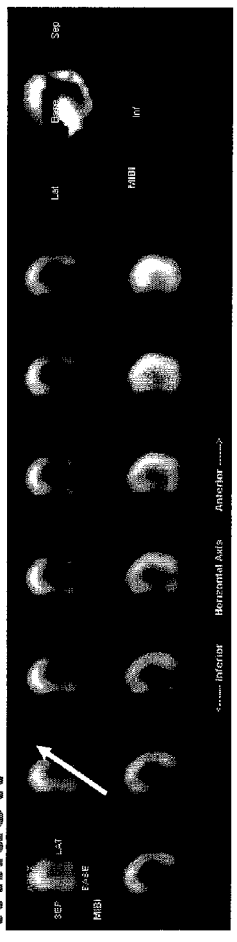

Dual Isotope- 2cm Tc99m-filled insert- Tc99m window

Fig. 101D

Apparent perfusion defect where insert is placed- the insert is filled with Tc99m, but the wall of the insert makes up for ~30% of its volume and therefore is not filled with Tc-99m- this theoretically simulates a ~30% perfusion defect. ~30% "perfusion defect" cannot be resolved in conventional camera

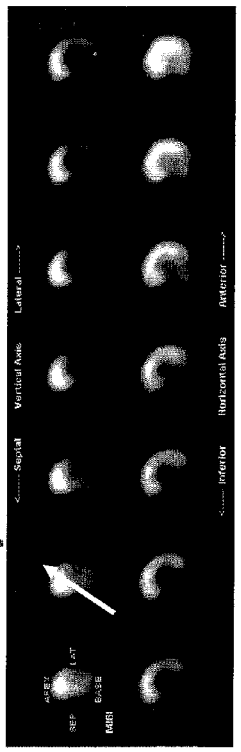

Dual Isotope- 2cm Tc99m-filled insert- Tl-201 window

Fig. 101E

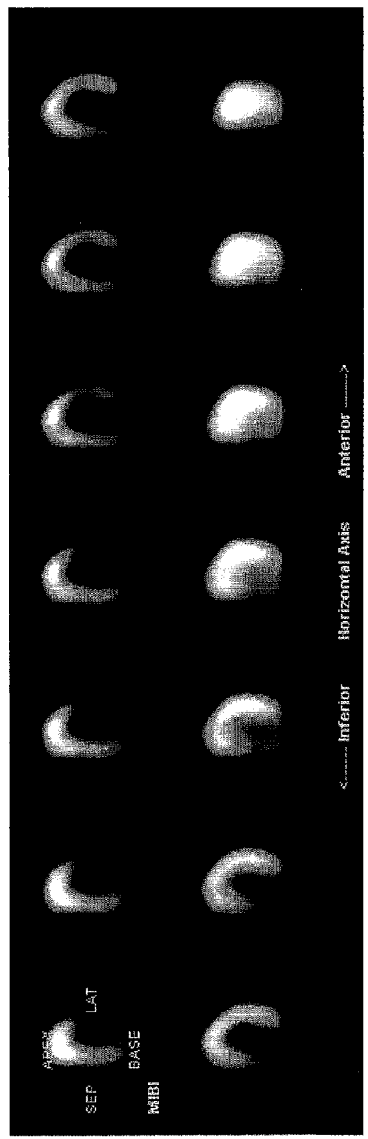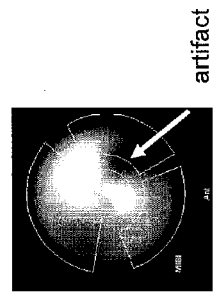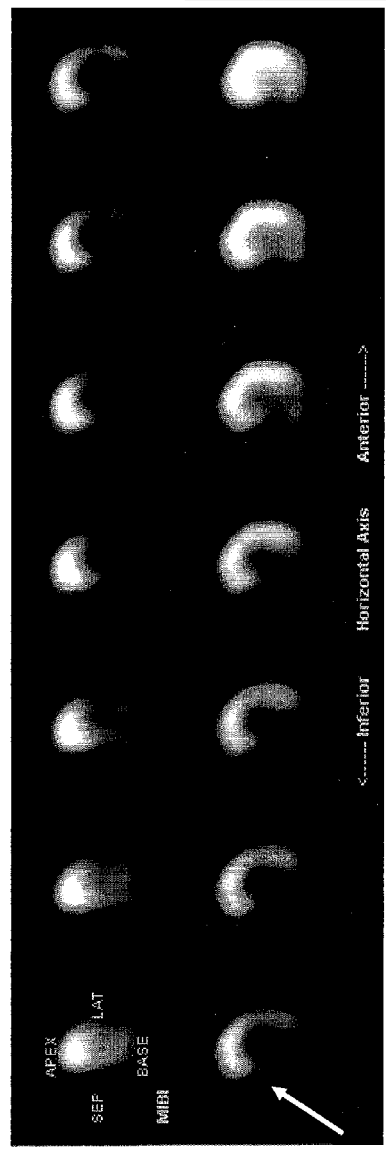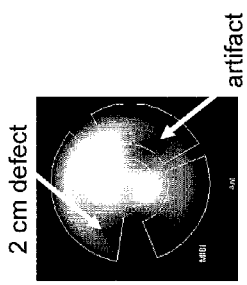

IMAGING PROTOCOLS

RELATED APPLICATIONS

This Application is a National Phase of PCT Patent Application No. PCT/IL2006/000834 having International Filing Date of Jul. 19, 2006, which claims the benefit of the following U.S. Provisional Patent Applications: 60/816,970 filed on Jun. 28, 2006, 60/800,846 filed on May 17, 2006, 60/800,845 filed on May 17, 2006, 60/799,688 filed on May 11, 2006, 60/763,458 filed on Jan. 31, 2006, 60/750,597 filed on Dec. 15, 2005, 60/750,334 filed on Dec. 15, 2005, 60/750,287 filed on Dec. 13, 2005, 60/741,440 filed on Dec. 2, 2005, 60/720,652 filed on Sep. 27, 2005, 60/720,541 filed on Sep. 27, 2005, 60/720,034 filed on Sep. 26, 2005, 60/702,979 filed on Jul. 28, 2005, 60/700,753 filed on Jul. 20, 2005, 60/700,752 filed on Jul. 20, 2005, 60/700,318 filed on Jul. 19, 2005, 60/700,299 filed on Jul. 19, 2005 and 60/700,317 filed on Jul. 19, 2005.

PCT Patent Application No. PCT/IL2006/000834 is also a Continuation-in-Part of the following PCT Patent Applications: PCT/IL2006/000562 filed on May 11, 2006, PCT/IL2006/000059 filed on Jan. 15, 2006, PCT/IL2005/001215 filed on Nov. 16, 2005 and PCT/IL2005/001173 filed on Nov. 9, 2005.

PCT Patent Application No. PCT/IL2006/000834 claims the benefit of Israel Patent Applications: 172349 filed on Nov. 27, 2005 and 171346 filed on Oct. 10, 2005.

The contents of the above Applications are all incorporated herein by reference.

FIELD AND BACKGROUND OF THE INVENTION

The present invention relates to protocols for nuclear imaging, and more particularly, to protocols for nuclear imaging, without coincidence, with sensitivity which meets, and even outperforms that of PET, in terms of speed and spatial resolution, and with a high spectral resolution not available in PET.

Radionuclide imaging aims at obtaining an image of a radioactively labeled substance, that is, a radiopharmaceutical, within the body, following administration, generally, by injection. The substance is chosen so as to be picked up by active pathologies to a different extent from the amount picked up by the surrounding, healthy tissue; in consequence, the pathologies are operative as radioactive-emission sources and may be detected by radioactive-emission imaging. A pathology may appear as a concentrated source of high radiation, that is, a hot region, as may be associated with a tumor, or as a region of low-level radiation, which is nonetheless above the background level, as may be associated with carcinoma.

A reversed situation is similarly possible. Dead tissue has practically no pick-up of radiopharmaceuticals, and is thus operative as a cold region.

The mechanism of localization of a radiopharmaceutical in a particular organ of interest depends on various processes in that particular organ such as antigen-antibody reactions, physical trapping of particles, receptor site binding, removal of intentionally damaged cells from circulation, and transport of a chemical species across a cell membrane and into the cell by a normally operative metabolic process. A summary of the mechanisms of localization by radiopharmaceuticals is found in http://www.lunis.luc.edu/nucmed/tutorial/radpharm/i.htm.

The particular choice of a radionuclide for labeling antibodies depends upon the chemistry of the labeling procedure and the isotope nuclear properties, such as the number of gamma rays emitted, their respective energies, the emission of other particles such as beta or positrons, the isotope half-life, and the decay scheme.

In PET imaging, positron emitting radio-isotopes are used for labeling, and the imaging camera detects coincidence photons, the gamma pair of 0.511 Mev, traveling in opposite directions. Each coincident detection defines a line of sight, along which annihilation takes place. As such, PET imaging collects emission events, which occurred in an imaginary tubular section enclosed by the PET detectors. A gold standard for PET imaging is PET $NH_3$ rest myocardial perfusion imaging with N-13-ammonia ($NH_3$), at a dose level of 740 MBq, with attenuation correction. Yet, since the annihilation gamma is of 0.511 Mev, regardless of the radio-isotope, PET imaging does not provide spectral information, and does not differentiate between radio-isotopes.

In SPECT imaging, primarily gamma emitting radio-isotopes are used for labeling, and the imaging camera is designed to detect the actual gamma emission, generally, in an energy range of approximately 11-511 KeV. Generally, each detecting unit, which represents a single image pixel, has a collimator that defines the solid angle from which radioactive emission events may be detected.

Because PET imaging collects emission events, in the imaginary tubular section enclosed by the PET detectors, while SPECT imaging is limited to the solid collection angles defined by the collimators, generally, PET imaging has a higher sensitivity and spatial resolution than does SPECT. Therefore, the gold standard for spatial and time resolutions in nuclear imaging is defined for PET.

Although radiopharmaceuticals are powerful labeling tools, their recommended maximum dose must be taken into account when using these agents for imaging. In order to minimize exposure to the tissue, radiopharmaceuticals, which have a long half life, and radiopharmaceuticals, which have radioactive daughters, are generally avoided.

The recommended maximum doses of radiopharmaceuticals are 5 rems for a whole body dose and 15 rads per organ, while the allowable dose for children is one tenth of the adult level. The per-organ criterion protects organs where accumulation takes place. For example, radiopharmaceuticals for which removal is primarily by the liver should be administered at a lower dose than those for which removal is partly by the liver and partly by the kidney, because in the former, a single organ is involved with the removal, and in the latter, there is sharing of the removal.

Radiopharmaceutical behavior in vivo is a dynamic process. Some tissues absorb radiopharmaceuticals faster than others or preferentially to others, and some tissues flush out the radiopharmaceuticals faster than others or preferentially to others, so the relative darkness of a given tissue is related to a time factor. Since the uptake clearance of such a radiopharmaceutical by the various tissues (target and background) varies over time, standard diagnosis protocols usually recommend taking an image at the time at which the ratio of target emission versus background emission is the highest.

Yet, this approach produces a single parameter per voxel of the reconstructed image, a level of gray, at a specific time, and ignores the information that could be obtained from the behavior of a radiopharmaceutical as a function of time.

Dynamic imaging, on the other hand, attempts to acquire the behavior of a radiopharmaceutical as a function of time, for example, to measure perfusion in myocardial tissue. Dynamic imaging is advantageous to static imaging, as it provides a better measure of blood flow, it is more sensitive to ischemia than static imaging, and both perfusion as absolute blood flow and coronary flow reserve as well as myocardial viability may be obtained from a single imaging session.

It is possible to design highly sensitive SPECT imaging cameras with the sensitivity and resolution of PET imaging cameras. For example, PCT IL2006/000059 assigned to Spectrum Dynamics LLC., discloses a highly sensitive radioactive-emission camera, which opens a new realm in SPECT-type imaging. Unlike other SPECT imaging cameras, this camera is viable for dynamic studies. Accordingly, it may be used to compare the rates of change of radiopharmaceutical in a tissue with spectral resolution. Other SPECT imaging cameras are only capable of measuring the total concentration of a radiopharmaceutical in a tissue. As mentioned above, this is particularly important for measuring cardiac functions such as cardiac ejection parameters.

The camera disclosed in PCT IL2006/000059 is capable of faster and lower dose imaging compared to other SPECT cameras. The higher sensitivity of this camera also allows for use of new agents which in existing systems would not produce sufficient radioactivity.

The camera is also able to make use of radiopharmaceutical cocktails and dynamic imaging of multiple isotopes. Thus, dual and multiple isotope studies may be performed using spectral resolution. This may be particularly relevant for tumor diagnosis, since in some cases the difference between tumor and healthy tissue is that one picks up two agents whilst the other picks up only one of the agents as well as different radiopharmaceutical kinetics between tumor and healthy tissue.

There is an urgent need for and it would be particularly advantageous to have novel protocols with clear guidelines that may be used for nuclear imaging with SPECT cameras of high sensitivity and resolution.

SUMMARY OF THE INVENTION

According to one aspect of the present invention there is provided a method of radioimaging a myocardial perfusion, the method comprising in sequence:
(a) administering to a subject about 3 mCi Tl201 thallous chloride;
(b) allowing the subject to rest;
(c) radioimaging a heart of the subject;
(d) subjecting the subject to a physical stress;
(e) administering to the subject at a peak of the physical stress about 20-30 mCi Tc99m sestamibi; and
(f) radioimaging the heart of the subject, thereby radioimaging a myocardial perfusion.

According to further features in preferred embodiments of the invention described below, the method comprises at least one or more of the following:
(1) step (b) is for about 10-15 minutes;
(2) step (c) is for about 2 minutes;
(3) step (d) is effected about 2 minutes following step (c);
(4) step (f) is effected about 30-60 minutes following step (d); and
(5) step (f) is for about 2 minutes.

According to still further features in the described preferred embodiments the method is affected as described in Table 1.

According to another aspect of the present invention there is provided a method of radioimaging a myocardial perfusion, the method comprising in sequence:
(a) administering to a subject about 8-10 mCi Tc99m sestamibi;
(b) allowing the subject to rest;
(c) radioimaging a heart of the subject;
(d) subjecting the subject to a physical stress;
(e) administering to the subject at a peak of the physical stress about 20-30 mCi Tc99m sestamibi; and
(f) radioimaging the heart of the subject, thereby radioimaging a myocardial perfusion.

According to further features in preferred embodiments of the invention described below, the method comprises at least one or more of the following:
(1) step (b) is for about 30 minutes;
(2) step (c) is for about 2 minutes;
(3) step (d) is effected immediately following step (c);
(4) step (f) is effected about 30-60 minutes following step (e); and
(5) step (f) is for about 2 minutes.

According to still further features in the described preferred embodiments the method is affected as described in Table 2.

According to yet another aspect of the present invention there is provided a method of radioimaging a myocardial perfusion, the method comprising in sequence:
(a) administering to a subject about 3 mCi Tl201 thallous chloride;
(b) allowing the subject to rest;
(c) radioimaging a heart of the subject;
(d) subjecting the subject to a pharmacological stress;
(e) administering to the subject at a peak of the pharmacological stress about 20-30 mCi Tc99m sestamibi; and
(f) radioimaging the heart of the subject, thereby radioimaging a myocardial perfusion.

According to further features in preferred embodiments of the invention described below, the method comprises at least one or more of the following:
(1) step (b) is for about 2 minutes;
(2) step (c) is for about 2 minutes;
(3) step (d) is effected immediately following step (c);
(4) step (e) is effected about 2 minutes following step (d);
(5) step (f) is effected immediately following step (e);
(6) step (f) is for about 2 minutes; and
(7) the pharmacological stress is adenosine or dipyridamole.

According to still further features in the described preferred embodiments the method is effected as described in Table 3.

According to still another aspect of the present invention there is provided a method of radioimaging a myocardial perfusion, the method comprising in sequence:
(a) administering to a subject about 8-10 mCi Tc99m sestamibi;
(b) radioimaging a heart of the subject;
(c) subjecting the subject to a pharmacological stress;
(d) administering to the subject at a peak of the pharmacological stress about 20-30 mCi Tc99m sestamibi; and
(e) radioimaging the heart of the subject, thereby radioimaging a myocardial perfusion.

According to further features in preferred embodiments of the invention described below, the method comprises at least one or more of the following:
(1) step (b) is immediately following step (a);
(2) step (b) is for about 2 minutes; v
(3) step (c) is effected immediately following step (b);
(4) step (d) is effected about 2 minutes following step (c);
(5) step (e) is effected immediately following step (d);
(6) step (e) is for about 2 minutes; and
(7) the pharmacological stress is adenosine or dipyridamole.

According to still further features in the described preferred embodiments the method is effected as described in Table 4.

According to an additional aspect of the present invention there is provided a method of radioimaging a myocardial perfusion, the method comprising in sequence:
(a) administering to a subject about 3 mCi Tl201 thallous chloride;
(b) allowing the subject to rest;
(c) radioimaging a heart of the subject;
(d) subjecting the subject to a physical stress;
(e) administering to the subject at a peak of the physical stress about 20-30 mCi Tc99m sestamibi; and
(f) radioimaging the heart of the subject immediately following the peak stress, thereby radioimaging a myocardial perfusion.

According to further features in preferred embodiments of the invention described below, the method comprises at least one or more of the following:
(1) step (b) is for about 15 minutes;
(2) step (c) is for about 2 minutes;
(3) step (e) is effected about 30-60 minutes following step (d); and
(4) step (f) is for about 2 minutes.

According to still further features in the described preferred embodiments the method is effected as described in Table 5.

According to yet an additional aspect of the present invention there is provided method of radioimaging a myocardial perfusion, the method comprising in sequence:
(a) administering to a subject about 20-30 mCi Tc99m sestamibi;
(b) allowing the subject to rest;
(c) radioimaging a heart of the subject;
(d) subjecting the subject to a physical stress;
(e) administering to the subject at a peak of the physical stress about 3 mCi Tl201 thallous chloride;
(f) radioimaging the heart of the subject; and
(g) radioimaging the heart of the subject, thereby radioimaging a myocardial perfusion.

According to further features in preferred embodiments of the invention described below, the method comprises at least one or more of the following:
(1) step (b) is for about 15-30 minutes;
(2) step (c) is for about 2 minutes;
(3) step (d) is effected immediately following step (c);
(4) step (f) is effected about 10-15 minutes following step (e);
(5) step (f) is for about 4 minutes;
(6) step (g) is effected about 4 hours following step (f); and
(7) step (g) is for about 6 minutes.

According to still further features in the described preferred embodiments the method is effected as described in Table 6.

According to still an additional aspect of the present invention there is provided a method of radioimaging a myocardial perfusion, the method comprising in sequence:
(a) administering to a subject about 3 mCi Tc99m sestamibi;
(b) allowing the subject to rest;
(c) radioimaging a heart of the subject;
(d) subjecting the subject to a pharmacological stress;
(e) administering to the subject at a peak of the pharmacological stress about 3 mCi Tl201 thallous chloride;
(f) radioimaging the heart of the subject; and
(g) radioimaging the heart of the subject, thereby radioimaging a myocardial perfusion.

According to further features in preferred embodiments of the invention described below, the method comprises at least one or more of the following:
(1) step (b) is for about 15-30 minutes;
(2) step (c) is for about 2 minutes;
(3) step (d) is effected immediately following step (c);
(4) step (e) is effected about 2 minutes following step (d);
(5) step (f) is effected immediately following step (e);
(6) step (f) is for about 4 minutes;
(7) step (g) is effected about 4 hours following step (f);
(8) step (g) is for about 6 minutes; and
(9) the pharmacological stress is adenosine or dipyridamole.

According to still further features in the described preferred embodiments the method is effected as described in Table 7.

According to a further aspect of the present invention there is provided method of radioimaging a myocardial perfusion, the method comprising in sequence:
(a) administering to a subject about 3 mCi Tc99m sestamibi;
(b) radioimaging a heart of the subject;
(c) subjecting the subject to a pharmacological stress;
(d) administering to the subject at a peak of the pharmacological stress about 3 mCi Tl201 thallous chloride;
(e) radioimaging the heart of the subject; and
(f) radioimaging the heart of the subject, thereby radioimaging a myocardial perfusion.

According to further features in preferred embodiments of the invention described below, the method comprises at least one or more of the following:
(1) step (b) is effected immediately following step (a);
(2) step (b) is for about 2 minutes;
(3) step (c) is effected immediately following step (b);
(4) step (d) is effected about 2 minutes following step (c);
(5) step (e) is effected immediately following step (d);
(6) step (e) is for about 4 minutes;
(7) step (f) is effected about 4 hours following step (e);
(8) step (f) is for about 6 minutes;
(9) the pharmacological stress is adenosine or dipyridamole.

According to still further features in the described preferred embodiments the method is effected as described in Table 8.

According to yet a further aspect of the present invention there is provided a method of radioimaging a myocardial perfusion, the method comprising in sequence:
(a) administering to a subject about 3 mCi Tc99m sestamibi;
(b) allowing the subject to rest;
(c) radioimaging a heart of the subject;
(d) subjecting the subject to a pharmacological stress;
(e) administering to the subject at a peak of the pharmacological stress about 3 mCi Tl201 thallous chloride;
(f) allowing the subject to rest; and
(g) radioimaging the heart of the subject, thereby radioimaging a myocardial perfusion.

According to further features in preferred embodiments of the invention described below, the method comprises at least one or more of the following:
(1) step (b) is for about 30 minutes;
(2) step (c) is for about 2 minutes;
(3) step (d) is effected immediately following step (c);
(4) step (e) is effected about 2 minutes following step (d);
(5) step (f) is for about 2 minutes;
(6) step (g) is effected immediately following step (f);

(7) step (g) is for about four minutes; and (8) the pharmacological stress is adenosine or dipyridamole.

According to still further features in the described preferred embodiments the method is effected as described in Table 9.

According to still a further aspect of the present invention there is provided a method of radioimaging a myocardial perfusion, the method comprising in sequence:

(a) administering to a subject about 8-10 mCi Tc99m Teboroxime;

(b) radioimaging a heart of the subject;

(c) subjecting the subject to a pharmacological stress;

(d) administering to the subject at a peak of the pharmacological stress about 20-30 mCi Tc99m Teboroxime; and (e) radioimaging the heart of the subject, thereby radioimaging a myocardial perfusion.

According to further features in preferred embodiments of the invention described below, the method comprises at least one or more of the following:

(1) step (b) is effected immediately following or during step (a);

(2) step (b) is for about 2-10 minutes;

(3) step (c) is effected immediately following step (b);

(4) step (d) is effected about 2 minutes following step (c);

(5) step (e) is effected immediately following or during step (d);

(6) step (e) is for about 2-10 minutes; and (7) the pharmacological stress is adenosine or dipyridamole.

According to still further features in the described preferred embodiments the method is effected as described in Table 10.

According to still a further aspect of the present invention there is provided a method of radioimaging a lung perfusion, the method comprising simultaneously:

(a) administering to a subject less than about 5 mCi Tc99m Diethylene triamine-pentacetic acid (DTPA);

(b) administering to a subject less than about 5 mCi Tc99m MAA;

(c) radioimaging a lung of the subject, thereby radioimaging a lung perfusion.

According to further features in preferred embodiments of the invention described below, the method comprises at least one or more of the following:

(1) the Tc99m Diethylene triamine-pentacetic acid (DTPA) is administered via a nebulizer;

(2) step (c) is for about 0-30 minutes;

According to still further features in the described preferred embodiments the method is effected as described in Table 11.

According to still a further aspect of the present invention there is provided a method of radioimaging a bone inflammation or a bone cancer, the method comprising simultaneously:

(a) administering to a subject about 20-30 mCi Tc99m MDP; and (b) radioimaging a bone of the subject, thereby radioimaging a bone inflammation or a bone cancer.

According to further features in preferred embodiments of the invention described below, the method comprises at least one or more of the following:

(1) step (b) is effected about 0-60 minutes following step (a);

(2) step (b) is for about six minutes.

According to still further features in the described preferred embodiments the method is effected as described in Table 12.

According to still a further aspect of the present invention there is provided a method of radioimaging an inflammatory process, the method comprising in sequence:

(a) administering to a subject about 2-3 mCi In 111 WBC; and (b) radioimaging the subject, thereby radioimaging an inflammatory process.

According to further features in preferred embodiments of the invention described below, the method comprises at least one or more of the following:

(1) step (b) is effected about 24 hours following step (a).

(2) step (b) is for about 1 minute.

According to still further features in the described preferred embodiments the method is effected as described in Table 13.

According to still a further aspect of the present invention there is provided a method of radioimaging a myocardial perfusion, the method comprising in sequence:

(a) administering to a subject about 0.3 mCi Tl201 thallous chloride;

(b) radioimaging a heart of the subject;

(c) subjecting the subject to a physical stress;

(d) administering to the subject at a peak of the physical stress about 3 mCi Tc99m sestamibi; and (e) radioimaging the heart of the subject, thereby radioimaging a myocardial perfusion.

According to further features in preferred embodiments of the invention described below, the method comprises at least one or more of the following:

(1) step (b) is effected about 10-15 minutes following step (a);

(2) step (b) is for about 15 minutes;

(3) step (c) is immediately following step (b);

(4) step (e) is effected about 30-60 minutes following step (d); and (5) step (e) is for about 15 minutes.

According to still further features in the described preferred embodiments the method is effected as described in Table 14.

According to still a further aspect of the present invention there is provided a method of radioimaging a myocardial perfusion, the method comprising in sequence:

(a) administering to a subject about 0.3 mCi Tc99m sestamibi;

(b) radioimaging a heart of the subject;

(c) subjecting the subject to a physical stress;

(d) administering to the subject at a peak of the physical stress about 3 mCi Tc99m sestamibi; and (e) radioimaging the heart of the subject, thereby radioimaging a myocardial perfusion.

According to further features in preferred embodiments of the invention described below, the method comprises at least one or more of the following:

(1) step (b) is effected about 15-30 minutes following step (a);

(2) step (b) is for about 15 minutes;

(3) step (c) is effected immediately following step (b);

(4) step (e) is effected about 30-60 minutes following step (d); and (5) step (e) is for about 15 minutes.

According to still further features in the described preferred embodiments the method is effected as described in Table 15.

According to still a further aspect of the present invention there is provided a method of radioimaging a myocardial perfusion, the method comprising in sequence:

(a) administering to a subject about 0.3 mCi Tl201 thallous chloride;

(b) subjecting the subject to a physical stress;

(c) administering to the subject at a peak of the physical stress about 3 mCi Tc99m sestamibi; and (d) radioimaging a heart of the subject, thereby radioimaging a myocardial perfusion.

According to further features in preferred embodiments of the invention described below, the method comprises at least one or more of the following:

(1) step (b) is effected immediately following step (a);

(2) step (d) is effected about 30-60 minutes following step (c); and (3) step (d) is for about 5-15 minutes.

According to still further features in the described preferred embodiments the method is effected as described in Table 16.

According to still a further aspect of the present invention there is provided a method of radioimaging a myocardial perfusion, the method comprising in sequence:

(a) administering to a subject about 0.3 mCi Tl201 thallous chloride;

(b) radioimaging a heart of the subject (c) subjecting the subject to a pharmacological stress;

(d) administering to the subject at a peak of the pharmacological stress about 3 mCi Tc99m sestamibi; and (e) radioimaging the heart of the subject, thereby radioimaging a myocardial perfusion.

According to further features in preferred embodiments of the invention described below, the method comprises at least one or more of the following:

(1) step (b) is effected about 2 minutes following step (a);

(2) step (b) is for about 15 minutes;

(3) step (c) is effected immediately following step (b);

(4) step (d) is effected about 2 minutes following step (c);

(5) step (e) is effected immediately following step (d);

(6) step (e) is for about 15 minutes; and (7) the pharmacological stress is adenosine or dipyridamole.

According to still further features in the described preferred embodiments the method is effected as described in Table 17.

According to still a further aspect of the present invention there is provided a method of radioimaging a breast cancer, the method comprising in sequence:

(a) administering to a subject about 0.3 mCi Tc99m sestamibi; and (b) radioimaging a breast of the subject, thereby radioimaging a breast cancer.

According to further features in preferred embodiments of the invention described below, the method comprises at least one or more of the following:

(1) step (b) is effected about 15-30 minutes following step (a);

(2) step (b) is for about 15 minutes.

According to still further features in the described preferred embodiments the method is, effected as described in Table 18.

According to still a further aspect of the present invention there is provided a method of radioimaging a brain perfusion, the method comprising in sequence:

(a) simultaneously administering to a subject no more than about 3 mCi Tc99m exametazine (HMPAO), no more than about 3 mCi Tc99m ECD and no more than about 5 mCi I123 isofetamine hydrochloride; and (b) radioimaging a brain of the subject, thereby radioimaging a brain perfusion.

According to further features in preferred embodiments of the invention described below, the method comprises at least one or more of the following:

(1) step (b) is effected about 1 hour following step (a);

(2) step (b) is no more than 30 minutes.

According to still further features in the described preferred embodiments the method is effected as described in Table 19.

According to still a further aspect of the present invention there is provided a method of radioimaging a brain perfusion, the method comprising in sequence:

(a) administering to a subject no more than about 3 mCi Tc99m exametazine (HMPAO); and (b) radioimaging a brain of the subject, thereby radioimaging a brain perfusion.

According to further features in preferred embodiments of the invention described below, the method comprises at least one or more of the following:

(1) step (b) is effected for no more than about 1 hour following step (a);

(2) step (b) is for no more than about 30 minutes.

According to still further features in the described preferred embodiments the method is effected as described in Table 20.

According to still a further aspect of the present invention there is provided a method of radioimaging a brain perfusion, the method comprising in sequence:

(a) administering to a subject no more than about 3 mCi Tc99m ECD; and (b) radioimaging a brain of the subject, thereby radioimaging a brain perfusion.

According to further features in preferred embodiments of the invention described below, the method comprises at least one or more of the following:

(1) step (b) is effected for no more than about 1 hour following step (a);

(2) step (b) is for no more than about 30 minutes.

According to still further features in the described preferred embodiments the method is effected as described in Table 21.

According to still a further aspect of the present invention there is provided a method of radioimaging a brain perfusion, the method comprising in sequence:

(a) administering to a subject no more than about 5 mCi I 123 isofetamine hydrochloride; and (b) radioimaging a brain of the subject, thereby radioimaging a brain perfusion.

According to further features in preferred embodiments of the invention described below, the method comprises at least one or more of the following:

(1) step (b) is effected for no more than about 1 hour following step (a);

(2) step (b) is for no more than about 30 minutes.

According to still further features in the described preferred embodiments the method is effected as described in Table 22.

According to still a further aspect of the present invention there is provided a method of radioimaging a brain perfusion, the method comprising simultaneously:

(a) administering to a subject no more than about 3 mCi Tc99m exametazine (HMPAO); and (b) radioimaging a brain of the subject, thereby radioimaging a brain perfusion.

According to further features in preferred embodiments of the invention described below, step (b) is for no more than 30 minutes.

According to still further features in the described preferred embodiments the method is effected as described in Table 23.

According to still a further aspect of the present invention there is provided a method of radioimaging a brain perfusion, the method comprising simultaneously:

(a) administering to a subject no more than about 3 mCi Tc99m ECD; and (b) radioimaging a brain of the subject, thereby radioimaging a brain perfusion.

According to further features in preferred embodiments of the invention described below, step (b) is for no more than about 30 minutes.

According to still further features in the described preferred embodiments the method is effected as described in Table 24.

According to still a further aspect of the present invention there is provided a method of radioimaging a brain perfusion, the method comprising simultaneously:

(a) administering to a subject no more than about 5 mCi I 123 isofetamine hydrochloride; and (b) radioimaging a brain of the subject, thereby radioimaging a brain perfusion.

According to further features in preferred embodiments of the invention described below, step (b) is for no more than about 30 minutes.

According to still further features in the described preferred embodiments the method is effected as described in Table 25.

According to still a further aspect of the present invention there is provided a method of radioimaging a liver structure, the method comprising simultaneously:

(a) administering to a subject about 0.5 mCi Tc99m mebrofenin; and (b) radioimaging a liver of the subject, thereby radioimaging a liver structure.

According to further features in preferred embodiments of the invention described below, step (b) is for about 30 minutes.

According to still further features in the described preferred embodiments the method is effected as described in Table 26.

According to still a further aspect of the present invention there is provided a method of radioimaging a lung perfusion, the method comprising simultaneously:

(a) administering to a subject no more than about 3 mCi of Tc99m DTPA and no more than 0.5 mCi of MAA or DTPA ln 111; and (b) radioimaging a lung of the subject, thereby radioimaging a lung perfusion.

According to further features in preferred embodiments of the invention described below, step (b) is for about 6 minutes.

According to still further features in the described preferred embodiments the method is effected as described in Table 27.

According to still a further aspect of the present invention there is provided a method of radioimaging a myocardial perfusion (thallium rest), the method comprising simultaneously:

(a) radioimaging a heart of the subject; and (b) administering to a subject about 4 mCi of Tl thallous chloride, thereby radioimaging a myocardial perfusion.

According to further features in preferred embodiments of the invention described below, wherein step (a) is for about 2-20 minutes.

According to still further features in the described preferred embodiments the method is effected as described in Table 28.

According to still a further aspect of the present invention there is provided a method of radioimaging a myocardial perfusion (thallium stress), the method comprising in sequence:

(a) subjecting a subject to a physical or pharmacological stress;

(b) administering to the subject at a peak of the physical stress about 4 mCi Tl201 thallous chloride; and (c) radioimaging a heart of the subject, thereby radioimaging a myocardial perfusion.

According to further features in preferred embodiments of the invention described below, the method comprises at least one or more of the following:

(1) step (c) is effected immediately following step (b); and (2) step (c) is for about 2-20 minutes; and (3) the pharmacological stress adenosine or dipyridamole.

According to still further features in the described preferred embodiments the method is effected as described in Table 29.

According to still a further aspect of the present invention there is provided a method of radioimaging a myocardial perfusion (teboroxime rest), the method comprising simultaneously:

(a) radioimaging a heart of the subject; and (b) administering to a subject about 30 mCi of Tc99m teboroxime, thereby radioimaging a myocardial perfusion.

According to further features in preferred embodiments of the invention described below, step (a) is for about 15 minutes.

According to still further features in the described preferred embodiments the method is effected as described in Table 30.

According to still a further aspect of the present invention there is provided a method of radioimaging a myocardial perfusion (teboroxime stress), the method comprising in sequence:

(a) subjecting a subject to a physical or pharmacological stress;

(b) administering to the subject at a peak of the physical stress about 4 mCi Tc99m Teboroxime; and (c) radioimaging a heart of the subject, thereby radioimaging a myocardial perfusion.

According to further features in preferred embodiments of the invention described below, the method comprises at least one or more of the following:

(1) step (c) is effected immediately following step (b);

(2) step (c) is for about 2-20 minutes; and (3) the pharmacological stress is adenosine or dipyridamole.

According to still further features in the described preferred embodiments the method is effected as described in Table 31.

According to still a further aspect of the present invention there is provided a method of radioimaging a myocardial perfusion (sestamibi rest), the method comprising simultaneously:

(a) radioimaging a heart of the subject; and (b) administering to a subject about 30 mCi of Tc99m sestamibi, thereby radioimaging a myocardial perfusion.

According to further features in preferred embodiments of the invention described below, step (a) is for about 15 minutes.

According to still further features in the described preferred embodiments the method is effected as described in Table 32.

According to still a further aspect of the present invention there is provided a method of radioimaging a myocardial perfusion (sestamibi stress), the method comprising in sequence:
(a) subjecting a subject to a physical or pharmacological stress;
(b) administering to the subject at a peak of the physical stress about 20-30 mCi of Tc99m sestamibi; and
(c) radioimaging a heart of the subject, thereby radioimaging a myocardial perfusion.

According to further features in preferred embodiments of the invention described below, the method comprises at least one or more of the following:
(1) step (c) is effected immediately following step (b); and
(2) step (c) is for about 15 minutes; and
(3) the pharmacological stress is adenosine or dipyridamole.

According to still further features in the described preferred embodiments the method is effected as described in Table 33.

According to still a further aspect of the present invention there is provided a method of radioimaging a myocardial perfusion (tetrofosmin rest), the method comprising simultaneously:
(a) radioimaging a heart of the subject; and
(b) administering to a subject about 30 mCi of Tc99m tetrofosmin, thereby radioimaging a myocardial perfusion.

According to further features in preferred embodiments of the invention described below, step (a) is for about 15 minutes.

According to still further features in the described preferred embodiments the method is effected as described in Table 34.

According to still a further aspect of the present invention there is provided a method of radioimaging a myocardial perfusion (tetrofosmin stress), the method comprising in sequence:
(a) subjecting a subject to a physical or pharmacological stress;
(b) administering to the subject at a peak of the physical stress about 20-30 mCi of Tc99m tetrofosmin; and
(c) radioimaging a heart of the subject, thereby radioimaging a myocardial perfusion.

According to further features in preferred embodiments of the invention described below, the method comprises at least one or more of the following:
(1) step (c) is effected immediately following or during step (b);
(2) step (c) is for about 15 minutes; and
(3) the pharmacological stress is adenosine or dipyridamole.

According to still further features in the described preferred embodiments the method is effected as described in Table 35.

According to still a further aspect of the present invention there is provided a method of radioimaging a myocardial perfusion (Q12 rest), the method comprising simultaneously:
(a) radioimaging a heart of the subject; and
(b) administering to a subject about 30 mCi of Tc99m Q12, thereby radioimaging a myocardial perfusion.

According to further features in preferred embodiments of the invention described below, step (a) is for about 15 minutes.

According to still further features in the described preferred embodiments the method is effected as described in Table 36.

According to still a further aspect of the present invention there is provided a method of radioimaging a myocardial perfusion (Q12 stress), the method comprising in sequence:
(a) subjecting a subject to a physical or pharmacological stress;
(b) administering to the subject at a peak of the physical stress about 30 mCi of Tc99m Q12; and
(c) radioimaging a heart of the subject, thereby radioimaging a myocardial perfusion.

According to further features in preferred embodiments of the invention described below, the method comprises at least one or more of the following:
(1) step (c) is effected immediately following step (b);
(2) step (c) is for about 15 minutes; and
(3) the pharmacological stress is adenosine or dipyridamole.

According to still further features in the described preferred embodiments the method is effected as described in Table 37.

According to still a further aspect of the present invention there is provided a method of radioimaging a myocardial perfusion (BMIPP-I-123 rest), the method comprising simultaneously:
(a) radioimaging a heart of the subject; and
(b) administering to a subject about 5 mCi of BMIPP I-123, thereby radioimaging a myocardial perfusion.

According to further features in preferred embodiments of the invention described below, step (a) is for about 15 minutes.

According to still further features in the described preferred embodiments the method is effected as described in Table 38.

According to still a further aspect of the present invention there is provided a method of radioimaging a myocardial perfusion (BMIPP I-123 stress), the method comprising in sequence:
(a) subjecting a subject to a physical or pharmacological stress;
(b) administering to the subject at a peak of the physical stress about 5 mCi of BMIPP I-123; and
(c) radioimaging a heart of the subject, thereby radioimaging a myocardial perfusion.

According to further features in preferred embodiments of the invention described below, the method comprises at least one or more of the following:
(1) step (c) is effected immediately following step (b);
(2) step (c) is for about 15 minutes; and
(3) the pharmacological stress is adenosine or dipyridamole.

According to still further features in the described preferred embodiments the method is effected as described in Table 39.

According to still a further aspect of the present invention there is provided a method of radioimaging a myocardial perfusion, the method comprising in sequence:
(a) subjecting a subject to a physical or pharmacological stress;
(b) administering to the subject at a peak of the physical stress about 30 mCi of a radiopharmaceutical; and
(c) radioimaging a heart of the subject, thereby radioimaging a myocardial perfusion.

According to further features in preferred embodiments of the invention described below, the method comprises at least one or more of the following:
(1) step (c) is effected immediately following step (b);
(2) step (c) is for about 10 minutes; and
(3) the pharmacological stress is adenosine or dipyridamole.

According to still further features in the described preferred embodiments the method is effected as described in Table 40.

According to still a further aspect of the present invention there is provided a method of radioimaging a myocardial perfusion, the method comprising simultaneously:
(a) radioimaging a heart of a subject; and
(b) administering to the subject about 30 mCi of a PET radiopharmaceutical, thereby radioimaging a myocardial perfusion.

According to further features in preferred embodiments of the invention described below, the method comprises at least one or more of the following:
(1) step (c) is effected immediately following step (b); and
(2) step (c) is for about 10 minutes.

According to still further features in the described preferred embodiments the method is effected as described in Table 41.

According to still a further aspect of the present invention there is provided a method of radioimaging a tumor, the method comprising simultaneously:
(a) radioimaging a tumor of a subject; and
(b) administering to the subject about 30 mCi of Tc99m Teboroxime, 30 mCi of Tc99m sestamibi, 30 mCi of Tc99m tetrofosmin or 4 mCi of Tl-201, thereby radioimaging a myocardial perfusion.

According to further features in preferred embodiments of the invention described below, step (a) is no more than about 5 minutes.

According to still further features in preferred embodiments of the invention described below, the method is effected as described in Table 42.

According to still a further aspect of the present invention there is provided a method of radioimaging a tumor, the method comprising simultaneously:
(a) radioimaging a tumor of a subject; and
(b) administering to the subject about 4 mCi of Tl201 thallous chloride and no more than about 30 mCi of Tc99m sestamibi, thereby radioimaging a tumor.

According to further features in preferred embodiments of the invention described below, step (a) is no more than about 5 minutes.

According to still further features in the described preferred embodiments the method is effected as described in Table 43.

According to still a further aspect of the present invention there is provided a method of radioimaging a renal function, the method comprising simultaneously:
(a) radioimaging a kidney of a subject; and
(b) administering to the subject about 1 mCi of Tc99mDTPA and about 3-10 mCi of Tc99 mMAG3, thereby radioimaging a renal function.

According to further features in preferred embodiments of the invention described below, step (a) is 10 minutes.

According to still further features in the described preferred embodiments the method is effected as described in Table 44.

According to still a further aspect of the present invention there is provided a method of radioimaging a renal function, the method comprising simultaneously:
(a) radioimaging a kidney of a subject; and
(b) administering to the subject about 1 mCi of Tc99m DTPA and about 1 mCi of HippuranI-123, thereby radioimaging a renal function.

According to further features in preferred embodiments of the invention described below, step (a) is about 10 minutes.

According to still further features in the described preferred embodiments the method is effected as described in Table 45.

According to still a further aspect of the present invention there is provided a method of radioimaging a brain perfusion, the method comprising simultaneously:
(a) radioimaging a brain of a subject; and
(b) administering to the subject about 20 mCi of Tc99m ECD (neurolite) and about 20 mCi of HPMAO 99m labeled and about 5 mCi of Spectaminel123, thereby radioimaging a brain perfusion.

According to further features in preferred embodiments of the invention described below, step (a) is no more than about 30 minutes.

According to still further features in the described preferred embodiments the method is effected as described in Table 46.

According to still a further aspect of the present invention there is provided a method of radioimaging a brain perfusion, the method comprising simultaneously:
(a) radioimaging a brain of a subject; and
(b) administering to the subject no more than about 20 mCi of teboroxime, thereby radioimaging a brain perfusion.

According to further features in preferred embodiments of the invention described below, step (a) is no more than 30 minutes.

According to still further features in the described preferred embodiments the method is effected as described in Table 47.

According to still a further aspect of the present invention there is provided a method of radioimaging a liver structure, the method comprising simultaneously:
(a) radioimaging a liver of the subject; and
(b) administering to the subject no more than about 5 mCi of Tc99m sulfur colloid, thereby radioimaging a liver structure.

According to further features in preferred embodiments of the invention described below, step (a) is no more than 10 minutes.

According to still further features in the described preferred embodiments the method is effected as described in Table 48.

According to still a further aspect of the present invention there is provided a method of radioimaging a liver function, the method comprising simultaneously:
(a) radioimaging a liver of the subject; and
(b) administering to the subject no more than about 10 mCi of Tc99m disida, thereby radioimaging a liver structure.

According to further features in preferred embodiments of the invention described below, step (a) is effected every five minutes for up until 1 hour.

According to still further features in the described preferred embodiments the method further comprises administering an agent for gall bladder contraction 1 hour following step (b).

According to still further features in the described preferred embodiments the method is effected as described in Table 49.

According to still a further aspect of the present invention there is provided a method of radioimaging a gastric emptying, the method comprising simultaneously:

(a) radioimaging a stomach of a subject; and (b) administering to the subject about 3 MBq of Tc99m Sulfer colloid or labeled solid food or 0.5 MBq In-111 DTPA labeled liquid food, thereby radioimaging a gastric emptying.

According to further features in preferred embodiments of the invention described below, step (a) is for a time until the stomach is empty of the labeled food.

According to still further features in the described preferred embodiments the method is effected as described in Table 50.

According to still a further aspect of the present invention there is provided a method of radioimaging a cardiac vulnerable plaque, the method comprising in sequence:

(a) administering to a subject no more than about 5 mCi Tc99m annexin and no more than about 5 mCi Tc99m AccuTec; and (b) radioimaging a blood vessel of the subject, thereby radioimaging a cardiac vulnerable plaque.

According to further features in preferred embodiments of the invention described below, the method comprises at least one or more of the following:

(1) step (b) is effected about 1 hour following step (a);

(2) step (b) is less than about 30 minutes.

According to still further features in the described preferred embodiments the method is effected as described in Table 51.

According to still a further aspect of the present invention there is provided a method of radioimaging for prostate cancer, the method comprising in sequence:

(a) administering to a subject no more than about 5 mCi Prostascint containing 111In capromab pendetide; and (b) radioimaging a prostate of the subject, thereby radioimaging for prostate cancer.

According to further features in preferred embodiments of the invention described below, the method comprises comprising at least one or more of the following:

(1) step (b) is effected about 24-72 hours following step (a);

(2) step (b) is less than 30 minutes.

According to still further features in the described preferred embodiments the method is effected as described in Table 52.

According to still a further aspect of the present invention there is provided a method of radioimaging for SST receptor expressing tumors, the method comprising in sequence:

(a) administering to a subject no more than about 5 mCi Octreotide containing 111In DTPA; and (b) radioimaging a body of the subject, thereby radioimaging for SST receptor expressing tumors.

According to further features in preferred embodiments of the invention described below, the method comprises at least one or more of the following:

(1) step (b) is effected about 24 hours following step (a);

(2) step (b) is less than about 30 minutes.

According to still further features in the described preferred embodiments the method is effected as described in Table 53.

According to still a further aspect of the present invention there is provided a method of radioimaging for neuroendocrine tumors, the method comprising in sequence:

(a) administering to a subject no more than about 20 mCi Tc99m Neotec; and (b) radioimaging a body of the subject, thereby radioimaging for neuroendocrine tumors.

According to further features in preferred embodiments of the invention described below, the method comprises at least one or more of the following:

(1) step (b) is effected about 1 hour following step (a);

(2) step (b) is less than about 30 minutes;

According to still further features in the described preferred embodiments the method is effected as described in Table 54.

According to still a further aspect of the present invention there is provided a method of radioimaging for thrombii, the method comprising in sequence:

(a) administering to a subject no more than about 20 mCi Tc99m Acutec; and (b) radioimaging blood vessels of the subject.

According to further features in preferred embodiments of the invention described below, the method comprises at least one or more of the following:

(1) step (b) is effected from about 0-20 minutes following step (a);

(2) step (b) is less than about 30 minutes.

According to still further features in the described preferred embodiments the method is effected as described in Table 55.

According to still a further aspect of the present invention there is provided a method of radioimaging a pheochromocytoma and/or myocardial failure, the method comprising in sequence:

(a) administering to a subject no more than about 5 mCi I-123 isofetamine hydrochloride MIBG; and (b) radioimaging an adrenal gland and/or heart of the subject, thereby radioimaging a pheochromocytoma and/or myocardial failure.

According to further features in preferred embodiments of the invention described below, the method comprises at least one or more of the following:

(1) step (b) is effected about 24 hours following step (a);

(2) step (b) is less than about 30 minutes;

According to still further features in the described preferred embodiments the method is effected as described in Table 56.

According to still a further aspect of the present invention there is provided a method of radioimaging a cardiac stress, the method comprising in sequence:

(a) administering to a subject about 4 mCi Tl201 thallous chloride;

(b) radioimaging a heart of the subject;

(c) subjecting the subject to a physical or pharmacological stress, wherein the pharmacological stress is at least one vasodilatory agent; and (d) radioimaging a heart of the subject, thereby radioimaging a cardiac stress.

According to further features in preferred embodiments of the invention described below, the method comprises at least one or more of the following:

(1) step (b) is effected no more than about 2 minutes following step (a);

(2) step (b) is for about 2-5 minutes;

(3) step (c) is effected immediately following step (b);

(4) step (d) is effected no more than about 5 minutes following step (c);

(5) step (d) is for about 2-10 minutes; and (6) the at least one vasodilatory agent is adenosine or dipyridamole.

According to still further features in the described preferred embodiments the method is effected as described in Table 57.

According to still a further aspect of the present invention there is provided a method of radioimaging a renal function, the method comprising in sequence:

(a) administering to a subject about 2-4 mCi DTPA and/or Tc99 mMAG3;

(b) radioimaging a kidney of the subject;

(c) subjecting the subject to a physical and/or at least one pharmacological stress; and (d) radioimaging a kidney of the subject.

According to further features in preferred embodiments of the invention described below, the method comprises at least one or more of the following:

(1) step (b) is for about 10-30 minutes;

(2) step (c) is effected immediately following step (b);

(3) step (d) is for about 10-30 minutes (4) the pharmacological stress is selected from the group consisting of captopril fuside, a vasodilatory agent and a diuretic agent.

According to still further features in the described preferred embodiments the method is effected as described in Table 58.

According to still a further aspect of the present invention there is provided a method of radioimaging to determine Bexaar dosimetry, the method comprising simultaneously:

(a) radioimaging a body of a subject; and (b) administering to the subject about 5 MCi/35 mg of I123 iofetamine hydrochloride, thereby radioimaging to determine Bexaar dosimetry.

According to further features in preferred embodiments of the invention described below, step (a) is for about 5 minutes.

According to still further features in the described preferred embodiments the method is effected as described in Table 59.

According to still a further aspect of the present invention there is provided a method of radioimaging a parathyroid adenoma, the method comprising in sequence:

(a) administering to a subject about 1 mCi thallium 201thallous chloride and about 15 mCi Tc99m pertechnetate;

(b) radioimaging a parathyroid of the subject, thereby radioimaging a parathyroid adenoma.

According to further features in preferred embodiments of the invention described below, the method comprises at least one or more of the following:

(1) step (b) is effected about 10 minutes following step (a); and (2) step (b) is for about 5 minutes.

According to still further features in the described preferred embodiments the method is effected as described in Table 60.

According to still a further aspect of the present invention there is provided a method of radioimaging a parathyroid adenoma, the method comprising in sequence:

(a) administering to a subject about 15 mCi Tc99m sestamibi and about 100 µCi I123;

(b) radioimaging a parathyroid of the subject, thereby radioimaging a parathyroid adenoma.

According to further features in preferred embodiments of the invention described below, the method comprises at least one or more of the following:

(1) step (b) is effected about 10 minutes following step (a); and (2) step (b) is for about 5 minutes.

According to still further features in the described preferred embodiments the method is effected as described in Table 61.

According to still a further aspect of the present invention there is provided a method of radioimaging a thyroid cancer, the method comprising in sequence:

(a) administering to a subject about 10 mCi Tc99m MDP and about 4 mCi I-131;

(b) radioimaging a thyroid of the subject, thereby radioimaging a thyroid cancer.

According to further features in preferred embodiments of the invention described below, the method comprises at least one or more of the following:

(1) step (b) is effected about 2 hours following step (a); and (2) step (b) is for about 30 minutes.

According to still further features in the described preferred embodiments the method is effected as described in Table 62.

According to still a further aspect of the present invention there is provided a method of radioimaging an endocrine tumor, the method comprising in sequence:

(a) administering to a subject about 15 mCi Tc99m MDP and about 4 mCi ln111 octeotride;

(b) radioimaging a body of the subject, thereby radioimaging an endocrine tumor.

According to further features in preferred embodiments of the invention described below, the method comprises at least one or more of the following:

(1) step (b) is effected no more than about 2 hours following step (a); and (2) step (b) is for about 30 minutes.

According to still further features in the described preferred embodiments the method is effected as described in Table 63.

According to still a further aspect of the present invention there is provided a method of radioimaging an endocrine tumor, the method comprising in sequence:

(a) administering to a subject about 4 mCi ln111 octeotride;

(b) administering to a subject about 15 mCi Tc99m MDP;

(c) radioimaging a body of the subject, thereby radioimaging an endocrine tumor.

According to further features in preferred embodiments of the invention described below, the method comprises at least one or more of the following:

(1) step (b) is effected no more than about 3 days following step (a);

(2) step (c) is effected no more than about 2 hours following step (b); and (3) step (c) is for about 30 minutes.

According to still-further features in the described preferred embodiments the method is effected as described in Table 64.

According to still a further aspect of the present invention there is provided a method of radioimaging a prostate tumor, the method comprising in sequence:

(a) administering to a subject about 3 mCi ln111 capromab pentitide;

(b) administering to a subject about 15 mCi Tc99m RBCs;

(c) radioimaging a pelvis/abdomen of the subject, thereby radioimaging a prostate tumor.

According to further features in preferred embodiments of the invention described below, the method comprises at least one or more of the following:

(1) step (b) is effected no more than about 3 days following step (a);

(2) step (c) is effected no more than about 2 hours following step (b); and (3) step (c) is for about 30 minutes.

According to still further features in the described preferred embodiments the method is effected as described in Table 65.

According to still a further aspect of the present invention there is provided a method of radioimaging a bone infection, the method comprising in sequence:
(a) administering to a subject about 3 mCi In111 WBC;
(b) administering to a subject about 15 mCi Tc99m colloid;
(c) radioimaging a bone of the subject, thereby radioimaging a bone infection.

According to further features in preferred embodiments of the invention described below, the method comprises at least one or more of the following:
(1) step (b) is effected no more than 3 days following step (a);
(2) step (c) is effected no more than 2 hours following step (b); and
(3) step (c) is for about 30 minutes.

According to still further features in the described preferred embodiments the method is effected as described in Table 66.

According to still a further aspect of the present invention there is provided a method of radioimaging a neck or head cancer invasion of a bone or cartilage, the method comprising in sequence:
(a) administering to a subject about 2 mCi Tl201 thallous chloride and about 15 mCi Tc99m MDP;
(b) radioimaging a bone or cartilage of the subject, thereby radioimaging a neck or head cancer invasion of a bone or cartilage.

According to further features in preferred embodiments of the invention described below, the method comprises at least one or more of the following:
(1) step (b) is effected about 2 hours following step (a); and
(2) step (b) is for about 30 minutes.

According to still further features in the described preferred embodiments the method is effected as described in Table 67.

According to still a further aspect of the present invention there is provided a method of radioimaging a pathological condition, the method comprising in sequence:
(a) administering to a subject about 2 mCi In111 WBCs;
(b) administering to the subject about 1 mCi Tl201 thallous chloride and about 10 mCi Tc99m sestamibi; and
(c) radioimaging a body of the subject, thereby radioimaging a pathological condition.

According to further features in preferred embodiments of the invention described below, the method comprises at least one or more of the following:
(1) step (b) is effected about 2 days following step (a); and
(2) step (c) is for about 30 minutes.
(3) the pathological condition is selected from the group consisting of an infection, a tumor and a myocardial infection.

According to still further features in the described preferred embodiments the method is effected as described in Table 68.

According to still a further aspect of the present invention there is provided a method of radioimaging a myocardial ischemia, the method comprising in sequence:
(a) administering to a subject about 2 mCi I123 BMIPP;
(b) administering to the subject about 1 mCi Tl201 thallous chloride and about 10 mCi of a Tc99m labeled chemical selected from the group consisting of sestamibi and teboroxime; and
(c) radioimaging a heart of the subject, thereby radioimaging a myocardial ischemia.

According to further features in preferred embodiments of the invention described below, the method comprises at least one or more of the following:
(1) step (b) is effected about 48 hours following step (a); and
(2) step (c) is for about 30 minutes;
(3) step (c) is effected immediately following step (b).

According to still further features in the described preferred embodiments the method is effected as described in Table 69.

According to still a further aspect of the present invention there is provided a method of radioimaging a pathological condition or a fever of unknown origin, the method comprising in sequence:
(a) administering to a subject about 2 mCi In111 WBC;
(b) administering to the subject about 15 mCi 99m Fanoselomab; and
(c) radioimaging a body of the subject, thereby radioimaging a pathological condition or a fever of unknown origin.

According to further features in preferred embodiments of the invention described below, the method comprises at least one or more of the following:
(1) step (b) is effected about 24 hours following step (a); and
(2) step (c) is for about 30 minutes.
(3) step (c) is effected immediately following step (b).

According to still further features in the described preferred embodiments the method is effected as described in Table 70.

According to still a further aspect of the present invention there is provided a method of radioimaging to indicate schizophrenia or Parkinson's disease, the method comprising in sequence:
(a) administering to a subject about 2 mCi I123 IBZM;
(b) administering to the subject about 15 mCi Tc99m HMPAO; and
(c) radioimaging a brain of the subject, thereby radioimaging to indicate schizophrenia or Parkinson's disease.

According to further features in preferred embodiments of the invention described below, the method comprises at least one or more of the following:
(1) step (b) is effected about 24 hours following step (a); and
(2) step (c) is for about 30 minutes.
(3) step (c) is effected immediately following step (b).

According to still further features in the described preferred embodiments the method is effected as described in Table 71.

According to still a further aspect of the present invention there is provided a method of radioimaging a tumor, a tumor perfusion and/or for differentiating a tumor from infection the method comprising in sequence:
(a) administering to a subject about 2 mCi In111 WBC;
(b) administering to the subject Tc99m sestamibi, Tc99m ArcitumoMab and Tl201 thallous chloride; and
(c) radioimaging an organ and/or a body of the subject, thereby radioimaging for identifying a tumor.

According to further features in preferred embodiments of the invention described below, the method comprises at least one or more of the following:
(1) step (b) is effected about 24 hours following step (a);
(2) step (c) is for about 30 minutes;
(3) step (c) is effected about 5 minutes following step (b);
(4) a dose of Tc99m sestamibi and Tc99m Arcitumo Mab is each about 10 mCi; and
(5) a dose of Tl201 thallous chloride is about 1 mCi.

According to still further features in the described preferred embodiments the method is effected as described in Table 72.

According to still a further aspect of the present invention there is provided a method of radioimaging a renal function, the method comprising in sequence:
(a) administering to a subject about 2 mCi Iln111 DTPA;
(b) administering to the subject about 15 mCi Tc99m MAG3; and
(c) radioimaging a kidney of the subject, thereby radioimaging a renal function.

According to further features in preferred embodiments of the invention described below, the method comprises at least one or more of the following:
(1) step (b) is effected about 24 hours following step (a);
(2) step (c) is for about 30 minutes;
(3) step (c) is effected about 5 minutes following step (b);

According to still further features in the described preferred embodiments the method is effected as described in Table 73.

According to still a further aspect of the present invention there is provided a method of radioimaging a tumor perfusion, the method comprising in sequence:
(a) administering to a subject about 1 mCi Tl thallous chloride;
(b) administering to the subject about 15 mCi Tc99m teboroxime or about 15 mCi Tc99m sestamibi; and
(c) radioimaging an organ of the subject, thereby radioimaging a tumor perfusion.

According to further features in preferred embodiments of the invention described below, the method comprises at least one or more of the following:
(1) step (b) is effected simultaneously with step (a);
(2) step (c) is for about 30 minutes;
(3) step (c) is effected immediately following step (b);

According to still further features in the described preferred embodiments the method is effected as described in Table 74.

According to still a further aspect of the present invention there is provided a method of radioimaging a myocardial perfusion and apoptosis in blood vessel plaque, the method comprising in sequence:
(a) administering to a subject about 1 mCi Tl thallous chloride;
(b) administering to the subject about 15 mCi Tc99m Annexin; and
(c) radioimaging a heart and blood vessels of the subject, thereby radioimaging a myocardial perfusion and apoptosis in blood vessel plaque.

According to further features in preferred embodiments of the invention described below, the method comprises at least one or more of the following:
(1) step (b) is effected simultaneously with step (a);
(2) step (c) is for about 30 minutes;
(3) step (c) is effected less than about 1 hour following step (b);

According to still further features in the described preferred embodiments the method is effected as described in Table 75.

According to still a further aspect of the present invention there is provided a method of radioimaging to differentiate between infection and bone marrow activation, the method comprising in sequence:
(a) administering to a subject about 2 mCi ln111 WBC;
(b) administering to the subject about 15 mCi Tc99m sulfur colloid; and
(c) radioimaging a body of the subject, thereby radioimaging a tumor perfusion.

According to further features in preferred embodiments of the invention described below, the method comprises at least one or more of the following:
(1) step (b) is effected about 24 hours following step (a);
(2) step (c) is for about 30 minutes;
(3) step (c) is effected immediately following step (b);

According to still further features in the described preferred embodiments the method is effected as described in Table 76.

According to still a further aspect of the present invention there is provided a method of radioimaging an osteomyelitis, the method comprising in sequence:
(a) administering to a subject about 2 mCi ln111WBC;
(b) administering to the subject about 15 mCi Tc99m MDP; and
(c) radioimaging a bone of the subject, thereby radioimaging an osteomyelitis.

According to further features in preferred embodiments of the invention described below, the method comprises at least one or more of the following:
(1) step (b) is effected about 24 hours following step (a);
(2) step (c) is for about 30 minutes;
(3) step (c) is effected immediately following step (b);

According to still further features in the described preferred embodiments the method is effected as described in Table 77.

According to still a further aspect of the present invention there is provided a method of radioimaging an inflammation, the method comprising in sequence:
(a) administering to a subject about 5 mCi Gallium 67;
(b) administering to the subject about 15 mCi ln111WBCs; and
(c) radioimaging a body of the subject, thereby radioimaging an inflammation.

According to further features in preferred embodiments of the invention described below, the method comprises at least one or more of the following:
(1) step (b) is effected simultaneously with step (a);
(2) step (c) is for about 30 minutes; and
(3) step (c) is effected about 72 hours following step (b).

According to still further features in the described preferred embodiments the method is effected as described in Table 78.

According to still a further aspect of the present invention there is provided a method of radioimaging a myocardial perfusion and apoptosis in blood vessel plaque, the method comprising in sequence:
(a) administering to a subject about 2 mCi ln111 annexin;
(b) administering to the subject about 15 mCi Tc99m teboroxime or about 2 mCi Tl201 thallous chloride; and
(c) radioimaging a heart of the subject, thereby radioimaging a myocardial perfusion and apoptosis in blood vessel plaque.

According to further features in preferred embodiments of the invention described below, the method comprises at least one or more of the following:
(1) step (b) is effected about 24 hours following step (a);
(2) step (c) is for about 30 minutes;
(3) step (c) is effected no more than about 3 minutes following step (b);

According to still further features in the described preferred embodiments the method is effected as described in Table 79.

According to still a further aspect of the present invention there is provided a method of radioimaging a myocardial perfusion, the method comprising in sequence:

(a) administering to a subject about 2 mCi Tl201 thallous chloride;

(b) administering to the subject about 15 mCi Tc99m pyrophosphate; and (c) radioimaging a heart of the subject, thereby radioimaging a myocardial infusion.

According to further features in preferred embodiments of the invention described below, the method comprises at least one or more of the following:

(1) step (b) is effected simultaneously with step (a);

(2) step (c) is for about 30 minutes; and (3) step (c) is effected about 1 hour following step (b).

According to still further features in the described preferred embodiments the method is effected as described in Table 80.

A method of radioimaging a myocardial perfusion, the method comprising simultaneously:

(a) radioimaging a heart of the subject; and (b) administering to a subject about 15 mCi of Tc99m pyrophsophate and about 2 mCi of Tl 201 thallous chloride, thereby radioimaging a myocardial perfusion.

According to further features in preferred embodiments of the invention described below, step (a) is for about 30 minutes.

According to still further features in the described preferred embodiments the method is effected as described in Table 81.

According to still a further aspect of the present invention there is provided a method of radioimaging a myocardial perfusion or cardiac vulnerable plaque, the method comprising simultaneously:

(a) administering to a subject about 5 mCi In111 annexin;

(b) administering to the subject about 5 mCi Tc99m Accutec;

(c) subjecting the subject to a pharmacological stress;

(d) administering to the subject about 1 mCi Tl201 thallous chloride; and (e) radioimaging a heart and blood vessels of the subject, thereby radioimaging a myocardial perfusion or cardiac vulnerable plaque.

According to further features in preferred embodiments of the invention described below, the method comprises at least one or more of the following:

(1) step (b) is effected about 24 hours following step (a);

(2) step (c) is effected immediately following step (b);

(3) the pharmacological stress is adenosine or dipyridamole;

(4) step (d) is effected about 2 minutes following step (c);

(5) step (e) is for about 30 minutes.

According to still further features in the described preferred embodiments the method is effected as described in Table 82.

According to still a further aspect of the present invention there is provided a method of radioimaging a glucose metabolism, the method comprising simultaneously:

(a) administering to a subject about 30-50 mCi FDG; and (b) radioimaging a body of the subject, thereby radioimaging a glucose metabolism.

According to further features in preferred embodiments of the invention described below, the method comprises at least one or more of the following:

(1) step (b) is effected immediately following step (a); and (2) step (b) is for less than about 30 minutes.

According to still further features in the described preferred embodiments the method is effected as described in Table 83.

According to further features in preferred embodiments of the invention described below the imaging is effected using a camera which comprises:

(i) at least one radioactive-emission detector designed and constructed to image radioactive emission from the tissue or body;

(ii) a position-tracking device communicating with the at least one radioactive-emission detector and configured to provide positional information for the at least one radioactive-emission; and (iii) a data processor, designed and configured for receiving data inputs from the position tracking device and the at least one radioactive-emission detector, and for generating an image of the tissue or body.

According to still another aspect of the present invention there is provided a method of packaging a radiopharmaceutical selected from the group consisting of Tl201 thallous chloride, Tc99m sestamibi, Tc 99m Teboroxime, Tc 99m DTPA, MAA, Tc 99m MDP, In 111 WBC, Tc 99m exametazine (HMPAO), Tc 99m ECD, I 123 isofetamine hydrochloride, I 123 isofetamine hydrochloride, Tc 99m mebrofenin, DTPA In 111, tetrofosmin, Tc 99m MAG3, Hippuran I-123, neurolite, Tc 99m sulfur colloid, Tc 99m disida, Tc99m Annexin, Tc99m AccuTec, Prostascint containing 111 In DTPA, Octreotide containing 111 In DTPA, Tc 99m neotec, MIBG containing I 123 iofetamine hydrochloride, Tc 99m pertechnetate, I 123, Tc 99m MDP, In 111 capromab pentitide, Tc 99m RBC, I 123 BMIPP, Tc 99m Fanoselomab, I 123 IBZM, Tc 99m ArcitumoMab, Gallium 67, Tc 99m pyrophosphate, In 111 annexin, F-18-Fluorodeoxyglucose (FDG), F-18-Fluoromisonidazole, F-18-3'-Fluoro-3'-deoxythymidine (FLT), F-18-Fluoromethyl choline (FCH), F-18-4-Fluoro-m-tyrosine (FMT), F-18-6-Fluoro-L-DOPA, F-18-FP-β-CIT, F-18-Pencyclovir (FHBG), F-18-Fluoroestradiol (FES), C-11-Methionine, Tc-99m-P280, Acutect®, C-11-Raclopride, I-123-iodobenzamide (IBZM), C-11-carfentanil, C-11-α-methyl-L-tryptophan, C-115-Hydroxytryptophan, F-18-MPPF, F-18-Altanserin, C-11-Acetate, C-11-Palmitate and F-18-Fluorodopamine, the method comprising packaging the radiopharmaceutical in a package and providing in association with the package in printed and/or electronic form instruction of use according to any of the methods of the preceding claims.

According to yet another aspect of the present invention there is provided an article of manufacturing produced according to the above packaging method.

According to yet another aspect of the present invention there is provided a diagnostic pharmaceutical kit comprising a packaged dose unit of a diagnostic radiopharmaceutical having a dose equivalent of 2.5 mrem or less per kg body weight.

According to yet another aspect of the present invention there is provided a packaged dose unit has a dose equivalent of 2 mrem or less per kg body weight.

According to further features in preferred embodiments of the invention described below packaged dose unit has a dose equivalent of 1 mrem or less per kg body weight.

According to yet another aspect of the present invention there is provided a packaged dose unit of diagnostic radiopharmaceutical having a dose equivalent of 150 mrem or less.

According to further features in preferred embodiments of the invention described below the diagnostic radiopharmaceutical is a radiotracer.

According to further features in preferred embodiments of the invention described below a radioisotope and a recognition binding moiety of the radiotracer are packaged in individual containers.

According to further features in preferred embodiments of the invention described below a purity of a radioisotope of the diagnostic radiopharmaceutical is at least 60%.

According to further features in preferred embodiments of the invention described below a purity of a radioisotope of the diagnostic radiopharmaceutical is at least 90%.

According to further features in preferred embodiments of the invention described below the diagnostic radiopharmaceutical is $^{13}$N-Ammonia and whereas the packaged dose unit comprises 0.01-5 mCi.

According to further features in preferred embodiments of the invention described below the diagnostic radiopharmaceutical is $^{18}$F-Fludeoxyglucose and whereas the packaged dose unit comprises 0.1-3 mCi.

According to further features in preferred embodiments of the invention described below the diagnostic radiopharmaceutical is $^{18}$F-Sodium Fluoride and whereas the packaged dose unit comprises 0.1-3 mCi.

According to further features in preferred embodiments of the invention described below the diagnostic radiopharmaceutical is $^{81m}$Kr-Krypton and whereas the packaged dose unit comprises 0.05-2 mCi.

According to further features in preferred embodiments of the invention described below the diagnostic radiopharmaceutical is $^{111}$In-Indium Capromab pendetide and whereas the packaged dose unit comprises 0.01-2 mCi.

According to further features in preferred embodiments of the invention described below the diagnostic radiopharmaceutical is $^{99m}$Tc-Technetium Arcitumomab and whereas the packaged dose unit comprises 0.05-5 mCi.

According to further features in preferred embodiments of the invention described below the diagnostic radiopharmaceutical is $^{111}$In-Indium Pentetreotide and whereas the packaged dose unit comprises 0.005-1 mCi.

According to further features in preferred embodiments of the invention described below the diagnostic radiopharmaceutical is $^{125}$I-Iodide Albumin and whereas the packaged dose unit comprises 0.0005-0.005 mCi.

According to further features in preferred embodiments of the invention described below the diagnostic radiopharmaceutical is $^{51}$Cr-Sodium Chromate and whereas the packaged dose unit comprises 0.001-0.05 mCi.

According to further features in preferred embodiments of the invention described below the diagnostic radiopharmaceutical is $^{99m}$Tc-Technetium Disofenin and whereas the packaged dose unit comprises 0.005-1 mCi.

According to further features in preferred embodiments of the invention described below the diagnostic radiopharmaceutical is $^{99m}$Tc-Technetium Sestamibi and whereas the packaged dose unit comprises 0.01-5 mCi.

According to yet another aspect of the present invention there is provided a composition of matter comprising a low dose of at least one radiopharmaceutical intended for administration in whole to a human subject of a particular age and/or weight.

According to further features in preferred embodiments of the invention described below the low dose is a dose below the maximal dose allowable to be administered to the human subject of the particular age and/or weight.

According to further features in preferred embodiments of the invention described below the maximal dose is the lower of 5 REM and a dose that following administration and distribution in a body of the subject does note accumulate in any specific organ in the body in excess of 15 Rads.

According to further features in preferred embodiments of the invention described below the radiopharmaceutical is selected from the group consisting of [18F]Fluorodeoxyglucose (FDG), [18F]-Fluoromisonidazole, [18F]3'-Fluoro-3'-deoxythymidine (FLT), [18F]Fluoromethyl choline (FCH), [18F]4-Fluoro-m-tyrosie (FMT), [18F]6-Fluoro-L-DOPA, [18F]FP-βCIT, [18F]Pencyclovir (FHBG), [18F]Fluoroestradiol (FES), [11C]Methionine, 111In-Pentetreotide, 99mTc-P829, 99mTc-P280, 123I-VIP (vasoactive intestinal peptide), 131I-NP-59, [11C]Raclopride, 123I-IBZM, [11C]Carfentanil, [11C]α-methyl-L-tryptophan, [11C]5-Hydroxytryptophan, [18F]MPPF, [18F]Altanserin, [11C]Acetate, [11C]Palmitate, [18F]Fluorodopamine, $^3$H-water, $^3$H-inulin, $^{11}$C-carbonmonoxide, $^{13}$N-ammonia, $^{14}$C-inulin, $^{15}$O—H$_2$O, $^{15}$O—O$_2$, $^{18}$F-fluorodeoxyglucose, $^{18}$F-sodium fluoride, $^{51}$Cr-erythrocytes (RBC), $^{57}$Co-vitamin B$_{12}$ (cyanocobalamin), $^{58}$Co-vitamin B$_{12}$ (cyanocobalamin), $^{59}$Fe-citrate, $^{60}$Co-vitamin B$_{12}$ (cyanocobalamin), $^{67}$Ga-citrate, $^{68}$Ga-citrate, $^{75}$Se-selenomethionine, $^{81m}$Kr-krypton for inhalation, oral administration or injections, $^{82}$Rb, $^{85}$Sr-nitrate, $^{90}$Y/$^{111}$In-ibritumomab tiuxetan ($^{90}$Y/$^{111}$In-Zevalin), $^{99m}$Tc-albumin microspheres, $^{99m}$Tc-disofenin, lidofenin and mebrofenin, $^{99m}$Tc-DMSA, $^{99m}$Tc-DTPA (injection), $^{99m}$Tc-DTPA (aerosol), $^{99m}$Tc-ECD (ethylene cystate dimer), $^{99m}$Tc-exametazime (HMPAO), $^{99m}$Tc-glucoheptonate, $^{99m}$Tc-HEDP, $^{99m}$Tc-HMDP, $^{99m}$Tc-HSA, $^{99m}$Tc-MAA, $^{99m}$Tc-MAG$_3$, $^{99m}$Tc-MDP, $^{99m}$Tc-tetrofosmin, $^{99m}$Tc-sestamibi, $^{99m}$Tc-oral administrations, $^{99m}$Tc-pertechnetate, $^{99m}$Tc-pyrophosphate, $^{99m}$Tc-RBC in vitro and in vivo labeling, $^{99m}$Tc-sulfur colloid, $^{99m}$Tc-teboroxime, $^{99m}$Tc-white blood cells, $^{111}$In-ibritumomab tiuxetan ($^{111}$In-Zevalin), $^{111}$In-DTPA, $^{111}$In-platelets, $^{111}$In-RBC, $^{111}$In-white blood cells, $^{123}$I-hippuran, $^{123}$I-IMP, $^{123}$I-mIBG, $^{123}$I-sodium iodide, $^{124}$I-sodium iodide, $^{125}$I-fibrinogen, $^{121}$I-IMP, $^{125}$I-mIBG, $^{125}$I-sodium iodide, $^{126}$I-sodium iodide, $^{130}$I-sodium iodide, $^{131}$I-hippuran, $^{131}$I-HSA, $^{131}$I-MAA, $^{131}$I-mIBG, $^{131}$I-Rose Bengal, $^{131}$I-sodium iodide, $^{127}$Xe-inhalation and injection, $^{133}$Xe-inhalation and injection, $^{197}$Hg-chlormerodrin, $^{198}$Au-colloid and $^{201}$Tl-chloride, Cu-62, Ga-68, Indium-111 Capromab pendetide, Indium In-111 Satumomab Pendetide, Technetium Tc 99m Arcitumomab (CEA-Scan), Technetium Tc 99m Fanolesomab, Technetium Tc 99m Nofetumomab Merpentan, Indium In 111 Oxyquinoline, Indium In 111 Pentetate, Indium In 111 Pentetreotide, Iobenguane, Radioiodinated, Iofetamine1 123, Iothalamate Sodium I 125, Iodide 125 Albumin, Radioiodinated Albumin, SodiumChromate Cr 51, (Sodium) Pertechnetate Tc 99m, Technetium Tc 99m Depreotide, Technetium Tc 99m Apcitide, TechnetiumTc 99m Bicisate, Technetium Tc 99m Disofenin (HIDA), Chromic Phosphate, SR 89 Chloride (Metastron), Technetium Tc 99m Oxidronate, Technetium Tc 99m (Pyro- and trimeta-) Phosphates, Technetium Tc 99m Sulfur Colloid, Technetium Tc 99m HDP, Technetium Tc 99m Sulpher colloid and radiopharmaceuticals which comprise an idsotope selected from the group consisting of $^{198}$Au, $^{11}$C, $^{14}$C, $^{51}$Cr, $^{57}$Co, $^{58}$Co, $^{60}$Co, $^{62}$Cu $^{18}$F, $^{59}$Fe, $^{67}$Ga, $^{68}$Ga, $^3$H, $^{153}$Sm, $^{197}$Hg, $^{111}$I, $^{123}$I, $^{124}$I, $^{125}$I, $^{126}$I, $^{131}$I, $^{131}$I, $^{133}$I, $^{111}$In, $^{81}$Kr, $^{127}$Xe, $^{133}$Xe, $^{67}$Cu, $^{177}$Lu, $^{13}$N, $^{15}$O, $^{82}$Rb, $^{117m}$Sn, $^{85}$Sr, $^{89}$Sr $^{52}$Fe, $^{113m}$In, $^{99m}$Tc, $^{201}$Tl.

According to further features in preferred embodiments of the invention described below the low dose is selected from the group consisting of:
(i) less than 90% of the maximal dose;
(ii) less than 85% of the maximal dose;
(iii) less than 80% of the maximal dose;

(iv) less than 75% of the maximal dose;
(v) less than 70% of the maximal dose;
(vi) less than 65% of the maximal dose;
(vii) less than 60% of the maximal dose;
(viii) less than 55% of the maximal dose;
(ix) less than 50% of the maximal dose;
(x) less than 45% of the maximal dose;
(xi) less than 40% of the maximal dose;
(xii) less than 35% of the maximal dose;
(xiii) less than 30% of the maximal dose;
(xiv) less than 25% of the maximal dose;
(xv) less than 20% of the maximal dose;
(xvi) less than 15% of the maximal dose;
(xvii) less than 10% of the maximal dose;
(xviii) less than 9% of the maximal dose;
(xix) less than 8% of the maximal dose;
(xx) less than 7% of the maximal dose;
(xxi) less than 6% of the maximal dose;
(xxii) less than 5% of the maximal dose;
(xxiii) less than 4% of the maximal dose;
(xxiv) less than 3% of the maximal dose;
(xxv) less than 2% of the maximal dose;
(xxvi) less than 1% of the maximal dose;
(xxvii) less than 0.9% of the maximal dose;
(xxviii) less than 0.8% of the maximal dose;
(xxix) less than 0.7% of the maximal dose;
(xxx) less than 0.6% of the maximal dose;
(xxxi) less than 0.5% of the maximal dose;
(xxxii) less than 0.4% of the maximal dose;
(xxxiii) less than 0.3% of the maximal dose;
(xxxiv) less than 0.2% of the maximal dose;
(xxxv) less than 0.1% of the maximal dose;
(xxxvi) less than 0.05% of the maximal dose; or
(xxxvii) less than 0.01% of the maximal dose;

According to yet another aspect of the present invention there is provided a method of radioimaging a region of interest in a subject, the method comprising:
(a) administering to the subject the low dose composition of matter as described hereinabove; and
(b) using a high sensitivity radioactive-emission camera for collecting radioactive-emission data from the subject, thereby radioimaging the region of interest in the subject.

According to further features in preferred embodiments of the invention described below the high sensitivity is selected from the group consisting of:
(a) sensitivity in terms of speed of data collection and spatial resolution, at least as good as a gold standard for PET imaging for at rest myocardial perfusion with N-13-ammonia ($NH_3$), at a dose of 740 MBq with attenuation correction;
(b) sensitivity sufficient for reconstructing an image under a Cobalt wire Nema test of a line source of 5 mCi cobalt with a line spread function of less than 7 mm Full Width Half Maximum (FWHM) through air at a distance of at least 100 mm;
(c) sensitivity sufficient for resolving through air at a distance of at least 100 mm under a Nema Bar Phantom test of gaps formed between 1 mm wide led bars positioned less than 7 mm apart from one another over a uniform cobalt disc;
(d) sensitivity operative for image acquisition of a full organ in less than 10 seconds at a spatial resolution, capable of identifying objects not greater than about 7 mm×7 mm×7 mm with a signal-to-noise ratio of at least 4 to 1 or better; and/or
(e) sensitivity allowing aquizition of at least 1 out of every 5000 emitted photons while allowing a reconstructions of a 3D image with a resolution of not more than 5 mm and energy resolution of not more than 15%.

According to further features in preferred embodiments of the invention described below the sensitivity is selected from the group consisting of:
at least 2 fold that of the gold standard for PET imaging;
at least 3 fold that of the gold standard for PET imaging;
at least 4 fold that of the gold standard for PET imaging;
at least 5 fold that of the gold standard for PET imaging;
at least 6 fold that of the gold standard for PET imaging;
at least 7 fold that of the gold standard for PET imaging;
at least 8 fold that of the gold standard for PET imaging;
at least 9 fold that of the gold standard for PET imaging;
at least 10 fold that of the gold standard for PET imaging;
at least 20 fold that of the gold standard for PET imaging;
at least 30 fold that of the gold standard for PET imaging;
at least 50 fold that of the gold standard for PET imaging;
at least 100 fold that of the gold standard for PET imaging;
sufficient for reconstructing an image under a Cobalt wire Nema test of the line source of 5 mCi cobalt with a line spread function of less than 6 mm Full Width Half Maximum (FWHM) through air at the distance of at least 100 mm;
sufficient for reconstructing an image under a Cobalt wire Nema test of the line source of 5 mCi cobalt with a line spread function of less than 5 mm Full Width Half Maximum (FWHM) through air at the distance of at least 100 mm;
sufficient for reconstructing an image under a Cobalt wire Nema test of the line source of 5 mCi cobalt with a line spread function of less than 4 mm Full Width Half Maximum (FWHM) through air at the distance of at least 100 mm;
sufficient for reconstructing an image under a Cobalt wire Nema test of the line source of 5 mCi cobalt with a line spread function of less than 3 mm Full Width Half Maximum (FWHM) through air at the distance of at least 100 mm;
sufficient for reconstructing an image under a Cobalt wire Nema test of the line source of 5 mCi cobalt with a line spread function of less than 2 mm Full Width Half Maximum (FWHM) through air at the distance of at least 100 mm;
sufficient for reconstructing an image under a Cobalt wire Nema test of the line source of 5 mCi cobalt with a line spread function of about 1 mm Full Width Half Maximum (FWHM) through air at the distance of at least 100 mm;
sufficient for resolving through air at the distance of at least 100 mm under the Nema Bar Phantom test of the gaps formed between the 1 mm wide led bars positioned less than 6 mm apart from one another over the uniform cobalt disc;
sufficient for resolving through air at the distance of at least 100 mm under the Nema Bar Phantom test of the gaps formed between the 1 mm wide led bars positioned less than 5 mm apart from one another over the uniform cobalt disc;
sufficient for resolving through air at the distance of at least 100 mm under the Nema Bar Phantom test of the gaps formed between the 1 mm wide led bars positioned less than 4 mm apart from one another over the uniform cobalt disc;
sufficient for resolving through air at the distance of at least 100 mm under the Nema Bar Phantom test of the gaps formed between the 1 mm wide led bars positioned less than 3 mm apart from one another over the uniform cobalt disc;
sufficient for resolving through air at the distance of at least 100 mm under the Nema Bar Phantom test of the gaps formed between the 1 mm wide led bars positioned less than 2 mm apart from one another over the uniform cobalt disc;
sufficient for resolving through air at the distance of at least 100 mm under the Nema Bar Phantom test of the gaps formed between the 1 mm wide led bars positioned less than 1 mm apart from one another over the uniform cobalt disc;
sufficient for resolving through air at the distance of at least 100 mm under the Nema Bar Phantom test of the gaps formed between the 1 mm wide led bars positioned less than 0.5 mm apart from one another over the uniform cobalt disc;

sufficient for resolving through air at the distance of at least 100 mm under the Nema Bar Phantom test of the gaps formed between the 1 mm wide led bars positioned less than 0.1 mm apart from one another over the uniform cobalt disc;

operative for image acquisition of the full organ in less than 10 seconds at the spatial resolution, capable of identifying objects not greater than about 6 mm×6 mm×6 mm with the signal-to-noise ratio of at least 4 to 1 or better;

operative for image acquisition of the full organ in less than 10 seconds at the spatial resolution, capable of identifying objects not greater than about 5 mm×5 mm×5 mm with the signal-to-noise ratio of at least 4 to 1 or better;

operative for image acquisition of the full organ in less than 10 seconds at the spatial resolution, capable of identifying objects not greater than about 4 mm×4 mm×4 mm with the signal-to-noise ratio of at least 4 to 1 or better;

operative for image acquisition of the full organ in less than 10 seconds at the spatial resolution, capable of identifying objects not greater than about 3 mm×3 mm×3 mm with the signal-to-noise ratio of at least 4 to 1 or better;

operative for image acquisition of the full organ in less than 10 seconds at the spatial resolution, capable of identifying objects not greater than about 2 mm×2 mm×2 mm with the signal-to-noise ratio of at least 4 to 1 or better;

operative for image acquisition of the full organ in less than 10 seconds at the spatial resolution, capable of identifying objects not greater than about 1 mm×1 mm×1 mm with the signal-to-noise ratio of at least 4 to 1 or better;

operative for image acquisition of the full organ in less than 10 seconds at the spatial resolution, capable of identifying objects not greater than about 0.5 mm×0.5 mm×0.5 mm with the signal-to-noise ratio of at least 4 to 1 or better; and/or operative for image acquisition of the full organ in less than 10 seconds at the spatial resolution, capable of identifying objects not greater than about 0.1 mm×0.1 mm×0.1 mm with the signal-to-noise ratio of at least 4 to 1 or better.

According to yet another aspect of the present invention there is provided a method of packaging the low dose composition-of matter as described hereinabove, the method comprising placing the low dose of the at least one radiopharmaceutical intended for the administration in whole to the human subject of the particular age and/or weight in a container or a syringe.

According to yet another aspect of the present invention there is provided a method of manufacturing the low dose composition-of matter as described hereinabove, the method comprising generating the at least one radiopharmaceutical and collecting the at least one radiopharmaceutical at a time needed for having the low dose.

According to yet another aspect of the present invention there is provided a method of radioimaging comprising:

(a) administering to a human subject a low dose of a first radiopharmaceutical; and (b) acquiring data representing a distribution of the first radiopharmaceutical in at least a section of the body of the subject during at least one time window.

According to yet another aspect of the present invention there is provided a method of radioimaging comprising:

(a) administering to a human subject a low dose of a first radiopharmaceutical; and (b) acquiring data representing a distribution of the first radiopharmaceutical in at least a section of the body of the subject during at least one short time window.

According to further features in preferred embodiments of the invention described below the section of a body comprises the heart.

According to further features in preferred embodiments of the invention described below the method further comprises:

(c) subjecting the human subject to stress following the administering of the first radiopharmaceutical; and (d) administering to the human subject a dose of at least a second radiopharmaceutical, prior to acquiring the data.

According to further features in preferred embodiments of the invention described below the method further comprises acquiring from the subject data representing a distribution of the first radiopharmaceutical in the subject during at least one short time window prior to subjecting the human subject to the stress.

According to further features in preferred embodiments of the invention described below the first radiopharmaceutical comprises thallium-201 at a dose of about 3 mCi.

According to further features in preferred embodiments of the invention described below the first radiopharmaceutical comprises technetium-99m-methoxyisobutylisonitrile (sestamibi).

According to further features in preferred embodiments of the invention described below the second radiopharmaceutical comprises technetium-99m-methoxyisobutylisonitrile (sestamibi) at a dose of from about 20 to about 30 mCi.

According to further features in preferred embodiments of the invention described below the second radiopharmaceutical comprises thallium-201 at a dose of about 3 mCi.

According to further features in preferred embodiments of the invention described below the first radiopharmaceutical comprises technetium-99m-methoxyisobutylisonitrile (sestamibi) at a dose of from about 8 to about 10 mCi.

According to further features in preferred embodiments of the invention described below the first radiopharmaceutical comprises technetium-99m-methoxyisobutylisonitrile (sestamibi) at a dose of about 3 mCi.

According to further features in preferred embodiments of the invention described below the short time window is not greater than about 6 minutes.

According to further features in preferred embodiments of the invention described below the first radiopharmaceutical comprises thallium-201 at a dose of about 3 mCi and the short window time is not greater than about 4 minutes.

According to further features in preferred embodiments of the invention described below the first radiopharmaceutical comprises thallium-201 at a dose of about 3 mCi, the second radiopharmaceutical comprises technetium-99m-methoxyisobutylisonitrile (sestamibi) at a dose of from about 20 to about 30 mCi and the short time window is not greater than about 4 minutes.

According to further features in preferred embodiments of the invention described below the data representing a distribution of the first radiopharmaceutical in the subject is acquired during a short time window of up to about 2 minutes.

According to further features in preferred embodiments of the invention described below the data representing a distribution of the second radiopharmaceutical in the subject is acquired during a short time window of up to about 2 minutes.

According to further features in preferred embodiments of the invention described below a time period of from about 10 to about 15 minutes is allowed to elapse between the administering of the first radiopharmaceutical and the acquiring of data representing a distribution of the first pharmaceutical.

According to further features in preferred embodiments of the invention described below a time period from about 30 to about 60 minutes is allowed to elapse between the administering of the second radiopharmaceutical and the acquiring of data representing a distribution of the second pharmaceutical.

According to further features in preferred embodiments of the invention described below a time period of from about 2 minutes is allowed to elapse between the administering of the first radiopharmaceutical and the acquiring of data representing a distribution of the first pharmaceutical.

According to further features in preferred embodiments of the invention described below the acquiring of data representing a distribution of the second pharmaceutical is performed immediately following administering of the second radiopharmaceutical.

According to further features in preferred embodiments of the invention described below the stress comprises exercise stress.

According to further features in preferred embodiments of the invention described below the stress comprises pharmacological stress.

According to further features in preferred embodiments of the invention described below the first radiopharmaceutical comprises technetium-99m-methoxyisobutylisonitrile (sestamibi) at a dose of from about 8 to about 10 mCi, the second radiopharmaceutical comprises technetium-99m-methoxyisobutylisonitrile (sestamibi) at a dose of from about 20 to about 30 mCi and the short time window is not greater than about 4 minutes.

According to further features in preferred embodiments of the invention described below the data representing a distribution of the first radiopharmaceutical in the subject is acquired during a short time window of up to about 2 minutes.

According to further features in preferred embodiments of the invention described below the data representing a distribution of the second radiopharmaceutical in the subject is acquired during a short time window of up to about 2 minutes.

According to further features in preferred embodiments of the invention described below a time period of about 30 minutes is allowed to elapse between the administering of the first radiopharmaceutical and the acquiring of data representing a distribution of the first pharmaceutical.

According to further features in preferred embodiments of the invention described below a time period from about 30 to about 60 minutes is allowed to elapse between the administering of the second radiopharmaceutical and the acquiring of data representing a distribution of the second pharmaceutical.

According to further features in preferred embodiments of the invention described below the stress comprises exercise stress.

According to further features in preferred embodiments of the invention described below the acquiring of data representing a distribution of the first pharmaceutical is performed immediately following administering of the first radiopharmaceutical.

According to further features in preferred embodiments of the invention described below the acquiring of data representing a distribution of the second pharmaceutical is performed immediately following administering of the second radiopharmaceutical.

According to further features in preferred embodiments of the invention described below the stress comprises pharmacological stress.

According to further features in preferred embodiments of the invention described below the first radiopharmaceutical comprises technetium-99m-methoxyisobutylisonitrile (sestamibi) at a dose of about 3 mCi, the second radiopharmaceutical comprises thallium-201 at a dose of about 3 mCi, and the short time window is not greater than about 6 minutes.

According to further features in preferred embodiments of the invention described below the data representing a distribution of the first radiopharmaceutical in the subject is acquired during a short time window of up to about 2 minutes.

According to further features in preferred embodiments of the invention described below the data representing a distribution of the second radiopharmaceutical in the subject is acquired during a short time window of up to about 4 minutes.

According to further features in preferred embodiments of the invention described below a time period of about 30 minutes is allowed to elapse between the administering of the first radiopharmaceutical and the acquiring of data representing a distribution of the first pharmaceutical.

According to further features in preferred embodiments of the invention described below a time period from about 10 to about 15 minutes is allowed to elapse between the administering of the second radiopharmaceutical and the acquiring of data representing a distribution of the second pharmaceutical.

According to further features in preferred embodiments of the invention described below the stress comprises exercise stress.

According to further features in preferred embodiments of the invention described below the acquiring of data representing a distribution of the second pharmaceutical is performed immediately following administering of the second radiopharmaceutical.

According to further features in preferred embodiments of the invention described below the stress comprises pharmacological stress.

According to further features in preferred embodiments of the invention described below the acquiring of data representing a distribution of the first pharmaceutical is performed immediately following administering of the first radiopharmaceutical.

According to further features in preferred embodiments of the invention described below the acquiring of data representing a distribution of the second pharmaceutical is performed immediately following administering of the second radiopharmaceutical.

According to further features in preferred embodiments of the invention described below the stress comprises pharmacological stress.

According to further features in preferred embodiments of the invention described below the first radiopharmaceutical comprises thallium-201 at a dose of about 3 mCi, the second radiopharmaceutical comprises technetium-99m-methoxyisobutylisonitrile (sestamibi) at a dose of from about 20 to about 30 mCi, and the short time window is not greater than about 2 minutes.

According to further features in preferred embodiments of the invention described below the acquiring of data representing a distribution of the first radiopharmaceutical and the acquiring of data representing a distribution of second radiopharmaceutical are performed simultaneously.

According to further features in preferred embodiments of the invention described below a time period of from about 30 to about 60 minutes is allowed to elapse between the administering of the second radiopharmaceutical and the acquiring of data representing a distribution of the first and the second radiopharmaceuticals.

According to further features in preferred embodiments of the invention described below the stress comprises exercise stress.

According to further features in preferred embodiments of the invention described below the first radiopharmaceutical comprises technetium-99m-methoxyisobutylisonitrile (sestamibi) at a dose of about 3 mCi, the second radiopharmaceutical comprises thallium-201 at a dose of about 3 mCi, and the short time window is not greater than about 4 minutes.

According to further features in preferred embodiments of the invention described below the acquiring of data representing a distribution of the first radiopharmaceutical and the acquiring of data representing a distribution of second radiopharmaceutical are performed simultaneously.

According to further features in preferred embodiments of the invention described below a time period of from about 2 minutes is allowed to elapse between the administering of the second radiopharmaceutical and the acquiring of data representing a distribution of the first and the second radiopharmaceuticals.

According to further features in preferred embodiments of the invention described below the section of a body comprises the lung.

According to further features in preferred embodiments of the invention described below the first radiopharmaceutical comprises a combination of Tc-99m-diethylene triamine pentaacetate (DTPA), Tc-99m-macro-aggregated albumin, and iodine-123.

According to further features in preferred embodiments of the invention described below a concentration of the Tc-99m-macro-aggregated albumin is up to about 5 mCi.

According to further features in preferred embodiments of the invention described below the acquiring of data is performed immediately following administering of the first radiopharmaceutical.

According to further features in preferred embodiments of the invention described below the section of a body comprises the bones.

According to further features in preferred embodiments of the invention described below the first radiopharmaceutical comprises Tc-99m-disodium dihydrogen methylenediphosphate at a dose of from about 20 to about 30 mCi.

According to further features in preferred embodiments of the invention described below a time period of up to about 60 minutes is allowed to elapse between the administering of the radiopharmaceutical and the acquiring of data, and wherein, wherein the acquiring of data is performed at an energy window of from about 3 to about 15 percent.

According to further features in preferred embodiments of the invention described below the first radiopharmaceutical comprises technetium-99m-teboroxime at a dose of from about 8 to about 10 mCi, the second radiopharmaceutical comprises technetium-99m-teboroxime at a dose of from about 20 to about 30 mCi and the short time window is not greater than about 4 minutes.

According to further features in preferred embodiments of the invention described below the data representing a distribution of the first radiopharmaceutical in the subject is acquired during a short time window of up to about 2 minutes.

According to further features in preferred embodiments of the invention described below the data representing a distribution of the second radiopharmaceutical in the subject is acquired during a short time window of up to about 2 minutes.

According to further features in preferred embodiments of the invention described below the acquiring of data representing a distribution of the first pharmaceutical is performed immediately following administering of the first radiopharmaceutical.

According to further features in preferred embodiments of the invention described below a time period of about 10 minutes is allowed to elapse between the acquiring of data representing a distribution of the first pharmaceutical and the subjecting to the stress.

According to further features in preferred embodiments of the invention described below the acquiring of data representing a distribution of the second pharmaceutical is performed immediately following administering of the second radiopharmaceutical.

According to further features in preferred embodiments of the invention described below the stress comprises pharmacological stress.

According to further features in preferred embodiments of the invention described below the section of a body comprises the heart.

According to further features in preferred embodiments of the invention described below the method further comprises:

(c) subjecting the human subject to stress following the administering of the first radiopharmaceutical; and (d) administering to the human subject a low dose of at least a second radiopharmaceutical, prior to acquiring the data.

According to further features in preferred embodiments of the invention described below the method further comprises acquiring from the subject data representing a distribution of the first radiopharmaceutical in the subject during at least one time window prior to subjecting the human subject to the stress.

According to further features in preferred embodiments of the invention described below the first radiopharmaceutical comprises thallium-201 at a dose of about 0.3 mCi.

According to further features in preferred embodiments of the invention described below the first radiopharmaceutical comprises technetium-99m-methoxyisobutylisonitrile (sestamibi) at a dose about 0.3 mCi.

According to further features in preferred embodiments of the invention described below the second radiopharmaceutical comprises technetium-99m-methoxyisobutylisonitrile (sestamibi) at a dose about 3 mCi.

According to further features in preferred embodiments of the invention described below the second radiopharmaceutical comprises technetium-99m-methoxyisobutylisonitrile (sestamibi) at a dose about 30 mCi.

According to further features in preferred embodiments of the invention described below the data representing a distribution of the first radiopharmaceutical in the subject is acquired during a time window of about 15 minutes.

According to further features in preferred embodiments of the invention described below the data representing a distribution of the second radiopharmaceutical in the subject is acquired during a time window of about 15 minutes.

According to further features in preferred embodiments of the invention described below the first radiopharmaceutical comprises thallium-201 201 at a dose of about 0.3 mCi, and wherein the data representing a distribution of the second radiopharmaceutical in the subject is acquired during a time window of about 2 minutes According to further features in preferred embodiments of the invention described below a time period from about 30 to about 60 minutes is allowed to elapse between the administering of the second radiopharmaceutical and the acquiring of data representing a distribution of the second pharmaceutical.

According to further features in preferred embodiments of the invention described below the first radiopharmaceutical comprises thallium-201 at a dose of about 0.3 mCi, and wherein a time period from about 10 to about 15 minutes is allowed to elapse between the administering of the thallium-201 and the acquiring of data representing a distribution of the thallium-201.

According to further features in preferred embodiments of the invention described below the first radiopharmaceutical comprises technetium-99m-methoxyisobutylisonitrile (sestamibi) at a dose about 0.3 mCi, and wherein a time period from about 30 minutes is allowed to elapse between the administering of technetium-99m-methoxyisobutylisonitrile (sestamibi) and the acquiring of data representing a distribution of technetium-99m-methoxyisobutylisonitrile (sestamibi).

According to further features in preferred embodiments of the invention described below the stress comprises exercise stress.

According to further features in preferred embodiments of the invention described below the first radiopharmaceutical comprises thallium-201 at a dose of about 0.3 mCi, and wherein a time period of about 2 minutes is allowed to elapse between the administering of the thallium-201 and the acquiring of data representing a distribution of the thallium-201.

According to further features in preferred embodiments of the invention described below the first radiopharmaceutical comprises technetium-99m-methoxyisobutylisonitrile (sestamibi) at a dose about 0.3 mCi, and wherein the acquiring of data representing a distribution of the first radiopharmaceutical is performed immediately following administering of the first radiopharmaceutical.

According to further features in preferred embodiments of the invention described below the acquiring of data representing a distribution of the second radiopharmaceutical is performed immediately following administering of the second radiopharmaceutical.

According to further features in preferred embodiments of the invention described below the stress comprises pharmacological stress.

According to further features in preferred embodiments of the invention described below the first radiopharmaceutical comprises thallium-201 at a dose of about 0.3 mCi, the second radiopharmaceutical comprises technetium-99m-methoxyisobutylisonitrile (sestamibi) at a dose of from about 3 to about 5 mCi, and wherein the acquiring of data representing a distribution of the thallium-201 and the technetium-99m-methoxyisobutylisonitrile (sestamibi) is performed simultaneously.

According to further features in preferred embodiments of the invention described below the data representing a distribution of the thallium-201 and the technetium-99m-methoxyisobutylisonitrile (sestamibi) in the subject is acquired during a time window of from about 5 to about 15 minutes.

According to further features in preferred embodiments of the invention described below a time period of from about 30 to about 60 minutes is allowed to elapse between the administering of technetium-99m-methoxyisobutylisonitrile (sestamibi) and the acquiring of data representing a distribution of the thallium-201 and the technetium-99m-methoxyisobutylisonitrile (sestamibi).

According to further features in preferred embodiments of the invention described below the acquiring of data is performed at an energy window of from about 3 to about 15 percent.

According to further features in preferred embodiments of the invention described below the first radiopharmaceutical comprises thallium-201 at a dose of up to about 4 mCi, and the time window is from about 2 to about 20 minutes.

According to further features in preferred embodiments of the invention described below the first radiopharmaceutical is selected from the group consisting of Tc-99m-teboroxime, Tc-99m-methoxyisobutylisonitrile (sestamibi), Tc-99m-tetrofosmin, Tc-99m-furifosmin (Q12), and Tc-99m-beta-methyl-p-iodophenylpentadecanoic acid (BMIPP).

According to further features in preferred embodiments of the invention described below a dose of the first radiopharmaceutical is up to about 30 mCi, and the time window is up to about 15 minutes.

According to further features in preferred embodiments of the invention described below the subject is subjected to stress prior to acquiring of the data.

According to further features in preferred embodiments of the invention described below the methods are applied to cardiac perfusion studies.

According to further features in preferred embodiments of the invention described below the first radiopharmaceutical is Tc-99m-methoxyisobutylisonitrile (sestamibi), applied to tumor imaging.

According to further features in preferred embodiments of the invention described below the radiopharmaceutical is a combination of thallium-201 at a dose of up to 4 mCi and Tc-99m-methoxyisobutylisonitrile (sestamibi) at a dose of up to about 30 mCi, applied to tumor imaging.

According to further features in preferred embodiments of the invention described below the radiopharmaceutical is a combination of In-111-diethylene triamine pentaacetate (DTPA) at a dose of 0.2 mCi and Tc-99m-mercaptoacetyl-triglycine (MAG3) at a dose of up to about 10 mCi, and the section of the body is the kidney.

According to further features in preferred embodiments of the invention described below the radiopharmaceutical is a combination of In-111-diethylene triamine pentaacetate (DTPA) at a dose of from about 0.3 to about 1 mCi and I-123-iodohippurate sodium (hippuran) at a dose of up to about 10 mCi, and the section of the body is the kidney.

According to further features in preferred embodiments of the invention described below the radiopharmaceutical is Tc-99m at a dose of up to about 5 mCi, applied to brain perfusion mapping.

According to further features in preferred embodiments of the invention described below the radiopharmaceutical is a combination of Tc-99m-Exametazine (HMPAO) at a dose of up to about 20 mCi, Tc-99m N,N'(1,2-ethlenediyl)bis-L-cysteine diethyl ester (Tc-99m ECD) at a dose of up to about 20 mCi, and I-123 iofetamine hydrochloride, at a dose of up to about 5 mCi, applied to brain perfusion mapping.

According to further features in preferred embodiments of the invention described below the radiopharmaceutical is a combination of Tc-99m-diisopropyl iminodiacetic acid (disulfenine), Tc-99m-2,2'-[[2-[(3-bromo-2,4,6-trimethylphenyl)-amino]-2-oxoethyl]imino]bisacetic acid (Tc-99m-mebrofenin), and Tc-99m-dimethyl iminodiacetic acid (HIDA), applied to liver function study.

According to further features in preferred embodiments of the invention described below the data is acquired immediately following administering of the first radiopharmaceutical at an energy window of from about 3 to about 15 percent.

According to further features in preferred embodiments of the invention described below the methods are applied to dynamic process imaging.

According to further features in preferred embodiments of the invention described below the methods are applied to the study of ventricular function study.

According to further features in preferred embodiments of the invention described below the first radiopharmaceutical comprises a combination of Tc-99m-colloid and In-111-diethylene triamine pentaacetate (DTPA), applied to the study of dual phase gastric emptying.

According to yet another aspect of the present invention there is provided a method of radioimaging comprising:

(a) administering to a human subject a dose of the composition as described hereinabove; and (b) acquiring data representing a distribution of each of the radiopharmaceutical of the composition in at least a section of the body of the subject.

According to yet another aspect of the present invention there is provided a composition comprising a first radiopharmaceutical and a second radiopharmaceutical being different from the first radiopharmaceutical, provided that if the fist radiopharmaceutical is Tc-99m the second radiopharmaceutical is not Thalium 201 and vice versa.

According to further features in preferred embodiments of the invention described below both the first and the second radiopharmaceuticals are at low doses.

According to yet another aspect of the present invention there is provided a low dose of a first radiopharmaceutical and a low dose of a second radiopharmaceutical being different from the first radiopharmaceutical.

According to yet another aspect of the present invention there is provided a kit comprising at least two compositions for generating at least two radiopharmaceuticals, wherein the at least two radiopharmaceuticals are:

Tl-201-thallous chloride; and

Tc-99m-pertechnetate.

According to further features in preferred embodiments of the invention described below the dose of the Tl-201-thallous chloride is up to about 1 mCi and a dose of the Tc-99m-pertechnetate is up to about 15 mCi.

According to yet another aspect of the present invention there is provided a kit comprising at least two compositions for generating at least two radiopharmaceuticals, wherein the at least two radiopharmaceuticals are:

Tc-99m-methoxyisobutylisonitrile (sestamibi); and

I-123.

According to further features in preferred embodiments of the invention described below the dose of the Tc-99m-methoxyisobutylisonitrile (sestamibi) is about 15 mCi and a dose of the I-123 is up to about 100 μCi.

According to yet another aspect of the present invention there is provided a kit comprising at least two compositions for generating at least two radiopharmaceuticals, wherein the at least two radiopharmaceuticals are:

I-123: and

Tc-99m-red blood cells or Tc-99m-dihygrogen methylenediphosphate (medronate).

According to further features in preferred embodiments of the invention described below the dose of the I-123 is about 4 mCi, a dose of the Tc-99m-red blood cells is up to about 10 mCi and a dose of the Tc-99m-dihygrogen methylenediphosphate (medronate) is up to about 10 mCi.

According to yet another aspect of the present invention there is provided a kit comprising at least two compositions for generating at least two radiopharmaceuticals, wherein the at least two radiopharmaceuticals are:

In-111-L-Cysteinamide, D-phenylalanyl-L-cysteinyl-L-phenylalanyl-D-tryptophyl-L-lysyl-L-threonyl-N-[2-hydroxy-1-(hydroxy-methyl)propyl]-, cyclic 7)-disulfide (In-111-octreotide); and Tc-99m-dihygrogen methylenediphosphate (medronate).

According to further features in preferred embodiments of the invention described below the dose of the In-111-octreotide is up to about 3 mCi and a dose of the Tc-99m-medronate is up to about 15 mCi.

According to yet another aspect of the present invention there is provided a kit comprising at least two compositions for generating at least two radiopharmaceuticals, wherein the at least two radiopharmaceuticals are:

In-111-capromab pendetide; and

Tc-99m-red blood cells.

According to further features in preferred embodiments of the invention described below the dose of the In-111-capromab pendetide is of up to about 2 mCi and a dose of the Tc-99m-red blood cells is up to about 15 mCi.

According to yet another aspect of the present invention there is provided a kit comprising at least two compositions for generating at least two radiopharmaceuticals, wherein the at least two radiopharmaceuticals are:

Tc-99m-colloid; and

In-111-white blood cells.

According to further features in preferred embodiments of the invention described below the dose of the Tc-99m-colloid is up to about 15 mCi and a dose of the In-111-white blood cells is up to about 3 mCi.

According to yet another aspect of the present invention there is provided a kit comprising at least two compositions for generating at least two radiopharmaceuticals, wherein the at least two radiopharmaceuticals are:

Tl-201-thallous chloride; and

Tc-99m-dihygrogen methylenediphosphate (medronate).

According to further features in preferred embodiments of the invention described below the dose of the Tl-201-thallous chloride is up to about 2 mC and a dose of the Tc-99m-dihygrogen methylenediphosphate (medronate) is up to about 15 mCi.

According to yet another aspect of the present invention there is provided a kit comprising at least two compositions for generating at least two radiopharmaceuticals, wherein the at least two radiopharmaceuticals are:

Tl-201-thallous chloride;

Te-99-m-methoxyisobutylisonitrile (sestamibi); and

In-111-white blood cells.

According to further features in preferred embodiments of the invention described below the dose of the Tl-201-thallous chloride is up to about 1 mCi, a dose of the Te-99-m-methoxyisobutylisonitrile (sestamibi) is up to about 10 mCi, and a dose of the In-111-white blood cells is up to about 2 mCi.

According to yet another aspect of the present invention there is provided a kit comprising at least two compositions for generating at least two radiopharmaceuticals, wherein the at least two radiopharmaceuticals are:

Tl-201-thallous chloride;

dihygrogen methylenediphosphate (medronate); and

In-111-white blood cells.

According to further features in preferred embodiments of the invention described below the dose of the Tl-201-thallous chloride is up to about 1 mCi, a dose of the dihygrogen methylenediphosphate (medronate) is up to about 10 mCi, and a dose of the In-111-white blood cells is up to about 2 mCi.

According to yet another aspect of the present invention there is provided a comprising at least two compositions for generating at least two radiopharmaceuticals, wherein the at least two radiopharmaceuticals are:

Tl-201-thallous chloride;

Tc-99m-teboroxime or Tc-99m-methoxyisobutylisonitrile (sestamibi); and

I-123-beta-methyl-p-iodophenylpentadecanoic acid (BMIPP).

According to further features in preferred embodiments of the invention described below the dose of the Tc-99m-teboroxime or Tc-99m-methoxyisobutylisonitrile (sestamibi) is up to 10 mCi, and a dose of the I-123-beta-methyl-p-iodophenylpentadecanoic acid (BMIPP) is up to about 2 mCi.

According to yet another aspect of the present invention there is provided a kit comprising at least two compositions for generating at least two radiopharmaceuticals, wherein the at least two radiopharmaceuticals are:
Tc-99m-Fanoselomab; and
In-111-white blood cells.

According to further features in preferred embodiments of the invention described below the a dose of the Tc-99m-Fanoselomab is up to about 15 mCi and a dose of the In-111-white blood cells is up to about 2 mCi.

According to yet another aspect of the present invention there is provided a kit comprising at least two compositions for generating at least two radiopharmaceuticals, wherein the at least two radiopharmaceuticals are:
I-123-iodobenzamide (IBZM); and
Tc-99m-Exametazine (HMPAO).

According to further features in preferred embodiments of the invention described below the dose of the I-123-iodobenzamide (IBZM) is up to about 2 mCi and a dose of the Tc-99m-Exametazine (HMPAO) is about 15 mCi.

According to yet another aspect of the present invention there is provided a kit comprising at least two compositions for generating at least two radiopharmaceuticals, wherein the at least two radiopharmaceuticals are:
In-111-labeled antibody;
Tc-99m-methoxyisobutylisonitrile (sestamibi) or Tc-99m-Arcitumomab; and
Tl-201-thallous chloride.

According to further features in preferred embodiments of the invention described below the dose of the In-111-labeled antibody is up to about 1 mCi, a dose of the Tc-99m-methoxyisobutylisonitrile (sestamibi) or Tc-99m-Arcitumomab is up to about 10 mCi and a dose of the Tl-201-thallous chloride is up to about 1 mCi.

According to yet another aspect of the present invention there is provided a kit comprising at least two compositions for generating at least two radiopharmaceuticals, wherein the at least two radiopharmaceuticals are:
In-111-diethylene triamine pentaacetate (DTPA); and
Tc-99m-mercaptoacetyltriglycine (MAG3).

According to further features in preferred embodiments of the invention described below the dose of the In-111-diethylene triamine pentaacetate (DTPA) is up to about 2 mCi and a dose of the Tc-99m-mercaptoacetyltriglycine (MAG3) is up to about 15 mCi.

According to yet another aspect of the present invention there is provided a kit comprising at least two compositions for generating at least two radiopharmaceuticals, wherein the at least two radiopharmaceuticals are:
Tl-201-thallous chloride; and
Tc-99m-teboroxime or Tc-99m-methoxyisobutylisonitrile (sestamibi).

According to further features in preferred embodiments of the invention described below the dose of the Tl-201-thallous chloride is up to about 1 mCi and a dose of the Tc-99m-teboroxime or Tc-99m-methoxyisobutylisonitrile (sestamibi) is up to about 15 mCi.

According to yet another aspect of the present invention there is provided a kit comprising at least two compositions for generating at least two radiopharmaceuticals, wherein the at least two radiopharmaceuticals are:
Tc-99m-sulfur colloid; and
In-111-white blood cells.

According to further features in preferred embodiments of the invention described below the dose of the Tc-99m-sulfur colloid is up to about 15 mCi and a dose of the In-111-white blood cells is up to about 2 mCi.

According to yet another aspect of the present invention there is provided a kit comprising at least two compositions for generating at least two radiopharmaceuticals, wherein the at least two radiopharmaceuticals are:
Tc-99m-dihygrogen methylenediphosphate (medronate); and
In-111-white blood cells.

According to further features in preferred embodiments of the invention described below the dose of the Tc-99m-dihygrogen methylenediphosphate (medronate) is up to about 15 mCi and a dose of the In-111-white blood cells is up to about 2 mCi.

According to yet another aspect of the present invention there is provided a kit comprising at least two compositions for generating at least two radiopharmaceuticals, wherein the at least two radiopharmaceuticals are:
gallium-67; and
In-111-white blood cells.

According to further features in preferred embodiments of the invention described below the dose of the gallium-67 is up to about 5 mCi and a dose of the In-111-white blood cells is up to about 2 mCi.

According to yet another aspect of the present invention there is provided a kit comprising at least two compositions for generating at least two radiopharmaceuticals, wherein the at least two radiopharmaceuticals are:
Tc-99m-teboroxime Tl-201-thallous chloride; and
In-111-annexin.

According to further features in preferred embodiments of the invention described below the dose of the Tc-99m-teboroxime is up to about 15 mCi, a dose of the Tl-201-thallous chloride is up to about 2 mCi, and a dose of the In-111-annexin is up to about 2 mCi.

According to yet another aspect of the present invention there is provided a kit comprising at least two compositions for generating at least two radiopharmaceuticals, wherein the at least two radiopharmaceuticals are:
Tl-201-thallous chloride; and
Tc-99m-pyrophosphate.

According to further features in preferred embodiments of the invention described below the dose of the Tl-201-thallous chloride is up to about 2 mCi and a dose of the Tc-99m-pyrophosphate is up to about 15 mCi.

According to yet another aspect of the present invention there is provided a use of F-18-Fluorodeoxyglucose (FDG), as a substrate for hexokinase in glucose metabolism, for the study of glucose metabolism of cells including tumor, heart and brain cells.

According to yet another aspect of the present invention there is provided a use of F-18-Fluoromisonidazole for imaging of hypoxia and oxidative metabolism, with the clinical application of radiotherapy treatment planning.

According to yet another aspect of the present invention there is provided a use of F-18-3'-Fluoro-3'-deoxythymidine (FLT) for the study of DNA synthesis.

According to yet another aspect of the present invention there is provided a use of F-18-Fluoromethyl choline (FCH) as a choline precursor for cell membrane synthesis, for the study of choline metabolism of tumors.

According to yet another aspect of the present invention there is provided a use of F-18-4-Fluoro-m-tyrosine (FMT) as a precursor for dopamine synthesis and as a substrate for aromatic amino acid decarboxylase (AAAD), with the clinical application of imaging brain tumors.

According to yet another aspect of the present invention there is provided a use of F-18-6-Fluoro-L-DOPA as a precursor for dopamine synthesis and as a precursor for AAAD, with the clinical applications of imaging and grading Parkinson's disease and imaging neuroendocrine tumors.

According to yet another aspect of the present invention there is provided a use of F-18-FP-β-CIT for binding to the dopamine transporter in dopaminergic axons, with the clinical application of imaging and grading Parkinson's disease and imaging neuroendocrine tumors.

According to yet another aspect of the present invention there is provided a use of F-18-Pencyclovir (FHBG) to target thymidine kinase, with the clinical application of imaging reporter gene expression.

According to yet another aspect of the present invention there is provided a use of F-18-Fluoroestradiol (FES) to target estrogen receptors, with the clinical application of breast tumor imaging.

According to yet another aspect of the present invention there is provided a use of C-11-Methionine to target amino acid synthesis, with the clinical application of imaging brain tumors.

According to yet another aspect of the present invention there is provided a use of Tc-99m-P280, Acutect® to target GP IIb/IIIa receptors on platelets, with the clinical applications of detection of thrombosis, such as deep vein thrombosis (DVT) and intratererial thrombosis in coronary and carotid arteries.

According to yet another aspect of the present invention there is provided a use of C-11-Raclopride to target dopamine D2 receptors, for brain imaging of dopamine D2 receptors in schizophrenia, and assessment of dose for neuroleptics.

According to yet another aspect of the present invention there is provided a use of I-123-iodobenzamide (IBZM) to target dopamine D2 receptors, for brain imaging of dopamine D2 receptors in schizophrenia, and assessment of dose for neuroleptics.

According to yet another aspect of the present invention there is provided a use of C-1-carfentanil to target Mu opioid receptors in brain, with the clinical application of imaging drug addiction.

According to yet another aspect of the present invention there is provided a use of C-11-α-methyl-L-tryptophan as a precursor for α-methyl serotonin synthesis and as a substrate for AAAD enzyme, with the clinical application of imaging depression.

According to yet another aspect of the present invention there is provided a use of C-115-Hydroxytryptophan as a precursor for serotonin synthesis with the clinical application of imaging neuroendocrine tumors.

According to yet another aspect of the present invention there is provided a use of F-18-MPPF to bind to 5-HT1A (5-hydroxytryptamine-1A) serotonin receptors, with the clinical application of imaging depression and epilepsy.

According to yet another aspect of the present invention there is provided a use of F-18-Altanserin to bind to 5-HT2A serotonin receptors with the clinical application of imaging depression and epilepsy.

According to yet another aspect of the present invention there is provided a use of C-11-Acetate for the study of tricarboxylic acid cycle activity and oxidative metabolism with the clinical application of studying myocardial oxygen metabolism.

According to yet another aspect of the present invention there is provided a use of C-11-Palmitate as a precursor for fatty acid metabolism with the clinical application of imaging myocardial metabolism.

According to yet another aspect of the present invention there is provided a use of F-18-Fluorodopamine to target presynaptic adrenergic receptors.

According to yet another aspect of the present invention there is provided a method for treating a patient, comprising:

(a) applying a therapy to the patient;

(b) performing on the patient a functional imaging procedure according to any of the methods described hereinabove to measure a property indicative of biochemical activity of at least one tissue of the patient; and modifying at least one parameter of the therapy responsively to the measured biochemical activity.

According to further features in preferred embodiments of the invention described below performing the imaging procedure comprises performing a SPECT imaging procedure on the patient.

According to further features in preferred embodiments of the invention described below the performing the SPECT imaging procedure comprises performing the SPECT imaging procedure using a high-definition SPECT camera.

According to further features in preferred embodiments of the invention described below the therapy comprises a therapeutic radiopharmaceutical.

According to yet another aspect of the present invention there is provided an apparatus for use with any of the methods, kits and compositions of the embodiments described hereinabove, the apparatus comprising:

a container containing at least one radiopharmaceutical of the methods, kits or compositions of the embodiments described hereinabove; and a portable computer-communicatable data carrier associated with the container, the data carrier containing imaging protocol information of any of the methods described hereinabove for use with the at least one radiopharmaceutical.

According to further features in preferred embodiments of the invention described below the apparatus comprises a device configured to write the imaging protocol information to the data carrier.

According to further features in preferred embodiments of the invention described below the data carrier additionally contains administration protocol information useful for administering the at least one radiopharmaceutical.

According to further features in preferred embodiments of the invention described below the imaging protocol information comprises instructions for performing an imaging procedure using the at least one radiopharmaceutical.

According to further features in preferred embodiments of the invention described below the imaging protocol information comprises an identifier of an imaging protocol.

According to further features in preferred embodiments of the invention described below the imaging protocol information comprises a parameter of the at least one radiopharmaceutical.

According to further features in preferred embodiments of the invention described below the imaging protocol information comprises a parameter useful for configuring at least one aspect of an imaging procedure performed using the at least one radiopharmaceutical.

According to further features in preferred embodiments of the invention described below the container contains a single dose of the radiopharmaceutical agent, which dose is appropriate for use with the imaging protocol information.

According to further features in preferred embodiments of the invention described below the container contains a plurality of radiopharmaceuticals mixed together.

According to further features in preferred embodiments of the invention described below the container is shaped so as to define a plurality of chambers, each of which contains a respective one of a plurality of radiopharmaceuticals.

According to further features in preferred embodiments of the invention described below the data carrier comprises a first data carrier, which contains a first identifier value, wherein the apparatus further comprises a second computer-communicatable data carrier, which contains a second identifier value, and wherein the apparatus is configured to operate responsively to a detection of a correspondence between the first and second identifier values.

According to further features in preferred embodiments of the invention described below at least one of the first and second data carriers is configured to perform the detection of the correspondence.

According to further features in preferred embodiments of the invention described below the apparatus comprises a correspondence-detection element configured to perform the detection of the correspondence.

According to further features in preferred embodiments of the invention described below at least one of the first and second data carriers contains an identifier of a patient to whom the radiopharmaceutical is to be administered.

According to further features in preferred embodiments of the invention described below at least one of the first and second identifier values comprises an identifier of a patient to whom the radiopharmaceutical is to be administered.

According to further features in preferred embodiments of the invention described below exactly one of the first and second data carriers comprises a coupling mechanism configured to be coupled to a patient to whom the radiopharmaceutical is to be administered.

According to further features in preferred embodiments of the invention described below the apparatus comprises an imaging system comprising imaging functionality, the imaging system configured, responsively to the detection of the correspondence, to drive the imaging functionality to perform an imaging procedure using the at least one radiopharmaceutical.

According to further features in preferred embodiments of the invention described below the data carrier is physically coupled to the container.

According to further features in preferred embodiments of the invention described below the data carrier contains an identifier of a patient to whom the radiopharmaceutical is to be administered, and wherein the imaging protocol information comprises imaging protocol information selected for the patient.

According to further features in preferred embodiments of the invention described below the imaging protocol information comprises an identifier of an imaging protocol.

According to further features in preferred embodiments of the invention described below the imaging protocol information comprises imaging protocol information customized for the patient.

According to further features in preferred embodiments of the invention described below the imaging protocol information comprises SPECT imaging protocol information.

According to further features in preferred embodiments of the invention described below the SPECT imaging protocol information comprises dynamic SPECT imaging protocol information.

According to further features in preferred embodiments of the invention described below the SPECT imaging protocol information comprises at least one kinetic parameter of the at least one radiopharmaceutical, the at least one kinetic parameter useful for performing a dynamic SPECT imaging procedure using the at least one radiopharmaceutical.

According to further features in preferred embodiments of the invention described below the apparatus comprises an imaging system, which comprises:

a communication element, configured to read the imaging protocol information from the data carrier; and a control unit, comprising imaging functionality, which is configured to perform an imaging procedure, and to configure the procedure at least in part responsively to the imaging protocol information read from the data carrier by the communication element.

According to further features in preferred embodiments of the invention described below the imaging system comprises a camera, wherein the imaging functionality comprises image acquisition functionality, and wherein the image acquisition functionality is configured to perform an image acquisition procedure using the camera, and to configure the procedure at least in part responsively to the imaging protocol information read from the data carrier by the communication element.

According to further features in preferred embodiments of the invention described below the image acquisition functionality configures a total acquisition time of the image acquisition procedure at least in part responsively to the imaging protocol information.

According to further features in preferred embodiments of the invention described below the camera comprises a plurality of detectors, and wherein the image acquisition functionality is configured to configure, at least in part responsively to the imaging protocol information, at least one motion of at least one of the detectors during the image acquisition procedure.

According to further features in preferred embodiments of the invention described below the control unit is configured to configure, at least in part responsively to the imaging protocol information, a waiting time between administration of the radiopharmaceutical and commencement of the image acquisition procedure.

According to further features in preferred embodiments of the invention described below the image acquisition functionality is configured to perform a gated image acquisition procedure at least in part responsively to the imaging protocol information.

According to further features in preferred embodiments of the invention described below the imaging functionality comprises image reconstruction functionality, and wherein the image reconstruction functionality is configured to perform an image reconstruction procedure, and to configure the procedure at least in part responsively to the imaging protocol information read from the data carrier by the communication element.

According to further features in preferred embodiments of the invention described below the imaging functionality comprises image analysis functionality, and wherein the image analysis functionality is configured to perform an image analysis procedure, and to configure the procedure at least in part responsively to the imaging protocol information read from the data carrier by the communication element.

According to further features in preferred embodiments of the invention described below the imaging functionality comprises diagnosis functionality, and wherein the diagnosis functionality is configured to perform a diagnostic procedure, and to configure the procedure at least in part responsively to the imaging protocol information read from the data carrier by the communication element.

According to further features in preferred embodiments of the invention described below the imaging procedure includes a three-dimensional dynamic imaging study, and wherein the imaging functionality is configured to perform the three-dimensional dynamic imaging study, and to configure the study at least in part responsively to the imaging protocol information read from the data carrier by the communication element.

According to further features in preferred embodiments of the invention described below the data carrier is not physically coupled to the container, and wherein the data carrier contains an identifier of a patient to whom the radiopharmaceutical is to be administered.

According to further features in preferred embodiments of the invention described below the data carrier comprises a coupling mechanism configured to be coupled to the patient.

According to further features in preferred embodiments of the invention described below the data carrier comprises a first data carrier, and wherein the apparatus further comprises a second computer-communicatable data carrier physically coupled to the container, the second data carrier containing radiopharmaceutical information regarding the at least one radiopharmaceutical.

According to further features in preferred embodiments of the invention described below the apparatus is for use with at least one radiopharmaceutical of any of the kits, compositions or methods as described hereinabove, the apparatus comprising:

a container containing the at least one radiopharmaceutical; and a computer-communicatable data carrier associated with the container, the data carrier containing authenticatable information regarding a commercial license for use of the imaging protocol information of any of the methods described hereinabove with the at least one radiopharmaceutical.

According to further features in preferred embodiments of the invention described below the apparatus comprises an imaging system, which comprises:

a communication element, configured to read the authenticatable license information from the data carrier;

a control unit, comprising imaging functionality, the control unit configured to:

authenticate the authenticatable license information, and only upon authentication, drive the imaging functionality to perform an imaging procedure using the SPECT imaging protocol information.

According to further features in preferred embodiments of the invention described below the apparatus comprises a device configured to write the authenticatable license information to the data carrier.

According to further features in preferred embodiments of the invention described below the data carrier is physically coupled to the container.

According to yet another aspect of the present invention, there is provided an apparatus comprising a portable computer-communicatable data carrier containing authenticatable information regarding a commercial license for use of any of the imaging methods described hereinabove.

According to further features in preferred embodiments of the invention described below the data carrier additionally contains patient information regarding a patient upon whom an imaging procedure using the SPECT imaging protocol information is to be performed.

According to further features in preferred embodiments of the invention described below the authenticatable license information is encrypted.

According to further features in preferred embodiments of the invention described below the apparatus comprises a device configured to write the authenticatable license information to the data carrier.

According to further features in preferred embodiments of the invention described below the data carrier comprises a coupling mechanism configured to be coupled to a patient upon whom an imaging procedure using the SPECT imaging protocol information is to be performed.

According to further features in preferred embodiments of the invention described below the apparatus comprises an imaging system, which comprises:

a communication element, configured to read the authenticatable license information from the data carrier;

a control unit, comprising imaging functionality, the control unit configured to:

authenticate the authenticatable license information, and only upon authentication, drive the imaging functionality to perform an imaging procedure using the SPECT imaging protocol information.

According to another aspect of the present invention, there is provided an apparatus for use with at least one radiopharmaceutical of the methods and kits described hereinabove for administration to a patient, the apparatus comprising:

a container containing the at least one radiopharmaceutical;

a first computer-communicatable data carrier physically coupled to the container, the first data carrier containing radiopharmaceutical information regarding the at least one radiopharmaceutical; and a second portable computer-communicatable data carrier containing patient information regarding the patient, and imaging protocol information for use with the at least one radiopharmaceutical.

According to further features in preferred embodiments of the invention described below the imaging protocol information comprises SPECT imaging protocol information.

According to further features in preferred embodiments of the invention described below the patient information comprises an identifier of the patient.

According to further features in preferred embodiments of the invention described below the second data carrier comprises a coupling mechanism configured to be coupled to the patient.

According to further features in preferred embodiments of the invention described below the first data carrier contains a first patient identifier, wherein the patient information contained in the second data carrier comprises a second patient identifier, and comprising an administration system, which comprises:

a first communication element, configured to read the first patient identifier from the first data carrier;

a second communication element, configure to read the second patient identifier from the second data carrier; and a control unit, configured to compare the first patient identifier to the second patient identifier, and, upon detecting a match, generate an administration signal that triggers administration to the patient of the at least one radiopharmaceutical contained in the container.

According to further features in preferred embodiments of the invention described below the first data carrier contains a first protocol identifier, wherein the imaging protocol information contained in the second data carrier comprises a second protocol identifier, and comprising an administration system, which comprises:

a communication element, configured to read the first and second protocol identifiers from the first and second data carriers, respectively; and a control unit, configured to compare the first protocol identifier to the second protocol identifier, and, upon detecting a match, generate an administration signal that triggers administration to the patient of the at least one radiopharmaceutical contained in the container.

According to further features in preferred embodiments of the invention described below the first data carrier contains a first protocol identifier, wherein the imaging protocol information contained in the second data carrier comprises a second protocol identifier, and comprising an administration system, which comprises:

a first communication element, configured to read the first protocol identifier from the first data carrier;

a second communication element, configured to read the second protocol identifier from the second data carrier; and a control unit, configured to compare the first protocol identifier to the second protocol identifier, and, upon detecting a match, generate an administration signal that triggers administration to the patient of the at least one radiopharmaceutical contained in the container.

According to further features in preferred embodiments of the invention described below the apparatus comprises an administration system, which comprises:

a communication element; and a control unit, configured to:

generate an administration signal that triggers administration to the patient of the at least one radiopharmaceutical contained in the container, and drive the communication element to transmit information regarding the administration to the second data carrier.

According to further features in preferred embodiments of the invention described below the apparatus comprises a device configured to write the imaging protocol information to the first data carrier.

According to further features in preferred embodiments of the invention described below the apparatus comprises a device configured to write the patient information to the second data carrier.

According to further features in preferred embodiments of the invention described below the imaging protocol information comprises imaging protocol information selected for the patient.

According to further features in preferred embodiments of the invention described below the imaging protocol information comprises an identifier of an imaging protocol.

According to further features in preferred embodiments of the invention described below the imaging protocol information comprises imaging protocol information customized for the patient.

According to further features in preferred embodiments of the invention described below the first data carrier contains a first patient identifier, wherein the patient information contained in the second data carrier includes a second patient identifier, and comprising an administration system, which comprises:

a communication element, configured to read the first and second patient identifiers from the first and second data carriers, respectively; and a control unit, configured to compare the first patient identifier to the second patient identifier, and, upon detecting a match, generate an administration signal that triggers administration to the patient of the at least one radiopharmaceutical contained in the container.

According to further features in preferred embodiments of the invention described below the administration system comprises an automated administration device, configured to administer the at least one radiopharmaceutical to the patient upon being triggered by the administration signal.

According to further features in preferred embodiments of the invention described below the control unit is configured to generate the administration signal to trigger the administration of the at least one radiopharmaceutical by instructing a healthcare worker to administer the at least one radiopharmaceutical to the patient.

According to further features in preferred embodiments of the invention described below the apparatus comprises:

a container containing the at least one radiopharmaceutical;

a computer-communicatable data carrier associated with the container, the data carrier containing data regarding at least one of: the radiopharmaceutical and the patient; and a SPECT imaging system comprising:

a communication element, configured to read the data; and a control unit, configured to utilize the read data to customize at least one function of the system selected from the group consisting of: administration of the radiopharmaceutical, acquisition of a SPECT image of the patient to whom the radiopharmaceutical is administered, reconstruction of the SPECT image, analysis of the SPECT image, and diagnosis of a condition of the patient based at least in part on the analysis.

According to further features in preferred embodiments of the invention described below the data carrier contains the data regarding the radiopharmaceutical.

According to further features in preferred embodiments of the invention described below the data carrier contains the data regarding the patient.

According to further features in preferred embodiments of the invention described below the control unit is configured to utilize the read data to customize the administration of the radiopharmaceutical.

According to further features in preferred embodiments of the invention described below the control unit is configured to utilize the read data to customize the acquisition of a SPECT image of the patient to whom the radiopharmaceutical is administered.

According to further features in preferred embodiments of the invention described below the control unit is configured to utilize the read data to customize the reconstruction of the SPECT image.

According to further features in preferred embodiments of the invention described below the control unit is configured to utilize the read data to customize the analysis of the SPECT image.

According to further features in preferred embodiments of the invention described below the control unit is configured to utilize the read data to customize the diagnosis of a condition of the patient based at least in part on the analysis.

According to further features in preferred embodiments of the invention described below the apparatus comprises a device configured to write the data to the data carrier.

According to yet another aspect of the present invention there is provided a SPECT imaging system for use with a container containing at least one radiopharmaceutical for administration to a patient according to the methods described hereinabove, and data regarding at least one of: the radiopharmaceutical and the patient, the system comprising:

a communication element, configured to read the data; and a control unit, configured to utilize the read data to customize at least one function of the system selected from the group consisting of: administration of the radiopharmaceutical, acquisition of a SPECT image of the patient to whom the radiopharmaceutical is administered, reconstruction of the SPECT image, analysis of the SPECT image, and diagnosis of a condition of the patient based at least in part on the analysis.

According to further features in preferred embodiments of the invention described below the system comprises a device configured to write the data to the container.

According to yet another aspect of the present invention, there is provided an automated radiopharmaceutical dispensing system for use with a container and a computer-communicatable container data carrier associated with the container and for using of any of the kits described hereinabove and/or executing any of the methods described hereinabove, the system comprising:

a robot, configured to manipulate the container;
a communication element; and
a control unit, configured to:
receive radiopharmaceutical information regarding at least one radiopharmaceutical, the radiopharmaceutical information selected from the group consisting of: imaging protocol information for use with the at least one radiopharmaceutical, and authenticatable information regarding a commercial license for use of an imaging protocol with the at least one radiopharmaceutical,
receive patient information regarding a patient,
drive the robot to automatically dispense a dose of the radiopharmaceutical to the container, and
drive the communication element to transmit to the container data carrier at least a portion of the radiopharmaceutical information and at least a portion of the patient information.

According to further features in preferred embodiments of the invention described below the control unit is configured to receive the radiopharmaceutical information regarding a plurality of radiopharmaceuticals, and drive the robot to automatically dispense respective doses of the radiopharmaceuticals to the container.

According to further features in preferred embodiments of the invention described below the patient information includes an identifier of an imaging protocol assigned to the patient for performance using the dose, and wherein the control unit is configured to drive the communication element to transmit the imaging protocol identifier to the container data carrier.

According to further features in preferred embodiments of the invention described below the control unit is configured to drive the communication element to transmit to the container data carrier at least one of: a time of dispensing of the radiopharmaceutical to the container, and information regarding a radioactivity of the dose at the time of dispensing.

According to further features in preferred embodiments of the invention described below the system comprises:
a mother vial that contains the radiopharmaceutical prior to dispensing thereof; and
a computer-communicatable mother vial data carrier associated with the mother vial, which mother vial data carrier contains the radiopharmaceutical information,
wherein the control unit is configured to receive the radiopharmaceutical information from the mother vial data carrier.

According to further features in preferred embodiments of the invention described below the radiopharmaceutical information comprises the imaging protocol information.

According to further features in preferred embodiments of the invention described below the imaging protocol information comprises SPECT imaging protocol information.

According to further features in preferred embodiments of the invention described below the imaging protocol information comprises at least one kinetic parameter of the at least one radiopharmaceutical.

According to further features in preferred embodiments of the invention described below the radiopharmaceutical information comprises the authenticatable information regarding the commercial license.

According to further features in preferred embodiments of the invention described below the information regarding the commercial license comprises information regarding the commercial license for use of a SPECT imaging protocol with the at least one radiopharmaceutical.

According to further features in preferred embodiments of the invention described below the control unit is configured to authenticate the authenticatable license information, and to drive the robot to automatically dispense the dose only upon authentication.

According to yet another aspect of the present invention, there is provided an imaging system for implementing any of the methods or using any of the kits or compositions described hereinabove, the imaging system comprising a radioimaging camera, which comprises a plurality of solid state detectors, configured for independent movement during data acquisition.

According to yet another aspect of the present invention, there is provided an imaging system for implementing any of the methods described hereinabove, or using any of the kits described hereinabove the system comprising a radioactive-emission-measuring-camera system which comprises:

a housing;
at least one detecting unit, located within the housing and adapted for at least one form of motion with respect to the housing;
at least one motion provider, in mechanical communication with the at least one detecting unit, for providing it with the at least one form of motion;
a controller, in signal communication with the at least one motion provider, for instructing it regarding the at least one form of motion of the at least one detecting unit, thus automatically providing the at least one detecting unit with the at least one form of motion.

According to further features in preferred embodiments of the invention described below the at least one detecting unit includes a plurality of detecting units, each detecting unit moving independently.

The present invention successfully addresses the shortcomings of the presently known configurations by providing novel protocols for radioimaging.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1B schematically illustrate detecting units and blocks for radioactive emission detection;

FIG. 2 schematically illustrates the basic component of a system, comprising a radioactive-emission camera and a position-tracking device, both in communication with a data-processing system;

FIGS. 3A-3B schematically illustrate the manner of operating the radioactive-emission camera with the position-tracking device;

FIGS. 4A-4C schematically illustrate extracorporeal and intracorporeal radioactive-emission camera operative with position-tracking devices;

FIGS. 5A-5F present the principles of modeling, for obtaining an optimal set of views, in accordance with embodiments of the present invention;

FIG. 8 illustrates, in flowchart form, a method of predefining a set of views for functional imaging, tailored for imaging a specific body structure, and optimized with respect to the functional information gained about the body structure, in accordance with embodiments of the present invention;

FIGS. 9A-9F schematically illustrate possible models and collections of views, for a body structure, in accordance with embodiments of the present invention;

FIG. 10 illustrates, in flowchart form, a method of functional imaging, tailored for imaging from esophagus, and optimized with respect to the functional information gained about the body structure, in accordance with embodiments of the present invention;

FIGS. 17A-17N schematically illustrate various detecting units and blocks, which may be incorporated in camera designs, in accordance with embodiments of the present invention;

FIGS. 18A-18D schematically illustrate possible motions of a radioactive-emission camera, for a single detecting unit and a single block, in accordance with embodiments of the present invention;

FIGS. 19A-19E schematically illustrate other possible motions of a radioactive-emission camera, for a single block, in accordance with embodiments of the present invention;

FIGS. 20A-20H schematically illustrate possible motions of a radioactive-emission camera, having a plurality of pairs of radioactive-emission blocks;

FIGS. 21A-21D schematically illustrate other possible motions of a radioactive-emission camera, having a plurality of pairs of radioactive-emission blocks;

FIGS. 22A-22X schematically illustrate a radioactive-emission camera system, comprising a plurality of assemblies, motions of individual blocks, and characteristics of an optimal camera, in accordance with embodiments of the present invention;

FIG. 22Y-22AA schematically illustrate a center of viewing, for a given camera design, in accordance with embodiments of the present invention;

FIGS. 23A-23D schematically illustrate a radioactive-emission camera system, in accordance with embodiments of the present invention;

FIGS. 25A-25E schematically illustrate the external appearance and the internal structure of the radioactive-emission camera for the prostate, in accordance with an embodiment of the present invention;

FIGS. 37-39 schematically illustrate the modeling of the heart as a process of two iterations, in accordance with embodiments of the present invention;

FIG. 51 schematically illustrates a cardiac model, in accordance with an embodiment of the present invention;

FIGS. 52A-52E schematically illustrate radiation detection blocks arranged for viewing a cardiac model, in accordance with an embodiment of the present invention;

FIGS. 55A-55C schematically illustrate the internal structure of the radioactive-emission camera for the dual imaging system, in accordance with an embodiment of the present invention;

FIGS. 56A-56B schematically illustrate the internal structure of the radioactive-emission camera for the dual imaging system, in accordance with an embodiment of the present invention;

FIGS. 57A-57B schematically illustrate a cranial model, in accordance with an embodiment of the present invention;

FIGS. 59A-59C schematically illustrate an imaging system for radioactive-emissions of the head, in accordance with an embodiment of the present invention;

FIGS. 60A-60K schematically illustrate the internal structure of the radioactive-emission camera for the head, in accordance with an embodiment of the present invention;

FIGS. 62A-62C schematically illustrate an imaging system for radioactive-emissions of the breast, in accordance with an embodiment of the present invention;

FIGS. 63A-63E schematically illustrate an imaging camera for radioactive-emissions of the breast, in accordance with an embodiment of the present invention;

FIGS. 64A-64K schematically illustrate an imaging system for radioactive-emissions of the breast, in accordance with an embodiment of the present invention;

FIGS. 64L-64M illustrates, in flowchart form, a method of examining a breast, in accordance with embodiments of the present invention;

FIGS. 66A-66G schematically illustrate an imaging system for radioactive-emissions of the breast, in accordance with an embodiment of the present invention;

FIGS. 67A-67B schematically illustrate effect of distance on detection efficiency of a radiation detector;

FIGS. 68A-68D schematically illustrate effect of distance on resolution of a radiation detector;

FIGS. 69A-69D schematically illustrate "wasteful viewing" by an array of radiation detectors;

FIGS. 70A-70C describe experimental results with grid point sources.

FIG. 71 schematically illustrates a non-wasteful radiation detector array, in accordance with an embodiment of the present invention;

FIGS. 74A and 74B schematically illustrate the use of a non-wasteful radiation detector array, in accordance with an embodiment of the present invention;

FIGS. 76A-80D schematically illustrate experimental data with the camera of the present invention.

FIG. 98 is a tabulation of events collected at temporal resolution of 1 ms in accordance with an embodiment of the present invention.

FIG. 99 A-E are tables showing exemplary preconfigured SPECT protocols and parameters thereof, in accordance with respective embodiments of the present invention;

FIG. 100 is a schematic illustration of an end-to-end automated system 10 for medical imaging, in accordance with an embodiment of the present invention. System 10 comprises a plurality of integrated elements that are configured to electronically exchange information among one another. The elements include an automated radiopharmaceutical dispensing system 20, a portable information-bearing radiopharmaceutical agent container 22, a portable patient-specific data carrier 24, an automated administration system 26, and an automated imaging system 28. Other exemplary components are indicated in the figure and further described hereinbelow.

Figure 5C:
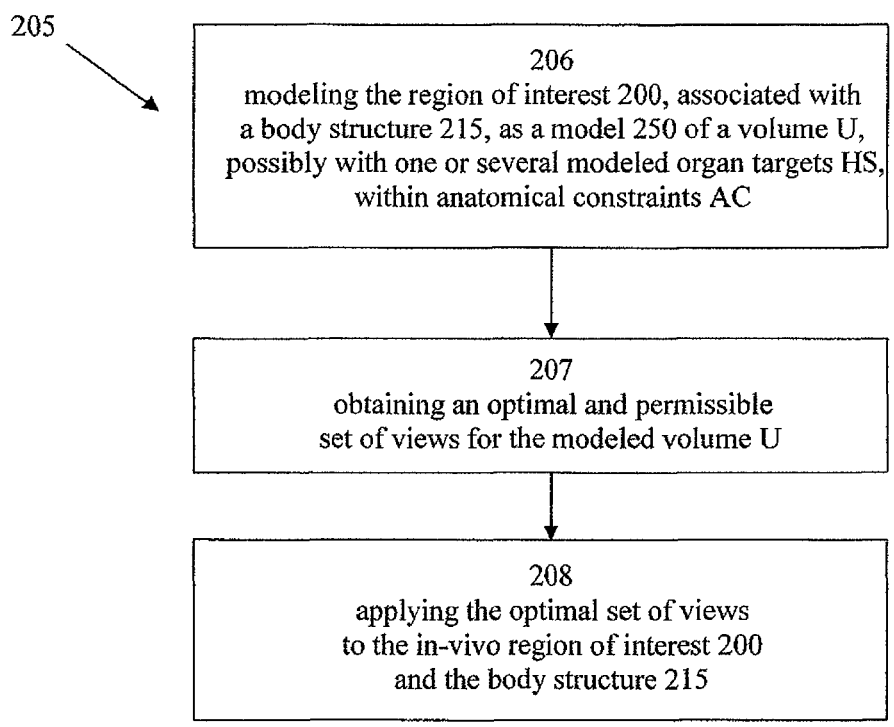

The systems perform their respective automated functions at least in part responsively to the exchanged information. The elements typically authenticate one another via the exchanged information, in order to ensure that only authorized elements participate in the system, and that only authorized and appropriate functions are performed. Each of the elements is described in detail hereinbelow.

FIGS. 101A-101H are experimental results, in accordance with embodiments of the present invention.

DESCRIPTION OF THE PREFERRED EMBODIMENTS

The present invention relates to novel radioimaging protocols which may be used for the visualization of specific tissues or regions of the body.

The principles and operation of the novel protocols according to the present invention may be better understood with reference to the accompanying description.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

The following is a list of terminology related to the protocols of the present invention:

TERMINOLOGY

As used herein a "subject" refers to a mammal, preferably a human subject.

As used herein the term "rest" refers to a non-exertion of physical activity for a period of time between the injection of the radio-isotope and acquisition of a resting scan.

As used herein the term "waiting" refers to the period of time between the injection and acquisition during which a subject is not engaged in a particular overt behavior. Typically the waiting period is to allow for distribution of the radioisotope in the body and clearance from organs such as the liver. The scan which is imaged following this period may be a resting scan or a stress scan.

As used herein the phrase "physical stress" refers to any physical activity which results in dilation of the blood vessels to the heart. Typically, the physical stress is an exercise treadmill.

As used herein the phrase "pharmacological stress" refers to any agent which results in dilation of the blood vessels to the heart. Examples of pharmacological stress include but are not limited to administration of adenosine, dipyridamole or dobutamine. Typically, the pharmacological stress is adenosine or dipyridamole.

As used herein the phrase "peak physical stress" refers to a safe amount of physical stress that will cause a sufficient vasodilation for myocardial perfusion imaging. Thus, the peak physical stress depends on patient parameters such as, but not limited to BMI, sex and medical conditions, as further described hereinbelow.

As used herein the phrase "peak pharmacological stress" refers to an amount of vasodilation exerted by an agent, sufficient for myocardial perfusion imaging. The peak pharmacological stress depends on patient parameters such as, but not limited to BMI, sex and medical conditions.

As used herein the term "about refers to 60%. Alternatively the term about refers to ±59%, alternatively the term about refers to ±58%, alternatively the term about refers to ±57%, alternatively the term about refers to ±56%, alternatively the term about refers to ±55%, alternatively the term about refers to ±54%, alternatively the term about refers to ±53%, alternatively the term about refers to ±52%, alternatively the term about refers to ±51%, alternatively the term about refers to ±50%, alternatively the term about refers to ±49%, alternatively the term about refers to ±48% alternatively the term about refers to ±47%, alternatively the term about refers to ±46%, alternatively the term about refers to ±45%, alternatively the term about refers to ±44%, alternatively the term about refers to ±43%, alternatively the term about refers to ±42%, alternatively the term about refers to ±41%, alternatively the term about refers to ±40%, alternatively the term about refers to ±39%, alternatively the term about refers to ±38%, alternatively the term about refers to ±37%, alternatively the term about refers to ±36%, alternatively the term about refers to ±35%, alternatively the term about refers to ±34%, alternatively the term about refers to ±33%, alternatively the term about refers to ±32%, alternatively the term about refers to ±31%, alternatively the term about refers to ±30%, alternatively the term about refers to ±29%, alternatively the term about refers to ±28%, alternatively the term about refers to ±27%, alternatively the term about refers to ±26% alternatively the term about refers to ±25%, alternatively the term about refers to ±24%, alternatively the term about refers to ±23%, alternatively the term about refers to ±22%, alternatively the term about refers to ±21%, alternatively the term about refers to ±20%, alternatively the term about refers to 19%, alternatively the term about refers to ±18%, alternatively the term about refers to ±17%, alternatively the term about refers to ±16%, alternatively the term about refers to ±15%, alternatively the term about refers to ±14%, alternatively the term about refers to ±13%, alternatively the term about refers to ±12%, alternatively the term about refers to ±11%, alternatively the term about refers to ±10%, alternatively the term about refers to ±9%, alternatively the term about refers to ±8%, alternatively the term about refers to ±7%, alternatively the term about refers to 6%, alternatively the term about refers to ±5%, alternatively the term about refers to ±4%, alternatively the term about refers to ±3%, alternatively the term about refers to ±2% and alternatively the term about refers to ±1%.

Unless a numeral is already preceded by the term "about", each numeral recited herein and describing a dose or a time period referred to in the protocols of the present invention (e.g., the numerals describing the doses or the time periods referred to in Tables 1-83 and in the Claims section and the dose and time ranges described below) should be read as if the term "about" precedes it.

The term "immediately" as used herein refers to an immediate time. For example if step "x" immediately follows step "y", this may be understood to mean that there is no enforced waiting period between the two steps. It may be that a time interval passes between step "x" and "y" due to, for example, patient or apparatus preparation. Preferably, the time interval is less than 5 minutes, more preferably less than 3 minutes and even more preferably less than 1 minute.

As used herein the term "simultaneously" refers to two events occurring at the same time with no enforced waiting period occurring between the two.

The term "radioimaging" as used herein refers to the imaging of the spatial distribution of a radiopharmaceutical which accumulates in a particular cell or sub-cellular component or cellular fluid.

The term "radiopharmaceutical" refers to a radioactive compound used for therapeutic, imaging, or diagnostic purposes in a mammalian subject.

The phrase "PET radiopharmaceutical" refers to any radiopharmaceutical that may be imaged using PET. An example of a PET radiopharmaceutical is 2-[F-18]fluoro-2-deoxy-D-glucose (FDG).

The phrase "myocardial perfusion" as used herein, refers to a normal or abnormal heart blood flow either at rest and/or following stress.

As used herein the phrase "lung perfusion" refers to a normal or abnormal lung blood flow.

The phrase "inflammatory process" as used herein, refers to the migration or infiltration of leukocytes into a pathological tissue. The process is typically driven by cytokines and/or chemokines as well as intracellular messengers) and involving vascular permeability, active migration of blood cells and passage of plasma constituents, resulting in tissue damage. The inflammatory process may be associated with any chronic or acute inflammation associated disease including, but not limited to inflammatory diseases associated with hypersensitivity, autoimmune diseases, infectious diseases, Graft rejection diseases, allergic diseases and cancerous diseases. Examples of diseases related to a bone inflammatory process include, but are not limited to muscular dystrophy, structural myopathy, inflammatory myopathy, a myotonic disorder, channelopathy, a metabolic muscle disease and arthritic disorders such as osteoporosis and osteoarthritis The phrase "bone cancer" as used herein, refers to benign or malignant growth situated in the bone. The bone cancer may be a primary or secondary tumor.

As used herein, the phrase "breast cancer" refers to any type of malignant growth in the breast tissue.

The phrase "brain perfusion" as used herein, refers to a normal or abnormal blood flow to the brain. Typically, blood perfusion is imaged for the diagnosis of brain pathologies including but not limited to ischemia, stroke and dementia.

The phrase "tumor perfusion" as used herein refers to a blood flow to a tumor. Typically, tumor perfusion is imaged to identify a tumor and/or to monitor treatment, treatment response and multi-drug resistance.

As used herein, the phrase "liver structure" refers to any normal or abnormal structure in the liver including but not limited to a hemangioma, an abscess and overall liver enlargement.

Herein, the phrase "renal function" refers to any normal or abnormal function of the kidney including but not limited to filtration, tubular secretion, perfusion and secretion.

The phrase "liver function" refers to any normal or abnormal function of the liver, including but not limited to production of bile, production of blood plasma proteins, production of cholesterol, conversion of excess glucose into glycogen, regulation of blood levels of amino acids, processing of hemoglobin, conversion of ammonia to urea, clearing the blood of drugs and other poisonous substances, regulating blood clotting, producing immune factors and removing bacteria from the blood stream.

The phrase "cardiac vulnerable plaque", as used herein, refers to a deposit of fat, cholesterol and/or other materials that collect in arteries rendering same vulnerable to rupture.

As used herein, "prostate cancer" is defined as cancer of the prostate gland, typically adenocarcinoma of the prostate gland.

As used herein, the phrase "neuroendocrine tumor" refers to any tumor derived from cells that release a hormone in response to a signal from the nervous system. Examples of neuroendocrine tumors include, but are not limited to carcinoid tumors, islet cell tumors, medullary thyroid carcinoma, and pheochromocytoma. These tumors typically secrete hormones in excess, causing a variety of symptoms.

The term "thrombi" as used herein refers to blood clots that have not been released into the blood system.

As used herein, the phrase "parathyroid adenoma" refers to benign tumors of the parathyroid glands.

As used herein, the phrase "endocrine tumor" refers to a tumor derived from cells that release a hormone.

The phrase "pathological condition" as used herein, refers to a medical condition (e.g., a disease or a syndrome) including but not limited to cardiac pathological conditions, cancer and infection.

The phrase "myocardial ischemia" as used herein, refers to a state of inadequate blood supply to the heart, associated with impairment in the relaxation and contraction of the myocardium.

The term "schizophrenia" as used herein refers to a psychiatric disorder that includes at least two of the following: delusions, hallucinations, disorganized speech, grossly disorganized or catatonic behavior, or negative symptoms. Patients can be diagnosed as schizophrenic using the DSM-IV criteria (APA, 1994, Diagnostic and Statistical Manual of Mental Disorders (Fourth Edition), Washington, D.C.).

The term "Parkinson's disease" as used herein refers to a neurodegenerative disease associated with the destruction of brain cells that produce dopamine.

As used herein, the phrase "bone marrow activation" refers to an up-regulation of any of the functions of the bone marrow.

The term "osteomyelitis" refers to any inflammation of the bone marrow and adjacent bone.

Single photon emission computerized tomography (SPECT) and positron emission tomography (PET) are well known nuclear imaging systems in medicine. Generally, in nuclear imaging, a radioactive isotope is injected to, inhaled by or ingested by a patient. The isotope, provided as a radioactive-labeled pharmaceutical (radio-pharmaceutical) is selected based on bio-kinetic properties that cause preferential uptake by different tissues. The gamma photons emitted by the radio-pharmaceutical are detected by radiation detectors outside the body, giving its spatial and uptake distribution within the body, with little trauma to the patient.

SPECT imaging is based on the detection of individual gamma rays emitted from the body, while PET imaging is based on the detection of gamma-ray pairs that are emitted in coincidence, in opposite directions, due to electron-positron annihilations. In both cases, data from the emitted photons is used to produce spatial images of the "place of birth" of a detected photon and a measure of its energy.

Because PET imaging collects emission events, in the imaginary tubular section enclosed by the PET detectors, while SPECT imaging is limited to the solid collection angles defined by the collimators, generally, PET imaging has a higher sensitivity and spatial resolution than does SPECT. In PET, photon detectors also provide an indication of the time when a photon is detected.

It is possible to design SPECT imaging cameras with the sensitivity and resolution of PET imaging cameras. Furthermore, SPECT cameras comprising high spectral resolution are also available enabling their use in dual and multiple isotope studies. Voxel dynamic modeling allows the use of SPECT cameras for dynamic studies. For example, U.S. Pat. Appl. No. PCT IL2006/000059 assigned to Spectrum Dynamics LLC discloses the capabilities of a highly sensitive radioactive-emission SPECT camera, a result of a meticulous search for the many different effects that combine synergistically to increase sensitivity and spatial, spectral, and time resolutions.

Inclusion of additional properties to the traditional SPECT imaging cameras requires the design of novel protocols which may be used for nuclear imaging. Such protocols may be used for diagnosing a myriad of diseases providing a higher degree of accuracy than presently used radioimaging protocols.

Thus, according to one aspect of the present invention there is provided a method of radioimaging a myocardial perfusion, the method comprising in sequence:

(a) administering to a subject about 3 mCi Tl201 thallous chloride;
(b) allowing the subject to rest;
(c) radioimaging a heart of the subject;
(d) subjecting the subject to a physical stress;
(e) administering to the subject at a peak of the physical stress about 20-30 mCi Tc99m sestamibi; and
(f) radioimaging the heart of the subject, thereby radioimaging a myocardial perfusion.

According to further features in preferred embodiments of the invention described below, the method comprises at least one or more of the following:

(1) step (b) is for about 10-15 minutes;
(2) step (c) is for about 2 minutes;
(3) step (d) is effected about 2 minutes following step (c);
(4) step (f) is effected about 30-60 minutes following step (d); and
(5) step (f) is for about 2 minutes.

According to still further features in the described preferred embodiments the method is affected as described in Table 1.

According to another aspect of the present invention there is provided a method of radioimaging a myocardial perfusion, the method comprising in sequence:

(a) administering to a subject about 8-10 mCi Tc99m sestamibi;
(b) allowing the subject to rest;
(c) radioimaging a heart of the subject;
(d) subjecting the subject to a physical stress;
(e) administering to the subject at a peak of the physical stress about 20-30 mCi Tc99m sestamibi; and
(f) radioimaging the heart of the subject, thereby radioimaging a myocardial perfusion.

According to further features in preferred embodiments of the invention described below, the method comprises at least one or more of the following:

(1) step (b) is for about 30 minutes;
(2) step (c) is for about 2 minutes;
(3) step (d) is effected immediately following step (c);
(4) step (f) is effected about 30-60 minutes following step (e); and
(5) step (f) is for about 2 minutes.

According to still further features in the described preferred embodiments the method is affected as described in Table 2.

According to yet another aspect of the present invention there is provided a method of radioimaging a myocardial perfusion, the method comprising in sequence:

(a) administering to a subject about 3 mCi Tl201 thallous chloride;
(b) allowing the subject to rest;
(c) radioimaging a heart of the subject;
(d) subjecting the subject to a pharmacological stress;
(e) administering to the subject at a peak of the pharmacological stress about 20-30 mCi Tc99m sestamibi; and
(f) radioimaging the heart of the subject, thereby radioimaging a myocardial perfusion.

According to further features in preferred embodiments of the invention described below, the method comprises at least one or more of the following:

(1) step (b) is for about 2 minutes;
(2) step (c) is for about 2 minutes;
(3) step (d) is effected immediately following step (c);
(4) step (e) is effected about 2 minutes following step (d);
(5) step (f) is effected immediately following step (e);
(6) step (f) is for about 2 minutes; and
(7) the pharmacological stress is adenosine or dipyridamole.

According to still further features in the described preferred embodiments the method is effected as described in Table 3.

According to still another aspect of the present invention there is provided a method of radioimaging a myocardial perfusion, the method comprising in sequence:

(a) administering to a subject about 8-10 mCi Tc99m sestamibi;

(b) radioimaging a heart of the subject;

(c) subjecting the subject to a pharmacological stress;

(d) administering to the subject at a peak of the pharmacological stress about 20-30 mCi Tc99m sestamibi; and (e) radioimaging the heart of the subject, thereby radioimaging a myocardial perfusion.

According to further features in preferred embodiments of the invention described below, the method comprises at least one or more of the following:

(1) step (b) is immediately following step (a);

(2) step (b) is for about 2 minutes;

(3) step (c) is effected immediately following step (b);

(4) step (d) is effected about 2 minutes following step (c);

(5) step (e) is effected immediately following step (d);

(6) step (e) is for about 2 minutes; and (7) the pharmacological stress is adenosine or dipyridamole.

According to still further features in the described preferred embodiments the method is effected as described in Table 4.

According to an additional aspect of the present invention there is provided a method of radioimaging a myocardial perfusion, the method comprising in sequence:

(a) administering to a subject about 3 mCi Tl201 thallous chloride;

(b) allowing the subject to rest;

(c) radioimaging a heart of the subject;

(d) subjecting the subject to a physical stress;

(e) administering to the subject at a peak of the physical stress about 20-30 mCi Tc99m sestamibi; and (f) radioimaging the heart of the subject immediately following the peak stress, thereby radioimaging a myocardial perfusion.

According to further features in preferred embodiments of the invention described below, the method comprises at least one or more of the following:

(1) step (b) is for about 15 minutes;

(2) step (c) is for about 2 minutes;

(3) step (e) is effected about 30-60 minutes following step (d); and (4) step (f) is for about 2 minutes.

According to still further features in the described preferred embodiments the method is effected as described in Table 5.

According to yet an additional aspect of the present invention there is provided method of radioimaging a myocardial perfusion, the method comprising in sequence:

(a) administering to a subject about 20-30 mCi Tc99m sestamibi;

(b) allowing the subject to rest;

(c) radioimaging a heart of the subject;

(d) subjecting the subject to a physical stress;

(e) administering to the subject at a peak of the physical stress about 3 mCi Tl201 thallous chloride;

(f) radioimaging the heart of the subject; and (g) radioimaging the heart of the subject, thereby radioimaging a myocardial perfusion.

According to further features in preferred embodiments of the invention described below, the method comprises at least one or more of the following:

(1) step (b) is for about 15-30 minutes;

(2) step (c) is for about 2 minutes;

(3) step (d) is effected immediately following step (c);

(4) step (f) is effected about 10-15 minutes following step (e);

(5) step (f) is for about 4 minutes;

(6) step (g) is effected about 4 hours following step (f); and (7) step (g) is for about 6 minutes.

According to still further features in the described preferred embodiments the method is effected as described in Table 6.

According to still an additional aspect of the present invention there is provided a method of radioimaging a myocardial perfusion, the method comprising in sequence:

(a) administering to a subject about 3 mCi Tc99m sestamibi;

(b) allowing the subject to rest;

(c) radioimaging a heart of the subject;

(d) subjecting the subject to a pharmacological stress;

(e) administering to the subject at a peak of the pharmacological stress about 3 mCi Tl201 thallous chloride;

(f) radioimaging the heart of the subject; and (g) radioimaging the heart of the subject, thereby radioimaging a myocardial perfusion.

According to further features in preferred embodiments of the invention described below, the method comprises at least one or more of the following:

(1) step (b) is for about 15-30 minutes;

(2) step (c) is for about 2 minutes;

(3) step (d) is effected immediately following step (c);

(4) step (e) is effected about 2 minutes following step (d);

(5) step (f) is effected immediately following step (e);

(6) step (f) is for about 4 minutes;

(7) step (g) is effected about 4 hours following step (f);

(8) step (g) is for about 6 minutes; and (9) the pharmacological stress is adenosine or dipyridamole.

According to still further features in the described preferred embodiments the method is effected as described in Table 7.

According to a further aspect of the present invention there is provided method of radioimaging a myocardial perfusion, the method comprising in sequence:

(a) administering to a subject about 3 mCi Tc99m sestamibi;

(b) radioimaging a heart of the subject;

(c) subjecting the subject to a pharmacological stress;

(d) administering to the subject at a peak of the pharmacological stress about 3 mCi Tl201 thallous chloride;

(e) radioimaging the heart of the subject; and (f) radioimaging the heart of the subject, thereby radioimaging a myocardial perfusion.

According to further features in preferred embodiments of the invention described below, the method comprises at least one or more of the following:

(1) step (b) is effected immediately following step (a);

(2) step (b) is for about 2 minutes;

(3) step (c) is effected immediately following step (b);

(4) step (d) is effected about 2 minutes following step (c);

(5) step (e) is effected immediately following step (d);

(6) step (e) is for about 4 minutes;

(7) step (f) is effected about 4 hours following step (e);

(8) step (f) is for about 6 minutes;

(9) the pharmacological stress is adenosine or dipyridamole.

According to still further features in the described preferred embodiments the method is effected as described in Table 8.

According to yet a further aspect of the present invention there is provided a method of radioimaging a myocardial perfusion, the method comprising in sequence:

(a) administering to a subject about 3 mCi Tc99m sestamibi;

(b) allowing the subject to rest;
(c) radioimaging a heart of the subject;
(d) subjecting the subject to a pharmacological stress;
(e) administering to the subject at a peak of the pharmacological stress about 3 mCi Tl201 thallous chloride;
(f) allowing the subject to rest; and
(g) radioimaging the heart of the subject, thereby radioimaging a myocardial perfusion.

According to further features in preferred embodiments of the invention described below, the method comprises at least one or more of the following:
(1) step (b) is for about 30 minutes;
(2) step (c) is for about 2 minutes;
(3) step (d) is effected immediately following step (c);
(4) step (e) is effected about 2 minutes following step (d);
(5) step (f) is for about 2 minutes;
(6) step (g) is effected immediately following step (f);
(7) step (g) is for about four minutes; and
(8) the pharmacological stress is adenosine or dipyridamole.

According to still further features in the described preferred embodiments the method is effected as described in Table 9.

According to still a further aspect of the present invention there is provided a method of radioimaging a myocardial perfusion, the method comprising in sequence:
(a) administering to a subject about 8-10 mCi Tc99m Teboroxime;
(b) radioimaging a heart of the subject;
(c) subjecting the subject to a pharmacological stress;
(d) administering to the subject at a peak of the pharmacological stress about 20-30 mCi Tc99m Teboroxime; and
(e) radioimaging the heart of the subject, thereby radioimaging a myocardial perfusion.

According to further features in preferred embodiments of the invention described below, the method comprises at least one or more of the following:
(1) step (b) is effected immediately following or during step (a);
(2) step (b) is for about 2-10 minutes;
(3) step (c) is effected immediately following step (b);
(4) step (d) is effected about 2 minutes following step (c);
(5) step (e) is effected immediately following or during step (d);
(6) step (e) is for about 2-10 minutes; and
(7) the pharmacological stress is adenosine or dipyridamole.

According to still further features in the described preferred embodiments the method is effected as described in Table 10.

According to still a further aspect of the present invention there is provided a method of radioimaging a lung perfusion, the method comprising simultaneously:
(a) administering to a subject less than about 5 mCi Tc99m Diethylene triamine-pentacetic acid (DTPA);
(b) administering to a subject less than about 5 mCi Tc99m MAA;
(c) radioimaging a lung of the subject, thereby radioimaging a lung perfusion.

According to further features in preferred embodiments of the invention described below, the method comprises at least one or more of the following:
(1) the Tc99m Diethylene triamine-pentacetic acid (DTPA) is administered via a nebulizer;
(2) step (c) is for about 0-30 minutes;

According to still further features in the described preferred embodiments the method is effected as described in Table 11.

According to still a further aspect of the present invention there is provided a method of radioimaging a bone inflammation or a bone cancer, the method comprising simultaneously:
(a) administering to a subject about 20-30 mCi Tc99m MDP; and
(b) radioimaging a bone of the subject, thereby radioimaging a bone inflammation or a bone cancer.

According to further features in preferred embodiments of the invention described below, the method comprises at least one or more of the following:
(1) step (b) is effected about 0-60 minutes following step (a);
(2) step (b) is for about six minutes.

According to still further features in the described preferred embodiments the method is effected as described in Table 12.

According to still a further aspect of the present invention there is provided a method of radioimaging an inflammatory process, the method comprising in sequence:
(a) administering to a subject about 2-3 mCi In 111 WBC; and
(b) radioimaging the subject, thereby radioimaging an inflammatory process.

According to further features in preferred embodiments of the invention described below, the method comprises at least one or more of the following:
(1) step (b) is effected about 24 hours following step (a).
(2) step (b) is for about 1 minute.

According to still further features in the described preferred embodiments the method is effected as described in Table 13.

According to still a further aspect of the present invention there is provided a method of radioimaging a myocardial perfusion, the method comprising in sequence:
(a) administering to a subject about 0.3 mCi Tl201 thallous chloride;
(b) radioimaging a heart of the subject;
(c) subjecting the subject to a physical stress;
(d) administering to the subject at a peak of the physical stress about 3 mCi Tc99m sestamibi; and
(e) radioimaging the heart of the subject, thereby radioimaging a myocardial perfusion.

According to further features in preferred embodiments of the invention described below, the method comprises at least one or more of the following:
(1) step (b) is effected about 10-15 minutes following step (a);
(2) step (b) is for about 15 minutes;
(3) step (c) is immediately following step (b);
(4) step (e) is effected about 30-60 minutes following step (d); and
(5) step (e) is for about 15 minutes.

According to still further features in the described preferred embodiments the method is effected as described in Table 14.

According to still a further aspect of the present invention there is provided a method of radioimaging a myocardial perfusion, the method comprising in sequence:
(a) administering to a subject about 0.3 mCi Tc99m sestamibi;
(b) radioimaging a heart of the subject;
(c) subjecting the subject to a physical stress;

(d) administering to the subject at a peak of the physical stress about 3 mCi Tc99m sestamibi; and (e) radioimaging the heart of the subject, thereby radioimaging a myocardial perfusion.

According to further features in preferred embodiments of the invention described below, the method comprises at least one or more of the following:

(1) step (b) is effected about 15-30 minutes following step (a);

(2) step (b) is for about 15 minutes;

(3) step (c) is effected immediately following step (b);

(4) step (e) is effected about 30-60 minutes following step (d); and (5) step (e) is for about 15 minutes.

According to still further features in the described preferred embodiments the method is effected as described in Table 15.

According to still a further aspect of the present invention there is provided a method of radioimaging a myocardial perfusion, the method comprising in sequence:

(a) administering to a subject about 0.3 mCi Tl201 thallous chloride;

(b) subjecting the subject to a physical stress;

(c) administering to the subject at a peak of the physical stress about 3 mCi Tc99m sestamibi; and (d) radioimaging a heart of the subject, thereby radioimaging a myocardial perfusion.

According to further features in preferred embodiments of the invention described below, the method comprises at least one or more of the following:

(1) step (b) is effected immediately following step (a);

(2) step (d) is effected about 30-60 minutes following step (c); and (3) step (d) is for about 5-15 minutes.

According to still further features in the described preferred embodiments the method is effected as described in Table 16.

According to still a further aspect of the present invention there is provided a method of radioimaging a myocardial perfusion, the method comprising in sequence:

(a) administering to a subject about 0.3 mCi Tl201 thallous chloride;

(b) radioimaging a heart of the subject (c) subjecting the subject to a pharmacological stress;

(d) administering to the subject at a peak of the pharmacological stress about 3 mCi Tc99m sestamibi; and (e) radioimaging the heart of the subject, thereby radioimaging a myocardial perfusion.

According to further features in preferred embodiments of the invention described below, the method comprises at least one or more of the following:

(1) step (b) is effected about 2 minutes following step (a);

(2) step (b) is for about 15 minutes;

(3) step (c) is effected immediately following step (b);

(4) step (d) is effected about 2 minutes following step (c);

(5) step (e) is effected immediately following step (d);

(6) step (e) is for about 15 minutes; and (7) the pharmacological stress is adenosine or dipyridamole.

According to still further features in the described preferred embodiments the method is effected as described in Table 17.

According to still a further aspect of the present invention there is provided a method of radioimaging a breast cancer, the method comprising in sequence:

(a) administering to a subject about 0.3 mCi Tc99m sestamibi; and (b) radioimaging a breast of the subject, thereby radioimaging a breast cancer.

According to further features in preferred embodiments of the invention described below, the method comprises at least one or more of the following:

(1) step (b) is effected about 15-30 minutes following step (a);

(2) step (b) is for about 15 minutes.

According to still further features in the described preferred embodiments the method is, effected as described in Table 18.

According to still a further aspect of the present invention there is provided a method of radioimaging a brain perfusion, the method comprising in sequence:

(a) simultaneously administering to a subject no more than about 3 mCi Tc99m exametazine (HMPAO), no more than about 3 mCi Tc99m ECD and no more than about 5 mCi I123 isofetamine hydrochloride; and (b) radioimaging a brain of the subject, thereby radioimaging a brain perfusion.

According to further features in preferred embodiments of the invention described below, the method comprises at least one or more of the following:

(1) step (b) is effected about 1 hour following step (a);

(2) step (b) is no more than 30 minutes.

According to still further features in the described preferred embodiments the method is effected as described in Table 19.

According to still a further aspect of the present invention there is provided a method of radioimaging a brain perfusion, the method comprising in sequence:

(a) administering to a subject no more than about 3 mCi Tc99m exametazine (HMPAO); and (b) radioimaging a brain of the subject, thereby radioimaging a brain perfusion.

According to further features in preferred embodiments of the invention described below, the method comprises at least one or more of the following:

(1) step (b) is effected for no more than about 1 hour following step (a);

(2) step (b) is for no more than about 30 minutes.

According to still further features in the described preferred embodiments the method is effected as described in Table 20.

According to still a further aspect of the present invention there is provided a method of radioimaging a brain perfusion, the method comprising in sequence:

(a) administering to a subject no more than about 3 mCi Tc99m ECD; and (b) radioimaging a brain of the subject, thereby radioimaging a brain perfusion.

According to further features in preferred embodiments of the invention described below, the method comprises at least one or more of the following:

(1) step (b) is effected for no more than about 1 hour following step (a);

(2) step (b) is for no more than about 30 minutes.

According to still further features in the described preferred embodiments the method is effected as described in Table 21.

According to still a further aspect of the present invention there is provided a method of radioimaging a brain perfusion, the method comprising in sequence:

(a) administering to a subject no more than about 5 mCi I 123 isofetamine hydrochloride; and (b) radioimaging a brain of the subject, thereby radioimaging a brain perfusion.

According to further features in preferred embodiments of the invention described below, the method comprises at least one or more of the following:

(1) step (b) is effected for no more than about 1 hour following step (a);

(2) step (b) is for no more than about 30 minutes.

According to still further features in the described preferred embodiments the method is effected as described in Table 22.

According to still a further aspect of the present invention there is provided a method of radioimaging a brain perfusion, the method comprising simultaneously:

(a) administering to a subject no more than about 3 mCi Tc99m exametazine (HMPAO); and (b) radioimaging a brain of the subject, thereby radioimaging a brain perfusion.

According to further features in preferred embodiments of the invention described below, step (b) is for no more than 30 minutes.

According to still further features in the described preferred embodiments the method is effected as described in Table 23.

According to still a further aspect of the present invention there is provided a method of radioimaging a brain perfusion, the method comprising simultaneously:

(a) administering to a subject no more than about 3 mCi Tc99m ECD; and (b) radioimaging a brain of the subject, thereby radioimaging a brain perfusion.

According to further features in preferred embodiments of the invention described below, step (b) is for no more than about 30 minutes.

According to still further features in the described preferred embodiments the method is effected as described in Table 24.

According to still a further aspect of the present invention there is provided a method of radioimaging a brain perfusion, the method comprising simultaneously:

(a) administering to a subject no more than about 5 mCi I 123 isofetamine hydrochloride; and (b) radioimaging a brain of the subject, thereby radioimaging a brain perfusion.

According to further features in preferred embodiments of the invention described below, step (b) is for no more than about 30 minutes.

According to still further features in the described preferred embodiments the method is effected as described in Table 25.

According to still a further aspect of the present invention there is provided a method of radioimaging a liver structure, the method comprising simultaneously:

(a) administering to a subject about 0.5 mCi Tc99m mebrofenin; and (b) radioimaging a liver of the subject, thereby radioimaging a liver structure.

According to further features in preferred embodiments of the invention described below, step (b) is for about 30 minutes.

According to still further features in the described preferred embodiments the method is effected as described in Table 26.

According to still a further aspect of the present invention there is provided a method of radioimaging a lung perfusion, the method comprising simultaneously:

(a) administering to a subject no more than about 3 mCi of Tc99m DTPA and no more than 0.5 mCi of MAA or DTPA ln 111; and (b) radioimaging a lung of the subject, thereby radioimaging a lung perfusion.

According to further features in preferred embodiments of the invention described below, step (b) is for about 6 minutes.

According to still further features in the described preferred embodiments the method is effected as described in Table 27.

According to still a further aspect of the present invention there is provided a method of radioimaging a myocardial perfusion (thallium rest), the method comprising simultaneously:

(a) radioimaging a heart of the subject; and (b) administering to a subject about 4 mCi of Tl thallous chloride, thereby radioimaging a myocardial perfusion.

According to further features in preferred embodiments of the invention described below, wherein step (a) is for about 2-20 minutes.

According to still further features in the described preferred embodiments the method is effected as described in Table 28.

According to still a further aspect of the present invention there is provided a method of radioimaging a myocardial perfusion (thallium stress), the method comprising in sequence:

(a) subjecting a subject to a physical or pharmacological stress;

(b) administering to the subject at a peak of the physical stress about 4 mCi Tl201 thallous chloride; and (c) radioimaging a heart of the subject, thereby radioimaging a myocardial perfusion.

According to further features in preferred embodiments of the invention described below, the method comprises at least one or more of the following:

(1) step (c) is effected immediately following step (b); and (2) step (c) is for about 2-20 minutes; and (3) the pharmacological stress adenosine or dipyridamole.

According to still further features in the described preferred embodiments the method is effected as described in Table 29.

According to still a further aspect of the present invention there is provided a method of radioimaging a myocardial perfusion (teboroxime rest), the method comprising simultaneously:

(a) radioimaging a heart of the subject; and (b) administering to a subject about 30 mCi of Tc99m teboroxime, thereby radioimaging a myocardial perfusion.

According to further features in preferred embodiments of the invention described below, step (a) is for about 15 minutes.

According to still further features in the described preferred embodiments the method is effected as described in Table 30.

According to still a further aspect of the present invention there is provided a method of radioimaging a myocardial perfusion (teboroxime stress), the method comprising in sequence:

(a) subjecting a subject to a physical or pharmacological stress;

(b) administering to the subject at a peak of the physical stress about 4 mCi Tc99m Teboroxime; and (c) radioimaging a heart of the subject, thereby radioimaging a myocardial to perfusion.

According to further features in preferred embodiments of the invention described below, the method comprises at least one or more of the following:

(1) step (c) is effected immediately following step (b);

(2) step (c) is for about 2-20 minutes; and (3) the pharmacological stress is adenosine or dipyridamole.

According to still further features in the described preferred embodiments the method is effected as described in Table 31.

According to still a further aspect of the present invention there is provided a method of radioimaging a myocardial perfusion (sestamibi rest), the method comprising simultaneously:

(a) radioimaging a heart of the subject; and (b) administering to a subject about 30 mCi of Tc99m sestamibi, thereby radioimaging a myocardial perfusion.

According to further features in preferred embodiments of the invention described below, step (a) is for about 15 minutes.

According to still further features in the described preferred embodiments the method is effected as described in Table 32.

According to still a further aspect of the present invention there is provided a method of radioimaging a myocardial perfusion (sestamibi stress), the method comprising in sequence:

(a) subjecting a subject to a physical or pharmacological stress;

(b) administering to the subject at a peak of the physical stress about 20-30 mCi of Tc99m sestamibi; and (c) radioimaging a heart of the subject, thereby radioimaging a myocardial perfusion.

According to further features in preferred embodiments of the invention described below, the method comprises at least one or more of the following:

(1) step (c) is effected immediately following step (b); and (2) step (c) is for about 15 minutes; and (3) the pharmacological stress is adenosine or dipyridamole.

According to still further features in the described preferred embodiments the method is effected as described in Table 33.

According to still a further aspect of the present invention there is provided a method of radioimaging a myocardial perfusion (tetrofosmin rest), the method comprising simultaneously:

(a) radioimaging a heart of the subject; and (b) administering to a subject about 30 mCi of Tc99m tetrofosmin, thereby radioimaging a myocardial perfusion.

According to further features in preferred embodiments of the invention described below, step (a) is for about 15 minutes.

According to still further features in the described preferred embodiments the method is effected as described in Table 34.

According to still a further aspect of the present invention there is provided a method of radioimaging a myocardial perfusion (tetrofosmin stress), the method comprising in sequence:

(a) subjecting a subject to a physical or pharmacological stress;

(b) administering to the subject at a peak of the physical stress about 20-30 mCi of Tc99m tetrofosmin; and (c) radioimaging a heart of the subject, thereby radioimaging a myocardial perfusion.

According to further features in preferred embodiments of the invention described below, the method comprises at least one or more of the following:

(1) step (c) is effected immediately following or during step (b);

(2) step (c) is for about 15 minutes; and (3) the pharmacological stress is adenosine or dipyridamole.

According to still further features in the described preferred embodiments the method is effected as described in Table 35.

According to still a further aspect of the present invention there is provided a method of radioimaging a myocardial perfusion (Q12 rest), the method comprising simultaneously:

(a) radioimaging a heart of the subject; and (b) administering to a subject about 30 mCi of Tc99m Q12, thereby radioimaging a myocardial perfusion.

According to further features in preferred embodiments of the invention described below, step (a) is for about 15 minutes.

According to still further features in the described preferred embodiments the method is effected as described in Table 36.

According to still a further aspect of the present invention there is provided a method of radioimaging a myocardial perfusion (Q12 stress), the method comprising in sequence:

(a) subjecting a subject to a physical or pharmacological stress;

(b) administering to the subject at a peak of the physical stress about 30 mCi of Tc99m Q12; and (c) radioimaging a heart of the subject, thereby radioimaging a myocardial perfusion.

According to further features in preferred embodiments of the invention described below, the method comprises at least one or more of the following:

(1) step (c) is effected immediately following step (b);

(2) step (c) is for about 15 minutes; and (3) the pharmacological stress is adenosine or dipyridamole.

According to still further features in the described preferred embodiments the method is effected as described in Table 37.

According to still a further aspect of the present invention there is provided a method of radioimaging a myocardial perfusion (BMIPP-I-123 rest), the method comprising simultaneously:

(a) radioimaging a heart of the subject; and (b) administering to a subject about 5 mCi of BMIPP I-123, thereby radioimaging a myocardial perfusion.

According to further features in preferred embodiments of the invention described below, step (a) is for about 15 minutes.

According to still further features in the described preferred embodiments the method is effected as described in Table 38.

According to still a further aspect of the present invention there is provided a method of radioimaging a myocardial perfusion (BMIPP I-123 stress), the method comprising in sequence:

(a) subjecting a subject to a physical or pharmacological stress;

(b) administering to the subject at a peak of the physical stress about 5 mCi of BMIPP I-123; and (c) radioimaging a heart of the subject, thereby radioimaging a myocardial perfusion.

According to further features in preferred embodiments of the invention described below, the method comprises at least one or more of the following:

(1) step (c) is effected immediately following step (b);

(2) step (c) is for about 15 minutes; and (3) the pharmacological stress is adenosine or dipyridamole.

According to still further features in the described preferred embodiments the method is effected as described in Table 39.

According to still a further aspect of the present invention there is provided a method of radioimaging a myocardial perfusion, the method comprising in sequence:

(a) subjecting a subject to a physical or pharmacological stress;

(b) administering to the subject at a peak of the physical stress about 30 mCi of a radiopharmaceutical; and (c) radioimaging a heart of the subject, thereby radioimaging a myocardial perfusion.

According to further features in preferred embodiments of the invention described below, the method comprises at least one or more of the following:

(1) step (c) is effected immediately following step (b);

(2) step (c) is for about 10 minutes; and (3) the pharmacological stress is adenosine or dipyridamole.

According to still further features in the described preferred embodiments the method is effected as described in Table 40.

According to still a further aspect of the present invention there is provided a method of radioimaging a myocardial perfusion, the method comprising simultaneously:

(a) radioimaging a heart of a subject; and (b) administering to the subject about 30 mCi of a PET radiopharmaceutical, thereby radioimaging a myocardial perfusion.

According to further features in preferred embodiments of the invention described below, the method comprises at least one or more of the following:

(1) step (c) is effected immediately following step (b); and (2) step (c) is for about 10 minutes.

According to still further features in the described preferred embodiments the method is effected as described in Table 41.

According to still a further aspect of the present invention there is provided a method of radioimaging a tumor, the method comprising simultaneously:

(a) radioimaging a tumor of a subject; and (b) administering to the subject about 30 mCi of Tc99m Teboroxime, 30 mCi of Tc99m sestamibi, 30 mCi of Tc99m tetrofosmin or 4 mCi of Tl-201, thereby radioimaging a myocardial perfusion.

According to further features in preferred embodiments of the invention described below, step (a) is no more than about 5 minutes.

According to still further features in preferred embodiments of the invention described below, the method is effected as described in Table 42.

According to still a further aspect of the present invention there is provided a method of radioimaging a tumor, the method comprising simultaneously:

(a) radioimaging a tumor of a subject; and (b) administering to the subject about 4 mCi of Tl201 thallous chloride and no more than about 30 mCi of Tc99m sestamibi, thereby radioimaging a tumor.

According to further features in preferred embodiments of the invention described below, step (a) is no more than about 5 minutes.

According to still further features in the described preferred embodiments the method is effected as described in Table 43.

According to still a further aspect of the present invention there is provided a method of radioimaging a renal function, the method comprising simultaneously:

(a) radioimaging a kidney of a subject; and (b) administering to the subject about 1 mCi of Tc99mDTPA and about 3-10 mCi of Tc99 mMAG3, thereby radioimaging a renal function.

According to further features in preferred embodiments of the invention described below, step (a) is 10 minutes.

According to still further features in the described preferred embodiments the method is effected as described in Table 44.

According to still a further aspect of the present invention there is provided a method of radioimaging a renal function, the method comprising simultaneously:

(a) radioimaging a kidney of a subject; and (b) administering to the subject about 1 mCi of Tc99m DTPA and about 1 mCi of HippuranI-123, thereby radioimaging a renal function.

According to further features in preferred embodiments of the invention described below, step (a) is about 10 minutes.

According to still further features in the described preferred embodiments the method is effected as described in Table 45.

According to still a further aspect of the present invention there is provided a method of radioimaging a brain perfusion, the method comprising simultaneously:

(a) radioimaging a brain of a subject; and (b) administering to the subject about 20 mCi of Tc99m ECD (neurolite) and about 20 mCi of HPMAO 99m labeled and about 5 mCi of Spectaminel123, thereby radioimaging a brain perfusion.

According to further features in preferred embodiments of the invention described below, step (a) is no more than about 30 minutes.

According to still further features in the described preferred embodiments the method is effected as described in Table 46.

According to still a further aspect of the present invention there is provided a method of radioimaging a brain perfusion, the method comprising simultaneously:

(a) radioimaging a brain of a subject; and (b) administering to the subject no more than about 20 mCi of teboroxime, thereby radioimaging a brain perfusion.

According to further features in preferred embodiments of the invention described below, step (a) is no more than 30 minutes.

According to still further features in the described preferred embodiments the method is effected as described in Table 47.

According to still a further aspect of the present invention there is provided a method of radioimaging a liver structure, the method comprising simultaneously:

(a) radioimaging a liver of the subject; and (b) administering to the subject no more than about 5 mCi of Tc99m sulfur colloid, thereby radioimaging a liver structure.

According to further features in preferred embodiments of the invention described below, step (a) is no more than 10 minutes.

According to still further features in the described preferred embodiments the method is effected as described in Table 48.

According to still a further aspect of the present invention there is provided a method of radioimaging a liver function, the method comprising simultaneously:

(a) radioimaging a liver of the subject; and (b) administering to the subject no more than about 10 mCi of Tc99m disida, thereby radioimaging a liver structure.

According to further features in preferred embodiments of the invention described below, step (a) is effected every five minutes for up until 1 hour.

According to still further features in the described preferred embodiments the method further comprises administering an agent for gall bladder contraction 1 hour following step (b).

According to still further features in the described preferred embodiments the method is effected as described in Table 49.

According to still a further aspect of the present invention there is provided a method of radioimaging a gastric emptying, the method comprising simultaneously:

(a) radioimaging a stomach of a subject; and (b) administering to the subject about 3 MBq of Tc99m Sulfer colloid or labeled solid food or 0.5 MBq In-111 DTPA labeled liquid food, thereby radioimaging a gastric emptying.

According to further features in preferred embodiments of the invention described below, step (a) is for a time until the stomach is empty of the labeled food.

According to still further features in the described preferred embodiments the method is effected as described in Table 50.

According to still a further aspect of the present invention there is provided a method of radioimaging a cardiac vulnerable plaque, the method comprising in sequence:

(a) administering to a subject no more than about 5 mCi Tc99m annexin and no more than about 5 mCi Tc99m AccuTec; and (b) radioimaging a blood vessel of the subject, thereby radioimaging a cardiac vulnerable plaque.

According to further features in preferred embodiments of the invention described below, the method comprises at least one or more of the following:

(1) step (b) is effected about 1 hour following step (a);

(2) step (b) is less than about 30 minutes.

According to still further features in the described preferred embodiments the method is effected as described in Table 51.

According to still a further aspect of the present invention there is provided a method of radioimaging for prostate cancer, the method comprising in sequence:

(a) administering to a subject no more than about 5 mCi Prostascint containing 111In capromab pendetide; and (b) radioimaging a prostate of the subject, thereby radioimaging for prostate cancer.

According to further features in preferred embodiments of the invention described below, the method comprises comprising at least one or more of the following:

(1) step (b) is effected about 24-72 hours following step (a);

(2) step (b) is less than 30 minutes.

According to still further features in the described preferred embodiments the method is effected as described in Table 52.

According to still a further aspect of the present invention there is provided a method of radioimaging for SST receptor expressing tumors, the method comprising in sequence:

(a) administering to a subject no more than about 5 mCi Octreotide containing 111 In DTPA; and (b) radioimaging a body of the subject, thereby radioimaging for SST receptor expressing tumors.

According to further features in preferred embodiments of the invention described below, the method comprises at least one or more of the following:

(1) step (b) is effected about 24 hours following step (a);

(2) step (b) is less than about 30 minutes.

According to still further features in the described preferred embodiments the method is effected as described in Table 53.

According to still a further aspect of the present invention there is provided a method of radioimaging for neuroendocrine tumors, the method comprising in sequence:

(a) administering to a subject no more than about 20 mCi Tc99m Neotec; and (b) radioimaging a body of the subject, thereby radioimaging for neuroendocrine tumors.

According to further features in preferred embodiments of the invention described below, the method comprises at least one or more of the following:

(1) step (b) is effected about 1 hour following step (a);

(2) step (b) is less than about 30 minutes;

According to still further features in the described preferred embodiments the method is effected as described in Table 54.

According to still a further aspect of the present invention there is provided a method of radioimaging for thrombii, the method comprising in sequence:

(a) administering to a subject no more than about 20 mCi Tc99m Acutec; and (b) radioimaging blood vessels of the subject.

According to further features in preferred embodiments of the invention described below, the method comprises at least one or more of the following:

(1) step (b) is effected from about 0-20 minutes following step (a);

(2) step (b) is less than about 30 minutes.

According to still further features in the described preferred embodiments the method is effected as described in Table 55.

According to still a further aspect of the present invention there is provided a method of radioimaging a pheochromocytoma and/or myocardial failure, the method comprising in sequence:

(a) administering to a subject no more than about 5 mCi I-123 iofetamine hydrochloride MIBG; and (b) radioimaging an adrenal gland and/or heart of the subject, thereby radioimaging a pheochromocytoma and/or myocardial failure.

According to further features in preferred embodiments of the invention described below, the method comprises at least one or more of the following:

(1) step (b) is effected about 24 hours following step (a);

(2) step (b) is less than about 30 minutes;

According to still further features in the described preferred embodiments the method is effected as described in Table 56.

According to still a further aspect of the present invention there is provided a method of radioimaging a cardiac stress, the method comprising in sequence:

(a) administering to a subject about 4 mCi Tl201 thallous chloride;

(b) radioimaging a heart of the subject;

(c) subjecting the subject to a physical or pharmacological stress, wherein the pharmacological stress is at least one vasodilatory agent; and (d) radioimaging a heart of the subject, thereby radioimaging a cardiac stress.

According to further features in preferred embodiments of the invention described below, the method comprises at least one or more of the following:

(1) step (b) is effected no more than about 2 minutes following step (a);

(2) step (b) is for about 2-5 minutes;

(3) step (c) is effected immediately following step (b);

(4) step (d) is effected no more than about 5 minutes following step (c);

(5) step (d) is for about 2-10 minutes; and (6) the at least one vasodilatory agent is adenosine or dipyridamole.

According to still further features in the described preferred embodiments the method is effected as described in Table 57.

According to still a further aspect of the present invention there is provided a method of radioimaging a renal function, the method comprising in sequence:

(a) administering to a subject about 2-4 mCi DTPA and/or Tc99 mMAG3;

(b) radioimaging a kidney of the subject;

(c) subjecting the subject to a physical and/or at least one pharmacological stress; and (d) radioimaging a kidney of the subject.

According to further features in preferred embodiments of the invention described below, the method comprises at least one or more of the following:

(1) step (b) is for about 10-30 minutes;

(2) step (c) is effected immediately following step (b);

(3) step (d) is for about 10-30 minutes (4) the pharmacological stress is selected from the group consisting of captopril fuside, a vasodilatory agent and a diuretic agent.

According to still further features in the described preferred embodiments the method is effected as described in Table 58.

According to still a further aspect of the present invention there is provided a method of radioimaging to determine Bexaar dosimetry, the method comprising simultaneously:

(a) radioimaging a body of a subject; and (b) administering to the subject about 5 MCi/35 mg of I123 iofetamine hydrochloride, thereby radioimaging to determine Bexaar dosimetry.

According to further features in preferred embodiments of the invention described below, step (a) is for about 5 minutes.

According to still further features in the described preferred embodiments the method is effected as described in Table 59.

According to still a further aspect of the present invention there is provided a method of radioimaging a parathyroid adenoma, the method comprising in sequence:

(a) administering to a subject about 1 mCi thallium 201thallous chloride and about 15 mCi Tc99m pertechnetate;

(b) radioimaging a parathyroid of the subject, thereby radioimaging a parathyroid adenoma.

According to further features in preferred embodiments of the invention described below, the method comprises at least one or more of the following:

(1) step (b) is effected about 10 minutes following step (a); and (2) step (b) is for about 5 minutes.

According to still further features in the described preferred embodiments the method is effected as described in Table 60.

According to still a further aspect of the present invention there is provided a method of radioimaging a parathyroid adenoma, the method comprising in sequence:

(a) administering to a subject about 15 mCi Tc99m sestamibi and about 100 µCi I123;

(b) radioimaging a parathyroid of the subject, thereby radioimaging a parathyroid adenoma.

According to further features in preferred embodiments of the invention described below, the method comprises at least one or more of the following:

(1) step (b) is effected about 10 minutes following step (a); and (2) step (b) is for about 5 minutes.

According to still further features in the described preferred embodiments the method is effected as described in Table 61.

According to still a further aspect of the present invention there is provided a method of radioimaging a thyroid cancer, the method comprising in sequence:

(a) administering to a subject about 10 mCi Tc99m MDP and about 4 mCi I-131;

(b) radioimaging a thyroid of the subject, thereby radioimaging a thyroid cancer.

According to further features in preferred embodiments of the invention described below, the method comprises at least one or more of the following:

(1) step (b) is effected about 2 hours following step (a); and (2) step (b) is for about 30 minutes.

According to still further features in the described preferred embodiments the method is effected as described in Table 62.

According to still a further aspect of the present invention there is provided a method of radioimaging an endocrine tumor, the method comprising in sequence:

(a) administering to a subject about 15 mCi Tc99m MDP and about 4 mCi ln111 octeotride;

(b) radioimaging a body of the subject, thereby radioimaging an endocrine tumor.

According to further features in preferred embodiments of the invention described below, the method comprises at least one or more of the following:

(1) step (b) is effected no more than about 2 hours following step (a); and (2) step (b) is for about 30 minutes.

According to still further features in the described preferred embodiments the method is effected as described in Table 63.

According to still a further aspect of the present invention there is provided a method of radioimaging an endocrine tumor, the method comprising in sequence:

(a) administering to a subject about 4 mCi ln111 octeotride;

(b) administering to a subject about 15 mCi Tc99m MDP;

(c) radioimaging a body of the subject, thereby radioimaging an endocrine tumor.

According to further features in preferred embodiments of the invention described below, the method comprises at least one or more of the following:

(1) step (b) is effected no more than about 3 days following step (a);

(2) step (c) is effected no more than about 2 hours following step (b); and (3) step (c) is for about 30 minutes.

According to still further features in the described preferred embodiments the method is effected as described in Table 64.

According to still a further aspect of the present invention there is provided a method of radioimaging a prostate tumor, the method comprising in sequence:

(a) administering to a subject about 3 mCi ln111 capromab pentitide;

(b) administering to a subject about 15 mCi Tc99m RBCs;

(c) radioimaging a pelvis/abdomen of the subject, thereby radioimaging a prostate tumor.

According to further features in preferred embodiments of the invention described below, the method comprises at least one or more of the following:

(1) step (b) is effected no more than about 3 days following step (a);

(2) step (c) is effected no more than about 2 hours following step (b); and (3) step (c) is for about 30 minutes.

According to still further features in the described preferred embodiments the method is effected as described in Table 65.

According to still a further aspect of the present invention there is provided a method of radioimaging a bone infection, the method comprising in sequence:

(a) administering to a subject about 3 mCi ln111 WBC;

(b) administering to a subject about 15 mCi Tc99m colloid;

(c) radioimaging a bone of the subject, thereby radioimaging a bone infection.

According to further features in preferred embodiments of the invention described below, the method comprises at least one or more of the following:

(1) step (b) is effected no more than 3 days following step (a);

(2) step (c) is effected no more than 2 hours following step (b); and (3) step (c) is for about 30 minutes.

According to still further features in the described preferred embodiments the method is effected as described in Table 66.

According to still a further aspect of the present invention there is provided a method of radioimaging a neck or head cancer invasion of a bone or cartilage, the method comprising in sequence:

(a) administering to a subject about 2 mCi Tl201 thallous chloride and about 15 mCi Tc99m MDP;

(b) radioimaging a bone or cartilage of the subject, thereby radioimaging a neck or head cancer invasion of a bone or cartilage.

According to further features in preferred embodiments of the invention described below, the method comprises at least one or more of the following:

(1) step (b) is effected about 2 hours following step (a); and (2) step (b) is for about 30 minutes.

According to still further features in the described preferred embodiments the method is effected as described in Table 67.

According to still a further aspect of the present invention there is provided a method of radioimaging a pathological condition, the method comprising in sequence:

(a) administering to a subject about 2 mCi ln111 WBCs;

(b) administering to the subject about 1 mCi Tl201 thallous chloride and about 10 mCi Tc99m sestamibi; and (c) radioimaging a body of the subject, thereby radioimaging a pathological condition.

According to further features in preferred embodiments of the invention described below, the method comprises at least one or more of the following:

(1) step (b) is effected about 2 days following step (a); and (2) step (c) is for about 30 minutes.

(3) the pathological condition is selected from the group consisting of an infection, a tumor and a myocardial infection.

According to still further features in the described preferred embodiments the method is effected as described in Table 68.

According to still a further aspect of the present invention there is provided a method of radioimaging a myocardial ischemia, the method comprising in sequence:

(a) administering to a subject about 2 mCi I123 BMIPP;

(b) administering to the subject about 1 mCi Tl201 thallous chloride and about 10 mCi of a Tc99m labeled chemical selected from the group consisting of sestamibi and teboroxime; and (c) radioimaging a heart of the subject, thereby radioimaging a myocardial ischemia.

According to further features in preferred embodiments of the invention described below, the method comprises at least one or more of the following:

(1) step (b) is effected about 48 hours following step (a); and (2) step (c) is for about 30 minutes;

(3) step (c) is effected immediately following step (b).

According to still further features in the described preferred embodiments the method is effected as described in Table 69.

According to still a further aspect of the present invention there is provided a method of radioimaging a pathological condition or a fever of unknown origin, the method comprising in sequence:

(a) administering to a subject about 2 mCi ln111WBC;

(b) administering to the subject about 15 mCi 99m Fanoselomab; and (c) radioimaging a body of the subject, thereby radioimaging a pathological condition or a fever of unknown origin.

According to further features in preferred embodiments of the invention described below, the method comprises at least one or more of the following:

(1) step (b) is effected about 24 hours following step (a); and (2) step (c) is for about 30 minutes.

(3) step (c) is effected immediately following step (b).

According to still further features in the described preferred embodiments the method is effected as described in Table 70.

According to still a further aspect of the present invention there is provided a method of radioimaging to indicate schizophrenia or Parkinson's disease, the method comprising in sequence:

(a) administering to a subject about 2 mCi I123 IBZM;

(b) administering to the subject about 15 mCi Tc99m HMPAO; and (c) radioimaging a brain of the subject, thereby radioimaging to indicate schizophrenia or Parkinson's disease.

According to further features in preferred embodiments of the invention described below, the method comprises at least one or more of the following:

(1) step (b) is effected about 24 hours following step (a); and (2) step (c) is for about 30 minutes.

(3) step (c) is effected immediately following step (b).

According to still further features in the described preferred embodiments the method is effected as described in Table 71.

According to still a further aspect of the present invention there is provided a method of radioimaging a tumor, a tumor perfusion and/or for differentiating a tumor from infection the method comprising in sequence:

(a) administering to a subject about 2 mCi ln111 WBC;

(b) administering to the subject Tc99m sestamibi, Tc99m Arcitumo Mab and Tl201 thallous chloride; and (c) radioimaging an organ and/or a body of the subject, thereby radioimaging a tumor.

According to further features in preferred embodiments of the invention described below, the method comprises at least one or more of the following:

(1) step (b) is effected about 24 hours following step (a);
(2) step (c) is for about 30 minutes;
(3) step (c) is effected about 5 minutes following step (b);
(4) a dose of Tc99m sestamibi and Tc99m Arcitumo Mab is each about 10 mCi; and
(5) a dose of Tl201 thallous chloride is about 1 mCi.

According to still further features in the described preferred embodiments the method is effected as described in Table 72.

According to still a further aspect of the present invention there is provided a method of radioimaging a renal function, the method comprising in sequence:

(a) administering to a subject about 2 mCi Iln111 DTPA;
(b) administering to the subject about 15 mCi Tc99m MAG3; and
(c) radioimaging a kidney of the subject, thereby radioimaging a renal function.

According to further features in preferred embodiments of the invention described below, the method comprises at least one or more of the following:

(1) step (b) is effected about 24 hours following step (a);
(2) step (c) is for about 30 minutes;
(3) step (c) is effected about 5 minutes following step (b);

According to still further features in the described preferred embodiments the method is effected as described in Table 73.

According to still a further aspect of the present invention there is provided a method of radioimaging a tumor perfusion, the method comprising in sequence:

(a) administering to a subject about 1 mCi Tl thallous chloride;
(b) administering to the subject about 15 mCi Tc99m teboroxime or about 15 mCi Tc99m sestamibi; and
(c) radioimaging an organ of the subject, thereby radioimaging a tumor perfusion.

According to further features in preferred embodiments of the invention described below, the method comprises at least one or more of the following:

(1) step (b) is effected simultaneously with step (a);
(2) step (c) is for about 30 minutes;
(3) step (c) is effected immediately following step (b);

According to still further features in the described preferred embodiments the method is effected as described in Table 74.

According to still a further aspect of the present invention there is provided a method of radioimaging a myocardial perfusion and apoptosis in blood vessel plaque, the method comprising in sequence:

(a) administering to a subject about 1 mCi Tl thallous chloride;
(b) administering to the subject about 15 mCi Tc99m Annexin; and
(c) radioimaging a heart and blood vessels of the subject, thereby radioimaging a myocardial perfusion and apoptosis in blood vessel plaque.

According to further features in preferred embodiments of the invention described below, the method comprises at least one or more of the following:

(1) step (b) is effected simultaneously with step (a);
(2) step (c) is for about 30 minutes;
(3) step (c) is effected less than about 1 hour following step (b);

According to still further features in the described preferred embodiments the method is effected as described in Table 75.

According to still a further aspect of the present invention there is provided a method of radioimaging to differentiate between infection and bone marrow activation, the method comprising in sequence:

(a) administering to a subject about 2 mCi ln111WBC;
(b) administering to the subject about 15 mCi Tc99m sulfur colloid; and
(c) radioimaging a body of the subject, thereby radioimaging a tumor perfusion.

According to further features in preferred embodiments of the invention described below, the method comprises at least one or more of the following:

(1) step (b) is effected about 24 hours following step (a);
(2) step (c) is for about 30 minutes;
(3) step (c) is effected immediately following step (b);

According to still further features in the described preferred embodiments the method is effected as described in Table 76.

According to still a further aspect of the present invention there is provided a method of radioimaging an osteomyelitis, the method comprising in sequence:

(a) administering to a subject about 2 mCi ln111WBC;
(b) administering to the subject about 15 mCi Tc99m MDP; and
(c) radioimaging a bone of the subject, thereby radioimaging an osteomyelitis.

According to further features in preferred embodiments of the invention described below, the method comprises at least one or more of the following:

(1) step (b) is effected about 24 hours following step (a);
(2) step (c) is for about 30 minutes;
(3) step (c) is effected immediately following step (b);

According to still further features in the described preferred embodiments the method is effected as described in Table 77.

According to still a further aspect of the present invention there is provided a method of radioimaging an inflammation, the method comprising in sequence:

(a) administering to a subject about 5 mCi Gallium 67;
(b) administering to the subject about 15 mCi ln111WBCs; and
(c) radioimaging a body of the subject, thereby radioimaging an inflammation.

According to further features in preferred embodiments of the invention described below, the method comprises at least one or more of the following:

(1) step (b) is effected simultaneously with step (a);
(2) step (c) is for about 30 minutes; and
(3) step (c) is effected about 72 hours following step (b).

According to still further features in the described preferred embodiments the method is effected as described in Table 78.

According to still a further aspect of the present invention there is provided a method of radioimaging a myocardial perfusion and apoptosis in blood vessel plaque, the method comprising in sequence:

(a) administering to a subject about 2 mCi ln111 annexin;
(b) administering to the subject about 15 mCi Tc99m teboroxime or about 2 mCi Tl201 thallous chloride; and
(c) radioimaging a heart of the subject, thereby radioimaging a myocardial perfusion and apoptosis in blood vessel plaque.

According to further features in preferred embodiments of the invention described below, the method comprises at least one or more of the following:

(1) step (b) is effected about 24 hours following step (a);
(2) step (c) is for about 30 minutes;
(3) step (c) is effected no more than about 3 minutes following step (b);

According to still further features in the described preferred embodiments the method is effected as described in Table 79.

According to still a further aspect of the present invention there is provided a method of radioimaging a myocardial perfusion, the method comprising in sequence:

(a) administering to a subject about 2 mCi Tl201 thallous chloride;
(b) administering to the subject about 15 mCi Tc99m pyrophosphate; and
(c) radioimaging a heart of the subject, thereby radioimaging a myocardial infusion.

According to further features in preferred embodiments of the invention described below, the method comprises at least one or more of the following:

(1) step (b) is effected simultaneously with step (a);
(2) step (c) is for about 30 minutes; and
(3) step (c) is effected about 1 hour following step (b).

According to still further features in the described preferred embodiments the method is effected as described in Table 80.

A method of radioimaging a myocardial perfusion, the method comprising simultaneously:

(a) radioimaging a heart of the subject; and
(b) administering to a subject about 15 mCi of Tc99m pyrophsophate and about 2 mCi of Tl201 thallous chloride, thereby radioimaging a myocardial perfusion.

According to further features in preferred embodiments of the invention described below, step (a) is for about 30 minutes.

According to still further features in the described preferred embodiments the method is effected as described in Table 81.

According to still a further aspect of the present invention there is provided a method of radioimaging a myocardial perfusion or cardiac vulnerable plaque, the method comprising simultaneously:

(a) administering to a subject about 5 mCi ln111 annexin;
(b) administering to the subject about 5 mCi Tc99m Accutec;
(c) subjecting the subject to a pharmacological stress;
(d) administering to the subject about 1 mCi Tl201 thallous chloride; and
(e) radioimaging a heart and blood vessels of the subject, thereby radioimaging a myocardial perfusion or cardiac vulnerable plaque.

According to further features in preferred embodiments of the invention described below, the method comprises at least one or more of the following:

(1) step (b) is effected about 24 hours following step (a);
(2) step (c) is effected immediately following step (b);
(3) the pharmacological stress is adenosine or dipyridamole;
(4) step (d) is effected about 2 minutes following step (c);
(5) step (e) is for about 30 minutes.

According to still further features in the described preferred embodiments the method is effected as described in Table 82.

According to still a further aspect of the present invention there is provided a method of radioimaging a glucose metabolism, the method comprising simultaneously:

(a) administering to a subject about 30-50 mCi FDG; and
(b) radioimaging a body of the subject, thereby radioimaging a glucose metabolism.

According to further features in preferred embodiments of the invention described below, the method comprises at least one or more of the following:

(1) step (b) is effected immediately following step (a); and
(2) step (b) is for less than about 30 minutes.

According to still further features in the described preferred embodiments the method is effected as described in Table 83.

The protocols of the present invention are further exemplified in the Examples section which follows.

The protocols of the present invention generally comprise administration of a radiopharmaceutical to a subject followed by imaging of a target organ. A waiting period may be added between the two steps to allow for distribution of the radioisotope in the body and clearance from organs such as the liver. According to various protocols of the present invention, the subject is also subjected to either a physical or pharmacological stress. In some case the subject may be subjected to both stresses (in sequence) in a single imaging protocol.

These individual steps may be further customized according to a patient's specific parameters. Thus, the dose of the radiopharmaceutical, waiting time/resting time, length of physical stress, degree of physical stress, dose of pharmacological stress and/or acquisition time may all be further fine-tuned and adjusted (customized) according to specific patient parameters. Examples of such parameters include, but are not limited to the patient's age, patient's sex, BMI, rate of metabolism, smoking, the nature of therapeutic treatments which the patient has undergone and the patient's medical condition (e.g. blood pressure, pregnancy, breast feeding, diabetes).

Thus, for some applications, one or more of the following parameters of the radiopharmaceutical agent are customized:
the dose, or for multiple radiopharmaceutical agents, the respective doses;
the radioactivity;
for cocktails, the ratio of the different radiopharmaceutical agents; and/or
the volume of the dose, or for multiple radiopharmaceutical agents, the volumes of the respective doses.

For some applications, one or more of the following parameters of the administration are customized:
the dose administered, or for multiple radiopharmaceutical agents, the respective doses per administration;
the type of administration, e.g., a single bolus, a plurality of boluses (e.g., two boluses), pulsatile administration, or constant drip administration;
the labeled radiopharmaceutical agent for each administration, whether a single agent or a cocktail of agents;
the time of the administration with respect to the time of imaging;
the timings of multiple administrations with respect to each other and with respect to other activities, such as rest or stress (physical or pharmacological);
the administration device, e.g., a syringe, a dual-needle syringe, a pump, or an IV line; and/or
the mode of administration, e.g., manual, automatic, or computer driven.

Further details on customization are provided in FIGS. 99A-E.

As mentioned, all the protocols of the present invention comprise administration of at least one radiopharmaceutical.

Selection of a radiopharmaceutical for imaging a particular process/organ is dependant on its distribution in the body. For example $^{201}$Tl Thallium Chloride mimics the biochemical and physiological distribution of potassium in the heart muscle and thus may be used to radioimage cardiac perfusion. The myocardial uptake of Tc99m sestamibi appears to occur by a passive diffusion process. The rate of passive uptake is determined by the membrane permeability of the radiopharmaceutical and the surface area of the vascular beds to which it is exposed; thus myocardial uptake is related to myocardial blood flow. While the mechanism of myocardial retention is not completely understood, it has been suggested that Tc99m sestamibi is trapped in the proximity of the mitochondria mostly due to its charge. Other radiopharmaceuticals suitable for cardiac imaging include but are not limited to Tc99m teboroxime and Tc99m tetrofosmine. When injected at rest, these radiopharmaceuticals accumulate in viable myocardial tissue; infarcts are thus delineated as areas of lack of accumulation. When injected at stress (either exercise or pharmacologic vasodilation), they accumulate in myocardial tissue in relation to myocardial blood flow; thus ischemic areas (e.g., those supplied by stenotic vessels) are detected as areas of less accumulation.

According to the protocols of the present invention, Tc99m sestamibi may also be used to image tumors such as parathyroid and thyroid tumors and breast cancer. Although the precise mechanism of tumor localization is unclear, it has been suggested that Tc99m sestamibi passively crosses cell membranes and is concentrated primarily within cytoplasm and mitochondria. It has been proposed that malignant cells, because of their increased metabolic rate, maintain greater negative mitochondrial and transmembrane potentials, thus enhancing intracellular accumulation of Tc99m sestamibi. In thyroid glands with hyperthyroidism, blood flow and the number of mitochondria are increased, which may explain the uptake of Tc99m sestamibi in hyperthyroid glands. Localization of Tc99m sestamibi appears to be dependent on blood flow to the tissue, the concentration of Tc99m sestamibi presented to the tissue, and the size of the gland.

The radiopharmaceuticals used in the protocols of the present invention may be dispensed to the subject using any mode of administration. Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. Typically, the radiopharmaceuticals are administered parenterally. Thus, the radiopharmaceuticals described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

According to some aspects of the present invention, two radiopharmaceuticals are administered simultaneously to a subject. Typically, the radiopharmaceuticals are administered one after the other, preferably in separate syringes and not administered as a co-formulation.

It will be appreciated that the dose of the radiopharmaceutical may be selected from a range of acceptable low, medium or high doses, as further described hereinbelow. Preferred doses of radiopharmaceuticals used in each protocol are provided in the Examples section which follows. It should be appreciated, though, that each of the protocols of the present invention may also be practiced using other doses which fall under their corresponding low, medium or high doses. The doses provided in Tables 1-83 of the Examples section hereinbelow have been grouped into low range, medium range and high range doses as detailed infra.

An exemplary range of a low dose of tagged Tc 99m is up to about 20 mCi or more specifically about 2-12 mCi e.g. about 3.

An exemplary range of a medium dose of tagged Tc 99m is between about 20-30 mCi or more specifically about 22-28 mCi e.g. about 25 mCi.

An exemplary range of a high dose of tagged Tc 99m is above 30 mCi or more specifically 30-40 mCi e.g. 35+/−25%.

An exemplary range of a low dose of tagged Tl 201 is up to about 1 mCi or more specifically about 0.1-0.5 mCi e.g. about 0.3 mCi.

An exemplary range of a medium dose of tagged Tl 201 is between about 1-3 mCi or more specifically about 1.5-2.5 mCi e.g. about 2 mCi.

An exemplary range of a high dose of tagged Tl 201 is above about 3 mCi or more specifically about 3-5 mCi e.g. about 4 mCi.

An exemplary range of a low dose of tagged In 111 is up to about 2 mCi or more specifically about 0.5-1.5 mCi e.g. about 1 mCi.

An exemplary range of a medium dose of tagged In 111 medium dose is between about 2-3 mCi or more specifically about 2.2-2.8 mCi e.g. about 2.5 mCi.

An exemplary range of a high dose of tagged In 111 is above about 3 mCi or more specifically about 3-5 mCi e.g. about 4 mCi.

An exemplary range of a low dose of tagged I 123 is up to above 5 mCi or more specifically about 2-4 mCi e.g. about 3 mCi.

An exemplary range of a medium dose of tagged I 123 is between about 5-10 mCi or more specifically about 6-8 mCi e.g. about 7 mCi.

An exemplary range of a high dose of tagged I 123 is above about 10 mCi or more specifically about 10-15 mCi e.g. about 13 mCi.

An exemplary range of a low dose of tagged Gallium is up to about 5 mCi or more specifically about 2-4 mCi e.g. about 3 mCi.

An exemplary range of a medium dose of tagged Gallium is between about 5-10 mCi or more specifically about 6.5-8.5 mCi e.g. about 7 mCi.

An exemplary range of a high dose of tagged Gallium is above about 10 mCi.

An exemplary range of a medium dose of free I 123 medium is between about 0.05-2 mCi or more specifically between about 0.1-0.5 mCi e.g. about 0.25 mCi.

An exemplary range of a high dose of free I 123 is above about 2 mCi or more specifically about 2-5 mCi e.g. about 3 mCi.

The radiopharmaceuticals used in the protocols of the present invention are all commercially available. For example, thallous chloride tl201 is commercially available from Mallinckrodt Inc, St. Louis, U.S.A. $^{18}$fluorine-labeled-2-fluoro-2-deoxyglucose is commercially available from such Companies as Health Imaging Isotopes. Tc99m Sestamibi is commercially available as Cardiolite®, or Miraluma® (Bristol Myers Squib—Medical Imaging) and Tc99m tetrofosmin is commercially available as Myoview, (Amersham Int.). I-123 BMIPP is a fatty acid imaging agent that has been available in Japan for many years, and is currently in Phase III clinical trials in the United States.

As mentioned above, the protocols of the present invention may comprise administration of a pharmacological agent. Typically, such pharmacological agents are administered by infusion I.V.

Regardless of the radioisotope employed, concomitantly with of following radioisotope administration, radioimaging is effected. Since the imaging technique is performed in vivo, preferably nuclear imaging is utilized.

Generally, nuclear imaging is aimed at visualizing molecular and cellular processes occurring in living tissues. As such, nuclear imaging typically serves as a medical tool for measuring signals of molecules within the tissue and thus for generating quantitative images of physiological, biochemical and pharmacological function.

PET or SPECT imaging may be used to execute the protocols of the present invention. Preferably SPECT radioimaging is performed. SPECT imaging detects isotopes that decay by electron capture and/or gamma emissions. Certain proton-rich radioactive isotopes, such as $^{123}$I and Tc99m are capable of capturing an orbiting electron, transforming a proton to a neutron [Sorenson J A, and Phelps M E. Philadelphia: W. B. Saunders; 1987]. The resulting daughter nucleus often remains residually excited. This meta-stable arrangement subsequently dissipates, thereby achieving a ground state and producing a single gamma photon in the process. Because gamma photons are emitted directly from the site of decay, no comparable theoretical limit on spatial resolution exists for SPECT. However, instead of coincidence detection, SPECT utilizes a technique known as collimation [Jaszczak R J. Boca Raton: CRC Press; (1991): 93-118]. A collimator may be thought of as a lead block containing many tiny holes that is interposed between the subject and the radiation detector. Given knowledge of the orientation of a collimator's holes, the original path of a detected photon is linearly extrapolated and the image is reconstructed by computer-assisted tomography.

Position tracking devices per se are well known in the art and may use any one of a plurality of approaches for the determination of position in a three-dimensional space as is defined by a system of coordinates in three and up to six degrees-of-freedom. Some position tracking devices employ movable physical connections and appropriate movement monitoring devices to keep track of positional changes. Thus, such devices, once zeroed, keep track of position changes to thereby determine actual positions at all times.

Radioactive emission detectors are well known in the art and may use any one of a number of approaches for the determination of the amount of radioactive emission emanating from an object or portion thereof. Depending on the type of radiation, such detectors typically include substances which when interacting with radioactive decay emitted particles emit either electrons or photons in a level which is proportional over a wide linear range of operation to the level of radiation impinging thereon. The emission of electrons or photons is measurable and therefore serves to quantitatively determine radiation levels. Solid-state radioactive emission detectors include CdZnTe detectors, CdTe detectors, HgI detectors, Si detectors, Ge detectors. etc. Scintillation detectors include NaI(Tl) detectors, GSO detectors, CsI detectors, CaF detectors, etc. Also known are gas detectors and scintillation fiber detectors.

Thus, as now afforded by the present embodiments, connecting one or more radioactive emission detectors to the position tracking system permits simultaneous radioactivity detecting and position tracking at the same time. This enables the accurate calculation of the shape, size and contour of the radiating object and its precise position in a three-dimensional space.

Preferably, the SPECT cameras used in the protocols of the present invention have a high sensitivity and resolution.

Properties which may be combined to increase a traditional SPECT imaging camera's sensitivity and resolutions include:

1. solid collection angles greater than 0.1 or 0.15 steradians;
2. close proximity of the detectors to the body, in order to increase both:
i. detection efficiency, which falls as a proportionally to the square of the distance from an object; and
ii. resolution, where the number of detector pixels which view an object also falls proportionally to the square of the distance from the object;
3. windshield-wiper sweeping motions, with a center of rotation outside the patient's body, to maximize the information obtained from each x; y; z detector position;
4. trio-vision of each voxel, wherein each voxel is viewed with x, y, and z, components, as opposed to stereo vision in a plane, with only x and y components of state-of-the-art cameras;
5. Focus on a region of interest, by:
i. prescanning;
ii. independent motion of detectors, for independent focusing on ROI, by each detector;
iii. applying algorithm which select a preferred set of views to for ROI focusing, based on the geometry of the organ to be imaged;
iv. zooming in, by a second algorithm tic iteration, to select a preferred set of views based on earlier findings;
v. active vision, which ensures that each detector obtains the maximum information from any position;
6. calibration sources, which may be placed on the body, within a body lumen, or near the camera;
7. the use of the calibration sources of (6) to obtain an attenuation map;
8. ultrasound-based, or MRI based attenuation correction;
9. ultrasound-based attenuation correction using ultrasound patches, such as patch-sensor devices, described in U.S. Pat. Nos. 5,807,268; 5,913,829 and 5,885,222, all of which are assigned to MedAcoustics, Inc., Raleigh, N.C., USA, both for structural mapping, for correlating the structural map with the functional map, and for attenuation correction. The ultrasound patches may be incorporated with the radiopharmaceutical calibration sources; and
10. minimal multiplexing between the detectors and the analyzer, to prevent saturation;

The camera may comprise a plurality of detectors, each of which is coupled to a respective angular orientator. Each of the detectors comprises a plurality of gamma ray sensors, such as a pixelated CZT array, and a collimator. For example, the array may include 16×64 pixels. A control unit drives, typically separately, each of the orientators to orient its respective detector in a plurality of orientations with respect to a region of interest (ROI). The control unit produces a SPECT image from a plurality of radiation acquisitions acquired with the detectors in different relative orientations.

The camera may be configured to begin an image acquisition procedure by performing a relatively brief, preliminary scan, and, based on the results of this preliminary scan, to determine one or more parameters of the full image acquisition procedure, such as dwell time per orientation of each detector. Typically, this determination further takes into account imaging protocol and/or patient-specific information received by imaging system from patient-specific data carrier, such as the activity of the labeled radiopharmaceutical agent at the time of administration, the time of administration, the patient's BMI (which may be used to estimate a perfusion percentage), and the pharmacokinetics of the labeled radiopharmaceutical agent.

In another embodiment, the camera may be configured to individually set a total angular range of each of the detectors responsively to the detector's orientation with respect to the ROI. For example, at least one detector closer to the ROI (a "proximal detector" or an "inner detector") may have a greater total angular range than at least one detector further from the ROI (a "distal detector" or an "outer detector"). The distal detectors are typically located nearer to the ends of a frame holding the detectors, while the proximal detectors are typically located nearer to center of the frame. The use of narrower angular ranges for some of the detectors generally reduces the photon acquisition time spent by these detectors in orientations aimed outside of the ROI. Alternatively, at least one distal detector has a greater total angular range than at least one proximal detector. In order to reduce the total angular range for a given detector, the camera typically drives the associated angular orientator to: (a) increase the dwell time of the detector in at least a portion of its orientations, and/or (b) reduce the angle by which the detector is moved during each orienting of the detector. For some applications, the camera sets the angular range of the detectors based on protocol information received by imaging system from patient-specific data carrier. For example, the number of distal and proximal detectors, and their respective angular ranges, may be specified by the protocol information.

The camera may also comprise a plurality of detectors, each of which is coupled to a respective angular orientator. Each of the detectors comprises a plurality of gamma ray sensors, such as a pixelated CZT array, and a collimator. The control unit drives, typically separately, each of the orientators to orient its respective detector in a plurality of orientations with respect to a region of interest (ROI). The control unit produces a SPECT image from a plurality of radiation acquisitions acquired with the detectors in different relative orientations.

In another embodiment, the camera is configured to drive one of the orientators to move its respective detector through a plurality of sequential angular positions, e.g., positions 1, 2, 3, . . . , 18, 19, and 20. Typically, a linear relationship relates the sequential positions, such that, for example, positions 1, 2, 3, . . . , 20 represent 1°, 2°, 3°, . . . , 20°, or, 2°, 4°, 6°, . . . , 40°. Alternatively, a non-linear relationship relates the sequential positions. Higher or lower angular resolutions are typically obtainable, as well.

For some applications, the camera steps the orientator in a first pass through a subset of the positions spanning most of the range of positions, and in a second pass the camera steps the orientator through a different subset of the positions. At each position, data are acquired by the detector. For example, during the first pass, the camera may drive the orientator to step through positions 1, 5, 9, 13, and 17, and the detector acquires data at each of these positions. During the second pass, the orientator steps through positions 2, 6, 10, 14, and 18. During two subsequent passes, data are acquired at the remainder of the positions. In this manner, a single-direction interlaced scan of the data is acquired by camera 452.

In an embodiment, a back-and-forth interlaced scan is acquired in which data are sampled when the orientator is moving in both directions. For example, during the first pass, the camera may drive the orientator to step through positions 1, 5, 9, 13, and 17. During the second pass, the orientator steps through positions 18, 14, 10, 6, and 2. During the third pass, the orientator steps through positions 3, 7, 11, 15, and 19, while during the fourth pass, the orientator steps through positions 20, 16, 12, 8, and 4. Fifth and higher passes, if desired, typically repeat the motions used in the earlier passes.

For some applications, the positions in a pass are not ordered from lowest-to-highest or highest-to-lowest. For example the positions of a pass may be 1, 15, 11, 19, and 17. Typically, the positions are, however, distributed generally evenly throughout the range of positions, in order to acquire photon counts representative of the entire region of interest.

As appropriate for a given scanning protocol using interlaced scanning, one or more, or even all of the orientators are driven to step through their respective positions in an interlaced fashion.

Typically, execution of an interlaced scan as provided by these embodiments of the present invention allows an operator of the camera, such as an imaging technician or other healthcare worker, to acquire a high-resolution image of the ROI in about 105% to 115% of the amount of time as would be used if orientator 456 were stepped through the positions sequentially. (Typically, each orientation takes between about 50 and about 200 msec, depending upon the angle of the step.) The high-resolution image is completely acquired after the orientator has stepped through each of its positions. In some cases, additional value is attained by interlacing the scanning, however, as this allows the performance of dynamic studies, in which a plurality of images are acquired during a respective plurality of the time periods, i.e., during each complete pass of the orientator. Although each these images is typically of lower resolution than the high-resolution image acquired using photon counts acquired during all of the passes, the images nevertheless have sufficient resolution to produce clinically-meaningful data for each time period of a dynamic study.

For some applications, interlacing the scanning allows an operator to see an initial, lower-resolution scan of the ROI. If, for example, an adjustment of any form is desired, this can often be seen within the first few seconds of a scan. The present scan is terminated, the adjustment made, and a second scan initiated. In the absence of interlacing, it is typically necessary to wait until a scan has completed until an assessment of the scan's results can be made.

For some applications, it is desirable to know whether the patient has moved during a scan. Patient movement is one reason for lower quality images, and when identified it can typically be corrected by suitable instruction and then a second scanning procedure initiated. Interlaced scanning, as provided by these embodiments of the present invention, allows the operator to immediately assess whether there has been patient movement between one pass and a subsequent pass. In an embodiment, the imaging system displays to an operator the scans obtained from the various passes in rapid succession at the same location on a monitor. As appropriate, the imaging system cycles quickly through the scans repeatedly (e.g., pass 1, pass 2, pass 3, pass 4, pass 1, pass 2, pass 3, pass 4 . . . ), e.g., displaying each scan for between about 0.2 and about 2 seconds, allowing an operator to see whether there is jitter between successive scans. If so, patient movement is typically the cause and image acquisition is repeated. For some applications, the scan is acquired in exactly two passes, e.g., the orientator steps through positions 1, 3, 5, . . . , 19 during a first pass, and through positions 2, 4, 6, . . . , 20 during a second pass, or through positions 20, 18, 16, . . . , 2 during the second pass.

Images acquired using these techniques, or other non-interlacing techniques described herein, are generally used to perform one or more of the following image reconstructions: (a) reconstruction of intensity image, (b) reconstruction of intensity over time, followed by fitting a model of the kinetics (which describe for each voxel a parameter set describing its time curve), and followed by presenting a three-dimensional map of the parameters, and/or (c) direct reconstruction of a three-dimensional parametric representation, without performing a reconstruction of an intensity map, typically by plugging an equation of a kinetic model into a reconstruction algorithm, and generating a result directly in terms of the value of the parameters per voxel (the parameters may include, for example, flow, diffusion coefficients, metabolism rate, or bio-clearance rate).

The camera sensitivity may be determined by at least one of the following:

1. a sensitivity in terms of speed of data collection and spatial resolution, at least as good as a gold standard for PET imaging for at rest myocardial perfusion with N-13-ammonia ($NH_3$);

2. a sensitivity sufficient for reconstructing an image under a Cobalt wire Nema test of a line source of 5 mCi cobalt with a line spread function of less than 7 mm Full Width Half Maximum (FWHM) through air at a distance of at least 100 mm;

3. a sensitivity sufficient for resolving through air at a distance of at least 100 mm under a Nema Bar Phantom test of gaps formed between 1 mm wide led bars positioned less than 7 mm apart from one another over a uniform cobalt disc;

4. a sensitivity operative for image acquisition of a full organ in less than 10 seconds at a spatial resolution, capable of identifying objects not greater than about 7 mm×7 mm×7 mm with a signal-to-noise ratio of at least 4 to 1 or better;

5. a sensitivity for detecting at least 1 out of every 5000 emitted photons while allowing a reconstructions of a 3D image with a resolution of not more than 5 mm and energy resolution of not more than 15%; and 6. having a sensitivity to image a volume of about 5 cm diameter located about 150 mm from the detectors, with a total sensitivity of about 1 photons detected out of 65 emitted.

According to some embodiments of the aspects of the present invention, the SPECT imaging apparatus comprises voxel kinetic compartmental modeling allowing its use for dynamic studies i.e. a quantitative measurement of flow. Alternatively, or additionally, a two step imaging for dynamic studies may be performed, based on small anatomic region of interest. For example, as a first step, conventional injection and imaging is performed, using standard voxel division, for example, of 5×5×5 mm, to obtain an image of the target, for example, the heart.

An anatomical region of interest is then defined on the image, and a new voxel map is generated, along the anatomical boundary lines. The anatomical region of interest may be a small portion of the overall image.

As a second step, a second injection is made, followed by scanning with detecting recourses aimed at the anatomical region of interest.

In a way, this approach is suggestive of a zooming in approach, for example, as taught in commonly owned PCT/IL2005/001173. But there, voxel reconstruction was rigorous throughout, and here, the first step employs cubical voxels, as known, but these are used to define anatomical voxels for the second step.

Several radioimaging protocols may be employed for this purpose, for example, as follows:

Step 1: a first injection, for example, a single bolus of a first marker, such as Tl-201, at a low dose of between 0.5 and 2 mCi, and imaging the heart for example, for about 1 minutes, to acquire a high quality image, to be used for constructing the anatomical image, and for defining a finer region of interest; and Step 2: while the patient is immobile, injecting 20-40 mCi, preferably of a second marker, for example, Tc-99m-sestamibi, and performing an up to 10 minute dynamic study, with image reconstruction every several seconds, for example, every 5 or 10 or 20 seconds, the dynamic image being superimposed on the first image.

On the one hand, when the image reconstruction is anatomically defined, the number of variables decrease drastically, for example, by a factor of 10;

Additionally, where only a small anatomically defined region is of interest, the scanning sweep is considerably shortened.

Both these factors together reduce the scanning time necessary for obtaining informative images for the anatomically defined region of interest.

In consequence, the two step rigorous-to-anatomic protocol is a highly effective technique for dynamic studies, providing anatomically reconstructed data, at very short time intervals of several seconds, and enabling the acquisition of kinetic parameters of specific tissues and across different tissues.

It will be appreciated that other markers may be used, and for other durations, provided the basic scheme of a first image for defining the anatomical boundaries, and the second image for dynamic reconstruction of anatomical voxels is maintained.

According to a particular embodiment the imaging apparatus is a high-definition SPECT camera, for example, which during imaging, is capable of acquiring at least one of 5000 photons emitted from the region of interest during the image acquisition procedure, such as at least one of 4000, 3000, 2500, 2000, 1500, 1200, 1000, 800, 600, 400, 200, 100, or 50 photons emitted from the region of interest. In one particular embodiment, the camera is capable of acquiring at least one of 2000 photons emitted from the ROI during the image acquisition procedure.

According to another embodiment, the imaging apparatus is a high-definition SPECT camera, for example, which during imaging, is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI having a volume of no more than 500 cc, such as a volume of no more than 500 cc, 400 cc, 300 cc, 200 cc, 150 cc, 100 cc, or 50 cc. In one particular embodiment, the camera is capable of acquiring at least 1,000,000 photons emitted from a volume of the region of interest having a volume of no more than 200 cc A particularly preferred imaging apparatus which may be used during the protocols of the present invention is that taught in PCT IL2006/000059 assigned to Spectrum Dynamics LLC.

Whichever camera is selected for use, the imaging parameters may be specifically tailored to an individual subject. For instance, individual detector integration time may be set according to the patient BMI, injected dose and time of injection. According to one embodiment of this aspect of the present invention, patients are categorized into 3 or more different groups based on BMI and individual detector integration times are set accordingly. Detector span may also be individually customized according to the physical characteristics of the patient (e.g. chest width) and the size of the region of interest specified in the protocol.

Thus, for some applications, one or more of the following parameters of the imaging procedure are customized. For some applications, such parameters are separately specified for individual components of the camera of the imaging system or groups of components.

- total acquisition time, and/or acquisition time for a plurality of phases of acquisition;
- detector scanning plan, including detector motions, such as detector angular and translational motions, detector step size (i.e., the density of the step size, typically expressed in degrees), number of detectors utilized for image acquisition, and detector dwell time at each view;
- detector sensitivity;
- detection energy resolution;
- detector calibration plan;
- definition of the region of interest (ROI);
- gating parameters;
- energy bands, i.e., a plurality of non-overlapping energy windows;
- collimator positioning, shape, structure, and orientation;
- multiple/interlaced scans;
- zooming parameters;
- uniformity/non-uniformity of scan;
- Compton scatter map calculation and correction parameters;
- optimal energy window;
- optimal energy resolution, i.e., the range of energy level windows for which detection is enabled; and/or
- adaptivity of scan pattern to acquired counts, e.g., active vision parameters (as described in the above-mentioned International Application PCT/IL2005/001173).

Similarly, in some embodiments, the protocols are performed with a range of acquisition durations (total scan times). It will be appreciated that the duration of the acquisition time (or any other time mentioned in the protocols e.g., resting, waiting) may be selected from a range of acceptable short, medium or long durations, as further described hereinbelow. Preferred acquisition time durations used in each protocol are provided in the Examples section which follows. It should be appreciated, though, that each of the protocols of the present invention may also be practiced using other acquisition durations which fall under their corresponding short, medium or long times as further exemplified for a single organ in Table 84 of the Examples section hereinbelow and for a whole body/multisegment scan in Table 85 of the Examples section hereinbelow. A typical duration of a dynamic study may last from about 5 sec-30 min, about 10 sec-20 min, about 20 sec-10 min, about 30 sec-7 min, about 60 sec-360 sec, about 90 sec-240 sec, for example about 120 sec.

Other protocol values, such as waiting times, energy windows/resolution, angular range, angular step, and dwell time, may also have a range from 50%, 75%, 90%, or 100% of the value given for the respective protocol, up to 5 times the value given for the respective protocols.

The protocols of the present invention may be selected according to a patient's indications, physical status and medical condition. The cardiac imaging protocols of the present invention may comprise a single imaging stage or two imaging stages. Such cardiac imaging protocols typically differentiate between healthy cardiac tissue and scarred or poorly perfused cardiac tissue. Perfusion defects that appear after exercise or pharmacologic stress suggest either vascular occlusion or myocardial infarction. For some applications, such studies are performed gated to the patient's ECG, in order to study cardiac wall motion. Wall motion studies allow calculation of key cardiac function parameters, such as ejection fraction and estimated cardiac output.

In respective embodiments of the present invention, all of the protocols described herein and/or in the co-assigned patent applications incorporated herein by reference are enabled to generate clinically-valuable images. A "clinically-valuable image" is an image of an intra-body region of interest (ROI) containing the labeled radiopharmaceutical agent(s), which image may be used for diagnosing a disease and/or evaluating a treatment regimen.

The image may have a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the labeled radiopharmaceutical agent as distributed within the ROI has a range of emission-intensities R (which is measured as emitted photons/unit time/volume), and wherein at least 50% of the voxels of the reconstructed three-dimensional emission-intensity image of the ROI have inaccuracies of less than 30% of range R, such as less than 25%, 20%, 15%, 10%, 5%, 2%, 1%, or 0.5% of range R. For example, the agent may emit over a range from 0 photons/second/cc to 105 photons/second/cc, such that the range R is 105 photons/second/cc, and at least 50% of the voxels of the reconstructed three-dimensional intensity image of the ROI have inaccuracies of less than 15% of range R, i.e., less than 1.5×104 photons/second/cc. For some applications, the study produce a parametric image related to a physiological process occurring in each voxel. In one particular embodiment, the image has a resolution of at least 5×5×5 mm, and at least 50% of the voxel have inaccuracies of less than 15% of range R;

The image may be generated according to a protocol, including at the radiopharmaceutical dose and image acquisition duration specified by the protocol, the image has a resolution of at least 7×7×7 mm, such as at least 6×6×6 mm, 5×5×5 mm, 4×4×4 mm, 4×3×3 mm, or 3×3×3 mm, wherein the labeled radiopharmaceutical agent has a range of intensities R (photons/unit time/volume), and wherein at least 50% of the voxels of the reconstructed three-dimensional intensity image of the ROI have inaccuracies of less than 30% of range R, such as less than 25%, 20%, 15%, 10%, 5%, 2%, 1%, or 0.5% of range R. For some applications, the study produce a parametric image related to a physiological process occurring in each voxel; and/or The image may also have a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values R, and wherein at least 50% of the voxels of the reconstructed parametric three-dimensional image have inaccuracies less than 100% of range R, such as less than 70%, 50%; 40%, 30%, 25%, 20%, 15%, 10%, 5%, 2%, 1%, or 0.5% of range R. For example, the physiological process may include blood flow, the values of the parameters of the physiological process may have a range from 0 to 100 cc/minute, such that the range R is 100 cc/minute, and at least 50% of the voxels of the reconstructed parametric three-dimensional image have inaccuracies less than 25% of range R, i.e., less than 25 cc/minute. In one particular embodiment, the image has a resolution of at least 5×5×5 mm, and at least 50% of the voxels have inaccuracies of less than 25% of range R.

The information gleaned from the protocols of the present invention may be used for diagnosis of a disease or disorder. Accordingly, using the imaging data obtained from the protocols of the present invention, together with other criteria such as age, obesity, cholesterol level, HDL and LDL levels, smoking, and the like which are well known to those skilled in the art, a skilled artisan will be able to predict the likelihood that the subject will develop a vascular disease or disorder or is at risk for developing a vascular disease or disorder. Following obtaining an accurate diagnosis, an appropriate treatment regimen may be selected. The protocols of the present invention may also be used for evaluating a treatment regimen.

Optimization of Treatment

In an embodiment of the present invention, the results of one or more imaging procedures, such as SPECT imaging procedures, are used to optimize a treatment. For some applications, the imaging procedures are performed using imaging protocols described herein, or in the co-assigned applications incorporated herein by reference. For some applications, a therapeutic radiopharmaceutical agent is administered at a low dose, and an imaging procedure, e.g., a SPECT imaging procedure, is performed, such as by using the imaging techniques described herein or in the co-assigned applications incorporated herein by reference, to determine information regarding the uptake of the radiopharmaceutical agent, such as areas in the body at which the radiopharmaceutical agent concentrates, levels of concentration of the radiopharmaceutical, actual bioavailability of the radiopharmaceutical, and kinetic information. This information is used in order to limit the toxicity of a subsequent administration of the radiopharmaceutical agent at a higher, therapeutic dose. For some applications, software calculates the maximum dose of radiopharmaceutical that can be delivered without exceeding the maximum accumulation of the radiopharmaceutical in sensitive organs and/or tissues. The use of this technique thus enables treatment to be customized per patient, rather than relying on textbook curves of bioavailability applicable to large patient populations.

In an embodiment of the present invention, a therapeutic radiopharmaceutical agent is administered at a therapeutically-effective dose, and an imaging procedure, e.g., a SPECT imaging procedure, is performed, such as by using the imaging techniques described herein or in the co-assigned applications incorporated herein by reference, to determine the bioclearance of the radiopharmaceutical. Further treatment sessions are planned based on the determined bioclearance. For example, a subsequent administration of the therapeutic radiopharmaceutical is performed once the concentration of the initially administered dose falls below a certain level, e.g., in particular sensitive organs and/or tissues, and/or in the target organ and/or tissue. Alternatively, the therapeutic radiopharmaceutical agent is administered continuously in a closed loop at a rate determined responsively to the bioclearance of the radiopharmaceutical, as determined periodically or substantially continuously by imaging. For some applications, such continuous administration is configured to maintain a generally constant level of the radiopharmaceutical in the target organ or tissue, or another desired time curve of concentration.

In an embodiment of the present invention, a method for treating a patient comprises applying a therapy to the patient (either a drug therapy or a non-drug therapy), administering a radiopharmaceutical agent to the patient, performing a functional imaging procedure, e.g., a SPECT imaging procedure, on the patient to measure a property indicative of biochemical activity of at least one tissue of the patient, and modifying at least one parameter of the therapy responsively to the measured biochemical activity, typically to optimize the therapy and/or customize the therapy for the patient, either on a long- or short-term basis. For some applications, this technique is used to monitor: (a) a therapeutic effect of a therapy (e.g., an antibiotic or a chemotherapy agent) on target cells, tissue, or an organ, and/or (b) an undesired effect of the therapy on non-target cells, tissue, or organs. For some applications, such monitoring is performed by repeating the imaging procedure at least once per day, such as at least once per hour, at least once per minute, at least once per ten second period, or substantially continuously during administration of the therapy. The measured property of the tissue may include, for example, size, perfusion, a marker of viability or apoptosis, an inflammatory process, metabolism, expression of specific proteins and/or mRNA, or cancer-specific activity. Modifying the parameter of the therapy may include, for example, increasing or decreasing dose, changing a cycle of the therapy, or changing a timing of the therapy. For some applications, the method comprises keeping records of the measured properties. For some applications, at least one parameter of the imaging process is customized, such as a parameter of the radiopharmaceutical (e.g., a dose), a parameter of image acquisition (e.g., timing), a parameter of administration of the radiopharmaceutical agent (e.g., timing of administration), or a parameter of image analysis.

The functional imaging procedure is typically a high sensitivity imaging procedure, e.g., a SPECT imaging procedure, which is typically performed using the imaging techniques described herein or in the co-assigned applications incorporated herein by reference. Such high sensitivity enables both the observation of the effect of the therapy on the target tissue, and adverse side effects of the therapy on non-target tissue. In addition, such high sensitivity enables the use of a low dose of the radiopharmaceutical agent, which allows the imaging procedure to be safely repeated a plurality of times, if necessary, without exceeding maximum radiation exposure limits. For some applications, the use of such high-sensitivity imaging procedures enables the monitoring of long-term processes ordinarily not detectible using cameras having conventional resolutions.

In an embodiment, the therapy includes administering a cocktail of drugs having differing respective therapeutic benefits and side effects. These techniques are used to determine doses and/or relative doses of the plurality of drugs in the cocktail, in order to achieve an optimized, customized balance between the benefits and side-effects of each of the drugs, for a specific patient or group of patients. In contrast, the relative doses of drugs in conventional cocktail therapies are typically pre-defined for all patients, rather than customized for each individual patient or group of patients.

A number of drugs suffer from lack of specificity because they do not sufficiently distinguish target cells from non-target cells when applied to an entire patient population. However, customization of the dose of such drugs for a particular patient enables the drugs to sufficiently distinguish target cells from non-target cells. For example, if a certain drug binds to target cells on average ten times more than it does to non-target cells, but the patient-to-patient variability is 50 times, it may be impossible to determine a single recommended dose that would apply to all patients, and the drug thus may not receive regulatory approval. Using the techniques described herein, a precise dose of the drug is determined for the specific patient, which dose is high enough to be therapeutically effective in the specific patient, but as low as possible to avoid side effects for the specific patient. Alternatively or additionally, these techniques are used during a drug development process, a regulatory approval process, or thereafter to determine recommended doses for segments of a population upon which the drug has differing effects.

Reagents of the above-described protocols can be incorporated into a commercial kit or system for imaging as further described hereinbelow, detecting, and evaluating the herein described medical conditions such as cardiac plaques and tumors as described herein. In addition, reagent of the herein described protocols can be incorporated into a kit for determining myocardial perfusion in response to treatment measures. For example, the kit may contain radiopharmaceutical and pharmacological agents and instructions for use and may further contain directions on the administration and use of such agents in conjunction with the appropriate imaging technology and dosage requirement for the intended use.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

This application claims the benefit of:
International Application PCT/IL2005/001215, filed Nov. 16, 2005;
International Application PCT/IL2005/001173, filed Nov. 9, 2005,
U.S. Application 60/700,318, filed Jul. 19, 2005;
U.S. Application 60/700,299, filed Jul. 19, 2005;
U.S. Application 60/700,317, filed Jul. 19, 2005;
U.S. Application 60/700,753, filed Jul. 20, 2005;
U.S. Application 60/700,752, filed Jul. 20, 2005;
U.S. Application 60/702,979, filed Jul. 28, 2005;
U.S. Application 60/720,034, filed Sep. 26, 2005;
U.S. Application 60/720,652, filed Sep. 27, 2005;
U.S. Application 60/720,541, filed Sep. 27, 2005,
U.S. Application 60/750,287, filed Dec. 13, 2005;
U.S. Application 60/750,334, filed Dec. 15, 2005;
U.S. Application 60/750,597, filed Dec. 15, 2005;
U.S. Application 60/800,845, filed May 17, 2006;
U.S. Application 60/800,846, filed May 17, 2006;
Israel Application 171346, filed Oct. 10, 2005;
Israel Application 172349, filed Nov. 27, 2005;
U.S. Application 60/741,440, filed Dec. 2, 2005;
International Application PCT/IL2006/000059, filed Jan. 15, 2006;
U.S. Application 60/763,458, filed Jan. 31, 2006;
International Application PCT/IL2006/000562, filed May 11, 2006; and
U.S. Application 60/799,688, filed May 11, 2006;
U.S. Application 60/816,970, filed Jun. 28, 2006; and
Information of all of which is herein incorporated in entirety by reference.

This application further incorporates by reference all the information of the International Application entitled "RECONSTRUCTION STABILIZER AND ACTIVE VISION" which is being co-filed by the same assignee of the present invention on Jul. 19, 2006.

EXAMPLES

Reference is now made to the following examples, which together with the above descriptions, illustrate the invention in a non limiting fashion.

Example 1

Exemplary Imaging Protocols

TABLE 1

Description: A fast, dual isotope, imaging protocol
Indication: Myocardial perfusion

| Length of time | Patient flow | Radiopharmaceutical | Dose (mCi) | Mode of administration | Type of stress |
|---|---|---|---|---|---|
| 10-15 min | Injection | Tl 201 thallous chloride | Medium dose for example 3 | Bolus IV | |
| 2 min | Rest Imaging | | | | |
| variable | Stress Peak stress injection | Tc 99m sestamibi | Medium dose for example 20-30 | Bolus IV | Physical |
| 30-60 min | waiting | | | | |
| 2 min | Imaging | | | | |

Timeframe summary:
Total imaging time: 4 min.
Total patient time: 60-90 min.
Clinical protocol advantages: fast imaging time compared to standard imaging methods.

TABLE 2

Description: A fast, single isotope, imaging protocol
Indication: Myocardial perfusion

| Length of time | Patient flow | Radiopharmaceutical | Dose (mCi) | Mode of administration | Type of stress |
|---|---|---|---|---|---|
| | Injection | Tc 99m sestamibi | Low dose for example 8-10 | Bolus IV | |

TABLE 2-continued

Description: A fast, single isotope, imaging protocol
Indication: Myocardial perfusion

| Length of time | Patient flow | Radiopharmaceutical | Dose (mCi) | Mode of administration | Type of stress |
|---|---|---|---|---|---|
| 30 min | rest | | | | |
| 2 min | imaging | | | | |
| variable | Stress | | | | physical |
| | Peak stress injection | Tc 99m sestamibi | Medium dose for example 20-30 | Bolus IV | |
| 30-60 min | waiting | | | | |
| 2 min | Imaging | | | | |

Timeframe summary:
Total imaging time: 4 min.
Total patient time: 60-90 min.
Clinical protocol advantages: Fast imaging time compared to standard imaging methods.

TABLE 3

Description: An ultra fast, dual isotope, imaging protocol
Indication: Myocardial perfusion

| Length of time | Patient flow | Radiopharmaceutical | Dose (mCi) | Mode of administration | Type of stress |
|---|---|---|---|---|---|
| | Injection | Tl 201 thallous chloride | Medium dose for example 3 | Bolus IV | |
| 2 min | rest | | | | |
| 2 min | imaging | | | | |
| 2 min | Stress | | | Infusion IV | Pharmacological - for example adenosine or dipyridamole |
| | Peak stress injection | Tc 99m sestamibi | Medium dose for example 20-30 | Bolus IV | |
| 2 min | Imaging | | | | |

Timeframe summary:
Total imaging time: 4 min.
Total patient time: 20-30 min.

Clinical protocol advantages:

1. Fast imaging time compared to standard imaging methods.

2. Avoidance of liver radioactivity since imaging takes place substantially immediately after injection, before buildup of radioactivity in the liver takes place.

TABLE 4

Description: An ultra fast, single isotope, imaging protocol
Indication: Myocardial perfusion

| Length of Time | Patient flow | Radiopharmaceutical | Dose (mCi) | Mode of administration | Type of stress |
|---|---|---|---|---|---|
| | Injection | Tc 99m sestamibi | low dose for example 8-10 | Bolus IV | |
| 2 min | imaging | | | | |
| 2 min | Stress | | | Infusion IV | Pharmacological - for example adenosine or dipyridamole |
| | Peak stress injection | Tc 99m sestamibi | Medium dose | Bolus IV | |

TABLE 4-continued

Description: An ultra fast, single isotope, imaging protocol
Indication: Myocardial perfusion

| Length of Time | Patient flow | Radiopharmaceutical | Dose (mCi) | Mode of administration | Type of stress |
|---|---|---|---|---|---|
| 2 min | Imaging | | for example 20-30 | | |

Timeframe summary:
Total imaging time: 4 min.
Total patient time: 20-30 min.
Clinical protocol advantages:
1. Fast imaging time compared to standard imaging methods.
2. Avoidance of liver radioactivity since imaging takes place substantially immediately after injection, before buildup of radioactivity in the liver takes place.

Timeframe summary:
Total imaging time: 2 min.
Total patient time: 45-90 min.
Clinical protocol advantages:
1. Fast imaging time compared to standard imaging methods.
2. Dual registration of the two isotopes, when imaged simultaneously avoiding patient movement between acquisitions.

TABLE 5

Description: A dual isotope, simultaneous imaging protocol
Indication: Myocardial perfusion

| Length of Time | Patient flow | Radiopharmaceutical | Dose (mCi) | Mode of administration | Type of stress |
|---|---|---|---|---|---|
| | Injection | Tl 201 thallous chloride | Medium dose for example 3 | Bolus IV | |
| 15 min | rest | | | | |
| 2 min | imaging | | | | |
| 30-60 min | Stress | | | | physical |
| | Peak stress injection | Tc 99m sestamibi | Medium dose for example 20-30 | Bolus IV | |
| 2 min | Imaging | | | | |

TABLE 6

Description: A fast, dual isotope, thallium-stress-perfusion, imaging protocol
Indication: Myocardial perfusion

| Length of time | Patient flow | Radiopharmaceutical | Dose (mCi) | Mode of administration | Type of stress |
|---|---|---|---|---|---|
| | Injection | Tc 99 sestamibi | Medium dose for example 20-30 | Bolus IV | |
| 15-30 min | Rest | | | | |
| 2 min | Imaging | | | | |
| variable | Stress | | | | Physical |
| | Peak stress injection | Tl 201 thallous chloride | Medium dose for example 3 | Bolus IV | |
| 10-15 min | waiting | | | | |
| 4 min | Imaging | | | | |
| 4 hours | waiting | | | | |
| 6 min | imaging | | | | |

Timeframe summary:
Total imaging time: 6 min.
Total patient time: 45-60 min.
Clinical protocol advantages:
1. Fast imaging time compared to standard imaging methods.
2. Better flow linearity.
3. Ability to detect small lesions
4. Ability to determine viability
5. High quality Thallium images

TABLE 7

Description: A fast, dual isotope, Tl-stress-perfusion, imaging protocol
Indication: Myocardial perfusion

| Length of time | Patient flow | Radiopharmaceutical | Dose (mCi) | Mode of administration | Type of stress |
|---|---|---|---|---|---|
| | Injection | Tc 99m sestamibi | low dose for example 3 | Bolus IV | |
| 15-30 min | Rest | | | | |
| 2 min | Imaging | | | | |
| 2 min | Stress | | | Infusion IV | Pharmacological - for example adenosine or dipyridamole |
| | Peak stress injection | Tl 201 thallous chloride | Medium dose for example 3 | Bolus IV | |
| 4 min | Imaging | | | | |
| 4 hours | waiting | | | | |
| 6 min | imaging | | | | |

Timeframe summary:
Total imaging time: 6 min.
Total patient time: 20-30 min. Additional redistribution time of 4 h.
Clinical protocol advantages:
1. Fast imaging time compared to standard imaging methods.
2. Better flow linearity.
3. Ability to detect small lesions
4. Ability to determine viability
5. High quality Thallium images

TABLE 8

Description: An ultra fast, dual isotope, thallium-stress-perfusion
and redistribution, imaging protocol
Indication: Myocardial perfusion

| Length of Time | Patient flow | Radiopharmaceutical | Dose (mCi) | Mode of administration | Type of stress |
|---|---|---|---|---|---|
| | Injection | Tc 99m sestamibi | low dose for example 3 | Bolus IV | |
| 2 min | Imaging | | | | |
| 2 min | Stress | | | Infusion IV | Pharmacological - for example adenosine or dipyridamole |
| | Peak stress injection | Tl 201 thallous chloride | Medium dose for example 3 | Bolus IV | |
| 4 min | Imaging | | | | |
| 4 hours | waiting | | | | |
| 6 min | imaging | | | | |

Timeframe summary:
Total imaging time: 6 min.
Total patient time: 10-20 min. Additional redistribution time of 4 h.
Clinical protocol advantages:
1. Fast imaging time compared to standard imaging methods.
2. Better flow linearity.
3. Ability to detect small lesions
4. Ability to determine viability.
5. A single acquisition.
6. Dual registration of the two isotopes imaged simultaneously avoiding patient movement during acquisition.

TABLE 9

Description: A fast, dual isotope, simultaneous imaging protocol
Indication: Myocardial perfusion

| Length of time | Patient flow | Radiopharmaceutical | Dose (mCi) | Mode of administration | Type of stress |
|---|---|---|---|---|---|
| | Injection | Tc 99m sestamibi | low dose for example 3 | Bolus IV | |
| 30 min | Rest | | | | |
| 2 min | Imaging | | | | |
| 2 min | Stress | | | Infusion IV | Pharmacological - for example adenosine or dipyridamole |
| | Peak stress injection | Tl 201 thallous chloride | Medium dose for example 3 | Bolus IV | |
| 2 min | Rest | | | | |
| 4 min | Imaging | | | | |

Timeframe summary:
Total imaging time: 6 min.
Total patient time: 10-20 min.
Clinical protocol advantages:
1. Fast imaging time compared to standard imaging methods.
2. Single imaging time.
3. Better flow linearity.
4. Ability to detect small lesions
5. A single acquisition.
6. Dual registration of the two isotopes imaged simultaneously avoiding patient movement during acquisition.

TABLE 10

Description: A fast, single isotope, Tc 99m teboroxime imaging protocol
Indication: Myocardial perfusion

| Length of time | Patient flow | Radiopharmaceutical | Dose (mCi) | Mode of administration | Type of stress |
|---|---|---|---|---|---|
| | Injection | Tc 99m Teboroxime | Medium dose for example 8-10 | Bolus IV | |
| 2-10 min | Imaging | | | | |
| 2 min | Stress | | | Infusion IV | Pharmacological - for example adenosine or dipyridamole |
| | Peak stress | Tc 99m Teboroxime | Medium dose for example 20-30 | Bolus IV | |
| 2-10 min | Imaging | | | | |

Timeframe summary:
Total imaging time: 12 min.
Total patient time: 20 min.
Clinical protocol advantages:
Fast imaging time compared to standard imaging methods.

TABLE 11

Description: Lung V/P-DTPA aerosol and macro-aggregated albumin (lung perfusion agent) protocol
Indication: for studying lung perfusion by quantitative parameters

| Length of time | Patient flow | Radiopharmaceutical | Patient relevant diagnosis (diabetes, BP, etc. . . . ) | Dose (mCi) | Mode of administration | Acquisition parameters (detector; windowing, etc.) |
|---|---|---|---|---|---|---|
| | Injection | Tc 99m DTPA | | low dose for example Up to 5 | Bolus IV | |
| | Injection | MAA | | Low dose for example Up to 5 (up to 1 M particles) | Bolus IV | |
| 0-30 min | Imaging | | | | | Energy window 3-15% |

Timeframe summary:
Total imaging time: 12 min.
Clinical protocol advantages:
Fast imaging time compared to standard imaging methods.

TABLE 12

Description: Fast MDP bone scan whole body scan protocol.
Indication: to look for bone cancers or inflammatory processes of the bone (e.g. osteomyelitis)

| Length of time | Patient flow | Radiopharmaceutical | Dose (mCi) | Mode of administration | Acquisition parameters (detector; windowing, etc.) |
|---|---|---|---|---|---|
| | Injection | Tc 99m MDP | Medium dose for example 20-30 | Bolus IV | |
| 0-60 min | Waiting | | | | |
| 6 min | Imaging | | | | Energy window 3-15% |

Timeframe summary:
Total imaging time: 0-60 min.
Clinical protocol advantages:
Fast imaging time compared to standard imaging methods.

TABLE 13

Description: In 111 WBC scan protocol.
Indication: imaging of inflammatory processes

| Length of Time | Patient flow | Radio-pharmaceutical | Dose (mCi) | Mode of admin-istration | Acquisition parameters (detector; windowing, etc.) |
|---|---|---|---|---|---|
| | Injection | In 111 WBC | Medium dose | Bolus IV | |
| | | | for example 2-3 | | |
| 24 h 1 min | Waiting Imaging | | | | Energy window 3-15% |

Timeframe summary:
Total imaging time: 1 min.
Clinical protocol advantages:
Fast imaging time compared to standard imaging methods.

TABLE 14

Description: A low dose, dual isotope, myocardial perfusion imaging protocol
Indication: myocardial perfusion

| Length of Time | Patient flow | Radiopharmaceutical | Dose (mCi) | Mode of administration | Type of stress | Acquisition parameters (detector; windowing, etc.) |
|---|---|---|---|---|---|---|
| | Injection | Tl 201 thallous chloride | low dose for example 0.3 | Bolus IV | | |
| 10-15 min | waiting | | | | | |
| 15 min | Imaging | | | | | Energy window 3-15% |
| variable | Stress Peak stress injection | Tc 99m sestamibi | low dose for example 3 | Bolus IV | physical | |
| 30-60 min | Waiting | | | | | |
| 15 min | Imaging | | | | | Energy window 3-15% |

Timeframe summary:
Total imaging time: 30 min.
Total patient time: 90 min.
Clinical protocol advantages:
1. Fast imaging time compared to standard imaging methods.
2. Low dose. 3. Better spectral resolution.

TABLE 15

Description: A low dose, single isotope, myocardial perfusion imaging protocol
Indication: myocardial perfusion

| Length of Time | Patient flow | Radiopharmaceutical | Dose (mCi) | Mode of administration | Type of stress | Acquisition parameters (detector; windowing, etc.) |
|---|---|---|---|---|---|---|
| | Injection | Tc 99m sestamibi | Low dose for example 0.3 | Bolus IV | | |
| 15-30 min | waiting | | | | | |
| 15 min | Imaging | | | | | Energy window 3-15% |
| variable | Stress Peak stress injection | Tc 99m sestamibi | Low dose for example 3 | Bolus IV | physical | |
| 30-60 min | Waiting | | | | | |
| 15 min | Imaging | | | | | Energy window 3-15% |

Timeframe summary:
Total imaging time: 30 min.
Total patient time: 90 min.
Clinical protocol advantages:
1. Fast imaging time compared to standard imaging methods.
2. Low dose.
3. better spectral resolution

TABLE 16

Description: A low dose, simultaneous dual isotope, imaging protocol
Indication: myocardial perfusion

| Length of Time | Patient flow | Radiopharmaceutical | Dose (mCi) | Mode of administration | Type of stress | Acquisition parameters (detector; windowing, etc.) |
|---|---|---|---|---|---|---|
| | Injection | Tl 201 thallous chloride | Low dose for example 0.3 | Bolus IV | | |
| variable | Stress Peak stress injection | Tc 99m sestamibi | Low dose for example 3-5 | Bolus IV | physical | |
| 30-60 min | Waiting | | | | | |
| 5-15 min | Imaging | | | | | Energy window 3-15% |

Timeframe summary:
Total imaging time: 5-15 min.
Total patient time: 90 min.
Clinical protocol advantages:
1. Fast imaging time compared to standard imaging methods.
2. Low dose.
3. Better spectral resolution
4. Better registration of rest and stress due to avoidance of patient movement

TABLE 17

Description: A low dose, dual isotope, fast imaging protocol
Indication: Myocardial perfusion

| Length of Time | Patient flow | Radiopharmaceutical | Dose (mCi) | Mode of administration | Type of stress | Acquisition parameters (detector; windowing, etc.) |
|---|---|---|---|---|---|---|
| | Injection | Tl 201 thallous chloride | Low dose for example 0.3 | Bolus IV | | |
| 2 min | waiting | | | | | |
| 15 min | Imaging | | | | | Energy window 3-15% |
| 2 min | Stress | | | Infusion IV | Pharmacological - for example adenosine or dipyridamole | |
| | Peak stress injection | Tc 99m sestamibi | Low dose for example 3 | Bolus IV | | |
| 15 min | Imaging | | | | | Energy window 3-15% |

Timeframe summary:
Total imaging time: 30 min.
Total patient time: 45 min.
Clinical protocol advantages:
1. Fast imaging time compared to standard imaging methods.
2. Low dose.

TABLE 18

Description: A low dose, single isotope, breast cancer imaging protocol
Indication: Detection of breast cancer

| Time Since previous step | Patient flow | Radiopharmaceutical | Dose (mCi) | Mode of administration | Acquisition parameters (detector; windowing, etc.) |
|---|---|---|---|---|---|
| | Injection | Tc 99m sestamibi | Low dose for example 0.3 | Bolus IV | |
| 15-30 min | waiting | | | | |
| 15 min | Imaging | | | | Energy window 3-15% |

Timeframe summary:
Total imaging time: 25 min.
Total patient time: 30-45 min.
Clinical protocol advantages:
1. Fast imaging time compared to standard imaging methods.
2. Low dose.
3. Better spectral resolution
4. High resolution breast cancer imaging

TABLE 19

Description: brain perfusion mapping protocol
Indication: Brain perfusion for the diagnosis of brain pathologies such as ischemia, stroke, and types of dementia

| Time Since previous step | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc 99m exametazine (HMPAO) | Low dose for example Up to 3 | Bolus IV | | |
| | Injection | Tc 99m ECD | Low dose for example Up to 3 | Bolus IV | | |
| | Injection | I 123 isofetamine hydrochloride | Low dose for example Up to 5 | Bolus IV | | |
| 1 h | Waiting | | | | | |
| up to 30 min. | imaging | | | | Energy window 3-15% | 1. Mg/min/gr 2. Cerebral flow reserve in rest and stress 3. Parametric quantitation Identification of disease signature |

ECD = N,N'(1'2-ethylenediyl)bis-L-cysteine diethyl ester

Timeframe summary:
Total patient time—Up to 1 h
Clinical protocol advantages:
This protocol can show stroke and other brain pathologies at an early stage and the extent of the event in an accurate way.

TABLE 20

Description: brain perfusion mapping protocol
Indication: Brain perfusion for the diagnosis of brain pathologies such as ischemia, stroke, and types of dementia

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| Up to 1 h | Injection | Tc 99m exametazine (HMPAO) | Low dose for example Up to 3 | Bolus IV | | |
| 0-30 min | Waiting imaging | | | | Energy window 3-15% | Brain perfusion |

Timeframe summary:
Total patient time—up to 1 h
Clinical protocol advantages:
This protocol can show stroke and other brain pathologies at an early stage and the extent of the event in an accurate way.

TABLE 21

Description: brain perfusion mapping protocol
Indication: Brain perfusion for the diagnosis of brain pathologies such as ischemia stroke, and types of dementia

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| Up to 1 h | Injection | Tc 99m ECD | Up to 3 | Bolus IV | | |
| 0-30 min | Waiting imaging | | | | Energy window 3-15% | Brain perfusion |

ECD = N,N'(1'2-ethylenediyl)bis-L-cysteine diethyl ester

Timeframe summary:
Total patient time: up to 1 h
Clinical protocol advantages:
This protocol can show stroke and other brain pathologies at an early stage and the extent of the event in an accurate way.

TABLE 22

Description: brain perfusion mapping protocol
Indication: Brain perfusion for the diagnosis of brain pathologies such as ischemia, stroke, and types of dementia

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | I 123 isofetamine hydrochloride | High dose for example | Bolus IV | | |

TABLE 22-continued

Description: brain perfusion mapping protocol
Indication: Brain perfusion for the diagnosis of brain pathologies such as
ischemia, stroke, and types of dementia

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| Up to 1 h 0-30 min | Waiting imaging | | Up to 5 | | Energy window 3-15% | Brain perfusion |

Timeframe summary:
Total patient time—up to 1 h
Clinical protocol advantages:
This protocol can show stroke and other brain pathologies at an early stage and the extent of the event in an accurate way.

TABLE 23

Description: Dynamic brain perfusion mapping protocol
Indication: Brain perfusion for the diagnosis of brain pathologies such as ischemia,
stroke, and types of dementia

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc 99m exametazine (HMPAO) | Low dose for example Up to 3 | Bolus IV | | |
| 0-30 min | imaging | | | | Energy window 3-15%; detectors sweep the brain every 10-15 seconds | 1. Mg/min/gr 2. Cerebral flow reserve in rest and stress 3. Parametric quantitation Identification of disease signatrue |

Timeframe summary:
Total patient time—up to 30 min
Clinical protocol advantages:
1. This protocol can show stroke at an early stage and the extent of the event in an accurate way.
2. Provides quantitative measurements of blood flow
3. Provides disease signature

TABLE 24

Description: Dynamic brain perfusion mapping protocol
Indication: Brain perfusion for the diagnosis of brain pathologies such as ischemia,
stroke, and types of dementia

| Time Since previous step | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc 99m ECD | Low dose for | Bolus IV | | |

TABLE 24-continued

Description: Dynamic brain perfusion mapping protocol
Indication: Brain perfusion for the diagnosis of brain pathologies such as ischemia, stroke, and types of dementia

| Time Since previous step | Patient flow | Radiopharmaceutical | Dose (mCi) | Mode of administration | Acquisition parameters (detector; windowing, etc.) | Clinical parameters acquired after processing |
|---|---|---|---|---|---|---|
|  |  |  | example Up to 3 |  |  |  |
| 0-30 min | imaging |  |  |  | Energy window 3-15%; detectors sweep the brain every 10-15 seconds | 1. Mg/min/gr 2. Cerebral flow reserve in rest and stress 3. Parametric quantitation Identification of disease signatrue |

ECD = N,N'(1'2-ethylenediyl)bis-L-cysteine diethyl ester

Timeframe summary:
Total patient time—up to 30 min
Clinical protocol advantages:
1. This protocol can show stroke at an early stage and the extent of the event in an accurate way.
2. Provides quantitative measurements of blood flow
3. Provides disease signature

TABLE 25

Description: Dynamic brain perfusion mapping protocol
Indication: Brain perfusion for the diagnosis of brain pathologies such as ischemia, stroke, and types of dementia

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
|  | Injection | I 123 isofetamine hydrochloride | High dose for example Up to 5 | Bolus IV |  |  |
| 0-30 min | imaging |  |  |  | Energy window 3-15%; detectors sweep the brain every 10-15 seconds | 1. Mg/min/gr 2. Cerebral flow reserve in rest and stress 3. Parametric quantitation Identification of disease signatrue |

Timeframe summary:
Total patient time—up to 30 min
Clinical protocol advantages:
1. This protocol can show stroke at an early stage and the extent of the event in an accurate way.
2. Provides quantitative measurements of blood flow
3. Provides disease signature

TABLE 26

Description: Dynamic hepatobiliary imaging
Indication: studying the structure of the liver including identification of hemangiomas, abscesses, and liver enlargement.

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| 0 | Injection | Tc 99m mebrofenin | Low dose for example 0.5 | Bolus IV | | |
| 30 min | imaging | | | | Energy window 3-15%; detectors sweep the region of interest every 10-15 seconds | 1. Fluid flow 2. rate of tracer uptake (passive or active) 3. accumulation and redistribution of tracer 4. tracer metabolism 5. secretion and or washout of tracer or metabolite (passive or active) |

Timeframe summary:
Total imaging time: 30 min.
Total patient time: 30 min.

TABLE 27

Description: lung V/P DTPA aerosol and macro aggregated albumin (lung perfusion agent) protocol)
Indication: for studying lung perfusion

| Length of Time | Patient flow | Radiopharmaceutical | Dose (mCi) | Mode of administration | Acquisition parameters (detector; windowing, etc.) |
|---|---|---|---|---|---|
| | Injection | Tc 99m DTPA | Low dose for example Up to 3 (up to 1 M particles) | Bolus IV | |
| | Injection | MAA or DTPA In 111 | Up to 0.5 | Bolus IV | |
| 6 min | imaging | | | | Energy window 3-15% |

Timeframe summary:
Total imaging time: 6 min.
Total patient time: 6 min.
Clinical protocol advantages:
Fast imaging time compared to standard imaging methods.

TABLE 28

Description: Dynamic myocardial perfusion (thallium rest) protocol
Indication: imaging of cardiac perfusion under rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tl 201 thallous chloride | High dose for example 4 | Bolus IV | | 1. Ml/min/gr 2. coronary flow reserve 3. parametric quantitation |
| 2-20 min | Imaging | | | | Energy window 3-15%; detectors sweep the region of interest every 10-15 seconds | |

Timeframe summary:
Total imaging time: 2-20 min.
Total patient time: 2-20 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 29

Description: Dynamic cardiac perfusion (thallium stress) protocol
Indication: imaging of cardiac perfusion under stress conditions

| Time Since previous step | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| Variable | Stress | | | Infusion IV | Physical or pharmacological - for example adenosine or dipyridamole | | |
| 2-20 min | Injection at peak stress imaging | Tl 201 thallous chloride | High dose for example 4 | Bolus IV | | Energy window 3-15%; detectors sweep the region of interest every 10-15 seconds | 1. Ml/min/gr 2. coronary flow reserve 3. parametric quantitation |

Timeframe summary:
Total imaging time-2-20 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 30

Description: Dynamic cardiac perfusion (teboroxime rest) protocol
Indication: imaging of cardiac perfusion under rest conditions

| Length of time | Patient flow | Radiopharmaceutical | Dose (mCi) | Mode of administration | Acquisition parameters (detector; windowing, etc.) | Clinical parameters acquired after processing |
|---|---|---|---|---|---|---|
|  | Injection | Teboroxime | medium dose for example 30 | Bolus IV |  | 1. Ml/min/gr 2. coronary flow reserve 3. parametric quantitation |
| 15 min | Imaging |  |  |  | Energy window 3-15%; detectors sweep the region of interest every 10-15 seconds |  |

Timeframe summary:
Total imaging time: 2-20 min.
Total patient time: 2-20 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 31

Description: Dynamic cardiac perfusion (teboroxime stress) protocol
Indication: imaging of cardiac perfusion under stress conditions

| Length of Time | Patient flow | Radio Pharmaceutical | Dose (mCi) | Mode of administration | Type of stress | Acquisition parameters (detector; windowing, etc.) | Clinical parameters acquired after processing |
|---|---|---|---|---|---|---|---|
| variable | Stress |  |  |  | Physical or pharmacological - for example adenosine or dipyridamole |  |  |
| 2-20 min | Injection at peak stress imaging | Teboroxime | Low dose for example 4 | Bolus IV |  | Energy window 3-15%; detectors sweep the region of interest every 10-15 seconds | 1. Ml/min/gr 2. coronary flow reserve 3. parametric quantitation |

Timeframe summary:
Total imaging time-2-20 min.
Total patient time-2-20 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 32

Description: Dynamic cardiac perfusion (sestamibi rest) protocol
Indication: imaging of cardiac perfusion under rest conditions

| Length of time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc 99m sestamibi | Medium dose for example 30 | Bolus IV | | 1. Ml/min/gr 2. coronary flow reserve 3. parametric quantitation |
| 15 min | Imaging | | | | Energy window 3-15%; detectors sweep the region of interest every 10-15 seconds | |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 33

Description: Dynamic cardiac perfusion (sestamibi stress) protocol
Indication: imaging of cardiac perfusion under stress conditions

| Length of time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| Variable | Stress | | | Infusion IV | Physical or pharmacological - for example adenosine or dipyridamole | | |
| | Injection at peak stress | Tc 99m sestamibi | Medium dose for example 30 | Bolus IV | | | |
| 15 min | imaging | | | | | Energy window 3-15%; detectors sweep the region of | 1. Ml/min/gr 2. coronary flow reserve 3. parametric |

TABLE 33-continued

Description: Dynamic cardiac perfusion (sestamibi stress) protocol
Indication: imaging of cardiac perfusion under stress conditions

| Length of time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| | | | | | | interest every 10-15 seconds | quantitation |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 34

Description: Dynamic cardiac perfusion (tetrofosmin rest) protocol
Indication: imaging of cardiac perfusion under rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | tetrofosmin | Medium dose for example 30 | Bolus IV | | 1. Ml/min/gr 2. coronary flow reserve 3. parametric quantitation |
| 15 min | Imaging | | | | Energy window 3-15%; detectors sweep the region of interest every 10-15 seconds | |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 35

Description: Dynamic cardiac perfusion (tetrofosmin stress) protocol
Indication: imaging of cardiac perfusion under stress conditions

| Length of Time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| variable | Stress | | | Infusion IV | Physical or pharmacological- | | |

TABLE 35-continued

Description: Dynamic cardiac perfusion (tetrofosmin stress) protocol
Indication: imaging of cardiac perfusion under stress conditions

| Length of Time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| | | | | | for example adenosine or dipyridamole | | |
| | Injection at peak stress | tetrofosmin | Medium dose for example 30 | Bolus IV | | | |
| 15 min | imaging | | | | | Energy window 3-15%; detectors sweep the region of interest every 10-15 seconds | 1. Ml/min/gr 2. coronary flow reserve 3. parametric quantitation |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 36

Description: Dynamic cardiac perfusion (Q12 rest) protocol
Indication: imaging of cardiac perfusion under rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc 99m sestamibi | Medium dose for example 30 | Bolus IV | | 1. Ml/min/gr 2. coronary flow reserve 3. parametric quantitation |
| 15 min | Imaging | | | | Energy window 3-15%; detectors sweep the region of interest every 10-15 seconds | |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 37

Description: Dynamic cardiac perfusion (Q12 stress) protocol
Indication: imaging of cardiac perfusion under stress conditions

| Length of Time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| Variable | Stress | | | Infusion IV | Physical or pharmacological- for example adenosine or dipyridamole | | |
| | Injection at peak stress | Tc sestamibi | Medium dose for example 30 | Bolus IV | | | |
| 15 min | imaging | | | | | Energy window 3-15%; detectors sweep the region of interest every 10-15 seconds | 1. Ml/min/gr 2. coronary flow reserve 3. parametric quantitation |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 38

Description: cardiac perfusion (BMIPP rest) protocol
Indication: Dynamic imaging of cardiac perfusion under rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc 99m sestamibi | Medium dose for example 30 | Bolus IV | | 1. Ml/min/gr 2. coronary flow reserve 3. parametric quantitation |
| 15 min | Imaging | | | | Energy window 3-15%; detectors sweep the | |

TABLE 38-continued

Description: cardiac perfusion (BMIPP rest) protocol
Indication: Dynamic imaging of cardiac perfusion under rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | | | | | region of interest every 10-15 seconds | |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 39

Description: Dynamic cardiac perfusion (BMIPP stress) protocol
Indication: imaging of cardiac perfusion under stress conditions

| Length of Time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| variable | Stress | | | Infusion IV | Physical or pharmacological- for example adenosine or dipyridamole | | |
| | Injection at peak stress | Tc sestamibi | Medium dose for example 30 | Bolus IV | | | |
| 15 min | imaging | | | | | Energy window 3-15%; detectors sweep the region of interest every 10-15 seconds | 1. Ml/min/gr 2. coronary flow reserve 3. parametric quantitation |

Timeframe summary:
Total imaging time: 15 min.
Total patient time: 15 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 40

Description: Dynamic cardiac perfusion protocol
Indication: imaging of cardiac perfusion under stress or rest conditions

| Length of time | Patient flow | Radiopharmaceutical | Dose (mCi) | Mode of administration | Type of stress | Acquisition parameters (detector; windowing, etc.) | Clinical parameters acquired after processing |
|---|---|---|---|---|---|---|---|
| Variable | Stress or rest | | | Infusion IV | Physical or pharmacological - for example adenosine or dipyridamole | | |
| | Injection at peak stress | Any radiopharmaceutical | Medium dose for example 30 | Bolus IV | | | |
| 10 min | imaging | | | | | Energy window 3-15%; detectors sweep the region of interest every 10-15 seconds | 1. Ml/min/gr 2. coronary flow reserve 3. parametric quantitation |

Timeframe summary:
Total imaging time: 10 min.
Total patient time: 10 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 41

Description: Dynamic cardiac perfusion protocol utilizing PET pharmaceuticals within the currently used PET protocols.
Indication: imaging of cardiac perfusion under stress or rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Rest injection | Any PET radiopharmaceutical | Medium dose for example 30 | Bolus IV | | |

TABLE 41-continued

Description: Dynamic cardiac perfusion protocol utilizing PET pharmaceuticals within the currently used PET protocols.
Indication: imaging of cardiac perfusion under stress or rest conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| Up to 15 minutes | Imaging | | | | Energy window 3-15% | 1. Ml/min/gr 2. coronary flow reserve 3. parametric quantitation |

Timeframe summary:
Total imaging time: 10 min.
Total patient time: 10 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 42

Description: Cancer - dynamic single isotope tumor perfusion protocol under rest or stress.
Indication: Diagnosis and evaluation of tumors

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | injection | Teboroxime Tc 99m or Tc 99m sestamibi or Tl 201 or Tc 99m tetrofosmin | Medium dose for example 30 mCi Tc or high dose for example 4 mCi Tl | Bolus IV | | |
| Up to 5 min | Imaging | | | | Energy window 3-15%; detectors sweep the region of interest every 10-15 seconds | 1. quantitative parameters (Ml/min/gr) 2. parametric quantitation |

Timeframe summary:
Total imaging time: 5 min.
Total patient time: 5 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.
3. Tumor blood flow measurements
4. Accurate tumor diagnosis
5. Evaluation of multi drug resistance
6. Monitoring of treatment response

TABLE 43

Description: Cancer - Dynamic simultaneous dual isotope tumor perfusion protocol under rest or stress.
Indication: Diagnosis and evaluation of tumors by simultaneous dual isotope.

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | injection | Tl 201 thallous chloride and Tc 99m sestamibi | High dose for example Tl –4 Medium doe for example Tc- up to 30 | Bolus IV | | |
| Up to 5 min | Imaging | | | | Energy window 3-15%; detectors sweep the region of interest every 10-15 seconds | 1. quantitative parameters (Ml/min/gr) 2. parametric quantitation |

Timeframe summary:
Total imaging time: 5 min.
Total patient time: 5 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.
3. Blood flow measurements
4. Accurate tumor diagnosis
5. Evaluation of multi drug resistance
6. Monitoring of treatment response

TABLE 44

Description: kidney - Dynamic renal function protocol.
Indication: assessment of filtration and tubular secretion, perfusion and secretion.

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc99m DTPA and Tc 99m- MAG3 | low dose for example Tc99m DTPA - 1 Tc MAG3 - 10 | Bolus IV | | |

TABLE 44-continued

Description: kidney - Dynamic renal function protocol.
Indication: assessment of filtration and tubular secretion, perfusion and secretion.

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| 10 min | Imaging | | | | Energy window 3-15%; detectors sweep the region of interest every 10-15 seconds | 1. quantitative parameters (Ml/min/gr) 2. parametric quantitation |

Timeframe summary:
Total imaging time—10 min.
Total patient time—10 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 45

Description: Dynamic renal function protocol.
Indication: assessment of filtration and tubular secretion, perfusion and secretion.

| Time Since previous step | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | Tc99m DTPA and Hippuran I-123 | Low dose for example 1 each | Bolus IV | | |
| 10 min | Imaging | | | | Energy window 3-15%; detectors sweep the region of interest every 10-15 seconds | 1. quantitative parameters (Ml/min/gr) 2. parametric quantitation |

Timeframe summary:
Total imaging time: 10 min.
Total patient time: 10 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 46

Description: Dynamic brain perfusion protocol.
Indication: perfusion mapping under rest or pharmacological stress conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | HMPAO 99m labeled Tc 99m ECD (neurolite | Medium dose for example 20 | Bolus IV | | |
| | | Spectamine I 123 | Low dose for example Up to 5 | Bolus IV | | |
| Up to 30 min | Imaging | | | | Energy window 3-15%; detectors sweep the region of interest every 10-15 seconds | 1. quantitative parameters (Ml/min/gr) 2. cerebral flow reserve 3. parametric quantitation 4. disease signature |

Timeframe summary:
Total imaging time: 30 min.
Total patient time: 30 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 47

Description: Dynamic brain perfusion protocol.
Indication: perfusion mapping under rest or pharmacological stress conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | Injection | teboroxime | Low dose for example Up to 20 | Bolus IV | | |
| Up to 30 min | Imaging | | | | Energy window 3-15%; detectors sweep the region of interest | 1. quantitative parameters (Ml/min/gr) 2. cerebral flow reserve |

TABLE 47-continued

Description: Dynamic brain perfusion protocol.
Indication: perfusion mapping under rest or pharmacological stress conditions

| Length of Time | Patient flow | Radiopharmaceutical | Dose (mCi) | Mode of administration | Acquisition parameters (detector; windowing, etc.) | Clinical parameters acquired after processing |
|---|---|---|---|---|---|---|
| | | | | | every 10-15 seconds | 3. parametric quantitation 4. disease signature |

Timeframe summary:
Total imaging time: 30 min.
Total patient time: 30 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 48

Description: hepatobiliary protocol
Indication: liver structure (hemangiomas, abscesses, liver enlargement, etc.)

| Length of Time | Patient flow | Radiopharmaceutical | Dose (mCi) | Mode of administration | Acquisition parameters (detector; windowing, etc.) |
|---|---|---|---|---|---|
| | Injection | Tc 99m sulfur colloid | low dose for example UP to 5 | Bolus IV | |
| Up to 10 min | Imaging | | | | Energy window 3-15%; detectors sweep the region of interest every 10-15 seconds |

Timeframe summary:
Total imaging time: 10 min.
Total patient time: 10 min.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 49

Description: liver function study rest or stress protocol
Indication: Pathological liver function

| Length of Time | Patient flow | Radiopharmaceutical | Dose (mCi) | Mode of administration | Acquisition parameters (detector; windowing, etc.) |
|---|---|---|---|---|---|
| | Injection | Tc 99m disida | Up to 10 | Bolus IV | |

TABLE 49-continued

Description: liver function study rest or stress protocol
Indication: Pathological liver function

| Length of Time | Patient flow | Radiopharmaceutical | Dose (mCi) | Mode of administration | Acquisition parameters (detector; windowing, etc.) |
|---|---|---|---|---|---|
| | | (disulfenine, or choletec), | | | |
| 5 min Every 5 minutes up to an hour | Imaging | | | | Energy window 3-15%; detectors sweep the region of interest every 10-15 seconds |
| | Injection of agent for gall bladder contraction Only if no activity is seen in the intestine after 1 hour of imaging | | | | |

Timeframe summary:
Total imaging time: 1 h.
Total patient time: 1 h.
Clinical protocol advantages:
1. Fast imaging time compared to standard imaging methods.
2. Enables the study of fluid flow, rate of tracer uptake (passive or active), tracer accumulation and redistribution, tracer metabolism, and secretion and/or washout (active or passive) of tracer/metabolites.

TABLE 50

Description: dual phase gastric emptying study protocol
Indication: determining the rate the stomach empties of food

| Length of time | Patient flow | Radiopharmaceutical | Dose (mCi) | Mode of administration |
|---|---|---|---|---|
| | Ingestion of labeled food | Solid food labled with Tc 99m S colloidor or liquid food labeled with IN 111 DTPA | Medium dose for example 3MBq solid 0.5 MBqliquid | PO |
| Until the stomach is approximately empty of all tracer | Imaging | | | |

Clinical protocol advantages: dynamic SPECT imaging for increased resolution

TABLE 51

Description: Cardiac vulnerable plaque study protocol
Indication: for identifying plaque in blood vessels that may be released in the blood stream and initiate a CVA or cardiac infarct

| Length of Time | Patient flow | Radio-pharmaceutical | Dose (mCi) | Mode of administration |
|---|---|---|---|---|
| | Injection | Annexin labeled with Tc 99m | low dose for example Up to 5 | Bolus IV |
| | Injection | AccuTec labeled with Tc 99m | low dose for example Up to 5 | Bolus IV |
| 24 h | waiting | | | |
| 30 min | imaging | | | |

Timeframe summary:

Total imaging time: 1 h.

Total patient time: 1 h.

Clinical protocol advantages:

1. Fast imaging time compared to standard imaging methods.

2. The AccuTec attaches to activated platelets and shows thrombus. The Annexin attaches to apoptotic cells. Apoptotic cells being human neutrophils that have died and broken up demonstrating inflammatory infiltrate. The protocol enables the study of dynamic plaques that are associated with cardiac plaque tissue damage and repair.

TABLE 52

Description: Prostate imaging study protocol
Indication: determining the presence and/or extent of metastatic and/or primary cancer in the prostate.

| Length of Time | Patient flow | Radio-pharmaceutical | Dose (mCi) | Mode of administration |
|---|---|---|---|---|
| | Injection | Prostascint containing 111 In DTPA | high dose for example Up to 5 | |
| 24-72 h | waiting | | Up to 10 | Bolus IV |
| up to 60 min | imaging | | | |

Timeframe summary:

Total patient time: 24-72 h.

Clinical protocol advantages:

1. Fast imaging time compared to standard imaging methods.

2. enables the study of dynamic plaques that are associated with tissue damage and repair.

TABLE 53

Description: SST receptor imaging study protocol
Indication: for determining the presence and/or extent of SST receptor expressing tumors, whether metastatic and/or primary cancerous tumors.

| Length of Time | Patient flow | Radio-pharmaceutical | Dose (mCi) | Mode of administration |
|---|---|---|---|---|
| | Injection | Octreotide containing 111 In DTPA | high dose for example Up to 5 | Bolus IV |
| 24 h | waiting | | | |
| up to 60 min | Imaging | | | |

Timeframe summary:

Total patient time: 24 h.

Clinical protocol advantages:

1. Fast imaging time compared to standard imaging methods.

2. enables the study of SST receptor expressing tumors metastatic and/or primary cancerous tumors.

TABLE 54

Description: neuroendocrine tumors imaging study protocol.
Indication: for determining the presence and/or extent of metastatic and/or primary neuroendocrine tumors by binding t associated somatostatin receptors.

| Length of Time | Patient flow | Radio-pharmaceutical | Dose (mCi) | Mode of administration |
|---|---|---|---|---|
| | Injection | Neotec labeled with Tc 99m | low dose for example Up to 20 | Bolus IV |
| 1 h | waiting | | | |
| up to 30 min | Imaging | | | |

Timeframe summary:

Total patient time—1 h.

Clinical protocol advantages:

1. Fast imaging time compared to standard imaging methods.

2. enables the study of neuroendocrine tumors.

TABLE 55

Description: Thrombus detection imaging study protocol.
Indication: for imaging DVT and intraarterial thrombusin coronary and carotidarteries, by binding to GP IIb/IIIa.

| Length of Time | Patient flow | Radio-pharmaceutical | Dose (mCi) | Mode of administration |
|---|---|---|---|---|
| | Injection | Acutec labeled with Tc 99m | low dose for example Up to 20 | Bolus IV |
| 0-20 min | waiting | | | |
| up to 60 min | Imaging | | | |

Timeframe summary:

Total patient time—20 min.

Clinical protocol advantages:

1. Fast imaging time compared to standard imaging methods.

2. enables the study of thrombus detection including DVT and intraarterial thromus in coronary and carotid arteries.

TABLE 56

Description: Pheochromocytoma and or myocardial failure imaging study protocol.
Indication: for imaging pancreatic adrenergic tissue uptake and presynaptic adrenergic receptors, adrenergic being associated with adrenaline bu binding to GP IIb/IIIa receptors on platelets.

| Length of Time | Patient flow | Radio-pharmaceutical | Dose (mCi) | Mode of administration |
|---|---|---|---|---|
| | Injection | MIBG containing I 123 iofetamine hydrochloride | high dose for example Up to 5 | Bolus IV |
| 24 h up to 30 min | waiting Imaging | | | |

Timeframe summary:

Total patient time: 24 h.

Clinical protocol advantages:

1. Fast imaging time compared to standard imaging methods.
2. enables the study of tissue and receptors that are associated with adrenergic uptake.

TABLE 57

Description: Dynamic gated cardiac stress imaging protocol
Indication a dynamic study to investigate the effects of stress for example adenosine or dipyridamole, ice water and/or vasodilatation agents, on blood flow kinetics.

| Length of Time | Patient flow | Radiopharmaceutical | Dose (mCi) | Mode of administration | Type of stress | Acquisition parameters (detector; windowing, etc.) |
|---|---|---|---|---|---|---|
| | Injection | Tl 291 thallous chloride | high dose for example 4 | Bolus IV | | |
| 0-2 min | waiting | | | | | |
| 2-5 min | imaging | | | | | |
| | Stress injection | | | Bolus IV | For example adenosine or dipyridamole and/or vasodilatation agents or hand in submerged into icewater | |
| 0-5 min | waiting | | | | | |
| 2-10 min | imaging | | | | | detectors sweep the region of interest every 10-15 seconds |

Timeframe summary:
Total imaging time: 15 min.
Total patient time: 20 min.
Clinical protocol advantages:
1. Fast imaging time compared to standard imaging methods.
2. enables the investigation of the effects of stress on blood flow kinetics

TABLE 58

Description: a kidney function imaging protocol
Indication: a dynamic study to investigate the effects of stress on blood flow kinetics of the kidneys.

| Length of Time | Patient flow | Radiopharmaceutical | Dose (mCi) | Mode of administration | Type of stress |
|---|---|---|---|---|---|
| | Injection | DTPA and/or Tc MAG3 | low dose for example 2-4 | Bolus IV | |
| | Stress injection | | | Bolus IV | captopril, fuside and/or vasodilatation or diuretic agents or hand in submerged into icewater |
| 10-30 min | Imaging | | | | |

Timeframe summary:
Total imaging time: 32 min.
Total patient time: 1 h.
Clinical protocol advantages:
1. Fast imaging time compared to standard imaging methods.
2. Enables the investigation of the effects of stress on blood flow kinetics (captopril, fuside etc.) of the kidney.

TABLE 59

Description: Bexaar dosimetry imaging protocol
Indication: a study to determine the dose required to inject in order to administer an effective dose of 75 REM.

| Length of Time | Patient flow | Radiopharmaceutical | Dose (mCi) | Mode of administration | Acquisition parameters (detector; windowing, etc.) |
|---|---|---|---|---|---|
| | Injection | I123 iofetamine hydrochloride | 5 Mci/ 35 mg | Bolus IV | |
| 5 min | Imaging | | | | Energy window 3-15% |

3 acquisitions are acquired during the week to produce a graph of metabolism.

Timeframe summary per scan:
Total imaging time: 5 min.
Total patient time: 5 h.
Clinical protocol advantages:
1. Fast imaging time compared to standard imaging methods.
2. Enables the determination of the dose required to inject in order to administer an effective dose of 75 REM.

TABLE 60

Description: Multi isotope combination protocol
Indication: parathyroid adenoma imaging and anatomical differentiation of the parathyroid from the thyroid.

| Length of time | Patient flow | Radiopharmaceutical | remarks | Dose (mCi) | Mode of administration | Acquisition parameters (detector; windowing, etc.) |
|---|---|---|---|---|---|---|
| | Injection | Thallium 201 thallous chloride | Parathyroid avid agent | low dose for example 1 | Bolus IV | |
| | Injection | Tc 99m pertechnetate | Thyroid agent | low dose for example 15 | Bolus IV | |
| 10 min | Waiting | | | | | |
| 5 min | imaging | | | | | Energy window 2-10%; |

Timeframe summary:
Total imaging time: 5 min.
Total patient time: 15 min.
Clinical protocol advantages:
1. Fast imaging time compared to standard imaging methods.
2. Enables parathyroid adenoma imaging and anatomical differentiation of the parathyroid from the thyroid.

TABLE 61

Description: Multi-isotope combination protocol
Indication: parathyroid adenoma imaging and anatomical differentiation of the parathyroid from the thyroid.

| Length of time | Patient flow | Radiopharmaceutical | remarks | Dose (mCi) | Mode of administration | Acquisition parameters (detector; windowing, etc.) |
|---|---|---|---|---|---|---|
| | Injection | Tc 99m sestamibi | Parathyroid avid agent | low dose for example 15 | Bolus IV | |
| | Injection | I 123 | Thyroid agent | low dose for example 100 µCi | Bolus IV | |
| 10 min | Waiting | | | | | |
| 5 min | imaging | | | | | Energy window 2-10% |

Timeframe summary:
Total imaging time: 5 min.
Total patient time: 15 min.
Clinical protocol advantages:
1. Fast imaging time compared to standard imaging methods.
2. Enables parathyroid adenoma imaging and anatomical differentiation of the parathyroid from the thyroid.

TABLE 62

Description: Multi-isotope combination protocol
Indication: imaging of thyroid cancer identification of the location of the thyroid cancer.

| Length of Time | Patient flow | Radiopharmaceutical | remarks | Dose (mCi) | Mode of administration | Acquisition parameters (detector; windowing, etc.) |
|---|---|---|---|---|---|---|
| | Injection | Tc 99m MDP | Bone imaging agent | low dose for example 10 | Bolus IV | |
| | Injection | Tl201 thallium chloride | Thyroid agent | high dose for example 4 | Bolus IV | |
| 2 h 30 min | Waiting imaging | | | | | Energy window 2-10% |

Timeframe summary:
Total imaging time: 30 min.
Total patient time: 2 h and 30 min.
Clinical protocol advantages:
1. Fast imaging time compared to standard imaging methods.
2. imaging of thyroid cancer identification of the location of the thyroid cancer. Tc 99m MDP enables visualization of the skeleton to provide anatomical landmarks. Tc 99m labeling of red blood cells enables the larger blood vessels to be visualized to provide anatomical landmarks.

TABLE 63

Description: Multi-isotope combination protocol
Indication: localization of certain endocrine tumors.

| Length of Time | Patient flow | Radiopharmaceutical | remarks | Dose (mCi) | Mode of administration | Acquisition parameters (detector; windowing, etc.) |
|---|---|---|---|---|---|---|
| | Injection | In 111 octeotride | Possible to administer simultaneously | High dose for example 4 | Bolus IV | |
| | Injection | Tc 99m MDP | | low dose for example 15 | Bolus IV | |
| Up to 2 h 30 min | waiting imaging | | | | | Energy window 2-10% |

* Imaging may be done within 3 days of injection of In 111 octeotride but within 2 h after injection of Tc 99m MDP
* 3. In 111 Octeotide and Tc 99m MDP may be administered in combination to optimally localize certain endocrine tumors. In 111 octeotide is a tumor imaging agent for somastatin receptor expressing tumors. Tc 99m MDP is a bone imaging agent which enables visualiziation of the skeleton to provide anatomical landmarks.

Timeframe summary:
Total imaging time: 30 min.
Total patient time: 2 h and 30 min.
Clinical protocol advantages:
1. Fast imaging time compared to standard imaging methods.
2. localization of certain endocrine tumors.

TABLE 64

Description: Multi-isotope combination protocol
Indication: localization of certain endocrine tumors.

| Length of Time | Patient flow | Radiopharmaceutical | remarks | Dose (mCi) | Mode of administration | Acquisition parameters (detector; windowing, etc.) |
|---|---|---|---|---|---|---|
| Up to 3 days | Injection | In 111 octeotride | *It is Possible to administer simultaneously | high dose for example 4 | Bolus IV | |
| | waiting | | | | | |
| | Injection | Tc 99m MDP | | low dose for example 15 | Bolus IV | |
| Up to 2 hours | waiting | | | | | |
| 30 min | imaging | | | | | Energy window 2-10% |

*Imaging may be done within 3 days of injection of In 111 octeotride but within 2 h after injection of Tc 99
*3. In 111 Octeotide and Tc 99m MDP may be administered in combination to optimally localize certain endocrine tumors. In 111 octeotide is a tumor imaging agent for somatostatin receptor expressing tumors. Tc 99m MDP is a bone imaging agent which enables visualiziation of the skeleton to provide anatomical landmarks.

Timeframe summary:
Total imaging time: 30 min.
Total patient time: 3 days.
Clinical protocol advantages:
1. Fast imaging time compared to standard imaging methods.
2. localization of certain endocrine tumors.

TABLE 65

Description: Multi-isotope combination protocol
Indication: delineating vascular structures of the pelvis or abdomen to differentiate from prostate cancer

| Length of Time | Patient flow | Radiopharmaceutical | remarks | Dose (mCi) | Mode of administration | Acquisition parameters (detector; windowing, etc.) |
|---|---|---|---|---|---|---|
| Up to 3 days | Injection | In 111 capromab pentitde | *It is Possible to administer simultaneously | medium dose for example 3 | Bolus IV | |
| | waiting | | | | | |
| | Injection | Tc 99m RBCs | | low dose for example 15 | Bolus IV | |
| 2 hours | waiting | | | | | |
| 30 min | imaging | | | | | Energy window 2-10% |

*Imaging may be done within 3 days of injection of In 111 capromab penticde but within 2 h after injection of Tc 99m RBCs.

Timeframe summary:
Total imaging time: 30 min.
Total patient time: 30 min to 3 days.
Clinical protocol advantages:
1. Fast imaging time compared to standard imaging methods.
2. Enables the clinician to distinguish the blood vessels from the lymph nodes in the pelvis or abdomen.

TABLE 66

Description: Multi-isotope combination protocol
Indication: identification and localization of bone infection.

| Length of Time | Patient flow | Radiopharmaceutical | remarks | Dose (mCi) | Mode of administration | Acquisition parameters (detector; windowing, etc.) |
|---|---|---|---|---|---|---|
| Up to 3 days | Injection | In 111 WBC | *It is Possible to administer simultaneously | medium dose for example 3 | Bolus IV | |
| | waiting | | | | | |
| | Injection | Tc 99m colloid | | low dose for example 15 | Bolus IV | |
| 2 hours | waiting | | | | | |
| 30 min | imaging | | | | | Energy window 2-10% |

*Imaging may be done within 3 days of injection of In 111 WBC but within 2 h after injection of Tc 99m colloid.

Timeframe summary:
Total imaging time: 30 min.
Total patient time: 30 min to 3 days.
Clinical protocol advantages:
1. Fast imaging time compared to standard imaging methods.
2. Identification and localization of bone infection.

TABLE 67

Description: Multi-isotope combination protocol
Indication: Evaluation of invasion of bone or cartilage by head or neck cancer.

| Length of Time | Patient flow | Radiopharmaceutical | remarks | Dose (mCi) | Mode of administration | Acquisition parameters (detector; windowing, etc.) |
|---|---|---|---|---|---|---|
| | Injection | Tl 201 thallous chloride | *It is Possible to administer simultaneously | Medium dose for example 2 | Bolus IV | |
| | Injection | Tc 99m MDP | | low dose for example 15 | Bolus IV | |
| 2 h | Waiting | | | | | |
| 30 min | imaging | | | | | Energy window 2-10% |

Timeframe summary:
Total imaging time: 30 min.
Total patient time: 2 h.
Clinical protocol advantages:
1. Fast imaging time compared to standard imaging methods.
2. Evaluation of invasion of bone or cartilage by head or neck cancer.

TABLE 68

Description: Dynamic multi-isotope combination protocol for multiple pathologies:
Indication: assessment of various pathological conditions, including cardiac, tumors and infection

| Length of Time | Patient flow | Radiopharmaceutical | Dose (mCi) | Mode of administration | Acquisition parameters (detector; windowing etc.) |
|---|---|---|---|---|---|
|  | Injection | In 11 WBCs | low dose for example 2 | Bolus IV |  |
| 24 h | Waiting |  |  |  |  |
|  | Injection | Tl 201 thallous chloride | low dose for example 1 | Bolus IV |  |
|  | Injection | Tc 99m sestamibi | low dose for example 10 | Bolus IV |  |
| 3 min | Waiting |  |  |  |  |
| 30 min | imaging |  |  |  | Energy window 2-10%; detectors sweep the region of interest every 10-15 seconds |

Timeframe summary:
Total imaging time: 30 min.
Total patient time: 25 h.
Clinical protocol advantages:
1. Fast imaging time compared to standard imaging methods.
2. Assessment of various pathological conditions, including cardiac, tumors and infection with only one acquisition
3. Easy registration as a result of simultaneous imaging

TABLE 69

Description: Dynamic multiple isotope combination protocol for different pathological processes of the same organ
Indication: study of acute myocardial ischemia

| Length of Time | Patient flow | Radiopharmaceutical | Patient relevant diagnosis (diabetes, BP, etc. . . . ) | Dose (mCi) | Mode of administration | Acquisition parameters (detector; windowing etc.) |
|---|---|---|---|---|---|---|
|  | Injection | I 123 BMIPP |  | low dose for example 2 | Bolus IV |  |
| 48 h | Waiting |  |  |  |  |  |
|  | Injection | Tl 201 thallous chloride |  | low dose for example 1 | Bolus IV |  |
|  | Injection | Tc 99m sestamibi or Tc |  | low dose for | Bolus IV |  |

TABLE 69-continued

Description: Dynamic multiple isotope combination protocol for different
pathological processes of the same organ
Indication: study of acute myocardial ischemia

| Length of Time | Patient flow | Radiopharmaceutical | Patient relevant diagnosis (diabetes, BP, etc. . . . ) | Dose (mCi) | Mode of administration | Acquisition parameters (detector; windowing etc.) |
|---|---|---|---|---|---|---|
| 30 min | imaging | 99m teboroxime | | example 10 | | Energy window 2-10%; detectors sweep the region of interest every 10-15 seconds |

Timeframe summary:
Total imaging time: 30 min.
Total patient time: 48 h.
Clinical protocol advantages:
1. Fast imaging time compared to standard imaging methods.
2. study of acute myocardial ischemia
3. BMIPP identifies the ischemic/infracted area while the other isotopes identify the perfused area; simultaneous imaging provides a more accurate means of identifying myocardial perfusion pathologies

TABLE 70

Description: combination protocol for different pathological processes of the same organ
Indication: fever of unknown origin

| Length of Time | Patient flow | Radiopharmaceutical | Dose (mCi) | Mode of administration | Acquisition parameters (detector; windowing, etc.) |
|---|---|---|---|---|---|
| | Injection | In 11 WBC | low dose for example 2 | Bolus IV | |
| 24 h | Waiting | | | | |
| | Injection | Tc 99m Fanoselomab | low dose for example 15 | Bolus IV | |
| 30 min | imaging | | | | Energy window 2-10% |

Timeframe summary:
Total imaging time: 30 min.
Total patient time: 24 h.
Clinical protocol advantages:
1. Fast imaging time compared to standard imaging methods.
2. study of fever of unknown origin
3. Differential diagnosis in one scan

TABLE 71

Description: Dynamic multi-isotope combination protocol for different pathological processes of the same organ
Indication: schizophrenia or Parkinson's disease.

| Length of Time | Patient flow | Radiopharmaceutical | Dose (mCi) | Mode of administration | Acquisition parameters (detector; windowing, etc.) |
|---|---|---|---|---|---|
| | Injection | I 123 IBZM | low dose for example 2 | Bolus IV | |
| 24 h | Waiting | | | | |
| | Injection | Tc 99m HMPAO | low dose for example 15 | Bolus IV | |
| 30 min | imaging | | | | Energy window 2-10%; detectors sweep the region of interest every 10-15 seconds |

Timeframe summary:
Total imaging time: 30 min.
Total patient time: 24 h.
Clinical protocol advantages:
1. Fast imaging time compared to standard imaging methods.
2. study of schizophrenia or Parkinson's disease.
3. Mapping of brain activity in different pathological states.

TABLE 72

Description: Dynamic multi-isotope combination protocol for different pathological processes of the same organ
Indication: tumor identification and characterization by perfusion studies.

| Length of Time | Patient flow | Radiopharmaceutical | Dose (mCi) | Mode of administration | Acquisition parameters (detector; windowing, etc.) |
|---|---|---|---|---|---|
| | Injection | In 111 WBC | low dose for example 2 | Bolus IV | |
| 24 h | Waiting | | | | |
| | Injection | Tc 99m sestamibi or Tc 99m Arcitumo Mab Or Tl 201 thallous chloride | low dose for example Tc - 10 Tl - 1 | Bolus IV | |

TABLE 72-continued

Description: Dynamic multi-isotope combination protocol for different pathological processes of the same organ
Indication: tumor identification and characterization by perfusion studies.

| Length of Time | Patient flow | Radiopharmaceutical | Dose (mCi) | Mode of administration | Acquisition parameters (detector; windowing, etc.) |
|---|---|---|---|---|---|
| 5 min | Waiting | | | | |
| 30 min | imaging | | | | Energy window 2-10%; detectors sweep the region of interest every 10-15 seconds |

Timeframe summary:
Total imaging time—30 min.
Total patient time—24 h.
Clinical protocol advantages:
1. Fast imaging time compared to standard imaging methods.
2. Tumor identification and characterization by perfusion studies.
3. Differentiation between tumors and inflammation
4. Accurate registration due to simultaneous imaging of all isotopes
5. Differential diagnosis in one scan

TABLE 73

Description: combination protocol for different pathological processes of the same organ.
Indication: Dynamic flow studies for the investigation of renal function.

| Length of Time | Patient flow | Radiopharmaceutical | Dose (mCi) | Mode of administration | Acquisition parameters (detector; windowing, etc.) |
|---|---|---|---|---|---|
| | Injection | In 111 DTPA | low dose for example 2 | Bolus IV | |
| 24 h | Waiting | | | | |
| | Injection | Tc 99m MAG3 | low dose for example 15 | Bolus IV | |
| 5 min | Waiting | | | | |
| 30 min | imaging | | | | Energy window 2-10% |

Timeframe summary:
Total imaging time: 30 min.
Total patient time: 24 h.
Clinical protocol advantages:
1. Fast imaging time compared to standard imaging methods.
2. Dynamic flow studies for the investigation of renal function.

TABLE 74

Description: Dynamic multi-isotope combination protocol for different pathological processes of the same organ
Indication: Tumor perfusion and therapeutic response.

| Length of Time | Patient flow | Radiopharmaceutical | Dose (mCi) | Mode of administration | Acquisition parameters (detector; windowing, etc.) |
|---|---|---|---|---|---|
| | Injection | Tl thallous chloride | low dose for example 1 | Bolus IV | |
| | Injection | Tc 99m teboroxime or Tc 99m sestamibi | low dose for example 15 | Bolus IV | |
| 1 h 30 min | Waiting imaging | | | | Energy window 2-10%; detectors sweep the region of interest every 10-15 seconds |

Timeframe summary:
Total imaging time: 30 min.
Total patient time: 1 h.
Clinical protocol advantages:
1. Fast imaging time compared to standard imaging methods.
2. Tumor perfusion and therapeutic response determined by absolute blood flow to and from tumor
3. Determination of multi-drug resistance by measurement of washout

TABLE 75

Description: Dynamic multi-isotope combination protocol for different pathological processes of the same organ
Indication: tumor perfusion and therapeutic response.

| Length of Time | Patient flow | Radiopharmaceutical | Dose (mCi) | Mode of administration | Acquisition parameters (detector; windowing, etc.) |
|---|---|---|---|---|---|
| | Injection | Tl thallous chloride | low dose for example 1 | Bolus IV | |
| | Injection | Tc 99m Annexin | low dose for example 15 | Bolus IV | |
| 1 h 30 min | Waiting imaging | | | | Energy window 2-10%; detectors sweep the |

TABLE 75-continued

Description: Dynamic multi-isotope combination protocol for different pathological processes of the same organ
Indication: tumor perfusion and therapeutic response.

| Length of Time | Patient flow | Radiopharmaceutical | Dose (mCi) | Mode of administration | Acquisition parameters (detector; windowing, etc.) |
|---|---|---|---|---|---|
| | | | | | region of interest every 10-15 seconds |

Timeframe summary:
Total imaging time: 30 min.
Total patient time: 1 h.
Clinical protocol advantages:
1. Fast imaging time compared to standard imaging methods.
2. Tumor perfusion with thallium and therapeutic response by monitoring apoptosis with annexin

TABLE 76

Description: Multi-isotope combination protocol for different pathological processes of the same organ
Indication: Differentiation between infection and bone marrow activation.

| Length of Time | Patient flow | Radiopharmaceutical | Dose (mCi) | Mode of administration | Acquisition parameters (detector; windowing, etc.) |
|---|---|---|---|---|---|
| | Injection | In 111 WBC | low dose for example 2 | Bolus IV | |
| 24 h | Waiting | | | | |
| | Injection | Tc 99m sulfur colloid | low dose for example 15 | Bolus IV | |
| 30 min | imaging | | | | Energy window 2-10% |

Timeframe summary:
Total imaging time: 30 min.
Total patient time: 24 h.
Clinical protocol advantages:
1. Fast imaging time compared to standard imaging methods.
2. Differentiation between infection and bone marrow activation
3. Differential diagnosis with one scan

TABLE 77

Description: Muti-isotope combination protocol for different pathological processes of the same organ
Indication: Differentiation between acute and chronic osteomyelitis.

| Length of Time | Patient flow | Radiopharmaceutical | Dose (mCi) | Mode of administration | Acquisition parameters (detector; windowing, etc.) |
|---|---|---|---|---|---|
| | Injection | In 111 WBC | low dose for example 2 | Bolus IV | |

TABLE 77-continued

Description: Muti-isotope combination protocol for different pathological processes of the same organ
Indication: Differentiation between acute and chronic osteomyelitis.

| Length of Time | Patient flow | Radiopharmaceutical | Dose (mCi) | Mode of administration | Acquisition parameters (detector; windowing, etc.) |
|---|---|---|---|---|---|
| 24 h | Waiting | | | | |
| | Injection | Tc 99m MDP | low dose for example 15 | Bolus IV | |
| 30 min | imaging | | | | Energy window 2-10% |

Timeframe summary:
Total imaging time: 30 min.
Total patient time: 24 h.
Clinical protocol advantages:
1. Fast imaging time compared to standard imaging methods.
2. Differentiation between acute and chronic osteomyelitis
3. Differential diagnosis in one scan

TABLE 78

Description: Multi-isotope combination protocol for different pathological processes of the same organ
Indication: Differentiation between acute and chronic inflammation.

| Length of Time | Patient flow | Radiopharmaceutical | Dose (mCi) | Mode of administration | Acquisition parameters (detector; windowing, etc.) |
|---|---|---|---|---|---|
| | Injection | Gallium 67 | low dose for example 5 | Bolus IV | |
| | Injection | In 111 WBCs | high dose for example 15 | Bolus IV | |
| 72 h 30 min | Waiting imaging | | | | Energy window 2-10% |

Timeframe summary:
Total imaging time: 30 min.
Total patient time: 72 h.
Clinical protocol advantages:
1. Fast imaging time compared to standard imaging methods.
2. Differentiation between acute and chronic inflammation.
3. Differential diagnosis in one scan

TABLE 79

Description: Multi-isotope combination protocol for different pathological processes of the same organ
Indication: Study myocardial perfusion and apoptosis.

| Length of Time | Patient flow | Radiopharmaceutical | Dose (mCi) | Mode of administration | Acquisition parameters (detector; windowing, etc.) |
|---|---|---|---|---|---|
| | Injection | In 111 annexin | low dose | Bolus IV | |

TABLE 79-continued

Description: Multi-isotope combination protocol for different pathological processes of the same organ
Indication: Study myocardial perfusion and apoptosis.

| Length of Time | Patient flow | Radiopharmaceutical | Dose (mCi) | Mode of administration | Acquisition parameters (detector; windowing, etc.) |
|---|---|---|---|---|---|
| 24 h | Waiting Injection | Tc 99m teboroxime or Tl 201 thallous chloride | for example 2 low dose for example Tc - 15 or medium dose for example Tl - 2 | Bolus IV | |
| 0-3 min 30 min | Waiting imaging | | | | Energy window 2-10%; detectors sweep the region of interest every 10-15 seconds |

Timeframe summary:
Total imaging time: 30 min.
Total patient time: 25 h.
Clinical protocol advantages:
1. Fast imaging time compared to standard imaging methods.
2. Study myocardial perfusion and apoptosis.

TABLE 80

Description: Multi-isotope combination protocol for different pathological processes of the same organ
Indication: Investigation of myocardial perfusion and infarct

| Length of Time | Patient flow | Radiopharmaceutical | Dose (mCi) | Mode of administration | Acquisition parameters (detector; windowing, etc.) |
|---|---|---|---|---|---|
| | Injection | Tl 201 thallous chloride | medium dose for example 2 | Bolus IV | |
| | Injection | Tc 99m pyrophosphate | low dose for example 15 | Bolus IV | |
| 1 h 30 min | Waiting imaging | | | | Energy window 2-10% |

Timeframe summary:
Total imaging time: 30 min.
Total patient time: 72 h.
Clinical protocol advantages:
1. Fast imaging time compared to standard imaging methods.
2. investigation of myocardial perfusion and infarct

TABLE 81

Description: Dynamic multi-isotope combination protocol for different pathological processes of the same organ
Indication: Investigation of myocardial perfusion and infarct

| Length of Time | Patient flow | Radiopharmaceutical | Patient relevant diagnosis (diabetes, BP, etc. . . . ) | Dose (mCi) | Mode of administration | Acquisition parameters (detector; windowing, etc.) |
|---|---|---|---|---|---|---|
| | Injection | Tl 201 thallous chloride | | medium dose for example 2 | Bolus IV | |
| | Injection | Tc 99m pyrophosphate | | low dose for example 15 | Bolus IV | |
| 30 min | imaging | | | | | Energy window 2-10%; detectors sweep the region of interest every 10-15 seconds |

Timeframe summary:
Total imaging time: 30 min.
Total patient time: 30 min.

Clinical protocol advantages:
1. Fast imaging time compared to standard imaging methods.
2. investigation of myocardial perfusion and infarct

TABLE 82

Description: Dynamic multi-isotope combination protocol for different pathological processes of the same organ
Indication: Cardiac vulnerable plaque and myocardial perfusion study protocol

| Length of Time | Patient flow | Radiopharmaceutical | Dose (mCi) | Mode of administration | Type of stress | Acquisition parameters (detector; windowing, etc.) |
|---|---|---|---|---|---|---|
| | Injection | *In 111 annexin | high dose for example 5 | Bolus IV | | |
| 24 h | Waiting | | | | | |
| | Injection | **Tc 99m AccuTec | low dose for example 5 | Bolus IV | | |
| | Pharmacological stress | | | infusion IV | For example adenosine or dipyridamole vasodilatation | |
| 2 min | Injection | Tl 201 thallous chloride | low dose for example 1 | Bolus IV | | |
| 30 min | imaging | | | — | | Energy window 2-10% |

**AccuTec attaches to activated platelets and shows thrombus.
*Annexin attaches to apoptotic cells. Apoptotic cells being human neutrophils that have died and broken up, demonstrate inflammatory infiltrate.

Timeframe summary:
Total imaging time: 30 min.
Total patient time: 25 h.
Clinical protocol advantages:
1. Fast imaging time compared to standard imaging methods.
2. Enables identification of intra vascular plaque that may be released into the blood stream and as a result initiate a CVA or cardiac infarct.
3. Enables identification of the perfusion defect if any that is caused by these events.
4. Enables the study of dynamic plaques that are associated with cardiac plaque tissue damage and repair.

TABLE 83

Description: Non coincidence imaging using PET radiopharmaceuticals
Indication: study of glucose metabolism of cells including tumor, heart and brain cells.

| Time Since previous step | Patient flow | Radiopharmaceutical | remarks | Dose (mCi) |
|---|---|---|---|---|
| | Injection | FDG as a substrate for hexokinase in glucose metabolism | | 30-50 |
| up to 60 min | imaging | | | |

Clinical protocol advantages:
1. Fast imaging time compared to standard imaging methods.
2. Enables study of glucose metabolism of cells including tumor, heart and brain cells using PET radiopharmaceuticals.
Protocols for Non-Coincidence Imaging Using PET Radiopharmaceuticals The following imaging protocols use non-coincidence imaging using PET radiopharmaceuticals.

1. Use of F-18-Fluorodeoxyglucose (FDG), as a substrate for hexokinase in glucose metabolism, for the study of glucose metabolism of cells including tumor, heart and brain cells.
2. Use of F-18-Fluoromisonidazole for imaging of hypoxia and oxidative metabolism, with the clinical application of radiotherapy treatment planning.
3. Use of F-18-3'-Fluoro-3'-deoxythymidine (FLT) for the study of DNA synthesis.
4. Use of F-18-Fluoromethyl choline (FCH) as a choline precursor for cell membrane synthesis, for the study of choline metabolism of tumors.
5. Use of F-18-4-Fluoro-m-tyrosine (FMT) as a precursor for dopamine synthesis and as a substrate for aromatic amino acid decarboxylase (AAAD), with the clinical application of imaging brain tumors.
6. Use of F-18-6-Fluoro-L-DOPA as a precursor for dopamine synthesis and as a precursor for AAAD, with the clinical applications of imaging and grading Parkinson's disease and imaging neuroendocrine tumors.
7. Use of F-18-FP-β-CIT for binding to the dopamine transporter in dopaminergic axons, with the clinical application of imaging and grading Parkinson's disease and imaging neuroendocrine tumors.
8. Use of F-18-Pencyclovir (FHBG) to target thymidine kinase, with the clinical application of imaging reporter gene expression.
9. Use of F-18-Fluoroestradiol (FES) to target estrogen receptors, with the clinical application of breast tumor imaging.
10. Use of C-11-Methionine to target amino acid synthesis, with the clinical application of imaging brain tumors.
11. Use of Tc-99m-P280, Acutect® to target GP IIb/IIIa receptors on platelets, with the clinical applications of detection of thrombosis, such as deep vein thrombosis (DVT) and intratererial thrombosis in coronary and carotid arteries.
17. Use of C-11-Raclopride to target dopamine D2 receptors, for brain imaging of dopamine D2 receptors in schizophrenia, and assessment of dose for neuroleptics.
18. Use of I-123-iodobenzamide (IBZM) to target dopamine D2 receptors, for brain imaging of dopamine D2 receptors in schizophrenia, and assessment of dose for neuroleptics.
19. C-11-carfentanil to target Mu opioid receptors in brain, with the clinical application of imaging drug addiction.
20. Use of C-11-α-methyl-L-tryptophan as a precursor for α-methyl serotonin synthesis and as a substrate for AAAD enzyme, with the clinical application of imaging depression.
21. Use of C-115-Hydroxytryptophan as a precursor for serotonin synthesis with the clinical application of imaging neuroendocrine tumors.
22. Use of F-18-MPPF to bind to 5-HT1A (5-hydroxytryptamine-1A) serotonin receptors, with the clinical application of imaging depression and epilepsy.
23. Use of F-18-Altanserin to bind to 5-HT2A serotonin receptors with the clinical application of imaging depression and epilepsy.
24. Use of C-11-Acetate for the study of tricarboxylic acid cycle activity and oxidative metabolism with the clinical application of studying myocardial oxygen metabolism.
25. Use of C-11-Palmitate as a precursor for fatty acid metabolism with the clinical application of imaging myocardial metabolism.
26. Use of F-18-Fluorodopamine to target presynaptic adrenergic receptors

TABLE 84

| | Short | Medium | Long |
|---|---|---|---|
| Heart | Up to 2 min | 2-20 min | Over 20 min |
| Lung | Up to 30 min | 30-60 min | Over 60 min |
| Breast | Up to 2 min | 2-15 min | Over 15 min |
| Brain | Up to 2 min | 2-20 min | Over 20 min |
| Liver | Up to 5 min | 5-10 min | Over 10 min |
| Kidney | Up to 10 min | 10-30 min | Over 30 min |
| Stomach | Up to 10 min | 10-30 min | Over 30 min |
| Prostate | Up to 10 min | 10-30 min | Over 30 min |
| Adrenal | Up to 10 min | 10-30 min | Over 30 min |
| Thyroid | Up to 10 min | 10-30 min | Over 30 min |
| Parathyroid | Up to 5 min | 5-10 min | Over 10 min |
| Bone | Up to 10 min | 10-30 min | Over 30 min |

TABLE 85

| | short | medium | long |
|---|---|---|---|
| Whole body | Up to 5 min | 5-30 min | Over 30 min |
| SST receptor expression | Up to 5 min | 5-10 min | Over 10 min |
| Endocrine tumors | Up to 5 min | 5-30 min | Over 30 min |
| Neuroendocrine tumors | Up to 5 min | 5-30 min | Over 30 min |
| FUO | Up to 5 min | 5-30 min | Over 30 min |
| Vascular structures in pelvis | Up to 5 min | 5-30 min | Over 30 min |

Example 2

Low Dose Radiopharmaceuticals

The protocols of the present invention are typically performed with low dose radiopharmaceuticals. The following example further describes such doses and provides kits of low dose pharmaceuticals that may be used together with the protocols of the present invention.

The main limitation associated with diagnostic nuclear imaging is the risk associated with humans coming in contact with radioactive materials. In 1901, five years after discovering radioactivity, Henri Becquerel recognized the risks involved in exposure to radioactive isotopes. A short time after he had carried a sample of uranium in his pocket, he observed that the underlying skin developed first erythema (reddening of the skin) and then tissue necrosis, which he attributed to the radioactive properties of the specimen.

Ionizing radiation sources can produce pathological damage by direct cell damage or by producing free radicals which are formed through ionization or excitation reactions and which destruct the chemical integrity of biological molecules such as DNA and proteins, leading to cell death and cancer. Radiation damage to DNA is due primarily to indirect action of radicals, which leads to the lethal and mutagenic effects attributed to ionizing radiation. On the other hand, the same effect is harnessed therapeutically as more rapidly dividing cells are more sensitive to ionizing radiation.

Other than being a source of ionizing radiation, most radioisotopes and radiopharmaceuticals such as heavy metals, and some targeting (recognition binding) moieties of radiotracers are chemically and/or metabolically toxic, and can disrupt enzymatic reactions and other metabolic processes in the body.

The current conservative hypothesis assumes that some risk is associated with even the smallest doses of radiation. Furthermore, it is long known that while there are safety guidelines for exposure to ionizing radiation such as radioactivity, any dose is harmful because radiative damage is cumulative over the life span. Today, after more than a century of careful review of the evidence for radiation effects from the radiation doses associated with diagnostic nuclear medicine, there appears to be little reason for apprehension about either genetic or somatic effects (including thyroid cancer) if exposure is controlled, monitored and utterly minimized. Most practitioners and regulation agencies base their dosage regimes on the Nuclear Regulation Committee (NRC) guidelines and follow NRC regulations.

In order to reduce the harmful effects of radiopharmaceuticals and radiotracers, medical use of these chemicals is closely monitored and controlled by the NRC which has issued strict guidelines for the manufacture, storage and maximal doses administered of such substances (Siegel, J. A., *Guide for Diagnostic Nuclear Medicine,* 2002, U.S. Nuclear Regulatory Commission).

Diagnostic dose guidelines are set according to the effect of the radiopharmaceutical on body tissue. One parameter which is useful in setting dose limits of diagnostic radiopharmaceuticals is the effective dose equivalence (EDE) which can be expressed as Roentgen Equivalent Man (rem, the amount of ionizing radiation required to produce the same biological effect as one rad of high-penetration x-rays) or Sievert (Sv) units, as this unit is defined hereinbelow, wherein 1 rem equals 0.01 Sv.

Following are the acceptable definitions of the units serving to measure radiation doses and effective dose equivalents (EDE, described supra).

The Sievert (symbol Sv) or millisievert (mSv) is an SI (International Standards and Units Organization) derived unit of equivalent dose or effective dose of radiation, and so is dependent upon the biological effects of radiation as opposed to the physical aspects, which are characterized by the absorbed dose, measured in grays (see, definition below). The millisievert (mSv) is commonly used to measure the effective dose in diagnostic medical procedures, e.g., X-rays, nuclear medicine, positron emission tomography (PET) and computed tomography (CT). For example, the natural background effective dose rate varies considerably from place to place, but typically is around 3.5 mSv/year. For a full body equivalent dose, 1 Sv causes slight blood changes, 2-5 Sv causes nausea, hair loss and hemorrhage, and will cause death in many cases. More than 3-6 Sv will lead to death in less than two months in more than 80% of cases.

The Becquerel (symbol Bq) is the SI derived unit of radioactivity, defined as the activity of a quantity of radioactive material in which one nucleus decays per second. It is therefore equivalent to second$^{-1}$. The older unit of radioactivity was the curie (Ci), defined as $3.7 \times 10^{10}$ becquerels or 37 GBq. It was named after Henri Becquerel, who shared a Nobel Prize with Marie Curie for their work in discovering radioactivity. In a fixed mass of radioactive material, the number of becquerels changes with time. In some circumstances, amounts of radioactive material are given after adjustment for some period of time. For example, one might quote a ten-day adjusted figure, that is, the amount of radioactivity that will still be present after ten days. This deemphasizes short-lived isotopes.

The curie (symbol Ci) or millicurie (mCi) is a former unit of radioactivity, defined as $3.7 \times 10^{10}$ decays per second. This is roughly the activity of 1 gram of the radium isotope $^{226}$Ra, a substance studied by the pioneers of radiology, Marie and Pierre Curie. The Ci has been replaced by Bq. One Bq=$2.7027 \times 10^{-11}$ Ci The gray (symbol Gy) or milligray (mGy) is the SI unit of energy for the absorbed dose of radiation. One gray is the absorption of one joule of radiation energy by one kilogram of matter. The gray replaced the rad, which was not coherent with the SI system. One Gy equals 100 rads.

Rem (symbol rem) is the amount of ionizing radiation required to produce the same biological effect as one rad of high-penetration x-rays.

Radiation absorbed dose (symbol rad) is a unit of radiation dose or the amount of radiation absorbed per unit mass of material. Rad was superseded in the SI by the Gy. The United States is the only country to still use the rad. Rads are often converted to units of rem by multiplication with quality factors to account for biological damage produced by different forms of radiation. The quality factor for X-rays is 1, so rads and rems are equivalent.

EDE (effective dose equivalence) takes into account the type of radiation, half life and distribution of an isotope to derive a number which represents the effect on human tissues for milliCurie (mCi, as this unit is defined hereinbelow) of the isotope administered.

For example, brain perfusion SPECT imaging performed by administration of a 20 mCi dose of $^{99m}$Tc is equivalent to 0.7 rem. This EDE value is similar to that received during a radionuclide bone scan, is 1.5 times that received from a CT of the abdomen and the pelvis, and is 43% of the annual average background radiation in the United States.

When administered to a 70 kg adult male, the average EDE of such doses falls within a range of 0.5 to 1.5 rem. Table 86 below presents typical doses from several commonly practiced nuclear medicine exams and scans based on a 70 kg individual, and provide information on prior art diagnostic radiopharmaceutical doses utilized to carry out these scans.

TABLE 86

| Nuclear Medical Scan | Radiopharmaceutical | Activity mCi (mBq) | Effective Dose mrem (mSv) |
|---|---|---|---|
| Brain | $^{99m+}$Tc DTPA | 20 (740) | 650 (6.5) |
| Brain | $^{15}$O water | 50 (1,850) | 170 (1.7) |
| Brain | $^{99m}$Tc HMPAO | 20 (740) | 690 (6.9) |
| Hepatobiliary | $^{99m}$Tc SCO | 5 (185) | 370 (3.7) |
| Bone | $^{99m}$Tc MDP | 20 (740) | 440 (4.4) |
| Lung Perfusion/Ventilation | $^{99m}$Tc MAA & $^{133}$Xe | 5 & 10 (185 & 370) | 150 (1.5) |
| Kidney | $^{99m}$Tc DTPA | 20 (740) | 310 (3.1) |
| Kidney | $^{99m}$Tc MAG3 | 20 (740) | 520 (5.2) |
| Tumor | $^{67}$Ga | 3 (110) | 1,220 (12.2) |
| Heart | $^{99m}$Tc sestimibi | 30 (1,100) | 890 (8.9) |
|  | $^{99m}$Tc pertechnetate | 30 (1,100) | 1,440 (14.4) |
| Heart | $^{201}$Tl chloride | 2 (74) | 1,700 (17) |
|  | $^{99m}$Tc tetrofosmi | 30 (1,100) | 845 (8.45) |
| Various | $^{18}$F FDG | 10 (370) | 700 (7.0) |

The regulations for use of radiopharmaceuticals changes in cases of patients with lower mass, such as fetuses, infants and children. If a pregnant patient undergoes a diagnostic nuclear medicine procedure, the embryo/fetus will be exposed to radiation. Typical embryo/fetus radiation doses for more than 80 radiopharmaceuticals have been determined by Russell et al. (*Health Phys.*, 1997, 73: 756-769). For the most common diagnostic procedures in nuclear medicine, the doses range from $0.5 \times 10^{-4}$ to 3.8 rad, the highest doses being for $^{67}$Ga. Most procedures result in a dose that is a factor of 10 or more lower than the 3.8 rad dose.

In situations involving the administration of radiopharmaceuticals to women who are lactating, the breastfeeding infant or child will be exposed to radiation through intake of radioactivity in the milk, as well as external exposure from close proximity to the mother. Radiation doses from the activity ingested by the infant have been estimated for the most common radiopharmaceuticals used in diagnostic nuclear medicine by Stabin and Breitz (*J. Nucl. Med*, 2000, 41:862-873). In most cases, no interruption in breast feeding is needed to maintain a radiation dose to the infant well below 100 mrem (1 mSv). Only brief interruption (hours to days) of breast feeding was advised for $^{99m}$Tc-macroaggregated albumin, $^{99m}$Tc-pertechnetate, $^{99m}$Tc-red blood cells, 99 mTc-white blood cells, $^{123}$I-metaiodobenzylguanidine, and $^{201}$Tl. Complete cessation was suggested for $^{67}$Ga-citrate, $^{123}$I-sodium iodide, and $^{131}$I-sodium iodide. The recommendation for $^{123}$I was based on a 2.5% contamination with $^{125}$I, which is no longer applicable.

Representative data of radiation dose estimates for a number of radiopharmaceuticals commonly used in nuclear medicine; each listed in a table for all major source organs, several other organs typically of interest, and the effect of an administered dose (per mCi) of a specific radiopharmaceutical on target organs expressed in rem per mCi, is presented in Appendix 1 hereinbelow. Data was collected from "Radiation Dose Estimates for Radiopharmaceuticals" by Michael G. Stabin, James B. Stubbs and Richard E. Toohey of the Radiation Internal Dose Information Center, Oak Ridge Institute for Science and Education, mail stop 51, P.O. Box 117, Oak Ridge, Tenn. 37831-0117.

Although the presently administered doses of radiopharmaceuticals are considered safe, there is a great need to substantially reduce the radiation and toxic effects attributed to use of such substances. Due to the finite sensitivity exhibited by today's imaging probes, currently established doses of radiopharmaceuticals are at the upper limits of those allowed by the NRC.

One inherent limitation of radioactive-emission imaging stems from the weighing of risks and benefits, namely the conflict between the requirement to limit the use of potentially harmful radioactive isotopes on one hand, and the need to generate sufficient photons from the diagnosed subject in order to produce a meaningful image on a camera or detector of limited sensitivity, on the other. Although low amounts of such radioisotopes are typically administered so as to not exceed recommended doses, currently available detectors require substantial and potentially hazardous amounts of radioisotopes in order to efficiently detect emission. This problem is intensified in cases where a patient is required to undergo several diagnostic procedures over the time of disease treatment, and more so in cases where the patient is a pregnant woman, an infant or a child.

Another limitation of the currently used techniques is the relatively short time periods which are available to the practitioner to collect diagnostic nuclear images due to decay of the radioisotopes (most diagnostic radiopharmaceuticals are characterized by short half-life), and rapid clearance of the diagnostic radiopharmaceuticals from the body by natural bio-processes. Moreover, the rapid decay and clearance of the radiopharmaceuticals prevents sufficient diagnosis of a dynamic system such as the body, wherein a series of images must be taken, so as to characterize a constantly changing environment. In these cases, a static image will not suffice but rather a series of images, much like in a movie. Again, this limitation could have been partially lessened if high dosage could be administered or images could be collected by more sensitive devices.

Thus, although the presently administered doses of diagnostic radiopharmaceuticals are considered safe there is still a widely recognized need for, and it would be highly advantageous to have radiopharmaceutical kits and methods in which the radiation and toxic effects of the radiopharmaceuticals are substantially reduced, whereby the diagnosis quality is at least maintained and desirably improved.

The present inventors have recently devised and constructed single and multi-collector emission detection probes which have vastly improved emission collection capabilities which enable highly sensitive and/or short-termed image capture. These novel emission detection/collection systems are at least ten-fold more efficient than presently utilized systems (the ratio of measured radiation to emitted radiation is at least 10 to 100-fold higher than prior art systems). This is primarily due to the use of either very sensitive radioactivity emission detectors coupled to high resolution position sensing detectors or to the use of multiple scannable detectors, and further to the use of dedicated algorithms as is disclosed, for example, in the following international applications: PCT/IL2005/000394, PCT/IL2005/000572, PCT/IL2005/000575, PCT/IL2005/000048, WO20040054248 and WO200216965, the contents of which are hereby incorporated by reference. These novel systems employ emission probes which are highly efficient in collecting emissions and thus enable, in combination with dedicated processing algorithms, more sensitive and accurate emission mapping.

The present inventors have now envisioned that the exceptional performance of the abovementioned device, can be efficiently utilized in diagnostic nuclear medicine and imaging, by opening a path to the desired minimization of exposure to ionizing radiation of patients and staff members and/or to the desired high resolution imaging.

The present invention is of diagnostic radiopharmaceutical dose units and methods of using same in diagnostic nuclear imaging. Specifically, the present invention can be used to image specific tissue such as pathological tissue and acquire dynamic imagery while minimizing the harmful effects of radiation caused by use of ionizing radiation sources in diagnostic radiopharmaceuticals. The present invention can further be used to image tissues while utilizing otherwise inefficient radiopharmaceuticals (e.g., having inherent low emission rate) and/or to perform dynamic imagery during short time periods and/or in high resolution.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The use of radioactive substances which produce ionizing radiation is necessary for advanced methods of pathologic diagnosis and for planning an optimal treatment regime of a growing number of medical conditions. Use of radioactive substances allows the practice of minimally invasive surgical techniques, which save the patients most of the trauma, pain, suffering, hospitalization, recovery and adverse complications associated with conventional "open surgical" procedures. Yet, the use of diagnostic radiopharmaceuticals in diagnostic nuclear medicine is associated with some risk since it exposes the probed subject as well as the medical and technical staff to harmful radiation, and further posses the obligation of expensive and complicated disposal of radioactive materials.

In view of the above, there is a constant need to minimize the exposure of any subject, to ionizing radiation. This can be achieved by minimizing the amount/concentration of the radioactive substance and/or the duration of the exposure to the radioactive substance.

A patient undergoing a nuclear medicine procedure will receive a radiation dose. Under present international guidelines it is assumed that any radiation dose, however small, presents a risk.

An effective dose of a nuclear medicine investigation is typically expressed by units of millisieverts (mSv). The effective dose resulting from an investigation is influenced by the amount of radioactivity administered in megabecquerels (MBq), the physical properties of the diagnostic radiopharmaceutical used (e.g., the type of ionizing radiation, the rate of emission and decay), its distribution in the body (e.g., the accumulation of the emitting agent per tissue) and its rate of clearance from the body. For example, effective doses can range from 0.006 mSv for a 3 MBq for $^{51}$Cr-EDTA measurement of glomerular filtration rate (measurement of the kidneys' waste filtration and removal) to 37 mSv for a 150 MBq $^{201}$Tl non-specific tumor imaging procedure. The common bone scan with 600 MBq of $^{99m}$Tc-MDP has an effective dose of 3 mSv.

As mentioned above, the present inventors have developed a system which employs emission probes that are highly efficient in collecting emissions and thus enable, in combination with dedicated processing algorithms, more sensitive and accurate emission mapping.

These novel systems have encouraged the present inventors to conceive novel diagnostic kits and diagnosis methods which enable (i) substantially lower diagnostic radiopharmaceutical doses (as compared with the presently used doses); (ii) shorter time of exposure (i.e., collecting the imaging data is a shorter time); (iii) use of radioisotopes that have short half-life and which are typically impractical when the presently known imaging devices are utilized; and (iv) mapping of organs in which rapid substance clearance is observed, and any combination of the foregoing.

Furthermore, the present inventors hypothesized that the heightened sensitivity and overall higher efficiency of the data acquisition device, which allows for the shorter exposure time for diagnostic nuclear imaging, will open the possibility of invasive, minimally invasive and noninvasive time-resolved imagery, or dynamic imagery of biological systems in a living organism.

Thus, the present inventors have now uncovered that the use of such probes facilitates the use of substantially lower amounts of diagnostic radiopharmaceuticals than those presently utilized and thus enables packaging and diagnostic use of novel radiopharmaceutical dose units of substantially lower radioactivity. As is illustrated above, the probe and imaging systems described in previous disclosures of the present inventors enable, for the first time, use of substantially lower doses of various diagnostic radiopharmaceuticals in nuclear imaging.

Thus, according to one aspect of the present invention, there is provided a diagnostic pharmaceutical kit which can be utilized in nuclear imaging techniques. The kit contains a packaged dose unit of a diagnostic radiopharmaceutical having an effective dose equivalence (EDE) of 2.5 millirem (mrem) or less per kg body weight of a subject. This packaged dose is considerably lower than the packaged dose of the prior art, and is in line with the general motivation to reduce to a minimum the exposure of the subject to substances which emit ionizing radiation. Preferably, the EDE of the packaged dose unit of the present invention is 0.01-2 millirem per kg body weight of a subject, and more preferably it is 0.01-1 millirem per kg body weight of a subject.

Similarly, the diagnostic pharmaceutical kit of the present invention contains a packaged dose unit of a diagnostic radiopharmaceutical having an effective dose equivalence (EDE) of 150 millirem (mrem) or less, which is a typical whole-body dose for a 70 kg person. Preferably, the EDE of the packaged whole-body dose unit of the present invention is 15-100 millirem per 70 kg subject, more preferably 15-50 millirem per 70 kg subject.

Compared to a typical whole-body dose of $^{99m+}$Tc DTPA of 650 mrem for a brain scan according to prior art, a whole-body dose of the present invention can be as low as 65 mrem and less; compared to a typical whole-body dose of $^{99m}$Tc-Sestimibi of 890 mrem for a heart scan according to prior art, a whole-body dose of the present invention can be as low as 89 mrem and less; and compared to a typical whole-body dose of $^{18}$F FDG of 700 mrem for a general somatic scan according to prior art, a whole-body dose of the present invention can be as low as 70 mrem and less.

Alternatively, the dose unit can include an amount of a diagnostic radiopharmaceutical which will result in an amount of detected counts sufficient for imaging when using the abovementioned imaging device having a heightened sensitivity. In nuclear medicine, the dose in mCi of a diagnostic radiopharmaceutical can also be determined according to the sensitivity of the detector utilized, the total time of scan and the total counts needed for imaging (typically about 2–4×10$^6$ for a scanned region and about 10$^5$ for a target organ such as the heart). These parameters can be utilized to determine the collection efficiency of prior art emission detection systems. For example, in a $^{99m}$Tc heart scan a typical administered dose is 20-30 mCi of which about 1.2-1.5% to 1.5-4% are uptaken by the heart (namely 0.3 mCi-1.2 mCi, typically 0.5-1.0 mCi) and a typical scan is conducted for approximately 10 minutes (600 seconds). Since a single mCi accounts for 3.7×10$^7$ counts per second, the efficiency of a typical detection system calculates to approximately 1.8 photons captured for every 10,000 photons emitted from the organ. Since the present system is at least 10 fold more efficient at photon capturing (e.g., capable of capturing at least 1 photon out of every 1000 photons emitted) a tenth of a diagnostic radiopharmaceutical dose can be utilized for scanning. Thus, for the above described example, a packaged dose unit of 2.5 mCi $^{99m}$Tc or less can be utilized for imaging a heart over a period of 10 minutes.

Since the dose reaching the target organ (e.g., the heart) is a fraction of the dose administered, for example, and as stated above, in the case of mapping the cardiac muscle, about 1.5-4% of the dose injected intravenously (20-30 mCi) reaches the heart (0.3 mCi in the heart), mapping a directly injected dose unit of 0.03 mCi or less is possible using the systems developed by the present inventors.

As used herein the phrase "packaged dose unit" refers to a dosage unit (or unit dose) which is packaged in one or more containers such as vials, ampoules or a delivery syringe. Preferably, the dose unit is manufactured and packaged for inhalation or injection (intravenous or subcutaneous) according to FDA regulatory guidelines for human use [Rules and Regulations, *Federal Register* (1999), Vol. 64, No. 94, pp 26657-70].

The dose unit may be ready for administration or may require premixing prior to administration. The latter case is exemplified by a radiotracer preparation which includes an isotope attached to a recognition binding moiety such as an antibody, as is detailed hereinbelow.

A diagnostic radiopharmaceutical can be a compound containing one or more radioisotopes per se, or, a radiotracer, in which the compound is bound to a recognition moiety, as follows.

In cases where the organ, tissue or cells to be imaged can be characterized by a known specific and localized (fixed) biochemical moieties, such as a peptide, a protein, a receptor, a membrane, a glycan, a nucleic acid (i.e., RNA and/or DNA) or any combination thereof, the radiopharmaceutical can be designed so as to specifically bind to one or more of these biochemical moieties by way of molecular recognition. This binding is afforded by virtue of one or more recognition moieties which form a part of the radiopharmaceutical. These recognition binding moieties are selected so as to have a high affinity to the specific biochemical moieties characterizing the target organ, tissue or cells to be imaged. This affinity allows for the radiopharmaceutical to concentrate at the target organ, tissue or cells at higher rates than the surrounding organs, tissues or cells, thereby affording an image wherein the target organ, tissue or cells are highlighted by the contrast of radioactive emission.

Radiopharmaceuticals having such binding moieties which act as a vehicle for transporting and delivering the radioactive isotope to a specific target are referred to herein as radiotracers. Therefore, the term "radiotracer", as used herein, refers to a radiopharmaceutical having one or more recognition binding (targeting) moieties attached thereto.

As used herein, the phrase "recognition binding moiety" or "targeting moiety" refers to a moiety that interacts (binds) with a target recognition site by means of molecular recognition, and include, without limitation, a ligand, an inhibitor, a co-factor, an antibody, a monoclonal antibody, an antibody fragment, an antigen, a hapten, a receptor, a receptor affine peptide, a peptide, a protein, a membrane, a nucleotide and a nucleic acid.

Molecular recognition, also known as "host-guest chemistry", is a phenomenon in which molecules are distinguished accurately from other molecules. Chemically, it indicates that certain molecules abnormally bond with certain molecules and are relatively inert with respect to other molecules found in the same environment. This phenomenon involves the three-dimensional positioning of various sub-molecular functionalities which can form interactions via reciprocal actions such as hydrogen bonds, hydrophobic interactions, ionic interactions, aromatic interactions and/or other non-covalent bond interactions and combination thereof. General examples of molecular recognition include ligand-receptor interactions, enzyme-substrate interactions, antibody-antigen interactions, biotin-avidin affinity interactions and the like.

Non-limiting examples of commonly used radiotracers include $^{99m}$Tc-Arcitumomab (CEA-Scan™) which is a monoclonal antibody for imaging colorectal tissues afflicted with colorectal cancer, $^{99m}$Tc-sestamibi (Cardiolite™) and $^{99m}$Tc-tetrofosmin (Myoview™) for imaging the heart of a subject for myocardial perfusion, $^{111}$In-Capromab pendetide (ProstaScint™) which is a monoclonal antibody for imaging prostate tissues afflicted with prostate cancer, $^{99m}$Tc-Fanolesomab (NeutroSpec™) which is a monoclonal antibody for imaging inflamed and infectious tissues and $^{90}$Y/$^{111}$In-Zevalin (Ibritumomab Tiuxetan) which is a monoclonal antibody directed against the CD20 antigen, whereby this antigen is found on the surface of normal and malignant B lymphocytes.

Any diagnostic radiopharmaceutical can be utilized in the kit of the present embodiments. In general, the kit of the present embodiments may contain a reduced radiation dose emitted from each radiopharmaceutical, which ranges from 0.1 of the dose of the prior art to 0.01 of the dose of the prior art.

Exemplary radiopharmaceuticals that can be utilized in this context of the present invention include, without limitation, $^3$H-water, $^3$H-inulin, $^{11}$C-carbonmonoxide, $^{13}$N-ammonia, $^{14}$C-inulin, $^{15}$O—H$_2$O, $^{15}$O—O$_2$, $^{18}$F-fluorodeoxyglucose, $^{18}$F-sodium fluoride, $^{51}$Cr-erythrocytes (RBC), $^{57}$Co-vitamin B$_{12}$ (cyanocobalamin), $^{58}$Co-vitamin B$_{12}$ (cyanocobalamin), $^{59}$Fe-citrate, $^{60}$Co-vitamin B$_{12}$ (cyanocobalamin), $^{67}$Ga-citrate, $^{68}$Ga-citrate, $^{75}$Se-selenomethionine, $^{81m}$Kr-krypton for inhalation, oral administration or injections, $^{82}$Rb, $^{85}$Sr-nitrate, $^{90}$Y/$^{111}$In-ibritumomab tiuxetan ($^{90}$Y/$^{111}$In-Zevalin), $^{99m}$Tc-albumin microspheres, $^{99m}$Tc-disofenin, lidofenin and mebrofenin, $^{99m}$Tc-DMSA, $^{99m}$Tc-DTPA (injection), $^{99m}$Tc-DTPA (aerosol), $^{99m}$Tc-ECD (ethylene cystate dimer), $^{99m}$Tc-exametazime (HMPAO), $^{99m}$Tc-glucoheptonate, $^{99m}$Tc-HEDP, $^{99m}$Tc-HMDP, $^{99m}$Tc-HSA, $^{99m}$Tc-MAA, $^{99m}$-Tc-MAG$_3$, $^{99m}$Tc-MDP, $^{99m}$Tc-tetrofosmin (Myoview), $^{99m}$Tc-sestamibi (Cardiolite), $^{99m}$Tc-oral administrations, $^{99m}$Tc-pertechnetate, $^{99m}$Tc-pyrophosphate, $^{99m}$Tc-RBC in vitro and in vivo labeling, $^{99m}$Tc-sulfur colloid, $^{99m}$Tc-teboroxime, $^{99m}$Tc-white blood cells, $^{111}$In-ibritumomab tiuxetan ($^{111}$In-Zevalin), $^{111}$In-DTPA, $^{111}$In-platelets, $^{111}$In-RBC, $^{111}$In-white blood cells, $^{123}$I-hippuran, $^{123}$I-IMP, $^{123}$I-mIBG, $^{123}$I-sodium iodide, $^{124}$I-sodium iodide, $^{125}$I-fibrinogen, $^{125}$I, IMP, $^{125}$I-mIBG, $^{25}$I-sodium iodide, $^{126}$I-sodium iodide, $^{130}$I-sodium iodide, $^{131}$I-hippuran, $^{131}$I-HSA, $^{131}$I-MAA, $^{131}$I-mIBG, $^{131}$I-Rose Bengal, $^{131}$I-sodium iodide, $^{127}$Xe-inhalation and injection, $^{133}$Xe-inhalation and injection, $^{197}$Hg-chlormerodrin, $^{198}$Au-colloid and $^{201}$Tl-chloride.

Following are several non-limiting examples of the radioactive dose of exemplary radiopharmaceuticals utilized in accordance with this aspect of the present invention. Since an administered dose is typically measured in mCi activity of the radioisotope, the following lists the radioactivity of a packaged dose unit in the kit of the present embodiments, compared to the radioactivity of the presently used doses.

Radioactive ammonia typically comprises a $^{13}$N isotope having a half-life of 9.96 minutes. A radioactive dose of $^{13}$N-ammonia is typically 20 mCi. According to a preferred embodiment of the present invention, a radiopharmaceutical kit comprises a radioactive dose of $^{13}$N-amminia that ranges from 5 mCi to 0.01 mCi, more preferably from 2 mCi to 0.02 mCi and thus can be, for example, 5, 2, 1, 0.5, 0.2, 0.1, 0.05, 0.02 or 0.01 mCi.

Radioactive fluorodeoxyglucose (FDG) typically comprises an $^{18}$F isotope having a half-life of 110 minutes. A radioactive dose of $^{18}$F-FDG is typically 10 mCi. According to a preferred embodiment of the present invention, a radiopharmaceutical kit comprises a radioactive dose of $^{18}$F-FDG that ranges from 3 mCi to 0.1 mCi, more preferably from 1 mCi to 0.1 mCi and thus can be, for example, 3, 1 or 0.1 mCi.

Radioactive capromab pendetide (ProstaScint), typically comprises an $^{111}$In isotope having a half-life of 72 hours. A radioactive dose of $^{111}$In-capromab pendetide is typically 5 mCi. According to a preferred embodiment of the present invention, a radiopharmaceutical kit comprises a radioactive dose of $^{111}$In-capromab pendetide that ranges from 2 mCi to 0.01 mCi, more preferably from 0.5 mCi to 0.01 mCi and thus can be, for example, 2, 1, 0.5, 0.1, 0.05 or 0.01 mCi.

Radioactive WBCs (non-protein peptide), typically comprises an $^{111}$In isotope. A radioactive dose of $^{111}$In-WBCs is typically 0.5 mCi. According to a preferred embodiment of the present invention, a radiopharmaceutical kit comprises a radioactive dose of $^{111}$In-WBCs that ranges from 0.2 mCi to 0.001 mCi, more preferably from 0.05 mCi to 0.001 mCi and thus can be, for example, 0.2, 0.1, 0.05, 0.01, 0.005 or 0.001 mCi.

Radioactive Satumomab Pendetide (OncoScint), typically comprises an $^{111}$In isotope. A radioactive dose of $^{111}$In-Satumomab Pendetide is typically 5 mCi. According to a preferred embodiment of the present invention, a radiopharmaceutical kit comprises a radioactive dose of $^{111}$In-Satumomab Pendetide that ranges from 2 mCi to 0.01 mCi, more preferably from 0.2 mCi to 0.01 mCi and thus can be, for example, 2, 1, 0.5, 0.1, 0.05 or 0.01 mCi.

Radioactive Pentetreotide typically comprises an $^{111}$In isotope. A radioactive dose of $^{111}$In-Pentetreotide is typically 6 mCi. According to a preferred embodiment of the present invention, a radiopharmaceutical kit comprises a radioactive dose of $^{111}$In-Pentetreotide that ranges from 1 mCi to 0.005 mCi, more preferably from 0.5 mCi to 0.005 mCi and thus can be, for example, 1, 0.5, 0.2, 0.1, 0.05, 0.01 or 0.005 mCi.

Radioactive Arcitumomab typically comprises a $^{99m}$Tc isotope having a half-life of 6 hours. A radioactive dose of $^{99m}$Tc-Arcitumomab typically ranges from 20 mCi to 30 mCi. According to a preferred embodiment of the present invention, a radiopharmaceutical kit comprises a radioactive dose of $^{99m}$Tc-Arcitumomab that ranges from 5 mCi to 0.05 mCi, more preferably from 3 mCi to 0.05 mCi and thus can be, for example, 5, 2, 1, 0.5, 0.1 or 0.05 mCi.

Radioactive Sodium pertechnetate typically comprises a $^{99m}$Tc isotope. A radioactive dose of $^{99m}$Tc-Sodium pertechnetate typically ranges from 10 mCi for a whole-body scan to 0.1 mCi, whereby the packaged dose unit is typically formulated as a drop for an eye scan. According to a preferred embodiment of the present invention, a radiopharmaceutical kit comprises a radioactive dose of $^{99m}$Tc-Sodium pertechnetate that ranges from 5 mCi to 0.01 mCi, more preferably from 1 mCi to 0.01 mCi and thus can be, for example, 5, 2, 1, 0.5, 0.2, 0.1, 0.05, 0.02 or 0.01 mCi.

A radioactive dose of Erythrocytes (RBC) comprising a $^{99m}$Tc isotope typically ranges from 10 mCi to 25 mCi. According to a preferred embodiment of the present invention, a radiopharmaceutical kit comprises a radioactive dose of $^{99m}$Tc-RBC that ranges from 5 mCi to 0.05 mCi, more preferably from 1 mCi to 0.05 mCi and thus can be, for example, 5, 2, 1, 0.5, 0.1, 0.05, 0.02 or 0.01 mCi.

Radioactive Depreotide (NeoTect), apcitide (AcuTect), pyrophosphate, medronate (MDP), exametazime (HMPAO) and bicisate (ECD, Neurolite) all comprise a $^{99m}$Tc isotope. A radioactive does of these radiopharmaceuticals is typically 20 mCi. According to a preferred embodiment of the present invention, radiopharmaceutical kits comprise a radioactive dose of such a $^{99m}$Tc-radiopharmaceuticals that ranges from 5 mCi to 0.05 mCi, more preferably from 1 mCi to 0.05 mCi and thus can be, for example, 5, 2, 1, 0.5, 0.2, 0.1, 0.05 mCi.

A radioactive dose of $^{99m}$Tc-Sestamibi typically ranges from 10 mCi (for stress) to 30 mCi (for rest). According to a preferred embodiment of the present invention, a radiopharmaceutical kit comprises a radioactive dose of such a $^{99m}$Tc-radiopharmaceutical that ranges from 5 mCi to 0.01 mCi, more preferably from 1 mCi to 0.01 mCi and thus can be, for example, 5, 2, 1, 0.5, 0.2, 0.1, 0.05, 0.02 or, 0.01 mCi.

Radioactive Cyanocobalamin typically comprises an $^{57}$Co isotope having a half-life of 271.8 days. A radioactive dose of $^{57}$Co-Cyanocobalamin is typically 0.001 mCi. According to a preferred embodiment of the present invention, a radiopharmaceutical kit comprises a radioactive dose of $^{57}$Co-Cyanocobalamin that ranges from 0.0003 mCi to 0.00001 mCi, more preferably from 0.0001 mCi to 0.00001 mCi and thus can be, for example, 0.0003, 0.0001, 0.00005 or 0.00001 mCi.

Radioactive Gallium Citrate, typically comprises a $^{67}$Ga isotope having a half-life of 271.8 days. A radioactive dose of $^{67}$Ga-Gallium citrate is typically 5 mCi for PET imaging and 10 mCi for SPEC imaging. According to a preferred embodiment of the present invention, a radiopharmaceutical kit comprises a radioactive dose of $^{67}$Ga-Gallium citrate that ranges from 1 mCi to 0.01 mCi, more preferably from 0.5 mCi to 0.01 mCi and thus can be, for example, 1, 0.5, 0.2, 0.1, 0.05 or 0.01 mCi.

$^{81}$Kr isotope, having a half-life of 210,000 years, is presently used as a gas for dynamic imaging. A radioactive dose of $^{81}$Kr is typically 10 mCi. According to a preferred embodiment of the present invention, a radiopharmaceutical kit comprises a radioactive dose of $^{81}$Kr that ranges from 2 mCi to 0.05 mCi, more preferably from 1 mCi to 0.05 mCi and thus can be, for example, 2, 1, 0.5, 0.1 or 0.05 mCi.

Radioactive sodium iodide typically comprises an $^{123}$I isotope having a half-life of 13.2 hours. A radioactive dose of $^{123}$I-sodium iodide typically ranges from 0.1 mCi to 0.4 mCi, and the radiopharmaceutical dose unit is often provided in capsules. According to a preferred embodiment of the present invention, a radiopharmaceutical kit comprises a radioactive dose of $^{123}$I-sodium iodide that ranges from 0.05 mCi to 0.001 mCi, more preferably from 0.01 mCi to 0.001 mCi and thus can be, for example, 0.1, 0.05, 0.02, 0.01, 0.005 or 0.001 mCi, whereby the $^{123}$I-sodium iodide can be packaged as capsules.

Radioactive Sodium iodide can alternatively comprise an $^{131}$I isotope having a half-life of 8 days. A radioactive does of $^{131}$I-sodium iodide typically ranges from 0.01 mCi to 0.004 mCi. According to a preferred embodiment of the present invention, a radiopharmaceutical kit comprises a radioactive dose of $^{131}$I-sodium iodide that ranges from 0.001 mCi to 0.00005 mCi, and thus can be, for example, 0.001, 0.0005, 0.0002, 0.0001 or 0.00005 mCi, whereby the $^{131}$I-sodium iodide can be packaged as capsules.

Radioactive albumin typically comprises an $^{125}$I isotope having a half-life of 59.4 days. A radioactive does of $^{125}$I-albumin is typically 0.02 mCi. According to a preferred embodiment of the present invention, a radiopharmaceutical kit comprises a radioactive dose of $^{125}$I-albumin that ranges from 0.005 mCi to 0.0001 mCi, more preferably from 0.001 mCi to 0.0001 mCi and thus can be, for example, 0.005, 0.002, 0.001, 0.0005 or 0.0001 mCi.

Radioactive sodium chromate typically comprises a $^{51}$Cr isotope having a half-life of 27.7 days. A radioactive dose of $^{51}$Cr-sodium chromate typically ranges from 0.15 mCi to 0.3 mCi. According to a preferred embodiment of the present invention, a radiopharmaceutical kit comprises a radioactive dose of $^{51}$Cr-sodium chromate that ranges from 0.05 mCi to 0.001 mCi, more preferably from 0.01 mCi to 0.001 mCi and thus can be, for example, 0.05, 0.02, 0.01, 0.005 or 0.001 mCi.

As is provided in the list above, the mCi dose range of the present dose unit of each listed exemplary diagnostic radiopharmaceutical is substantially lower than that of prior art dose units.

The kit of the present embodiments can be used with any suitable nuclear imaging technique.

The radiopharmaceutical of the diagnostic kit of the present embodiments can be prepared using any suitable prior art approach. Such approaches are well known to the ordinary skilled artisan and as such no further description of specific synthesis approaches of diagnostic radiopharmaceuticals and in particular radiotracers are provided herein.

However, in cases where the radiopharmaceutical is a radiotracer, it is sometimes preferred that the isotope be provided separate from the recognition binding moiety especially in cases of isotopes exhibiting a short half life, since a specific activity of such a radiotracer preparation will substantially decrease over a short time period.

As mentioned hereinabove, an effective dose of any given radiopharmaceutical is influenced, among other factors, by the amount of the radioisotope and the state of decay of the radioisotope, namely the radioactivity which is currently measured at any given time. In essence, an isotope which already decayed no longer contributes to the activity of the administered sample, and therefore is considered an impurity. In addition, radiopharmaceuticals which contain chelators or recognition moieties attached thereto may decompose, both in vivo and in vitro, so as to produce, for example, the radioisotope, the chelating moiety and/or the recognition moiety. The free chelators and recognition moieties are also considered impurities.

Radioisotopes utilized for synthesis are therefore typically >60% pure, and preferably are >90% pure; during radiotracer synthesis, a recognition binding moiety is mixed with a radioisotope and quality is checked to maintain approximately a 95% pure composition of the radiotracer. The remaining 5% is composed of non-radioactive isotopes, chelators, recognition moieties and the like.

Following mixing and prior to injection, isotope decay and chemical decomposition may reduce the specific activity of the diagnostic radiopharmaceutical in proportion to isotope decay time and the instability of the radiopharmaceutical.

Few diagnostic radiopharmaceuticals depend on "specific activity" or purity, since they "compete" for receptors with their decomposition products or their decomposition products produce adverse effects (e.g. to lungs).

The kit of the present invention can further include instructions for use in carrying out a nuclear scan as well as instructions for handling and additional packaging materials (e.g. pig) as required by federal regulations. Radioisotopes must be carefully handled, therefore vials or syringes containing such substances are delivered inside containers offering some degree of radiation shielding. Furthermore, government regulations require syringes to be disposed of in a disposal container that shields others from the risk of injury posed by their sharp, biologically-contaminated hypodermic needles. Such a container generally referred to herein as a "sharps" container, typically has an inner cavity or chamber that can hold one or more syringes.

One type of conventional delivery container currently used for the delivery of syringes containing radioactive drugs is known as a radiopharmaceutical pig. The radiopharmaceutical pig has a shielded inner chamber suitable for enclosing a syringe that is itself held inside of a sharps container. In particular, the chamber is lined with elemental lead to shield individuals from the radioactive drug in the syringe. The exterior of the radiopharmaceutical pig is a plastic polystyrene shell. The sharps container has an insert and a cap that can be engaged by two snaps that fit into two aligned slots formed on the insert.

Prior to administration, the syringe is loaded with the required dose of a radioactive drug and is placed in the insert, which is nested in the chamber of the radiopharmaceutical pig. The radiopharmaceutical pig is then closed and delivered to the hospital, whereupon the pig is disassembled and the syringe is used to inject the dose into the patient. The spent syringe may then be placed back into the sharps insert and the cap may then be placed on the housing to hold the spent syringe within the sharps container. The radiopharmaceutical pig is reassembled and taken to a disposal area, which may or may not be at the pharmacy.

While exposure to ionizing radiation presents a major, widely recognized limit to the presently known nuclear imaging techniques, these techniques are oftentimes limited by other factors. These include, for example, rapid decay of the radioisotope (i.e., short half-life), rapid clearance of the radiopharmaceutical from the targeted organ, and low energy and/or rate of disintegration of the radiopharmaceutical.

These characteristics determine the amount and energy of detectable photons which reach the detector per time unit. When used with the presently known emission detectors, low amount and/or energy of the detectable photons results in a weak or no signal and hence fail to provide a meaningful image. Thus, for example, radioisotopes that rapidly decay or are rapidly cleared from the target organ, fail to produce a sufficient amount of detectable photons at the time of data collection.

According to the present invention, the highly sensitive emission detector designed by the present inventors can be used to detect sufficient photons from such radioisotopes due to its higher efficiency and wider dynamic range, even for radioisotope characterized by a short half-life, low rate and low energy of disintegration, which may or may not be combined with a low rate of accumulation in the organ of interest and a rapid clearance from the body by metabolic and chemical processes.

The present inventors have now uncovered that the high sensitivity of the novel imaging probes described above can be used, due to higher efficiency and wider dynamic range, to collect sufficient imaging data even in cases of radiopharmaceuticals that are characterized by low amount and/or energy of the emitted photons within a time frame of a nuclear investigation. Thus, these highly sensitive probes enable to perform efficient imagery even with such radiopharmaceuticals that are incompatible or at least inefficient when utilized with the presently known techniques. These radiopharmaceuticals are collectively referred to herein as having an inherent low emission rate, as this phrase is defined hereinbelow.

Each of the radiopharmaceutical kits described herein can be efficiently utilized for obtaining nuclear images of tissue and organs of interest, by employing non- or minimally invasive techniques in vivo.

Thus, according to an additional the present invention there is provided a method of imaging a tissue of a subject. The method is effected by administering to the subject, either systemically or locally, a dose unit of a diagnostic radiopharmaceutical having a dose equivalent of 2.5 mrem or less per kg body weight, as detailed hereinabove; collecting the emission produced by the diagnostic radiopharmaceutical, as detailed hereinbelow; and translating the emission data collected into a two-dimensional or three-dimensional image data.

Typically, the radiopharmaceutical is administered systematically in order to achieve two main goals, a) reach the target organ which is typically out of reach when using non-invasive or minimally invasive techniques, and b) in order to create the appropriate background for the organ to be imaged and obtain the contrast between the areas of interest (those serving as targets for the radiopharmaceutical) and their surrounding. Systematic administration can be effected, for example, by intravenous injection, by inhalation or orally.

As the use of the abovementioned high sensitivity emission detector becomes available, the limitations associated with low signal are alleviated considerably. Thus, imaging of tissues or organs using radiopharmaceuticals that have low emission rate and hence presently lead to collection of insufficient data during a scan, is facilitated.

Thus, according to another aspect of the present invention, there is provided another method of imaging a tissue of a subject. The method, according to this aspect of the present invention is effected by administering to the subject, either systemically or locally, a dose unit of a radiopharmaceutical which is characterized by an inherent low emission rate, as detailed hereinabove; collecting the emission produced by the diagnostic radiopharmaceutical; and translating the emission data collected into a two-dimensional or three-dimensional image data.

The method, according to this aspect of the present invention, therefore allows to use radiopharmaceuticals and to image organs and/or tissues that are otherwise impractical.

The high sensitivity of the emission detector taught by the present inventors further enables to collect sufficient image data in a short time period. This feature is exceptionally advantageous since it allows to minimize the time during which a subject is exposed to radiation. Hence, using any diagnostic radiopharmaceuticals, including the radiopharmaceuticals described herein, nuclear imaging can be performed during a shorter time period, compared to the presently known imaging methods.

Thus, according to a further aspect of the present invention there is provided a method of imaging a tissue, which is effected by administering to the subject a dose unit of a diagnostic radiopharmaceutical; collecting emission of the diagnostic radiopharmaceutical during a time period that does not exceed, e.g., 1-30 minutes; and translating the emission collected into image data.

The method according to this aspect of the present invention is particularly advantageous in PET and SPECT imaging techniques.

Positron Emission Tomography (PET), is a nuclear medicine imagine technology which requires the administration to a subject of a molecule labeled with a positron-emitting nuclide. Single Photon Emission Computed Tomography (SPECT) is a form of chemical imaging in which emissions from radioactive compounds, labeled with gamma-emitting radionuclides, are used to create cross-sectional images of radioactivity distribution in vivo.

These techniques require relatively high emission levels for obtaining a meaningful image. In addition, radiopharmaceuticals that are suitable for use in these techniques are often characterized by relatively short half-lives. Thus, for example, $^{15}O$, $^{13}N$, $^{11}C$ and $^{18}F$, which are often used in PET, have half-lives of 2, 10, 20, and 110 minutes, respectively. Due to the high emission level required and the short half-lives of the radiopharmaceuticals, relatively high radiation doses of the radiopharmaceutical are administered to the subject.

Performing such nuclear imaging procedures in relatively short time periods is therefore exceptionally beneficial since it reduces the time the subject is exposed to high radiation level.

The ability to obtain all the required data during a short time period, which is not possible with other currently used detectors, further allows the investigator to collect several consecutive images during that time scan in which the emission rate is still sufficient for significant data collection.

These consecutive images can be used to provide time-resolved data of the tissue or organ of interest, showing the development in time of imaged system.

Thus, according to preferred embodiments of the present invention, for any of the methods described herein, a time-resolved data can be obtained by performing consecutive images of the investigated tissue.

Nuclear imaging techniques suffer from other limitations which are related to a weak signal or a low signal-to-noise ratio. Such limitations stem from the fact that any detector has a limited sensitivity, and at any dose of the radiopharmaceutical, only a fraction of the emitted radiation can be picked-up by the detector and/or be distinguished from the background noise.

Using the improved emission detector taught by the present invention can further enable and facilitate the provision of a high-resolution image of a tissue, which so far was impossible, difficult or required exceptionally high doses of the radiopharmaceutical and/or prolonged exposure of the subject to the radiopharmaceutical t.

Thus, according to an aspect of the present invention, there is provided a method of obtaining a high-resolution image of a tissue of a subject.

Any suitable extracorporeal or intracorporeal imaging technique employing any suitable probe types can be used to image the administered diagnostic radiopharmaceutical in the methods described herein. Preferably an imaging system employing a probe having a wide angle or a wide view of collection is employed.

Further preferably, the emission data is collected by one or more radioactive-emission probes which are characterized by a collection efficiency of 1%, each of which is separately adjustable within its housing.

Further preferably, the radioactive-emission probes, or emission detectors are scintillation probes which have a collection angle that enables a collection target area of 15 mm$^2$ when placed 15 cm away from the target area.

Extra and intra-corporeal probe types which are highly suitable for use with the kit of the present invention are described in detail in the PCT applications referenced hereinabove.

A non-limiting example of a widely used radiopharmaceutical, $^{99m}$Tc-sastamibi, is used herein to demonstrate the various novel features of the present invention. $^{99m}$Tc is characterized by a half-life ($t_{1/2}$) of 6.02 hours. Table 86a below presents the physical decay of $^{99m}$Tc, wherein the calibration time is set to 0 arbitrarily and the activity is defined as 100%. The remaining fraction of radioactivity is recorded every hour from that time point. This decay chart is used by the medical staff when preparing the sample for injection into a patient undergoing diagnostic imaging. The absolute activity of the product is measured at the manufacturer site on the day of shipment, and the complete assay data is provided on the tag attached to the vial.

TABLE 86a

| Hours | Fraction remaining |
|---|---|
| 0 | 1.000 (100%) |
| 1 | 0.891 (89.1%) |
| 2 | 0.794 (79.4%) |
| 3 | 0.708 (70.8%) |
| 4 | 0.631 (63.1%) |
| 5 | 0.562 (56.2%) |
| 6 | 0.501 (50.1%) |
| 7 | 0.447 (44.7%) |
| 8 | 0.398 (39.8%) |
| 9 | 0.355 (35.5%) |
| 10 | 0.316 (31.6%) |
| 11 | 0.282 (28.2%) |
| 12 | 0.251 (25.1%) |

Apart for radioactivity decay, the product is cleared from the body by natural processes. Myocardial uptake which is coronary flow dependent is 1.2% of the injected dose at rest and 1.5% of the injected dose at exercise. Table 87 below illustrates the biological clearance as well as effective clearance which include biological clearance and radionuclide decay of $^{99m}$Tc-Sestamibi from the heart and liver.

TABLE 87

| Time | Rest | | | | Stress | | | |
| | Heart | | Liver | | Heart | | Liver | |
| (minutes) | Biological | Effective | Biological | Effective | Biological | Effective | Biological | Effective |
|---|---|---|---|---|---|---|---|---|
| 5 | 1.2 | 1.2 | 19.6 | 19.4 | 1.5 | 1.5 | 5.9 | 5.8 |
| 30 | 1.1 | 1.0 | 12.2 | 11.5 | 1.4 | 1.3 | 4.5 | 4.2 |
| 60 | 1.0 | 0.9 | 5.6 | 5.0 | 1.4 | 1.2 | 2.4 | 2.1 |
| 120 | 1.0 | 0.8 | 2.2 | 1.7 | 1.2 | 1.0 | 0.9 | 0.7 |
| 240 | 0.8 | 0.5 | 0.7 | 0.4 | 1.0 | 0.6 | 0.3 | 0.2 |

The agent is excreted without any evidence of metabolism. The major pathway for clearance of $^{99m}$Tc-Sestamibi is the hepatobiliary system. Activity from the gall bladder appears in the intestines within one hour of injection. Twenty-seven percent of the injected dose is excreted in the urine, and approximately thirty-three percent of the injected dose is cleared through the feces in 48 hours.

A typical published preparation procedure of $^{99m}$Tc-Sestamibi [CARDIOLITE®, *Kit for the Preparation of Technetium Tc99m Sestamibi for Injection*, Document No. 513121-0300, March 2000, DuPont Pharmaceuticals Company, Billerica, Mass., USA] includes transferring a known volume of a solution containing the radioactive isotope sodium salt into a vial containing the rest of the ingredients, including the MIBI (2-methoxy isobutyl isonitrile) component. This amount should correspond to 925-5550 MBq (25-150 mCi) in approximately 1 to 3 ml. After heating the reaction mixture, the reaction vial sample is assayed using a suitable radioactivity calibration system, and the results of the assay determine the amount which will be injected into the patient. According to this prior art procedure, the prepared product should be stored at 15-25° C. before and after reconstitution and used within 6 hours after preparation. The patient dose and radiochemical purity (see the abovementioned Document No. 513121-0300 for procedures) should be measured by a suitable radioactivity calibration system immediately prior to patient administration.

As can be deduced from the above description, there are two major physical attributes which determine the time regime for the nuclear imaging process which are crucial for its effectiveness: the rate of decay and the rate of clearance.

According to the present invention, the above procedure can be altered in two principle ways; one addresses the decay chronology and the other addresses the quantity required for effective imaging of the relevant organ in the patient. Since the sensitivity of the emission detector associated with the present invention is 10-100 folds higher than the currently used detectors, a kit according to the present invention may contain a smaller amount of the radioactive isotope to be used, or may allow a longer time for data collection after administration, as compared to the presently known kits. The latter allows for data collection of dynamic processes which take place in the patient, i.e., following in-vivo changes in the organs which are monitored by the nuclear imaging technique, hence allowing for time-resolved analysis of the medical condition of interest.

Other examples for the preparation procedure of any commercially available radiopharmaceutical and radiotracer can be in the instruction documents provided in presently available kits, such as the kit for the preparation of $^{111}$Indium Capromab Pendetide. $^{111}$Indium Capromab Pendetide is a radiotracer containing a murine monoclonal antibody, 7E11-C5.3 (the site-specific delivery vehicle), which is covalently conjugated to the linker-chelator, glycyl-tyrosyl-(N,-diethylenetriaminepentaacetic acid)-lysine hydrochloride (GYK-DTPA-HCl). The 7E11-C5.3 antibody is of the IgG1, kappa subclass (IgG1K). This antibody is directed against a glycoprotein expressed by prostate epithelium known as prostate specific membrane antigen (PSMA). The PSMA epitope recognized by monoclonal antibody (MAb) 7E11-C5.3 is located in the cytoplasmic domain. The radioisotope $^{111}$In is brought in contact with the antibody-linker-chelator conjugate upon preparation of the sample prior to administration, and the indium is therefore incorporated into the site-specific delivery vehicle. Detailed quantities, characteristics and procedures for the preparation of this radiotracer for administration can be found in http://www.cytogen.com/professional/prostascint/pi.php.

As in the example of $^{99m}$Tc-sestamibi, $^{111}$Indium capromab pendetide (ProstaScint®) is provided as a two-vials kit which contain all of the non-radioactive ingredients necessary to produce a single unit dose of $^{111}$In ProstaScint®, an immunoscintigraphic agent for administration by intravenous injection only. The ProstaScint® vial contains 0.5 mg of capromab pendetide in 1 ml of sodium phosphate buffered saline solution adjusted to pH 6; a sterile, pyrogen-free, clear, colorless solution. The vial of sodium acetate buffer contains 82 mg of sodium acetate in 2 ml of water for injection adjusted to pH 5-7 with glacial acetic acid; it is a sterile, pyrogen-free, clear, and colorless solution. The sodium acetate solution must be added to the sterile, non-pyrogenic high purity $^{1111}$InCl solution to buffer it prior to radiolabeling ProstaScint®. The immunoscintigraphic agent $^{111}$In capromab pendetide is formed after radiolabeling with $^{111}$In.

Use of novel low doses of Radiopharmaceuticals, typically Radiopharmaceuticals which result in less than 2.5 mrem EDE per Kg body weight (e.g., less than 2 mCi of Tc-99m) is enabled through the use of more sensitive emission detectors such as those described in PCT/IL2005/000394, PCT/IL2005/000572, PCT/IL2005/000575, PCT/IL2005/000394 and PCT/IL2005/000048, hereby included in their entirety by reference.

Table 88 below provides typical prior art doses and novel low doses of radiopharmaceuticals that are effectively imaged using the emission detection systems described in the above referenced PCT applications.

TABLE 88

| Radiopharmaceutical | Typical Purity in % | Prior art dose in mCi (range) | Dose utilized by present invention mCi (range) |
|---|---|---|---|
| Positron Emission Isotopes | | | |
| ISOTOPE/Half-Life Time | | | |
| Ammonia N 13 | 9.96 min | 20 | 0.05-5 Preferably - 5, 2, 1, 0.5, 0.2, 0.1, 0.05, 0.02, 0.01 |
| Fludeoxyglucose F-18 | 110 min | 10 | 0.1-3 preferably - 3, 1, 0.1 |
| Sodium Fluoride F-18 | 110 min | | 0.1-3 preferably - 3, 1, 0.1 |
| Methionine C-11 | 20.4 min | | |
| O-15 | 2.04 min | | |
| Rubidium Rb-82 | 1.27 min | | |
| Cu-62 | 9.8 min | | |
| Ga-68 | 68.1 min | | |
| Protein/peptide/antibody + Isotopes | | | |
| Indium-111 Capromab pendetide (ProstaScint) | >90% (inject after up to 8 hours from mixing, isotope 1/2L ~72 hr) | 5 | 0.01-2 Preferably - 2, 1, 0.5, 0.1, 0.05, 0.01 |

TABLE 88-continued

| Radiopharmaceutical | Typical Purity in % | Prior art dose in mCi (range) | Dose utilized by present invention mCi (range) |
|---|---|---|---|
| Indium In-111 WBCs (non-protein,peptide) | | 0.5 | 0.001-0.2 Preferably - 0.2, 0.1, 0.05, 0.01, 0.005, 0.001 |
| Indium In-111 Satumomab Pendetide (OncoScint) | | 5 | 0.01-2 Preferably - 2, 1, 0.5, 0.1, 0.05, 0.01 |
| Technetium Tc 99m Arcitumomab (CEA-Scan) | >60% (shelf life up to 4 hr/6 hr half-life) | 20-30 | 0.05-5 Preferably - 5, 2, 1, 0.5, 0.1, 0.05 |
| Technetium Tc 99m Fanolesomab (Neutrospec) | | 75-25 mcg of Fanolesomab is labeled with 10-20 mCi | |
| Technetium Tc 99m Nofetumomab Merpentan† | | | |
| Non-peptide/protein based isotopes | | | |
| Cyanocobalamin Co 57 | | 0.001 | 0.00001-0.0003 Preferably - 0.0003, 0.0001, 0.00005, 0.00001 |
| Ferrous Citrate Fe 59 | | | |
| Gallium Citrate Ga 67 | | 5 10 for SPECT | 0.01-1 Preferably - 1, 0.5, 0.2, 0.1, 0.05, 0.01 |
| Indium In 111 Oxyquinoline | | | |
| Indium In 111 Pentetate | | | |
| Indium In 111 Pentetreotide | | 6 | 0.005-1 Preferably - 1, 0.5, 0.2, 0.1, 0.05, 0.01, 0.005 |
| Iobenguane, Radioiodinated | | | |
| Iodohippurate Sodium I 123 | | | |
| Iodohippurate Sodium I 131 | | | |
| Iofetamine I 123 | | | |
| Iothalamate Sodium I 125 | | | |
| Krypton Kr 81m | | 10 (as a gas, USED FOR DYNAMIC IMAGING) | 0.05-2 Preferably - 2, 1, 0.5, 0.1, 0.05 |
| Iodide 125 Albumin | | 0.02 | 0.0001-0.005 Preferably - 0.005, 0.002, 0.001, 0.0005, 0.0001 |
| Radioiodinated Albumin | | | |
| SodiumChromate Cr 51 | | 0.15 0.1-0.3 | 0.001-0.05 Preferably - 0.05, 0.02, 0.01, 0.005, 0.001 |
| Sodium Iodide I 123 | | 0.4, (also 0.1-0.2 as capsules) | 0.001-0.05 Preferably - 0.1, 0.05, 0.02, 0.01, 0.005, 0.001 Also as capsules |
| Sodium Iodide I 131 | | 0.004-0.01 | 0.00005-0.001 Preferably - 0.001, 0.0005, 0.0002, 0.0001, 0.00005 |
| (Sodium) Pertechnetate Tc 99m | | 10 100-200 micro for eye imaging (1 drop per eye) 1 mCi for cyctogram | 0.01-5 Preferably - 5, 2, 1, 0.5, 0.2, 0.1, 0.05, 0.02, 0.01 |
| Technetium Tc 99m Albumin | | | |
| Technetium Tc 99m Albumin Aggregated | NO LESS THAN 90% AT PREPARATION (Up to 6 additional hours on the shelf turns it into 45%), AS BEYOND A LEVEL IT MAY BLOCK LUNGS | 1-4 2 mCi in each leg | 0.001-0.5 Preferably - 0.5, 0.2, 0.1, 0.05, 0.02, 0.01, 0.005, 0.002, 0.001 |

TABLE 88-continued

| Radiopharmaceutical | Typical Purity in % | Prior art dose in mCi (range) | Dose utilized by present invention mCi (range) |
|---|---|---|---|
| | CAPILLARY - USED TO DETECT PULMONARY EMBOLISM DUE TO DVT | | |
| Technetium Tc 99m Albumin Colloid | | | |
| Technetium Tc 99m Erythrocytes (RBCs) | | 10-20 20-25 for liver perfusion & SPECT | 0.05-5 Preferably - 5, 2, 1, 0.5, 0.2, 0.1, 0.05, 0.02, 0.01 |
| Technetium Tc 99m Depreotide (NeoTect) | | 20 | 0.05-5 Preferably - 5, 2, 1, 0.5, 0.2, 0.1, 0.05 |
| Technetium Tc 99m Apcitide (AcuTect) | | 20 | 0.05-5 Preferably - 5, 2, 1, 0.5, 0.2, 0.1, 0.05 |
| TechnetiumTc 99m Bicisate (ECD, Neurolite) | | 20 | 0.05-5 Preferably - 5, 2, 1, 0.5, 0.2, 0.1, 0.05 |
| Technetium Tc 99m DMSA Dimercaptosuccinic acid (Succimer) | | 2-6 (typically 5) | 0.005-1 Preferably - 1, 0.5, 0.2, 0.1, 0.05, 0.01, 0.005 |
| Technetium Tc 99m Disofenin (HIDA) | | 5 | 0.005-1 Preferably - 1, 0.5, 0.2, 0.1, 0.05, 0.01, 0.005 |
| TechnetiumTc 99m Exametazime (HMPAO) | | 20 | 0.05-5 Preferably - 5, 2, 1, 0.5, 0.2, 0.1, 0.05 |
| Technetium Tc 99m Gluceptate | | | |
| TechnetiumTc 99m Lidofenin | | | |
| Technetium Tc 99m Mebrofenin | | 5mCi (non-jaundiced)8mCi (jaundiced) | |
| TechnetiumTc 99m Medronate (MDP) | | 20 15 | 0.05-5 Preferably - 5, 2, 1, 0.5, 0.2, 0.1, 0.05, 0.01 |
| Technetium Tc 99m Mertiatide (MAG3) | | 5-10 | 0.005-1 Preferably - 1, 0.5, 0.2, 0.1, 0.05, 0.01, 0.005 |
| Chromic Phosphate | | 4 | 0.05-1 Preferably - 1, 0.5, 0.2, 0.1, 0.05, 0.01 |
| SR 89 Chloride (Metastron) | | 4 (this is for palliative treatment) | 0.05-1 Preferably - 1, 0.5, 0.2, 0.1, 0.05, 0.01 |
| Technetium Tc 99m Oxidronate | | | |
| Technetium Tc 99m Pentetate (DTPA) | | 3-5 (for GFR), 10-20 (for brain, renal perfusion) | 3 (brain/renal perferred) 0.005-1 Preferably - 1, 0.5, 0.2, 0.1, 0.05, 0.02, 0.01, 0.005 |
| TechnetiumTc 99m Pyrophosphate | | 15 20 for muscle necrosis | 0.005-5 Preferably - 5, 2, 1, 0.5, 0.3, 0.1, 0.05, 0.02, 0.01, 0.005 |
| Technetium Tc 99m (Pyro- and trimeta-) Phosphates | | | |
| Technetium Tc 99m Sestamibi (Cardiolite, Miraluma - for breast imaging) | | 10-30 (typically 10 for rest and 30 for stress) | 0.01-5 preferably 5, 2, 1, 0.5, 0.2, 0.1, 0.05, 0.02, 0.01 |
| Technetium Tc 99m Sulfur Colloid | | | |
| Technetium Tc 99m Teboroxime | | | |
| Technetium Tc 99m Tetrofosmin (MyoView) | | 5-33 (typical 8-20) | |
| Technetium Tc 99m HDP | | 20-25 <30 years 25-30.30 yrs & obese | |
| Technetium Tc 99m Sulpher colloid | | 12 mCi/70 kg | |
| Thallous Chloride Tl 201 | | 0.055 mCi/kg | |

TABLE 88-continued

| Radiopharmaceutical | Typical Purity in % | Prior art dose in mCi (range) | Dose utilized by present invention mCi (range) |
|---|---|---|---|
| Xenon Xe 127 | | 5-10 | |
| Xenon Xe 133 | | 5-10 | |

Use of radiopharmaceutical cocktails yields generations of new products (premixed radiopharmaceutical pairs) and diagnostic procedures that enable multi-dimensional, differential diagnosis and use of one diagnostic procedure for revealing any pathology. Radiopharmaceutical cocktails also require significantly lower radiopharmaceutical dosage and results in several-fold increase in sensitivity as well as a 90% procedure time reduction and significant improvement in spatial and spectral resolution.

Radiopharmaceutical combinations are exemplified in a liver-spleen scan using+RBC+gallium (for cases of liver SOL/hemangioma/abscess/hepatoma). Bone scan+gallium or bone scan+In-WBC (for osteomyelitis). Perfusion rest/stress+MIBG for autonomic system in heart, mapping+BMIPP for heart failure with the addition of FDG for viability.

Assessment of the sentinel lymph node of tumors via Lymphoscintigraphy, (melanoma, breast, etc) with addition of FDG (and optionally MIBI) to assess the presence of tumor in these nodes (typically effected by peri-tumoral injection for lymphoscintigraphy and IV FDG). Although low doses are preferred for the reasons set forth hereinabove, higher doses can also be utilized in combinations provided one can effectively isolate the signal resultant from each radiopharmaceutical.

Example 4

Unified Management of Radiopharmaceutical Dispensing, Administration, and Imaging Methods and kits of the present invention may be administered and imaging followed using the following exemplary end-to-end automated system.

FIG. 100 is a schematic illustration of an end-to-end automated system 10a for medical imaging, in accordance with an embodiment of the present invention. System 10a comprises a plurality of integrated elements that are configured to electronically exchange information among one another. The elements include an automated radiopharmaceutical dispensing system 20a, a portable information-bearing radiopharmaceutical agent container 22a, a portable patient-specific data carrier 24a, an automated administration system 26a, and an automated imaging system 28a. The systems perform their respective automated functions at least in part responsively to the exchanged information. The elements typically authenticate one another via the exchanged information, in order to ensure that only authorized elements participate in the system, and that only authorized and appropriate functions are performed. Each of the elements is described in detail hereinbelow.

An end-to-end system of the present invention may comprise a plurality of integrated elements that are configured to electronically exchange information among one another. The elements include an automated radiopharmaceutical dispensing system, a portable information-bearing radiopharmaceutical agent container, a patient management system, a portable patient-specific data carrier, an automated administration system, and an automated imaging system. The systems perform their respective automated functions at least in part responsively to the exchanged information. The elements typically authenticate one another via the exchanged information, in order to ensure that only authorized elements participate in the system, and that the systems perform only authorized and appropriate functions.

The exchanged information typically includes patient-specific data, radiopharmaceutical agent-specific data, and/or patient- or radiopharmaceutical agent-specific imaging protocol data. Such data enable the systems to customize their respective automated functions for specific patients, radiopharmaceutical agents, indications, and/or imaging procedures. For some applications, the exchanged information includes commercial license information relating to the use of a specific protocol with a specific radiopharmaceutical agent, and one or more of the systems are configured to verify the license information before performing their respective functions.

In some embodiments of the present invention, the information-bearing radiopharmaceutical agent container and/or the patient-specific data carrier is configured to contain protocol information for performing an imaging procedure using the labeled radiopharmaceutical agent (also referred to herein and in the claims as "radiopharmaceutical") held by the container. For some applications, the protocol information includes SPECT imaging protocol information, and the imaging system uses the protocol information to perform a SPECT imaging procedure using the labeled radiopharmaceutical agent contained in the container. For some applications, the agent container contains a single dose of the labeled radiopharmaceutical agent, which dose is appropriate for use with the imaging protocol.

In some embodiments of the present invention, the information-bearing radiopharmaceutical agent container or the patient-specific data carrier is configured to contain at least one kinetic parameter of the labeled radiopharmaceutical agent contained in the container. The imaging system uses the kinetic parameter to perform a dynamic SPECT imaging procedure.

In some embodiments of the present invention, the information-bearing radiopharmaceutical agent container contains radiopharmaceutical information regarding the labeled radiopharmaceutical agent contained in the container. The portable patient-specific data carrier is configured to contain patient information regarding the patient, and imaging protocol information for use with the labeled radiopharmaceutical agent, such as SPECT imaging protocol information. The imaging system uses the protocol information to perform an imaging procedure, such as a dynamic SPECT imaging procedure. For some applications, the patient-specific data carrier comprises a coupling mechanism configured to be coupled to the patient. For example, the coupling mechanism may comprise a bracelet, a watch, a necklace, or another wearable article.

In some embodiments of the present invention, the information-bearing radiopharmaceutical agent container contains a first identifier value, and the patient-specific data carrier contains a second identifier value. The imaging system is configured to perform an imaging procedure responsively to a detection of a correspondence between the first and second identifier values. For some applications, the first identifier value equals the second identifier value, while for other applications the values do not equal one another, but instead correspond to one another based on information provided by an element of the end-to-end system. For some applications, the first and/or second identifier values are arbitrarily assigned, or pre-loaded into the data carrier my a manufacturer or distributor, while for other applications at least one of the identifier values comprises a patient identifier, or another meaningful value. For some applications, at least one of the information-bearing agent container and the patient-specific data carrier performs the detection of the correspondence, while for other applications the imaging system or another element of the end-to-end system performs the detection of the correspondence.

In some embodiments of the present invention, the imaging system comprises a SPECT imaging system configured to utilize the information contained in the labeled radiopharmaceutical agent container and/or the patient-specific data carrier to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

The integration of the elements of the end-to-end system, and the exchange of authenticatable information among the elements generally increase patient safety, by ensuring that each patient receives the prescribed labeled radiopharmaceutical agent and dosage, and undergoes the desired imaging protocol. For some applications, one or more elements of the end-to-end system are configured to perform their respective function only upon being triggered by another element of the system. For example, the administration or imaging system may perform its function only upon being triggered by the information-bearing radiopharmaceutical agent container, by the patient-specific data carrier, and/or, in the case of the administration system, by the imaging system.

In some embodiments of the present invention, the automated radiopharmaceutical dispensing system comprises an information manager that is configured to receive radiopharmaceutical information regarding a labeled radiopharmaceutical agent and patient information regarding a patient. Responsively to the information, the dispensing system automatically dispenses a dose of the labeled radiopharmaceutical agent to an agent container, and stores the radiopharmaceutical information and at least a portion of the patient information in a data carrier associated with the container. For some applications, the radiopharmaceutical information is selected from the group consisting of: imaging protocol information for use with the labeled radiopharmaceutical agent, such as a SPECT imaging protocol; at least one kinetic parameter useful for performing a dynamic SPECT imaging procedure using the at least one labeled radiopharmaceutical agent; and authenticatable information regarding a commercial license for use of a SPECT imaging protocol with the at least one labeled radiopharmaceutical agent.

In some embodiments of the present invention, the dispensing system is configured to receive a mother vial containing a labeled radiopharmaceutical agent in a quantity sufficient for preparation of a plurality of doses of the labeled radiopharmaceutical agent. Associated with the mother vial is a data carrier containing information regarding the labeled radiopharmaceutical agent, such as the formulation, radioactivity information, and protocol information. The information manager of the dispensing system receives at least a portion of the labeled radiopharmaceutical agent information from the data carrier.

In some embodiments of the present invention, use of the end-to-end automated system enables customization of one or more aspects of the imaging process, from dispensing to diagnosis. Customization typically includes one or more of the following:

The dispensing system customizes the dispensed dose for a specific patient, based on radiopharmaceutical information and patient-specific information. Typically, the dispensing system customizes the dispensed dose (e.g., the radioactivity level thereof) based in part on the scheduled time of the scheduled time of administration of the dose, and/or the scheduled time of the imaging procedure to be performed using the dose.

The administration system customizes the administered dose for a specific patient, based on radiopharmaceutical information and patient-specific information. For some applications in which the administration system customizes the administered dose, the radiopharmaceutical agent container contains a standard, non-customized dose.

The imaging system customizes image acquisition, image reconstruction, image analysis, and/or diagnosis, based on radiopharmaceutical information and patient-specific information, such as patient physiology and/or known and/or suspected disease of the patient.

Such customization is typically based at least in part on information provided by the manufacturer or distributor of the radiopharmaceutical agent. Such information may be in the form of lookup tables and/or expert system rules. A more detailed review of the customization parameters is provided hereinabove.

Of note, the term "labeled" means radiolabeled, and "unlabeled" means not radio labeled.

There is therefore provided, in accordance with an embodiment of the present invention, apparatus for use with at least one labeled radiopharmaceutical agent, the apparatus comprising:

a container containing the at least one labeled radiopharmaceutical agent; and a portable computer-communicatable data carrier associated with the container, the data carrier containing imaging protocol information for use with the at least one labeled radiopharmaceutical agent.

For some applications, the apparatus comprises a device configured to write the imaging protocol information to the data carrier.

For some applications, the data carrier additionally contains administration protocol information useful for administering the at least one labeled radiopharmaceutical agent.

In an embodiment, the imaging protocol information comprises instructions for performing an imaging procedure using the at least one labeled radiopharmaceutical agent. Alternatively or additionally, the imaging protocol information comprises an identifier of an imaging protocol. Further alternatively or additionally, the imaging protocol information comprises a parameter of the at least one labeled radiopharmaceutical agent. Still further alternatively or additionally, the imaging protocol information comprises a parameter useful for configuring at least one aspect of an imaging procedure performed using the at least one labeled radiopharmaceutical agent.

In an embodiment, the container contains a single dose of the radiopharmaceutical agent, which dose is appropriate for use with the imaging protocol information. Alternatively, the container contains a plurality of labeled radiopharmaceutical agents mixed together. For some applications, the container is shaped so as to define a plurality of chambers, each of which contains a respective one of a plurality of labeled radiopharmaceutical agents.

In an embodiment, the data carrier comprises a first data carrier, which contains a first identifier value, the apparatus further comprises a second computer-communicatable data carrier, which contains a second identifier value, and the apparatus is configured to operate responsively to a detection of a correspondence between the first and second identifier values. For some applications, at least one of the first and second data carriers is configured to perform the detection of the correspondence. Alternatively or additionally, the apparatus comprises a correspondence-detection element configured to perform the detection of the correspondence.

In an embodiment, at least one of the first and second data carriers contains an identifier of a patient to whom the labeled radiopharmaceutical agent is to be administered.

For some applications, at least one of the first and second identifier values comprises an identifier of a patient to whom the labeled radiopharmaceutical agent is to be administered.

In an embodiment, exactly one of the first and second data carriers comprises a coupling mechanism configured to be coupled to a patient to whom the labeled radiopharmaceutical agent is to be administered.

In an embodiment, the apparatus comprises an imaging system comprising imaging functionality, the imaging system configured, responsively to the detection of the correspondence, to drive the imaging functionality to perform an imaging procedure using the at least one labeled radiopharmaceutical agent.

In an embodiment, the data carrier is physically coupled to the container. For some applications, the data carrier contains an identifier of a patient to whom the labeled radiopharmaceutical agent is to be administered, and the imaging protocol information comprises imaging protocol information selected for the patient. For some applications, the imaging protocol information comprises an identifier of an imaging protocol.

For some applications, the imaging protocol information comprises imaging protocol information customized for the patient. Customization is described elsewhere in the application.

Description of the imaging system which may be used in the present system is provided in Example 3 hereinabove.

In an embodiment, the imaging procedure includes a three-dimensional dynamic imaging study, and wherein the imaging functionality is configured to perform the three-dimensional dynamic imaging study, and to configure the study at least in part responsively to the imaging protocol information read from the data carrier by the communication element.

In an embodiment, the data carrier is not physically coupled to the container, and wherein the data carrier contains an identifier of a patient to whom the labeled radiopharmaceutical agent is to be administered. For some applications, the data carrier comprises a coupling mechanism configured to be coupled to the patient. In an embodiment, the data carrier comprises a first data carrier, and wherein the apparatus further comprises a second computer-communicatable data carrier physically coupled to the container, the second data carrier containing radiopharmaceutical information regarding the at least one labeled radiopharmaceutical agent.

There is also provided, in accordance with an embodiment of the present invention, apparatus for use with at least one labeled radiopharmaceutical agent, the apparatus comprising:
a container containing the at least one labeled radiopharmaceutical agent; and a computer-communicatable data carrier associated with the container, the data carrier containing authenticatable information regarding a commercial license for use of SPECT imaging protocol information with the at least one labeled radiopharmaceutical agent.

In an embodiment, the apparatus comprises an imaging system, which comprises:
a communication element, configured to read the authenticatable license information from the data carrier;
a control unit, comprising imaging functionality, the control unit configured to: authenticate the authenticatable license information, and
only upon authentication, drive the imaging functionality to perform an imaging procedure using the SPECT imaging protocol information.

For some applications, the apparatus comprises a device configured to write the authenticatable license information to the data carrier.

For some applications, the data carrier is physically coupled to the container. There is further provided, in accordance with an embodiment of the present invention, apparatus comprising a portable computer-communicatable data carrier containing authenticatable information regarding a commercial license for use of SPECT imaging protocol information.

For some applications, the data carrier additionally contains patient information regarding a patient upon whom an imaging procedure using the SPECT imaging protocol information is to be performed.

For some applications, the authenticatable license information is encrypted.

In an embodiment, the apparatus comprises an imaging system, which comprises:
a communication element, configured to read the authenticatable license information from the data carrier;
a control unit, comprising imaging functionality, the control unit configured to:
authenticate the authenticatable license information, and
only upon authentication, drive the imaging functionality to perform an imaging procedure using the SPECT imaging protocol information.

For some applications, the apparatus comprises a device configured to write the authenticatable license information to the data carrier.

For some applications, the data carrier comprises a coupling mechanism configured to be coupled to a patient upon whom an imaging procedure using the SPECT imaging protocol information is to be performed.

There is still further provided, in accordance with an embodiment of the present invention, apparatus comprising:
a first portable computer-communicatable data carrier containing a first identifier value;
a second portable computer-communicatable data carrier containing a second identifier value; and
an imaging system comprising imaging functionality, the imaging system configured, responsively to a detection of a correspondence between the first and second identifier values, to drive the imaging functionality to perform an imaging procedure on a patient.

For some applications, at least one of the first and second data carriers is configured to perform the detection of the correspondence. Alternatively or additionally, the imaging system comprises a correspondence-detection element configured to perform the detection of the correspondence.

For some applications, at least one of the first and second data carriers contains an identifier of a patient to whom the labeled radiopharmaceutical agent is to be administered.

For some applications, at least one of the first and second identifier values comprises an identifier of a patient to whom the labeled radiopharmaceutical agent is to be administered.

In an embodiment, one of the first and second data carriers comprises a coupling mechanism configured to be coupled to a patient to whom the labeled radiopharmaceutical agent is to be administered.

For some applications, the apparatus comprises a device configured to write at least one of the first and second identifier values to the respective first and second data carriers.

In an embodiment, at least one of the first and second data carriers contains radiopharmaceutical information regarding at least one labeled radiopharmaceutical agent, the imaging system comprises a communication element, configured to read the radiopharmaceutical information from the at least one of the data carriers, and the imaging system is configured to configure the imaging procedure at least in part responsively to the read radiopharmaceutical information. For some applications, the apparatus comprises a container containing the at least one labeled radiopharmaceutical agent. For some applications, one of the first and second data carriers is physically coupled to the container.

In an embodiment, the imaging functionality comprises a nuclear camera. For some applications, the nuclear camera comprises a SPECT camera.

There is yet further provided, in accordance with an embodiment of the present invention, apparatus for use with first and second portable computer-communicatable data carriers containing first and second identifier values, respectively, the apparatus comprising an imaging system, which comprises: imaging functionality; and a control unit configured to drive the imaging functionality to perform an imaging procedure on a patient, responsively to a detection of a correspondence between the first and second identifier values.

For some applications, the imaging system comprises a correspondence-detection element configured to perform the detection of the correspondence.

There is additionally provided, in accordance with an embodiment of the present invention, apparatus for use with at least one labeled radiopharmaceutical agent for administration to a patient, the apparatus comprising:

a container containing the at least one labeled radiopharmaceutical agent;

a first computer-communicatable data carrier physically coupled to the container, the first data carrier containing radiopharmaceutical information regarding the at least one labeled radiopharmaceutical agent; and a second portable computer-communicatable data carrier containing patient information regarding the patient, and imaging protocol information for use with the at least one labeled radiopharmaceutical agent.

For some applications, the imaging protocol information comprises SPECT imaging protocol information.

For some applications, the patient information comprises an identifier of the patient.

For some applications, the second data carrier comprises a coupling mechanism configured to be coupled to the patient.

For some applications, the first data carrier contains a first patient identifier, the patient information contained in the second data carrier comprises a second patient identifier, and the apparatus comprises an administration system, which comprises:

a first communication element, configured to read the first patient identifier from the first data carrier;

a second communication element, configure to read the second patient identifier from the second data carrier; and a control unit, configured to compare the first patient identifier to the second patient identifier, and, upon detecting a match, generate an administration signal that triggers administration to the patient of the at least one labeled radiopharmaceutical agent contained in the container.

For some applications, the first data carrier contains a first protocol identifier, the imaging protocol information contained in the second data carrier comprises a second protocol identifier, and the apparatus comprises an administration system, which comprises:

a communication element, configured to read the first and second protocol identifiers from the first and second data carriers, respectively; and a control unit, configured to compare the first protocol identifier to the second protocol identifier, and, upon detecting a match, generate an administration signal that triggers administration to the patient of the at least one labeled radiopharmaceutical agent contained in the container.

For some applications, the first data carrier contains a first protocol identifier, the imaging protocol information contained in the second data carrier comprises a second protocol identifier, and the apparatus comprises an administration system, which comprises:

a first communication element, configured to read the first protocol identifier from the first data carrier;

a second communication element, configured to read the second protocol identifier from the second data carrier; and a control unit, configured to compare the first protocol identifier to the second protocol identifier, and, upon detecting a match, generate an administration signal that triggers administration to the patient of the at least one labeled radiopharmaceutical agent contained in the container.

In an embodiment, the apparatus comprises an administration system, which comprises:

a communication element; and a control unit, configured to:

generate an administration signal that triggers administration to the patient of the at least one labeled radiopharmaceutical agent contained in the container, and drive the communication element to transmit information regarding the administration to the second data carrier.

For some applications, the apparatus comprises a device configured to write the imaging protocol information to the first data carrier. Alternatively or additionally, the apparatus comprises a device configured to write the patient information to the second data carrier.

In an embodiment, the imaging protocol information comprises imaging protocol information selected for the patient. For some applications, the imaging protocol information comprises an identifier of an imaging protocol. For some applications, the imaging protocol information comprises imaging protocol information customized for the patient.

In an embodiment, the first data carrier contains a first patient identifier, the patient information contained in the second data carrier includes a second patient identifier, and the apparatus comprises an administration system, which comprises:

a communication element, configured to read the first and second patient identifiers from the first and second data carriers, respectively; and a control unit, configured to compare the first patient identifier to the second patient identifier, and, upon detecting a match, generate an administration signal that triggers administration to the patient of the at least one labeled radiopharmaceutical agent contained in the container.

For some applications, the administration system comprises an automated administration device, configured to administer the at least one labeled radiopharmaceutical agent to the patient upon being triggered by the administration signal.

For some applications, the control unit is configured to generate the administration signal to trigger the administration of the at least one labeled radiopharmaceutical agent by instructing a healthcare worker to administer the at least one labeled radiopharmaceutical agent to the patient.

There is yet additionally provided, in accordance with an embodiment of the present invention, apparatus for use with at least one labeled radiopharmaceutical agent for administration to a patient, the apparatus comprising:

a container containing the at least one labeled radiopharmaceutical agent;

a computer-communicatable data carrier associated with the container, the data carrier containing data regarding at least one of: the labeled radiopharmaceutical agent and the patient; and a SPECT imaging system comprising:

a communication element, configured to read the data; and
a control unit, configured to utilize the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

For some applications, the data carrier contains the data regarding the labeled radiopharmaceutical agent. Alternatively or additionally, the data carrier contains the data regarding the patient.

For some applications, the control unit is configured to utilize the read data to customize the administration of the labeled radiopharmaceutical agent. Alternatively or additionally, the control unit is configured to utilize the read data to customize the acquisition of a SPECT image of the patient to whom the labeled radiopharmaceutical agent is administered. Further alternatively or additionally, control unit is configured to utilize the read data to customize the reconstruction of the SPECT image. Still further alternatively or additionally, the control unit is configured to utilize the read data to customize the analysis of the SPECT image. Alternatively or additionally, the control unit is configured to utilize the read data to customize the diagnosis of a condition of the patient based at least in part on the analysis.

For some applications, the apparatus comprises a device configured to write the data to the data carrier.

There is also provided, in accordance with an embodiment of the present invention, a SPECT imaging system for use with a container containing at least one labeled radiopharmaceutical agent for administration to a patient, and data regarding at least one of: the labeled radiopharmaceutical agent and the patient, the system comprising:

a communication element, configured to read the data; and a control unit, configured to utilize the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

For some applications, the system comprises a device configured to write the data to the container.

There is further provided, in accordance with an embodiment of the present invention, an automated radiopharmaceutical dispensing system for use with a container and a computer-communicatable container data carrier associated with the container, the system comprising:

a robot, configured to manipulate the container;

a communication element; and a control unit, configured to:

receive radiopharmaceutical information regarding at least one labeled radiopharmaceutical agent, the radiopharmaceutical information selected from the group consisting of: imaging protocol information for use with the at least one labeled radiopharmaceutical agent, and authenticatable information regarding a commercial license for use of an imaging protocol with the at least one labeled radiopharmaceutical agent, receive patient information regarding a patient, drive the robot to automatically dispense a dose of the labeled radiopharmaceutical agent to the container, and drive the communication element to transmit to the container data carrier at least a portion of the radiopharmaceutical information and at least a portion of the patient information.

For some applications, the control unit is configured to receive the radiopharmaceutical information regarding a plurality of labeled radiopharmaceutical agents, and drive the robot to automatically dispense respective doses of the labeled radiopharmaceutical agents to the container.

For some applications, the patient information includes an identifier of an imaging protocol assigned to the patient for performance using the dose, and wherein the control unit is configured to drive the communication element to transmit the imaging protocol identifier to the container data carrier.

For some applications, the control unit is configured to drive the communication element to transmit to the container data carrier at least one of: a time of dispensing of the labeled radiopharmaceutical agent to the container, and information regarding a radioactivity of the dose at the time of dispensing.

In an embodiment, the apparatus comprises:

a mother vial that contains the labeled radiopharmaceutical agent prior to dispensing thereof; and
a computer-communicatable mother vial data carrier associated with the mother vial, which mother vial data carrier contains the radiopharmaceutical information,
wherein the control unit is configured to receive the radiopharmaceutical information from the mother vial data carrier.

For some applications, the radiopharmaceutical information comprises the imaging protocol information. For some applications, the imaging protocol information comprises SPECT imaging protocol information, which may comprise at least one kinetic parameter of the at least one labeled radiopharmaceutical agent.

In an embodiment, the radiopharmaceutical information comprises the authenticatable information regarding the commercial license. For some applications, the information regarding the commercial license comprises information regarding the commercial license for use of a SPECT imaging protocol with the at least one labeled radiopharmaceutical agent. For some applications, the control unit is configured to authenticate the authenticatable license information, and to drive the robot to automatically dispense the dose only upon authentication.

There is still further provided, in accordance with an embodiment of the present invention, apparatus for use with a container, the apparatus comprising:

a mother vial having a volume of at least 10 ml, which contains at least 5 ml of a non-diluted labeled radiopharmaceutical agent, and at least 5 ml of saline solution; and an automated radiopharmaceutical dispensing system, configured to contain the mother vial, and to dispense at least one dose from the mother vial to the container.

There is additionally provided, in accordance with an embodiment of the present invention, a method comprising:

placing at least one labeled radiopharmaceutical agent in a container;

associating a portable computer-communicatable data carrier with the container; and writing, to the data carrier, imaging protocol information for use with the at least one labeled radiopharmaceutical agent.

There is yet additionally provided, in accordance with an embodiment of the present invention, a method comprising:

placing at least one labeled radiopharmaceutical agent in a container;

associating a computer-communicatable data carrier with the container; and writing, to the data carrier, authenticatable information regarding a commercial license for use of SPECT imaging protocol information with the at least one labeled radiopharmaceutical agent.

There is also provided, in accordance with an embodiment of the present invention, a method comprising:

providing a portable computer-communicatable data carrier; and writing, to the data carrier, authenticatable information regarding a commercial license for use of SPECT imaging protocol information.

There is further provided, in accordance with an embodiment of the present invention, a method comprising:

writing first and second identifier values to first and second computer-communicatable data carriers, respectively;

detecting a correspondence between the first and second identifier values; and perform an imaging procedure on a patient responsively to the detecting.

There is still further provided, in accordance with an embodiment of the present invention, a method for use with at least one labeled radiopharmaceutical agent for administration to a patient, the method comprising:

placing at least one labeled radiopharmaceutical agent in a container;

physically coupling a first computer-communicatable data carrier to the container;

writing, to the first data carrier, radiopharmaceutical information regarding the at least one labeled radiopharmaceutical agent; and writing, to a second portable computer-communicatable data carrier, patient information regarding the patient, and imaging protocol information for use with the at least one labeled radiopharmaceutical agent.

There is additionally provided, in accordance with an embodiment of the present invention, a method comprising:

placing, in a container, at least one labeled radiopharmaceutical agent for administration to a patient;

associating a computer-communicatable data carrier with the container;

writing data to the data carrier regarding at least one of: the labeled radiopharmaceutical agent and the patient;

reading the data from the data carrier at a SPECT imaging system;

utilizing the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

There is yet additionally provided, in accordance with an embodiment of the present invention, a method for use with a container containing at least one labeled radiopharmaceutical agent for administration to a patient, and data regarding at least one of: the labeled radiopharmaceutical agent and the patient, the method comprising:

reading the data at a SPECT imaging system; and utilizing the read data to customize at least one function of the system selected from the group consisting of: administration of the labeled radiopharmaceutical agent, acquisition of a SPECT image of the patient to whom the labeled radiopharmaceutical agent is administered, reconstruction of the SPECT image, analysis of the SPECT image, and diagnosis of a condition of the patient based at least in part on the analysis.

There is also provided, in accordance with an embodiment of the present invention, a method for use with a container and a computer-communicatable container data carrier associated with the container, the method comprising:

receiving, by an automated radiopharmaceutical dispensing system, radiopharmaceutical information regarding at least one labeled radiopharmaceutical agent, the radiopharmaceutical information selected from the group consisting of: imaging protocol information for use with the at least one labeled radiopharmaceutical agent, and authenticatable information regarding a commercial license for use of an imaging protocol with the at least one labeled radiopharmaceutical agent;

receiving, by the dispensing system, patient information regarding a patient;

automatically robotically dispensing, by the dispensing system, a dose of the labeled radiopharmaceutical agent to the container; and transmitting to the container data carrier, by the dispensing system, at least a portion of the radiopharmaceutical information and at least a portion of the patient information.

There is further provided, in accordance with an embodiment of the present invention, a method for automatically dispensing a labeled radiopharmaceutical agent to a container, comprising:

providing a mother vial having a volume of at least 10 ml;

filling the mother vial with at least 5 ml of a non-diluted labeled radiopharmaceutical agent, and with at least 5 ml of saline solution;

placing the mother vial in an automated radiopharmaceutical dispensing system; and dispensing at least one dose from the mother vial to the container.

There is also provided, in accordance with an embodiment of the present invention, a method for setting a dose of a labeled radiopharmaceutical agent for use for performing an imaging procedure on a patient for studying a physiological characteristic of the patient, the method including:

selecting the radiopharmaceutical agent;

receiving information regarding a medical parameter of the patient not directly related to the physiological characteristic of the patient; and setting the dose at least in part responsively to the received information.

There is further provided, in accordance with an embodiment of the present invention, a substance associated with a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is still further provided, in accordance with an embodiment of the present invention, a computer controlled functionality employing a machine readable multi-parameter human physiological profile including at least one of a kinetic and intra-body location dependent parameter and a machine readable multi-parameter substance profile, including at least one kinetic parameter, for indicating a time-dependent substance intake program.

There is yet further provided, in accordance with an embodiment of the present invention, a substance associated with a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is also provided, in accordance with an embodiment of the present invention, a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is further provided, in accordance with an embodiment of the present invention, a substance formulated in accordance with a time-dependent substance intake program generated by a computer controlled functionality employing a machine readable multi-parameter human physiological profile including at least one of a kinetic and intra-body location dependent parameter and a machine readable multi-parameter substance profile, including at least one kinetic parameter.

There is still further provided, in accordance with an embodiment of the present invention, an apparatus, method, and/or functionality for generation of a machine readable multi-parameter human physiological profile including at least one of a kinetic and intra-body location dependent parameter, including providing a time-dependent substance intake program; a data acquisition system which acquires data from the patient passing through the intake program; and a computerized analysis using a machine readable multi-parameter substance profile, including at least one kinetic parameter.

There is yet further provided, in accordance with an embodiment of the present invention, an apparatus, method, and/or functionality for generation of a human physiological profile, including providing a substance intake program; a data acquisition system which acquires data from the patient passing through the intake program; and a computerized analysis using a substance profile, including at least one kinetic parameter.

There is also provided, in accordance with an embodiment of the present invention, an interactive pharmaceutical-containing, machine-readable information-bearing, customized medicine module suitable for use in computerized customized medicine, said customized medicine module including a computerized customized medicine machine-interfaceable pharmaceutical-containing delivery module and a computerized individualized medicine machine-readable information-containing carrier containing at least data regarding said pharmaceutical which is required for use of said pharmaceutical in computerized customized medicine, said data being useful in computerized customized medicine machine actuation of said pharmaceutical-containing delivery module.

There is additionally provided, in accordance with an embodiment of the present invention, a computerized customized medicine machine including:
  a computerized patient imager;
  a computerized pharmaceutical deliverer employing a pharmaceutical-containing, machine-readable information-bearing, customized medicine module; and
  a customized medicine protocol controller including:
    an interactive patient imager interface including patient information receiving functionality and patient imaging actuation functionality; and
    an interactive pharmaceutical deliverer interface including patient information receiving functionality and patient information-responsive pharmaceutical delivery actuation functionality.

There is also provided, in accordance with an embodiment of the present invention, an interactive pharmaceutical-containing, machine-readable authenticated, authenticated customized medicine module suitable for use in computerized customized medicine, said customized medicine module including a computerized customized medicine machine-interfaceable pharmaceutical-containing module and a computerized individualized medicine machine-readable authentication-containing carrier containing at least authentication data regarding said pharmaceutical which is required for use of said pharmaceutical in computerized customized medicine, said data being useful in said computerized customized medicine machine.

There is further provided, in accordance with an embodiment of the present invention, a computerized customized medicine preparation machine including:
  a computerized patient information manager;
  a computerized customized medicine pharmaceutical information manager;
  a computerized authenticated customized medicine module authenticator; and
  a computerized pharmaceutical-containing, machine-readable information-bearing, customized medicine module generator including:
    a computerized generator protocol manager operative to receive patient information from said patient information manager, to receive authentication of an authenticated customized medicine module from said authenticator, to receive customized medicine pharmaceutical information relating to at least one pharmaceutical contained in said authenticated customized medicine module from said pharmaceutical information manager and to prepare customized medicine information to be included in said customized medicine module; and
    a computerized pharmaceutical-containing, machine-readable information-bearing, customized medicine module preparer operative to associate said customized medicine information prepared by said protocol manager in an authenticatable machine readable form with a quantity of said pharmaceutical contained in said authenticated customized medicine module, thereby providing a pharmaceutical-containing, machine-readable information-bearing, customized medicine module.

There is still further provided, in accordance with an embodiment of the present invention, an interactive pharmaceutical-containing, machine-readable information-bearing, individualized medicine module suitable for use in computerized individualized medicine, said individualized medicine module including a computerized individualized medicine machine actuable pharmaceutical-containing delivery module and a computerized individualized medicine machine-readable information-containing carrier containing at least data regarding said pharmaceutical which is required for use of said pharmaceutical in computerized individualized medicine, said data being useful in computerized individualized medicine machine actuation of said pharmaceutical-containing delivery module.

For some applications, said data is in an encrypted format, readable by said computerized individualized medicine machine upon receipt of a predetermined authentication.

There is also provided, in accordance with an embodiment of the present invention, a computerized individualized medicine machine including:
- a computerized patient imager;
- a computerized pharmaceutical deliverer employing a pharmaceutical-containing, machine-readable information-bearing, individualized medicine module; and
- an individualized medicine protocol controller including:
  - an interactive patient imager interface including patient image receiving functionality and patient imaging actuation functionality; and
  - an interactive pharmaceutical deliverer interface including patient image receiving functionality and patient image-responsive pharmaceutical delivery actuation functionality.

There is further provided, in accordance with an embodiment of the present invention, use of a high definition, high sensitivity camera for determination of an optimal parameter for a labeled radiopharmaceutical agent, the optimal parameter selected from the group consisting of: optimal dose, optimal mode of administration, optimal mode of acquisition of data with respect to the labeled radiopharmaceutical agent, optimal mode of data processing with respect to the labeled radiopharmaceutical agent, and optimal mode of presentation of information acquired with respect to the labeled radiopharmaceutical agent.

There is still further provided, in accordance with an embodiment of the present invention, a labeled radiopharmaceutical agent that is manufactured or designed or indicated for use with or sold with any one of the above techniques.

Example 5

Imaging System

As mentioned hereinabove, the present invention relates to radioimaging cameras characterized by unprecedented high sensitivity allowing for high resolution image acquisition for use in clinical diagnostic protocols algorithms described hereinabove and systems operable in conjunction with the camera, the algorithms and systems include, but are not limited to, predetermined view selection algorithm and system, active vision (on the fly view selection) algorithm and system, closed loop administration of a radiopharmaceutical algorithm and system, expert system diagnostic algorithm and system, automatic dose preparation algorithm and kinetic parameter extraction algorithm and system; low dose radiopharmaceuticals; combinations of radiopharmaceuticals either as compositions (cocktails) and/or kits; an administering device of radiopharmaceuticals, which may include syringes, pumps and IV lines; mixers for mixing different radiopharmaceuticals; and an ERP system for controlling and monitoring each one or more of the above.

The present invention emerges from the development of a radioimaging camera characterized by unprecedented sensitivity. The sensitivity of the camera is attributed, as is further detailed hereinbelow, to at least the following constructual features: (a) a plurality of detecting units; (b) movability of the detecting units one with respect to the other; (c) thus allowing concentrated focus on a region-of-interest by the individual detecting units; and (d) wiring diagram with minimal multiplexing, thereby preventing saturation thereof.

As a result of this sensitivity, it is now possible using the camera of the present invention to (a) detect low dose radiopharmaceuticals; (b) perform fast kinetic studies; (c) extract kinetic parameters for the distribution of a radiopharmaceutical under different diagnostic setups, thereby allowing (i) formulating radiopharmaceuticals based on the newly achieved knowledge of the kinetic parameters; (ii) diagnostics based on the kinetic parameters; (iii) formulating new therapeutic drugs based on the kinetic parameters; and (iv) using the kinetic parameters as an input to the expert system for diagnostics; (d) provide images of co-administered radiopharmaceuticals; and (e) allow diagnostically meaningful imaging at a far faster rate as compared to conventional prior art radioimaging cameras.

In order to minimize the exposure of a subject to radioactive substances and in order to maximize the diagnostic capabilities using radioimaging, the inventors of the present invention developed low dose preparations of radiopharmaceuticals and compositions and kits comprising two or more radiopharmaceuticals adapted for use in conjunction with the camera and all other aspects of the invention (See Example 1 and 2).

Basic Imaging Concept

FIGS. 1A and 1B schematically illustrate a detecting unit 12 and a block 90 of detecting units 12, respectively.

As seen in FIG. 1A, the detecting unit 12 is formed of a single-pixel detector 91, having a thickness $\tau_d$ and a diameter D or, in the case of a non-circular detector, a diameter equivalent. Alternatively, several pixels may be summed up so as to operate, in effect, as a single pixel. Both the detector diameter D and the detector thickness $\tau_d$ affect the detecting efficiency. The detector diameter D determines the surface area on which radioactive emission impinges; the greater the surface area, the greater the efficiency. The detector thickness $\tau_d$ affects the stopping power of the detector. High-energy gamma rays may go through a thin detector; the probability of their detection increases with an increase in the detector thickness $\tau_d$.

FIG. 1A illustrates a single-pixel detector 91, which by itself cannot generate an image; rather, all counts are distributed over the surface area of the detector 91.

As seen in FIG. 1B, the block 90 includes a plurality of the detecting unit 12, formed by dividing the detector 91 into a plurality of electrically insulated pixels 106, each associated with a collimator 96. The collimators 96 are of the diameter or diameter equivalent D, a length L, and a septum thickness $\tau$. The collimators 96 may be, for example, of lead, tungsten or another material which substantially blocks gamma and beta rays. The collimators 96 may be shaped as tubes, rectangular grids, or grids of any other polygon. Wide-angle or narrow-angle collimators are also possible.

The collimator's geometry and specifically, the ratio of D/L, provides the detecting unit 12 with a collection solid angle δ analogous to the viewing solid angle of an optical camera. The collection solid angle δ limits the radioactive-emission detection to substantially only that radioactive emission which impinges on the detector 91 after passing through a "corridor" of the collimator 96 (although in practice, some high-energy gamma rays may penetrate the collimator's walls). With no collimator, the collection angle δ, is essentially a solid angle of 4π steradians.

Thus, the collimator's geometry affects both the detection efficiency and the image resolution, which are defined as follows:

i. The detection efficiency is the ratio of measured radiation to emitted radiation; and ii. The image resolution is the capability of making distinguishable closely adjacent manifestations of a pathology, or the capability to accurately determine the size and shape of individual manifestations of a pathology.

While it is naturally desired to optimize both the detection efficiency and the image resolution, they are inversely related to each other. The detection efficiency increases with an increase in the collimator collection angle, and the image resolution decreases with an increase in the collimator collection angle.

In other words, while a wide-aperture, single-pixel detecting unit, such as that of FIG. 1A provides high efficiency, it does not lend itself to the generation of a two-dimensional image, and the wide aperture blurs the information regarding the direction from which the radiation is emitted. Yet as the resolution is increased, for example, in the detecting unit 12 of FIG. 1B, the detection efficiency decreases.

Commonly owned US Applications 20040015075 and 20040054248 and commonly owned PCT publication WO2004/042546, all of whose disclosures are incorporated herein by reference, describe systems and methods for scanning a radioactive-emission source with a radioactive-emission camera of a wide-aperture collimator and, at the same time, monitoring the position of the radioactive-emission camera, at very fine time intervals, to obtain the equivalence of fine-aperture collimation. In consequence, high-efficiency, high-resolution images of a radioactivity emitting source are obtained. This is discussed below with regard to FIGS. 2-3B.

FIG. 2 schematically illustrates the basic component of a system 120 comprising a radioactive-emission camera 122, operative as a detection system, and a position-tracking device 124, both in communication with a data-processing system 126. The radioactive-emission camera 122 is associated with a first coordinate system 128, and the position-tracking device 124 is associated with a second coordinate system 128', wherein the position-tracking device 124 monitors the position of the radioactive-emission camera 122 as a function of time. The data-processing system 126 processes the measurements of both the radioactive-emission camera 122 and the position-tracking device 124 and combines them to form the image.

FIG. 3A schematically illustrates a manner of operating the radioactive-emission camera 122 with the position-tracking device 124 of the system 120. The radioactive-emission camera 122 moves about an area of radioactive emission 110, for example, in the direction of an arrow 118, so as to measure a radioactive emission distribution 112, as a function of time, while the position-tracking device 124 monitors the position of the camera 122. The radioactive-emission camera 122 may be a single-pixel detector of high efficiency, which is incapable, by itself, of producing images. Nonetheless, a data-processing system 126 processes a radioactive-count-rate input 121 together with a position-tracking input 123, using algorithms 125, to reconstruct an image 110' of the area of radioactive emission 110 for example, on a display unit 129.

Imaging according to this concept is illustrated in FIG. 3B. The area of radioactive emission 110 is located in a two-dimensional coordinate system u; v, and includes two hot points 115. The camera 122 moves from a position P(1), at a time t(1), to a position P(2), at a time t(2), while measuring the radioactive emission distribution 112 of the area of radioactive emission 110, including the hot points 115.

An example of a suitable position-tracking device 124 for use with system 120 is the miniBird™, which is a magnetic tracking and location system commercially available from Ascension Technology Corporation, P.O. Box 527, Burlington, Vt. 05402 USA (http://www.ascension-tech.com/graphic.htm). The miniBird™ measures the real-time position and orientation (in six degrees of freedom) of one or more miniaturized sensors, so as to accurately track the spatial location of cameras, instruments, and other devices. The dimensions of the miniBird™ are 18 mm×8 mm×8 mm for the Model 800 and 10 mm×5 mm×5 mm the Model 500. Alternatively, other optical tracking systems which may be used are NDI-POLARIS of Northern Digital Inc., Ontario, Canada, which provides passive or active systems, a magnetic tracking device of NDI-AURORA, an infrared tracking device of E-PEN system, or an ultrasonic tracking device of E-PEN system. Additionally or alternatively, the position-tracking device may be an articulated-arm position-tracking device, an accelerometer-based position-tracking device, a potentiometer-based position-tracking device, or a radio-frequency-based position-tracking device.

Commonly owned US application 20040054248 and commonly owned PCT publication WO2004/042546 further disclose various extracorporeal and intracorporeal systems 120 wherein the position-tracking devices 124 associated with the radioactive-emission cameras 122 have relatively wide apertures. Examples of extracorporeal and intracorporeal radioactive-emission cameras of this type are seen in FIGS. 4A-4C.

FIG. 4A schematically illustrates one embodiment of system 120, including a hand-held, extracorporeal device 170, which includes the camera 122, having a detector 132 and a collimator 134. The system 120 also includes a controller 130 and a position-tracking device 124, wherein the camera 122 and the position-tracking device 124 are associated with the data-processing system 126 discussed above with reference to FIGS. 2-3B.

FIG. 4B schematically illustrates another embodiment of system 120 wherein an intracorporeal camera device 180 includes the radioactive-emission camera 122 mounted on a catheter 136. The camera 122 includes the detector 132, the collimator 134, and the position-tracking device 124, wherein the camera 122 and the position tracking device 124 are associated with the data-processing system 126 discussed above with reference to FIGS. 2-3B. The camera 122 is configured so as to penetrate a tissue 135, via a Trocar valve 138. A structural imager 137, such as an ultrasound imager or an MRI camera may further be included.

FIG. 4C schematically illustrates yet another embodiment of system wherein an intracorporeal camera device 190 is adapted for rectal insertion. The device 190 includes the radioactive-emission camera 122, which includes a plurality of the detectors 132 and the collimators 134 associated with the position-tracking device 124. The intracorporeal 190 device may be further adapted for motion along the x and ω directions. For example, the intracorporeal device 190 may include a motor 154 for moving the device 190 in the x and ω directions, such that, once inserted into a rectum, it may be propelled therealong. A suitable motor 154 may be obtained, for example, from B-K Medical A/S, of Gentofte, DK, and may be adapted to transmit information to the data-processing system 126, regarding the exact position and orientation of the intracorporeal device. 190. In some embodiments, the motor 154 may be used in place of the position-tracking device 124. Alternatively, it may be used in addition thereto. The intracorporeal device 190 may further include the structural imager 137, such as an ultrasound imager or an MRI.

Initial View Determination

Predetermined Views, Based on a Model of a Body Structure

Definition of a View

Referring now to the drawings, FIGS. 5A-5F present the principles of modeling, for obtaining an optimal set of views, in accordance with embodiments of the present invention.

FIG. 5A schematically illustrates a body section 230 having a region-of-interest (ROI) 200. The region-of-interest 200 may be associated with a body structure 215 having a specific radioactive-emission-density distribution, possibly suggestive of a pathological feature, this feature termed herein organ target 213. Additionally, there may be certain physical viewing constraints associated with the region-of-interest 200.

In accordance with embodiments of the present invention, FIG. 5C illustrates, in flowchart form, a method 205 for best identifying an optimal and permissible set of views for measuring the radioactive-emissions of the region-of-interest 200, such that a three-dimensional image thereof may be reconstructed. The method 205 includes the following steps:

in a box 206: modeling the region-of-interest 200 as a model 250 of a volume U, wherein U is the region-of-interest volume, and wherein the volume U may include one or several radioactive-emission sources, operative as modeled organ targets HS located within anatomical constraints AC, as seen in FIG. 5B;

in a box 207: obtaining an optimal and permissible set of views for the modeled volume U FIG. 5B; and in a box 208: applying the optimal set of views to the in-vivo region-of-interest 200 and the body structure 215 of FIG. 5A.

It will be appreciated that the model 250 of the region-of-interest 200 may be based on general medical information of the body structure 215 and common pathological features associated with it. Additionally, the model may be based on information related to a specific patient, such as age, sex, weight, and body type. Furthermore, in order to facilitate generation of the model 250, a structural image, such as by ultrasound or MRI, may be used for providing information about the size and location of the body structure 215 in relation to the body section 230.

FIGS. 5D-5F schematically illustrate three types of the modeled organ targets HS, as follows:

i. a region of concentrated radiation, or a hot region, for example, as may be associated with a malignant tumor and as seen in FIG. 5D;

ii. a region of low-level radiation, which is nonetheless above background level, for example, as may be associated with carcinoma and as seen in FIG. 5E; and iii. a region of little radiation, or a cold region, below the background level, for example, as may be associated with dead tissue and as seen in FIG. 5F.

Figure 6B:
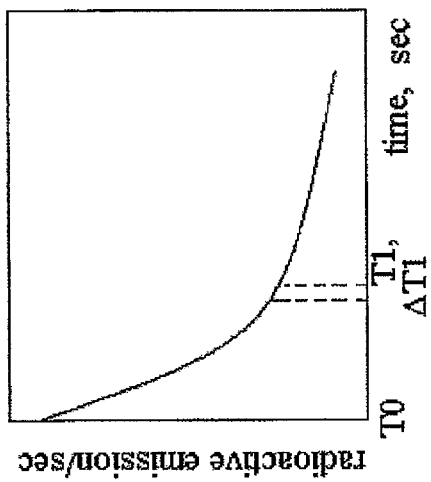
FIGS. 6A and 6B pictorially illustrate a view and viewing parameters associated with it, in accordance with definitions of the present invention.
Figure 6A:
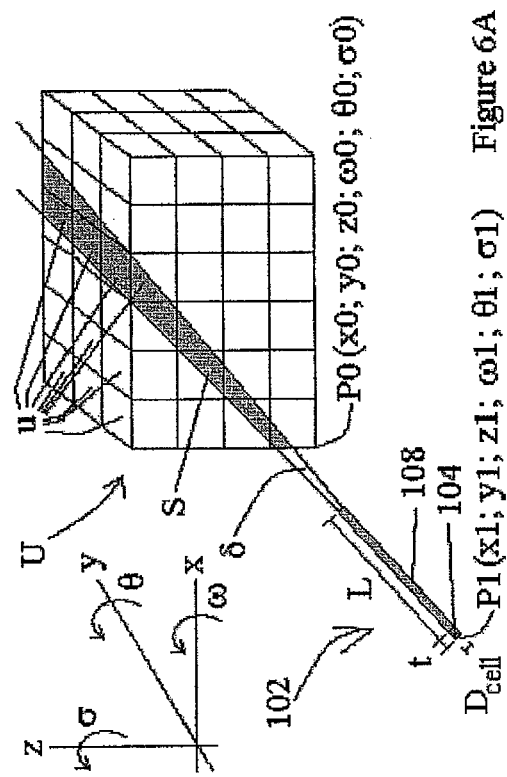

Referring further to the drawings, FIGS. 6A and 6B pictorially illustrate a view and viewing parameters associated therewith, in accordance with embodiments of the present invention.

FIG. 6A illustrates the volume U, subdivided into voxels u. The volume U is defined in a six-degree coordinate system x; y; z; ω; θ; σ having a point of origin P0(x0; y0; z0; ω0; θ0; σ0). A detecting unit 102 is positioned at a location and orientation P1(x1; y1; z1; ω1; θ1; σ1). The detecting unit 102 has a detector 104, formed of a specific detector material having a thickness $\tau_d$, and a collimator 108, having a diameter D and a length L and defining a collection angle δ.

FIG. 6B schematically illustrates the emission rate of the volume U, as a function of time, given that a radioactive material of a specific half-life has been administered at a time T0.

A view may thus be defined as a group of nonzero probabilities of detecting a radioactive emission associated with all the voxels that form a sector S (FIG. 6A). A view is sometimes referred to as a projection, and the two terms are synonymous. Furthermore, a view defined over a sector S can be naturally extended to be defined over the set of all voxels, by simply associating a zero probability with every voxel outside the sector S. This makes possible the application of mathematical operations over the entire volume U.

A view is dependent on the following viewing parameters:

Location and Orientation Parameters:

The location and orientation of the detecting unit 12 in a six-dimensional space, P1(x1; y1; z1; ω1; θ1; σ1), with respect to the origin P0(x0; y0; z0; ω0; θ0; σ0) of the volume U.

Detecting-Unit Parameters:

The collection angle δ which, together with the location and orientation parameters P1(x1; y1; z1; ω1; θ1; σ1) with respect to the origin P0(x0; y0; z0; ω0; θ0; σ0), define the sector S;

The detector material, which affects the detector efficiency;

The detector thickness $\tau_d$, which affects the detector's stopping power, hence, its efficiency; and The diameter of the detecting unit, or the effective diameter, calculated so as to produce a circle of the same area, when the geometry is not a circle.

Attenuation Parameters:

Attenuation properties of all the voxels within the sector S, as they affect the probabilities that radioactive emissions from a specific voxel will reach the detector, wherein different voxels within the sector S may have different attenuation properties, since several types of tissue may be involved.

Radiopharmaceutical Parameters:

The half life $t_{1/2}$ of the radiopharmaceutical, the types of radioactive emission, whether gamma or beta, and the energies of the radioactive emissions, which affect the probability of detection.

As used herein the phrase "kinetic profile" means a collection of one or more parameters describing the rate of distribution due to flow, uptake, bioclerance, diffusion, active transport, metabolism and the like.

A kinetic profile is either definable in general or per patient, per organ, per tissue and under various conditions, such as pathologies and stimulations.

Time Parameters:

T0 is the time of administrating the radiopharmaceutical, T1 is the time since administration, and the duration of the measurement is ΔT1, which affects the number of emissions that occur during the radioactive-emission measurement.

Some of these viewing parameters are fixed for a particular situation. Specifically, the tissue attenuation parameters are given. Additionally, the time T1 since administration of the radiopharmaceutical is generally governed by the blood pool radioactivity, since it is generally necessary to wait until the blood pool radioactivity dies out for low-level detection to be possible. For the remaining viewing parameters, optimization may be carried out.

The remaining viewing parameters may be divided into two categories:

i. viewing parameters in the design of a radioactive-emission camera;

ii. viewing parameters for an optimal set of views, for a given camera.

Viewing Parameters for an Optimal Set of Views, for a Given Camera

Figure 7C:
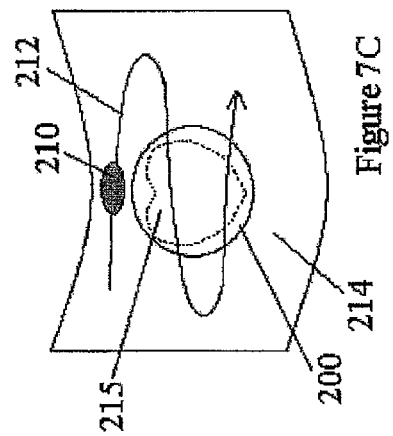
FIGS. 7A-7C schematically illustrate anatomical constraints, which are to be modeled, in accordance with embodiments of the present invention.
Figure 7B:
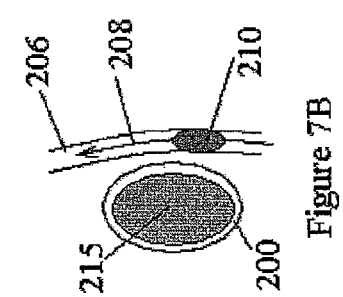
Figure 7A:
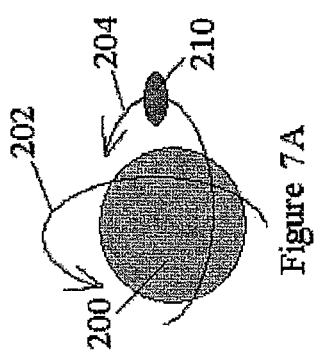

Referring further to the drawings, FIGS. 7A-7C schematically illustrate anatomical constraints, which may hinder measurements.

FIG. 7A schematically illustrates the region-of-interest 200, for which a three-dimensional radioactive-emission image is desired. The region-of-interest 200 is in free space, with no constraints to limit accessibility to it. Thus, a radioactive-emission camera 210 may travel, for example, along tracks 202 and 204, and any other track, unhindered.

In FIG. 7B, the region-of-interest 200 is associated with the body structure 215, such as a prostrate, in vivo. For obtaining a radioactive-emission image, the radioactive-emission camera 210 may be inserted transrectally, so as to travel in a rectum 206, for example, in the direction of an arrow 208. Its ability to image the prostrate is limited by anatomical constraints.

In FIG. 7C, the region-of-interest 200 is associated with the body structure 215, such as a heart, a breast, or another organ, in vivo, and the radioactive-emission camera 210 may be an extracorporeal camera, which may perform radioactive-emission measurements from outside the body, on an extracorporeal surface 214, for example when moving along a track 212.

In each of these cases, it is desired that a reconstructed three-dimensional radioactive-emission image of the region-of-interest 200 be obtained at a predetermined quality. This is achieved by predefining an optimal set of radioactive-emission measurement views, tailored to the specific body structure 215 and optimized with respect to the information gained regarding the body structure 215.

Referring further to the drawings, FIG. 8 illustrates, in flowchart form, a method 300 of predefining a set of views for functional imaging, tailored for imaging a specific body structure, and optimized with respect to the functional information gained about the body structure, in accordance with embodiments of the present invention. In effect, FIG. 8 is an expansion of FIG. 5C. The method 300 comprises:

in a box 302: providing a model of the body structure 215, based on its geometry;

in a box 304: providing a model of anatomical constraints, which limit accessibility to the body structure;

in a box 306: providing a collection of views of the modeled body structure obtained within the modeled anatomical constraints;

in a box 308: providing a scoring function, by which any set of at least one view, from a collection of views, is scorable with a score that rates information obtained from the modeled body structure by the set;

in a box 310: forming sets of views from the collection of views and scoring them with the scoring function; and in a box 312: selecting a set of views, from the collection of views, based on their scores, as the predefined set of views.

The model of the body structure is based on anatomical knowledge regarding its size, shape, and weight. In fact, different models may be provided, for example, for different ages, sexes, weights, and body types, such as heavy-built, medium-built, or small-built. In accordance with a first embodiment, the body structure is modeled assuming that there is no radioactive emission throughout its volume. In accordance with other embodiments, the body structure may be modeled with one or more modeled organ targets, simulating different pathological features. Specifically, the modeled organ targets may be hot regions, of a radioactive-emission intensity higher than the background level, regions of low-level radioactive-emission intensity, which is nonetheless above the background level, and cold regions, of a radioactive-emission intensity lower than the background level. These may be distributed in accordance with medical records, which teach of sites within the body structure that may be more susceptible to certain pathologies.

Similarly, the model of anatomical constraints which limit accessibility to the body structure is based on anatomical knowledge, and different models may be provided, for example, for different ages, sexes, weights, and body types.

The collection of views may be obtained by several methods. It may be calculated analytically for the modeled body, based on the view parameters. Additionally or alternatively, computer simulations of the modeled body and the view parameters may provide the collection of views. Additionally or alternatively, measurements may be performed using a point source and a detecting unit of appropriate parameters, at different locations and orientations of the detecting unit, so as to simulate the desired geometries.

It will be appreciated that a combination of these may be used. For example, the measurements may be performed in air, but corrected analytically or by computer simulations, for tissue attenuation.

Referring further to the drawings, FIGS. 9A-9F schematically illustrate possible models and collections of views for a body structure, in accordance with embodiments of the present invention.

FIG. 9A schematically illustrates four views, formed by sectors S1, S2, S3, and S4 through the volume U, which has an even distribution of radioactive emission.

FIG. 9B schematically illustrates three views, formed by sectors S1, S2, and S3, through the volume U, which includes a modeled pathological feature, which is the modeled organ target, HS.

FIG. 9C schematically illustrates three views, formed by sectors S1, S2, and S3 through the volume U, which includes a modeled organ target, HS', of the same type as that of the modeled organ target HS, (that is, either a hot region or a cold region) but somewhat displaced along the x; y; z coordinate system. Additionally, the modeled organ target HS of FIG. 9B is superimposed in FIG. 9C, for illustrative purposes, in order to show the displacement, delta1, of modeled organ target HS' from modeled organ target HS.

FIG. 9D schematically illustrates three views, formed by sectors S1, S2, and S3 through the volume U, which includes a modeled organ target, HS", of the same type as that of the modeled organ targets HS and HS', but somewhat displaced along the x; y; z coordinate system from them. Additionally, the modeled organ targets HS of FIG. 9B and HS' of FIG. 9C are superimposed in FIG. 9D, for illustrative purposes, in order to show the displacements delta2 and delta3, vis a vis HS" of FIG. 9D.

FIG. 9E schematically illustrates three views, formed by sectors S1, S2, and S3 through the volume U, which includes two modeled organ targets, HS1 and HS2.

Figure 9F:
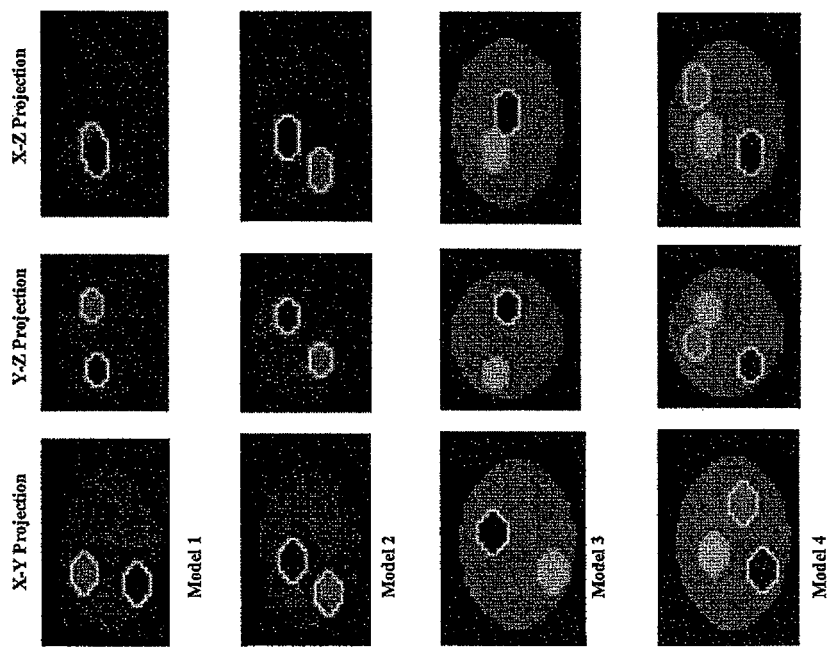

FIG. 9F schematically illustrates four possible models of organs, shown as elliptical volumes, each with a slightly different distribution of modeled organ targets.

The modeled organ targets may be termed emmitance models. In general, an emmitance model is based on a particular radiopharmaceutical, which fixes both the rate of emission and the change in the rate of emission with time, determining the difference between the modeled organ target and the background level, as a function of time. To study the effect of different radiopharmaceuticals on the views, one may provide different emmitance models, based on different radiopharmaceuticals and different elapsed times relative to their administration.

The choice of an optimal set of views from among a collection of views, such as any of those illustrated in FIGS. 9A-9E, is based on a scoring function, which rates different sets of views in terms of their information regarding the volume U. The scoring function is based on information theoretic measures that rate the quality of the data which each set of views provides.

Information Theoretic Measures

A brief description of the information theoretic measures, upon which the scoring function may be based, is as follows:

Uniformity:

The information theoretic measure of uniformity requires that the probability of detecting a radioactive emission from each voxel, by one of the views, be substantially equal, i.e., substantially uniform for all the voxels.

This is illustrated with reference to FIG. 9A. Basically, in one view, a voxel may have a high influence on the counts that are measured while, in another view, the same voxel may have a low influence on the counts that are measured. For example, consider a voxel u(1; 1; 1), in relation to the views associated with the sectors S2 and S4. The voxel u(1; 1; 1) has a high influence on the counts that are measured by the view associated with the sector S4, but a low influence on the counts that are measured by the view associated with the sector S2. The aim of uniformity is to identify a set of views that will balance the influence of each voxel for the entire set of views.

Separability:

The information theoretic measure of separability rates resolution, or the ability to distinguish between a pair of close models of the body structure, each having substantially identical dimensions, so as to define substantially identical volumes U having slightly different distributions of modeled organ targets.

For example, a pair of models of substantially identical volumes are illustrated in FIGS. 9B and 9C, wherein the respective modeled organ targets are HS, whose center is at a location $(x; y; z)_{Hs}$ and HS', whose center is at a location $(x; y; z)_{HS'}$. As noted above, the displacement along the x axis is delta1, which may be measured, for example, in mm.

An optimal set of views, from the standpoint of separability, is that which will best distinguish between HS of FIG. 9B and HS' FIG. 9C. Thus, a score, in terms of separability, is given for the pair of models, the score relating to a resolution as defined by the difference between the location of the two models. In the present example, the difference is delta1, so the score given by the information theoretic measure of separability will relate specifically to a resolution as defined by delta1 along the x-axis, relative to the locations of HS and HS'. Other portions of the volume U and other displacements may have different resolutions.

Additionally, as discussed above with regard to the model of FIG. 9D, volume U includes the modeled organ target HS", whose center is at a location $(x; y; z)_{HS''}$. HS" is displaced from HS of FIG. 9B, along the z-axis, the displacement denoted delta2, and is also displaced from HS' of FIG. 9C, along the x- and z-axes, the displacement denoted delta3.

Scores, in terms of separability, may be given to all the pairing combinations, i.e., to the models of FIGS. 9B-9C, with regard to delta1; to the models of FIGS. 9B-9D, with regard to delta2; and to the models of FIGS. 9C-9D, with regard to delta3. An optimal set of views may be selected based on the average scores for all the pairing combinations; for example, the optimal set may be that whose average score for all the pairing combinations is the highest. Alternatively, a weighted average may be applied.

It will be appreciated that more than one modeled organ target may be included in the volume U. It will be further appreciated that a set of views may be selected so as to provide high resolution for portions of the volume U known to be susceptible to pathologies, and so as to provide low resolution for portions of the volume U known to be generally free of pathological features.

With regard to FIG. 9F, any pair of models of organs having different distributions of modeled organ targets, may be utilized for identifying an optimal set of views in terms of separability.

Reliability:

The information theoretic measure of reliability rates repeatability in measurement, so that repeated reconstructions are not substantially different. Reliability may be scored with respect to a single model of a body structure, having a specific distribution of modeled organ targets, for example, any one of the models of FIGS. 9B-9E. Yet, preferably, several models of substantially identical volumes are provided, such as, for example, the four models of FIGS. 9B-9E. Substantially identical sets of views may be applied to all the models and may be scored with respect to reliability. The optimal set is selected based on its average score for the plurality of the models. For example, the optimal set may be that whose average score for the plurality of the models is the highest.

The four models of organs of FIG. 9F, each of which has a slightly different distribution of modeled organ targets, may also be used for identifying an optimal set of views in terms of reliability.

Weighted Combination:

A weighted combination of several information theoretic measures may also be used. For example, a plurality of models may be provided, all having substantially identical dimensions and volumes, as follows:

i. a first model of the volume U, free of modeled organ targets, as seen in FIG. 9A, for scoring sets of views in terms of uniformity;

ii. at least one pair of models of the volume U, with slightly different distributions of modeled organ targets, as seen in any pair of FIGS. 9B-9C, 9B-9D, and (or) 9C-9D, for scoring sets of views in terms of separability;

iii. at least one model of the volume U, with a given distribution of modeled organ targets, as seen in any one of FIGS. 9B, 9C, 9D, and (or) 9E, for scoring sets of views in terms of reliability.

Identical sets of views may be applied to all the models of the volume U, and each view may be scored in terms of uniformity, separability, and reliability. An optimal set of views may be selected based on a summation of the three scores, or based on a weighted average of the three scores.

The Greedy Construction

Some approaches for selecting an optimal set are based on determining a required quality of reconstruction, and finding a set of views that meets that requirement. Others are based on fixing the size for the set (i.e., the number of views in the set) and maximize the quality of the reconstruction for the given set size. Still other approaches define both a desired size for the set and a desired quality of reconstruction and search for a set of the desired size, which meets the desired quality of reconstruction.

However, given a desired size for a set of views and a desired quality of reconstruction, while it may be possible to search through all possible sets of the desired size, scoring each, in order to identify the set that meets the desired quality, the task may be monumental. For example, where the collection of views includes several thousand views, and a set size of 100 is desired, rating each combination of 100 views would be computationally impractical.

An alternative approach is the Greedy Construction. When applying the Greedy Construction, an information theoretic measure is chosen, for example, separability, and an initial set of a minimal number of views is defined. The set is gradually built up, so that with every addition, a view is picked so as to maximize the chosen information theoretic measure of the set.

This may be illustrated with reference to FIG. 9E. Given that separability is the chosen information theoretic measure, and an initial set of view S1 is defined, the additions of views S2 and S3 may then be compared in order to determine with which of them separability is maximized. Intuitively, for the present example, the addition of S3 will maximize the chosen information theoretic measure of the set.

It will be appreciated that other scoring functions, as known, may similarly be used.

Performing Measurements

The advantage of the method of the present invention, of predefining a set of views based on a model of a body structure, using an information theoretic measure, so as to optimize the functional information from the views of the corresponding body structure, in vivo, becomes apparent when compared with the prior art alternatives. The prior art relies on obtaining random views, in vivo, or views dictated by anatomical constraints, with no rigorous approach to the manner by which they are chosen.

The method of the present invention, of predefining a set of views, based on a model of a body structure, using an information theoretic measure, so as to optimize the functional information from the views of the corresponding body structure, in vivo, is further illustrated hereinbelow, with reference to FIG. 10.

FIG. 10 illustrates, in flowchart form, a method 320 of functional imaging, tailored for imaging a body structure optimized with respect to the functional information gained about the body structure, by using the predefined optimal set of views, in accordance with embodiments of the present invention. The method 320 comprises:

in a box 322: providing a model of a body structure, based on its geometry;

in a box 324: providing a model of anatomical constraints, which limit accessibility to the body structure;

in a box 326: providing a collection of views of the modeled body structure, obtained within the modeled anatomical constraints;

in a box 328: providing a scoring function, by which any set of at least one view, from a collection of views is scorable with a score that rates information, obtained from the modeled body structure by the set;

in a box 330: forming sets of views from the collection of views and scoring them, with the scoring function;

in a box 332: selecting a set of views from the collection of views of the modeled body structure, based on its score, as the predefined set of views; and in a box 334: performing radioactive-emission measurements of an in-vivo body structure that corresponds to the body structure that has been modeled, selectively at the predefined set of views.

It will be appreciated that the region-of-interest 200 may include an organ, such as a heart or a pancreas, a gland, such as a thyroid gland or a lymph gland, blood vessels, for example, the coronary artery or the pulmonary artery, a portion of an organ, such as a left atrium of a heart, a bone, a ligament, a joint, a section of the body, such as a chest or an abdomen, or a whole body.

A still more powerful approach may be achieved by taking the method of the present invention through second and third iterations, so as to zoom in on suspected pathological features that are identified. Specifically, when a suspected pathological feature is identified, a second, inner region-of-interest, limited to the region of the pathological feature and its surrounding anatomical structure, can be identified and modeled. An optimal pathology set of views, specifically for the second, inner region-of-interest, may be predefined, based on information theoretic measures, as before. This is illustrated hereinbelow, with reference to FIGS. 11 and 12.

Figure 11:
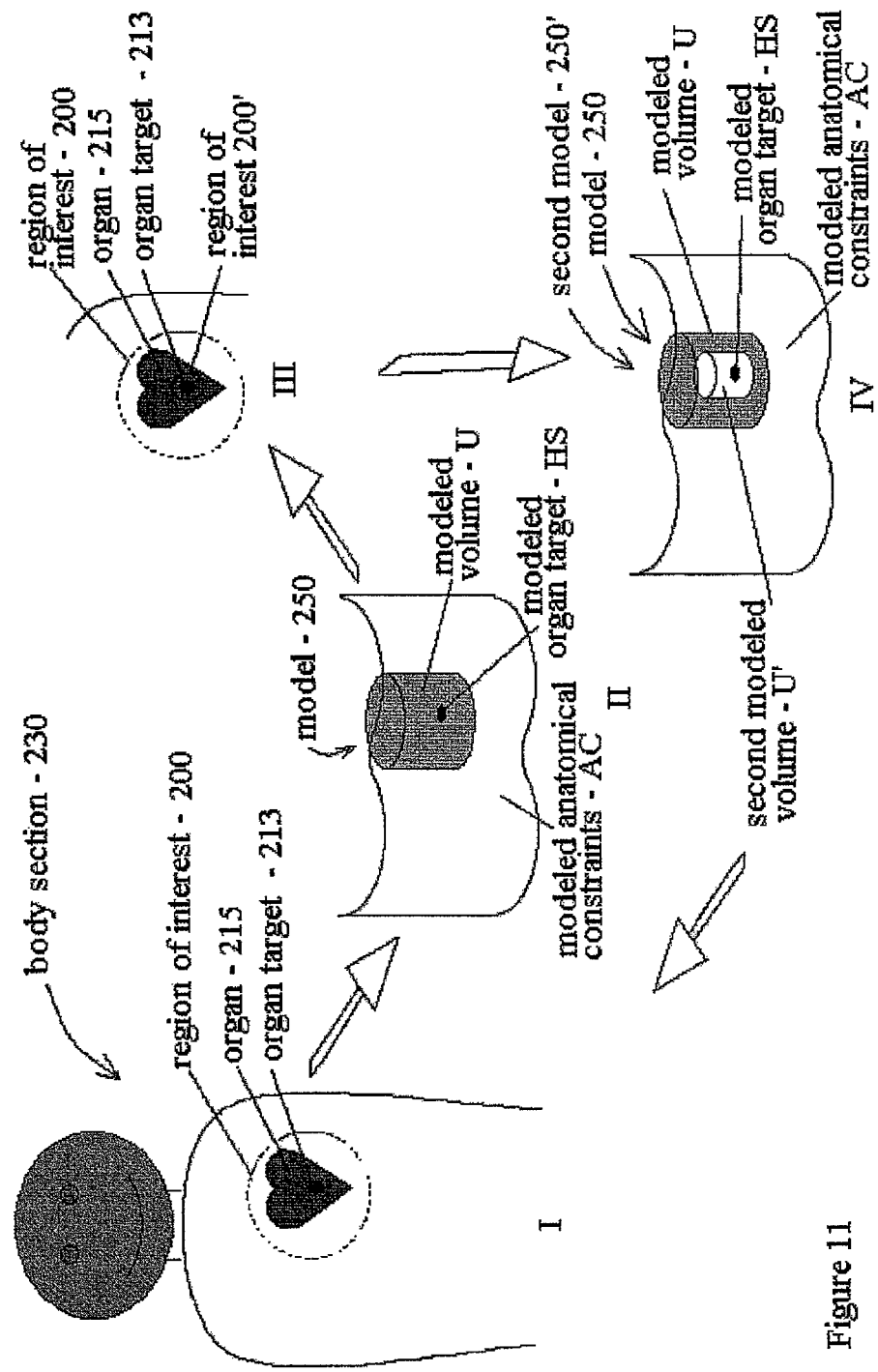
FIG. 11 schematically illustrates the process of modeling in two iterations, for zooming in on a pathological feature, in accordance with embodiments of the present invention.

Referring further to the drawings, FIG. 11 pictorially illustrates a method 340 for zooming in on a suspected pathological feature, as a process of two or more iterations, in accordance with embodiments of the present invention, as follows:

In I: The region-of-interest 200, associated with the body structure 215, is defined for the body section 230.

In II: The model 250 of the volume U is provided for the region-of-interest 200, possibly with one or several of the modeled organ targets HS, and within the anatomical constraints AC, for obtaining the optimal set of views for the region-of-interest 200. The optimal set of views is then applied to the body section 230.

In III: When a suspected organ target 213 is identified, in vivo, by radioactive-emission measurements at the optimal set of views, a second, inner region-of-interest 200' is defined, including the suspected pathological feature.

In IV: A model 250' of a volume U' is provided for the second, inner region-of-interest 200', preferably, with at least one modeled organ target HS, simulating the suspected organ target 213, for obtaining an optimal pathology set of views for the region-of-interest 200'. The second, pathology set of views is then applied to the body section 230.

Figure 12:
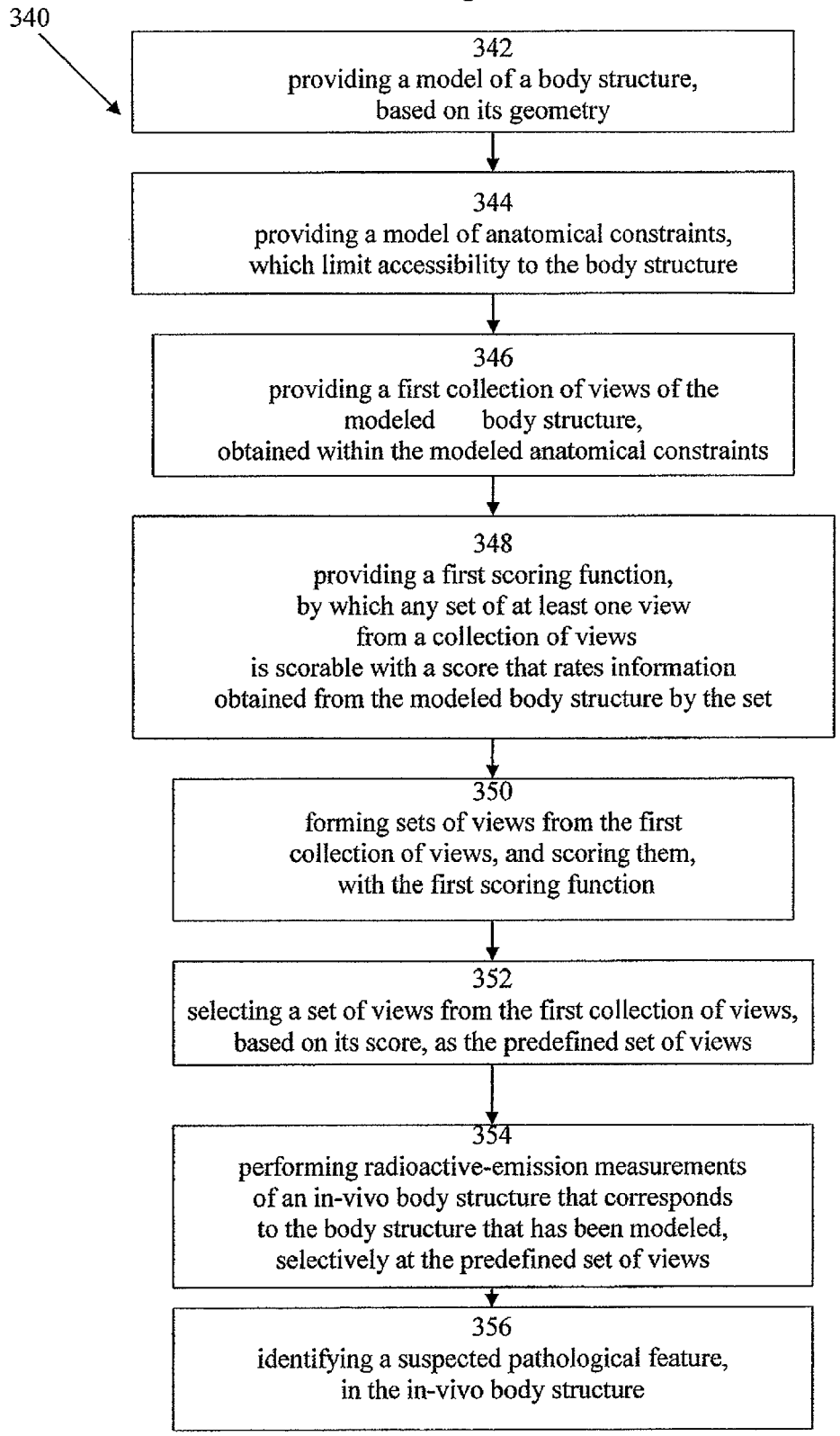
FIG. 12 illustrates, in flowchart form, a method of several iterations for zooming in on a pathological feature, when performing in vivo measurements, in accordance with embodiments of the present invention.
Figure 12:
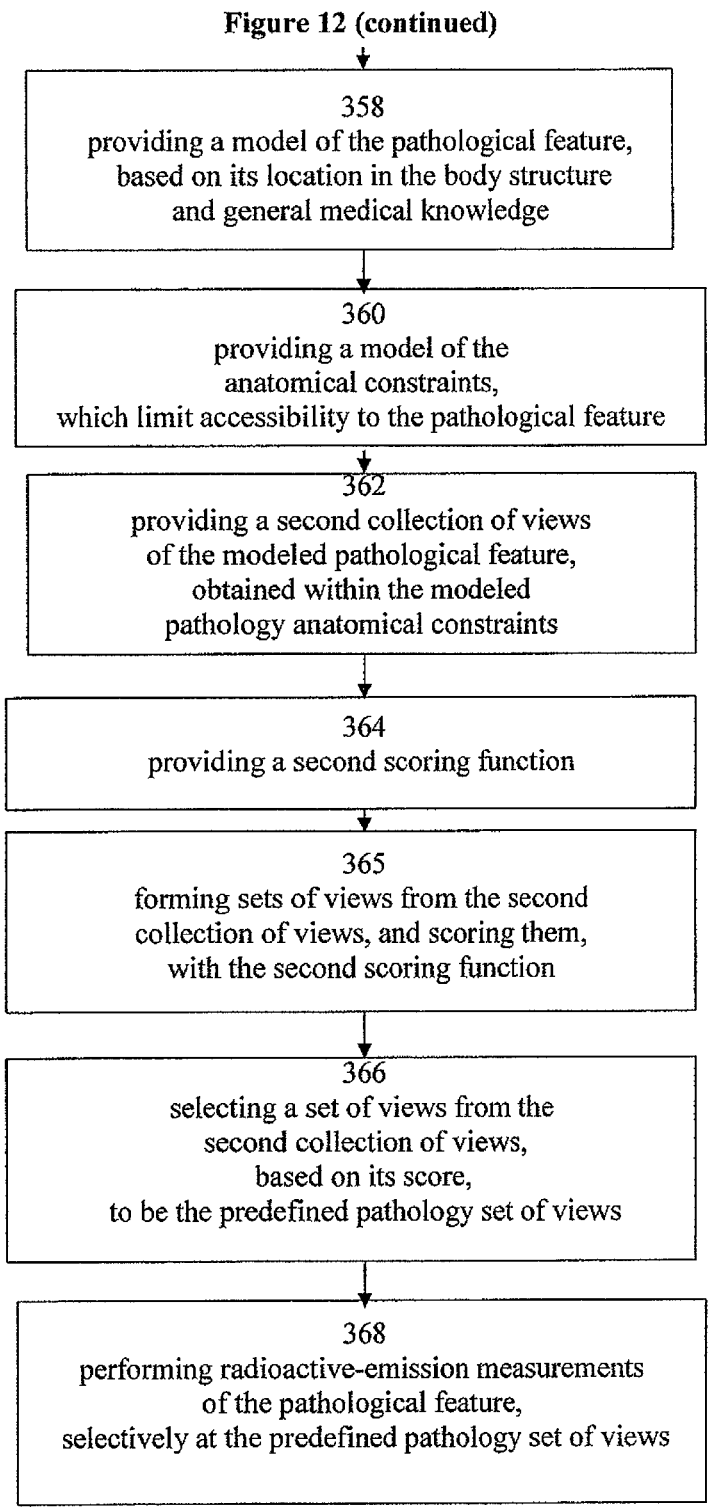

Referring further to the drawings, FIG. 12 illustrates, in flowchart form, the method 340, for zooming in on a suspected pathological feature of the body structure, as a process of two iterations, in accordance with embodiments of the present invention. The method 340 comprises:

in a box 342: providing a model of a body structure, based on its geometry;

in a box 344: providing a model of anatomical constraints, which limit accessibility to the body structure;

in a box 346: providing a first collection of views of the modeled body structure, obtained within the modeled anatomical constraints;

in a box 348: providing a first scoring function, by which any set of at least one view, from a collection of views, is scorable with a score that rates information, obtained from the modeled body structure by the set;

in a box 350: forming sets of views from the first collection of views, and scoring them, with the first scoring function;

in a box 352: selecting a set of views from the first collection of views of the modeled body structure, based on its score, as the predefined set of views;

in a box 354: performing radioactive-emission measurements of an in-vivo body structure that corresponds to the body structure that has been modeled, selectively at the predefined set of views;

in a box 356: identifying a suspected pathological feature, in the in-vivo body structure;

in a box 358: providing a model of the suspected pathological feature, based on its location in the body structure and general medical knowledge;

in a box 360: providing a model of the anatomical constraints, which limit accessibility to the suspected pathological feature;

in a box 362: providing a second collection of views of the modeled suspected pathological feature, obtained within the modeled pathology's anatomical constraints;

in a box 364: providing a second scoring function;

in a box 365: forming sets of views from the second collection of views, and scoring them, with the second scoring function;

in a box 366: selecting a set of pathology views from the second collection of views, based on its score, as the predefined pathology set of views; and in a box 368: performing radioactive-emission measurements of the suspected pathological feature, selectively at the predefined pathology set of views.

It will be appreciated that the model of the suspected pathological feature may be provided responsive to a patient's complaint, a physician's examination, or based on input from another imaging system, for example, x-rays, CT, MRI, ultrasound, and gamma scanning, for example, with a hand-held gamma camera, rather then based on the findings of the first set of measurements, of the step 356, hereinabove.

Design of the Radioactive-Emission Camera

While the embodiments described with reference to FIGS. 5A-12 relate to predefining a set of optimal views for a given radioactive-emission camera and a body structure, another side of the same coin relates to an optimal design of the radioactive-emission camera and camera system for the body structure, optimized with respect to functional information gained.

Thus, the embodiments described hereinbelow, with reference to FIGS. 13A-15 illustrate methods of designing cameras and camera systems, optimized with respect to information gained about a body structure.

Referring further to the drawings, FIGS. 13A-13E schematically illustrate possible designs of the radioactive-emission camera 10, and the process of obtaining views for a given camera design, in accordance with embodiments of the present invention.

Figures 13A, 13B, 13C:
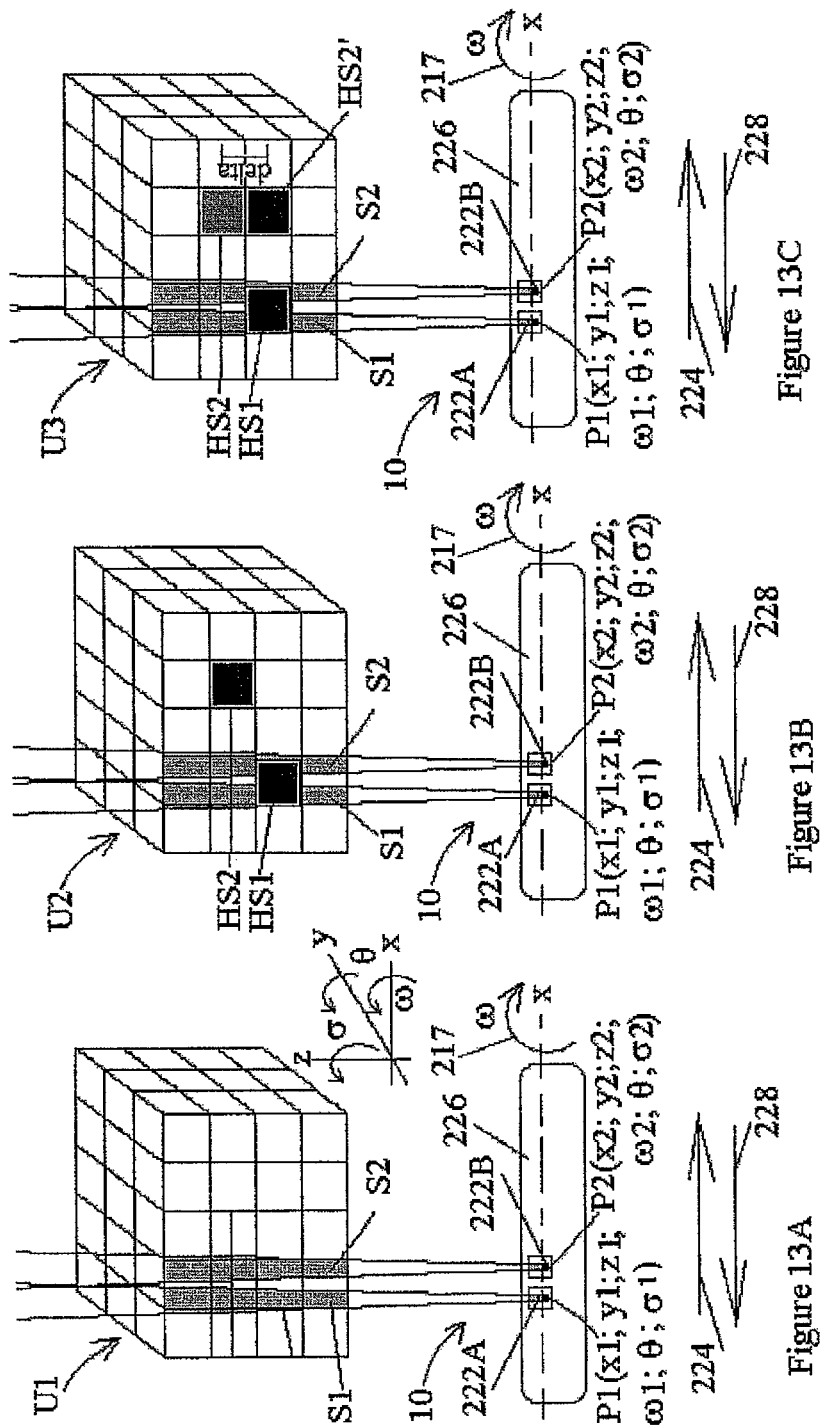
FIGS. 13A-13E schematically illustrate possible camera designs, and the process of obtaining views based on a model and a camera design, in accordance with embodiments of the present invention.

FIGS. 13A-13C schematically illustrate the radioactive-emission camera 10 as a radioactive-emission camera 226 arranged for measuring the radioactive-emission-density distribution of three bodies, U1, U2 and U3. The volume U1 of FIG. 13A has been modeled with no modeled organ targets, in order to score the radioactive-emission camera 226 in terms of uniformity. The volume U2 of FIG. 13B includes two modeled organ targets, HS1 and HS2, and may be used for scoring the radioactive-emission camera 226 in terms of reliability. The volume U3 of FIG. 13C includes two modeled organ targets, HS1 and HS2', so as to form a pair with the volume U2 of FIG. 13B, and the pair may be used for scoring the radioactive-emission camera 226 in terms of separability. Additionally, the volume U3 may be used to obtain a second score in terms of reliability, and the two reliability scores may be averaged. It will be appreciated that additional bodies, of different radioactive emission density distributions may be used, for obtaining additional scores in terms of reliability, and for forming additional pairs, for additional scores in terms of separability, wherein the scores in terms of each scoring function may be averaged. Additionally, the scores of the three functions may be combined, for example, as a sum, or as a weighted average. It will be appreciated that only one of the scoring functions, or only two of the scoring functions may be used. Additionally or alternatively, another scoring function or other scoring functions may be used.

According to the present example, the camera 226 has two detecting units 222A and 222B whose collimators are arranged in parallel. The two detecting units 222A and 222B are adapted for motion in the directions of ix, within the camera 226, as shown by arrows 224 and 228, so as to provide coverage of a plane within the bodies U1 U2 and U3, in parallel sectors. Upon reaching the end of the travel in the +x direction, as shown by the arrow 224, the two detecting units 222A and 222B may be rotated in the direction of ω, as shown by an arrow 217, and return in the −x direction of the arrow 228. In this manner, complete coverage of the whole body is provided. A representative collection of views of the camera 226 may be defined as a set of views of the bodies U1, U2, and U3, taken at predetermined increments of $\Delta x$ and $\Delta \omega$.

Intuitively, a set formed of parallel sectors may score poorly in terms of uniformity since radioactive emissions from voxels closer to the detecting unit have higher probabilities of being detected than radioactive emissions from voxels far from the detecting unit. Additionally, a set formed of parallel sectors may score poorly in terms of separability, since it cannot distinguish between two models, which only differ in the depth of a pathological feature, along the z-axis.

Figure 13D:
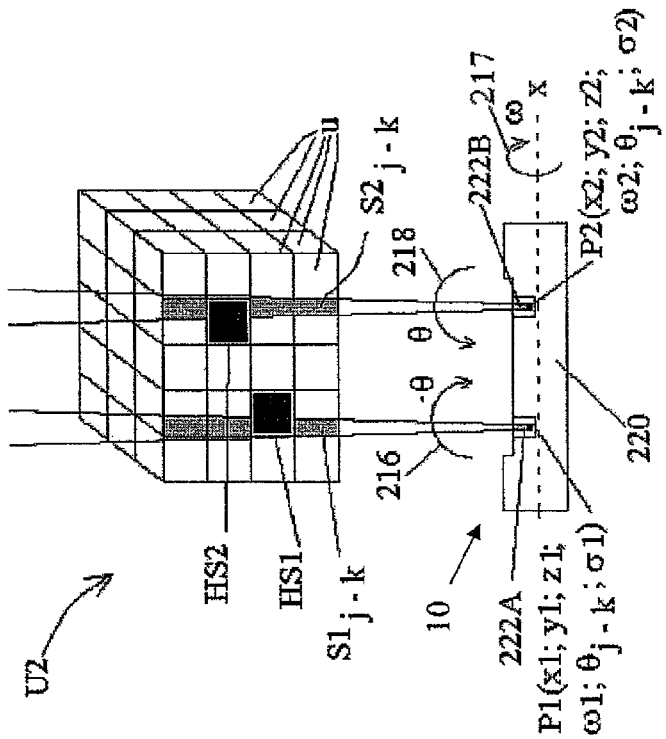

FIG. 13D schematically illustrate the radioactive-emission camera 10 as a radioactive-emission camera 220, arranged for measuring the radioactive-emission-density distribution of the volume U2, which may be used for scoring the radioactive-emission camera 220 in terms of reliability.

The camera 220 has the two detecting units 222A and 222B, arranged to sweep a plane within the volume U2, in a windshield-wiper-like manner, along $\pm \theta$, as illustrated by arrows 216 and 218. When sweeping along $\pm \theta$ is completed, the detecting units 222A and 222B rotate a few degrees along ω, as illustrated by the arrow 217, and sweeping along $\pm \theta$ is repeated in the new orientation. In this manner, coverage of the whole volume U2 is performed, from two locations and a large plurality of orientations. A representative collection of views of the camera 220 may be defined as a set of views of the volume U2, taken at predetermined increments of $\Delta \theta$ and $\Delta \omega$.

The significance of the present embodiment, is as follows:

i. The different detecting units 222A and 222B provide views from different orientations; and ii. The different detecting units 222A and 222B may change their view orientations.

A score may be applied to this set, based on the information theoretic measure of reliability.

It will be appreciated that similarly, the camera 220 may be arranged for measuring the radioactive-emission-density distribution of the volume U1 (FIG. 13A) and of the volume U3 (FIG. 13C), and possibly also of other bodies, in order to score the radioactive-emission camera 220 also in terms of uniformity and separability. The scores of the three functions may be combined, for example, as a sum, or as a weighted average. It will be appreciated that only one of the scoring functions, or only two of the scoring functions may be used. Additionally or alternatively, another scoring function or other scoring functions may be used.

Intuitively, the set of representative collection of views of the present example is likely to score more highly in terms of separability than that of the camera 226 of FIG. 13A, as it provides views from different locations and orientations.

Figure 13E:
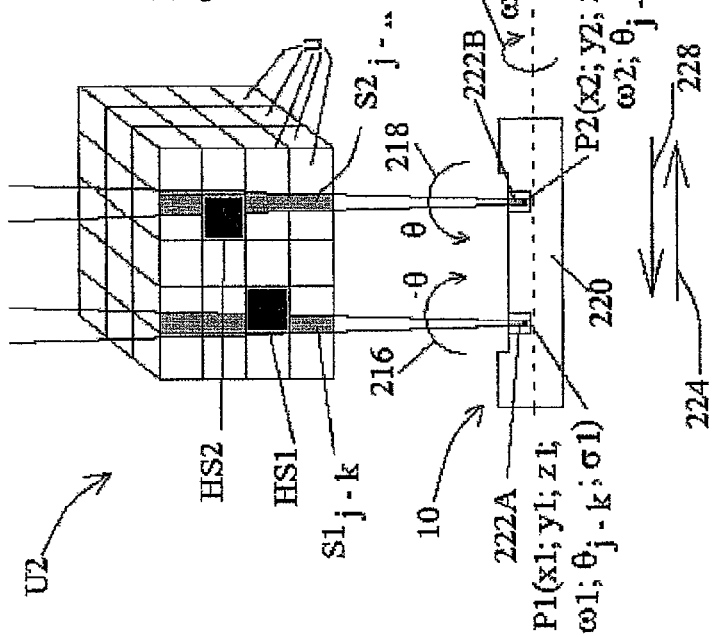

In FIG. 13E the detecting units 222A and 222B of the camera 220 are further adapted for motion in the directions of ix, within the camera 220, as shown by the arrows 224 and 228.

Intuitively, the set of representative collection of views of the present example is likely to score more highly in terms of all three information theoretic measures, than those of the camera of FIGS. 13A-13C and of the camera of FIG. 13D, as the present example provides views from a large plurality of locations and orientations.

In this manner, the information theoretic measures may be used for scoring representative collections of views of suggested camera designs, and an optimal camera design may be chosen based on this score, as described hereinbelow, with reference to FIG. 14, hereinbelow.

Figure 14:
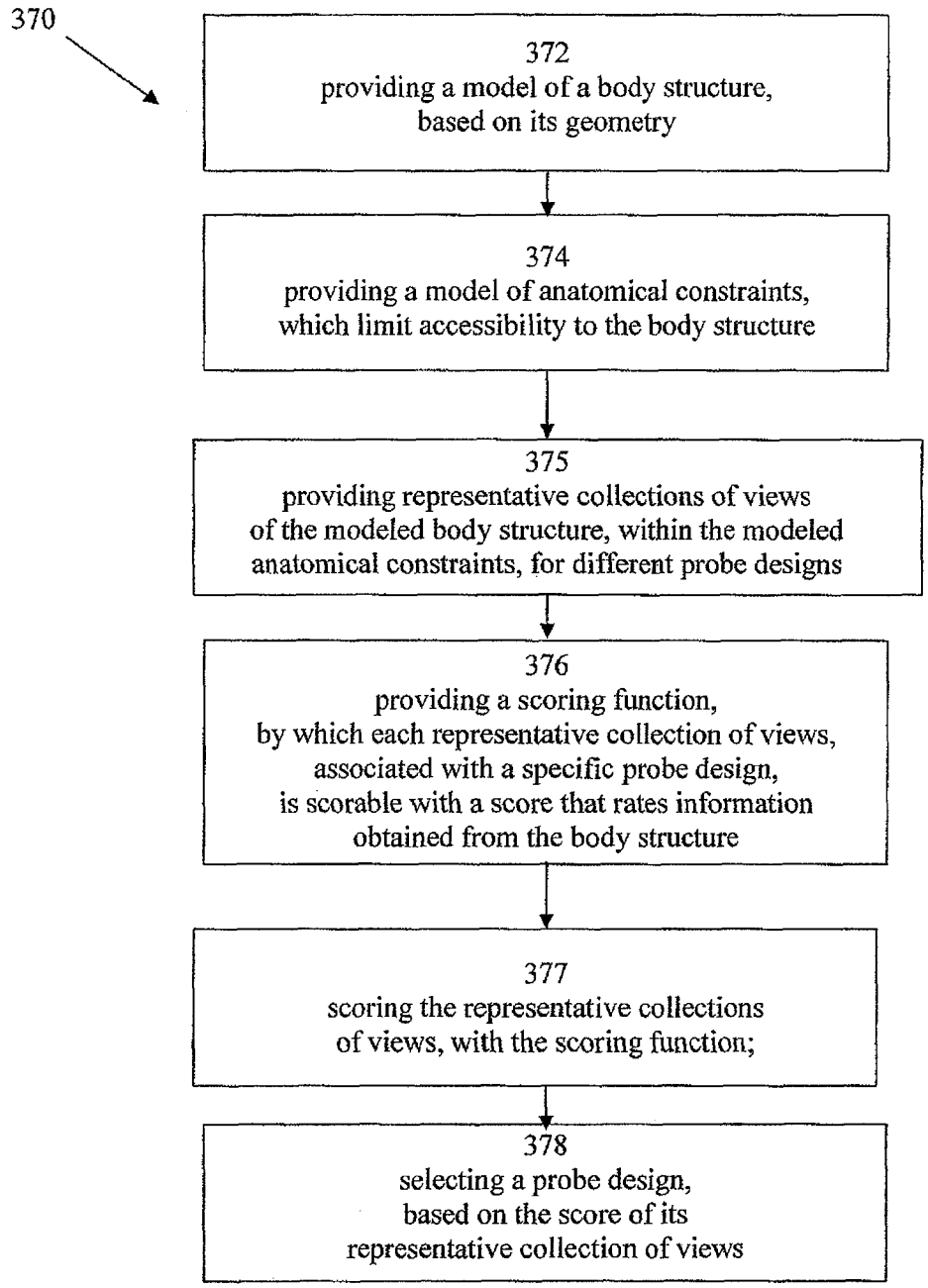
FIG. 14 illustrates, in flowchart form, a method of selecting a camera design optimized with respect to information gained about a body structure, in accordance with embodiments of the present invention.

FIG. 14 illustrates, in flowchart form, a method 370 for identifying a camera optimized with respect to information gained about the body structure. The method 370 comprises:

in a box 372: providing a model of a body structure, based on its geometry;

in a box 374: providing a model of anatomical constraints, which limit accessibility to the body structure;

in a box 375: providing representative collections of views of the modeled body structure, within the modeled anatomical constraints, for different camera designs;

in a box 376: providing a scoring function, by which each representative collection of views, associated with a specific camera design, is scorable with a score that rates information, obtained from the body structure;

in a box 377: scoring the representative collections of views, with the scoring function; and in a box 378: selecting a camera design, based on the score of its representative collection of views.

In this manner, a comparison of the quality of the data that may be produced by each camera design can be made. This analysis is important at the camera-design stage, in order to eliminate situations where views which are anatomically possible and which are desired from the standpoint of information theoretic measures, are unattainable because of camera design limitations. For example, the camera 190 of FIG. 4C, hereinabove, cannot be used for the windshield-wiper-like motion, shown in FIG. 13D, by the arrows 216 and 218; however, this type of coverage has proved very valuable. The method 370 may, however, be suitable for another camera design.

Additionally, when selecting a camera design, it is generally desired to consider secondary issues, such as the rate of data collection, the cost of the camera, the complexity of the design, for example, in terms of the number of motors, motion-transfer systems, and the like.

The rate of data collection is important both because it may be associated with patient discomfort and because it affects the number of patients that may be examined in a period of time. Where data collection with one camera design may take an hour and with another camera design may take 10 minutes, the design of the faster camera is highly advantageous. Complexity and cost are important because they affect the accessibility of the camera to the general public.

Thus, a design scoring function may be provided, for rating each camera design with a design score, based on any one or a combination of the secondary issues. The design scoring function may be used for selecting a camera design from several that have been found acceptable in terms of the quality of the data, by the method 370 of FIG. 14.

Figure 15:
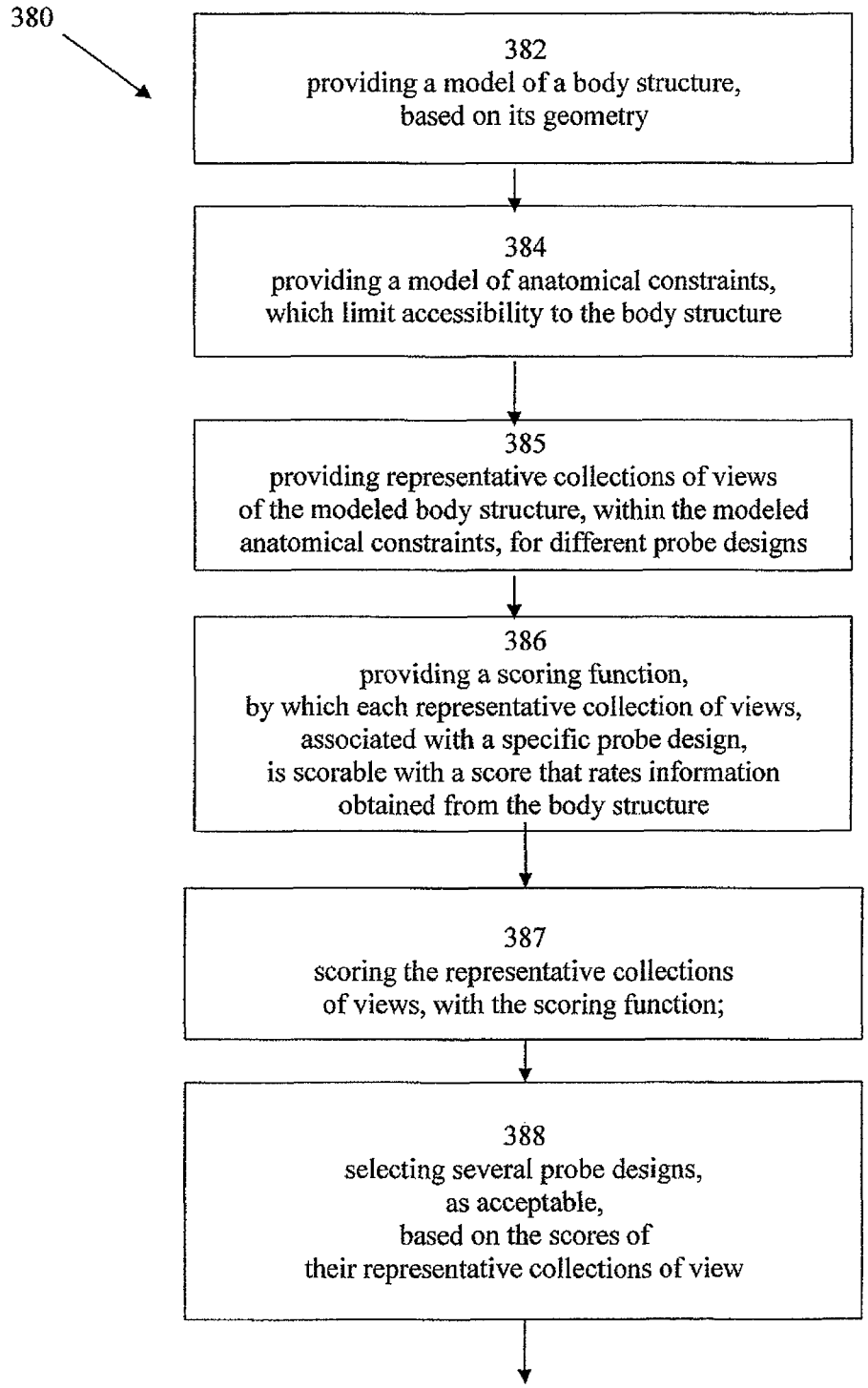
FIG. 15 illustrates, in flowchart form, a method of selecting a camera design, based on the rate of data collection and other design considerations, in accordance with embodiments of the present invention.
Figure 15:
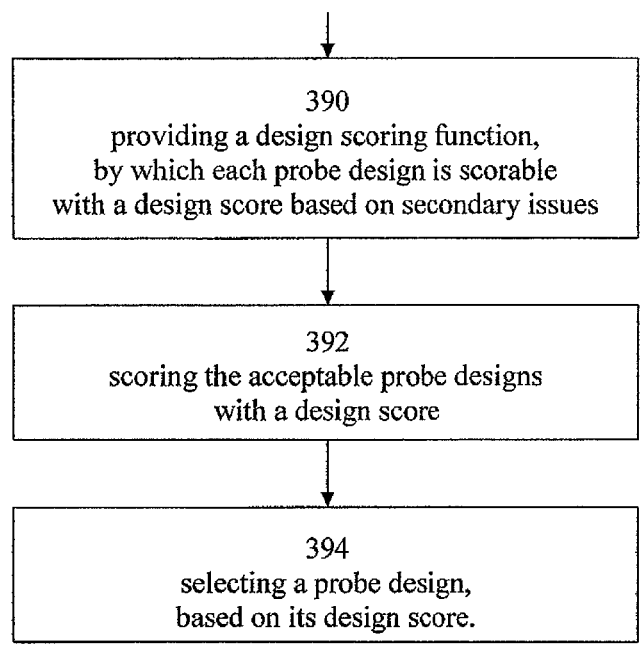

Referring further to the drawings, FIG. 15 illustrates, in flowchart form, a method 380 of selecting a camera design, optimized with respect to information gained about a body structure and secondary issues, in accordance with embodiments of the present invention. The method 380 comprises:

in a box 382: providing a model of a body structure, based on its geometry;

in a box 384: providing a model of anatomical constraints, which limit accessibility to the body structure;

in a box 385: providing representative collections of views of the modeled body structure, within the modeled anatomical constraints, for different camera designs;

in a box 386: providing a scoring function, by which each representative collection of views, associated with a specific camera design, is scorable with a score that rates information, obtained from the body structure;

in a box 387: scoring the representative collections of views, with the scoring function;

in a box 388: identifying several camera designs as acceptable, based on the scores of their representative collections of view;

in a box 390: providing a design scoring function, by which each camera design is scorable, based on the secondary issues;

in a box 392: scoring the acceptable camera designs with a design score;

in a box 394: selecting a camera design, based on its design score.

It will be appreciated other manners of combining the scoring function, which rates information, and the design scoring function, which rates secondary issues, are possible. For example, a combined scoring function, which takes all these factors into account, may be used.

As will be shown, hereinbelow, with reference to FIGS. 18A-22X, many different camera designs may provide substantially the same information, but are different in terms of their secondary considerations, that is, at different rates of data collection, different costs and different complexity of their designs, for example, in terms of the number of motors and motion-transfer systems. Thus these may score similarly in terms of functional information, and a design scoring function may be used to choose from amongst them.

Referring further to the drawings, FIGS. 16A-16L schematically illustrate viewing the elliptical model 250 of the volume U, with the camera 10, as illustrated specifically in FIGS. 20A-20H, hereinbelow.

Figure 16A:
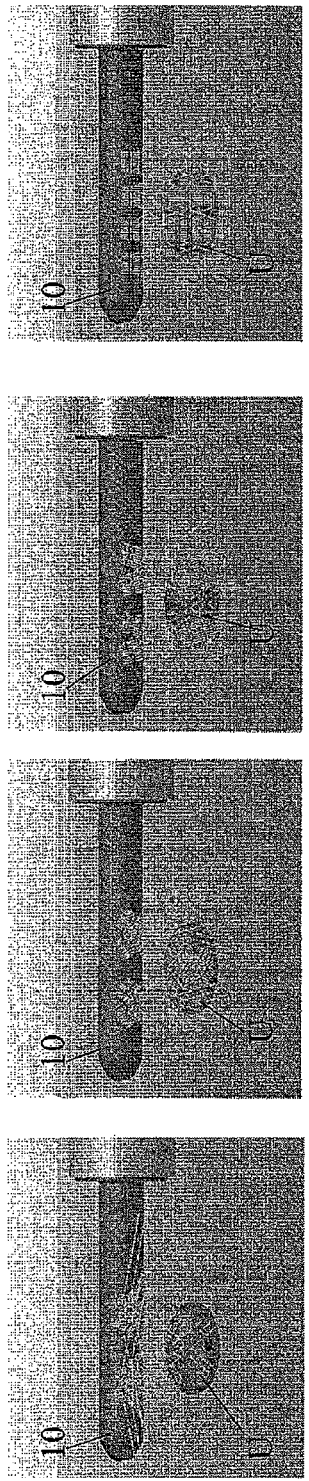
FIGS. 16A-16L schematically illustrate viewing of an elliptical modeled volume, by the radioactive-emission camera, in accordance with embodiments of the present invention.
Figure 16B:
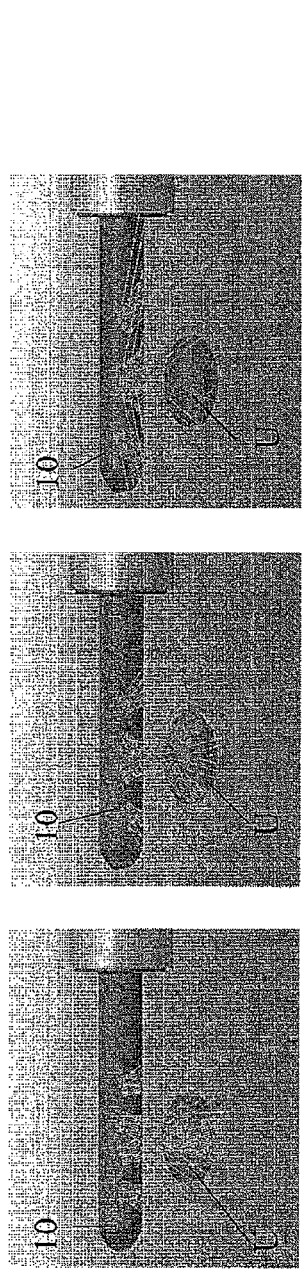
Figure 16C:
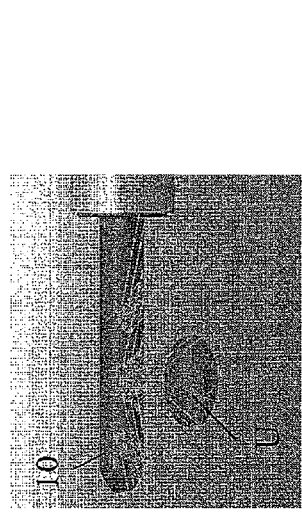
Figure 16D:
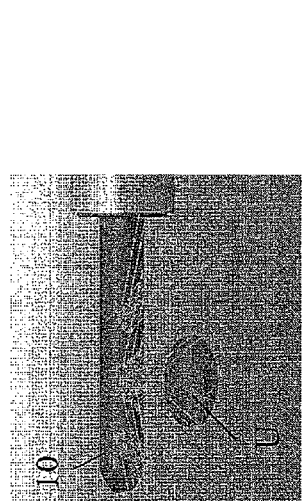
Figure 16E:
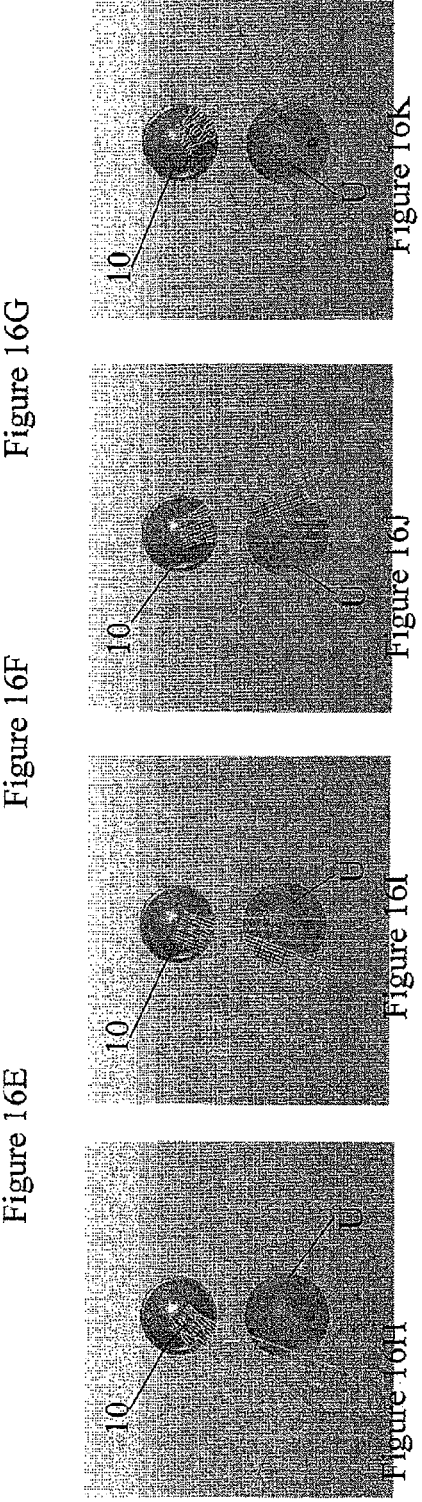
Figure 16F:
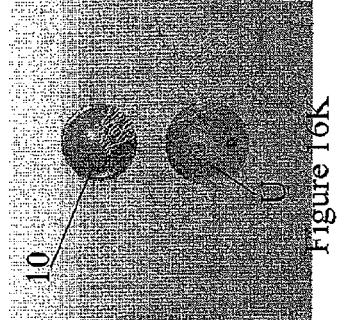
Figure 16G:
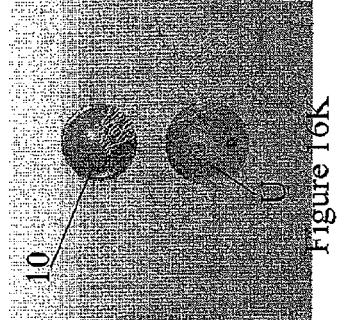
Figure 16H:
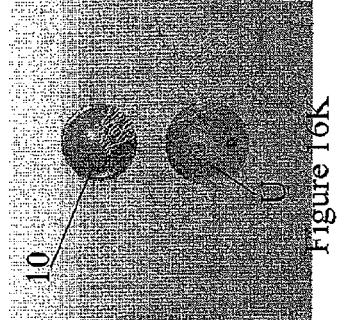
Figure 16I:
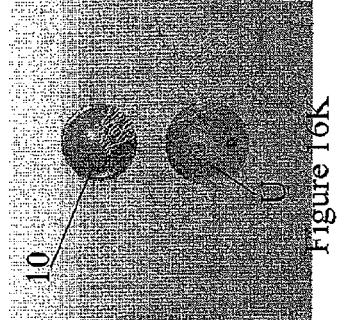
Figure 16J:
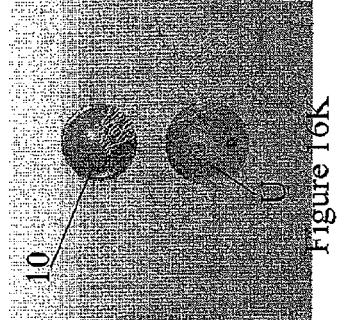
Figure 16K:
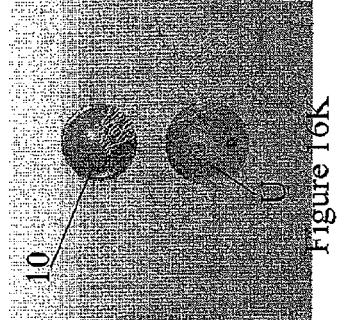
Figure 16L:
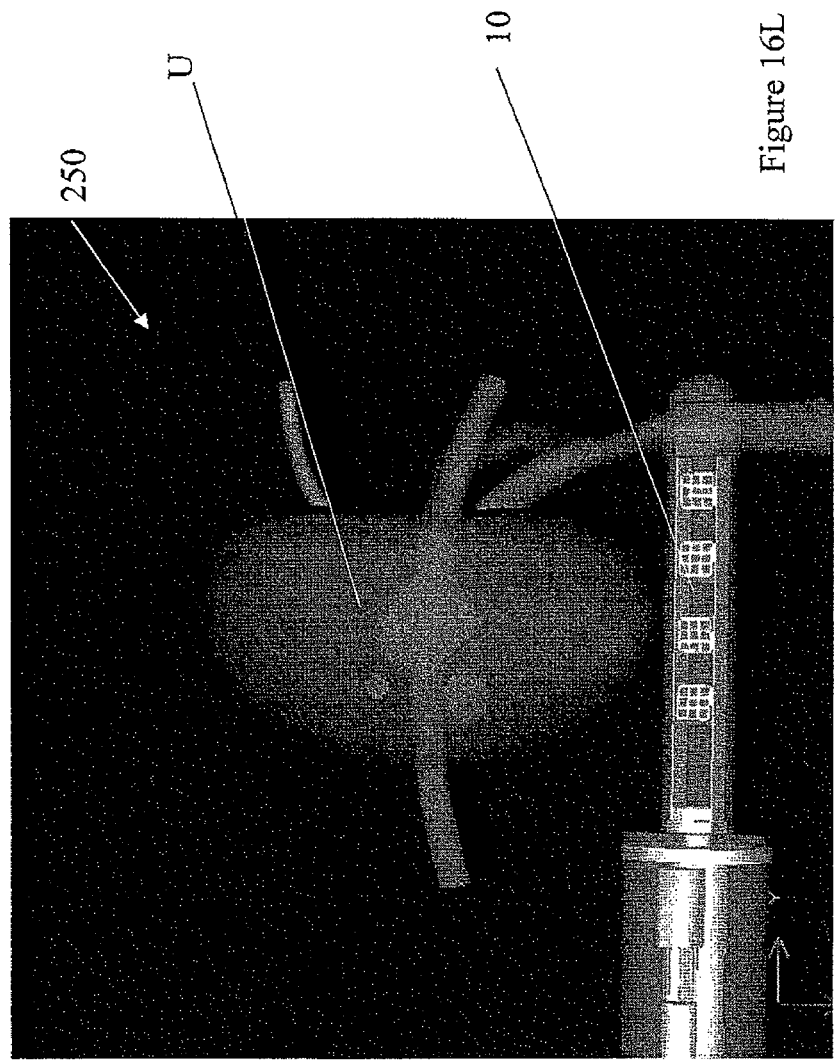

FIGS. 16A-16K show the spanning of the elliptical model 250 of the volume U, along an x-z plane, by the sweeping views. FIG. 16L is a pictorial representation of the camera 10 of FIGS. 20A-20H and the elliptical model 250 of the volume U, in accordance with embodiments of the present invention.

The views, obtained in FIGS. 16A-16K may be used both for:

i. a collection of views for the volume U, from which an optimal set of views may be chosen, specific to a body structure, in accordance with the teachings of FIGS. 8, 10, and 12, hereinabove, and ii. a representative collection of views of the camera 10, for optimizing a camera design, in accordance with the teachings of FIGS. 14 and 15, hereinabove.

Imaging Schemes—Stop-Go, Interlacing and Continuous Acquisition

According to embodiments of the present invention there may be several imaging schemes connected with the motion of the detecting units, blocks and/or assemblies as follows:

In a first embodiment the detecting units, blocks and/or assemblies are moved to a position and collect photon emission data while stationary (herein referred to as the Stop-Go imaging scheme).

In a second embodiment, a version of the Stop-Go imaging scheme, a motion of each detecting unit or block or assembly is at a predetermined angle per move (after each move data is collected while the detecting unit or block or assembly is stationary) and characterized by half the angle phase shift when scanning in opposite directions, so as to scan the scanned region every half angle (herein referred to as the Interlacing imaging scheme).

In a third embodiment a motion of each detecting unit or block or assembly is without pause between minimum and maximum sweeping angles (herein referred to as the Sweeping Imaging Scheme).

Prescanning

Oftentimes it is desirable to perform a fast prescan of a subject undergoing diagnosis, find a region-of-interest, thereafter collect higher quality data from the region-of-interest. A prescan according to embodiments of the present invention can be performed by any imaging device, including, but not limited to, ultrasound and MRI or by a physical inspection of the subject undergoing diagnosis. Alternatively, a prescan can be performed by the camera of the present invention preferably using the interlacing imaging scheme as is further described above or by broad view selection as is further described below.

Examples of Camera Systems

Reference is now made to the following examples of radioactive-emission cameras and camera systems, for a comparative study taught with reference to FIGS. 14 and 15.

Example 1A

Referring further to the drawings, FIGS. 18A and 18B schematically illustrate the radioactive-emission camera 10, of the single detecting unit 12 (see FIGS. 1A and 17A). The single detecting unit 12 has a motion with respect to the overall structure 20, which is a combination of a rotational motion around the x-axis, in the direction of ω, denoted by an arrow 44, and a translational motion along the x-axis, denoted by an arrow 46.

As a consequence, a spiral trace 48 is formed, for example, on an inner surface of a body lumen 232, as seen in FIG. 18B.

Preferably, the motions of the detecting unit 12 are contained within the overall structure 20, so that the external surface of the camera 10 remains stationary. The external surface of the camera may be formed of a carbon fiber, a plastic, or another material, which is substantially transparent to nuclear radiation.

Example 2A

Referring further to the drawings, FIGS. 18C and 18D schematically illustrate the radioactive-emission camera 10, of the single block 90 (FIGS. 1B and 17E). Note that all the detecting units 12 of the single block 90 move as a single body. The single block 90 has a motion with respect to the overall structure 20, which is a combination of the rotational motion around the x-axis, in the direction of ω, denoted by the arrow 44, and the translational motion along the x-axis, denoted by the arrow 46.

As a consequence, a plurality of spiral traces 49 is formed, for example, on an inner surface of a body lumen, as seen in FIG. 18D.

Preferably, the motions of the block 90 are contained within the overall structure 20, so that the external surface of the camera 10 remains stationary, wherein the external surface of the camera is substantially transparent to nuclear radiation.

Example 3A

Referring further to the drawings, FIGS. 19A-19E schematically illustrate the radioactive-emission camera 10, of the single block 90 of a plurality of the detecting units 12.

For understanding the motion of the camera 10 of the present example, it is desirable to define a cylindrical coordinate system of a longitudinal axis, x, and a radius r, wherein the motion around the longitudinal axis, x, is denoted by ω, while the motion around the radius r is denoted by φ.

The single block 90 has a motion with respect to the overall structure 20, which is performed in steps, as follows:

i. the windshield-wiper like oscillatory motion, around the radius r, in the direction of ±φ, as denoted by the arrow 50;

ii. the translational motion along the x-axis, by an amount Δω, to a new measuring position, as denoted by the arrow 46;

iii. after traversing the length of the camera, a rotational motion around the x-axis, in the direction of ω, by an amount Δω, as denoted by the arrow 44, in order to perform the same measurements at a new measuring position of ω.

As a consequence, a plurality of broken line traces 59 is formed, as seen in FIG. 19E.

Preferably, the motions of the block 90 are contained within the overall structure 20, so that the external surface of the camera 10 remains stationary, wherein the external surface of the camera is substantially transparent to nuclear radiation.

Example 4A

Referring further to the drawings, FIGS. 20A-20H schematically illustrate the radioactive-emission camera 10, having at least one pair, or a plurality of pairs of blocks 90, adapted for the windshield-wiper like oscillatory motion, around the radius r, as denoted by the arrows 50. The oscillatory motions may be synchronized in an antipodal manner, so as to be diametrically opposed to each other, as shown in FIGS. 20B and 20E, by the arrows 54, and as shown in FIGS. 20C and 21F by the arrows 56. It will be appreciated that the oscillatory motions need not be synchronized in an antipodal manner. Rather, all the blocks 90 may move in synchronized motion, or each block 90 may move independently. It will be appreciated that an odd number of blocks 90 is also possible.

Additionally, a rotational motion of the overall structure 20, around the x-axis in the direction of ω, an amount Δω, to a new measuring position along ω, is provided, after each step of the oscillatory motion, as shown in FIG. 20D, by an arrow 52.

The resultant traces are the plurality of broken line traces 59, as seen in FIG. 20G.

In essence, the camera 10 of FIGS. 20A-20F and 20H provides views which are essentially the same as those of FIGS. 19A-19E, but in a more efficient way, since a plurality of blocks is involved.

In accordance with the present example, i. The different blocks 90 provide views from different orientations; and ii. The different blocks 90 may change their view orientations.

Preferably, the motions of the blocks 90 are contained within the overall structure 20, so that the external surface of the camera 10 remains stationary, wherein the external surface of the camera is substantially transparent to nuclear radiation.

In particular, as seen in FIG. 20H, an internal structure 21 may contain all the blocks 90, configured to move together, as a rigid structure, while the overall structure 20 and the external surface of the camera 10 remain stationary.

The operational manner of the camera 10 of FIGS. 20A-20H is described with reference to FIG. 23C, hereinbelow.

It will be appreciated that the single detecting units 12 may be used in place of the single blocks 90.

Example 5A

Referring further to the drawings, FIGS. 21A-21D schematically illustrate the radioactive-emission camera 10, having at least one pair, or a plurality of pairs of blocks 90, adapted for the windshield-wiper like oscillatory motion, around the radius r, as denoted by the arrow 50. The oscillatory motions are preferably synchronized in an antipodal manner, so as to be diametrically opposed to each other, as in, for example, FIG. 20B. It will be appreciated that the oscillatory motions need not be synchronized in an antipodal manner. Rather, all the blocks 90 may move in synchronized motion, or each block 90 may move independently. It will be appreciated that an odd number of blocks 90 is also possible.

Additionally, a rotational motion of each of the blocks 90 around the x-axis, in the direction of ω, an amount Δω, to a new measuring position along ω, is provided, after each step of the oscillatory motion, as shown in FIG. 21B, by the arrows 44. This is unlike FIG. 20D, wherein the internal structure 21 moved as a rigid unit, as shown in FIGS. 20D and 20H.

The resultant traces are the plurality of broken line traces 59, as seen in FIG. 21D. In essence, the camera 10 of FIGS. 21A-21C provides views which are essentially the same as those of FIG. 19E, and of FIG. 20G, but in a different manner.

In accordance with the present example, i. The different blocks 90 provide views from different orientations; and ii. The different blocks 90 may change their view orientations.

Preferably, the motions of the blocks 90 are contained within the overall structure 20, so that the external surface of the camera 10 remains stationary, wherein the external surface of the camera is substantially transparent to nuclear radiation.

It will be appreciated that the detecting units 12 may be used in place of the blocks 90.

Example 6A

Referring further to the drawings, FIGS. 22A-22C and 22E-22G schematically illustrate the radioactive-emission camera 95, comprising the plurality of assemblies 92, each assembly 92 being similar in construction to the structure 21 of FIG. 20H, in accordance with embodiments of the present invention.

The plurality of assemblies 92 are preferably arranged in parallel, and their rotational motions, around the x-axis, may be synchronized in an antipodal manner, so as to be diametrically opposed to each other, as shown in FIG. 22C, by arrows 62, and in FIG. 22G, by arrows 64. It will be appreciated that the rotational motion around the x-axis need not be synchronized in an antipodal manner, and may be performed in parallel, or independently.

Thus, the resultant traces are a large plurality of the broken line traces 66 and 68, as seen in FIGS. 22D and 22H.

In essence, the camera 95 provides views which are essentially the same as those of FIGS. 19E, 20G, and 21D, but far more efficiently, since a plurality of assemblies is involved.

In accordance with the present example, i. The different blocks 90 provide views from different orientations;

ii. The different blocks 90 may change their view orientations;

iii. The different assemblies 92 provide views from different orientations; and iv. The different assemblies 92 may change their view orientations.

The operational manner of the camera 95 is described with reference to FIG. 23D, hereinbelow, for the at least two assemblies 92A and 92B.

Preferably, the motions of the blocks 90 and of the assemblies 92 are contained within the overall structure 20, so that the external surface of the camera 95 remains stationary, wherein the external surface of the camera 95 is substantially transparent to nuclear radiation.

It will be appreciated that camera 95 may include a plurality of assemblies 92, which are not parallel to each other. For example, the assemblies 92 may be at right angles to each other, or at some other angle.

It will be appreciated that the assemblies 92 may include the detecting units 12 rather then the blocks 90.

Referring further to the drawings, FIGS. 221-22X schematically illustrate possible individual motions for blocks 90, in accordance with embodiments of the present invention.

In essence, in the present example, the blocks 90 are not arranged in assemblies 92, and each moves independently of the other blocks 90.

In accordance with a first embodiment, of FIGS. 221-22M, each of the blocks 90 may be in communication with two motion providers, for providing the oscillatory motion about the r-axis, as seen by the arrows 50, and for providing the rotational motion around the x-axis, as seen by the arrows 44.

A first set of measurements is performed as the blocks 90 oscillate about the r-axis, as seen in FIG. 22J.

The blocks 90 then rotate around the x-axis, to a new measuring position, as seen in FIG. 22K.

A second set of measurements is performed at the new position, as the blocks 90 oscillate about the r-axis, as seen in FIG. 22M.

The blocks then rotate around the x-axis, to a new measuring position, as shown in FIG. 22K, and so on.

The resultant traces are a large plurality of the broken line traces 66 and 68, as seen in FIGS. 22J and 22M, and are substantially the same as those of FIGS. 22D and 22H.

In accordance with a second embodiment, each of the blocks 90 (FIG. 22N) may be in communication with two motion providers, for providing an oscillatory motion about the x-axis as seen by an arrow 61, and a rotational motion around the x-axis, as seen by an arrows 63. The resultant trace is star shaped, as seen by the lines 65 of FIG. 22O.

Additionally, a tertiary motion provider may be included, for providing a cluster 67 of overlapping lines, for a substantially complete coverage of a region, for example, as seen in FIG. 22P by a cluster 67 of the overlapping star-shaped lines 65.

It will be appreciated that many other forms of motion may be provided, and may include one, two, three or more motion providers.

FIGS. 22Q and 22R illustrate another set of dual motions and corresponding measurements for an individual one of the blocks 90, while FIGS. 22S and 22T illustrate those of a set of a tertiary motion, by three motion providers.

Similarly, FIGS. 22U and 22V illustrate still another set of two rotational motions and corresponding measurements, provided for each block individually, and FIGS. 22W and 22X illustrate still another set of a rotational motion, provided for each block individually, and coupled with a linear motion.

It will be appreciated that each block 90, or detecting unit 12 may be provided with at least one, and preferably, two, three, or possibly as many as six degrees of motion, for example, rotational motion around the x, y, and z, axis, or oscillatory motion about these axes, and possibly also translational motion, along the x, and (or) y, and (or) the z-axis. In this manner, each block 90 may be preprogrammed to view each portion of the body section 230, in accordance with some predetermined schedule, dedicated to the specific block 90. For example, one of the blocks 90 may perform oscillatory motion, while an adjacent one of the blocks 90 may perform rotational motion.

Referring further to the drawings, FIGS. 22Y and 22AA schematically illustrate a center of viewing 200A, for a given camera design, in accordance with embodiments of the present invention.

As the detecting units 12, or blocks 90, or assemblies 92 move or sweep across the region-of-interest volume U, for example, as illustrated by the arrows 203, different portions of the volume U are viewed at different frequencies and duration. The region which is viewed most heavily may be defined as the center of viewing 200A. It is surrounded by regions, which are viewed somewhat less. In essence, a shell-like viewing structure may be formed, with decreasing viewing intensities, as the distance from the center of viewing 200A increases. This is illustrated, for example, by the center of viewing 200A and surrounding shells 201, 209, and 211.

It will be appreciated that the center of viewing 200A may be a region of uniform viewing, rather than a mere point. For example, the region 201 may be a region of uniform viewing, which forms the center of viewing 200A.

Example 7A

Having designed a radioactive-emission camera capable of obtaining a collection of views, and having predefined a set of views, which is optimal for a body structure, based on its model, the task of performing measurements, selectively at the predefined set of views, would be quite impossible if it were to be performed manually. Generally, between several hundred and several thousand views are taken, and manually tuning each to a predetermined location, orientation, and possibly also duration would be impractical. Therefore, the camera and method of the present invention are operative with an overall system, in which computer controlled motion providers govern the motions of the detecting units or of the overall camera. The computer may be any one of a personal computer, a laptop, a palmtop, or another computer, adapted for communication with the camera, or a microcomputer, built into the camera. Additionally, a combination of a microcomputer, built into the camera, and an external computer such as a personal computer, a laptop, a palmtop, or the like, may be used.

Preferably, before measurements are performed, personal details are fed into the computer, and the models of the body structure and anatomical constraints are adapted to these details. The personal details may include age, sex, weight, body type, and the like.

Referring further to the drawings, FIGS. 23A-23D schematically illustrate a radioactive-emission camera system 400 in accordance with embodiments of the present invention.

Figure 23A:
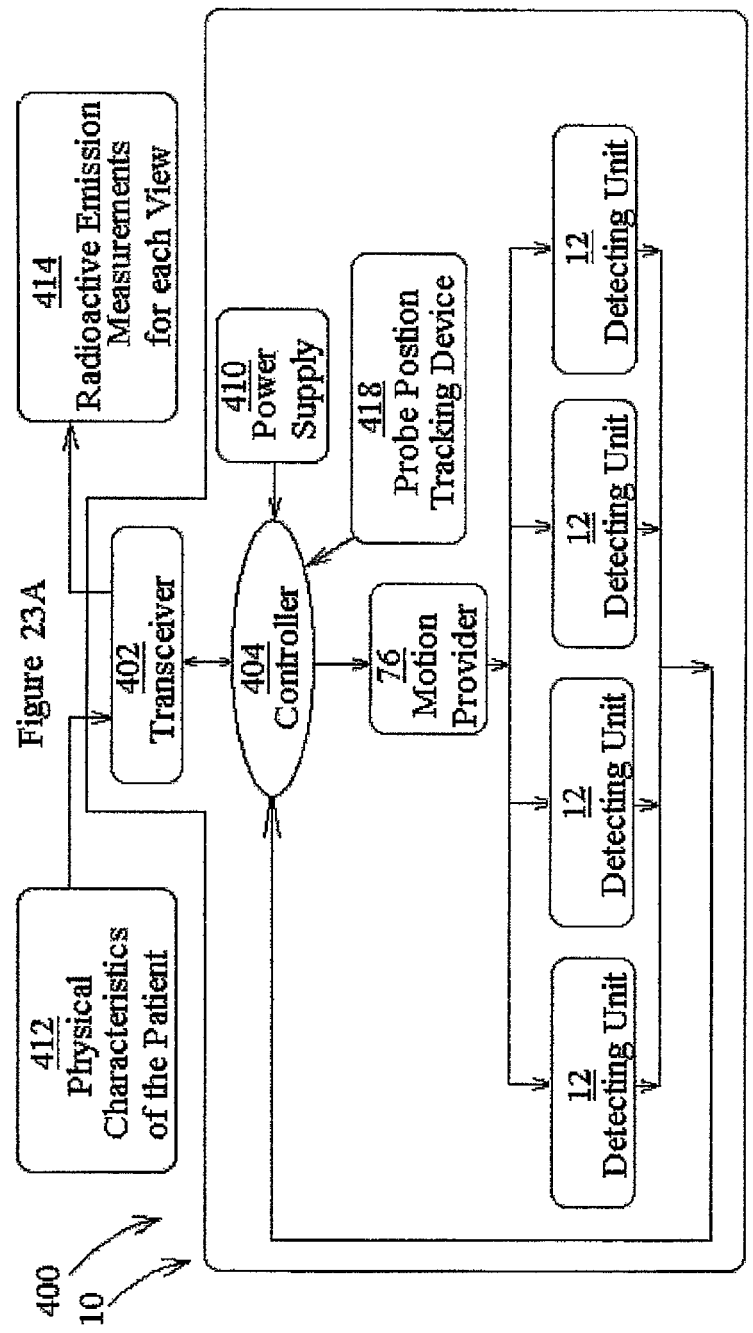

As seen in FIG. 23A, the camera system 400 includes the camera 10, having a controller 404, in communication with one or several motion providers 76, for sending signals of the locations and orientations of views to the one or several motion providers 76. The one or several motion providers 76, in turn, govern the motions of one or several of the detecting units 12. The one or several of the detecting units 12 collect the measurements at the predefined locations and orientations and communicate the data to the controller 404. Signals of new locations and orientations are then communicated by the controller 404 to the one or several motion providers 76. Each of the motion providers 76 may control the motion of one of the detecting units 12 or of a plurality of the detecting units 12.

Preferably, the controller 404 registers the location and orientation of each of the detecting unit 12 as it moves. Additionally or alternatively, a position-tracking device may be associated with each of the detecting units 12.

Preferably, a position-tracking device 418 is associated with the camera 10 as a whole, for registering its position with respect to, for example, the body structure 215 (FIG. 5A).

A power supply 410 powers the camera 10. Alternatively, power may be supplied from the grid.

Preferably, a transceiver or transmitter 402, reports the measurements to an external computer (not shown). Alternatively, a cable (not shown) may be used. Alternatively, the controller 404 includes a microcomputer, or the like, and performs the data analysis.

Additionally, the transceiver 402 may be adapted to receive input data relating to the personal details of the patient, such as the age, sex, weight, body type, and the like, in order to adjust the model of the body structure, hence the locations and orientations of the predefined, optimal set of views, to the particular patient.

Furthermore, the transceiver 402 may be adapted to receive input data from an ultrasound imager, for providing information such as location, size of the body structure and the like, by ultrasound imaging, in order to adjust the model of the body structure, hence the locations and orientations of the predefined, optimal set of views, to the particular patient.

Preferably, the motion of the one or several motion providers 76 relates to motion of the detecting units 12, with respect to the camera overall structure 20 (FIG. 20H), for example, by the motion of detecting units 222A and 222B (FIG. 13E), with respect to the overall structure 220, as shown by the arrows 216 and 218.

Alternatively or additionally, the motion of the one or several motion providers 76 may relate to motion of the overall structure 20 or 220 as a whole, for example, as taught with reference to FIG. 13E, by the motion the camera 220, as shown by the arrows 224 and 228.

It will be appreciated that the controller 404, while being part of the system 400, need not part of the actual camera 10. Rather it may be an external computer, communicating with the camera 10 either by cables or via a transceiver.

As seen in FIG. 23B, the camera 10 includes the blocks 90, each comprising a plurality of the detecting units 12, each block 90 moving as a single body.

Figure 23C:
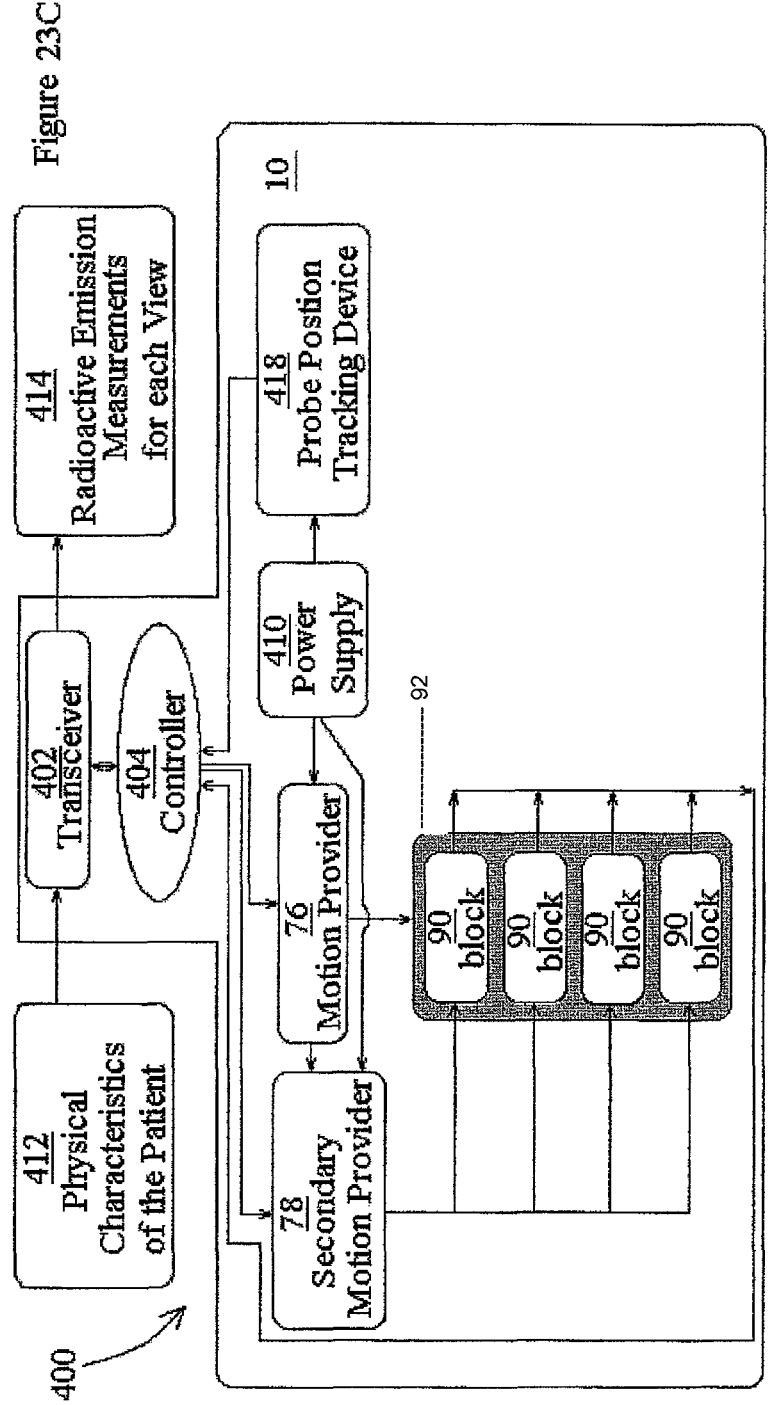

As seen in FIG. 23C, the individual motion of the blocks 90 is governed by a secondary motion provider 78. Additionally, all of the blocks 90 form an assembly 92, which moves by the motion provider 76, for example, within an internal structure 21, as illustrated hereinbelow with reference to FIG. 20H. For example, the secondary motion provider 78 may provide the motion described by the arrows 50 of FIGS. 20B and 20C or 20F and 20F, hereinbelow while the motion provider 76 may provide the motion described by the arrow 52 of FIG. 20H, hereinabove.

It will be appreciated that the multiple motions may be provided to the detecting units 12, rather then to the blocks 90.

It will be appreciated that a tertiary motion provider may also be used and that many arrangements for providing the motions are possible, and known.

Figure 23D:
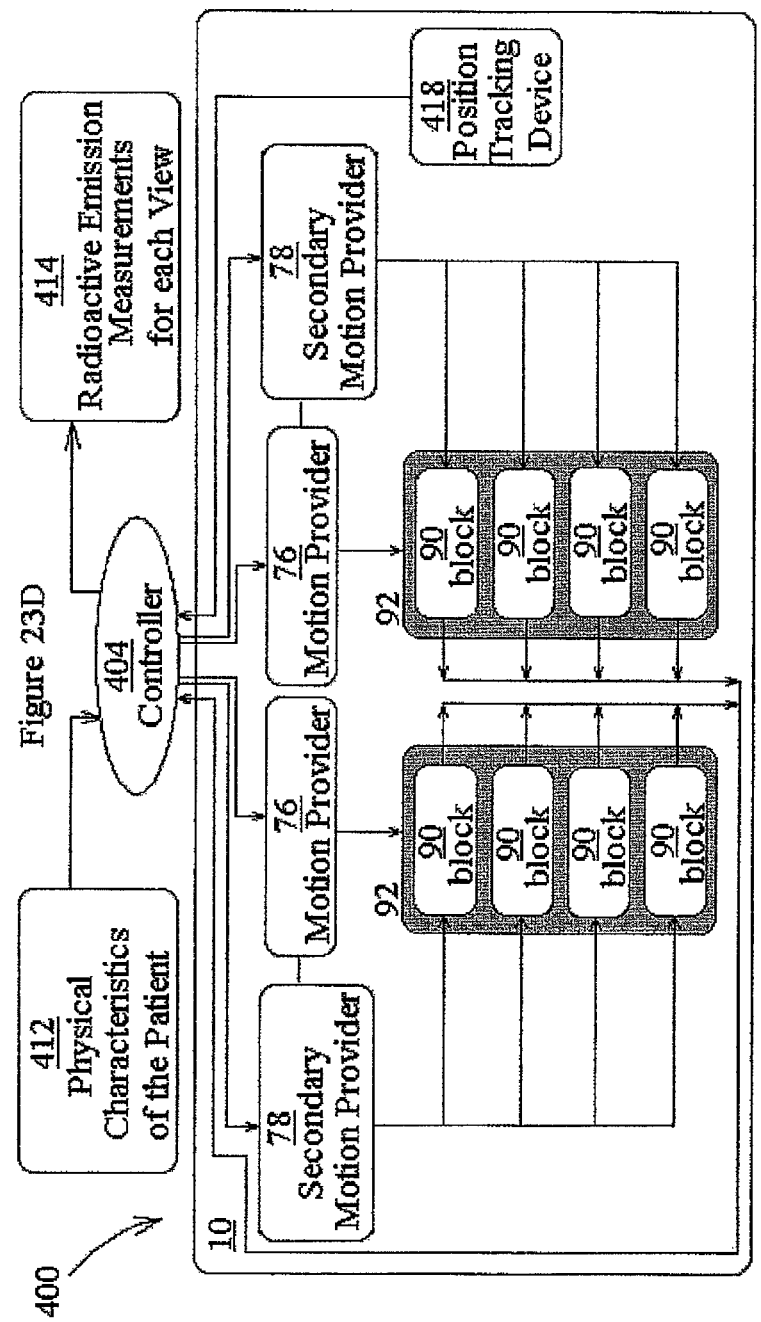

As seen in FIG. 23D, at least two assemblies 92 may be provided, each with a dedicated motion provider 76 and a dedicated secondary motion provider 78. It will be appreciated that the multiple motions may be provided to the detecting units 12, rather then to the blocks 90. It will be appreciated that tertiary motion providers may also be used and that many arrangements for providing the motions are possible, and known.

In the example of FIG. 23D, the controller 404, while being part of the system 400, may not be part of the actual camera 10. For example, it may be an external computer, communicating with the camera 10 either by cables or via a transceiver.

Examples of Camera Systems for Specific Applications

Reference is now made to the following examples of radioactive-emission cameras and camera systems, for specific applications.

Example 8A

Referring further to the drawings, FIGS. 24A-32 schematically illustrate the radioactive-emission camera 10, for the prostate, in accordance with an embodiment of the present invention.

Figure 24B:
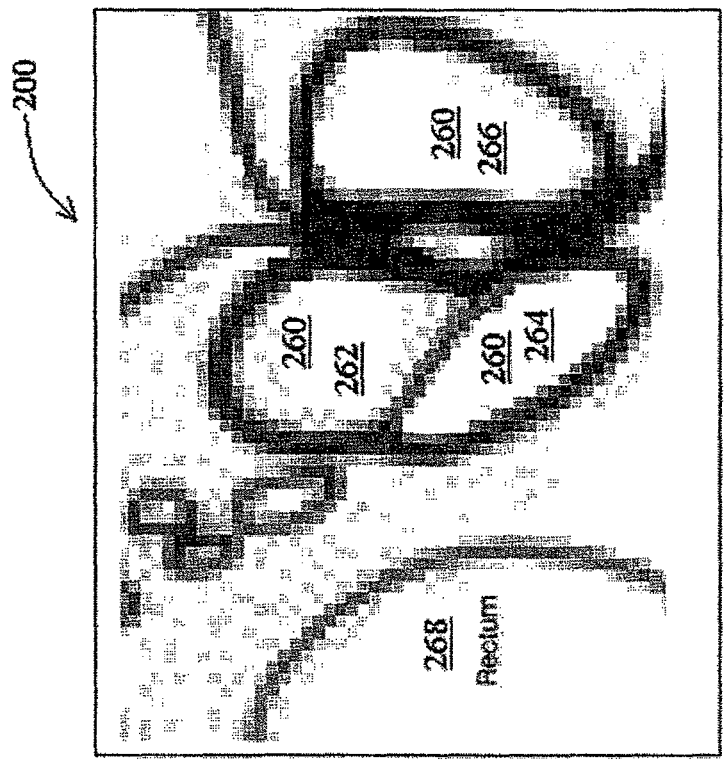
FIGS. 24A-24C schematically illustrate the modeling of a prostate as a process of two iterations, for zooming in on a pathology, in accordance with embodiments of the present invention.
Figure 24A:
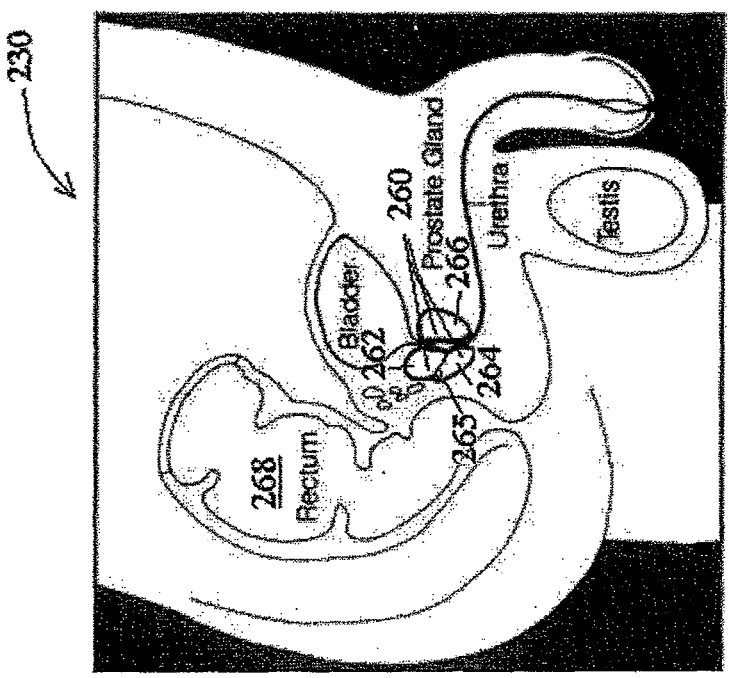
Figure 24C:
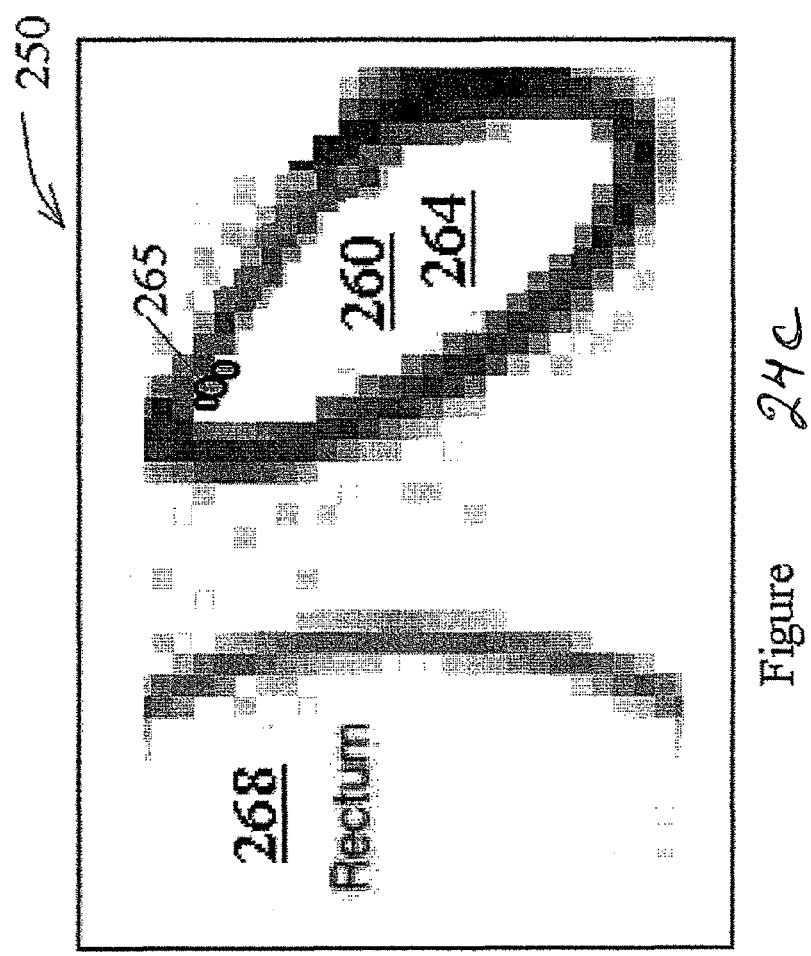
Figure 25D:
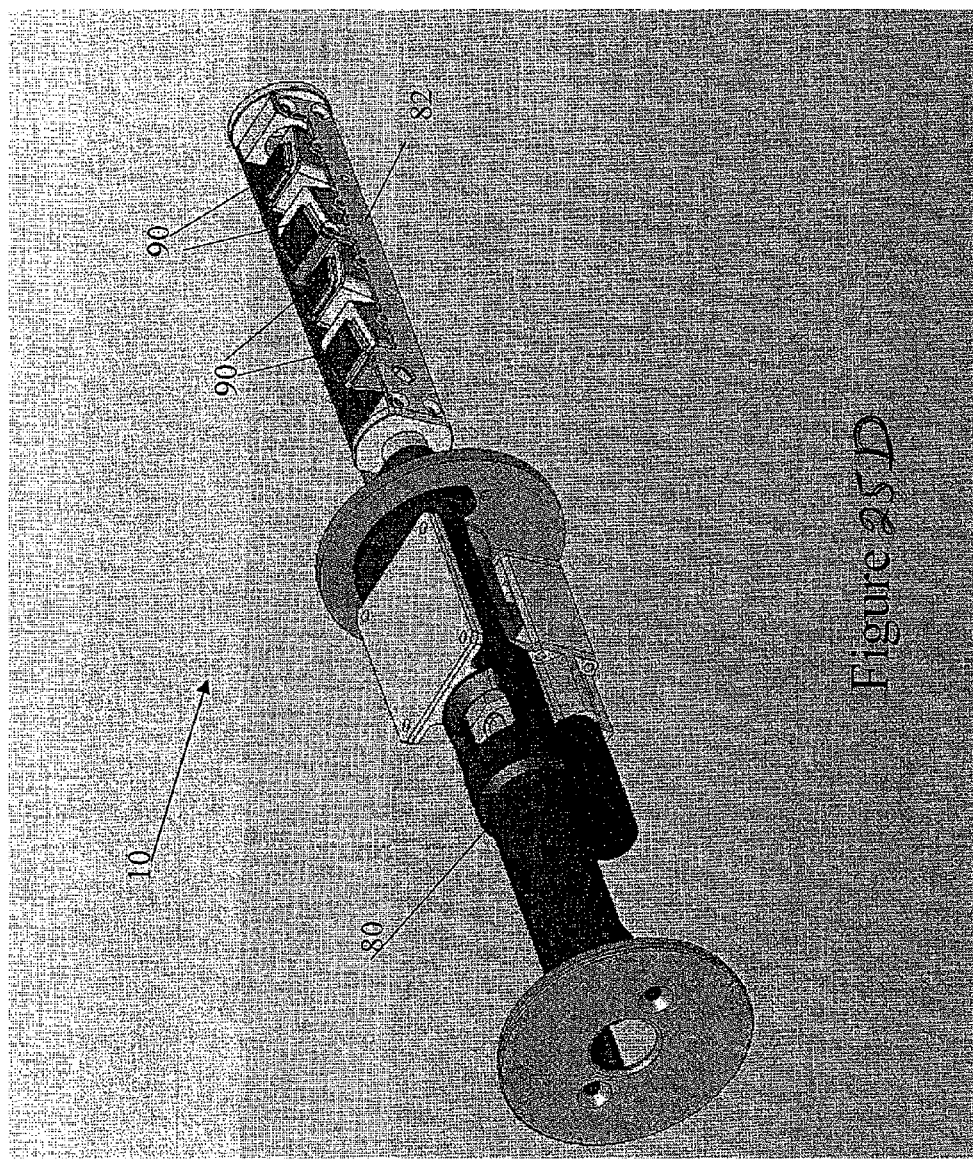

FIGS. 24A-24C schematically illustrate the modeling of a prostate and a location of pathology, as a process of two iterations, for zooming in on the pathology, in accordance with embodiments of the present invention.

FIG. 24A schematically illustrates a body section 230, which includes a prostate 260, which has sections 262, 264 and 266, and a pathology 265 in section 264. Additionally, the body section 230 includes a rectum 268, from which the prostate 260 may be viewed.

FIG. 24B schematically illustrates the model 200 of the body section 230, including the prostate 260, of sections 262, 264 and 266, and the rectum 268. An optimal set of views is predefined based on the model 200 and a first scoring function. The first scoring function may be based on regions of interest similar to the pathology 265, as known, from medical records of common pathologies. Measurements of radioactive emission are then taken at the predefined views, in vivo, for the prostate 260.

As seen in FIG. 24C, upon discovering the pathology 265, by the in-vivo measurements, a second model 250 of the section 264 is made, for zooming in on the pathology 265, and a second optimal set of views is predefined, based on the second model 250 of the section 264 and a second scoring function, for zooming in on the pathology 265. Measurements of radioactive emission are then taken at the predefined second set of views, in vivo, for the section 264 and the pathology 265.

It will be appreciated that the first and second scoring functions may be based on any one of or a combination of the information theoretic measures of uniformity, separability, and reliability. It will be further appreciated that the first and second scoring functions need not be the same.

FIGS. 25A-25E illustrate an external appearance and an internal structure, of the camera 10. The radioactive-emission camera 10 for the prostate has an extracorporeal portion 80 and an intracorporeal portion 82, which is adapted for insertion into a rectum. The overall structure 20 of the intracorporeal portion 82 is preferably shaped generally as a cylinder and defines a longitudinal axis along the x-axis, and a radius, perpendicular to the longitudinal axis. The intracorporeal portion 82 preferably includes two pairs of assemblies 90, arranged in the overall structure 20. It will be appreciated that another number of assemblies, for example, a single pair, or three pairs, is similarly possible. An odd number of assemblies is similarly possible. In essence, the camera 10 of the present example is analogous to the camera 10 of FIG. 23C and FIGS. 20A-20F and 20H, and particularly, to FIG. 20H. The rotational motion, in the direction of the arrow 52 of FIG. 20H, is provided by a motor 88 (FIG. 25C) and a main shaft 85. The motor 88 may be an electric motor, for example, a servo motor. The motor 88 and main shaft 85, together, form a motion provider 76 for the rotational motion in the direction of the arrow 52 of FIG. 20H. The oscillatory motion, in the direction of the arrows 50 of FIG. 20B, is provided by a secondary motor 86, a secondary shaft 84 and a motion transfer link 74. The secondary motor 86 may also be an electric motor, for example, a servo motor. The secondary motor 86, secondary shaft 84 and the motion transfer link 74, together, form the secondary motion provider 78, in the direction of the arrows 224 and 228 of FIG. 13E.

The significance of the present embodiment, is as follows:
  i. The different assemblies 90 provide views from different orientations; and
  ii. The different assemblies 90 may change their view orientations independent of each other.

It is important to point out that during the operation of the camera 10, the external surface of the intracorporeal portion 82 (FIG. 25A) remains stationary, while the internal structure 21 (FIG. 25C) rotates around the x-axis. The external surface of the intracorporeal portion 82 may be formed of a carbon fiber, a plastic, or another material, which is substantially transparent to nuclear radiation.

FIG. 25E illustrates further the internal structure of the radioactive-emission camera for the prostate, in accordance with an embodiment of the present invention, showing the assemblies 90 within the overall structure 20. Each assembly may be a single detecting unit 12, or a plurality of the detecting units 12, for example, 36 of the detecting units 12, for example, as an array of 6×6, or 99 of the detecting units 12, for example, as an array of 11×9, or another number of the detecting units 12, arranged as an array or arranged in another geometry.

Figure 26:
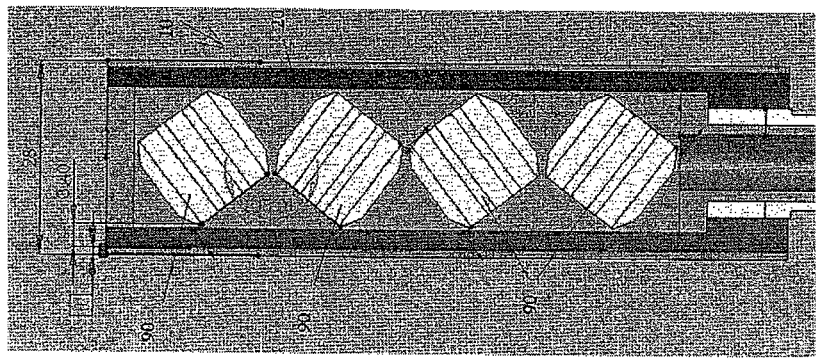
FIG. 26 illustrates further the internal structure of the radioactive-emission camera for the prostate, in accordance with an embodiment of the present invention.

Referring further to the drawings, FIG. 26 illustrates further the internal structure of the radioactive-emission camera for the prostate, in accordance with an embodiment of the present invention, showing the oscillatory motion (in the direction of the arrows 50 of FIGS. 20A, and 20C) of the assemblies 90 within the overall structure 20.

Figure 27:
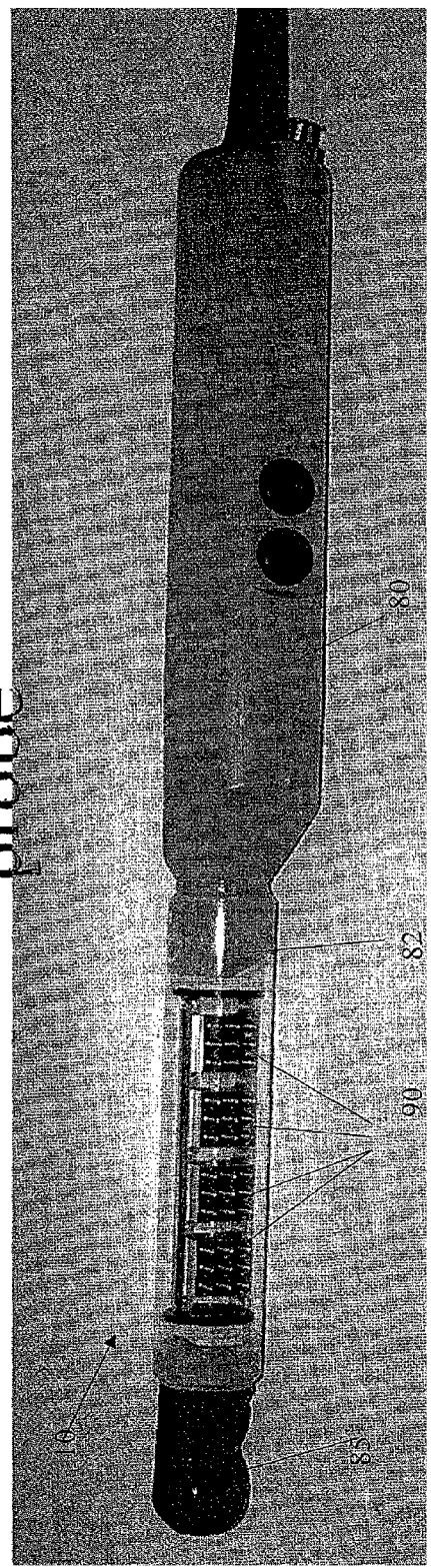
FIG. 27 schematically illustrates the radioactive-emission camera for the prostate, integrated with an ultrasound camera, in accordance with another embodiment of the present invention.
Figure 28:
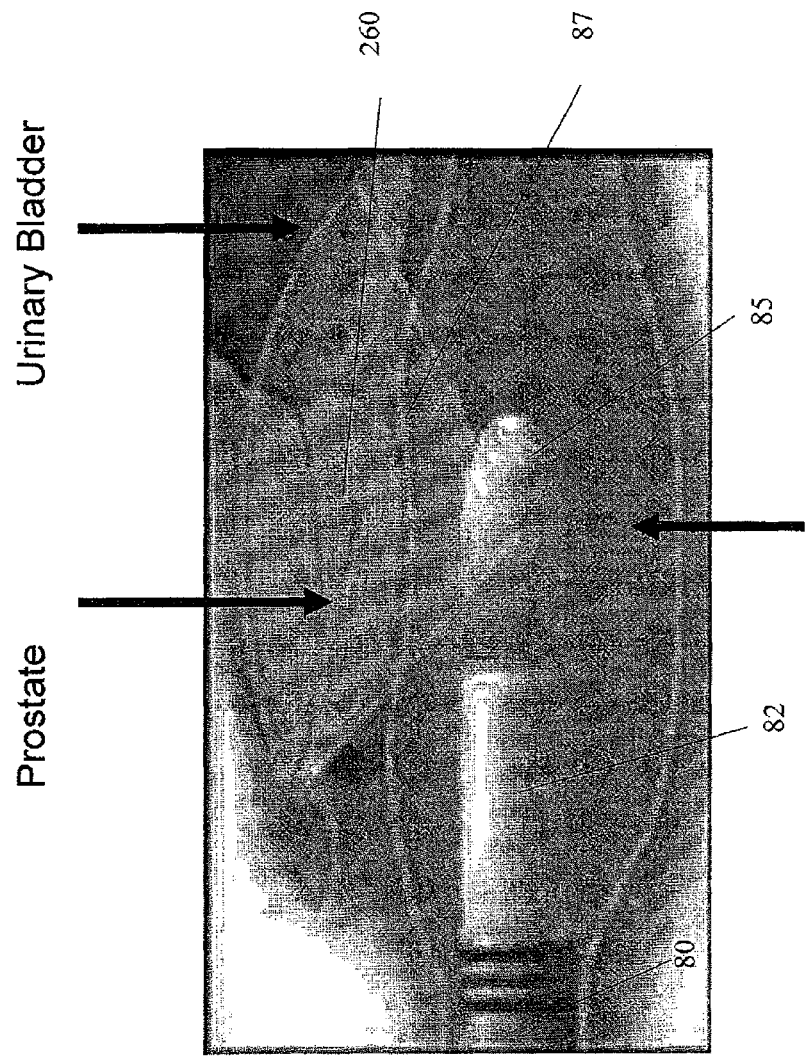
FIG. 28 schematically illustrates an ultrasound wave impinging on a prostate, in accordance with embodiments of the present invention.

FIGS. 27-28 schematically illustrate the radioactive-emission camera 10, for the prostate, in accordance with another embodiment of the present invention. In accordance with the present embodiment, the camera 10 further includes an ultrasound transducer 85, arranged, for example, at the tip of the intracorporeal portion 82.

FIG. 27 illustrates the external appearance of the camera 10 with the ultrasound transducer 85 at its tip.

FIG. 28 illustrates the ultrasound wave 87, impinging on the prostate 260.

Figures 29A, 29B, 29C:
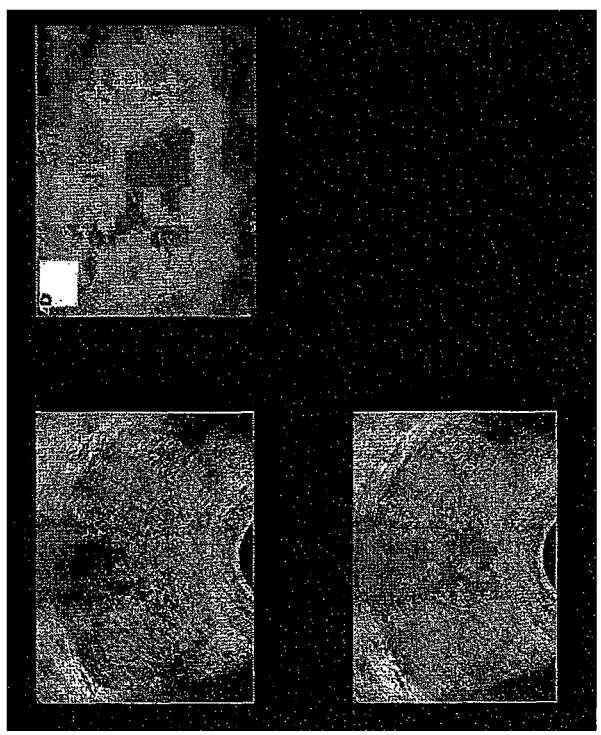
FIGS. 29A-29C illustrate the co-registering of a radioactive-emission image and an ultrasound image, in accordance with embodiments of the present invention.

FIGS. 29A-29C illustrate the co-registering of a radioactive-emission image and an ultrasound image, to illustrate the functional information of the radioactive-emission image with the structural information of the ultrasound image. The ultrasound image is seen in FIG. 29A, the radioactive-emission image is seen in FIG. 29B, and the co-registering of the two is seen in FIG. 29C.

Figure 30:
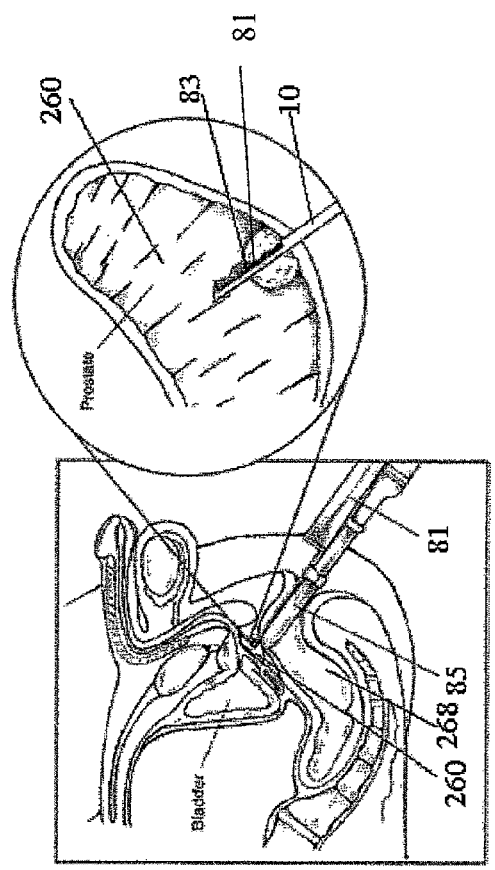
FIG. 30 schematically illustrates the radioactive-emission camera for the prostate, integrated with a surgical needle, in accordance with another embodiment of the present invention.

FIG. 30 schematically illustrates the radioactive-emission camera 10, for the prostate, in accordance with another embodiment of the present invention. In accordance with the present embodiment, the camera 10 further includes an ultrasound transducer 85, and a surgical needle 83, in a needle guide 81, arranged alongside the camera 10, for obtaining a biopsy or for other minimally invasive procedures. FIG. 30 schematically illustrates the surgical needle 83 as it penetrates the prostate 260 from the rectum 268.

Figure 31:
FIGS. 31 and 32 schematically illustrates the operation of the surgical needle of FIG. 30.
Figure 32:
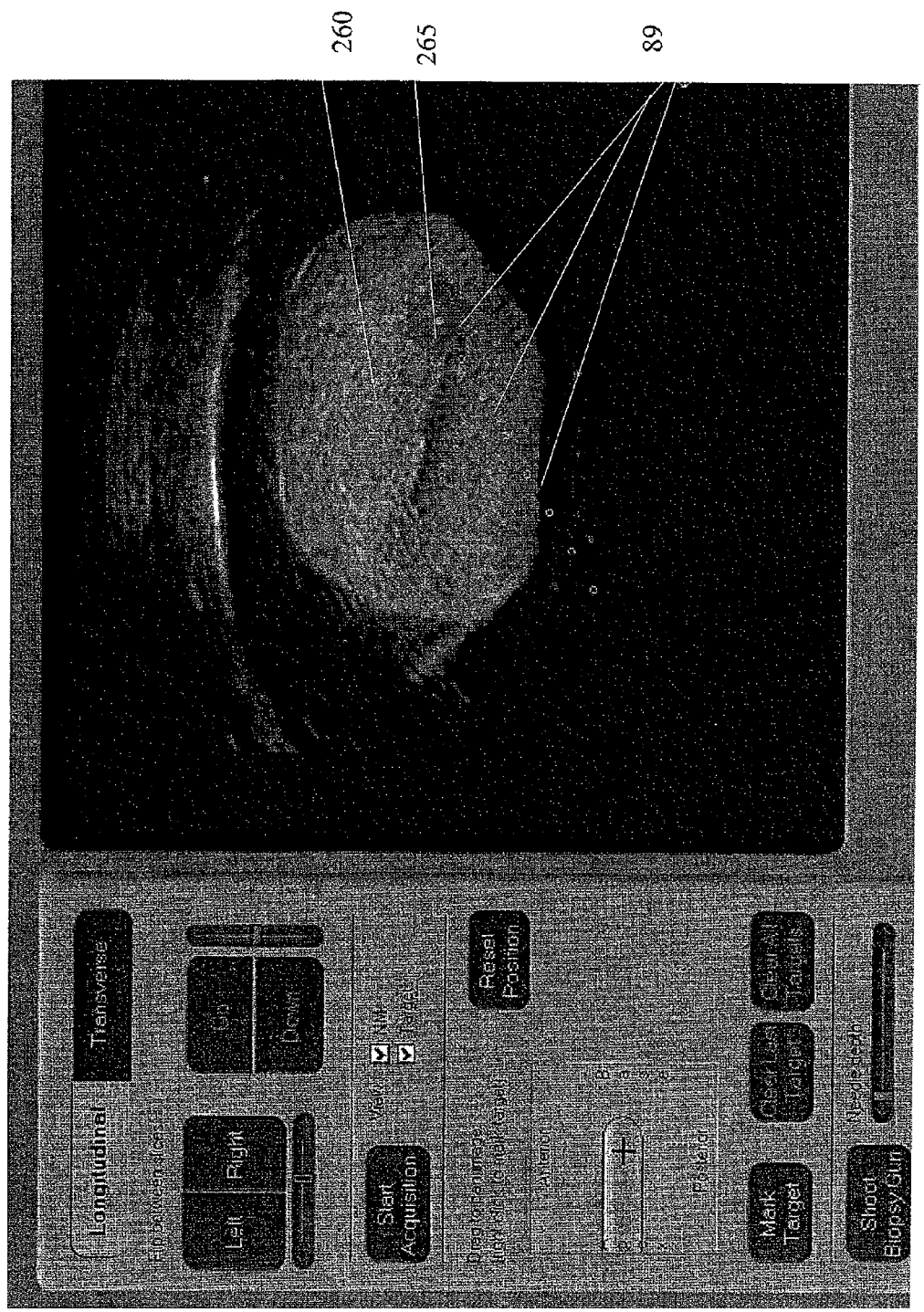

FIGS. 31 and 32 schematically illustrate the manner of guiding the needle 83. A track 89 shows the surgeon the direction of the needle, while the camera 10 produces the functional image of the pathology 265 in the prostate 260. By moving the camera 10, manually, the surgeon can align the track 89 with the pathology 265, as shown in FIG. 32. Once aligned, he can insert the needle 83, as shown in FIG. 30.

Example 9A

Figure 33:
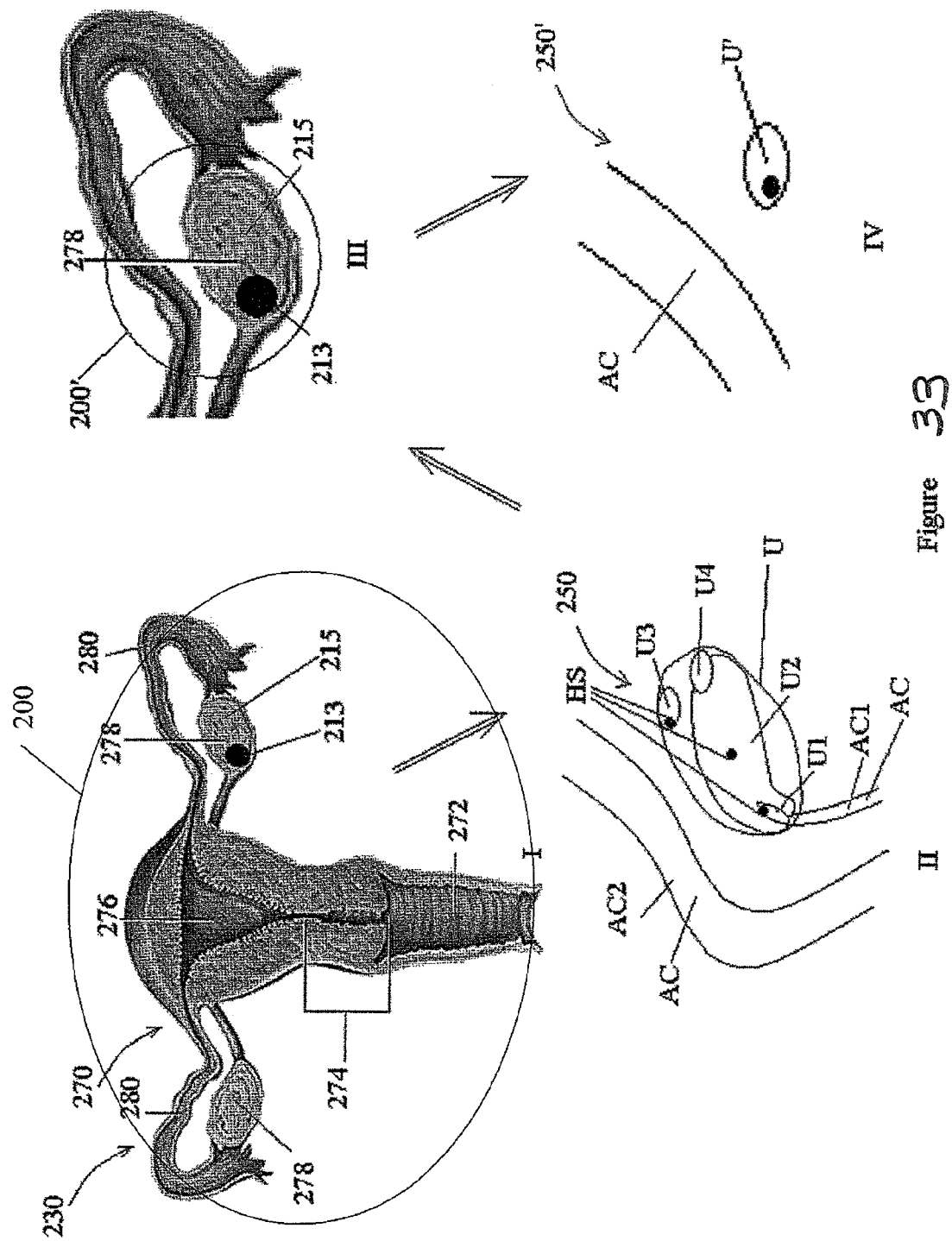
FIG. 33 schematically illustrates the modeling of the female reproductive system as a process of two iterations, for zooming in on a pathology, in accordance with embodiments of the present invention.

Referring further to the drawings, FIG. 33 pictorially illustrates the method 340 for zooming in on a suspected pathological feature in a woman's reproductive system, as a process of two or more iterations, in accordance with embodiments of the present invention, as follows:

As seen in FIG. 33, the method 340 may be described, pictorially, as follows:

In I: The region-of-interest 200, associated with a woman's reproductive system 270, is defined for the body section 230 having the body structure 215.

In II: The model 250 of the volume U, is provided for the region-of-interest 200, possibly with one or several of the modeled organ targets HS, and within the anatomical constraints AC, for obtaining the optimal set of views for the region-of-interest 200. The optimal set of views is then applied to the body section 230.

In III: When a suspected organ target 213 is identified, in vivo, by radioactive-emission measurements at the optimal set of views, a second, inner region-of-interest 200' is defined, encircling the suspected pathological feature.

In IV: A model 250' of a volume U' is provided for the second, inner region-of-interest 200', preferably, with at least one modeled organ target HS, simulating the suspected organ target 213, for obtaining an optimal pathology set of views for the region-of-interest 200'. The second, pathology set of views is then applied to the body section 230.

Figure 34A:
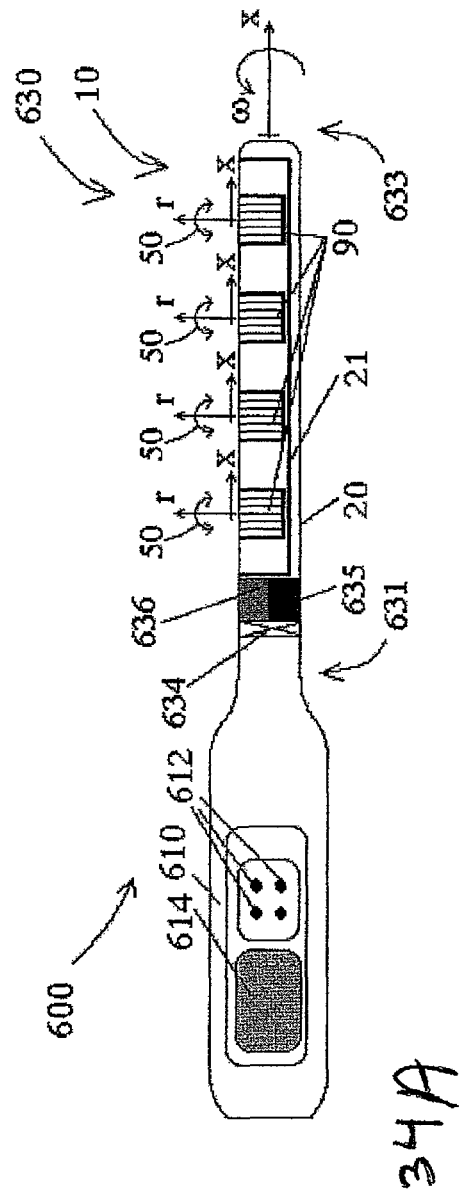
FIGS. 34A-34R schematically illustrate the external appearance and the internal structure of the radioactive-emission camera for the female reproduction tract, in accordance with an embodiment of the present invention.

Referring further to the drawings, FIGS. 34A-34R schematically illustrate radioactive-emission measuring cameras 600, tailored for imaging the woman's reproductive system 270 and optimized with respect to the functional information gained, regarding the body structures of the woman's reproductive system, such as the cervix 274, the uterus 276, the ovaries 278, and the fallopian tubes 280 (FIG. 33), in accordance with preferred embodiments of the present invention.

FIG. 34A schematically illustrates the basic radioactive-emission measuring camera 600, for a body lumen, for example, the vagina 272, the cervix 274, the uterus 276, the rectum (not shown), or the sigmoid colon (not shown). The camera 600 includes an extracorporeal portion 610, which preferably comprises a control unit, and an intracorporeal portion 630, having proximal and distal ends 631 and 633, with respect to an operator (not shown).

The control unit of the extracorporeal portion 610 may include control buttons 612 and possibly a display screen 614, and may provide connections with a computer station. It may receive power from a grid or be battery operated. The control unit of the extracorporeal portion 610 may further include a computer or a microcomputer. It will be appreciated that the control unit may be incorporated with the intracorporeal section 630, and operated remotely.

The intracorporeal portion 630 defines a cylindrical coordinate system of x; r, wherein x is the longitudinal axis. The plurality of blocks 90 along the length of the intracorporeal portion 630 is housed in an internal structure 21 (FIG. 20H).

Each of the blocks 90 is adapted for the windshield-wiper like oscillatory motion, around the radius r, as denoted by the arrows 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Additionally, the internal structure 21 is adapted for rotational motion around the x-axis, in the direction of $\omega$, wherein after each step of oscillatory motion at a certain orientation of $\omega$, the internal structure rotates by a step to a new orientation of $\omega$, and the oscillatory motion is repeated.

Figure 34K:
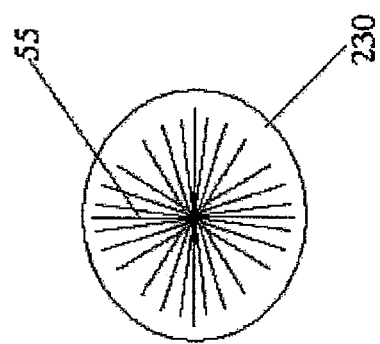
Figure 34J:
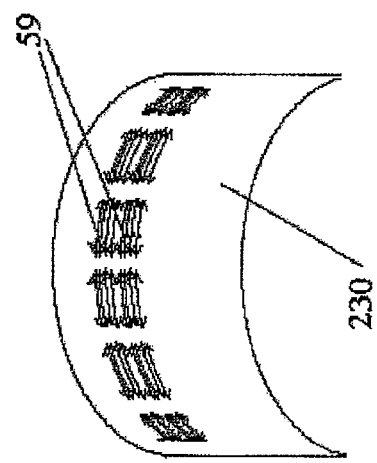

As a consequence, a plurality of broken line traces 59 are formed, in the body section 230, as seen in FIG. 34J.

Preferably, the controller or the computer registers the locations and orientations of each detecting unit or block and correlates the measurements with the corresponding positions and orientations.

A position-tracking device 635 may also be used, for providing information regarding the position of the camera 600 relative to a known reference. For example, if a structural scan, or another scan by another imager has been made, the position-tracking device 635 may be used to register that scan with the measurements of the camera 600.

It will be appreciated that the camera 600 may include detecting units 12 rather then blocks 90.

Preferably, the overall structure 20 remains stationary and is substantially transparent to nuclear radiation, formed, for example, of a hydrocarbon material.

The intracorporeal portion 630 may further include dedicated electronics 634 and motion providers 636, such as miniature motors and motion transfer systems, as known.

FIGS. 34B and 34C schematically illustrate side and distal views, respectively, of the radioactive-emission measuring camera 600, having an ultrasound imager 640 at its distal tip 633. The ultrasound imager 640 may provide a structural image which may be correlated with the functional image. Additionally, it may be used for providing the size and location of the body structure for modeling. Furthermore, it may be used for providing attenuation correction to the radioactive emission measurements.

FIGS. 34D and 34E schematically illustrate side and distal views, respectively, of the radioactive-emission measuring camera 600, having an MRI imager 642 at its distal tip 633. The MRI imager 642 may provide a structural image which may be correlated with the functional image. Additionally, it may be used for providing the size and location of the body structure for modeling. Furthermore, it may be used for providing attenuation correction to the radioactive emission measurements.

FIGS. 34F-34I schematically illustrate the radioactive-emission measuring camera 600, having a distal block 90A at its distal tip 633. The distal block 90A at the distal tip is also adapted for oscillatory motion, but about the x-axis, as seen by an arrow 53. When combined with the rotational motion around the x-axis, it produces traces 55 in the shape of a star, in the body section 230, as seen in FIG. 34K.

It will be appreciated that a single distal detecting unit may be employed in place of the distal block 90A.

FIGS. 34L-34Q schematically illustrates the radioactive-emission measuring camera 600, for a body lumen, having the distal block 90A at its distal tip 633, adapted for a deployed and a retracted position, and for oscillatory motion about the x-axis, when deployed. The camera 600 further has the ultrasound imager 640 at its distal tip 633, as a ring, similarly having a deployed and a retracted position.

FIGS. 34N-34P illustrate the distal block 90A deployed, and the ultrasound imager 640 retracted. In this manner, the ultrasound imager 640 does not obstruct the oscillatory motion of the distal block 90A at the distal tip 633.

FIG. 34Q illustrates the distal block 90A retracted and the ultrasound imager deployed so the distal block 90A does not obstruct the view of the ultrasound imager. It will be appreciated that the ultrasound image is to be taken once, from the distal tip 633, while the radioactive-emission measurements are to be taken at a plurality of orientations, from the distal tip 633.

FIG. 34R illustrates the camera 600 with a cable 620 connecting the intracorporeal portion 630 and the extracorporeal portion 610, for example, for imaging the ovaries and the fallopian tubes from the sigmoid colon.

It will be appreciated that the cameras 600 of the present invention may also be moved manually, both linearly, into the body lumen and rotationally, around its longitudinal axis, preferably while the position-tracking device 635 (FIG. 34A) registers its position.

It will be appreciated that a camera with a single block or a single detecting unit may also be used.

Example 10A

Figure 35A:
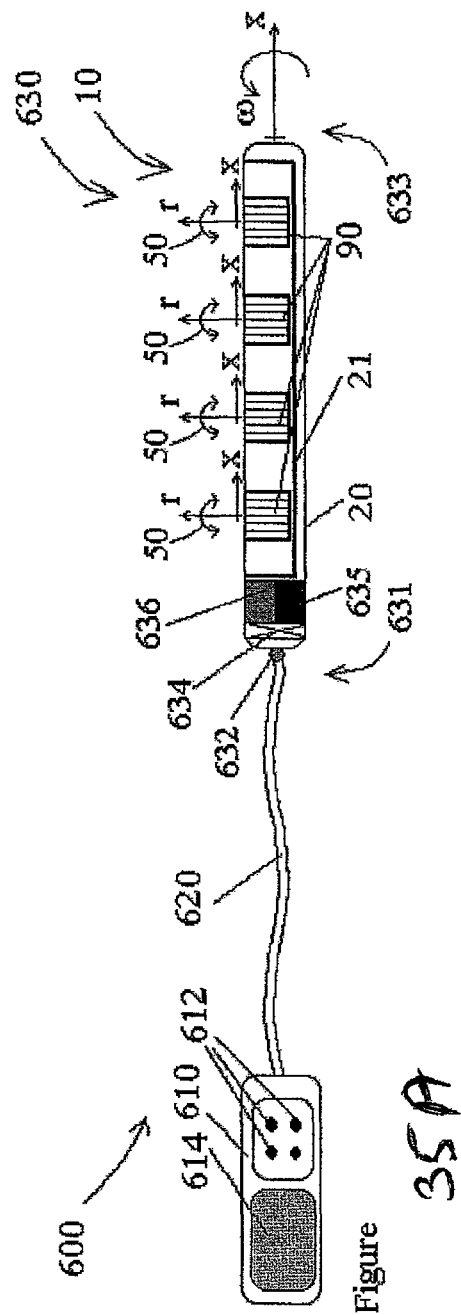
FIGS. 35A-35Q schematically illustrate the external appearance and the internal structure of the radioactive-emission camera for the esophagus, in accordance with an embodiment of the present invention.

Referring further to the drawings, FIGS. 35A-35Q schematically illustrate radioactive-emission measuring cameras 600, adapted for the esophagus, in accordance with preferred embodiments of the present invention.

FIG. 35A schematically illustrates the basic radioactive-emission measuring camera 600, for the esophagus. The camera 600 includes an extracorporeal portion 610, which comprises a control unit, and an intracorporeal portion 630, having proximal and distal ends 631 and 633, with respect to an operator (not shown). A flexible cable 620 connects between them.

The control unit 610 may include control buttons 612 and possibly a display screen 614, and may provide connections with a computer station. It may receive power from a grid or be battery operated. The control unit 610 may further include a computer or a microcomputer.

The intracorporeal portion 630 is constructed essentially as the camera 10 of FIG. 23C and FIGS. 20A-20H, and specifically, FIG. 20H.

Thus, the intracorporeal section 630 defines a cylindrical coordinate system of x; r, wherein x is the longitudinal axis. The plurality of blocks 90 along the intracorporeal portion 630 is housed in an internal structure 21.

Each of the blocks 90 is adapted for the windshield-wiper like oscillatory motion, around the radius r, as denoted by the arrows 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Additionally, the internal structure 21 is adapted for rotational motion around the x-axis, in the direction of ω, wherein after each step of oscillatory motion at a certain orientation of ω, the internal structure 21 rotates by a step to a new orientation of ω, and the oscillatory motion is repeated.

Figure 35K:
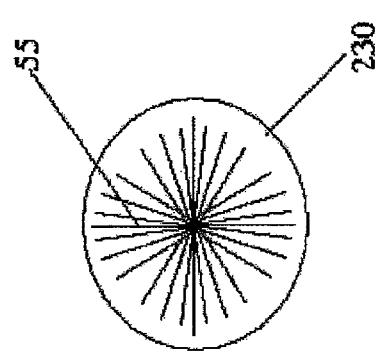
Figure 35J:
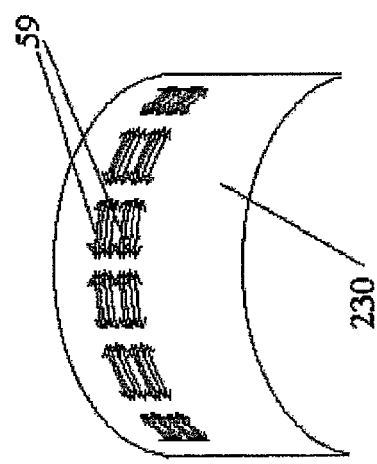

As a consequence, a plurality of broken line traces 59 are formed, in the body section 230, as seen in FIG. 35J.

Preferably, the controller or the computer registers the locations and orientations of each detecting unit or block and correlates the measurements with the corresponding positions and orientations.

A position-tracking device 635 may also be used, for providing information regarding the position of the camera relative to a known reference.

It will be appreciated that the camera 600 may include detecting units 12 rather then blocks 90.

Preferably, the overall structure 20 remains stationary, and has an external surface, which is substantially transparent to nuclear radiation.

A ball bearing 632 may be used at the connecting point with the cable 620, to enable the rotational motion.

The intracorporeal section 630 may further include dedicated electronics 634 and motion providers 636, such as miniature motors and motion transfer systems, as known. Alternatively, the motion may be transferred via the cable 620.

FIGS. 35B and 35C schematically illustrate side and distal views, respectively, of the radioactive-emission measuring camera 600, for the esophagus, having an ultrasound imager 640 at its distal tip 633. The ultrasound imager 640 may provide a structural image which may be correlated with the functional image. Additionally, it may be used for providing the size and location of the relevant organ for modeling. Furthermore, it may be used for providing attenuation correction to the radioactive emission measurements.

FIGS. 35D and 35E schematically illustrate side and distal views, respectively, of the radioactive-emission measuring camera 600, for the esophagus, having an MRI imager 642 at its distal tip 633. The MRI imager 642 may provide a structural image which may be correlated with the functional image. Additionally, it may be used for providing the size and location of the relevant organ for modeling. Furthermore, it may be used for providing attenuation correction to the radioactive emission measurements.

FIGS. 35F-35I schematically illustrate the radioactive-emission measuring camera 600, for the esophagus, having a block 90 at its distal tip 633. The block 90 at the distal tip is also adapted for oscillatory motion, but about the x-axis, as seen by an arrow 53. When combined with the rotational motion around the x-axis, it produces traces 55 in the shape of a star, in the body section 230, as seen in FIG. 35K.

FIGS. 35L-35Q schematically illustrates the radioactive-emission measuring camera 600, for the esophagus, having a block 90 at its distal tip 633, adapted for a deployed and a retracted position, and for oscillatory motion about the x-axis, when deployed. The camera 600 further has the ultrasound imager 640 at its distal tip 633, as a ring, similarly having a deployed and a retracted position.

FIGS. 35N-35P illustrate the block 90 deployed, and the ultrasound imager 640 retracted. In this manner, the ultrasound imager 640 does not obstruct the oscillatory motion of the block 90 at the distal tip 633.

FIG. 35Q illustrates the block 90 retracted and the ultrasound imager deployed so the block 90 does not obstruct the view of the ultrasound imager. It will be appreciated that the ultrasound image is to be taken once, from the distal tip 633, while the radioactive-emission measurements are to be taken at a plurality of orientations, from the distal tip 633.

Figure 36:
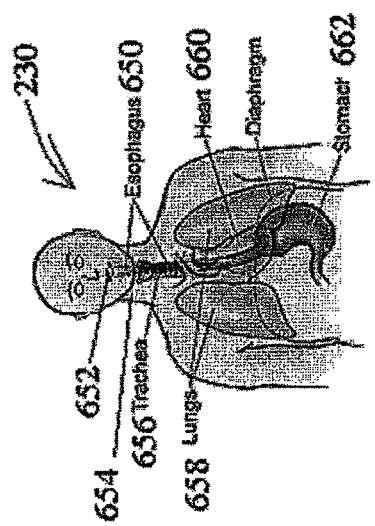
FIGS. 36A and 36B schematically illustrates body organs, including an esophagus.
Figure 36:
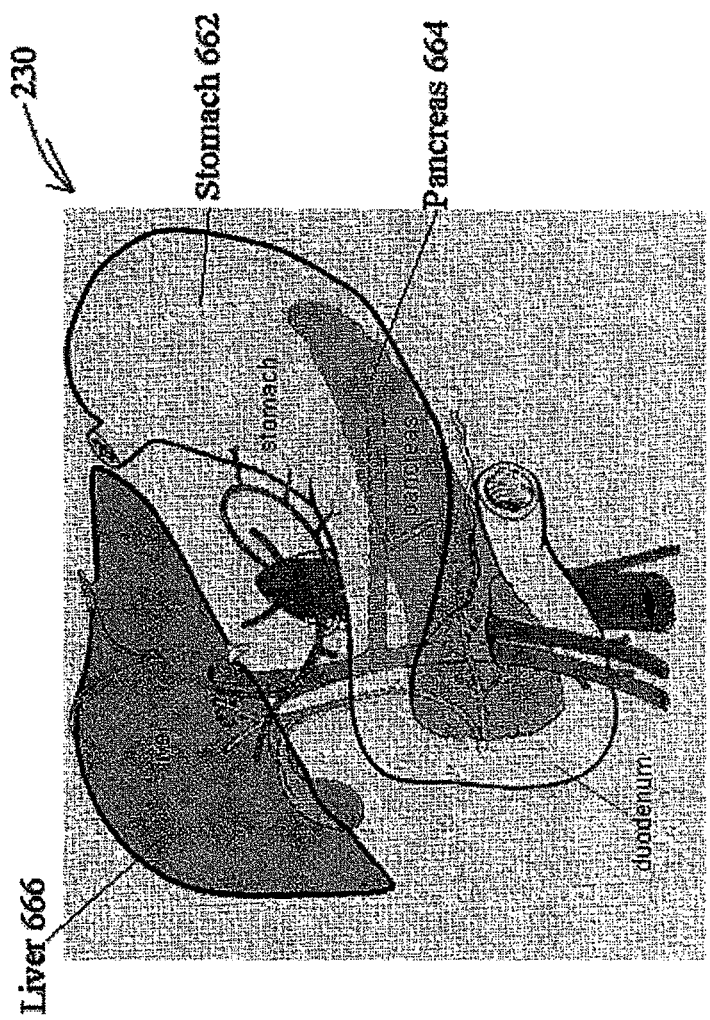
Figure 42:
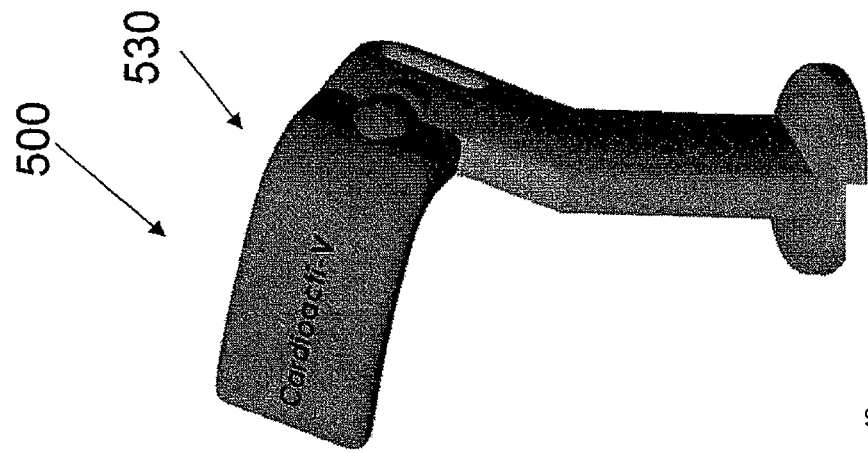
FIGS. 40-45 schematically illustrate the basic components of a cardiac camera system, in accordance with an embodiment of the present invention.
Figure 41:
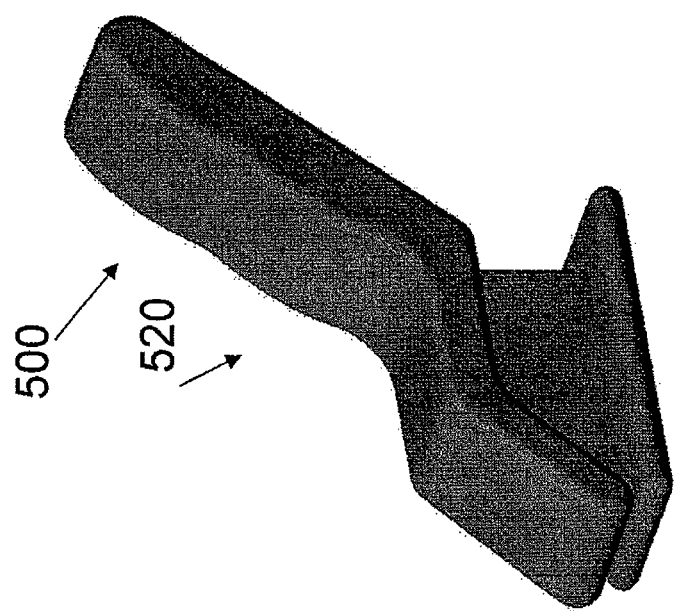
Figure 40:
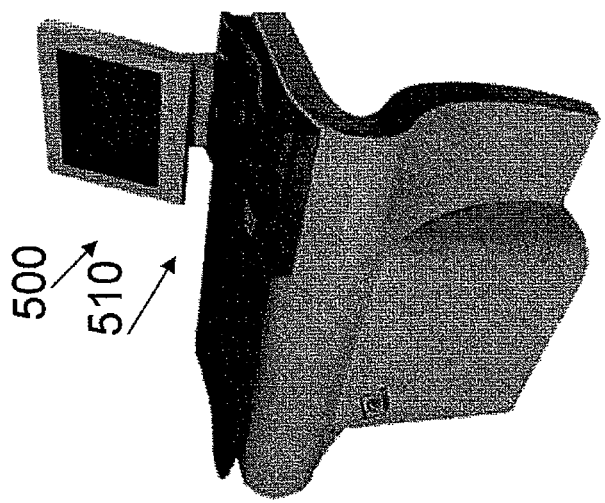

FIGS. 36A and 36B schematically illustrates the body section 230, showing an esophagus 650. The radioactive-emission measuring camera 600 for the esophagus (FIGS. 35A-35Q), is adapted for oral insertion, through a mouth 652, and is further designed for identifying pathological features in a neck area 654, for example, as relating to the vocal cords, the thyroid gland, the submandibular glands. Additionally, it is designed for identifying pathological features in the trachea 656, the lungs 658, the heart 660, the breasts, the stomach 662, the pancreas 664, and the liver 666, as well as other relevant organs and glands, for example, the lymph glands.

The camera system of the present invention allows imaging of internal organs from a close proximity. Additionally, it is particularly advantageous for overweight people and for women with large breasts, for whom extracorporeal imaging, for example, extracorporeal cardiac imaging by nuclear emission measurements, is ineffective, because of losses in the tissue.

For cardiac imaging, the radiopharmaceuticals associated with the camera of FIGS. 35A-35Q may be Myoview™ (technetium Tc-99m tetrofosmin), a cardiac imaging agent, of GE Healthcare, GE Medical Systems, http://www.ge-healthcare.com/contact/contact_details.html#diothers. Alternatively, it may be Cardiolite (Sestamibi radiolabeled with Tc-99m), of DuPont, http://www1.dupont.com/NASApp/dupontglobal/corp/index.jsp?page=/content/US/en_US/contactus.html. It will be appreciated that other agents may be used, as known, for other relevant organs, for example, for the detection of cancerous tissue or other pathologies.

In accordance with the preferred embodiment of the present invention, cardiac imaging is performed with Teboroxime, for example, for myocardial perfusion imaging.

It will be appreciated that the radioactive-emission measuring camera 600, for the esophagus of the present invention may also be used in parallel with the cardiac camera system 500 of Example 12, described hereinbelow.

Example 11A

Referring further to the drawings, FIGS. 37-39 schematically illustrate the body section 230, as a heart, which includes the region-of-interest 200, associated with the organ 215, being the heart, which includes an aorta 242, a left atrium 244 and a right atrium 246.

FIG. 38 schematically illustrates a second, inner region-of-interest 200', associated with the aorta 242.

Similarly, FIG. 39 schematically illustrates a second, inner region-of-interest 200', associated with the left atrium 244.

Referring further to the drawings, FIGS. 40-52E schematically illustrate a cardiac camera system 500, in accordance with a preferred embodiment of the present invention.

FIGS. 40-45 schematically illustrate the basic components of the cardiac camera system 500, in accordance with embodiments of the present invention. These include an operator computer station 510, a chair 520, and a radioactive-emission camera assembly 530.

Figure 43:
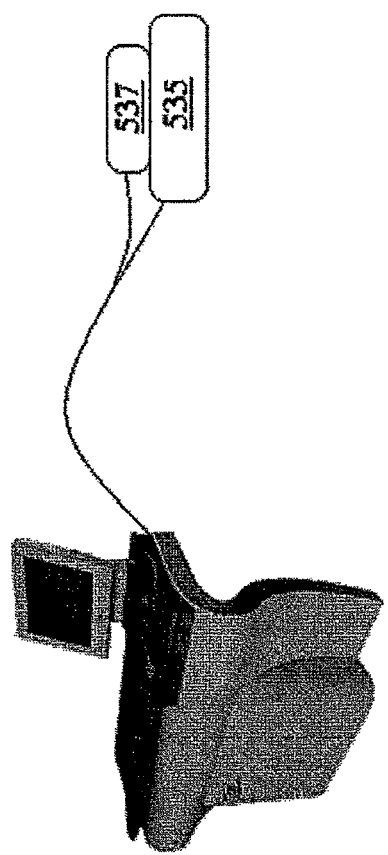

As seen in FIG. 43, computer station 510 may be further adapted for input of an ultrasound imager 535, for example, a handheld ultrasound imager 535, possibly with a position-tracking device 537, or a 3-D ultrasound imager. The data provided by the ultrasound imager 535 may be used in the modeling of the heart. Preferably, the data of the ultrasound imager may be co-registered with the radioactive emission measurements, on the same frame of reference, for providing co-registration of structural and functional images. It will be appreciated that the imager 535 may be an MRI imager.

A problem in cylindrical volumes, when viewed along the periphery of the cylinder is that the innermost information is blocked by the concentric information around it. Thus, it is often advisable to obtain views from the bases of the cylinder.

Figure 44:
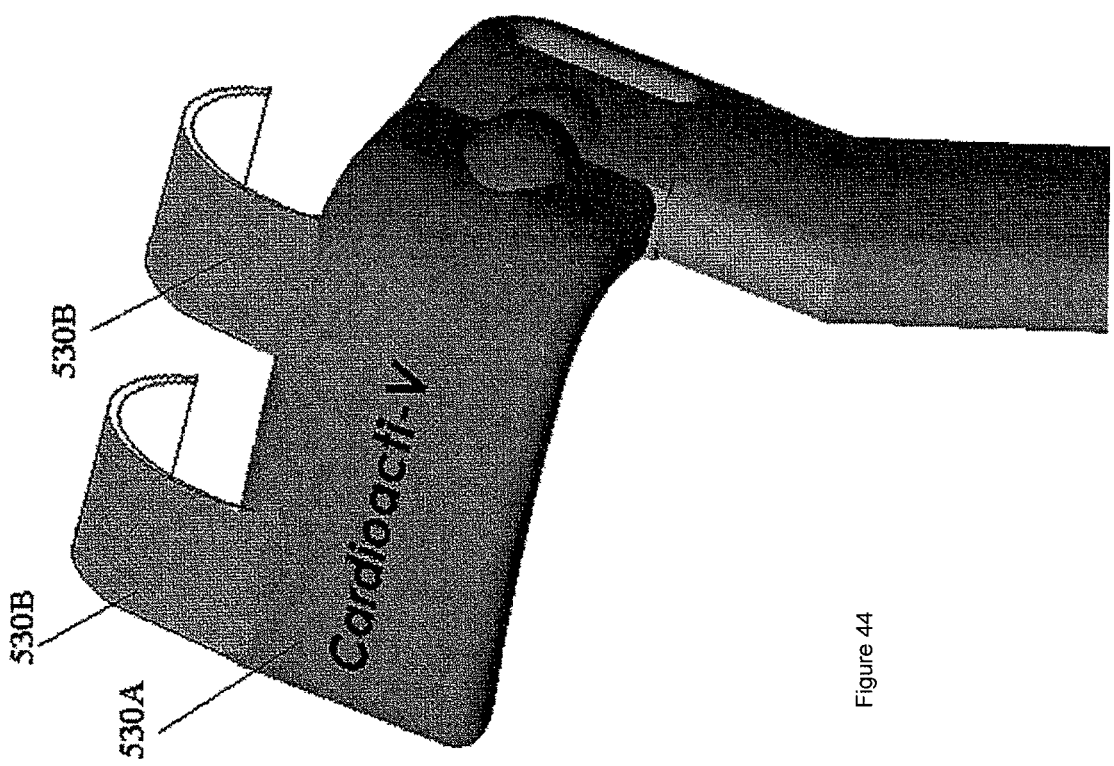

FIG. 44 schematically illustrate a camera 530A, which includes shoulder sections 530B, for viewing the heart essentially from a base of the cylindrical volume, in accordance with embodiments of the present invention.

Figure 45:
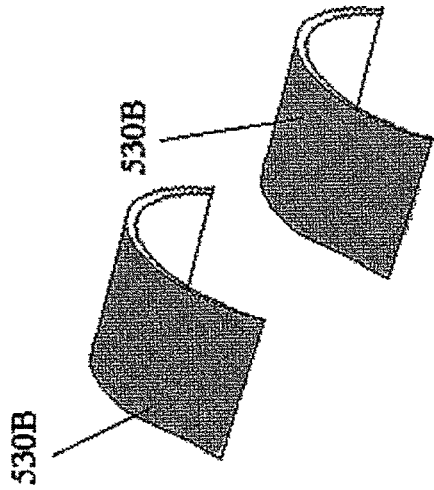

FIG. 45 schematically illustrate cameras 530B, formed as shoulder sections for viewing the heart essentially from a base of the cylindrical volume, in accordance with an alternative embodiment of the present invention.

Views from the shoulders, either as in FIG. 44 or 45 provides information not blocked or hidden by the chest.

It will be appreciated that the design of cameras 530B is possible because of the small size of the blocks 90 relative to the contour or of the body section 230.

Figure 46:
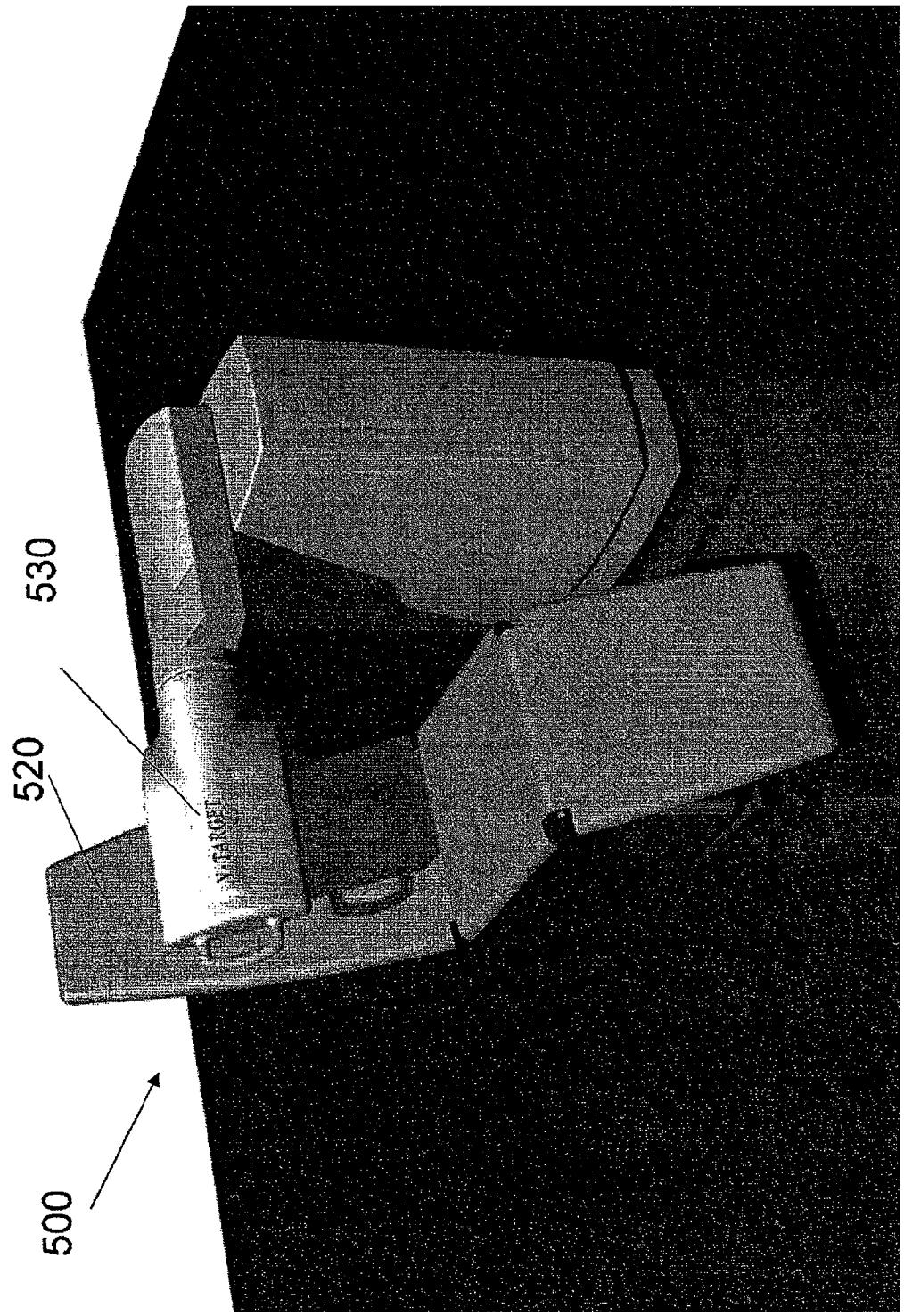
FIG. 46 schematically illustrates the external appearance of a radioactive-emission-camera system for the heart, in accordance with an embodiment of the present invention.

FIG. 46 schematically illustrates the chair 520 and the camera assembly 530, arranged for operation, in accordance with a preferred embodiment of the present invention. Preferably, the chair 520 is in a partial reclining position, and the camera assembly 530 is designed to face it, opposite the chest of a person sitting on the chair 520. Preferably, the camera assembly 530 includes a housing, operative as the overall structure, which is substantially transparent to radioactive emission. Alternatively, a skeleton, which is open on the side facing a patient, may be used as the overall structure.

It will be appreciated that another chair or a bed may be used rather than the chair 520. Alternatively, the patient may be standing.

Figure 47:
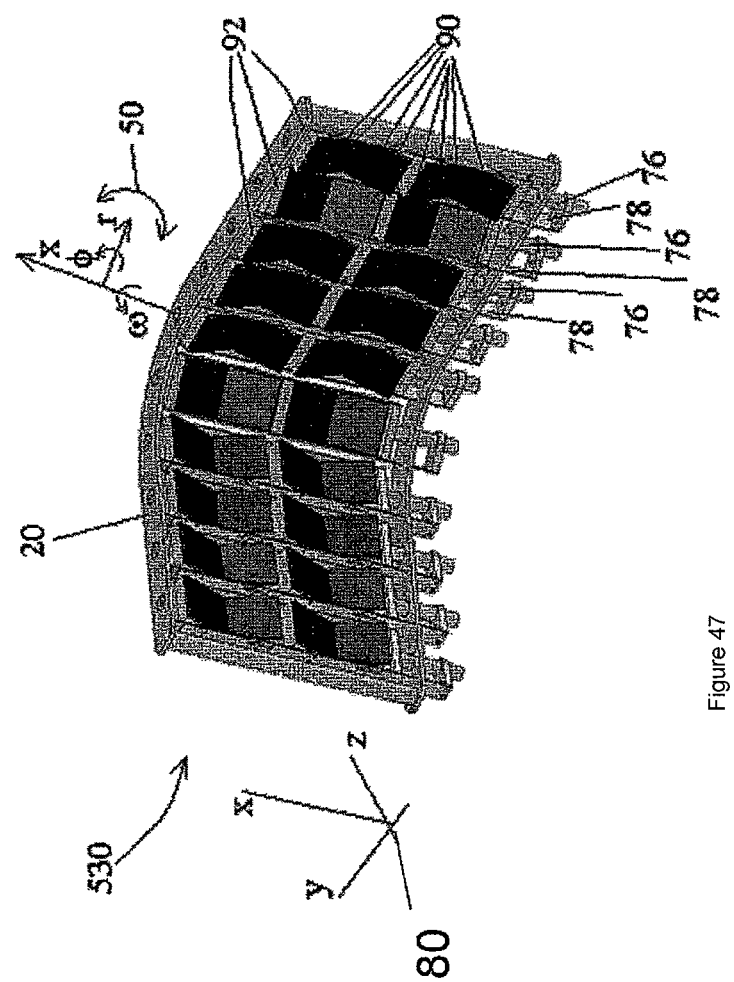
FIGS. 47 and 48 schematically illustrate the internal structure of the radioactive-emission camera for the heart, in accordance with an embodiment of the present invention.
Figure 48:
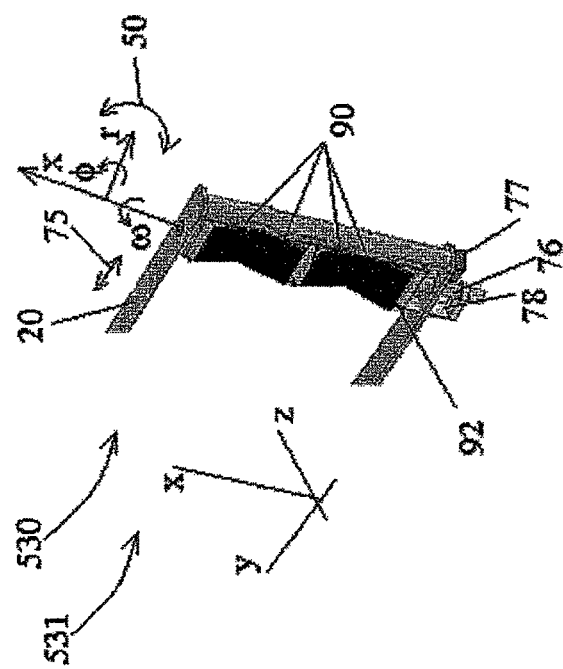
Figure 49:
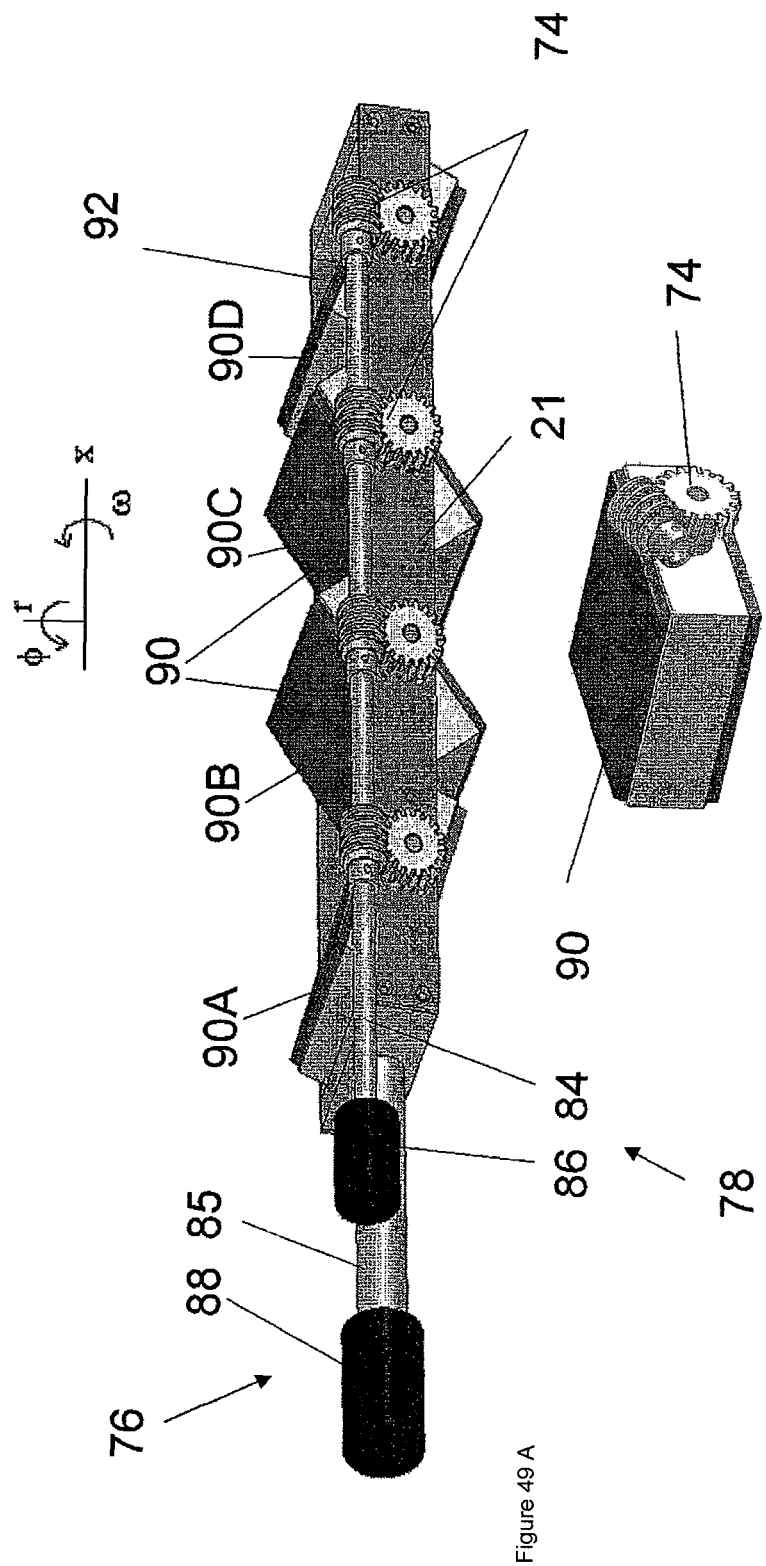
FIGS. 49A and 49B schematically illustrate the internal structure of the radioactive-emission camera for the heart, in accordance with an embodiment of the present invention.

FIGS. 47-48 schematically illustrate possible inner structures of the camera assembly, in accordance with preferred embodiments of the present invention.

FIG. 47 schematically illustrates the inner structure of the camera assembly 530, showing the overall structure 20, the parallel lines of assemblies 92, possibly of an even number, each with a dedicated motion provider 76 and a dedicated secondary motion provider 78, and the rows of blocks 90, possibly arranged in pairs, along the assemblies 92.

The camera assembly 530 defines an internal frame of reference 80, while each assembly 92 has a reference cylindrical coordinate system of x; r, with rotation around x denoted by $\omega$ and rotation around r denoted by $\phi$, wherein the oscillatory motion about r is denoted by the arrow 50.

Preferably, the motion of the camera assembly 530 corresponds to that described hereinabove, with reference to FIGS. 20A-20H and 22A-22H, as follows:

The plurality of blocks 90 is adapted for the windshield-wiper like oscillatory motion, around the radius r, as denoted by the arrow 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Furthermore, the plurality of assemblies 92 are preferably arranged in parallel, and their rotational motions, around the x-axis, in the direction of co, may also be synchronized in an antipodal manner, so as to be diametrically opposed to each other, as shown hereinabove, in FIG. 22C, by arrows 62, and as shown hereinabove in FIG. 22G, by arrows 64. However, other motions are also possible. For example, the assemblies 92 may move together, or independently. It will be appreciated that an odd number of assemblies 92 is also possible.

Thus, the resultant traces are a large plurality of the broken line traces 59, as seen hereinabove, with reference to FIGS. 22D and 22H, on the chest of the patient.

In accordance with the present example, i. The different blocks 90 provide views from different orientations;

ii. The different blocks 90 may change their view orientations;

iii. The different assemblies 92 provide views from different orientations; and iv. The different assemblies 92 may change their view orientations.

The operational manner of the camera 530 is described hereinbelow with reference to FIG. 23D, for the at least two assemblies 92.

Preferably, the motions of the blocks 90 and of the assemblies 92 are contained within the overall structure 20, so that the external surface of the camera assembly 530 remains stationary, wherein the external surface of the camera assembly 530 is substantially transparent to nuclear radiation. Alternatively, the overall structure may be a skeleton, open on the side facing the patient.

It will be appreciated that the oscillatory motions need not be synchronized in an antipodal manner. Rather, the blocks 90 may move together, or independently. It will be appreciated that an odd number of blocks 90 is also possible.

It will be appreciated that camera 530 may include a plurality of assemblies 92, which are not parallel to each other. For example, the assemblies 92 may be at right angles to each other, or at some other angle. It will be appreciated that the assemblies 92 may include detecting units 12 rather then blocks 90, for example, as in the camera 10 of FIGS. 20A-20G.

FIG. 48 schematically illustrates a section 531 of the camera assembly 530, showing the inner structure thereof, in accordance with another embodiment of the present invention. Accordingly, the camera assembly 530 may include the overall structure 20, and a single one of the assemblies 92, within the overall structure 20, having the dedicated motion provider 76, the dedicated secondary motion provider 78, and the rows of blocks 90. Additionally, in accordance with the present embodiment, the camera assembly 530 includes a tertiary motion provider 77, for sliding the assembly 90 laterally, in the directions of the arrow 75, along the chest of the patient (not shown). In this manner, imaging of the chest may be performed with the single assembly 92.

FIGS. 49A and 49B schematically illustrate the assembly 92 and the block 90, in accordance with a preferred embodiment of the present invention. In essence, the assembly 92 is constructed in a manner similar to the camera 10 of FIGS. 20A-20H, and specifically FIG. 20H, and according to FIG. 23D, hereinabove.

Thus the assembly 92 includes a row of at least two blocks 90, each adapted for oscillatory motion about r. The blocks 90 are arranged within the internal structure 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, for example, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

Figure 50:
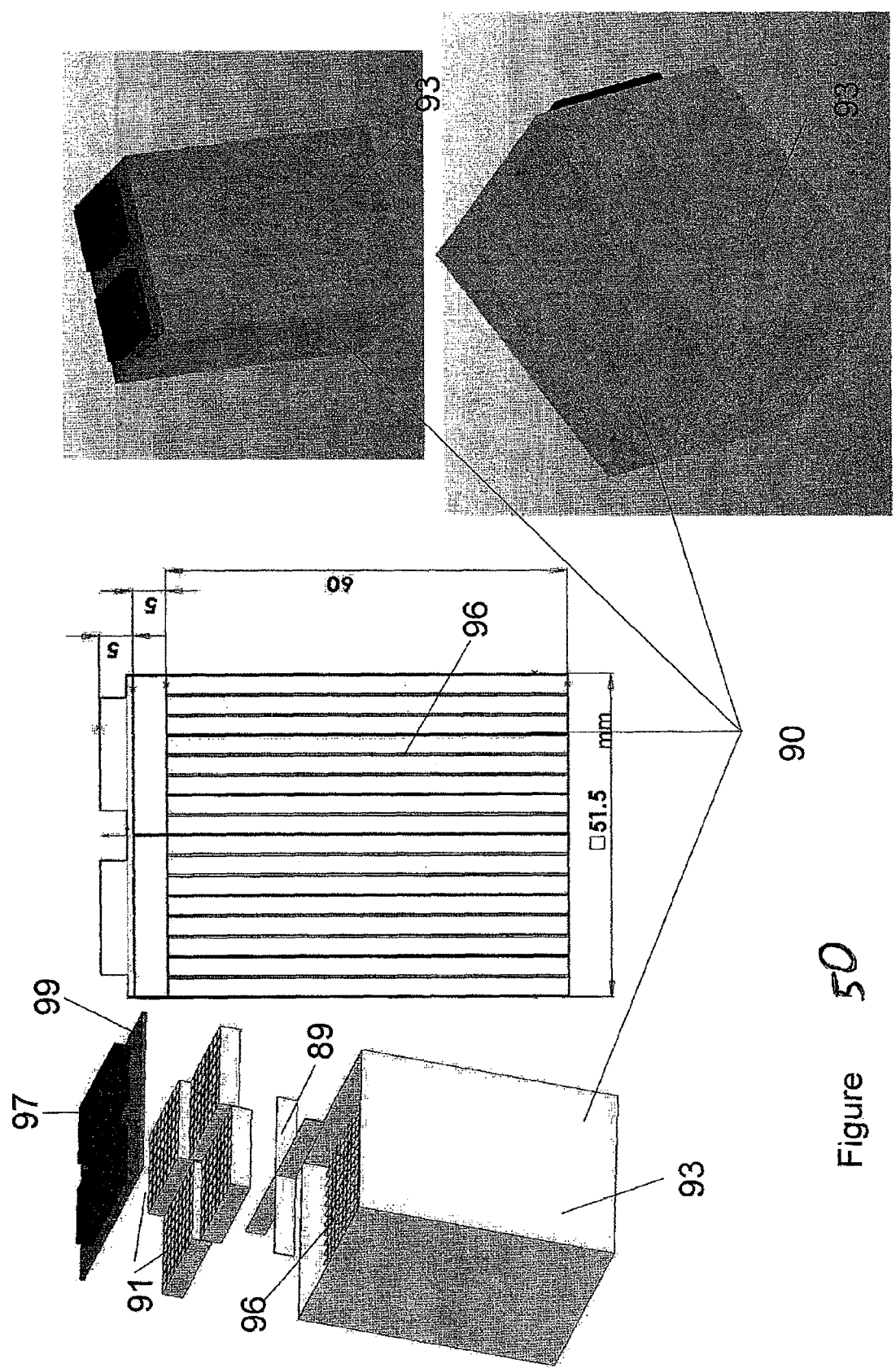
FIG. 50 schematically illustrates the construction of radiation detection blocks, in accordance with an embodiment of the present invention.

FIG. 50 schematically illustrates the block 90, in accordance with a preferred embodiment of the present invention. The block 90 includes a frame 93, which houses the detector material 91, which is preferably pixelated, and the collimators 96. Additionally, the frame 93 houses dedicated electronics 97, preferably on a PCB board 99. Furthermore, where several modules of the detector material 91 need to be used, a structural element 89 may be provided to hold the different modules of the detector material 91 together. It will be appreciated that a single pixel detector may be used. Alternatively, a single module of a pixelated detector may be used. Alternatively, the block 90 may be constructed as any of the examples taught with reference to FIGS. 17A-17N, or as another block, as known.

The dimensions, which are provided in FIG. 50, are in mm. It will be appreciated that other dimensions, which may be larger or smaller, may similarly be used.

FIG. 51 schematically illustrates the cardiac model 250, in accordance with a preferred embodiment of the present invention. The cardiac model 250 includes the volume U, for example, as a cylinder, and the anatomical constraints AC. The rows of blocks 90 are arranged around the volume U, as permissible by the anatomical constraints AC.

FIGS. 52A-52E schematically illustrate the blocks 90, arranged for viewing the cardiac model 250, in accordance with a preferred embodiment of the present invention.

In FIG. 52A, the block 90 is shown with the frame 93, which houses the detector material 91, which is preferably pixelated, and the collimators 96. Additionally, the frame 93 houses the dedicated electronics 97, on the PCB board 99.

In FIG. 52B, fields of view 98 of the blocks 90 are seen for a situation wherein adjacent blocks 90A and 90B move in an antipodal manner, while adjacent blocks 90B and 90C move in a nearly parallel manner. The figure illustrates that when moving in an antipodal manner, the blocks 90 do not obstruct each other's field of view 98. Yet, when moving in a parallel manner, or a near parallel manner, obstruction may occur.

A similar observation is made by FIG. 52C, wherein the adjacent blocks 90B and 90C move in an antipodal manner, while the adjacent blocks 90A and 90B move in a near parallel manner.

Again, it will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

FIG. 52D illustrates possible dimensions for the cardiac model 250. The dimensions are in mm. It will be appreciated that other dimensions are similarly possible. Furthermore, it will be appreciated that the model 250 may be based on general medical information of the organ 215 and common pathological features associated with it. Additionally, the model may be based on information related to a specific patient, such as age, sex, weight, and body type. Furthermore, a structural image, such as by ultrasound or MRI, may be used for providing information about the size and location of the heart 215 in relation to the body section 230 (FIG. 5A), for generating the model 250.

FIG. 52E schematically illustrates a possible arrangement of the blocks 90 for viewing the volume U of the model 250, within the anatomical constrains AC. The significance of the present invention, as illustrated by Figures and 52E is that all the blocks maintain a close proximity to the modeled volume U, and to the region-of-interest, in vivo, even as they move. This is in sharp contrast to the prior art, for example, as taught by U.S. Pat. No. 6,597,940, to Bishop, et al, and U.S. Pat. No. 6,671,541, to Bishop, in which the blocks are fixed within a rigid overall structure, so that as some of the blocks are placed in close proximity to the body, others are forced away from the body, and their counting efficiency deteriorates.

Preferably, the radiopharmaceuticals associated with the camera of FIGS. 40-52E may be Myoview™ (technetium Tc-99m tetrofosmin), a cardiac imaging agent, of GE Healthcare, GE Medical Systems, http://www.gehealthcare.com/contact/contact_details.html#diothers. Alternatively, it may be Cardiolite (Sestamibi radiolabeled with Tc-99m), of DuPont, http://www1.dupont.com/NASApp/dupontglobal/corp/index.jsp?page=/content/US/en_US/contactus.html. It will be appreciated that other agents may be used.

In accordance with the preferred embodiment of the present invention, esophagus imaging is performed with Teboroxime as the radiopharmaceutical.

It will be appreciated that cardiac imaging, in accordance with embodiments of the present invention relates to the imaging of the whole heart, or to a portion of the heart, or to blood vessels near the heart, for example, the coronary artery.

Example 12A

Figure 53:
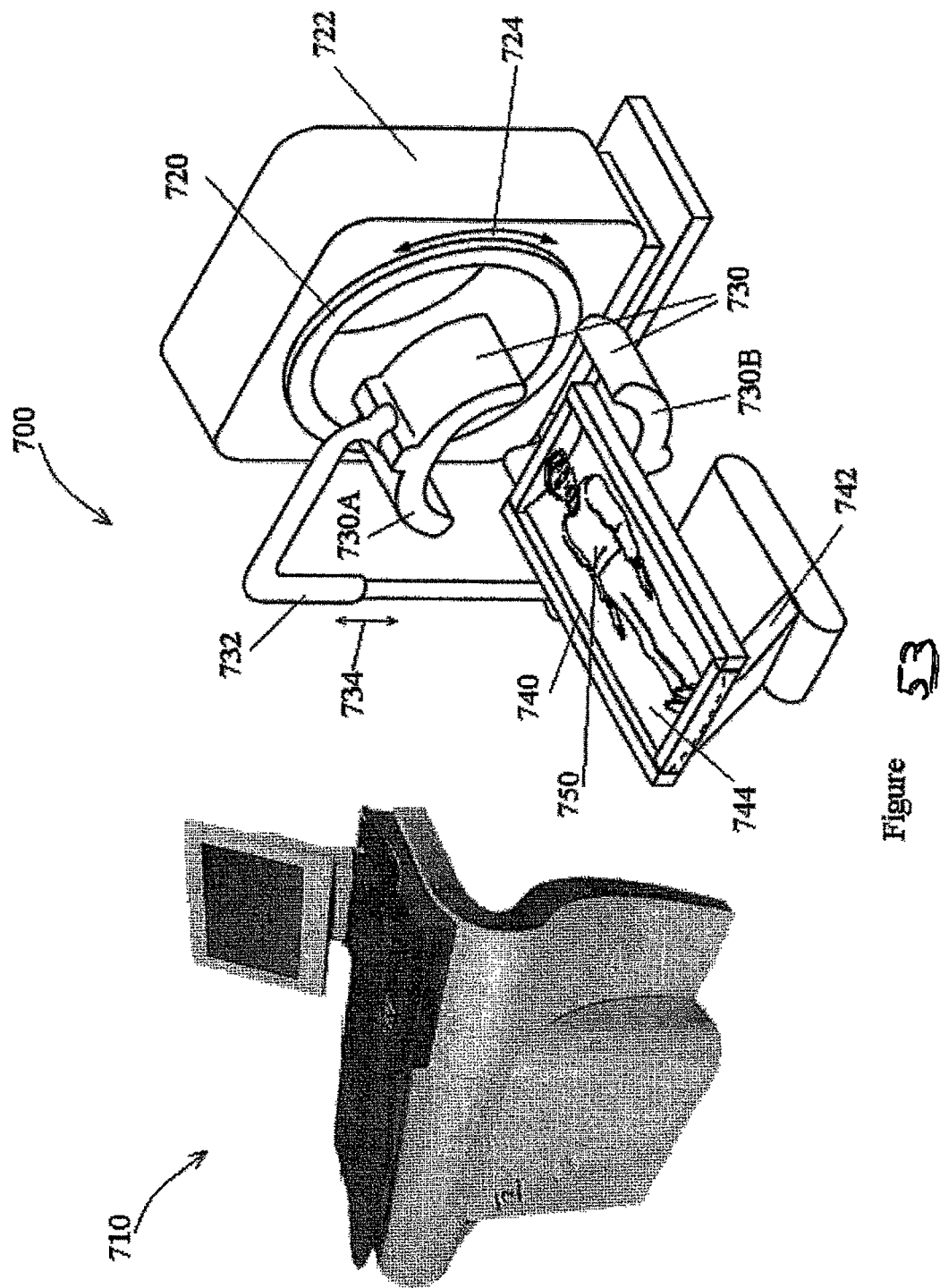
FIG. 53 schematically illustrates a dual imaging system for radioactive-emissions in tandem with a three-dimensional structural imager, in accordance with an embodiment of the present invention.

Referring further to the drawings, FIG. 53 schematically illustrates a dual imaging system 700 for radioactive-emissions in tandem with a three-dimensional structural imager, in accordance with a preferred embodiment of the present invention.

The dual imaging system 700 includes a three-dimensional structural imager 720, preferably, on a structural-imager gantry 722, and a radioactive-emission measuring camera 730, preferably, on a camera gantry 732. A patient 750 may lie on a bed 740, which is adapted for motion into the radioactive-emission measuring camera 730 and the three-dimensional structural imager 720, on a bed gantry 742.

A control unit 710 controls the operation of the dual system 700, including the three-dimensional structural imager 720, the radioactive-emission measuring camera 730, and the bed 740. The control unit 710 may also analyze the data.

Alternatively, two control units may be used, one for controlling the three-dimensional structural imager 720 and another for controlling the radioactive-emission measuring camera 730. It will be appreciated that the control system of the radioactive-emission measuring camera 730 generally controls the order of the operation of the dual system 700, wherein the radioactive-emission measuring may be performed before or after the structural imaging.

It will be further appreciated that the radioactive-emission measuring camera 730 may be configured as an add-on system, adapted for operating with an existing structural imager. It may be supplied with a dedicated software, for example, in a CD format, or with its own control unit, which is preferably adapted for communication with the structural imager control unit.

The three-dimensional structural imager 720 may be, for example, a CT or an MRI, which defines a frame of reference, wherein the radioactive-emission measuring camera 730 is co-registered to the frame of reference.

In this manner, co-registration of functional and structural images is possible. Additionally, the structural image may be used for providing tissue information for attenuation correction of the functional image, resulting in a more accurate functional image.

The radioactive-emission measuring camera 730 may be constructed as one arc 730A, preferably adapted for viewing a full width of a body from a single position of the camera 730. Alternatively, the radioactive-emission measuring camera 730 may be constructed as two arcs 730A and 730B, which are adapted for viewing a full circumference of a body, from a single position of the camera 730. It will be appreciated that the camera 730 may have other geometries, for example, a circle, an ellipse, a polygon, a plurality of arcs forming a circle, or a plurality of sections, forming a polygon, or other shapes.

Preferably, where the camera 730 is adapted for viewing a full circumference of a patient, from a single position, the bed 740 is formed as a stretcher, with a sheet 744, which is substantially transparent to radioactive emission, for example, of a hydrocarbon material.

Figure 54:
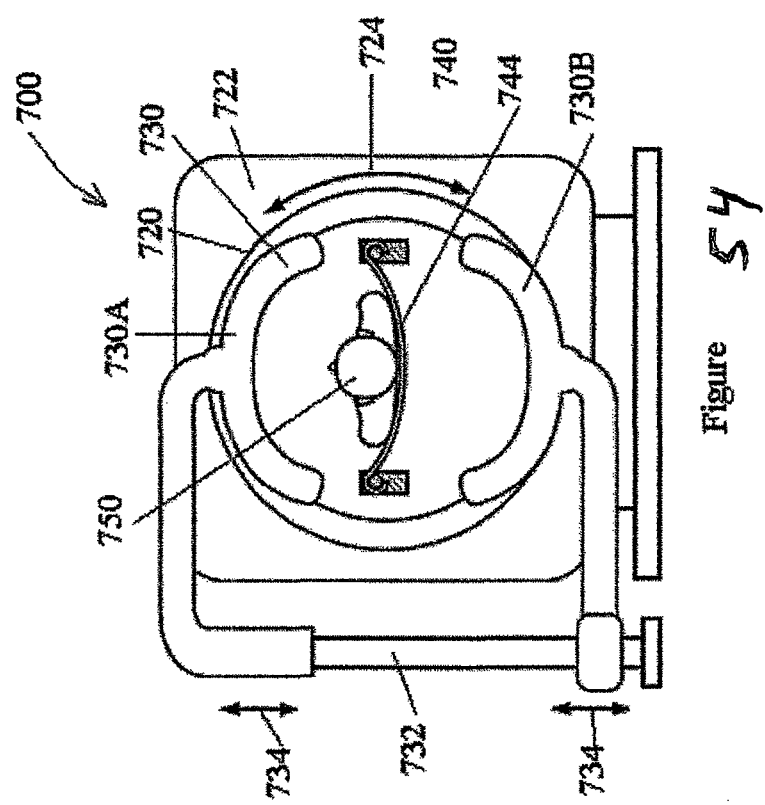
FIG. 54 schematically illustrates a dual imaging system for radioactive-emissions in tandem with a three-dimensional structural imager, in accordance with an embodiment of the present invention.

FIG. 54 schematically illustrates a cross-sectional view of dual imaging system 700 for radioactive-emissions in tandem with a three-dimensional structural imager, in accordance with a preferred embodiment of the present invention.

Preferably, the gantry 732 of the camera 730 is adapted for vertical motion, as described by the arrows 734, so as to bring the camera 730 closer to the patient 750.

Additionally, the gantry 722 of the three-dimensional structural imager 720 may be adapted for rotation, as described by an arrow 724.

The bed 740 is preferably adapted for motion into and out of the camera 730 and the three-dimensional structural imager 720.

Preferably, the rate of imaging by the three-dimensional structural imager 720 and by the radioactive-emission measuring camera is substantially the same, so the bed moves into the two imagers at a constant speed.

In accordance with embodiments of the present invention, the camera 730, formed of portions 730A and 730B, as illustrated in FIGS. 53 and 54 may also be a radioactive-emission measuring PET camera. Additionally, while the patient 750 appears lying, the patient may be sitting standing, lying on the back or lying on the stomach.

It will be appreciated that the body structure that may be imaged may be an organ, such as a heart or a pancreas, a gland, such as a thyroid gland or a lymph gland, blood vessels, for example, the coronary artery or the pulmonary artery, a portion of an organ, such as an aorta or a left atrium of a heart, a bone, a ligament, a joint, a section of the body, such as a chest or an abdomen, or a whole body.

Preferably, the radiopharmaceuticals associated with the camera of the present invention be any one of the following:

1. anti-CEA, a monoclonal antibody fragment, which targets CEA—produced and shed by colorectal carcinoma cells—and may be labeled by Tc-99m or by other radioisotopes, for example, iodine isotopes (Jessup J M, 1998, Tumor markers—prognostic and therapeutic implications for colorectal carcinoma, Surgical Oncology; 7: 139-151);

2. In-111-Satumomab Pendetide (Oncoscint®), designed to target TAG-72, a mucin-like glycoprotein, expressed in human colorectal, gastric, ovarian, breast and lung cancers, but rarely in healthy human adult tissues [Molinolo A; Simpson J F; et al., 1990, Enhanced tumor binding using immunohistochemical analyses by second generation anti-tumor-associated glycoprotein 72 monoclonal antibodies versus monoclonal antibody B72.3 in human tissue, Cancer Res., 50(4): 1291-8];

3. Lipid-Associated Sialic Acid (LASA), a tumor antigen, used for colorectal carcinoma, with a similar sensitivity as anti-CEA monoclonal antibody fragment but a greater specificity for differentiating between benign and malignant lesions (Ebril K M, Jones J D, Klee G G, 1985, Use and limitations of serum total and lipid-bound sialic acid concentrations as markers for colorectal cancer, Cancer; 55:404-409);

4. Matrix Metaloproteinase-7 (MMP-7), a proteins enzyme, believed to be involved in tumor invasion and metastasis (Mori M, Barnard G F et al., 1995, Overexpression of matrix metalloproteinase-7 mRNA in human colon carcinoma, Cancer; 75: 1516-1519);

5. Ga-67 citrate, used for detection of chronic inflammation (Mettler F A, and Guiberteau M J, Eds., 1998, Inflammation and infection imaging, Essentials of nuclear medicine, Fourth edition, Pgs: 387-403);

6. Nonspecific-polyclonal immunoglobulin G (IgG), which may be labeled with both In-111 or Tc-99m, and which has a potential to localize nonbacterial infections (Mettler F A, and Guiberteau M J, ibid);

7. Radio-labeled leukocytes, such as such as In-111 oxine leukocytes and Tc-99m HMPAO leukocytes, which are attracted to sites of inflammation, where they are activated by local chemotactic factors and pass through the endothelium into the soft tissue [Mettler F A, and Guiberteau M J, ibid; Corstens F H; van der Meer J W, 1999, Nuclear medicine's role in infection and inflammation, Lancet; 354 (9180): 765-70]; and 8. Tc-99m bound to Sodium Pertechnetate, which is picked up by red blood cells, and may be used for identifying blood vessels and vital organs, such as the liver and the kidneys, in order to guide a surgical instrument without their penetration.

Additionally, certain organic materials can replace normal atoms in organic molecules with radioactive atoms, and thus can be used to label metabolism. In general, these are used for PET imaging. However, they can be used for other nuclear imaging as well. The radionuclides may be, for example:

1. F-18 fluoro-deoxyglucose (FDG)
2. F-18 Sodium Fluoride
2. C-11 methionine
3. Other less common C-11 amino acid tracers, such as:
C-11 thymidine,
C-11 tyrosine,
C-11 leucine
4. N-13 ammonia
5. O-15 water
6. Rb-82 Rubidium Rb-82
7. Cu-62 copper
8. Ga-68 gallium In accordance with the preferred embodiment of the present invention, the dual imaging and any whole body imaging may be performed with Teboroxime as the radiopharmaceutical.

It will be appreciated that other agents may be used.

Figure 55C:
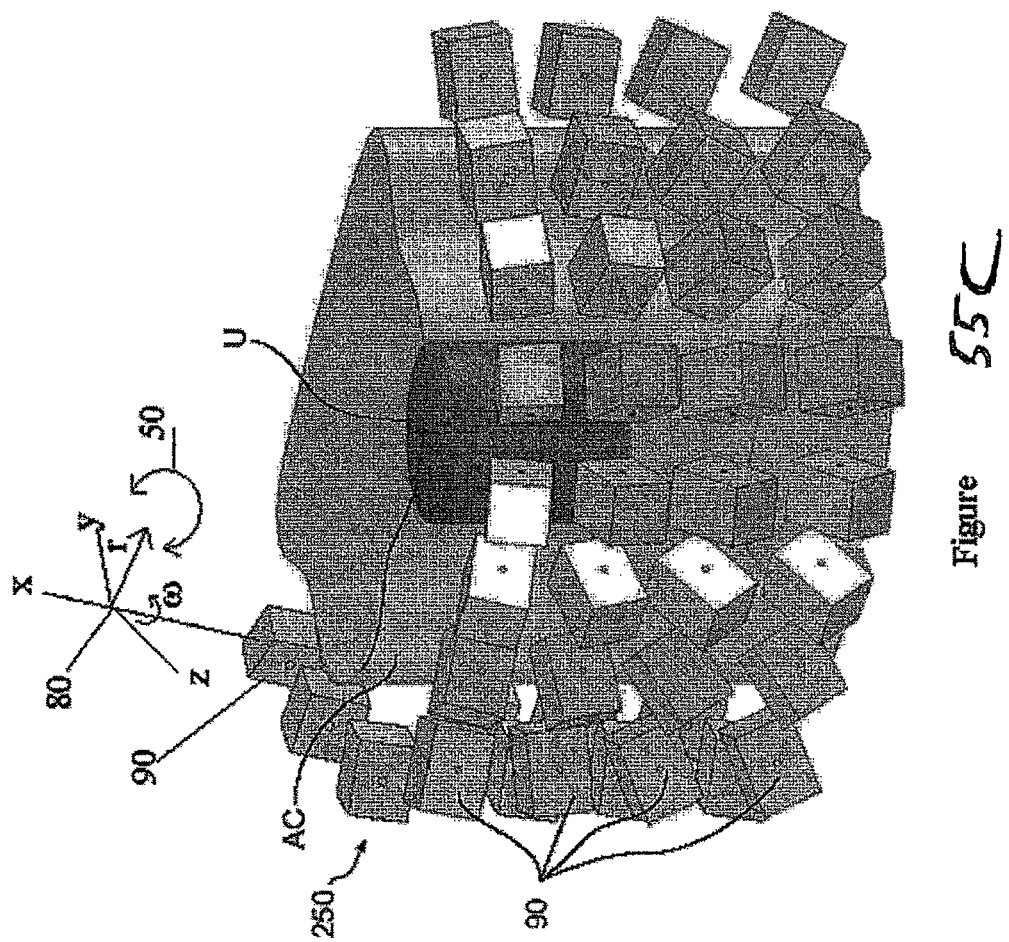

FIGS. 55A-55C schematically illustrate possible inner structures of the camera 730, in accordance with preferred embodiments of the present invention.

FIG. 55A schematically illustrates the inner structure of the camera 730, showing the overall structure 20 and the parallel lines of the assemblies 92, possibly of an even number, each with the row of blocks 90, possibly arranged in pairs. Each of the assemblies 92 preferably includes the dedicated motion provider 76, for providing the rotational motion around x, and the dedicated secondary motion provider 78, for providing the oscillatory motion about r in the direction of the arrow 50.

The camera 730 defines an internal frame of reference 80, while each assembly 92 has a reference cylindrical coordinate system of x; r, with rotation around x denoted by $\omega$ and rotation around r denoted by $\phi$, wherein the oscillatory motion about r is denoted by the arrow 50.

Preferably, the motions of the assemblies 92 and the blocks 90 correspond to those described hereinabove, with reference to FIGS. 20A-20H and 22A-22H, as follows:

The plurality of blocks 90 is adapted for the windshield-wiper like oscillatory motion, around the radius r, as denoted by the arrow 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Furthermore, the plurality of assemblies 92 are preferably arranged in parallel, and their rotational motions, around the x-axis, in the direction of $\omega$, may also be synchronized in an antipodal manner, so as to be diametrically opposed to each other, as shown hereinabove, in FIG. 22C, by arrows 62, and as shown hereinabove in FIG. 22G, by arrows 64. However, other motions are also possible. For example, the assemblies 92 may move together, or independently. It will be appreciated that an odd number of assemblies 92 is also possible.

Thus, the resultant traces are a large plurality of the broken line traces 59, as seen hereinabove, with reference to FIGS. 22D and 22H, on the skin of the patient.

In accordance with the present example, i. The different blocks 90 provide views from different orientations;

ii. The different blocks 90 change their view orientations;

iii. The different assemblies 92 provide views from different orientations; and iv. The different assemblies 92 change their view orientations.

The operational manner of the camera 730 is described hereinbelow with reference to FIG. 23D, for the at least two assemblies 92.

Preferably, the motions of the blocks 90 and of the assemblies 92 are contained within the overall structure 20, so that the overall structure 20 of the camera 730 remains stationary, wherein the external surface of the camera 730 is substantially transparent to nuclear radiation. Alternatively, the overall structure may be a skeleton, open on the side facing the patient.

It will be appreciated that the oscillatory motions need not be synchronized in an antipodal manner. Rather, the blocks 90 may move together, or independently. It will be appreciated that an odd number of blocks 90 is also possible.

It will be appreciated that the camera 730 may include a plurality of assemblies 92, which are not parallel to each other. For example, the assemblies 92 may be at right angles to each other, or at some other angle. It will be appreciated that the assemblies 92 may include detecting units 12 rather then blocks 90, for example, as in the camera 10 of FIGS. 20A-20G.

FIG. 55B schematically illustrates a section 731 of the camera 730, showing the inner structure thereof, in accordance with another embodiment of the present invention. Accordingly, the camera 730 may include the overall structure 20, and a single one of the assemblies 92, within the overall structure 20, having the dedicated motion provider 76, the dedicated secondary motion provider 78, and the rows of blocks 90. Additionally, in accordance with the present embodiment, the camera 730 includes a tertiary motion provider 77, for sliding the assembly 90 laterally, in the directions of an arrow 75.

FIG. 55C schematically illustrates an alternative arrangement of the blocks 90 around the volume U of the model 250, wherein each of the blocks 90 is provided with motion around the x-axis, in the direction of c, and with the oscillatory motion about r, preferably in the y-z plane, as illustrated by the arrow 50. Accordingly, the assemblies 92 need not be used. Rather, each of the blocks 90 may communicate with two motion providers which provide it with the two types of motion.

FIGS. 56A and 56B schematically illustrate the assembly 92 and the block 90, in accordance with a preferred embodiment of the present invention. In essence, the assembly 92 is constructed in a manner similar to the camera 10 of FIG. 20H, and according to FIG. 23D, hereinabove.

Thus the assembly 92 includes a row of at least two blocks 90, each adapted for oscillatory motion about r. The blocks 90 are arranged within the internal structure 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

It will be appreciated that many other cameras and camera systems may be considered and the examples here are provided merely to illustrate the many types of combinations that may be examined, in choosing and scoring a camera design, both in terms of information and in terms of secondary considerations, such as rate of data collection, cost, and complexity of the design.

Example 13A

Brain cancer is the leading cause of cancer-related death in patients younger than age 35, and in the United States, the annual incidence of brain cancer generally is 15-20 cases per 100,000 people.

There are two types of brain tumors: primary brain tumors that originate in the brain and metastatic (secondary) brain tumors that originate from cancer cells that have migrated from other parts of the body.

Approximately 17,000 people in the United States are diagnosed with primary cancer each year; nearly 13,000 die of the disease. Amongst children, the annual incidence of primary brain cancer is about 3 per 100,000.

Primary Brain Tumors are generally named according to the type of cells or the part of the brain in which they begin. The most common are gliomas, which begin in glial cells, and of which there are several types, as follows:

Astrocytoma, a tumor which arises from star-shaped glial cells called astrocytes, which most often arises in the cerebrum in adults, whereas, in children, it occurs in the brain stem, the cerebrum, and the cerebellum;

Brain stem glioma, a tumor that occurs in the lowest part of the brain and is diagnosed in young children as well as in middle-aged adults;

Ependymoma, a tumor most common in middle-aged adults, which arises from cells that line the ventricles or the central canal of the spinal cord, and also occurs in children and young adults; and Oligodendroglioma, a rare tumor, which arises from cells that make the fatty substance that covers and protects nerves and usually occurs in the cerebrum, grows slowly and generally does not spread into surrounding brain tissue.

Some types of brain tumors do not begin in glial cells. The most common of these are:

Medulloblastoma, also called a primitive neuroectodermal tumor, a tumor which usually arises in the cerebellum and is the most common brain tumor in children;

Meningioma, which arises in the meninges and usually grows slowly;

Schwannoma, also called an acoustic neuroma, and occurring most often in adults, it is a tumor that arises from a Schwann cell, of the cells that line the nerve that controls balance and hearing, in the inner ear;

Craniopharyngioma, a tumor which grows at the base of the brain, near the pituitary gland, and most often occurs in children;

Germ cell tumor of the brain, a tumor which arises from a germ cell, generally, in people younger than 30, the most common type of which is a germinoma; and Pineal region tumor, a rare brain tumor, which arises in or near the pineal gland, located between the cerebrum and the cerebellum.

Certain inherited diseases are associated with brain tumors, for example, Multiple endocrine neoplasia type 1 (pituitary adenoma), Neurofibromatosis type 2 (brain and spinal cord tumors), Retinoblastoma (malignant retinal glioma), Tuberous sclerosis (primary brain tumors), and Von Hippel-Lindau disease (retinal tumor, CNS tumors). Furthermore, genetic mutations and deletions of tumor suppressor genes (i.e., genes that suppress the development of malignant cells) increase the risk for some types of brain cancer.

Additionally, exposure to vinyl chloride is an environmental risk factor for brain cancer. Vinyl chloride is a carcinogen, used in the manufacturing of plastic products such as pipes, wire coatings, furniture, car parts, and house wares, and is present in tobacco smoke. Manufacturing and chemical plants may release vinyl chloride into the air or water, and it may leak into the environment as a result of improper disposal. People who work in these plants or live in close proximity to them have an increased risk for brain cancer.

Secondary brain cancer occurs in 20-30% of patients with metastatic disease and its incidence increases with age. In the United States, about 100,000 cases of secondary brain cancer are diagnosed each year. Patients with a history of melanoma, lung, breast, colon, or kidney cancer are at risk for secondary brain cancer.

Brain tumors can obstruct the flow of cerebrospinal fluid (CSF), which results in the accumulation of CSF (hydrocephalus) and increased intracranial pressure (IICP). Nausea, vomiting, and headaches are common symptoms. They can damage vital neurological pathways and invade and compress brain tissue. Symptoms usually develop over time and their characteristics depend on the location and size of the tumor.

The first step in diagnosing brain cancer involves evaluating symptoms and taking a medical history. If there is any indication that there may be a brain tumor, various tests are done to confirm the diagnosis, including a complete neurological examination, imaging tests, and biopsy.

Referring now to the drawings, FIGS. 57A-57F present the principles of modeling, for obtaining an optimal set of views, for a body organ 215, in accordance with embodiments of the present invention.

FIG. 57A schematically illustrates a body section 230, illustrating the organ 215, being the brain 215. The brain 215 is enclosed within a skull 830 and includes:

a cerebellum 802, the part of the brain below the back of the cerebrum, which regulates balance, posture, movement, and muscle coordination;

a corpus callosum 804, which is a large bundle of nerve fibers that connect the left and right cerebral hemispheres;

a frontal lobe of the cerebrum 806, which is the top, front regions of each of the cerebral hemispheres, and is used for reasoning, emotions, judgment, and voluntary movement;

a medulla oblongata 808, which is the lowest section of the brainstem (at the top end of the spinal cord) and controls automatic functions including heartbeat, breathing, and the like;

a occipital lobe of the cerebrum 810, which is the region at the back of each cerebral hemisphere, at the back of the head, and contains the centers of vision and reading ability;

a parietal lobe of the cerebrum 812, which is the middle lobe of each cerebral hemisphere between the frontal and occipital lobes, located at the upper rear of the head, and which contains important sensory centers;

a pituitary gland 814, which is a gland attached to the base of the brain that secretes hormones, and is located between the pons and the corpus callosum;

pons 816, which is the part of the brainstem that joins the hemispheres of the cerebellum and connects the cerebrum with the cerebellum, located just above the medulla oblongata;

a spinal cord 818, which is a thick bundle of nerve fibers that runs from the base of the brain to the hip area, through the spine (vertebrae);

a temporal lobe of the cerebrum 820, which is the region at the lower side of each cerebral hemisphere, located at the sides of the head and containing centers of hearing and memory.

The brain 215 may include a pathological feature 213, termed herein an organ target 213. A region-of-interest (ROI) 200 may be defined so as to encompass the brain 215 and the pathological feature 213.

As seen in FIG. 57B, the region-of-interest 200 of FIG. 57A is modeled as a model 250 of a volume U, and the organ target 213 is modeled as a modeled organ targets HS. Additionally, there are certain physical viewing constraints, associated with the region-of-interest 200, which are modeled as anatomical constraints AC. In the present case, the skull 830 creates viewing constraints, and generally, imaging the brain is performed extracorporeally.

Figure 58:
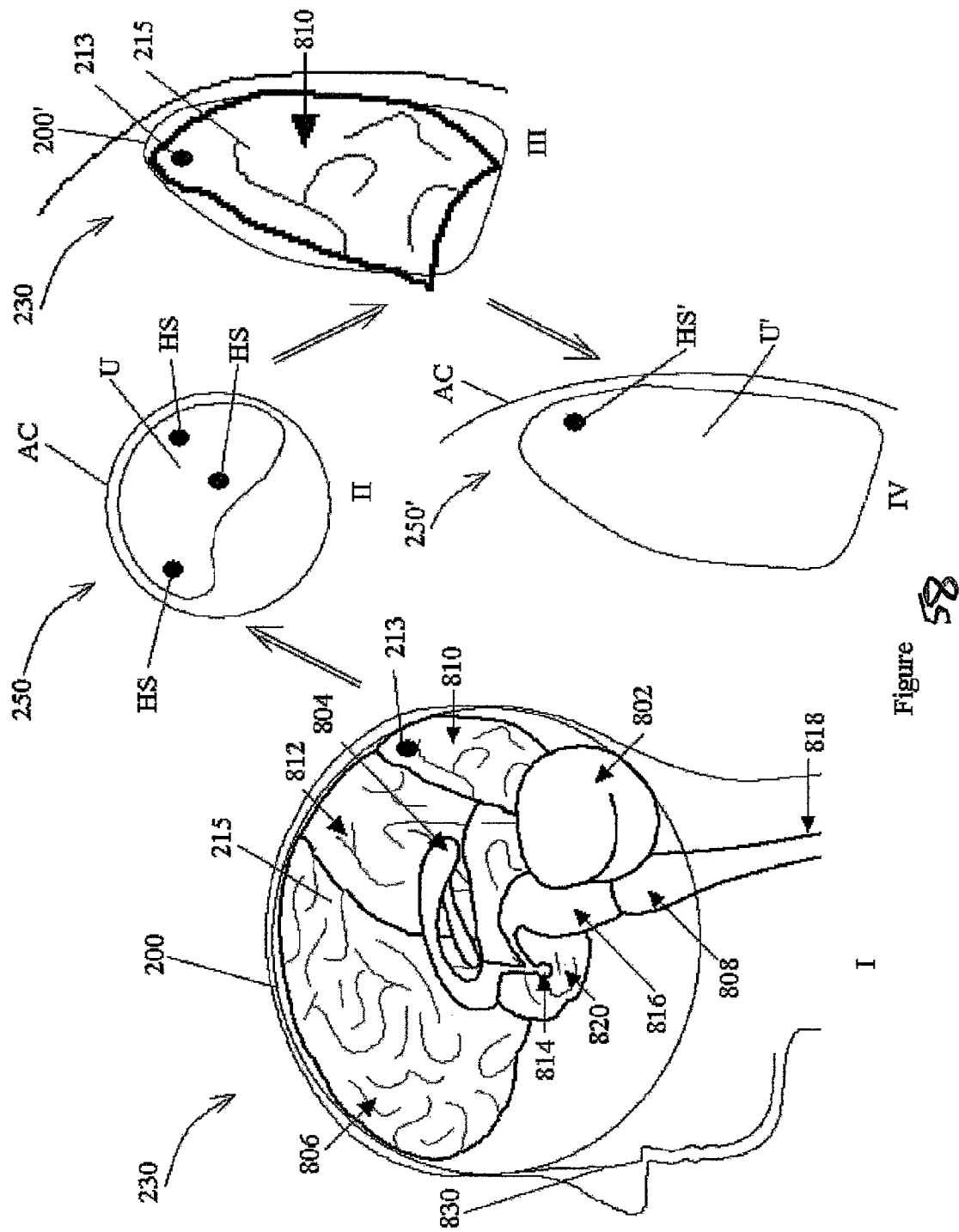
FIG. 58 schematically illustrates a cranial model, in accordance with an embodiment of the present invention.

Referring further to the drawings, FIG. 58 pictorially illustrates a method 340 for zooming in on a suspected pathological feature, as a process of two or more iterations, in accordance with embodiments of the present invention, as follows:

As seen in FIG. 58, the method 340 may be described, pictorially, as follows:

In I: The region-of-interest 200, associated with the organ 215, such as the brain 215, is defined for the body section 230.

In II: The model 250 of the volume U is provided for the region-of-interest 200, possibly with one or several of the modeled organ targets HS, and within the anatomical constraints AC, for obtaining the optimal set of views for the region-of-interest 200. The optimal set of views is then applied to the region-of-interest 200, encompassing the brain 215 of the body section 230.

In III: When the suspected organ target 213 is identified, in vivo, in the brain 215, by radioactive-emission measurements at the optimal set of views, a second, inner region-of-interest 200' is defined, encircling the suspected pathological feature. For example, if a suspected pathology 213 is identified in the occipital lobe 810 of the cerebrum, that is, the region at the back of each cerebral hemisphere at the back of the head, the second region-of-interest 200' is defined so as to encircle the occipital lobe 810 of the cerebrum.

In IV: A model 250' of a volume U' is provided for the second, inner region-of-interest 200', preferably, with at least one modeled organ target HS, simulating the suspected organ target 213, for obtaining an optimal pathology set of views for the region-of-interest 200'. The second, pathology set of views is then applied to the second, inner region-of-interest 200' of the body section 230. In the present example, the second, pathology set of views is then applied to the occipital lobe 810 of the cerebrum, in vivo.

Referring further to the drawings, FIGS. 59A-60J schematically illustrate a camera system 850 for the brain, in accordance with a preferred embodiment of the present invention.

FIGS. 59A-59C schematically illustrate the radioactive-emission camera for the brain, in accordance with embodiments of the present invention;

Preferably, radioactive-emission camera 850 for the brain is shaped as a helmet 860, adapted for wearing on a head 862. The helmet 860 is preferably mounted on a gantry 870, which may be adjustable in the directions of arrows 872, 874 and 876, for adapting to individual heights and comfort requirements.

Alternatively, no gantry is used, and the helmet 860 may be worn directly on the head 862, for example, like a motorcycle helmet.

A chair 880 may be provided for the comfort of the patient.

Preferably, the radioactive-emission camera 850 for the brain is operable with a control unit 890, which may be a desktop computer, a laptop, or the like. The control unit 890 is preferably used both for controlling the motions of the detecting units 12, blocks 90 and assemblies 92 of the radioactive-emission camera 850 for the brain and for analyzing the data.

It will be appreciated that the radioactive-emission camera 850 for the brain may be supplied merely as the camera helmet 860 and a data storage device, such as a CD 892, a disk 892, or the like, containing the appropriate software, for operation with an existing computer, at the site.

It will be appreciated that the present camera system for the brain may also be used as a PET system, for coincident counting.

It will be appreciated that the radioactive-emission camera 850 for the brain may be operable with a structural imager, as taught by commonly owned PCT publication WO2004/042546, whose disclosure is incorporated herein by reference. The structural imager may be a handheld ultrasound imager, possibly with a position-tracking device, a 3-D imager such as an ultrasound imager, a CT imager, or an MRI imager, as known. The data provided by the structural imager may be used for any one or a combination of the following:

i. obtaining accurate dimensional data for modeling the brain 215, as taught with reference to FIGS. 57A-58 and 11-12;

ii. providing attenuation correction for the radioactive-emissions, based on the structural data, as taught by commonly owned PCT publication WO2004/042546; and iii. co-registering the functional and structural images, as taught, for example, by commonly owned PCT publication WO2004/042546.

Referring further to the drawings FIGS. 60A-60K schematically illustrate inner structures of the camera 850 in accordance with several embodiments of the present invention.

FIG. 60A schematically illustrates the assembly 92, comprising, for example four of the blocks 90, adapted for oscillatory motion about the r-axis, as illustrated by the arrows 50, and adapted for rotational motion about the x-axis, as illustrated by the arrow 62, as taught, for example, with reference to FIGS. 22A-22H. It will be appreciated that detecting units 12 may be used in place of blocks 90.

FIG. 60B schematically illustrates a possible cross sectional view of the camera 850 (FIG. 59C), showing an arrangement of the assemblies 92, laterally around the head 862.

FIG. 60C schematically illustrates a top view of the camera 850, showing an arrangement of the assemblies 92, laterally around the head 862. It will be appreciated that the number of the blocks 90 may vary around the head 862.

Figure 60F:
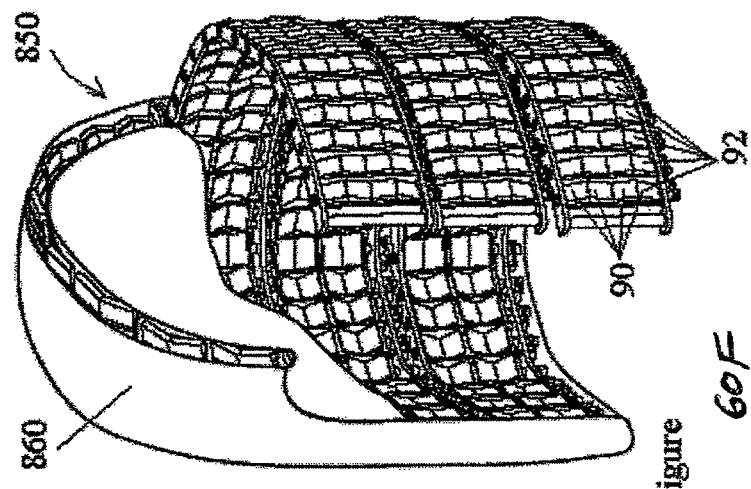
Figure 60E:
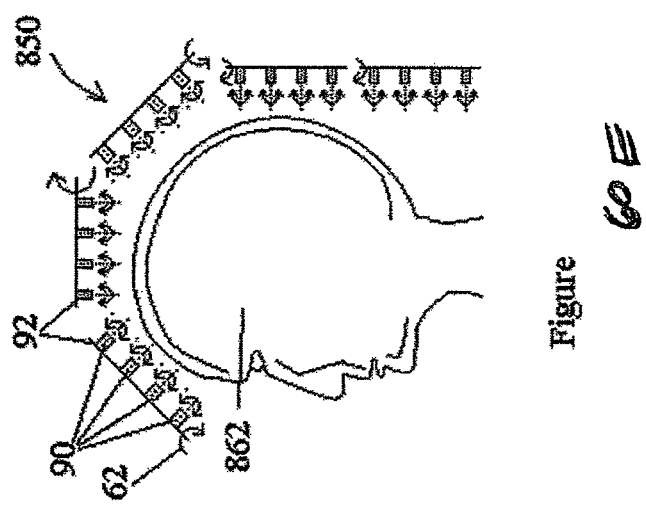
Figure 60D:
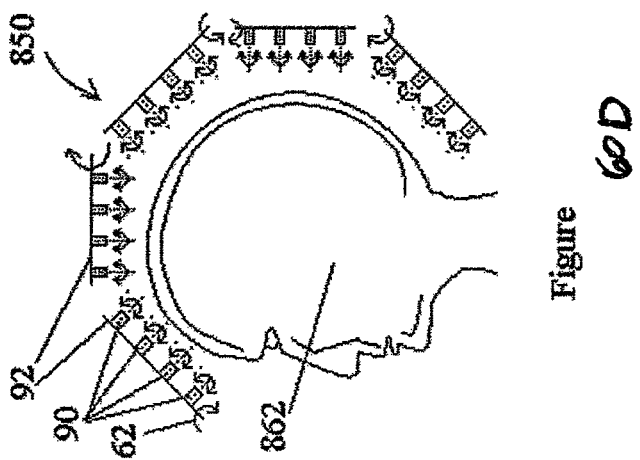

FIGS. 60D and 60E schematically illustrate other possible cross sectional views of the camera 850, showing arrangements of the assemblies 92, vertically around the head 862.

FIG. 60F schematically illustrates the camera 850 formed as the helmet 860, with the assemblies 92, arranged as illustrated by the cross sectional view of FIG. 60E. It will be appreciated that other arrangements are similarly possible. Preferably, the camera helmet 860 includes an overall structure 864. Preferably, the motions of the blocks 90 and of the assemblies 92 are contained within the overall structure 864.

Preferably, the proximal side of the overall structure 864 with respect to the head 862 (FIG. 59C) is transparent to nuclear radiation. Alternatively, the proximal side with respect to the head 862 is open.

FIG. 60G schematically illustrates another arrangement of the blocks 90 around the head 862, wherein the blocks 90 are not arranged in assemblies 92; rather each block 90 moves as an individual body. It will be appreciated that the detecting units 12 may be used in place of the blocks 90.

FIGS. 60H-60K schematically illustrate possible rotational motions of the blocks 90, each of the blocks 90 moving as an individual body for obtaining views of different orientations. As seen in FIG. 60H, the block 90 rotates around x as seen by an arrow 852 and at each position around x, oscillates about x, as seen by an arrow 851. The resultant traces are seen in FIG. 60I as a star of line traces 854.

Alternatively, as seen in FIG. 60J, the block 90 rotates around y as seen by an arrow 853 and at each position around y, oscillates about x, as seen by the arrow 851. The resultant traces are seen in FIG. 60K, as line traces 855.

The assembly 92 and the block 90, in accordance with a preferred embodiment of the present invention are described in FIGS. 49A and 49B, hereinabove.

Thus the assembly 92 includes a row of at least two blocks 90, each adapted for oscillatory motion about r. The blocks 90 are arranged within the internal structure 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

It will be appreciated that imaging, in accordance with embodiments of the present invention relates to the imaging of the whole brain, or to a portion of the brain, or to blood vessels near the brain, for example, the coronary artery.

Preferably, the radiopharmaceuticals associated with the camera of the present invention may be Tc99m-d, l-hexamethyl propylene amine oxime (1-HMPAO) commercially known as Ceretec by GE-Amersham, or Tc-99m-ECD, commercially known as Neurolite, and made by Bristol Myers Squibb.

The present invention applies to the two types of brain tumors: primary brain tumors, which originate in the brain and metastatic (secondary) brain tumors that originate from cancer cells that have migrated from other parts of the body.

Additionally, the primary brain tumors may be gliomas, which begin in glial cells, and of which there are several types, as follows:

Astrocytoma, a tumor which arises from star-shaped glial cells called astrocytes, and which in adults, most often arises in the cerebrum, whereas in children, it occurs in the brain stem, the cerebrum, and the cerebellum.

Brain stem glioma, a tumor that occurs in the lowest part of the brain, and is diagnosed in young children as well as in middle-aged adults.

Ependymoma, a tumor, most common in middle-aged adults, which arises from cells that line the ventricles or the central canal of the spinal cord and which occurs in children and young adults.

Oligodendroglioma, a rare tumor, which arises from cells that make the fatty substance that covers and protects nerves and usually occurs in the cerebrum, grows slowly and generally does not spread into surrounding brain tissue.

Additionally or alternatively, the present invention applies to other types of brain tumors, which do not begin in glial cells. The most common of these are:

Medulloblastoma, also called a primitive neuroectodermal tumor, a tumor which usually arises in the cerebellum and is the most common brain tumor in children.

Meningioma, which arises in the meninges and usually grows slowly.

Schwannoma, also called an acoustic neuroma, and occurring most often in adults, it is a tumor that arises from a Schwann cell, of the cells that line the nerve that controls balance and hearing, in the inner ear.

Craniopharyngioma, a tumor which grows at the base of the brain, near the pituitary gland, and most often occurs in children.

Germ cell tumor of the brain, a tumor which arises from a germ cell, generally, in people younger than 30, the most common type of which is a germinoma.

Pineal region tumor, a rare brain tumor, which arises in or near the pineal gland, located between the cerebrum and the cerebellum.

Additionally or alternatively, the present invention applies to tumors associated with certain inherited diseases, for example, Multiple endocrine neoplasia type 1 (pituitary adenoma), Neurofibromatosis type 2 (brain and spinal cord tumors), Retinoblastoma (malignant retinal glioma), Tuberous sclerosis (primary brain tumors), and Von Hippel-Lindau disease (retinal tumor, CNS tumors), and genetic mutations and deletions of tumor suppressor genes (i.e., genes that suppress the development of malignant cells), which increase the risk for some types of brain cancer.

Additionally or alternatively, the present invention applies to tumors associated with exposure to vinyl chloride.

Additionally or alternatively, the present invention applies to secondary brain cancer, for example, originating from the lungs, the breasts, or other parts of the body.

It will be appreciated that the present invention further applies to other types brain tumors, which may be malignant or benign, blood clots in the brain, and other brain pathologies. It will be appreciated that many other cameras and camera systems may be considered and the examples here are provided merely to illustrate the many types of combinations that may be examined, in choosing and scoring a camera design, both in terms of information and in terms of secondary considerations, such as rate of data collection, cost, and complexity of the design.

Example 14A

Figure 61A:
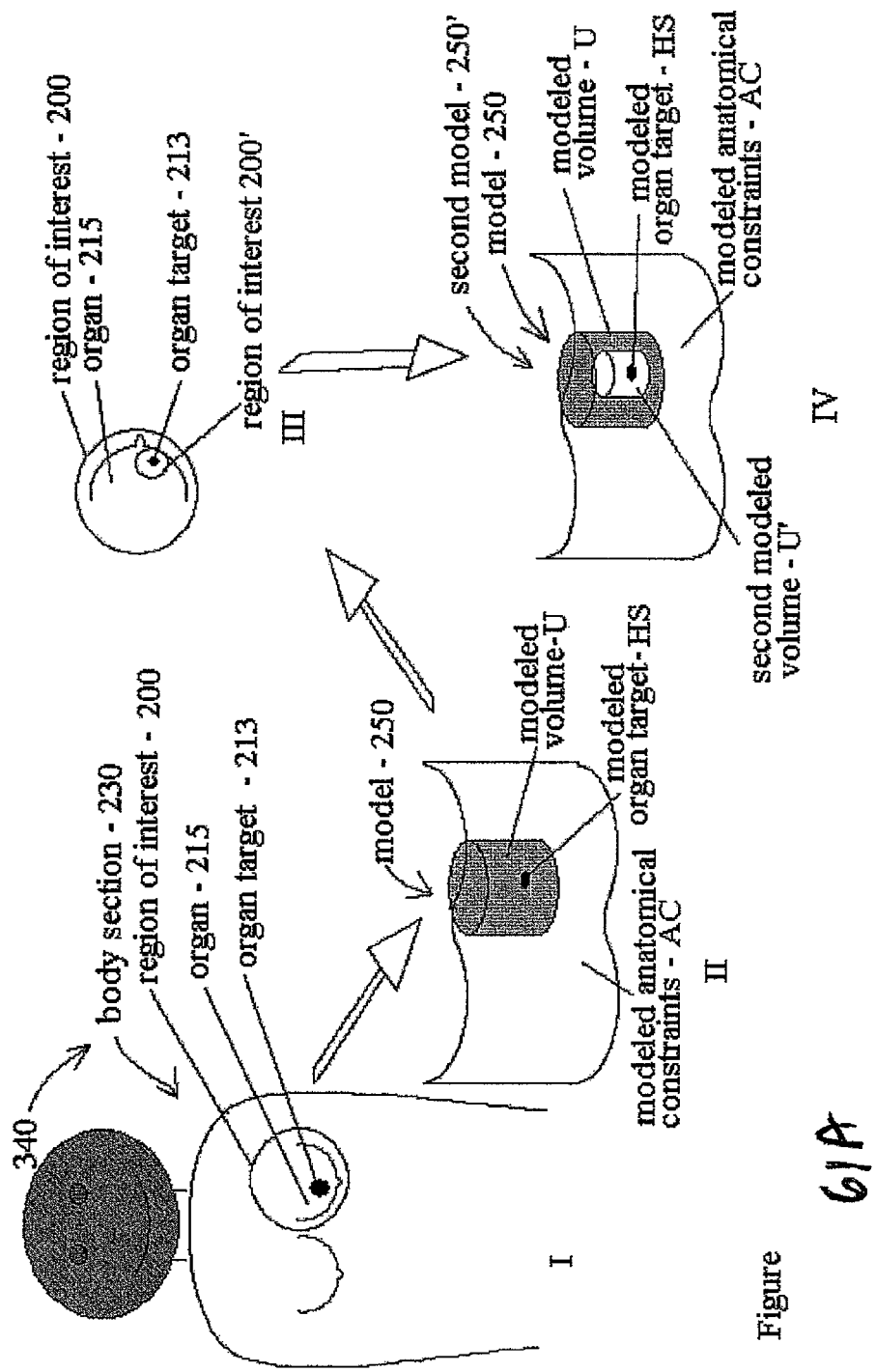
FIGS. 61A and 61B schematically illustrate a breast model, in accordance with an embodiment of the present invention.

Referring further to the drawings, FIG. 61A pictorially illustrates a method 340 for zooming in on a suspected pathological feature in a breast, as a process of two or more iterations, in accordance with embodiments of the present invention.

As seen in FIG. 61A, the method 340 may be described, pictorially, as follows:

In I: The region-of-interest 200, associated with the organ 215, such as the breast 215, is defined for the body section 230.

In II: The model 250 of the volume U is provided for the region-of-interest 200, possibly with one or several of the modeled organ targets HS, and within the anatomical constraints AC, for obtaining the optimal set of views for the region-of-interest 200. The optimal set of views is then applied to the region-of-interest 200, encompassing the breast 215 of the body section 230.

In III: When the suspected organ target 213 is identified, in vivo, in the breast 215, by radioactive-emission measurements at the optimal set of views, a second, inner region-of-interest 200' is defined, encircling the suspected pathological feature.

In IV: A second model 250' of a second volume U' is provided for the second, inner region-of-interest 200', preferably, with at least one modeled organ target HS, simulating the suspected organ target 213, for obtaining an optimal pathology set of views for the second region-of-interest 200'. The second, pathology set of views is then applied to the second, inner region-of-interest 200' of the body section 230.

Figure 61B:
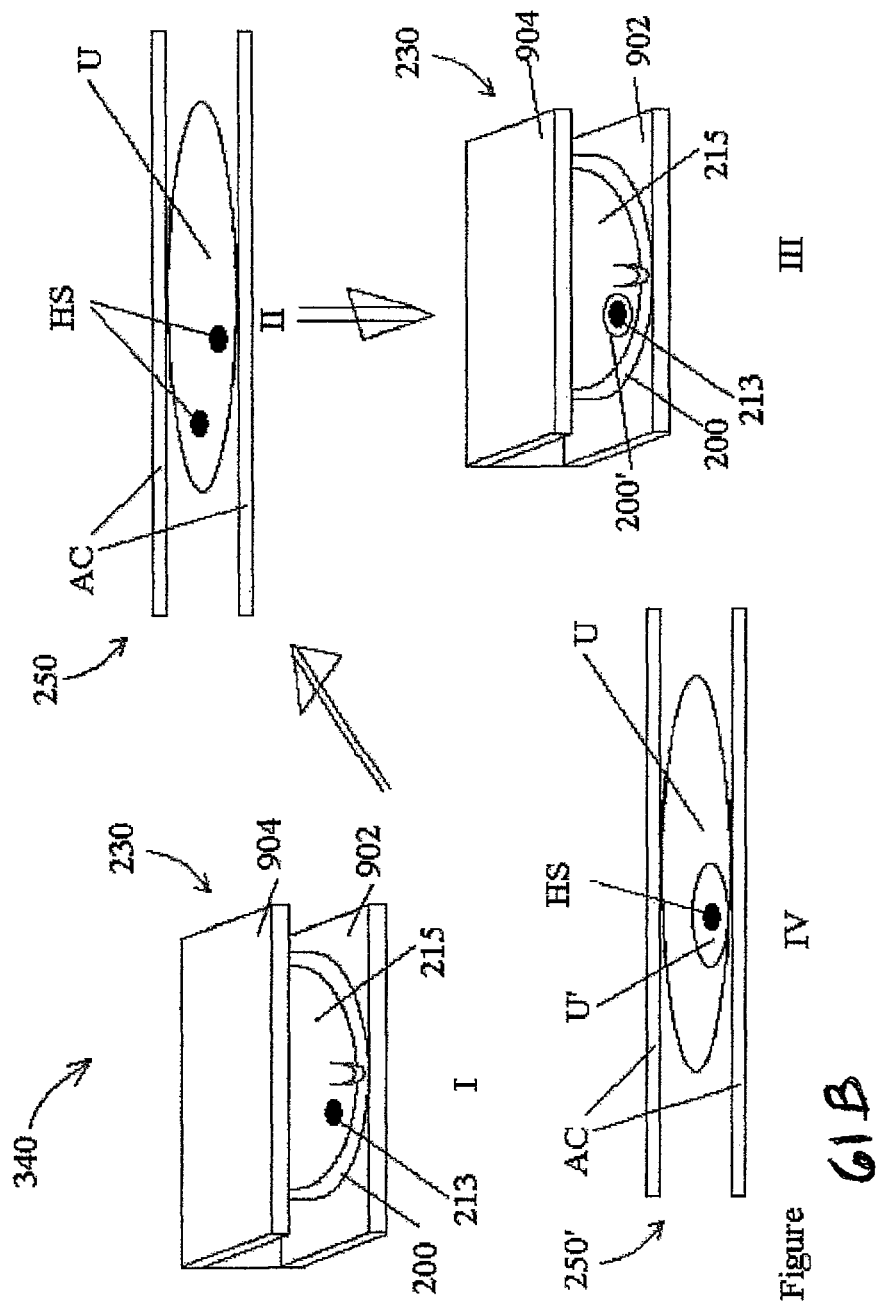

Alternatively, as seen in FIG. 61B, the method 340 may be described, pictorially, as follows:

In I: The region-of-interest 200, associated with the organ 215, such as the breast 215, is defined for the body section 230, when compressed between two plates 902 and 904, for example, mammograph plates.

In II: The model 250 of the volume U is provided for the region-of-interest 200, possibly with one or several of the modeled organ targets HS, and within the anatomical constraints AC, representing the mammograph plates, for obtaining the optimal set of views for the region-of-interest 200. The optimal set of views is then applied to the region-of-interest 200, encompassing the organ 215 of the body section 230.

In III: When the suspected organ target 213 is identified, in vivo, in the organ 215, by radioactive-emission measurements at the optimal set of views, a second, inner region-of-interest 200' is defined, encircling the suspected organ target 213.

In IV: A second model 250' of a second volume U' is provided for the second, inner region-of-interest 200', preferably, with at least one modeled organ target HS, simulating the suspected organ target 213, for obtaining an optimal pathology set of views for the second region-of-interest 200'. The second, pathology set of views is then applied to the second, inner region-of-interest 200' of the body section 230.

It will be appreciated that this camera system may also be used as a PET.

FIGS. 61A-61B schematically illustrate the modeling of a breast in accordance with embodiments of the present invention. However, generally the breast is tested when compressed, as described hereinbelow.

Mammography is currently the most effective method of screening for breast cancer, for the detection of early non-palpable tumors. In essence, it involves compressing the breast between two plates, a support plate and a compression plate, and passing x-rays through the compressed breast. The compression is desirous both in order to spread the breast fatty tissue thin, to reduce its attenuation, and in order to fix the breast tissue, with respect to a frame of reference, so that the x-ray image may be correlated with a surgical tool frame of reference, such as a biopsy needle frame of reference, for guiding the surgical tool to a suspected location on the x-ray image, without the breast tissue moving between the taking of the x-ray image and the guiding of the surgical tool.

Often stereotactic mammography is applied, meaning that the x-ray head is rotated with respect to the plates, so as to provide at least two views of the fixed breast, compressed between the plates, from at least two angles, for stereo imaging.

In general, each breast is imaged separately, generally, both in a vertical direction and from the side (laterally), preferably, stereotactically. In other words, generally, at least four views of each breast are taken, two vertically and two laterally.

A surgical instrument, for example, a biopsy needle, or an ablation device, such as a cryosurgery device, an ultrasound ablation device, a knife, or a laser ablation device, may be built onto the mammograph, its frame of reference correlated with that of the x-ray image.

FIG. 62A schematically illustrates the basic mammograph 900, showing a structural support 929, which defines a frame of reference 80, and which includes a support plate 902 and a compression plate 904, the compression plate 904 being adapted for motion along an arrow 906, so as to compress a breast 909 on the support plate 902.

An x-ray tube 905 is preferably arranged so as to move within a track 907, for obtaining x-ray images of the compressed breast 909 from at least two views, so as to obtain stereotactic viewing, for depth evaluation. A film 901 is preferably arranged under the breast 909, for example, under the support plate 902, for registering the x-ray image.

Additionally, the mammograph 900 is preferably adapted for rotation, as illustrated by an arrow 908, for compressing a breast from at least two orientations, for example vertically and laterally.

A surgical tool 903, for example, a biopsy needle 903 or an ablation device 903, such as by cryosurgery or laser, or a knife 903, may be built onto the mammograph 900, its frame of reference correlated with the frame of reference 80, using position tracking devices or a linkage system, as known.

FIGS. 62B and 62C schematically illustrate a system 925 of an ultrasound imager 915, operative with the two plates 902 and 904, in accordance with embodiments of the present invention. The importance of performing ultrasound between two plates, as in the case of x-rays, is that the two plates fix the breast with respect to the frame of reference 80, and in fact, convert the breast to a rigid-like tissue, so that any suspicious findings can be located by the surgical tool 903.

In FIG. 62B, the ultrasound imager 915 is arranged to slide along tracks 917, for example, on the compression plate 904, while a layer of gel 913 or hydrogel 913, between the compression plate 904 and the breast 909 ensures good contact for ultrasound imaging. In this manner, an ultrasound image, correlated to the frame of reference 80, when the breast is under compression, may be obtained.

Alternatively, as seen in FIG. 62C the ultrasound imager 915 may be built onto the structural support 929, its frame of reference correlated with the frame of reference 80, using position tracking devices or a linkage system, as known.

Referring further to the drawings, FIGS. 63A-63E schematically illustrate a radioactive-emission camera 1000 for the breast, for operation with the mammograph 900 of FIG. 62A, or for operation with another system, wherein a breast is compressed between two plates, in accordance with embodiments of the present invention.

Figure 63A:
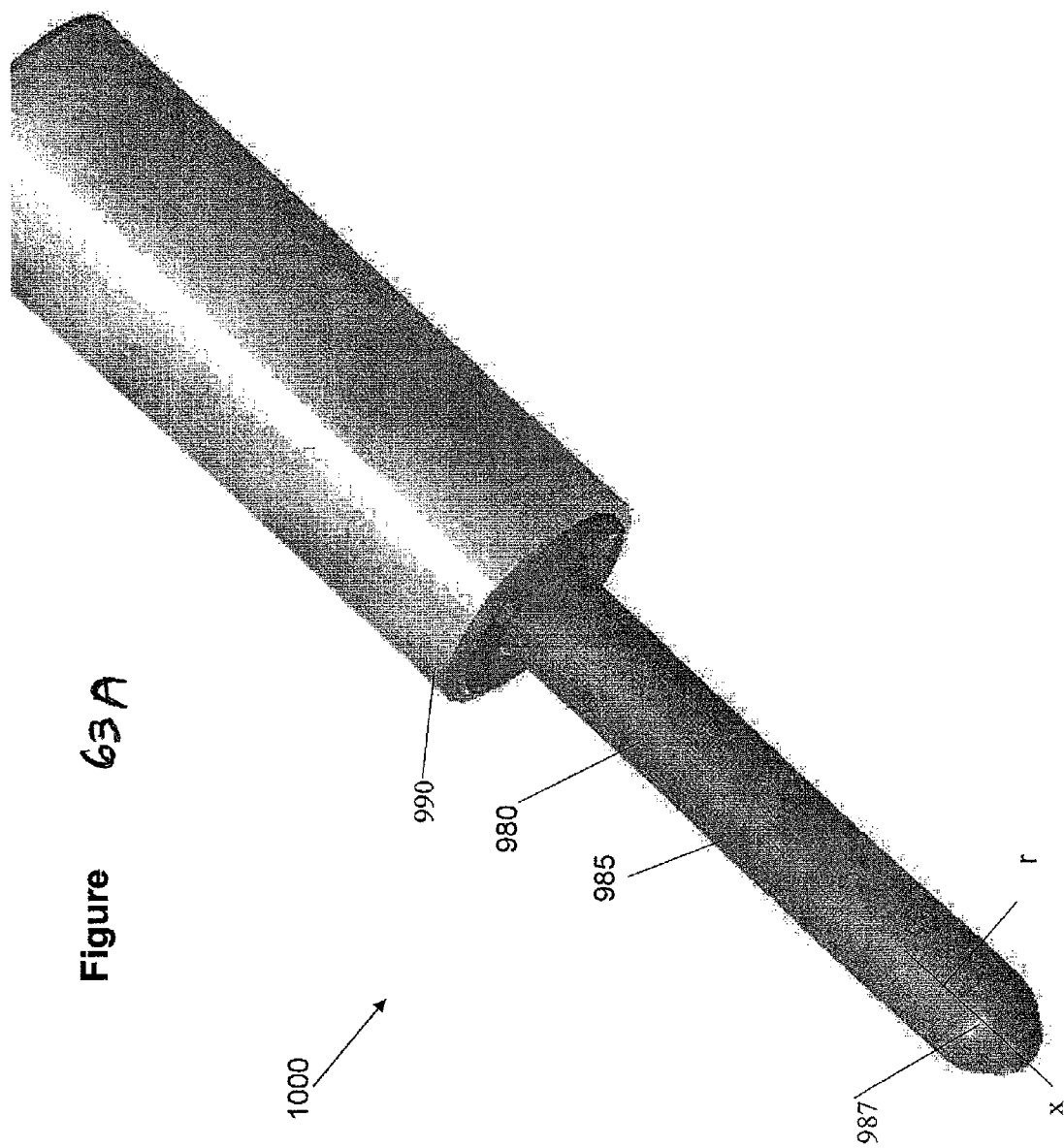

FIG. 63A schematically illustrates an external appearance of the radioactive-emission camera 1000, for the breast. The camera 1000 has a driving portion 990 and an imaging portion 980, enclosed in a sheath 985. The imaging portion 980 defines cylindrical coordinates 987 of a longitudinal axis along the x-axis, and an r-axis, perpendicular to the longitudinal axis.

Figure 63B:
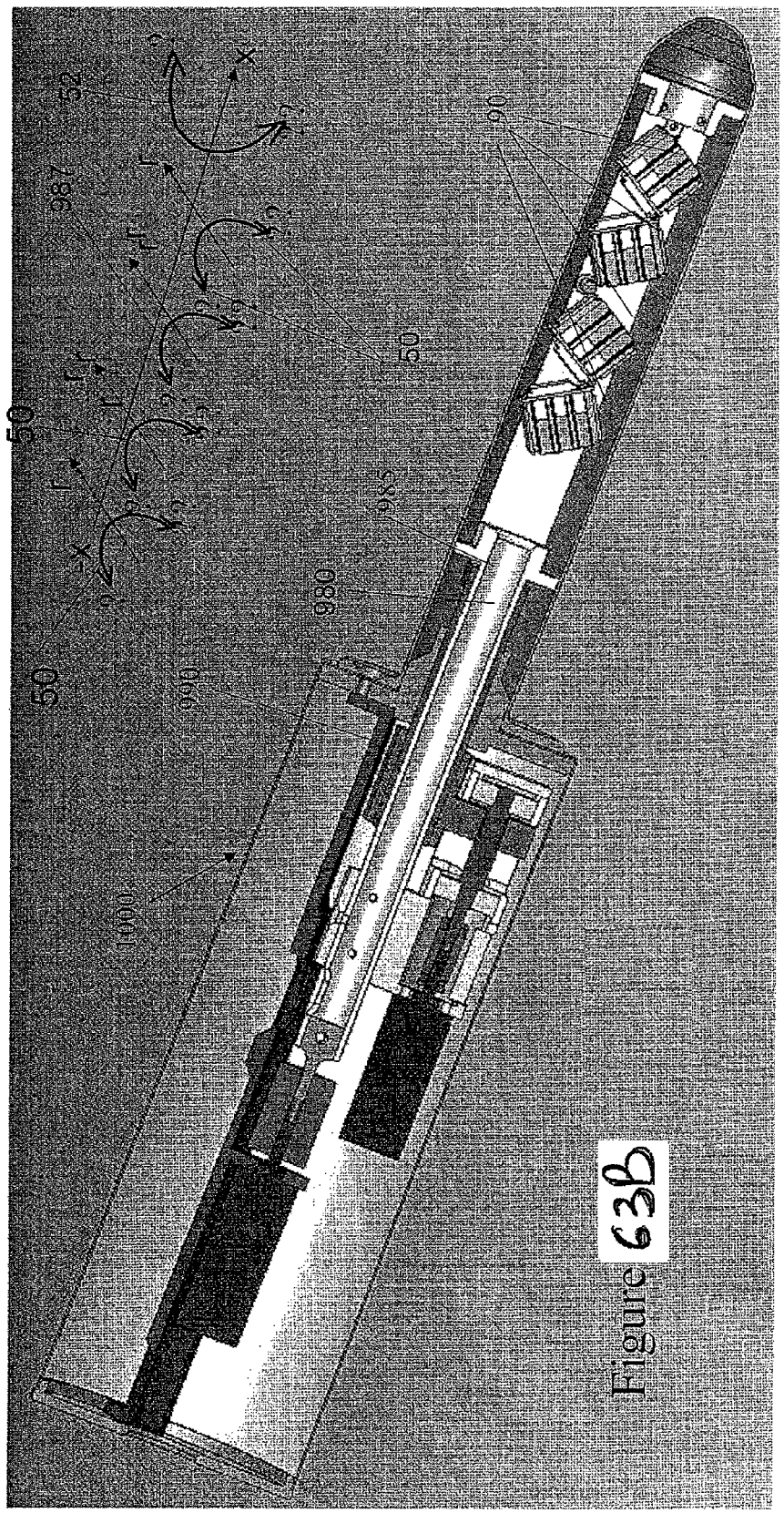
Figure 63C:
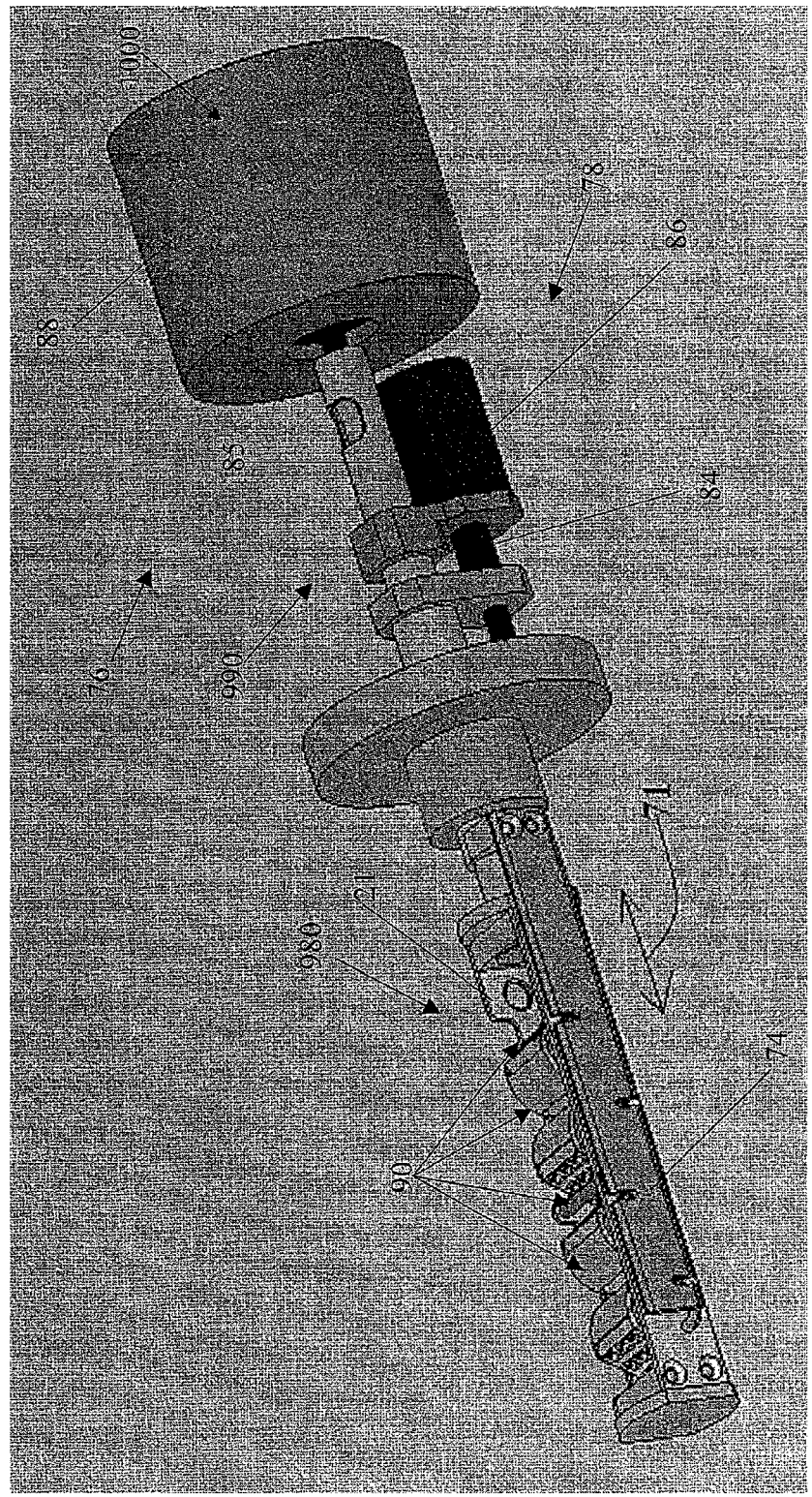

FIGS. 63B-63C schematically illustrate an internal structure of the radioactive-emission camera 1000, for the breast. The imaging portion 980 includes several of the blocks 90, for example, between two and six of the blocks 90, arranged within the sheath 985. It will be appreciated that another number, which may be larger or smaller, and which may be odd or even, may be employed.

In FIG. 63B, the motions experienced by the blocks 90 are illustrated with respect to the cylindrical coordinates 987 of x; r.

A first motion is a rotational motion of all the blocks 90, moving as a single body, with the shaft 85 and the internal structure 21, around the x-axis, in the direction between +ω and −ω, as illustrated by the arrow 52. The first motion is powered by the motor 88.

A second motion is an oscillatory motion of the individual blocks 90, powered by the secondary motor 86, the secondary shaft 84, and the motion transfer link 74, the motion transfer link 74 moving in a linear, sliding motion, as shown by the arrow 71.

At each orientation of the internal structure 21 with respect to ω, around x, the second, oscillatory motion about r takes place, individually by each of the block 90, the oscillatory motion about r being between −φ and +φ, as illustrated by the arrow 50, and as taught hereinabove, with reference to FIGS. 20A-20H.

Thus, the overall motion is as illustrated hereinabove, with reference to FIG. 23C and FIG. 20H.

Further as seen in FIG. 63C, the rotational motion in the direction of the arrow 52 is provided by a motor 88 and the shaft 85, which together form the motion provider 76. The motor 88 may be an electric motor, for example, a servo motor. The oscillatory motion in the direction of the arrow 50 is provided by a secondary motor 86, a secondary shaft 84 and a motion transfer link 74. The secondary motor 86 may also be an electric motor, for example, a servo motor. The secondary motor 86, secondary shaft 84 and the motion transfer link 74, together, form the secondary motion provider 78, for the oscillatory motion, in the direction of the arrow 50.

Thus, for the radioactive-emission camera 1000, for the breast:

i. The different blocks 90 provide views from different orientations; and ii. The different blocks 90 may change their view orientations independent of each other.

It is important to point out that during the operation of the camera 1000, the sheath 985 of the imaging portion 980 (FIGS. 63A and 63B) remains stationary, while the internal structure 21 (FIG. 63C) rotates around the x-axis. The sheath 985 may be formed of a carbon fiber, a plastic, or another material, which is substantially transparent to nuclear radiation.

FIGS. 63D and 63E illustrate further the oscillatory motion of the blocks 90, within the sheath 985, as described by the arrows 50, by showing the blocks 90 at different positions, along their oscillatory travel. FIGS. 63D and 63E further illustrate a viewing side 986 and a back side 988 for the camera 1000.

Referring further to the drawings, FIGS. 64A-64M schematically illustrate systems 910, which include the radioactive-emission cameras 1000 for the breast, operating with systems, in which a breast is compressed between two plates, for example, as in the mammograph 900, in accordance with embodiments of the present invention.

Preferably, as seen in FIGS. 64A and 64B, the cameras 1000 are mounted onto the two plates, the compression plate 904, and the support plate 902, such that their viewing sides 986 face each other. Preferably, the cameras 1000 are aligned with the x-axis, as seen. Alternatively, the cameras 1000 may be aligned with the y-axis. It will be appreciated that the cameras 1000 may be mounted only on one plate, the compression plate 904 or the support plate 902.

Additionally, as seen in FIG. 64C, one or several of the cameras 1000 may be mounted as edge cameras, for positioning at edges 992 and 994, supplementing the cameras 1000 mounted on the plates, for obtaining views from the sides of the compressed breast.

Figure 64E:
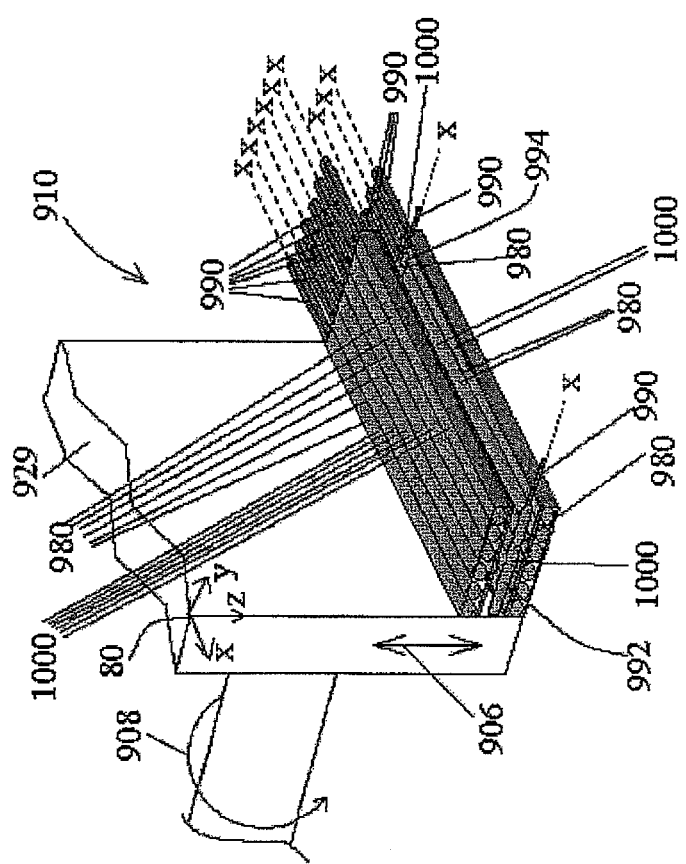
Figure 64E:
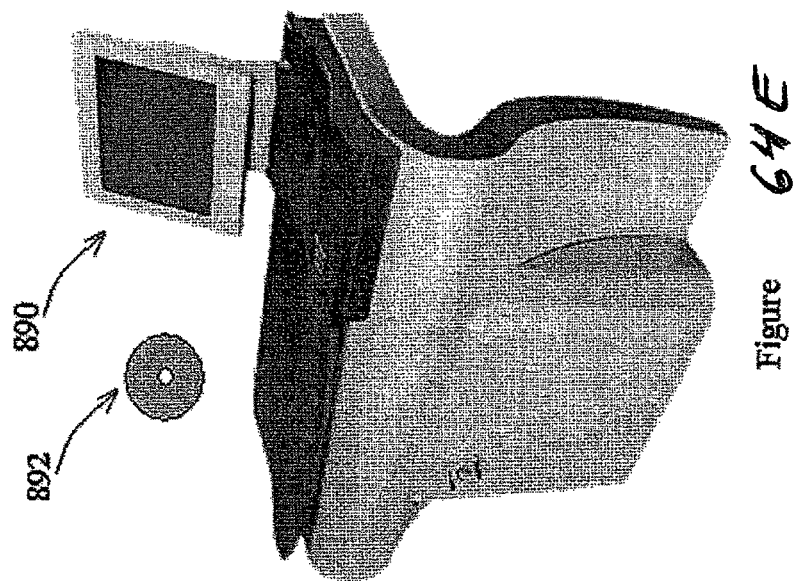
Figure 64D:
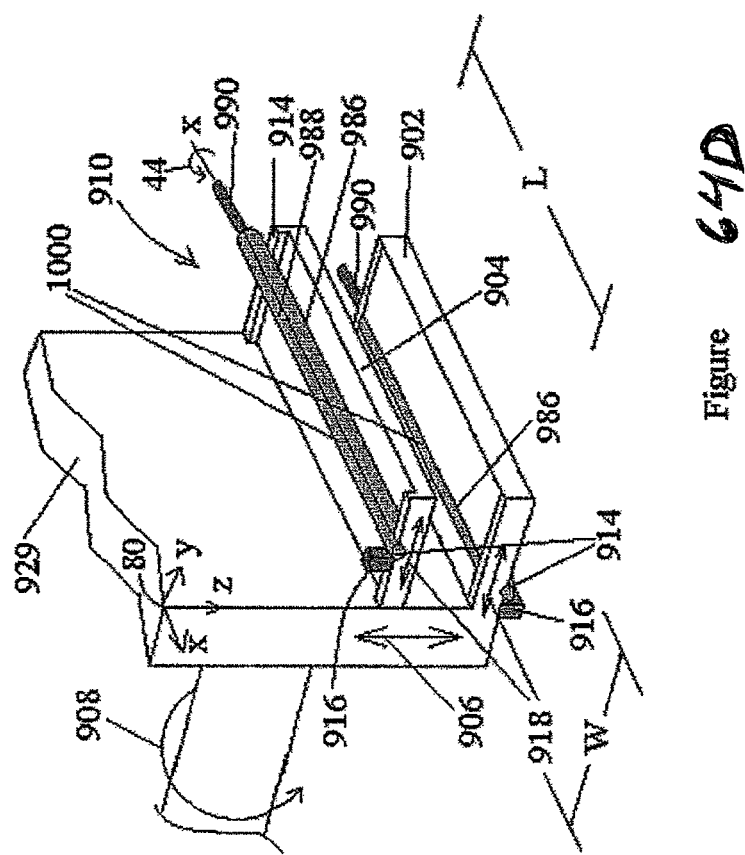

An alternative embodiment is illustrated in FIG. 64D, wherein a single one of the cameras 1000 may be mounted on each of the plates 902 and 904, the camera 1000 being adapted for travel along a track 914, in a direction of an arrow 918, by a dedicated motion provider 916, thus providing the views that a plurality of the cameras 1000 would have provided, as illustrated in FIGS. 64A-64B.

It will be appreciated that edge cameras 1000, may be added to the embodiment of FIG. 64D, in a manner similar to that of FIG. 64C.

FIG. 64E schematically illustrates a control unit 890, for controlling the motions of the blocks 90 (or the detecting units 12, when not arranged in blocks) of the cameras 1000 and for analyzing the measurements and constructing the images. Preferably, a single control unit is used both for the x-ray imager, or the ultrasound imager 915, on the one hand, and the radioactive-emission cameras 1000, on the other. Alternatively, individual control units may be used, one for each modality. Alternatively, the system 910 for the breast is provided with a storage device 892, such as a CD or a disk, which contains the software for operating the system 910 for the breast with an existing computer on the site. It will be appreciated that the control unit 890 may be a PC, a laptop, a palmtop, a computer station operating with a network, or any other computer as known.

In accordance with embodiments of the present invention, frames may be provided for mounting the radioactive-emission cameras 1000 on the plates 902 and 904.

Figure 64H:
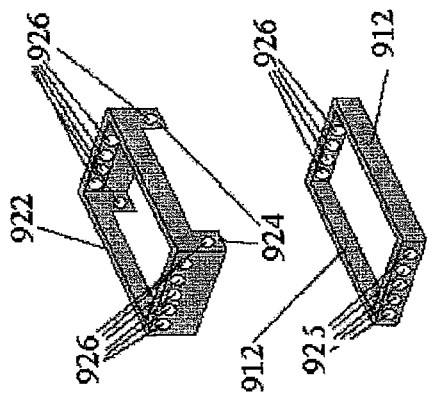
Figure 64I:
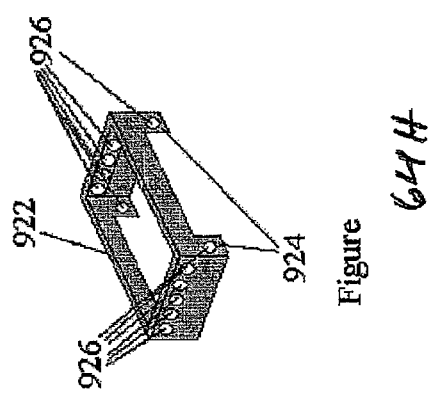
Figure 64G:
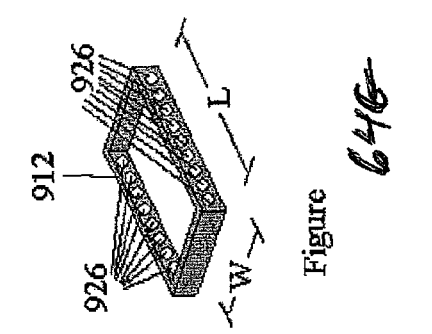
Figure 64F:
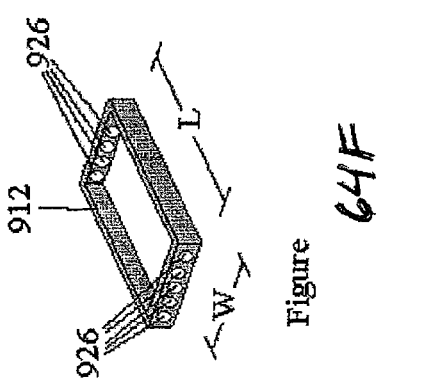

As seen in FIG. 64F, a frame 912 may be provided for either the support plate 902 or the compression plate 904, designed for accepting the cameras 1000 lengthwise, by inserting the cameras 1000 in holes 926.

Alternatively, as seen in FIG. 64G, the frame 912 may be designed for accepting the cameras 1000 widthwise.

Additionally, as seen in FIG. 64H, a frame 922 is designed for accepting the cameras 1000 widthwise or lengthwise, wherein the frame 922 further includes an edge section 924, for supporting the edge cameras of FIG. 64C.

Furthermore, as seen in FIG. 64I, two complementary frames may be provided, one designed as the frame 922, for accepting the cameras 1000 lengthwise (or widthwise) along the plate and for accepting the edge cameras, as illustrated in FIG. 64H, and the other, designed as the frame 912, for accepting the cameras 1000 lengthwise (or widthwise) along the plate.

Figure 64K:
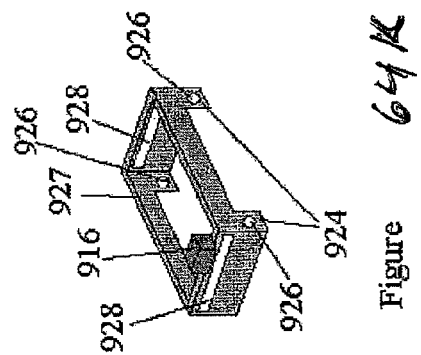
Figure 64J:
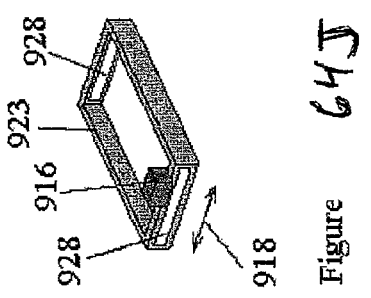

As seen in FIG. 64J, a frame 923 may be designed for accepting a single one of the cameras 1000, lengthwise, adapted for sliding widthwise along the plate, in a channel 928, by the dedicated motion provider 916. Alternatively, the frame 923 may be designed for accepting the camera 1000 widthwise, adapted for sliding lengthwise.

As seen in FIG. 64K, a frame 927 may be designed for accepting a single one of the cameras 1000, for example, lengthwise, adapted for sliding widthwise along the plate, in a channel 928, by the dedicated motion provider 916, wherein the frame 927 further includes the edge section 924, for supporting the edge camera 1000 of FIG. 64C.

In accordance with embodiments of the present invention, nuclear imaging by radioactive-emissions, co-registered with x-ray mammography, may be obtained by a method 1010, illustrated in FIG. 64L, in flowchart form, as follows:

in a box 1012: the breast is compressed between the plates;
in a box 1014: an x-ray mammography is performed, as seen in FIG. 62A, preferably from at least two orientations of the x-ray tube 905;
in a box 1016: the cameras 1000 are mounted on the plates, and radioactive-emission measurements are performed;
in a box 1018: where necessary, the surgical tool 903 may be employed, while the breast is still compressed between the two plates.

It will be appreciated that the order of the steps of boxes 1014 and 1016 may be reversed.

Preferably, the images of the x-ray mammography and the nuclear imaging are co-registered and analyzed together.

Figure 64M:
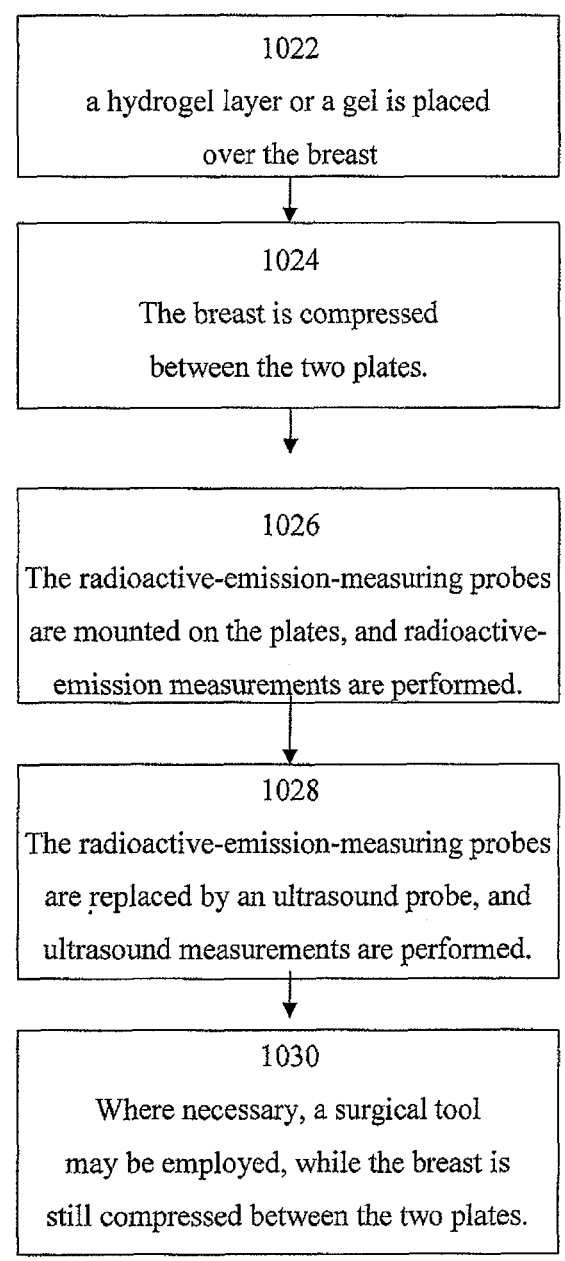

However, it will be appreciated that only nuclear imaging by radioactive-emission measurements may be performed, without x-ray imaging.

Where ultrasound imaging co-registered with nuclear imaging by radioactive-emissions is desired, a method 1020, illustrated in FIG. 64M, in flowchart form, applies, as follows:

in a box 1022: a hydrogel layer is placed between one of the plates, for example, the compression plate 904 and the breast, or a gel is spread over the breast, so as to serve as an ultrasound interface between the plate and the breast;
in a box 1024: the breast is compressed between the plates;
in a box 1026: the cameras 1000 are mounted on the plates, and radioactive-emission measurements are performed;
in a box 1028: the cameras 1000 are replaced by an ultrasound imager, for example as illustrated in FIG. 62B or 62C, and ultrasound imaging is performed;
in a box 1030: where necessary, the surgical tool 903 may be employed, while the breast is still compressed between the two plates.

It will be appreciated that the order of the steps 1026 and 1028 may be reversed.

Preferably, the images of the x-ray mammography and the nuclear imaging are co-registered and analyzed together.

Figure 65A:
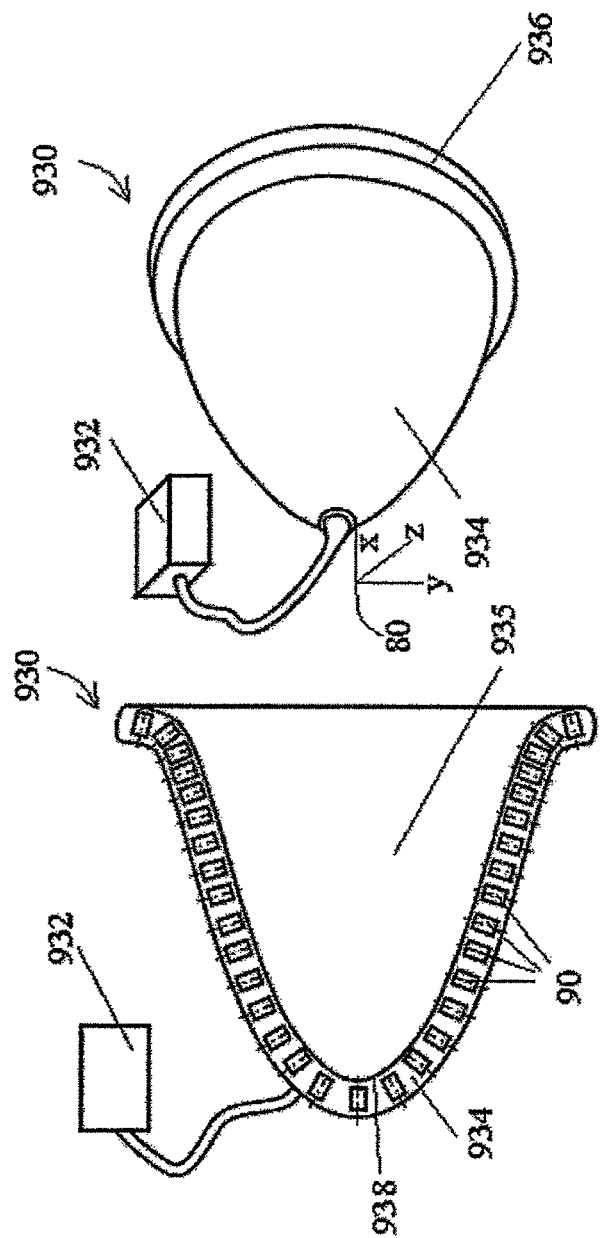
FIGS. 65A-65C schematically illustrate an imaging camera for radioactive-emissions of the breast, in accordance with an embodiment of the present invention.
Figures 65B, 65C:
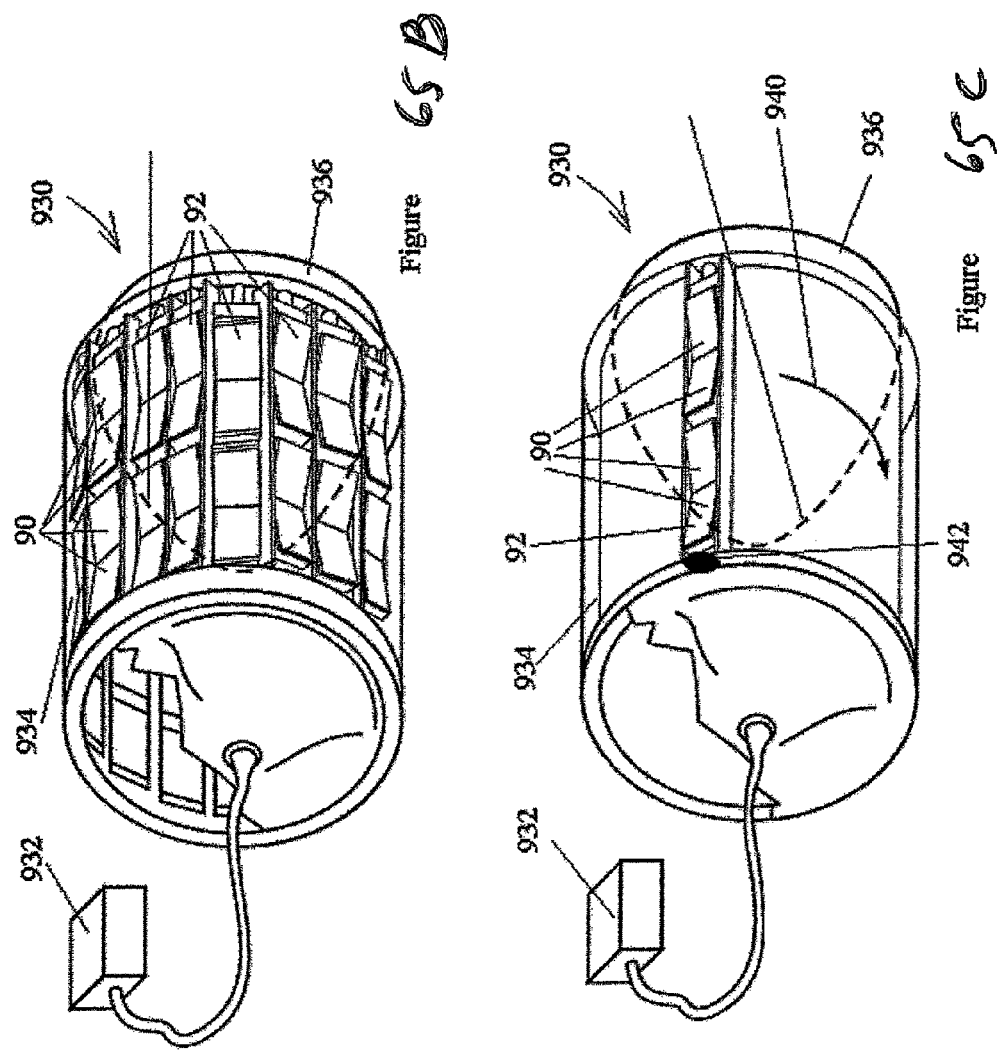

Referring further to the drawings, FIGS. 65A-65C schematically illustrate a radioactive-emission camera 930, for imaging a breast under vacuum, in accordance with another preferred embodiment of the present invention.

As seen in FIG. 65A, the camera 930 includes a vacuum cup 934, shaped as a cone and connected to a vacuum system 932, for creating a vacuum in a cavity 935 within. The vacuum in the cavity is used both to stretch the breast so as to spread the fatty tissue thin and to fix the breast tissue with respect to a frame of reference, so a surgical device may be employed, where needed, while the breast tissue remains fixed in place.

A vacuum ring 936, for example of natural or synthetic rubber, helps maintain the vacuum in the cup 934.

The vacuum cup 934 defines the frame of reference 80 and a plurality of the blocks 90 are arranged along the walls 938 of the suction cup 934, each adapted for at least one, and preferably two rotational motions, for example, as illustrated with reference to FIGS. 22I-22M and FIGS. 22Q-22R, or FIGS. 22N-22P, for imaging a breast in the cavity 935. Alternatively, the blocks 90 may be arranged in the assemblies 92, as illustrated with reference to FIGS. 22A-22H.

A surgical tool may be attached to the camera 930, and correlated to its frame of reference, for example as taught with reference to FIG. 62B.

The motions of the blocks 90 are preferably automatic, controlled by the control unit 890 (FIG. 64C).

Preferably, the inner walls 938 of the cup 934 are substantially transparent to radioactive emission.

FIG. 65B schematically illustrates an embodiment wherein a vacuum cylinder 934 is used in place of a conical cup, and the blocks 90 are arranged in assemblies 92, for example, as illustrated with reference to FIGS. 16E and 24A-24H.

FIG. 65C schematically illustrates an embodiment wherein the vacuum cylinder 934 is used, and a single one of the assemblies 92 is arranged for traveling around the cylinder 934, in the direction of an arrow 940, by a motion provider 942.

Referring further to the drawings, FIGS. 66A-66F schematically illustrate a radioactive-emission camera 950, for imaging the breasts in the natural state, in accordance with another preferred embodiment of the present invention.

As seen in FIG. 66A, the radioactive-emission camera 950, for imaging the breasts in a natural state, is designed as an extracorporeal unit which may be positioned against the breasts, operating as taught with reference to any one of FIGS. 20A-22R. Preferably, the radioactive-emission camera 950, for imaging the breasts is attached to a gantry 952, which may provide adjustments as seen by arrows 954 and 956.

Additionally, the patient may be positioned on a chair 960, as seen in FIG. 66B.

The control unit 890 may be used for controlling the motions of the blocks 90 (FIG. 22A-22H or 22I-22R) or the detecting units 12, when not arranged in blocks, and for analyzing the measurements and constructing the images. Alternatively, the radioactive-emission camera 910 for the breast is supplied with a storage device 892, which contains the software for operating the radioactive-emission camera 910 for the breast with an existing computer on the site. It will be appreciated that the control unit 890 may be a PC, a laptop, a palmtop, a computer station operating with a network, or any other computer as known.

Figures 66D, 66E:
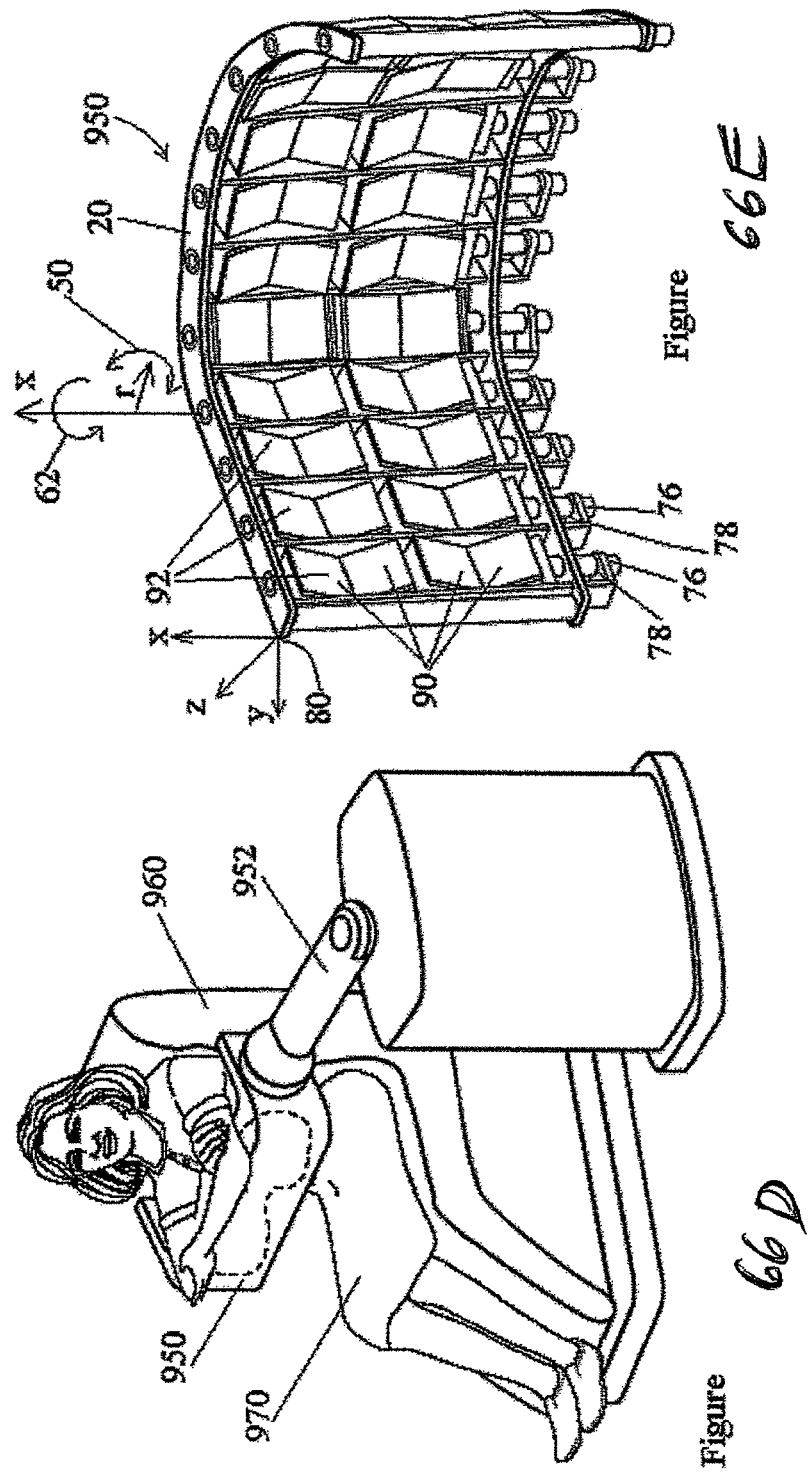

FIG. 66D schematically illustrates a woman 970 being examined by the radioactive-emission camera 950, when seated on the chair 960. It will be appreciated that the examination may also be conducted when the woman 970 is standing or lying on a bed.

FIG. 66E schematically illustrates the inner structure radioactive-emission camera 950 in accordance with a preferred embodiment of the present invention. FIG. 66E shows the overall structure 20, the parallel lines of assemblies 92, possibly of an even number, each with a dedicated motion provider 76 and a dedicated secondary motion provider 78, and the rows of blocks 90, possibly arranged in pairs, along the assemblies 92.

The camera 950 defines the frame of reference 80, while each assembly 92 has a reference cylindrical coordinate system of x; r, with rotation around x denoted by the arrow 62 and oscillatory motion about r, denoted by the arrow 50.

Figure 66F:
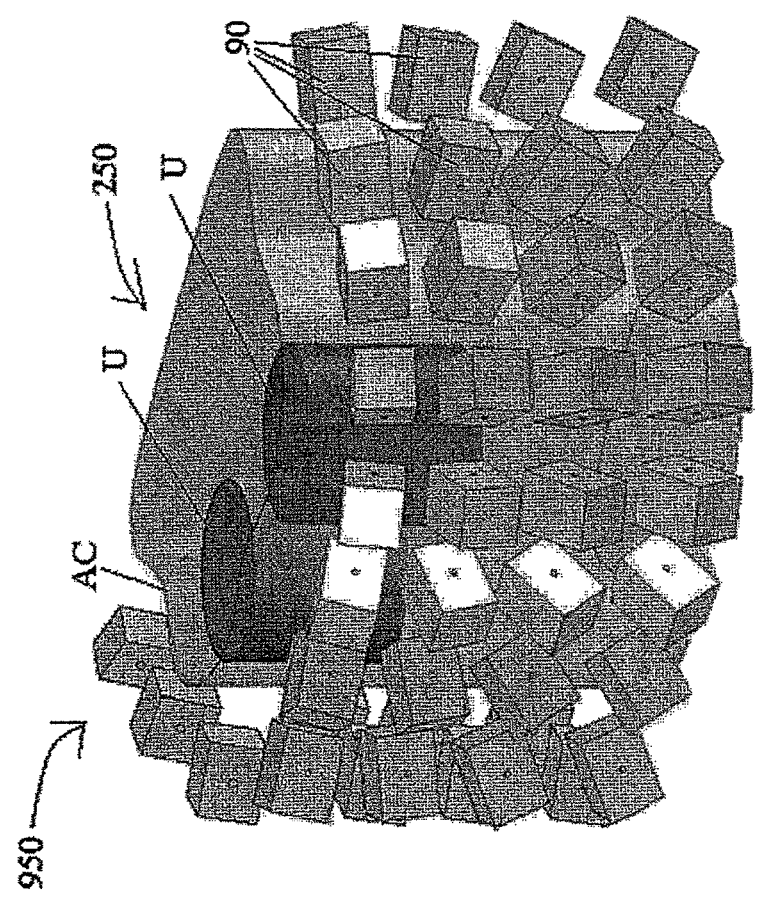

FIG. 66F schematically illustrates the model 250 of the two breasts, modeled as the volumes U, and the anatomical constraints associated with them, for determining an optimal set of views for radioactive-emission measurements.

It will be appreciated that imaging, in accordance with embodiments of the present invention relates to the imaging of the whole breast, or to a portion of the breast, the armpits near the breasts, (and) or the two breasts.

Preferably, the radiopharmaceuticals associated with the radioactive-emission camera for the breast may be Tc-99m bound to Sestamibi, a small protein molecule, made for example, by Bristol Myers Squibb, and marketed as Miraluma, used widely for breast cancer detection.

Figure 66G:
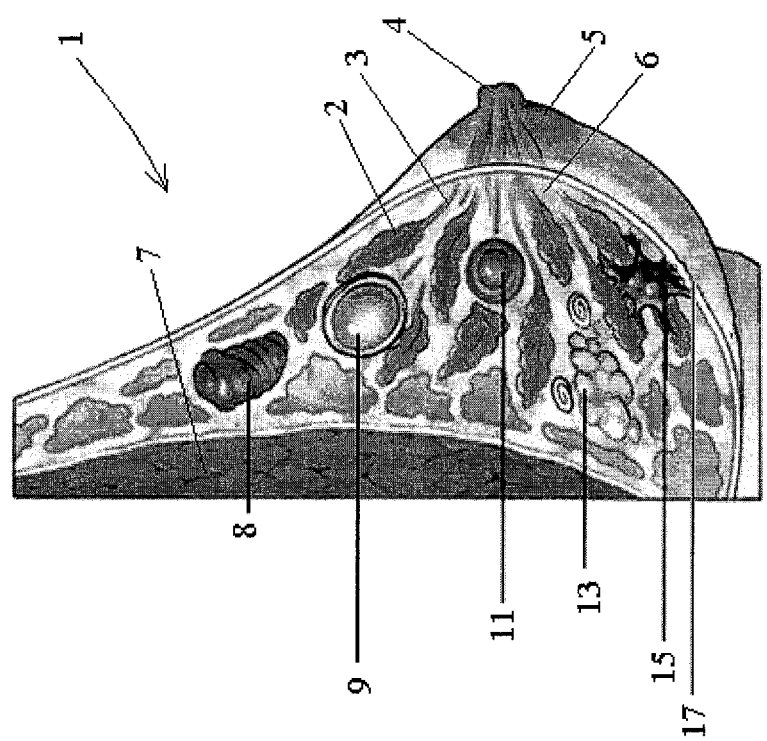

The present invention applies to detecting and differentiating between various types of breast disorders, for example as illustrated in FIG. 66G, hereinabove, as follows.

i. fibroadenomas 8, which are fibrous, benign growths in breast tissue.

ii. cysts 9, which are fluid-filled sacs and may disappear sometimes by themselves, or a doctor may draw out the fluid with a needle.

iii. a breast abscess 11, which is a collection of pus, resulting from an infection.

iv. fibrocystic breast disease 13, which is a common condition characterized by an increase in the fibrous and glandular tissues in the breasts, resulting in small, nodular cysts, noncancerous lumpiness, and tenderness, wherein treatment of the cysts may be all that is needed.

v. a tumor 15, which may be precancerous or cancerous, and which usually shows up as a white area on a mammogram even before it can be felt. In cases where the tumor 15 is cancerous, it may appear as a white area with radiating arms. A cancerous tumor 15 may have no symptoms or may cause swelling, tenderness, discharge from the nipple 4, indentation of the nipple 4, or a dimpled appearance 17 in the skin over the tumor.

Additionally, the present invention applies to detecting various types of breast cancers, such as:

i. ductal cancer, which affects the cells of the ducts;

ii. lobular cancer, which begins in the lobes or lobules of the breast; and iii. inflammatory breast cancer, which is an uncommon type of breast cancer and causes the breast to be warm, red, and swollen.

It will be appreciated that the present invention further applies to other types breast disorders, which may be cancerous, precancerous, or benign.

Additionally or alternatively, the present invention applies to secondary breast cancer, for example, originating from the lungs, or other parts of the body.

Furthermore, the radioactive-emission camera for the breast may be designed for and used on a single breast or designed for and used simultaneously on the two breasts.

It will be appreciated that although breast cancer in men and children is rare, the present invention may be used for the detection of breast cancer in men and children as well.

Overall Camera Performance

The following section reviews the overall camera performance for different camera designs and illustrates configurations which conform to body contours, so as to be as close as possible to the anatomical constraints (FIG. 5B). Additionally, the importance of distance between the organ target 213 and the detecting block 90 is explained. The camera performance is considered with respect to the following:

i. detecting efficiency;
ii. acquisition time;
iii. spatial resolution;
iv. wasteful viewing, in regard to ordinary gamma cameras;
v. adjustable design;
vi. independent viewing by each block or detecting unit;
vii. criteria for camera design;
viii. experimental results.

i. Detecting Efficiency

Referring further to the drawings, FIGS. 67A and 67B schematically illustrate the solid angle by which the radiation emission source 213 "sees" the detecting block 90. At a distance of R1, the solid angle is $\beta 1$ and at the distance of R2, the solid angle is $\beta 2$, wherein an inverse relation exists between R1 and R2 and $\beta 1$ and $\beta 2$, such that when R2>R1 then $\beta 1 > \beta 2$.

Furthermore, for the detecting block 90 of an area $\pi r^2$, at a distance R from a point source, the detecting efficiency is a function of the ratio of the detecting area $\pi r^2$ to the area of the sphere $4\pi R^2$, so as to behave as a function of $r^2/R^2$. Thus, for the detecting block 90 of a fixed detecting area, as the distance R from the source 213 increases, the detecting efficiency decreases, proportionally to $R^2$.

It will be appreciated that a similar analysis is valid for the detecting unit 12, on a pixel basis, as well.

ii. Acquisition Time

A related issue is the acquisition time, for statistically meaningful results. Radioactive emission may be described by the Poisson distribution, for which the counting error for N counts is described by $N^{1/2}$. For example, when 10,000 counts have been detected, the counting error is $10,000^{1/2}$, or 100, which is 1% of N. Where it is desired to obtain data at a predetermined level of accuracy, a minimal level of counts must be obtained. Thus, for an accuracy level of 1%, 10,000 counts must be obtained; for an accuracy level of 0.1%, 1,000, 000 counts must be obtained, and so on.

Yet, when the distance R between the source 213 and the detecting block 90 is increased, the counting efficiency falls proportionally to $R^2$ and the number of counts per minutes falls proportionally to $R^2$, and so the acquisition time required to reach a predetermined number of counts, for a predetermined accuracy level, increases proportionally to $R^2$.

iii. Spatial Resolution

Referring further to the drawings, FIGS. 68A-68B schematically illustrate the effect of the distance R on the spatial resolution.

As seen in FIG. 68A, the organ target 213 has a radius q, which may be, for example, of the order of magnitude of the radius r of the detecting block 90, so that q~r. The organ target 213 may have a distribution of activity, for example, a high-level portion 213A, a medium-level radiation portion 213B, and a relatively low-level radiation portion 213C.

As seen in FIG. 68B, given, for example, a 3×3 pixel arrangement and a collection angle β, when the block 90 is very close to the organ target 213, such that R1 is substantially zero, and given that q~r, the organ target 213 is viewed by practically all the 3×3 pixels, resulting in a high-resolution image.

As seen in FIG. 68C, at a distance R2, the organ target 213 is barely viewed by more than one pixel, resulting in a low-resolution image.

As seen in FIG. 68D, at a distance R3, the organ target 213 is viewed by less than one pixel, resulting in a very low-resolution image.

Thus, the number of pixels in the block 90 provides for a spatial resolution capability. In order for this resolution capability to be realized, however, the distance between the detecting block 90 and the organ target 213 should be as small as possible.

iv. Wasteful Viewing, in Regard to Ordinary Gamma Cameras

Referring further to the drawings, FIGS. 69A-69D schematically illustrate different view arrangements.

FIG. 69A illustrates four blocks 90A, 90B, 90C, and 90D for viewing the organ target 213, the blocks arranged around the body section 230. The block 90A, at the distance R1 from the organ target 213, is as close as possible to the external surface of the body section 230, such that it is substantially touching it. Therefore, the block 90A is at an optimal viewing position for the organ target 213. The block 90B is at a distance R2 from the organ target 213, where R2>R1, but it is still in position to view the target 213, from that distance. Therefore, the block 90B is at a suboptimal position for viewing the organ target 213. The block 90C does not view the organ target 213, yet it does view the body section 230, so it may also be considered at a suboptimal position. The block 90D does not view the body section 230, so the view of the block 90D is wasteful, in that it does not provide any information regarding the body section 230.

As FIG. 69A illustrates, blocks which substantially touch the surface of the body section 230 will always provide some information about it. Yet blocks 90 that are distant from the body section 230 may view areas altogether outside the body section 230, so their contribution is wasteful.

This point is further illustrated in FIGS. 69B-69D, which illustrate the use of a rigid camera of the prior art, for example, as taught by U.S. Pat. Nos. 6,597,940 and 6,671,541, both to Bishop et al. As may be understood from FIG. 69B-C, as the blocks 90A and 90B are brought into close proximity with the body section 230, blocks 90C, 90D, 90E and 90F are moved away from it, and their views become suboptimal or even wasteful. Conversely, as the blocks 90F and 90E are brought into close proximity with the body section 230, blocks 90D, 90C, 90B and 90A are moved away from it, and their views become suboptimal or even wasteful Similarly, as the blocks 90B, 90C, and 90D are brought into close proximity with the body section 230, the views of blocks 90F and 90A become suboptimal or even wasteful v. Adjustable Designs Referring further to the drawings, FIG. 71 schematically illustrates an adjustable PET camera 1150, in accordance with embodiments of the present invention. The PET camera 1150 is formed of a plurality of the blocks 90, placed substantially on the body section 230. Such a camera, when completely surrounding the body section 230, essentially sees all coincident emissions coming out of the body, and greatly increases the counting efficiency for PET.

Referring further to the drawings, FIGS. 72A-72E schematically illustrate adjustable cameras 1160 and 1170A-B mounted on adjustable overall structures, for conforming to contours of the body section 230, in accordance with embodiments of the present invention.

Figure 72C:
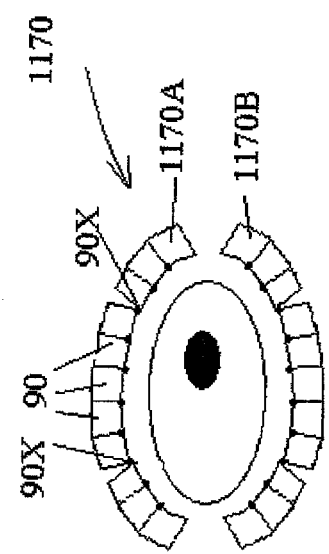
FIGS. 72A-72E schematically illustrate non-wasteful radiation detector arrays, in accordance with an embodiment of the present invention.
Figure 72A:
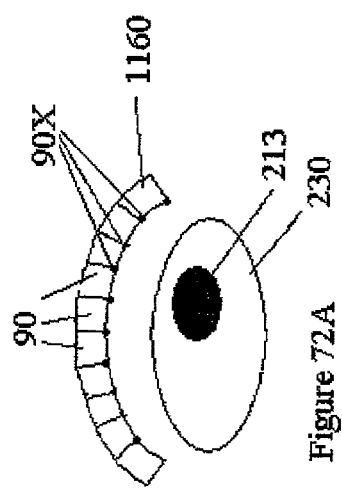
Figure 72B:
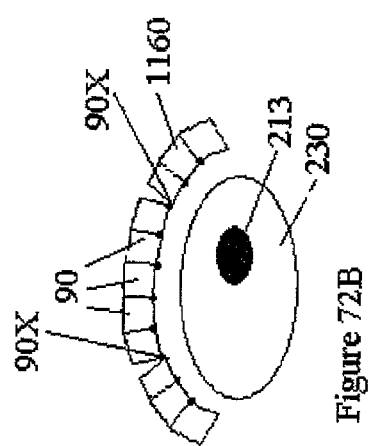

As seen in FIGS. 72A-72B, the cameras 1160 and 1170A-B include hinges 90X between the blocks 90, such that the positions of the blocks may be adjusted. Alternatively, as seen in FIG. 72C, several blocks 90 may be arranged in a row to form an assembly 92 and the camera may include hinges 90X between the assemblies 92, such that assemblies 92 may be adjusted. FIG. 72A illustrates the camera 1160 prior to the adjustment, and FIG. 72B illustrates the camera 1160 after adjustment. FIG. 72C illustrates the camera 1170, as may be used for coincident imaging or another whole body imaging.

Figure 72D:
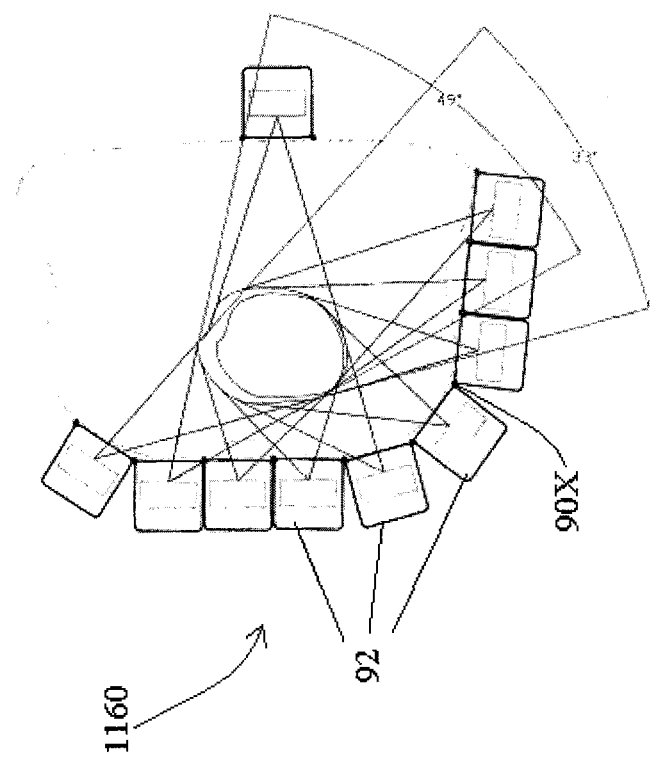

FIG. 72D schematically illustrates the viewing range of the camera 1160, in accordance with the present embodiment.

Figure 72E:
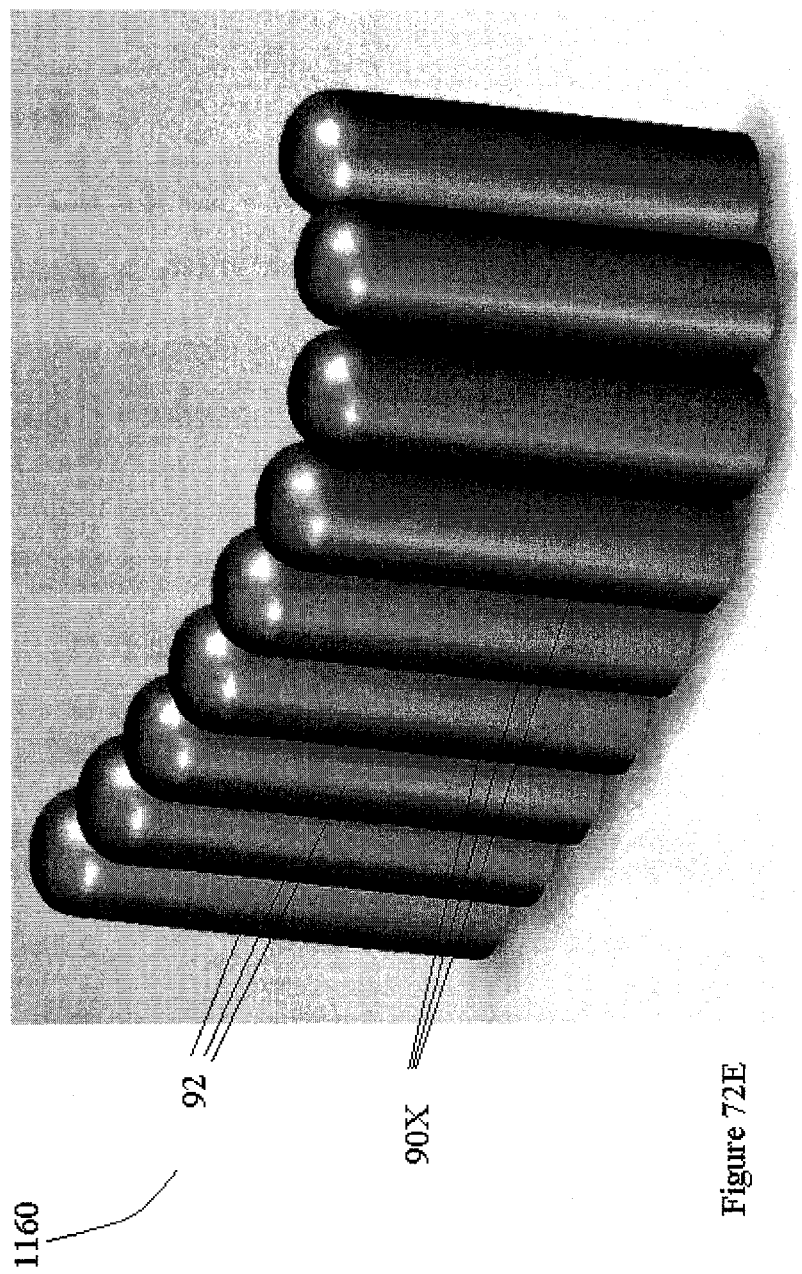

FIG. 72E schematically illustrates a pictorial view of the camera 1160, of the present embodiment.

Figure 73:
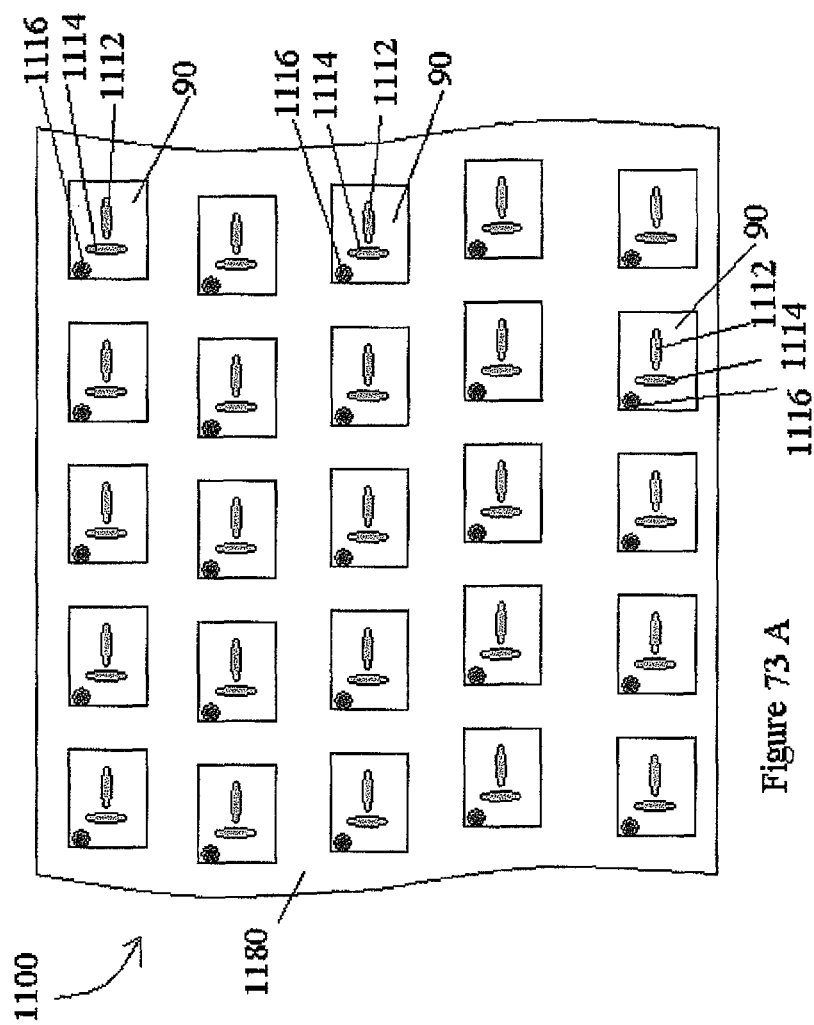
FIGS. 73A and 73B schematically illustrate non-wasteful radiation detector arrays, in accordance with an embodiment of the present invention.
Figure 73B:
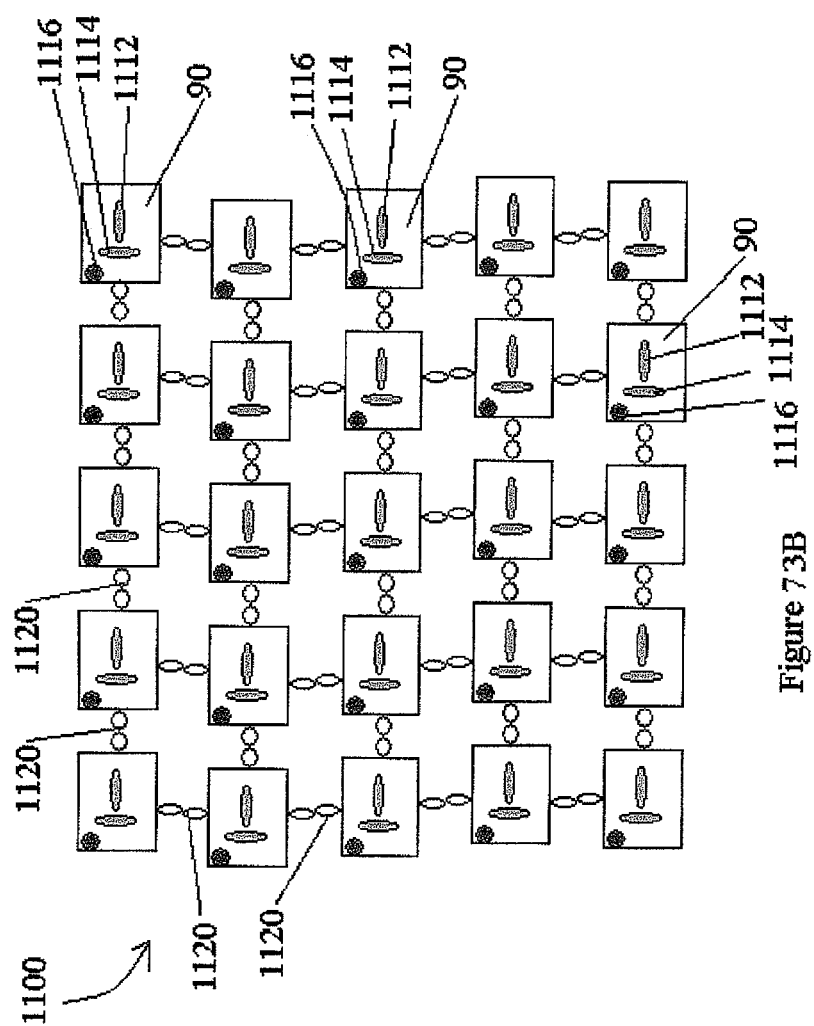

Referring further to the drawings, FIGS. 73A-73B schematically illustrate adjustable cameras 1100, in accordance with another embodiment of the present invention.

FIG. 73A illustrates the blocks 90 mounted on a flexible structure 1180 such as cloth, vinyl or the like. Each assembly 90 preferably includes a position tracking device 1116 and at least one but preferably two or more motion providers, such as motion providers 1114 and 1112, to provide the assembly 90 with at least one, but preferably two, three, or possibly up to six degrees of motion.

FIG. 73B illustrates the blocks 90 linked by chains 1120, to provide the adjustable character.

It will be appreciated that the position tracking device may be magnetic, electromagnetic, optical, or another device, as known. For example, each block 90 may include a Minibird™. Alternatively, two cameras may track the position of each block 90. Alternatively, other tracking methods may be used.

Referring further to the drawings, FIGS. 74A-74B schematically illustrate adjustable cameras 1200, in accordance with still another embodiment of the present invention. The cameras 1200 are constructed as detecting modules 1216, which contain blocks 90 or detecting units 12, the detecting modules 1216 being arranged on tracks 1212 which are associated with a coordinate system 1214. Each of the detecting modules 1216 includes an encoder 1218, operative as the position tracking device 124 (FIGS. 2 and 3A), as known. The modules move along the tracks 1212 by means of a motion provider (not shown) while sending information regarding their coordinates together with measurements taken to the data-processing system 126 (FIGS. 2 and 3A).

vi. Independent Viewing by Each Block or Detecting Unit

In accordance with embodiments of the present invention, each block 90 of the adjustable camera construction (FIGS. 71-73B) or each detecting unit 12, where single-pixel detecting units 12 are used, may be provided with at least one, and preferably, two, three, or as many as six degrees of motion such as, for example, rotational motion around the x, y, and z, axis, oscillatory motion about these axes, or translational motion along these axes. In this manner, each block 90 may be preprogrammed to view each portion of the body section 230, in accordance with some predetermined schedule. For example, one of the blocks 90 may perform oscillatory motion, while an adjacent one of the blocks 90 may perform rotational motion. Thus, areas that are known to pose little susceptibility to abnormalities may be viewed differently from areas that are more susceptible to abnormalities. Additionally, active vision may take place. For example, where something suspicious is viewed, a decision to view it for a longer period of time and to thus obtain better data may be made by the data-processing system 126 (FIG. 2), so that the associated blocks 90 may be instructed to view an area longer. Alternatively, where not enough data has been acquired for the desired level of accuracy, more data may be collected, i.e., the number of counts may be increased so as to reduce the margin or error to 1%. In other words, when using multiple, independent blocks 90 or detecting units 12, each may spend more time in one region than in another, and each may spend the time needed to reach a desired level of accuracy. Thus, one block or detector may spend a long time (within a predetermined limit) in one region, while another may spend less time and move on to another angle and position so as to provide a new view. Similarly, one block 90 or detecting unit 12 may use large steps, while another may use fine steps.

The present invention relates to situations that are unlike current systems, where the detecting units or blocks are fixed, with respect to each other, so individual optimization by block or by detecting unit is not possible.

The reverse is also possible, and a decision to obtain data for less than originally intended may be made. Also, cursory imaging may be performed and, where necessary, a decision may be made to acquire more data. It will be noted that the blocks along the camera may be designed differently and may include different collimators, for the different portions of the body section 230, such as those taught with reference to FIGS. 17C-17F. For example, the blocks 90 at the edge may have wide-angle collimators and those that are in the central portion of the blocks 90 may have narrow collimators.

vii. Criteria for Camera Design

An overall camera design may be based on the following criteria:

i. a distance from the surface of the body section 230 to the detecting unit 12 or the block 90 which is no greater than 5 cm and, preferably, no greater than 3 cm, and, more preferably, no greater than 2 cm.

ii. wasteful viewing for less than 50% of the viewing of each detecting unit 12 or block 90 and, preferably, less than 30% of the viewing time and, more preferably, less than 20% of the viewing time.

iii. Substantially no detecting unit 12 or block 90 is positioned so as not to view the body structure at all.

iv. a collimator solid collection angle of at least 0.0005 steradians, or at least 0.001 steradians, or at least 0.003 steradians, or at least 0.005 steradians, or at least 0.01 steradians, or at least 0.03 steradians, or at least 0.05 steradians, or at least 0.08 steradians.

v. alternatively, a collimator collection solid angle which is configured to view substantially a whole organ, such as a heart, or substantially a large portion of the organ.

vi. a block size along the rotational axis, for the block 90, of less than 10 cm and, preferably, of less than 6 cm and, more preferably, of less than 2 mm.

vii. independent motion control for each of the blocks 90, along at least one rotational axis, preferably along at least two rotational axes and, more preferably, along the three rotational axes and the three translational axes.

Wherein a portion of these or all of these may be incorporated into the camera design.

viii. Experimental Results

Figure 75A:
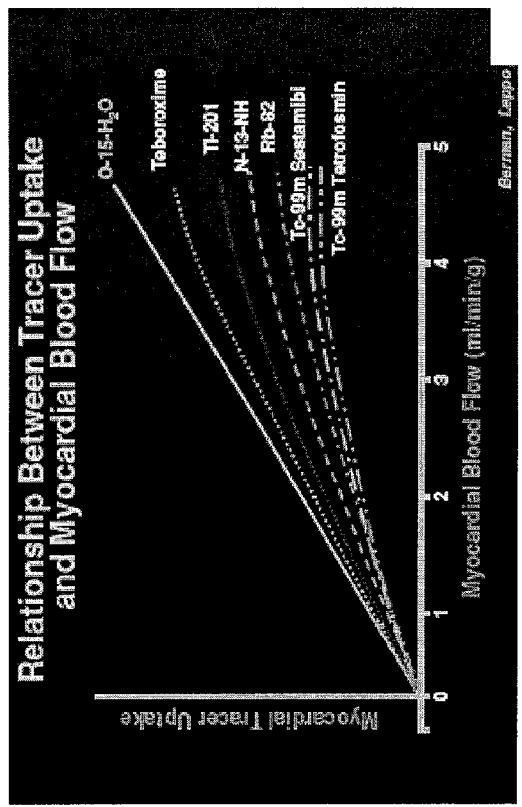
FIGS. 75A and 75B illustrate Teboroxime physiological behavior, according to Garcia et al. (Am. J. Cardiol. $51^{st}$ Annual Scientific Session, 2002).
Figure 75B:
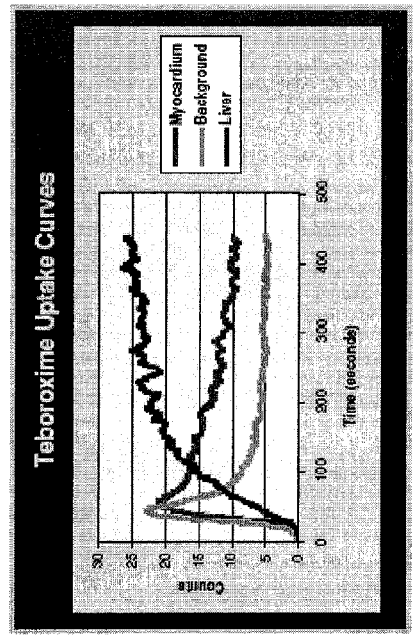

Referring to the drawings FIGS. 75A and 75B illustrate Teboroxime physiological behavior, according to Garcia et al. (Am. J. Cardiol. $51^{st}$ Annual Scientific Session, 2002).

Referring further to the drawings, FIGS. 76A-80D illustrate experimental results of the camera of the present invention and results of a conventional gamma camera, in terms of resolution, speed, and contrast. In all the experiments, the detectors used were 16×16 pixilated (2.54×2.54 mm in size) CZT arrays made by Imarad, Rehovot, Israel and driven by the XA controller system made by IDEAS asa., Norway.

Test No 1: Speed and Resolution

Performances of the camera of the present invention and of the conventional gamma camera were compared by equivalent setups, as follows:

For the camera of the present invention, a center of viewing was at a distance of 150 mm from the collimators' distal end with respect to an operator. A 5 mili Curie Cobalt 57 line source was placed at a distance of 1 cm from the center of viewing, so as to be off center for the viewing. A total of 13.5 million photon counts were taken. Acquisition time was 49 seconds.

For the conventional gamma camera, a center of rotation was at a distance of 150 mm from the collimators' distal end with respect to an operator. A 5 mili Curie Cobalt 57 line source was placed at a distance of 1 cm from the center of rotation, so as to be off center for the rotation, and the same number of counts, 13.5 million photon counts, was taken. Acquisition time was 600 seconds.

Thus, the camera of the present invention was about 12 times more sensitive than the conventional gamma camera.

The image of the source was reconstructed using dedicated reconstruction algorithms based on the EM method and developed by the inventors. The reconstruction algorithms used on the conventional unit were OSEM/MLEM based.

FIG. 76A represents results with the camera of the present invention.

FIG. 76B represents results of the conventional gamma camera.

The measured FWHM (Full Width at Half Maximum) resolutions are shown as follows:

| System/Reconstruction | Resolution FWHM (NEMA) [mm] |
| --- | --- |
| camera of the present invention | 5.5 |
| conventional gamma camera | 10.4 |

Test No. 2: Resolution as a Function of Scattering Distance

A standard NEMA cylindrical phantom was filled with water, and a 5 mili Curie Cobalt 57 line source of 190 mm in length and 1 mm in diameter was placed at its center, as illustrated in FIG. 76C. The cylindrical phantom was placed at a distance R from the distal end of the cameras' collimators.

Reconstruction images from two 40-second acquisitions were performed and analyzed, wherein the first acquisition was based on equal angle span for all views (Fixed Angle Spans), and the second acquisition was based on adjusted angle viewing, for viewing equal sectors of the region-of-interest (Fixed ROI).

Figure 76D:
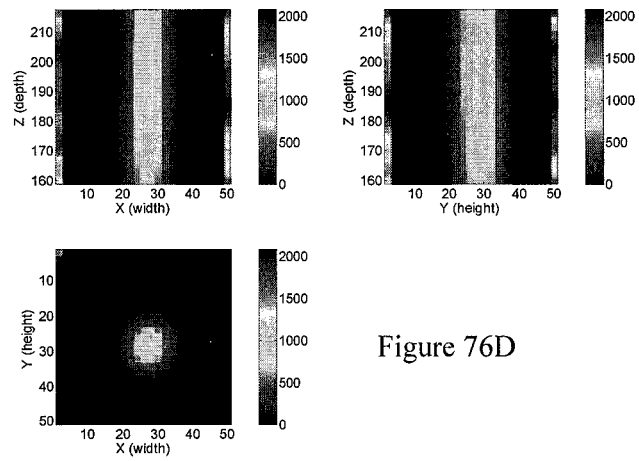

For image reconstruction, a maximal intensity projection (MIP) of the reconstruction without attenuation correction is given in FIG. 76D, based on the combined total of the two acquisitions. The x-z and the y-z planes each show the line source as a line, and the x-y plane provides a cross-sectional view of the line.

Figure 76E:
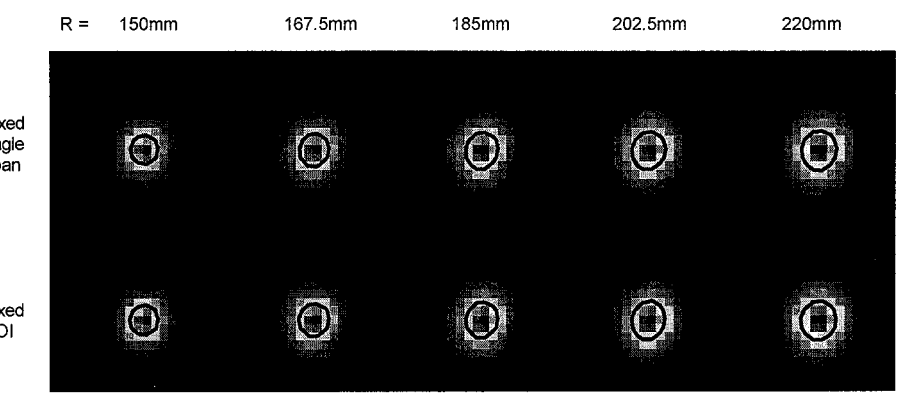

FIG. 76E illustrates the reconstructed cross-sectional intensity of the line source for the fixed scan angle and Fixed ROI cases, respectively, and for varying distances R from the camera. As expected, the FWHM increases with increasing R.

Figure 76F:
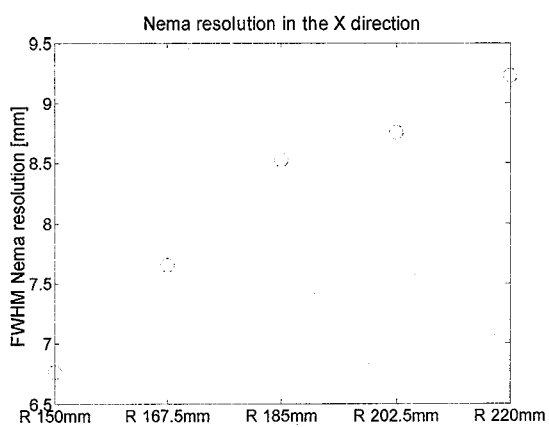
Figure 76G:
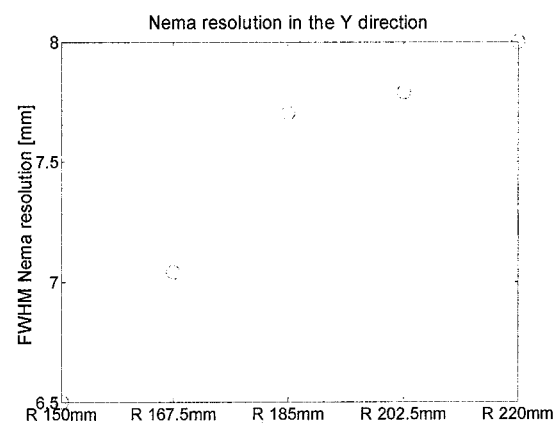
Figure 76H:
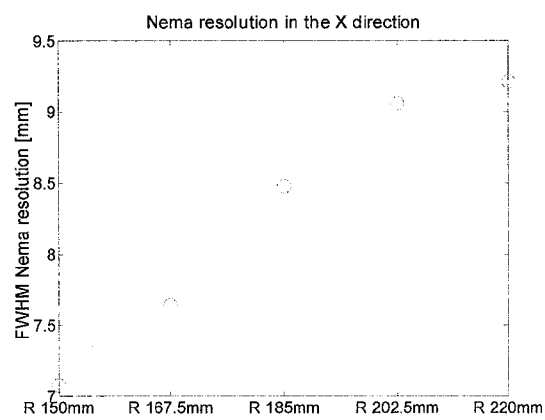
Figure 76I:
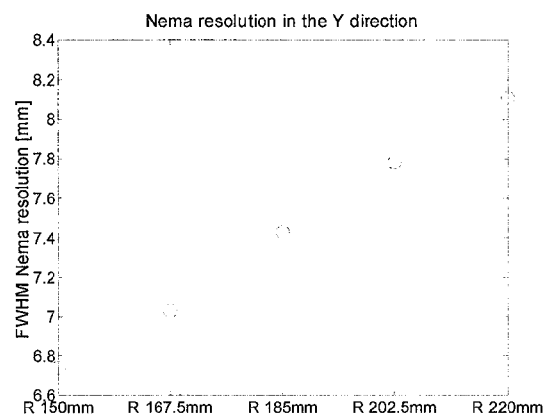

FIGS. 76F and 76G schematically show NEMA resolutions in the x and y directions, respectively, for the fixed-angle span acquisition, while FIGS. 76H and 76I schematically show NEMA resolutions in the x and y directions, respectively, for the fixed-ROI acquisition.

Test No. 3: NEMA Three Line Source Acquisition

Three Cobalt 57 line sources were placed inside a standard NEMA phantom, as seen in FIG. 77A.

Viewing coverage was 200 degrees, wherein the distance from the distal end of the collimators to the center of viewing was 150 mm. The total net acquisition time was 60 seconds. The images shown in FIGS. 77B-77D are based on raw reconstruction, without attenuation correction or smoothing.

After application of a simplistic, model-based attenuation correction, which is acceptable in the case of water as the scattering and absorbing medium and circular symmetry of an object, the results are shown in FIGS. 77E-77G.

Table 89 below provides resolution numbers for the pre- and post-attenuation correction results, as follows:

TABLE 89

| | NEMA resolution FWHM [mm] | | |
|---|---|---|---|
| | Point #1 | Point #2 (Center) | Point #3 |
| Without Attenuation Correction | | | |
| X-Direction | 5.6 | 7.7 | 4.4 |
| Y-Direction | 5.4 | 7 | 4.4 |
| With Attenuation Correction | | | |
| X-Direction | 6.1 | 7.6 | 3.9 |
| Y-Direction | 6.3 | 7.6 | 4 |

Test No. 4: Resolution, Acquisition Time, and Contrast

Figure 78A:
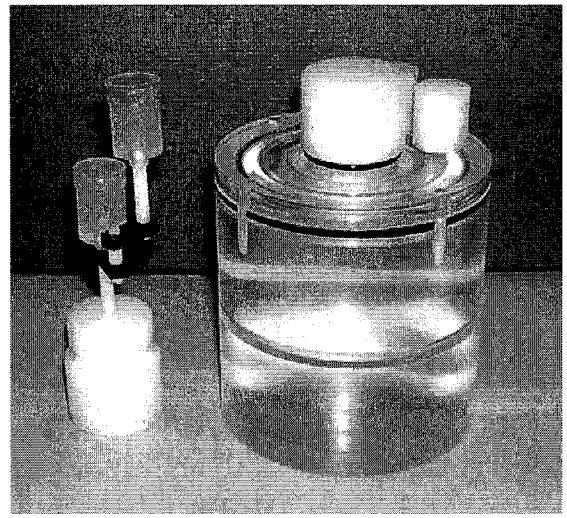
Figure 78C:
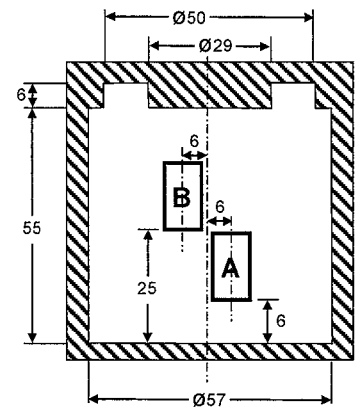
Figure 78B:
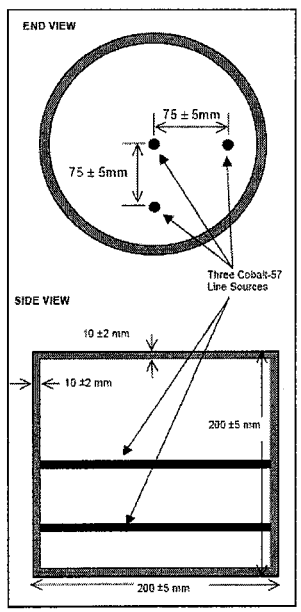

As shown in FIGS. 78A-78C, two sources, A and B, were placed in a cylindrical Perspex phantom, designed to allow the insertion of sources of different sizes and intensities.

A comparison of radioactive-emission imaging of the camera of the present invention and of a conventional gamma camera was made, and this included image evaluation, sensitivities, and contrast differences.

The cylindrical Perspex phantom was placed with its center at the center of viewing of the camera. The distance from the distal end of the collimators to the center of the phantom cylinder was 100 cm.

The total radiation coming from the cylinder, including radiation from background, insert A, and insert B, was 930 µCi of Tc-99m. The ratio of the amount of radiation from insert A to background radiation was 2:1, while that of radiation from insert B to background radiation was 3:1. Acquisition time was 40 seconds and 1.4 million counts were acquired. The reconstructed images are seen in FIGS. 79A-79C. Both the 2:1 and 3:1 Target to Background ratio targets are visible.

The resulting measured contrasts are 2.6:1 and 1.6:1 for the 3:1 and 2:1 input contrasts, respectively, in the case of the camera of the present invention.

Figure 79D:
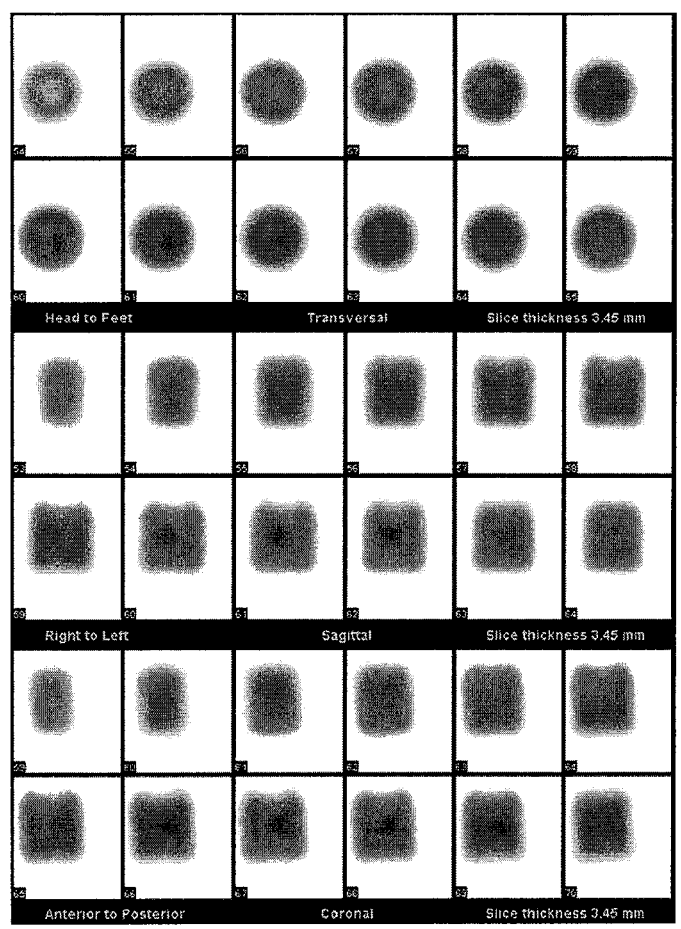

FIG. 79D represents the reconstructed results using the conventional camera, for which the acquisition time to reach the 1.4 million counts was 20 minutes. The 3:1 target was reconstructed as a 1.3:1 ratio while the 2:1 target was indistinguishable from the background radiation. The main reason for this loss of contrast is the poor spatial resolution of the conventional camera when compared to that of the camera of the present invention.

Test No. 5: Reconstruction of Complex Objects—Torso Phantom Acquisition

Figure 80A:
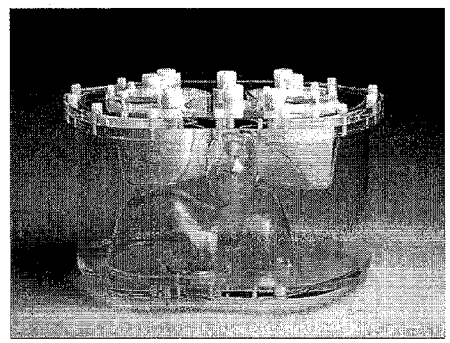

A standard torso phantom of Anthropomorphic Torso Phantom Model ECT/TOR/P, produced by Data Spectrum Corporation, USA, was provided, as seen in FIG. 80A.

The radioisotope Tc-99m was used as the tracer. The activity of the various organs was: Cardio—0.5 mCi, Background—2 mCi (0.19 mCi/liter) and Liver—0.23 mCi (0.19 mCi/liter).

An acquisition time of 1.25 minutes was used for the camera of the present invention, and an acquisition time of 12.5 minutes was used for the conventional camera. In both cases, 2.5 M counts were obtained.

Figure 80B:
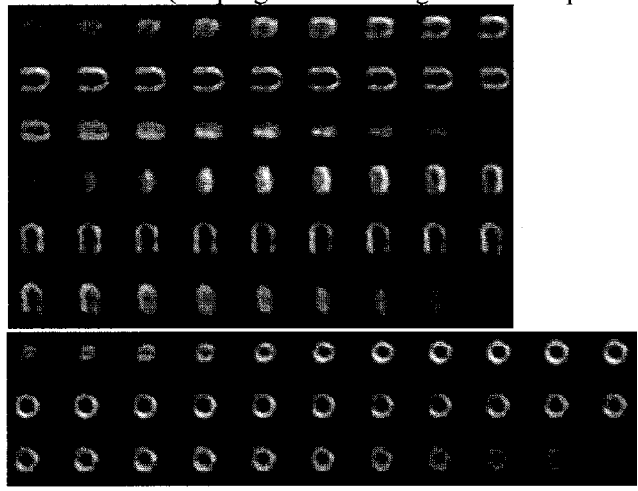

FIG. 80B illustrates the results using the camera of the present invention, and

Figure 80C:
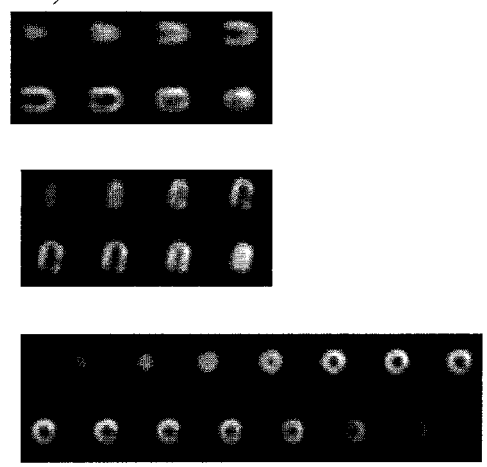

FIG. 80C illustrates the results using the conventional gamma camera.

The sensitivity ratio was thus 10:1. The reconstruction is visibly better in the case of the camera of the current invention.

Figure 80D:
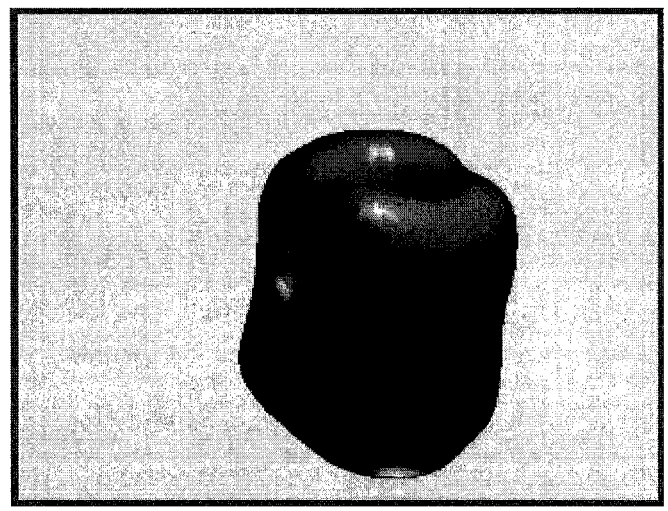

FIG. 80D illustrates a reconstructed three-dimensional image of the heart, from the phantom, using the camera of the present invention.

A cold area of 1 cm×1 cm×0.5 cm at a left side of the heart is clearly seen. Other cold areas are similarly visible.

Test No. 6: Sensitivity Studies

In another exemplary embodiment of the current invention, the probe system includes multiple blocks of detectors positioned in a structure encircling the imaged area, each is able to rotate about a longitudinal axis substantially parallel to the main axis of the subject.

In a further example case of 10 such blocks of detectors, each covering a 40×160 mm section covering about 180-200 deg of the circle around the imaged area, with 10 blocks of collimators each covering 1024 pixels arranged in a 16×64 pixel matrix, with square collimator opening of 2.46×2.46 mm, and a length of 20 mm], the system demonstrated ability to detect about one out of 1500 of the emitted photons from a 2.7 mCi $Co^{57}$ point source that was moved about in a 40×30×15 cm volume facing the probe.

When located in the center of the imaged area (about 150 mm from the detectors), while the energy window for acquisition was about 5%, and the detectors were sweeping a wide angular range.

In a further exemplary embodiment, substantially all detectors are able to simultaneously image the region of interest containing the point source and thus obtaining one out of every 500 of the emitted photons.

It is known to the skilled in the art that further opening the energy window of the detector to about 15%, enables acquisition of about one out of 250 photons of the photons emission in an experimental setting similar to the previous example.

In a further example, each such detector having multiple pixels is of about 5 cm wide or more, thus producing a region of interest of at least 5 cm in diameter, from which said sensitivity and said resolution is being obtained even without the need to move any of the detectors.

In a further possible embodiment of the present invention the width of each detector is about 10 cm wide, thus enabling regions of interest of even bigger diameters at said resolution and sensitivity with a smaller detector motion such that bigger objects are continuously viewed by the detector with only small angular detector motion.

In a further possible embodiment of the present invention the detectors array may encircle the imaged subject to the extent of 360 deg, for example by having two hemi circles from both sides of the subject. The sensitivity in such case is estimated be about 1 in 125.

In a further exemplary embodiment additional detectors may be positioned to obtain views not perpendicular to the subject's main longitudinal axis, for example by upper view (e.g. from the shoulders) and abdominal view of the target region (in the case of cardiac mapping). It is estimated that such addition may increase the sensitivity but a factor of about ×2.

As a result, an example embodiment of the present invention is estimated to be able to image a volume of about 5 cm diameter located about 150 mm from the detectors, with energy window of 15%, producing spatial resolution of about 5 mm in approximately 100 sec, with a total sensitivity of about 1 photons being detected out of 65 emitted.

It will be recognized by a person skilled in the art that a system built around the principles of this invention can thus reach the sensitivity necessary to detect substantially more than one photon from every 100 emitted. This result for an imaging system provides more than 100 time better sensitivity than commercially available cameras that have a sensitivity ranging from substantially from 170 counts/microCurie/minute (or 1 photon in 8500 photons emitted for a Low resolution low energy collimator to about 1 photon in every 15000 emitted for a high resolution medium energy collimator), while maintaining similar energy windows, and potentially similar or better resolution.

Test No. 7: Sensitivity Studies—Grid Point Source

Figure 70C:
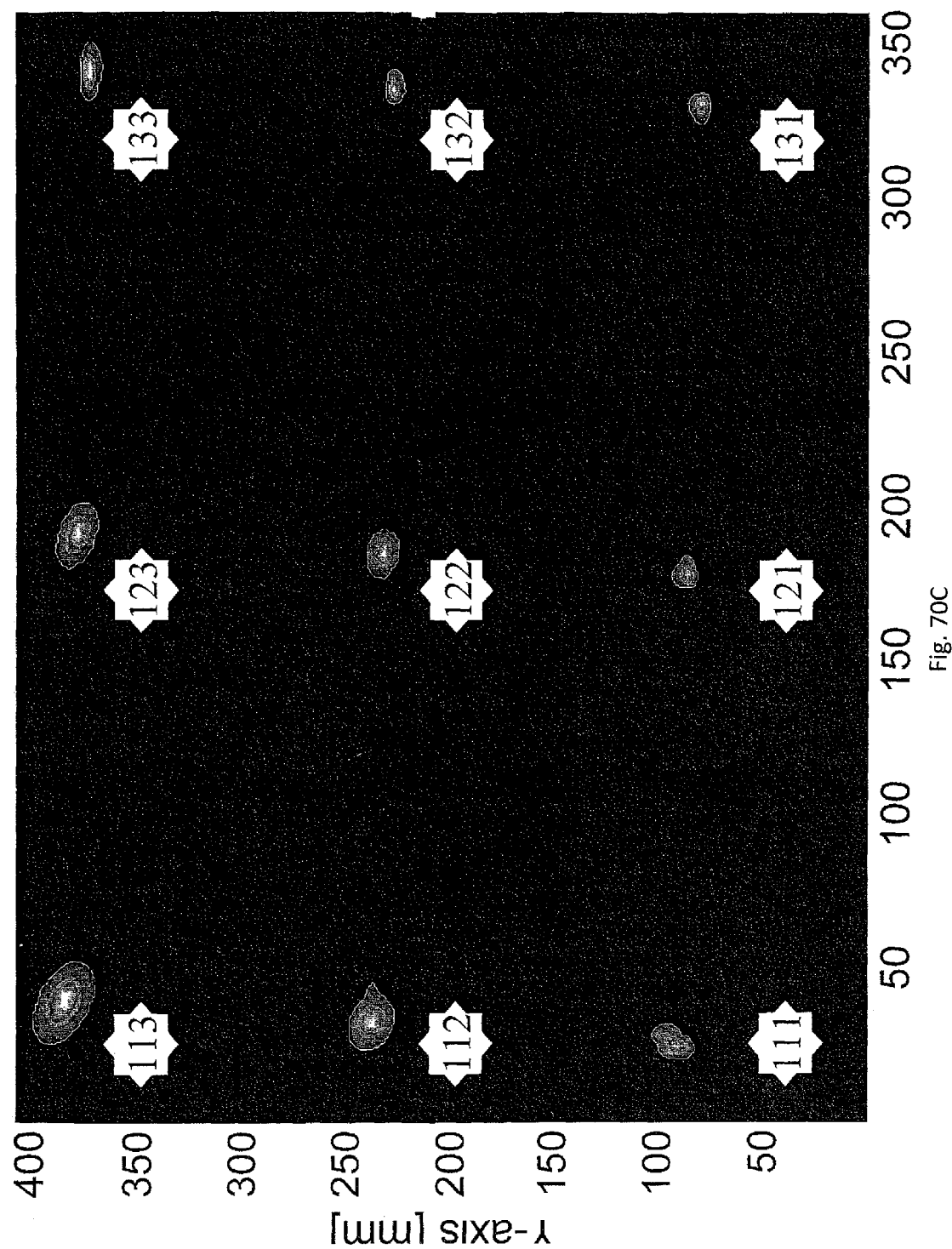

In a further experiment a $Co^{57}$ point source of 2.7 mCi activity was used in order to measure the sensitivity, resolution and geometric accuracy of the probe. A probe composed out of 10 detector columns, each containing detector pixels in a 16×64 pixel arrangement, where each pixel element had a dimension of 2.46×2.46 mm and being covered by a Tungsten collimator matrix with 0.2 mm septal thickness and 20 mm septal length was used to image the point source. The energy window was set at 5% FWHM (6 KeV total). A robotic arm was used to move the point source within a 40×30×15 cm rectangular volume at positions shown in FIG. 70A. FIG. 70B is a diagram showing the error of the reconstructed position relative to the nominal position as placed by the robot. It is evident that the deviation in position is less than 1 mm for most points and less than 2.5 mm for all points. FIG. 70C shows the FWHM diameter and the FWTM (Full Width Tenth Maximum) diameter for all points in the volume. It is noted that the resolutions measured according to the NEMA standards are substantially under 10 mm throughout the volume and do not exceed 15 mm for all points, a performance equal to or superior than existing nuclear cameras for similar fields of View. The total net acquisition time for each point was 120 seconds and the typical count rate for most points (with the exception of positions that could not be viewed by all columns due to mechanical limitations), and the collected number of photons was substantially 7-8 million counts for most positions fully viewed, yielding a sensitivity of I photon out of 1500 emitted in the energy window of 5%.

Electrical Scheme

FIG. 143 describes an example of a system that includes multiple detection, amplifications and signal processing paths, thereby avoiding saturation due to single hot source in space. Gamma-Ray photon (A) is hitting a pixelized CZT crystal. A hit is named 'Event'. The crystal is part of a 'CZT MODULE' (B) containing the CZT crystal divided into 256 pixels and 2 ASICS each receiving events from 128 pixels. The ASIC is OMS 'XAIM3.4' made by Orbotech Medical Systems, Rehovot, Israel, together with the CZT crystal. The 2 ASICs share a common output and transmit the data to 'ADC PCB' (C) that handles in parallel 4 'CZT MODULES'. Thus, a total of 1024 pixels are presently channeled through one ADC board. The system is capable of further increasing the accepted event rate by channeling every 2 ASICS through a single ADC. The 'ADC PCB' transmits the data to the 'NRG PCB' (D) that handles in parallel 10 'ADC PCBS', but could be further replicated should one want to further decrease "dead time". The 'NRG PCB' transmits the data to the 'PC' (E) where it is stored.

All in all, in the present embodiment, 40 'CZT MODULE' containing a total of 10240 pixels are transmitting in parallel to the PC.

The bottle neck, and hence the only constraint, of the system data flow is the ASICS in the 'CZT MODULE' and it's connection to the 'ADC PCB':

1. An ASIC (128 pixels) can process only one photon hit within 3.5 uSec, or 285,000 events/sec over 128 pixels, i.e. over 2200 events/px/sec-an exceedingly high rate.

2. 2 ASICS share the same output, and hence coincident event output of the 2 ASICS in a 'CZT MODULE' will cause a collision and information loss. The duration of an event output from the ASIC is 1 uSec.

General Designs of Detecting Units, Blocks, Assemblies and Cameras

Referring further to the drawings, FIGS. 17A-17H schematically illustrate detecting units 12 and blocks 90 that may be considered for possible camera designs.

FIGS. 17A and 17B schematically illustrate side and top views, respectively, of the basic detecting unit 12 (see also FIG. 1A), having a detector 91 and a collimator 96, formed as a tube, of a collection angle 61.

FIGS. 17C and 17D schematically illustrate side and top views, respectively, of the detecting unit 12, with the collimator 96 formed as a wide angle collimator, of a collection angle δ2.

FIGS. 17E and 17F schematically illustrate side and top views, respectively, of the block 90 (see also FIG. 1B) of the detecting units 12, with the collimator 96 formed as a grid, and each of the detecting unit 12 having a collection angle 63. As few as two or four, and as many as a hundred or several hundred of the detecting units 12 may be included in the block 90.

FIGS. 17G and 17H schematically illustrate side and top views, respectively, of the block 90 of the detecting units 12, with the collimator 96 formed as a grid, with two sizes of the detecting units 12, as follows: small detecting units 94A, of collection angles 64, at the center of the grid, and large detecting units 94B, of collection angles 65, at the periphery. It will be appreciated that other arrangements of detecting units of different sizes may be used.

It will be appreciated that a combination of these may be used. For example, the block 90 may include wide-angle collimators (FIG. 17C) at the periphery and normal collimators of 90-degrees (FIG. 17A) at the center.

It will be appreciated that the camera 10 may contain blocks 90 and (or) detecting units 12 of different collection angles.

Referring further to the drawings, FIGS. 17I and 17J schematically illustrate a detecting unit 12A with an adjustable collimator 96Z, for adjusting the collection angle, in accordance with embodiments of the present invention. Preferably, the detecting unit 12A includes the detector 91 and an adjustor 91A at the bottom of the collimator 96Z. Additionally, the collimator 96Z is formed of a plurality of petal collimators 96A, 96B, 96C, and so on, wherein the collimator 96Z may be partially open, as shown in FIG. 17I, or fully open, as shown in FIG. 17J, by the action of the adjustor 91A, which may be, for example, a rotating knob, controlled by the data-processing system 126 (FIGS. 2, 3A). Preferably, the extent of opening of the collimator 96Z is adjustable, so it may be essentially closed, with the petal collimators 96A, 96B, 96C and so on substantially vertical with the detector 91, partially open, or fully open, much like a flower.

FIGS. 17K-17N schematically illustrate the block 90, wherein the detector 91 is a single-pixel scintillation detector, such as NaI(Tl), LSO, GSO, CsI, CaF, or the like, operative with photomultipliers 103.

As seen in FIG. 17K, the block 90, having proximal and distal ends 109 and 111, respectively, vis a vis an operator (not shown), is formed of the scintillation detector 91, of a single pixel, and the collimators 96, to create the detecting units 12. A plurality of photomultipliers 103 is associated with the single pixel scintillation detector 91, and with dedicated algorithms, as known, their output can provide a two dimensional image of the scintillations in the single pixel scintillation detector 91. In essence, this is an Anger camera, as known.

The distal view 111 of the collimator grid is seen in FIG. 17L.

Two optional proximal views 109 of the photomultipliers 103 are seen in FIGS. 17M and 17N, as a square grid arrangement, and as an arrangement of tubes.

The detector may be a room temperature, solid-state CdZnTe (CZT) detector, configured as a single-pixel or a multi-pixel detector, obtained, for example, from eV Products, a division of II-VI Corporation, Saxonburg Pa., 16056, or from IMARAD IMAGING SYSTEMS LTD., of Rehovot, ISRAEL, 76124, www.imarad.com, or from another source. A detector thickness $\tau_d$ may range from about 0.5 mm to about 100 mm, depending on the energy of the radioactive emission and typically about 2 mm to about 50 mm, and in some cases about 5 mm to about 30 mm.

Alternatively, another solid-state detector such as CdTe, HgI, Si, Ge, or the like, or a scintillation detector (such as NaI(Tl), LSO, GSO, CsI, CaF, or the like, or a combination of a scintillation detector and a photomultiplier, to form an Anger camera, or another detector as known, may be used. Additionally, a combination of scintillation materials and photodiode arrays may be used.

It will be appreciated that the methods of the present invention apply to pathological features that may be modeled as regions of concentrated radiations, or hot regions, regions of low-level radiation, which is nonetheless above background level, and regions of little radiation, or cold regions, below the background level. However, in general, for identifying a pathological feature of the heart, they relate to cold regions.

It will be appreciated that the methods of the present inventions may be operable by computer systems and stored as computer programs on computer-readable storage media.

It will be appreciated that the body may be an animal body or a human body.

It will be appreciated that the radioactive-emission-camera systems, cameras and methods of the present invention may be used with commonly owned US Applications 20040015075 and 20040054248 and commonly owned PCT publication WO2004/042546, all of whose disclosures are incorporated herein by reference. These describe systems and methods for scanning a radioactive-emission source with a radioactive-emission camera of a wide-aperture collimator, and at the same time, monitoring the position of the radioactive-emission camera, at very fine time intervals, to obtain the equivalence of fine-aperture collimation. In consequence, high-efficiency, high-resolution, images of a radioactive-emission source are obtained.

Commonly owned US application 20040054248 and commonly owned PCT publication WO2004/042546 further disclose various extracorporeal and intracorporeal systems, of radioactive-emission cameras, of relatively wide apertures, associated with position-tracking devices.

It will be appreciated that the radioactive-emission-camera systems, cameras and methods of the present invention may be used with commonly owned U.S. Pat. No. 6,173,201 to Front, whose disclosure is incorporated herein by reference, as well as by M. W. Vannier and D. E. Gayou, "Automated registration of multimodality images", Radiology, vol. 169 pp. 860-861 (1988); J. A. Correia, "Registration of nuclear medicine images, J. Nucl. Med., vol. 31 pp. 1227-1229 (1990); J-C Liehn, A. Loboguerrero, C. Perault and L. Demange, "Superposition of computed tomography and single photon emission tomography immunoscinigraphic images in the pelvis: validation in patients with colorectal or ovarian carcinoma recurrence", Eur. J. Nucl. Med., vol. 19 pp. 186-194 (1992); F. Thomas et al., "Description of a prototype emission transmission computed tomography imaging system", J. Nucl. Med., vol. 33 pp. 1881-1887 (1992); D. A. Weber and M. Ivanovic, "Correlative image registration", Sem. Nucl. Med., vol. 24 pp. 311-323 (1994); and Hasegawa et al., U.S. Pat. No. 5,376,795.

These relate to the acquisition of both a functional image of the body, such as a radioactive-emission image, and a structural image, such as an ultrasound, an x-ray, or an MRI image, and their co-registration on a single frame of reference.

In essence, several images may be acquired and co-registered to the same frame of reference, as follows:

i. a first functional image scan, based for example, on anti-CEA monoclonal antibody fragment, labeled by iodine isotopes, may be acquired for targeting CEA—produced and shed by colorectal carcinoma cells for detecting a pathological feature, such as colorectal carcinoma;

ii. a second functional image, based for example, on non-specific-polyclonal immunoglobulin G (IgG), which may be labeled with $Tc^{99m}$, may be acquired for locating blood vessels and vital structures, such as the heart, or the stomach, co-registered with the first functional image and the pathological feature detected on it, in order to locate the pathological feature in reference to blood vessels and vital organs; and iii. a structural image, such as an ultrasound image, may be used for general structural anatomy, co-registered with the first and second functional images, in order to locate the pathological feature in reference to bones and the general anatomic structure.

Thus, a physician may locate the pathological feature in reference to the blood vessels, vital organs, and the bones, and guide a minimally invasive surgical instrument to the pathological feature, while avoiding the blood vessels, vital organs, and bones. The minimally invasive surgical instrument may be a biopsy needle, a wire, for hot resection, a knife for cold resection, an instrument of focused energy, to produce ablation, for example, by ultrasound, or by laser, an instrument for cryosurgery, an instrument for cryotherapy, or an instrument for brachytherapy, wherein seeds of a radioactive metal are planted close to a tumor, for operating as a radioactive source near the tumor.

Commonly owned PCT publication WO2004/042546 further discloses that the surgical instrument may be visible on at least one of the images, for example, on the structural image, to enable the physician to see the instrument, the pathological feature, and the surrounding anatomy on the display 129 (FIG. 3A). Additionally, the surgical instrument may be radioactively labeled, to be visible also on the functional image. PCT publication WO2004/042546 further disclose various extracorporeal and intracorporeal systems, of radioactive-emission cameras, and structural imagers such as an ultrasound camera or an MRI camera.

Commonly owned U.S. Pat. No. 6,173,201, to Front further discloses a method of stereotactic therapy, wherein a frame, which includes at least three markers, visible on a structural image, is rigidly secured to a patient. The structural image of a region inside the patient's body, which includes a pathological feature and the markers, is acquired. A functional image of the pathological feature is then acquired and co-registered with the structural image, to correlate the images to the same frame of reference. A stereotactic guide is rigidly attached to the frame and is used to guide a surgical instrument, such as a biopsy needle or a brachytherapy needle, to the pathological feature, with reference to the co-registered images.

Thus the radioactive-emission-camera systems, cameras and methods of the present invention may be used together with position tracking devices, for enhanced image acquisition, they may be used together with structural imager and structural imaging for correlating functional and structural images, and they may be used for guiding minimally invasive surgical instruments, such as a biopsy needle, a wire, for hot resection, a knife for cold resection, an instrument of focused energy, to produce ablation, for example, by ultrasound, or by laser, an instrument for cryosurgery, an instrument for cryotherapy, or an instrument for brachytherapy.

It will be appreciated that a structural image, such as by ultrasound may further be used and in order to provide information about the size and location of the body structure 215 for the purpose of creating the model 250 (FIG. 5A).

It will be appreciated that a structural image, such as by ultrasound may further be used and in order to provide information about tissue attenuation, for example, as taught in conjunction by commonly owned PCT publication WO2004/042546, whose disclosure is incorporated herein by reference. The information may then be used to correct the radioactive-emission measurements.

Active Vision

At present, radioactive-emission imaging of a body structure is a three-stage process. First the radiopharmaceutical is administered. Then measurements are taken at a set of predetermined views, that is at predetermined locations, orientations, and durations. Finally, the data is analyzed to reconstruct the emission distribution of the volume and an image of the body structure is formed. The imaging process is sequential, and there is no assessment of the quality of the reconstructed image until after the measurement process is completed. Where a poor quality image is obtained, the measurements must be repeated, resulting in inconvenience to the patient and inefficiency in the imaging process.

According to this embodiment, the present invention teaches using radioactive-emission measurements to define views for further radioactive-emission measurements of a body structure, to be performed during the current measurement process. Specifically, the methods teach analyzing the previously obtained measurement results to determine which further views are expected to provide a high quality of information. The analysis may be based directly on the photon counts obtained for the current or recent measurements and/or on a reconstruction of the body structure performed upon the completion of a set of measurements.

The present embodiments address the problem of ensuring that the quality of data gathered during the measurement process is adequate to provide a high quality image. The collected data and/or the image reconstructed from the collected data is analyzed the while the measurement process is taking place. Based on the analysis, further views are defined. Since each view is associated with known values of the viewing parameter(s), selecting a view effectively specifies known viewing parameter values. The defined further views thus define a set of viewing parameter values, which are used during the current measurement process in order to collect data which yields a high-quality reconstruction of the body structure.

The following embodiments are of a method for determining further views for the imaging of a body structure, and are not confined to a specific reconstruction algorithm. Further views are preferably defined based on one or more of the following:

1) Detector photon count
2) Geometric properties of the reconstructed body structure
3) Information theoretic measures that quantify the quality of the data fed to the reconstruction algorithm Each of these criteria is discussed in detail below.

Figure 81:
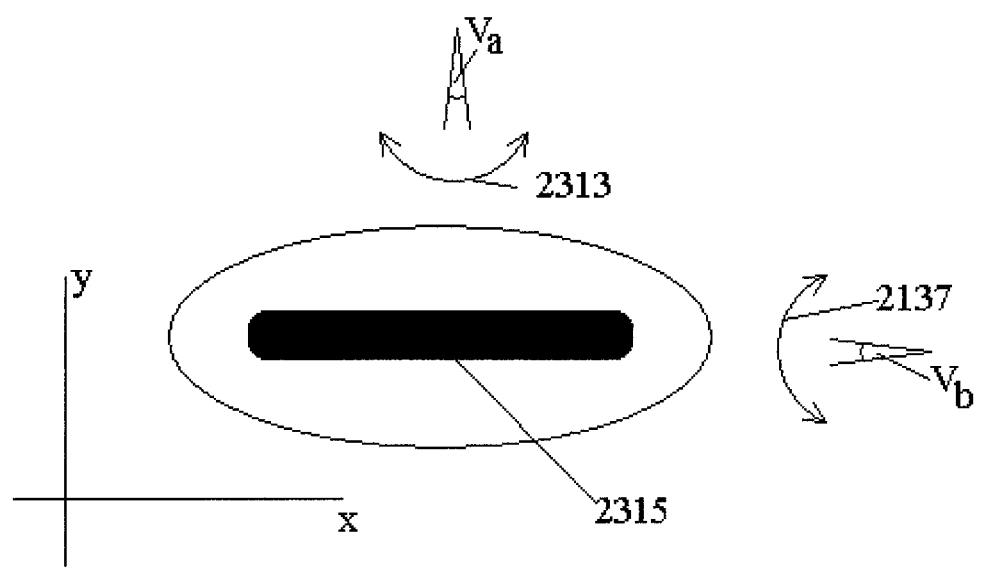
FIG. 81 is a description of advantageous and disadvantageous viewing positions according to embodiments of the present invention.

Reference is now made to FIG. 81 which is a self explanatory description of advantageous and disadvanatageous viewing positions according to embodiments of the present invention.

Figure 82:
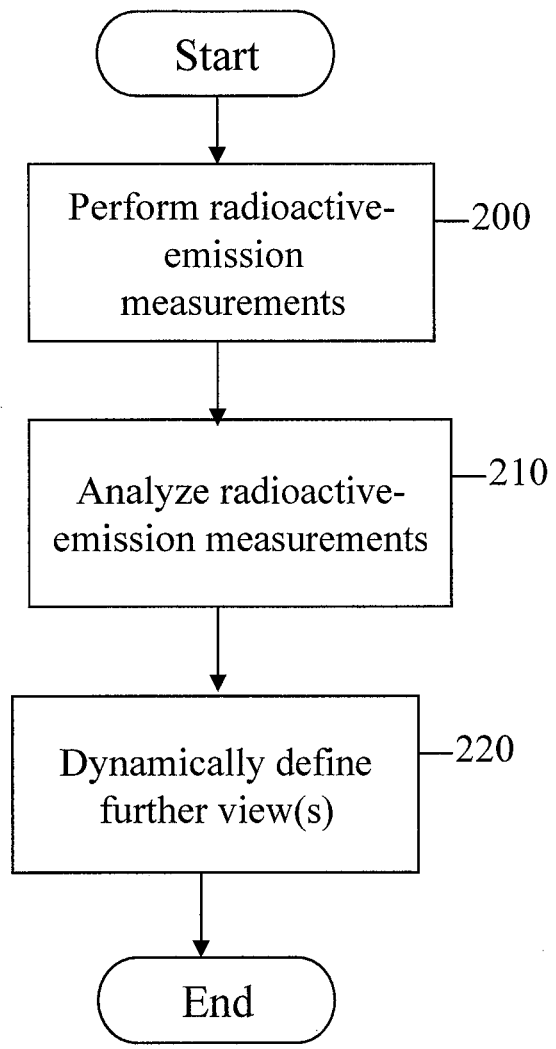
FIG. 82 is a simplified flowchart of a method of performing radioactive-emission measurements of a body structure, according to a preferred embodiment of the present invention.

Reference is now made to FIG. 82, which is a simplified flowchart of a method of performing radioactive-emission measurements of a body structure, according to a preferred embodiment of the present invention. In step 200, radioactive-emission measurements of the body structure are performed at predetermined views, preferably in vivo. Preferably the measurements are performed for diagnostic purposes. These predetermined views are selected prior to the measurement process, based on a model of the body structure being imaged. In the model more and less informative viewing directions have been identified. The predetermined views of step 200 preferably include those views expected to be informative, based on an analysis of the model.

Preferably the body structure is all or a portion of: a prostate, a heart, a brain, a breast, a uterus, an ovary, a liver, a kidney, a stomach, a colon, a small intestine, an oral cavity, a throat, a gland, a lymph node, the skin, another body organ, a limb, a bone, another part of the body, and a whole body.

In step 210 the radioactive-emission measurements are analyzed. Preferably the analysis includes one or more of:

1) Analyzing detector photon count(s)
2) Analyzing detector photon count(s) and rate changes from one view to another
3) Identifying detector saturation
4) Reconstructing a body structure image from emission measurements 5) Identifying geometric properties of the reconstructed image 6) Applying information-theoretic measures to the reconstructed image In step 220, further views for measurements are dynamically defined, based on the analysis performed in step 210. Preferably, each of the views is associated with viewing parameters selected from the group consisting of: detector unit location, detector unit orientation, collection angle, and measurement duration. Defining a view consists of providing a value for each of the parameters associated with the given view. The analysis (step 210) and/or dynamic view definition (step 220) may take into account external parameters including: measurement duration, time elapsed from the administration of the pharmaceutical to the measurement, radiopharmaceutical half life, radioactive emission type, and radioactive emission energy.

Each of these analysis techniques, and their application to view definition, is now discussed in turn. While each of the analysis/view determination techniques is discussed as a separate embodiment, multiple techniques may be used together to obtain the desired image quality.

In a first preferred embodiment, a photon count analysis ensures that the photon count at a given view yields an acceptable measurement error. As discussed above, the radiative emissions of the body structure being imaged is a Poisson process. In a Poisson process the Poisson noise grows inversely to the square root of the number of photons detected. In other words, if N photons are collected from a given view, the resulting signal to noise ratio (SNR) equals:

$$SNR = N/\sqrt{N} = \sqrt{N} \tag{12}$$

The unprocessed detector photon count at a given view thus provides significant information regarding the quality of the information obtained at a given view. If the photon count is too low, it may be desired to continue to collect photons at the current location/orientation in order to obtain a satisfactory SNR. Alternatively, it may be determined that enough photons have already been collected, and to terminate the current view and move on to the next view.

The analysis is preferably performed by defining a global or local required measurement error, and comparing the square root of the obtained photon count to the required measurement error. Photon count analysis can be applied to the current and/or previous views. When a photon count of a current view is found to be too low, the duration of the current view is preferably extended in order to obtain the required error value. When a photon count of a past view is found to be too low, an emission measurement at substantially the same location and orientation but having a longer duration than previously is preferably performed. Alternately or additionally, the collection angle at the given location/orientation is preferably increased.

In an additional preferred embodiment, a detector photon count is analyzed to identify detector saturation at a given view. Preferably, when a detector is determined to have saturated, a new view or views are selected to reinforce those views that have saturated. In an alternate preferred embodiment, further views are defined to avoid highly-radiating portions of the body structure.

In a second preferred embodiment, a photon collection rate at a given view is analyzed to determine if it is within a specified range. In the preferred embodiment, the photon count rate is used to identify regions of high or low interest. In prostate imaging, for example, a region of high interest may be identified by a high photon rate, indicative of a tumor. In a second example, a region of high interest may be identified in heart imaging by a low photon rate, indicative of non-functional tissues. After one or more areas of high and/or low interest are found, further views are preferably defined by selecting views to concentrate on regions of high interest and/or to avoid regions of low interest. It is thus possible to zoom in on a suspected pathology without repeating the emission measurement process.

In a further preferred embodiment, the analyzing of step 210 includes reconstructing a radioactive-emission density distribution of the body structure. Reconstruction may be performed according to any applicable technique known in the art. The reconstruction is then used as the basis for further analysis.

Reconstruction based on the data collected from the predetermined views provides information regarding the quality of information obtained from the preceding measurements, and which further views are likely to be most informative. Selecting new views based on reconstruction is intended to bring us into viewing from the more informative views or combinations of views.

Figure 83:
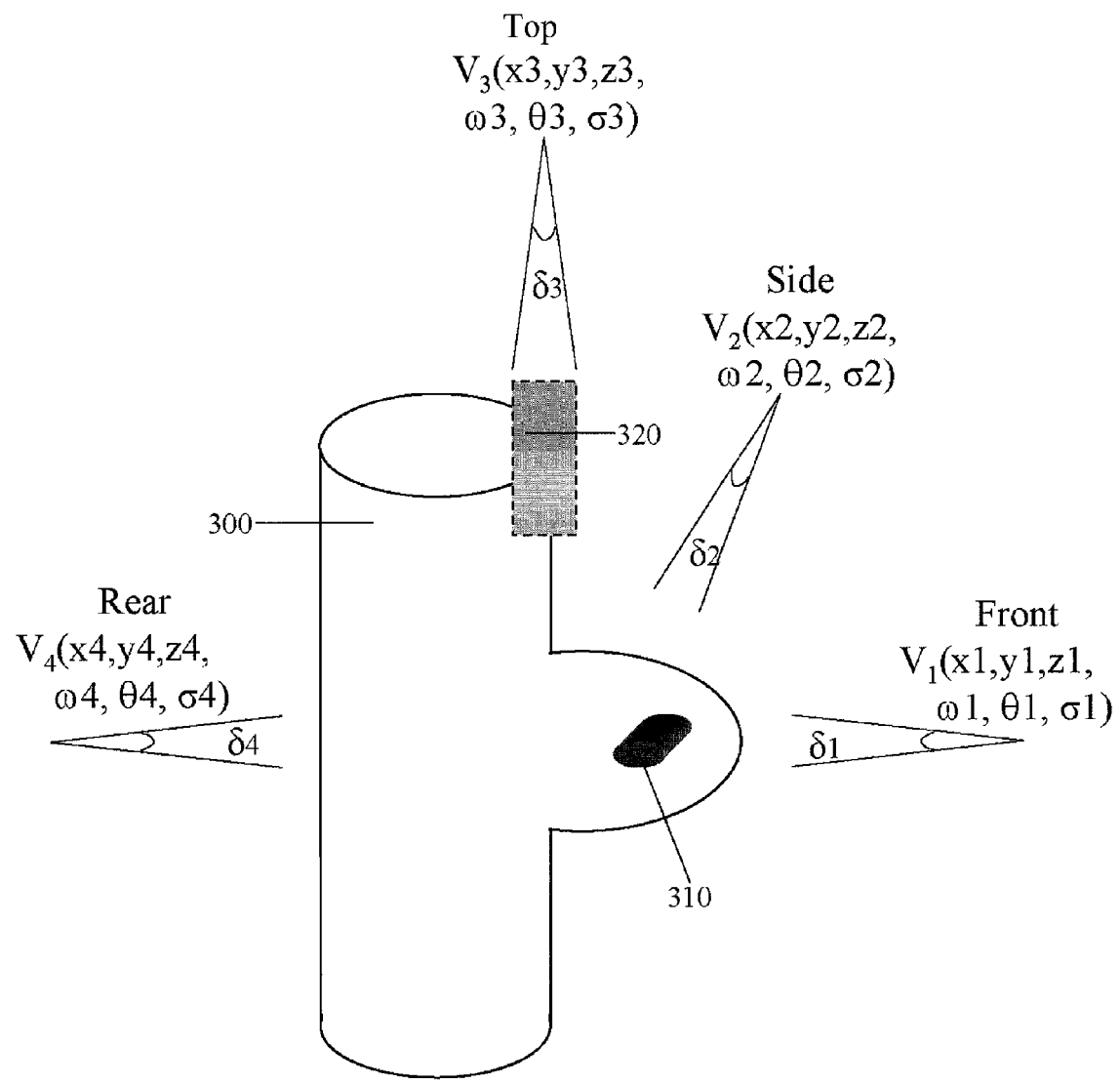
FIG. 83 shows an object shaped as a cylinder with a front protrusion, and having a high-remittance portion (hotspot).
Figure 84A:
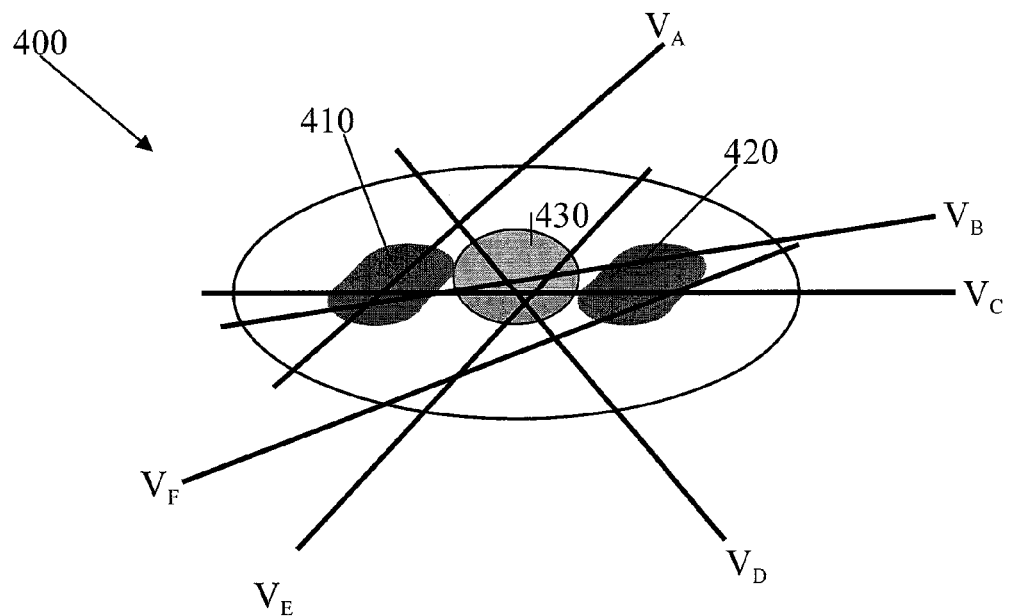
FIG. 84a illustrates an object having two high-emission regions of interest.
Figure 84B:
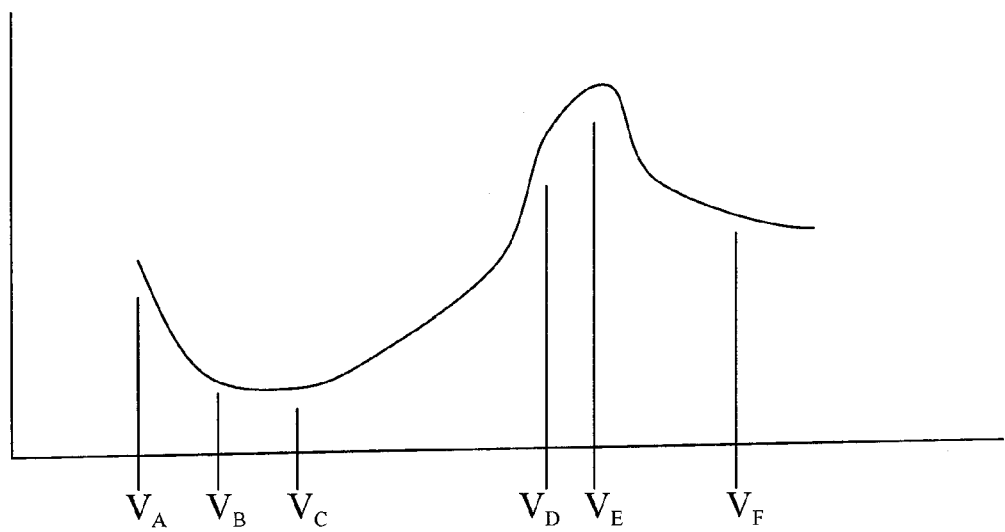
FIG. 84b illustrates the added information provided by each of views $V_A$ to $V_F$.

Reference is now made to FIGS. 83 and 84a-84b, which pictorially illustrate how different views provide differing types and quality of information. FIG. 3 shows an object 300 shaped as a cylinder with a front protrusion, and having a high-emmitance portion (hotspot) 310. Four views of object 300 are shown, which can be seen to provide different levels of information. Front views, such as $V_1$, provide little information regarding the shape of object 300 and have relatively little attenuation between the detector and hotspot 310. Side views, such as $V_2$, provide edge information regarding the object shape or profile, and when correlated with front views help locate hotspot 310 spatially within object 300. Top views, such as $V_3$, provide information regarding the cylinder edge region 320. Finally, rear views, such as $V_4$, are uninformative about the shape of object 300 and have high attenuation relative to hot region 310.

FIGS. 84a and 84b demonstrate how the proper selection of views may improve the quality of information obtained for the body structure, for example in distinguishing between two regions of interest within a given volume.

FIG. 84a illustrates an object 400 having two high-emission regions of interest (ROI), 410 and 420. For clarity the views $V_A$ to $V_F$ are shown as lines in FIG. 84a, however in practice they will each have a finite collection angle δ. The position of ROIs 410 and 420 are assumed to have been estimated based on a model of object 400 and/or a previously performed prescan. A goal of an aspect of the present invention is to select an additional new view or views which increase the information we have regarding the separation of ROIs 410 and 420 within object 400.

In simple terms, consider the object as having three regions: ROI 410 with intensity $I_1$, ROI 420 with intensity $I_2$, and a low-emission region 430 between the two ROIs with intensity $I_3$. The detected intensity at a given detector is proportional to $I_n/r_{ni}^2$, where $I_n$ is the emission intensity of region n and $r_i$ is the distance of region n from detector $V_i$.

FIG. 84b illustrates the added information provided by each of the shown views, $V_A$ to $V_F$. Views $V_B$ and $V_C$ collect emissions from all three regions, and are therefore least informative. Views $V_D$ and $V_E$ collect emissions from only low emmitance region 430, and therefore provide most information regarding the location of each ROI within the volume and the separation between ROIs 410 and 420. Views $V_A$ and $V_F$ pass only through a single ROI, and therefore provide an intermediate level of information. It is a goal of the present invention to determine, while the emission measurements of the body structure are taking place, that views in the vicinity of $V_D$ and $V_E$ are highly informative, and to add these further views to the measurement process.

A body structure reconstruction can be utilized in several ways to define further views. A first way is to identify interesting portions of the contour and structure of the reconstruction. For example, it is seen in FIG. 83 that top views are informative about edge region 320. Further top view measurements will therefore be informative re edge region 320, and may enable defining the edge more accurately.

In a preferred embodiment, the reconstruction is analyzed to identify textural edges within the reconstruction, and view definition preferably includes selecting views at an angle to the textural edges. In the preferred embodiment, the angle is a substantially sharp angle in order to provide information regarding the edge.

In another preferred embodiment, the reconstruction is analyzed to identify volumetric boundaries within the reconstruction, and view definition preferably includes selecting views at an angle to the volumetric boundaries. It is expected that the defined views will provide information regarding the boundary and differences in surrounding tissues on either side of the boundary. In the preferred embodiment, the angle is a substantially sharp angle.

Another way to utilize the reconstruction to define further views is to identify suspected organ targets within the reconstruction, and to select further view(s) in close proximity to the suspected organ targets. A suspected organ target is typically detected by identifying portions of the reconstruction whose emission intensity distribution and spatial characteristics are typical of a suspect region.

In a first preferred embodiment, a suspected organ target is defined as a high-emmitance portion of the reconstruction. In a second preferred embodiment, a suspected organ target is defined as a low-emmitance portion of the reconstruction.

In the preferred embodiment the further views are used immediately for radioactive-emission measurements. The results of the new measurements are then used in another analysis to define new further views for additional measurements. The radioactive-emission measurements may then be said to be performed iteratively.

Figure 85A:
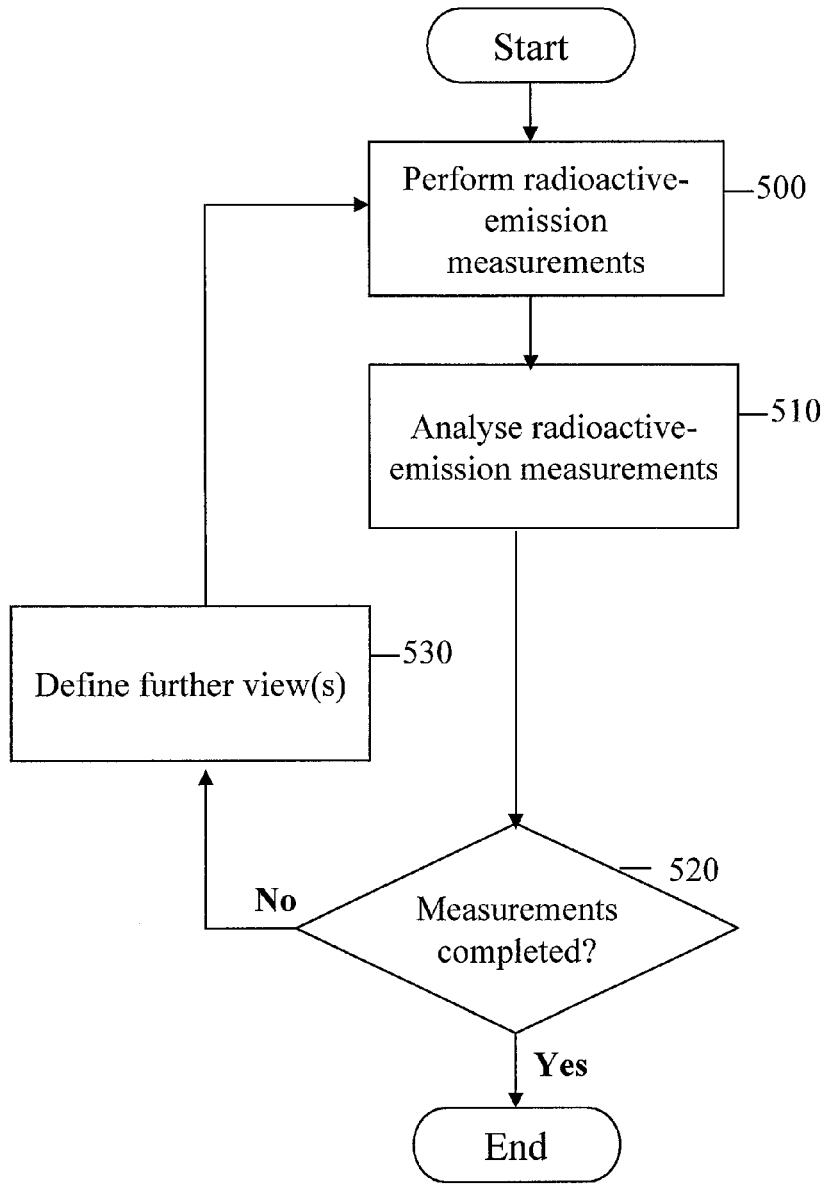
FIGS. 85a and 85b are simplified flowcharts of iterative methods of performing radioactive-emission measurements of a body structure, according to a first and a second preferred embodiment of the present invention.

Reference is now made to FIG. 85a, which is a simplified flowchart of an iterative method of performing radioactive-emission measurements of a body structure, according to a first preferred embodiment of the present invention. In step 500, radioactive-emission measurements of the body structure are performed at predetermined views. In step 510, an analysis is performed of the previously performed emission measurements. In step 520 a decision is made whether to continue with further measurements. If yes, in step 530 further views are defined based on the analysis. Subsequent iterations continue until the decision to end the emission measurement process. After the first iteration, the analysis performed at a given stage may include consideration of all or on part of the measurements performed during one or more previous iterations, in addition to the new measurements.

Figure 85B:
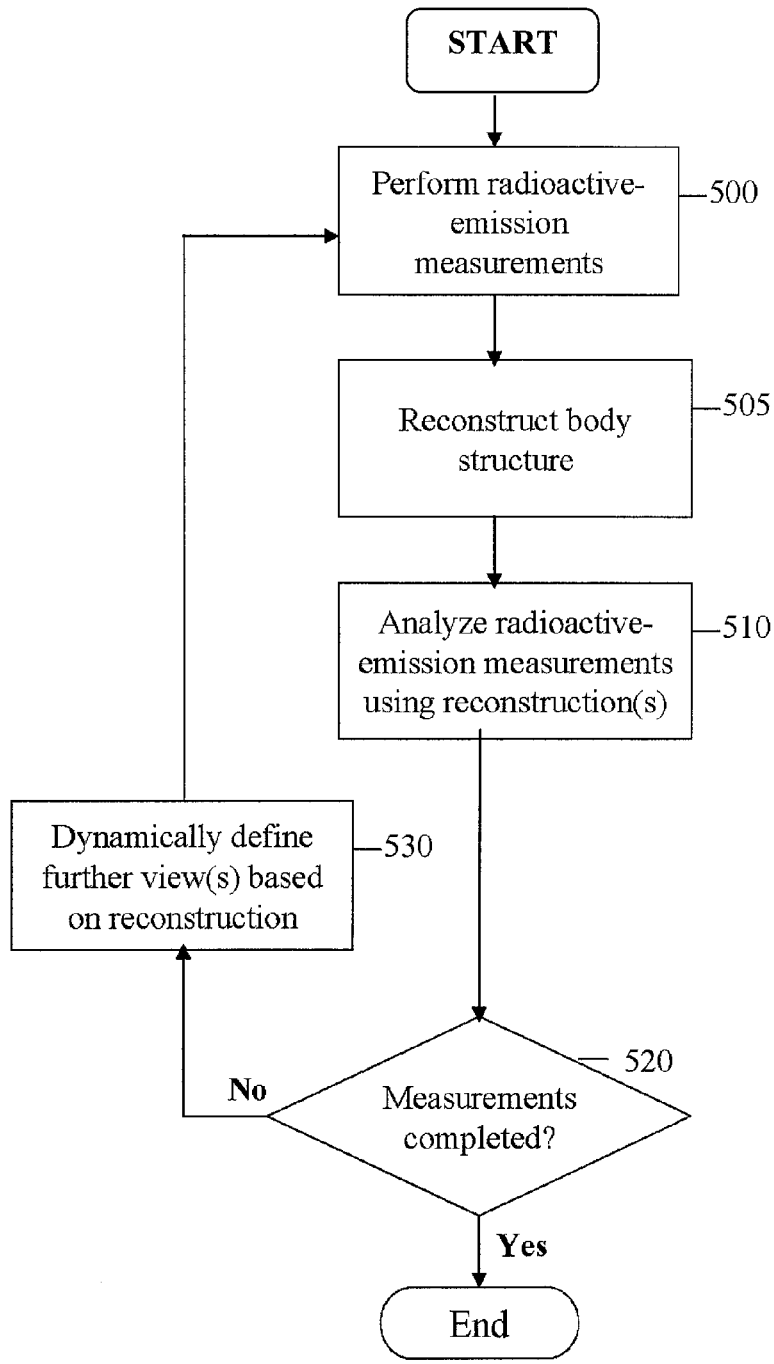

Reference is now made to FIG. 85b, which is a simplified flowchart of a iterative method of performing radioactive-emission measurements of a body structure, according to a second preferred embodiment of the present invention. In the present preferred embodiment, a reconstruction of the body structure is formed in step 505. The analysis step 510 is then performed utilizing data provided by the reconstruction(s).

Referring again to FIG. 82, preferably, analysis step 210 includes determining an accuracy of the reconstruction. Accuracy is preferably determined by analyzing the variance of the reconstructions formed over multiple iterations. Preferably, further views are defined in step 220 to concentrate on the region for which higher accuracy is required. Regions of the reconstruction having low variance provide a high degree of confidence regarding the accuracy of the reconstruction in the given region (where a portion may include the entirety of the body structure being imaged). Further views may be added to the current measurements until the variance is reduced to a required level.

Preferably, analysis step 210 includes determining a resolution of the reconstruction. Resolution is preferably determined by analyzing the full width at half maximum (FWHM) of peak values of the reconstruction. The FWHM is given by the distance between points at which the reconstructions reaches half of a peak value. Preferably, further views are defined in step 220 to concentrate on the region for which higher resolution is required.

An additional way to define future views using the reconstruction is on an information-theoretic basis. A quality function expressing an information theoretic measure is defined. The quality function rates the information that is obtainable from the body structure when one or more permissible views are added to current measurement process. Several examples of quality functions based on information-theoretic measures are discussed in detail below. The quality function is used to rate potential further views. The measurement process may then continue at those further views whose addition to the previous views yields a high rating.

Figure 86A:
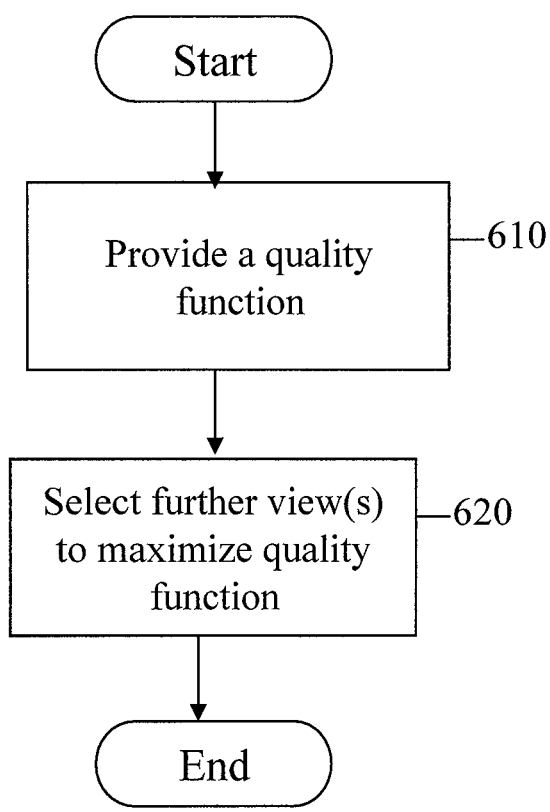
FIGS. 86a and 86b are simplified flowcharts of methods for dynamically defining further views, according to a first and a second preferred embodiment of the present invention.

Reference is now made to FIG. 86a, which is a simplified flowchart of a method for dynamically defining further views, according to a first preferred embodiment of the present invention. In step 610 a quality function is provided. The quality function expresses an information-theoretic measure which rates the quality of information obtainable from potential further views. In step 620 a set of further views is selected to maximize the quality function. Preferably the selected further views fulfill certain constraints; for example the further views may be selected from a predefined set or may be located in the vicinity of a region of interest within the body structure.

In the abovedescribed reconstruction-based analyses, the quality function is evaluated independently for a single reconstruction of the emission intensity of the body structure. However, quality functions may be defined which calculate the score for a given set in relation to one or more reconstructions and/or emmitance models. As is further discussed herein, given an object or class of objects, emmitance models may be devised to reflect expected or typical emission patterns for the given object.

For simplicity, the following discussion describes the evaluation of information-theoretic quality functions based on emmitance models only. It is to be understood that at least one of the emmitance models is a reconstruction of the body structure based on past measurements. Any remaining emmitance models are provided externally, and may be based on general medical knowledge or on information gathered during a previous round of emission measurements of the body structure.

Figure 86B:
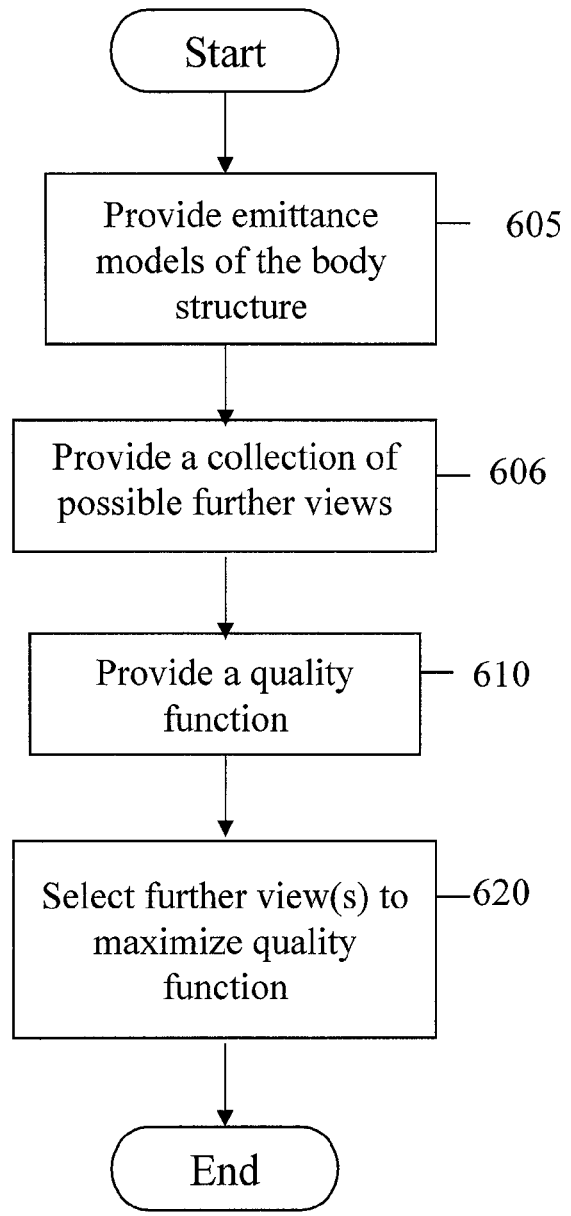

Reference is now made to FIG. 86b, which is a simplified flowchart of a method for dynamically defining further views, according to a second preferred embodiment of the present invention. The current method differs from the method of FIG. 86a by the addition of steps 605-606. In step 605 a set of one or more emmitance models is provided (where the set includes one or more reconstructions of the body structure). An emmitance model specifies the radiative intensity of each voxel in the body structure. As discussed above, some of the viewing parameters affect the radiative intensity of the voxels in the volume, for example the type of radiopharmaceutical and the time since administration of the radiopharmaceutical. Therefore, the emmitance models provided in step 605 preferably correspond to the relevant viewing parameters. In step 606 a collection of possible further views of the body structure is provided. The collection of views includes possible further views for future measurements, preferably based on anatomical and other constraints. Furthermore, the quality function provided in step 610 may utilize multiple emission models.

In the preferred embodiment, one or more of the emmitance models contains at least one high-emmitance portion (i.e. hot region). A prostate containing a tumor, for example, may be modeled as an ellipsoid volume with one or more high-emmitance portions.

In the preferred embodiment, one or more of the emmitance models contains at least one low-emmitance portion. A diseased heart may therefore be modeled as a heart-shaped volume with low-emmitance portions.

Note that an emmitance model need not contain high- or low-emmitance portions, but may have a uniform intensity or a slowly varying intensity.

In a first preferred embodiment the quality function implements a separability criterion. The implementation and evaluation of the separability criterion for active view determination is performed substantially as is further described herein.

In a second preferred embodiment, the quality function implements a reliability criterion. The implementation and evaluation of the reliability criterion for active view determination is performed substantially as described herein.

Maximization of the quality function may be performed utilizing any method known in the art such as simulated annealing and gradient ascent. In the simulated annealing (SA) method, each point of the search space is compared to a state of some physical system. The quality function to be maximized is interpreted as the internal energy of the system in that state. Therefore the goal is to bring the system from an arbitrary initial state to a state with the minimum possible energy.

The neighbors of each state and the probabilities of making a transition from each step to its neighboring states are specified. At each step, the SA heuristic probabilistically decides between moving the system to a neighboring state s' or staying put in states. The probabilities are chosen so that the system ultimately tends to move to states of lower energy. Typically this step is repeated until the system reaches and acceptable energy level.

Gradient ascent, on the other hand, is based on the observation that if a real-valued function $F(x)$, such as the quality function of the present embodiments, is defined and differentiable in a neighborhood of a point a, then $F(x)$ increases fastest if one goes from a in the direction of the gradient of F at a, $\nabla F(a)$. It follows that if:

$$b = a + \gamma \nabla F(a) \qquad (19)$$

for $\gamma > 0$ a small enough number, then $F(a) \leq F(b)$. Gradient ascent starts with a guess $x_0$ for a local maximum of F, and considers the sequence $x_0, x_1, x_2, \ldots$ such that:

$$x_{n+1} = x_n + \gamma \nabla F(x_n), n \geq 0. \qquad (20)$$

Since $F(x_0) \leq F(x_1) \leq F(x_2) \leq \ldots$, the sequence $(x_n)$ is expected converges to a local maximum.

Preferably, the set of views selected with the quality function is increased by at least one randomly selected view. The randomly selected view(s) increase the probability that the quality of information obtained with the further views is maximized globally rather than locally.

As discussed above, selecting the best set of size N from amongst a large set of candidate projections is computationally complex. Since the size of the collection of views and of the required set may be large, a brute force scheme might not be computationally feasible.

In an additional preferred embodiment, a so-called "greedy algorithm" is used to incrementally construct larger and larger sets, until the required number of further views is defined. When multiple further views are required, it is computationally complex to maximize the quality function over all possible combinations of further views. The greedy algorithm reduces the computational burden by selecting the further views one at a time. The algorithm starts with a current set of views, and for each iteration determines a single view that yields the maximum improvement of the set score (hence the name "greedy").

In theoretical terms, assume $\rho(\cdot)$ is the quality measure we are using for the view selection, and assume without loss of generality that we are trying to maximize this measure. We gradually build a set W of projections as follows. We start with an empty set $W=\emptyset$, and at every stage choose the projection that maximizes the quality measure when added to the current set:

$$W \leftarrow \arg\max_{W'} \{\rho(W') | W' = W \cup \{\phi\}, \phi \in \Phi\} \qquad (21)$$

In other words, during a given iteration, a respective score is calculated for a combination of the previous set with each of the views which is not a member of the current set. The current set is then expanded by adding the view which yielded the highest respective score, and the expanded current set serves as the input to the following iteration. Thus the number of times the scoring function is calculated per iteration drops from iteration to iteration. For a large collection of possible views, the greedy algorithm reduces the total number of computations required for set selection.

Figure 87:
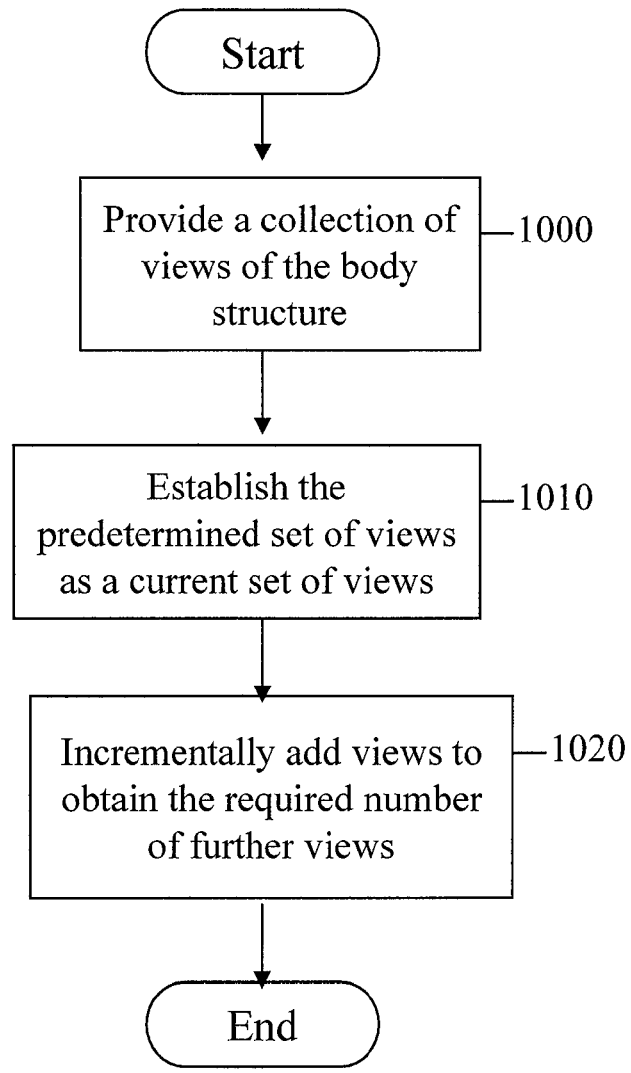
FIG. 87 is a simplified flowchart of an iterative method for selecting further views, according to a preferred embodiment of the present invention.

Reference is now made to FIG. 87, which is a simplified flowchart of an iterative "greedy" method for defining further views, according to a preferred embodiment of the present invention. The greedy algorithm is implemented substantially as described herein. In step 1000 a collection of views of the body structure is provided. The collection of views includes possible further views for future measurements, preferably based on anatomical and other constraints. In step 1010, the set of views used for the previous emission measurements is established as a current set of views. In step 1020 the view set is incrementally increased by a single further view during each iteration, until the required number of further views has been selected.

Figure 88:
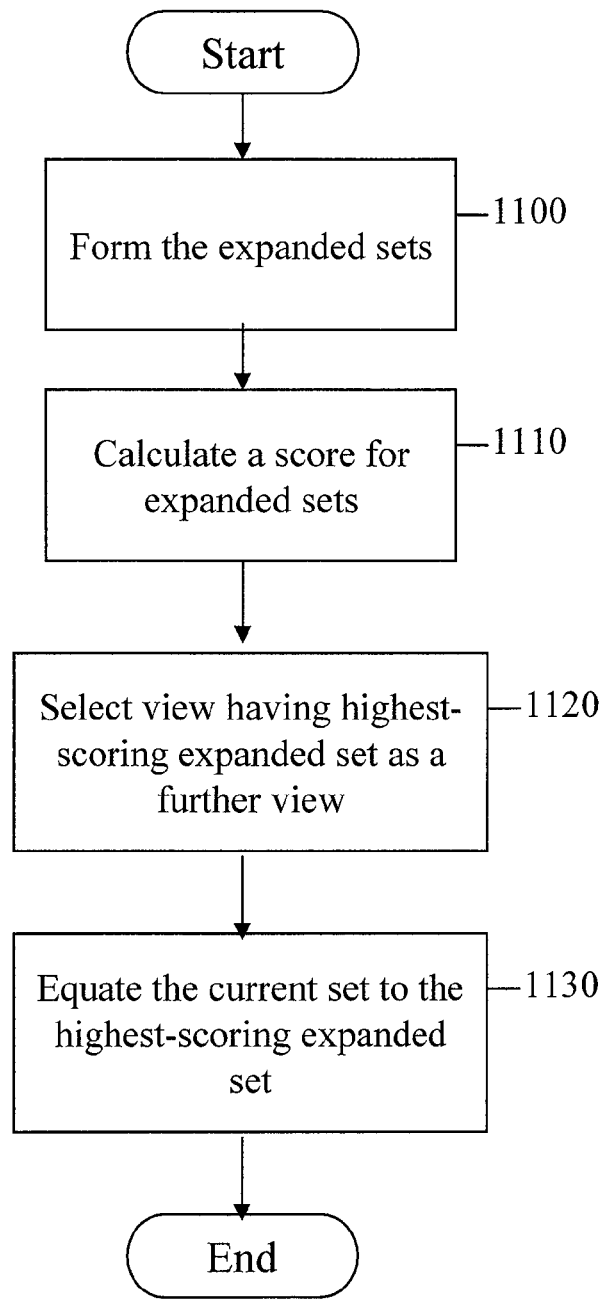
FIG. 88 is a simplified flowchart of a single iteration of a view selection method, according to a preferred embodiment of the present invention.

Reference is now made to FIG. 88, which is a simplified flowchart of a single iteration of the view selection method of FIG. 87, according to a preferred embodiment of the present invention. The method of FIG. 88 expands the current set of views by a single view. The method begins with a current set of views, which is the predetermined set (step 1010 above) for the first iteration of the greedy algorithm, or the set formed at the end of the previous iteration (step 1120 below) for all subsequent iterations. In step 1100, a respective expanded set is formed for each view not yet in the current set of views. A given view's expanded set contains all the views of the current set of views as well as the given view. In step 1110, a respective score is calculated for each of the expanded sets using the quality function. In step 1120, the view which yielded the highest-scoring expanded set is selected as a further view, to be used for further radioactive emission measurements. Finally, in step 1130, the current set is equated to the highest-scoring expanded set by adding the selected view to the current set. The newly formed current set serves as an input to the subsequent iteration, until the desired number of views is attained.

Figure 89:
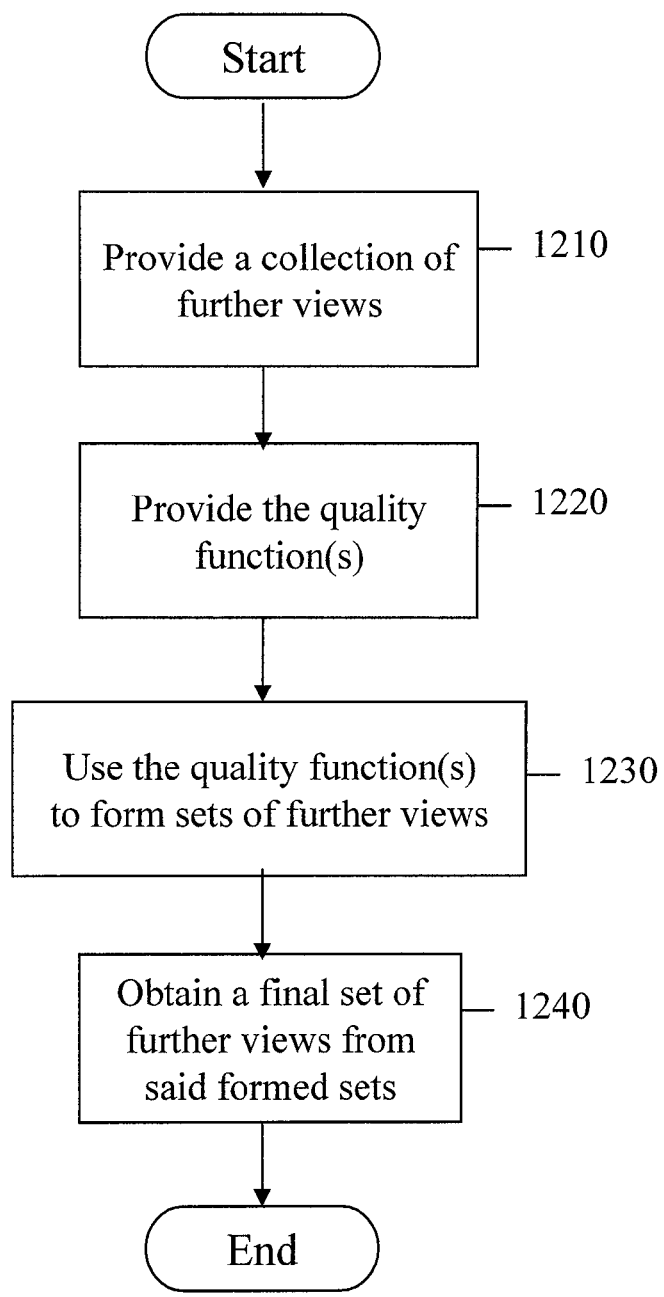
FIG. 89 is a simplified flowchart of a method for dynamically defining further views, according to a third preferred embodiment of the present invention.

Reference is now made to FIG. 89, which is a simplified flowchart of a method for dynamically defining further views, according to a third preferred embodiment of the present invention. In step 1210, a collection of possible further views for performing radioactive-emission measurements of the body structure are provided. Each of the views is associated with at least one viewing parameter. Preferably the viewing parameters consist of at least one the following: detector unit location, detector unit orientation, collection angle, and measurement duration.

In step 1220 at least one quality function is provided. Each quality function is for evaluating sets of views, essentially as described above. A single quality function may be used to select several sets of views, where each set of views contains a different number of views.

In step 1230, multiple sets of further views (where a set may include a single further view) are formed from the collection of views, using the quality function(s) provided in step 1220. In a first preferred embodiment, each of the sets is formed using a different one of the quality functions. In an alternate preferred embodiment, one or more of the quality functions are used to form more than one set of views, where sets formed with the same quality function have differing numbers of views.

In step 1240, a selected set of views is obtained from the sets formed in step 1230.

In a first preferred embodiment, the final set of views is obtained by choosing one of the sets formed in step 1230 using a set selection criterion. For example, a respective set is formed in step 1230 for the separability and reliability criteria independently. A set selection criterion which calculates an overall performance rating for a given set taking both criteria into account is defined, and the formed set with the highest overall rating is selected as the final set.

In another preferred embodiment, the selected set of views is obtained by merging the sets formed in step 1230 according to the relative importance of the respective quality function used to form each set.

In the preferred embodiment, the method further consists of providing at least one emmitance model and/or reconstruction representing the radioactive-emission density distribution of the volume, and of evaluating with at least one of the quality functions of step 1220 is performed in relation to the emmitance models.

As discussed above, since each view is associated with one or more parameters, the selected set yields a group of parameter values for performing effective detection of the intensity distribution of the body structure. For example, if each view is associated with a view location parameter the selected set defines a set of locations for collecting emission data from an object, in order to provide a high-quality reconstruction of the intensity distribution of the body structure.

Figure 90:
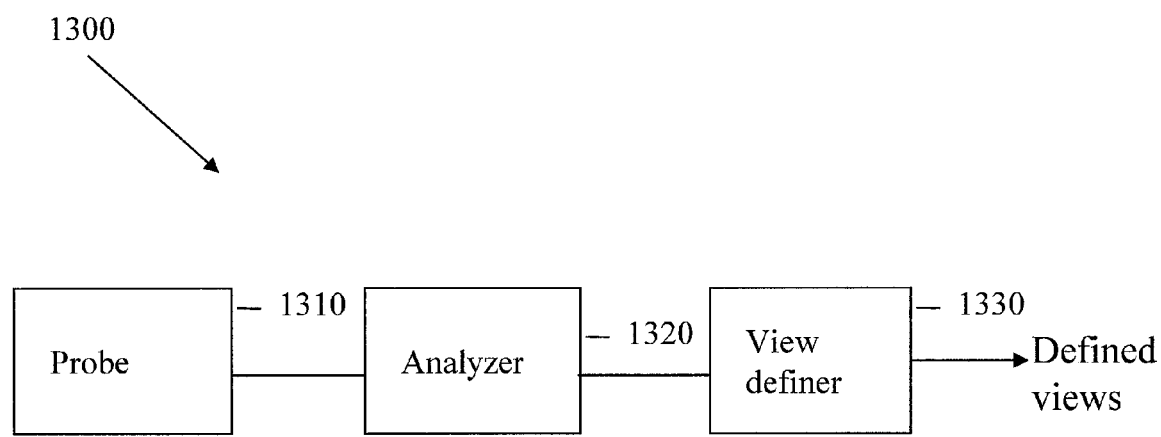
FIG. 90 is a simplified block diagram of measurement unit for performing radioactive-emission measurements of a body structure, according to a preferred embodiment of the present invention.

Reference is now made to FIG. 90, which is a simplified block diagram of measurement unit for performing radioactive-emission measurements of a body structure, according to a preferred embodiment of the present invention. Measurement unit 1300 includes probe 1310, analyzer 1320 and view definer 1330. Probe 1310 performs the radioactive-emission measurements of the body structure. Radioactive-emission-measuring probe 1310 preferably comprises several detecting units, which may be of different geometries and different collection angles δ, within a housing. Preferably, the orientation and/or collection angle of the individual collimators is controllable. Analyzer 1320 analyzes the radioactive-emission measurements obtained from probe 1310. View definer 1330 dynamically defines further views for measurements, based on the analysis provided by analysis unit 1320. The analysis and view definition are performed substantially as described above.

The abovedescribed methods for radioactive-emission measurements of a body structure begin by performing measurements at a predetermined set of views. The results of the initial measurements are then analyzed and further views are defined.

The initial set of views is preferably selected based on information theoretic measures that quantify the quality of the data fed to the reconstruction algorithm, in order to obtain the best data for reconstructing a three-dimensional image of the body structure, as described herein. The following section concentrates on the second step of the process, namely, obtaining the optimal and permissible set of initial views for performing the radioactive-emission measurements of the body structure. The initial predetermined set of views is denoted herein the optimal set of views.

The initial predetermined set of views is preferably selected in accordance with the method of the view selection as described herein. Preferably the initial predetermined set of views is selected on the basis of one or a combination of the separability, reliability, and uniformity criteria.

The abovedescribed methods may each be embodied as a computer program stored on a computer-readable storage medium. In the preferred embodiment, computer-readable storage medium contains a set of instructions for defining views for radioactive-emission measurements of the body structure. An analysis routine analyzes the radioactive-emission measurements obtained from a radioactive-emission-measuring probe, and a view definition routine dynamically defines further views for measurements, based on the analyzing.

By enabling high-quality reconstruction based on data collected from a limited collection of views, the abovedescribed view set selection techniques present a way to resolve the current conflict between the relatively large-pixel detectors needed for measurement speed and data processing considerations, with the small-pixel detectors needed until now to obtain a high-resolution reconstruction. The data obtained using the selected set of views enables a high-resolution reconstruction from a smaller number of measurements. Additionally, reconstructing the intensity distribution from a smaller quantity of collected data simplifies the computational process. The abovedescribed embodiments are particularly suitable for medical imaging purposes, where a high-resolution image is needed and it is desired to minimize the difficulties of the patient undergoing the diagnostic testing or treatment.

Voxel Dynamic Modeling

Dynamic modeling is a technique in which the parameters of a dynamic system are represented in mathematical language. Dynamic systems are generally represented with difference equations or differential equations. Measurements obtained from the modeled system can then be used to evaluate the values of parameters of interest that cannot be measured directly.

In the present case, the system being modeled is the body structure (or portion thereof) being imaged. During imaging, the emmitance from a given. voxel is affected by the chemical properties of the radiopharmaceuticals well as by the half-life of the tracer, as well as by the nature of the body structure being imaged. For example, the chemical properties of the antibody to which the tracer is attached govern factors such as binding to the tissue, accumulation, and clearance rate.

The goal of the presented models is to recover the kinetics per voxel of one or more parameters of interest. Each of the models reflects a different mechanism for the diffusion of the radiopharmaceutical into and out of the voxel, as well as the possibility of accumulation within the voxel. For a given measurement process the dynamic model should be selected to match the known properties of the radiopharmaceutical being used.

Figure 91:
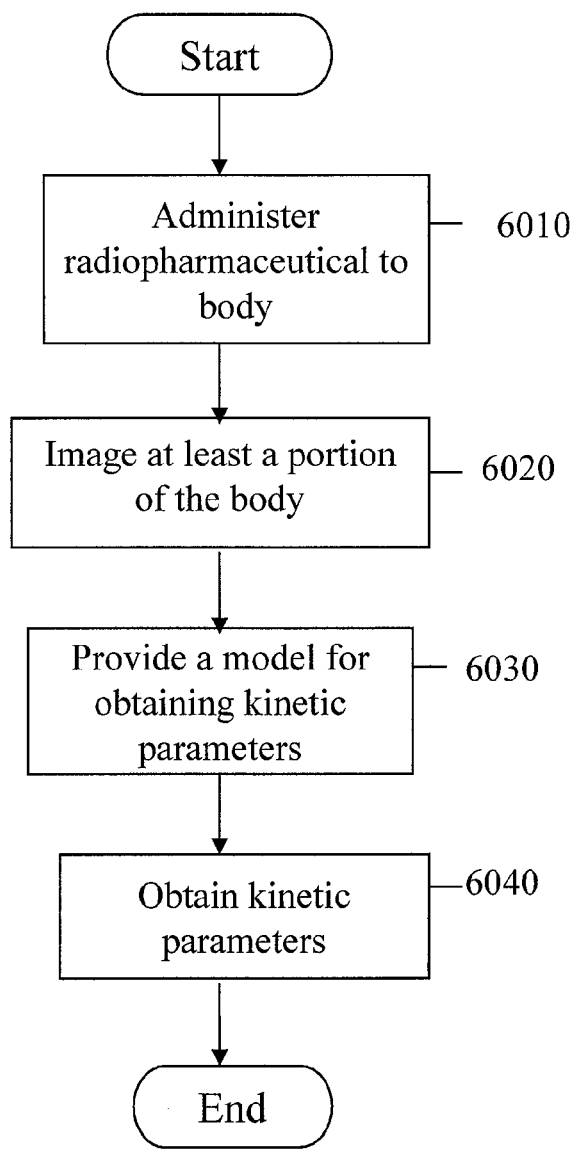
FIG. 91 is a simplified flowchart of a method for measuring kinetic parameters of a radiopharmaceutical in a body, according to a preferred embodiment of the present invention.

Reference is now made to FIG. 91, which is a simplified flowchart of a method for measuring kinetic parameters of a radiopharmaceutical in a body, according to a preferred embodiment of the present invention. In step 6010, the radiopharmaceutical is administered to the body. In step 6020, the body or a portion of the body are imaged. In step 6030, a model is provided for obtaining kinetic parameters from the imaging is provided. Several preferred embodiments of dynamic models are presented below. Finally, in step 6040, the kinetic parameters are obtained by applying the measurements to the provided model in order to extract the value of the required parameter(s). The kinetic parameters may provide information on factors such as actual uptake, rate of uptake, accumulation, and clearance of the radiopharmaceutical, which in turn provide information about the health of tissue in the voxel. The obtained parameter values can thus be analyzed to evaluate the health of the imaged body structure and of other portions of the body (for example renal functioning). (See description of expert system) The parameter values can also be analyzed and used to control future administration of the radiopharmaceutical (See description of closed loop injection system). The parameters obtained in step 6040 preferably include at least one of: local (in-voxel) representation of blood pool, blood flow, and diffusion to and/or from the local tissue as representative of function (e.g. viability).

Three preferred embodiments of dynamic models for provision in step 6030 are now presented. The following rationale and assumptions are common to all of the presented embodiments.

The analysis is of one voxel versus the rest of the body, not of the entire organ.

The dynamic model relates the per pixel emission levels to factors such as the blood in voxel, the tissue in voxel (and uptake from blood), and blood re-fill (perfusion/flow).

An additional assumption is that the amount of the tracer in the voxel is insignificant compared with the rest of the body and with the global blood pool. Therefore, the voxel in the region of interest (ROI) is affected by the global blood pool, but does not affect it. As a result, the concentration of tracer in the global blood pool can be recovered separately by one or more of: modeling the known kinetics given the exact injected dose, measuring the concentration at a pre-identified blood region using the imaging equipment, or by taking blood samples over time.

It is also assumed that the concentration of the tracer in the global blood may be controlled in a complex fashion by various injection profiles, such as:

1) Bolus injection
2) Constant drip
3) Smart injection—in which the radiopharmaceutical is injected in a controlled manner over time. The smart injection profile may be predetermined, or responsive to external events and/or feedback from the imaging equipment (see closed loop description). For example, rather than injecting a single bolus dose of radiopharmaceutical, one can inject a tenth of the dose for each of a series of ten injections. Examples of smart injection profiles are described below.

It is assumed that in ischemic conditions, not enough blood flow reaches the voxel, thus the concentration of the tracer in the blood of that voxel is different than in global blood pool. For example, if oxygen is the tracer, then ischemic region has lower oxygen concentration in the capillaries than in global blood pool due to poor refill.

An additional assumption is that the processes affecting the tracer concentration are slower than fractions a second, so that the volume and flow values (as defined below) relate to an average over the heart cycle. Thus gating will not separate the uptake into the tissue for different time slices in the heartbeat. Gated analysis (which is synchronized with the heart cycle) may be developed for fast processes which do not involve slow accumulation in the muscle tissue, or, alternatively, model the accumulation, both of which requires motion compensation.

A final assumption is that each voxel is large enough so that variables may be defined to relate to the voxel structure in global terms. The dynamic models described below are for voxels having a millimetric size, which are therefore significantly larger than the blood vessels (unlike during imaging of blood vessels). The models therefore include parameters for both blood and tissue parameters. In cases where a very high-resolution reconstruction (i.e. sub-millimetric) is required, a different model should be applied to handle voxels which are pure blood (e.g. voxels inside coronaries).

The following parameters are defined for all of the dynamic model embodiments presented below:

1) $V_t$—Volume of tissue in voxel.
2) $V_b$—Volume of blood within the capillaries in the given voxel. $V_b$ is normally constant for a given tissue type, but may vary for different tissue types such as blood vessel, connective tissue, or tumor before or after angiogenesis
3) V—Voxel volume. The voxel volume is the sum of the tissue volume and blood volume within the voxel:

$$V = V_t + V_b \quad (1)$$

V is a fixed value dictated by the imaging equipment (i.e. camera) performing the radioactive-emission measurements.

4) $R_b$—Density of blood within the voxel. $R_b$ is the ratio of the volume of the blood in the voxel to the total voxel volume:

$$R_b = V_b/V \quad (2)$$

For example, in cross section, the diameter of a capillary is about 10-15 um. To allow diffusion to cells the capillaries are spaced about 50-150 um apart. Therefore, it is reasonable to assume that healthy tissue has $R_b \sim 1\text{-}5\%$ 5) F—Blood flow to voxel. It is assumed that blood flow is not affected by neighboring voxels (i.e. blood flow is of "fresh" blood from the arteries).

6) $C_b$—Tracer concentration in blood within the voxel (reflects the capillaries in the voxel).

7) $C_t$—Tracer concentration in tissue within the voxel.

8) C—Tracer concentration in voxel, as measured by the imaging equipment.

9) $C_g$—Tracer concentration in global blood. The concentration in the global blood supply is assumed to be given. C may be determined with a separate model, or by measuring the global blood concentration directly. A full model of $C_g$ should reflect many of the patient's conditions, including cardiac output, prior diseases (such as metabolic disorders or diabetes), hyper/hypo-fluid volume, hyper/hypo-blood pressure, liver and/or kidney function, drugs (diuretics), and so forth.

Note that all of the above parameters other than $C_g$ are defined per voxel.

Figure 92:
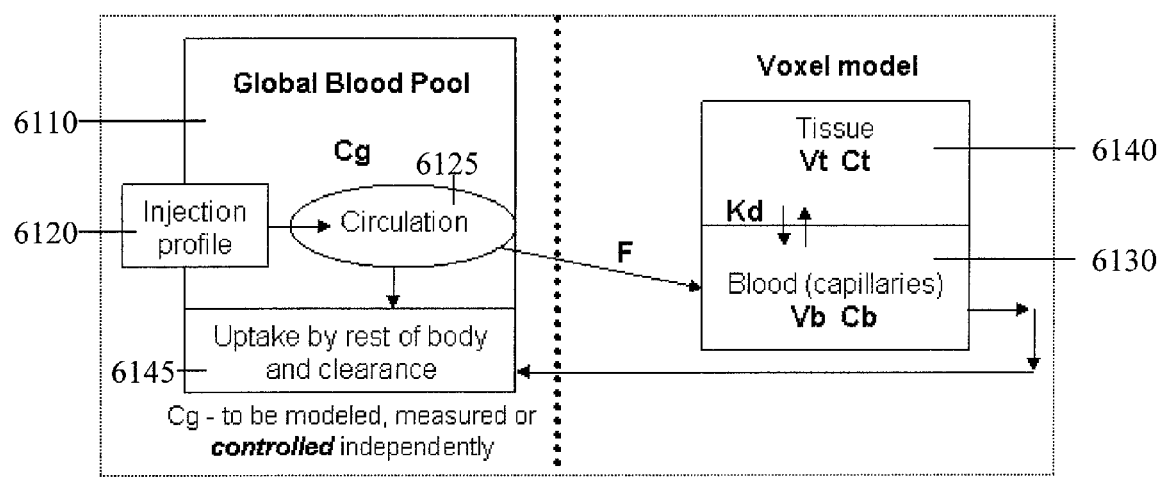
FIG. 92 is a schematic representation of a dynamic model of a voxel, according to a first preferred embodiment of the present invention.

Reference is now made to FIG. 92, which is a schematic representation of a dynamic model of a voxel, according to a first preferred embodiment of the present invention. The present embodiment (denoted herein model 1) assumes symmetric diffusion (i.e. the tracer diffusion coefficients into and out of the voxel are equal), and that there is no accumulation of the tracer within the voxel. FIG. 92 illustrates the role of each of the parameters described above.

The radioactive pharmaceutical is introduced into the global blood pool 6110 by injection according to an injection profile 6120. The radiopharmaceutical is conveyed to the voxel via the circulatory system 6125. The radiopharmaceutical flows through the voxel via the capillaries 6130 running through the voxel at flow rate F. Diffusion from the capillaries 6130 to the voxel tissue 6140 (uptake) and from the voxel tissue 6140 to the capillaries 6130 (release) occurs with a common diffusion coefficient Kd. Kd is an effective coefficient which takes into account both the uptake and outtake diffusion coefficients, and the surface area to volume ratio of the capillaries 6130. The remainder of the pharmaceutical is dispersed to the rest of the body for uptake and clearance 6145.

Similar or identical components are indicated with the same reference numbers throughout the figures.

Model 1 assumes tracer delivery to the voxel by diffusion to and from the local tissue, rather than by accumulation and dissolution. Therefore, model 1 can serve for applications with materials like Thallium and CardioTech, but not with Mibi which accumulates due to different diffusion rates in and out of the tissue. Models 2 and 3, which are presented below, allow for accumulation, and are therefore more suitable for radiopharmaceuticals such as Mibi.

Equations 3-5 present the relationship between the kinetic parameters for model 1:

$$C = \frac{Ct \cdot Vt + Cb \cdot Vb}{V} \qquad (3)$$
$$= Cb \cdot Rb + Ct \cdot (1 - Rb)$$

$$\frac{dCt}{dt} = Kd(Cb - Ct) \qquad (4)$$

$$\frac{dCb}{dt} = \frac{F}{Vb}(Cg - Cb) - Kd(Cb - Ct) \qquad (5)$$

Initial conditions: $Ct = 0$, $Cb = 0$

C is measured dynamically by the imaging equipment and Cg is determined separately by measurement or independent modeling from the art.

Figure 93:
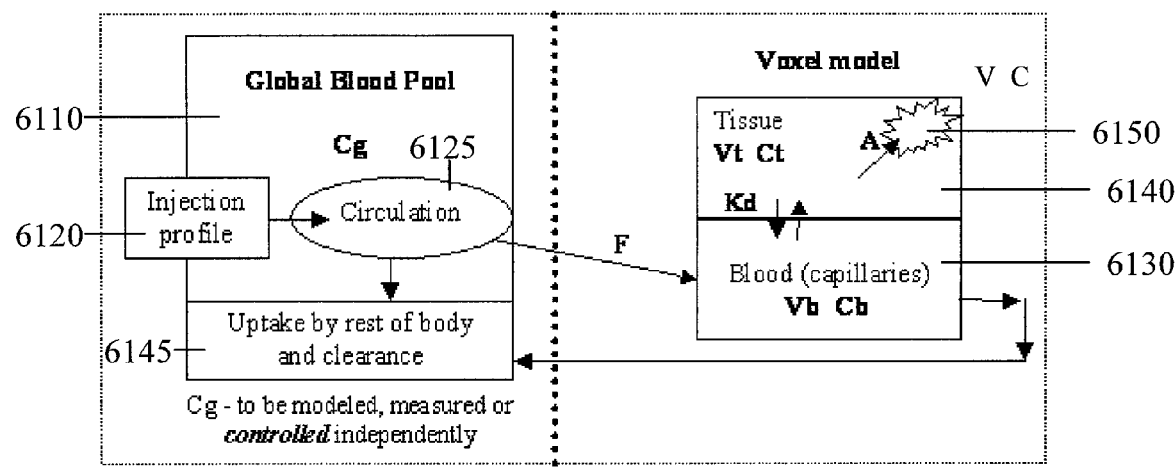
FIG. 93 is a schematic representation of a dynamic model of a voxel, according to a second preferred embodiment of the present invention.

Reference is now made to FIG. 93, which is a schematic representation of a dynamic model of a voxel, according to a second preferred embodiment of the present invention. The present embodiment (denoted herein model 2) assumes symmetric diffusion, with a diffusion coefficient of Kd. As in model 1, Kd is an effective coefficient which takes into account both the uptake and outtake diffusion coefficients, and the surface area to volume ratio of the capillaries 6130. However, in contrast with model 1, model 2 assumes that a fraction 6150 of the tracer concentration within the tissue is accumulated and is not diffused back to blood (for example by metabolism). The tracer accumulation within the voxel occurs at a rate of A.

Equations 6-9 present the relationship between the kinetic parameters for model 2:

$$C = \frac{Ct \cdot Vt + Cb \cdot Vb}{V} + Accum \qquad (6)$$
$$= Cb \cdot Rb + Ct \cdot (1 - Rb) + Accum$$

$$\frac{dCt}{dt} = Kd(Cb - Ct) - A \cdot Ct \qquad (7)$$

$$\frac{dCb}{dt} = \frac{F}{Vb}(Cg - Cb) - Kd(Cb - Ct) \qquad (8)$$

$$Accum = \int_0^t A \cdot Ct \, dt \qquad (9)$$

Initial conditions: $Ct = 0$, $Cb = 0$ $Accum = 0$

Figure 94:
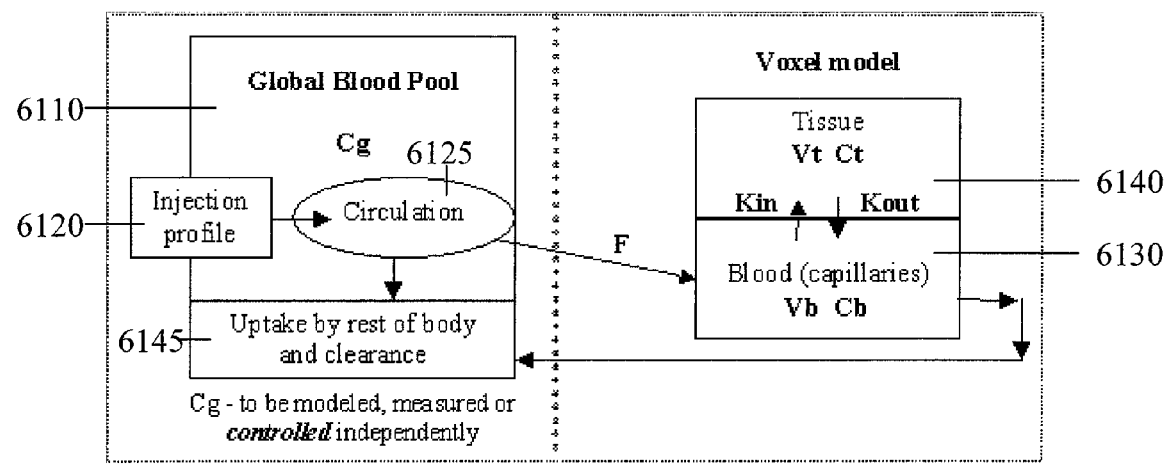
FIG. 94 is a schematic representation of a dynamic model of a voxel, according to a third preferred embodiment of the present invention.

Reference is now made to FIG. 94, which is a schematic representation of a dynamic model of a voxel, according to a third preferred embodiment of the present invention. The present embodiment (denoted herein model 3) assumes asymmetric diffusion, with uptake and release occurring according to the blood concentration (vs. zero) for uptake, and to the tissue concentration (vs. zero) for release, not according to the difference in concentrations (blood vs. tissue) as in model 1. Transport to the tissue is modeled by a diffusion coefficient of Kin, depending only on the outside concentration of capillary blood. Outgoing transport is modeled by a diffusion coefficient of Kout for outgoing transport, depending only on the internal (tissue) concentration. This way, accumulation is described by a high Kin and a low Kout. Kin and Kout are effective coefficients, which account for the surface area to volume ratio of capillaries.

Equations 10-12 present the relationship between the kinetic parameters for model 3:

$$C = \frac{Ct \cdot Vt + Cb \cdot Vb}{V} \qquad (10)$$
$$= Cb \cdot Rb + Ct \cdot (1 - Rb)$$

$$\frac{dCt}{dt} = Kin \cdot Cb - Kout \cdot Ct \qquad (11)$$

$$\frac{dCb}{dt} = \frac{F}{Vb}(Cg - Cb) - Kin \cdot Cb + Kout \cdot Ct \qquad (12)$$

Initial conditions: $Ct = 0$, $Cb = 0$

Models 2 and 3 are suitable for use with tracers like Thallium and Mibi, since they do not assume symmetric diffusion to/from the local tissue, but rather allow accumulation.

Regarding the parameters of the abovedescribed dynamic models, it may be possible to attribute the physiological meaning as follows:
1) F may correspond to perfusion
2) Kd+A may correspond to viability and metabolism (Model 2)
3) Kin may correspond to viability (Model 3)

Referring again to FIG. 92, in step 6040 the kinetic parameters for the voxel are obtained by applying the measured values to the provided model and extracting the value of the required parameters. Parameter extraction may be performed utilizing any technique known in the art, such as numerical analysis. Repeated measurements may be made of the given voxel, and the parameters calculated with increasing accuracy.

In a preferred embodiment, parameter extraction the dynamic system is provided in step 6030 as an analogous RLC electronic circuit. An RLC circuit is an electrical circuit consisting of resistors (R), inductors (L), and capacitors (C), connected in series and/or in parallel. Any voltage or current in an RLC circuit can be described by a second-order differential equation. Since all of the abovedescribed models present the voxel kinetic parameters as a second order system, the dynamic model provided in step 6030 may be described as an arrangement of resistors, capacitors, and inductors.

Voltage analysis of an RLC circuit is based on expressing the voltage over each of the circuit elements as a function of the circuit current as follows:

$$\text{Resistor: } V_R(t) = R \cdot i(t) \tag{13}$$

$$\text{Capacitor: } V_C(t) = \frac{1}{C} \int_{-\infty}^{t} i(\tau) d\tau \tag{14}$$

$$\text{Inductor: } V_L(t) = L \frac{di}{dt} \tag{15}$$

Figure 95:
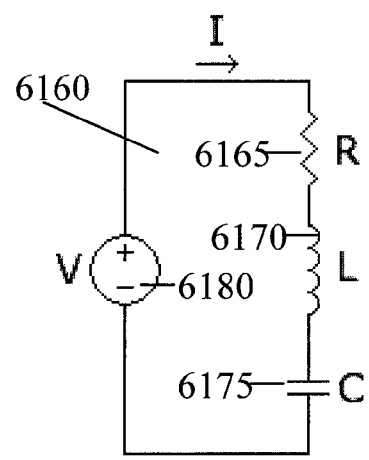
FIG. 95 is a circuit diagram of a series RLC electronic circuit.

As an example of RLC circuit analysis, consider the series RLC circuit 6160 shown in FIG. 95. RLC circuit 6160 consists of resistor 6165, inductor 6170, and capacitor 6175 connected in series, with an input voltage provided by voltage source 6180. In a series RLC circuit, the total voltage drop over the circuit is the sum of the voltage drop over each of the circuit elements, so that:

$$V(t) = R \cdot i(t) + L \frac{di}{dt} + \frac{1}{C} \int_{-\infty}^{t} i(\tau) d\tau \tag{16}$$

and:

$$\frac{dV}{dt} = L \frac{d^2 I}{dt^2} + R \frac{di}{dt} + \frac{1}{C} i(t) \tag{17}$$

Presenting the dynamic model as an RLC circuit enables using well-known circuit analysis techniques to derive the values of the desired parameters based on the measurements, and to analyze the behavior of the dynamic system. In terms of the abovedescribed dynamic modeling, the voltage, V, represents the administered radiopharmaceutical, and dV/dt represents the rate of change of the administered radiopharmaceutical, that is the administration protocol. The circuit function (e.g. the right hand side of equation 17) is analogous to the obtained image. Since the obtained image is dependent on Ø, the probability that a photon emitted by the given voxel is detected by the imaging equipment, the circuit function is a function of Ø. The RLC analogy can thus be used in order to determine the radiopharmaceutical input function, dV/dt, which optimizes Ø.

Possible forms for dV/dt include bolus injection (V(t) is a single pulse at t=0), constant drip (V(t) is a constant), and smart injection profile. Following are non-limiting examples of smart injection profiles:

1) Randomly (e.g. in the range of about every 1 to 200 sec)
2) Periodically every T seconds
3) Synchronized to the camera acquisition cycle. For example, if the camera produces a full volume scan every 5 seconds the injections are synchronized with each repetition of the scan. Synchronizing with camera acquisition allows better spatio-temporal coverage, as the injection and the scanning plans may be optimized together.

4) Synchronized to motion-related events. Motion-related events may include one or more of expiration, inspiration, cardiac movement, stomach contraction, gastro-intestinal movement, joint movement, organ movement, and so forth. For example, motion-synchronized injection may be used to inject and/or acquire during a relatively stable time period or a relatively motion-intensive time period.

5) Synchronized to physiological events (which may be acquired by another system). Physiological events may include a change in the activity of an organ or tissue (such as $O_2/CO_2$ concentration), glucose concentration, changes in perfusion, electrical activity (ECG, EMG, EEG, etc. . . . ), neuronal activity, muscular activity, gland activity, and so forth.

6) Synchronized to an external event, for example to an external stimulation (e.g. by motion, sound, or light) or drug administration. Synchronizing with a drug administration may be useful for procedures such as imaging of cerebral perfusion events (like in functional MRI), so that a small bolus may be injected per stimulus and the region that uptakes the radiopharmaceutical will be more likely to be related to the stimulus.

7) Responsive to the radiopharmaceutical concentration in the blood. By monitoring the level of the radiopharmaceutical in the blood (either by drawing blood samples or by determining the level with the camera or other measurement system) it is possible to control the pattern in the blood, for example to keep a desired level, a desired slope, cycles, and so forth. In particular, when the frequency domain is used for the final analysis it may be beneficial to have the injection profile in one or more fixed periods (frequencies) selected to fit the expected kinetic profile, and to keep the concentration in the blood controlled so as to produce a desired spectral performance of the blood concentration, for example an approximately sinusoidal, saw-tooth, other harmonic form. When the level in the blood is provided by the camera, a closed loop system is obtained (see closed loop description).

By synchronized to an event it is meant that the injection timing is substantially linked to the timing of the event; for example the injection is performed at the time of the event, at a predetermined delay after it, or at a predicted time before the event. Such synchronization may allow summing and/or averaging the collected data in a synchronized fashion, similar to gating. Such summing/averaging enables the analysis and amplification of information related to the desired event, while all events which are not synchronized become "blurred", and have less influence on the final result. For example, an injection profile of once every two seconds allows data accumulated for a dynamic event synchronized to a two second period to be collected and averaged. External interferences, such as breathing, heart motion, and sudden patient motion, become less influential as they are not synchronized with the two second cycle. Therefore the signal to noise ratio and errors in the reconstructed kinetic parameters are reduced.

Figure 96:
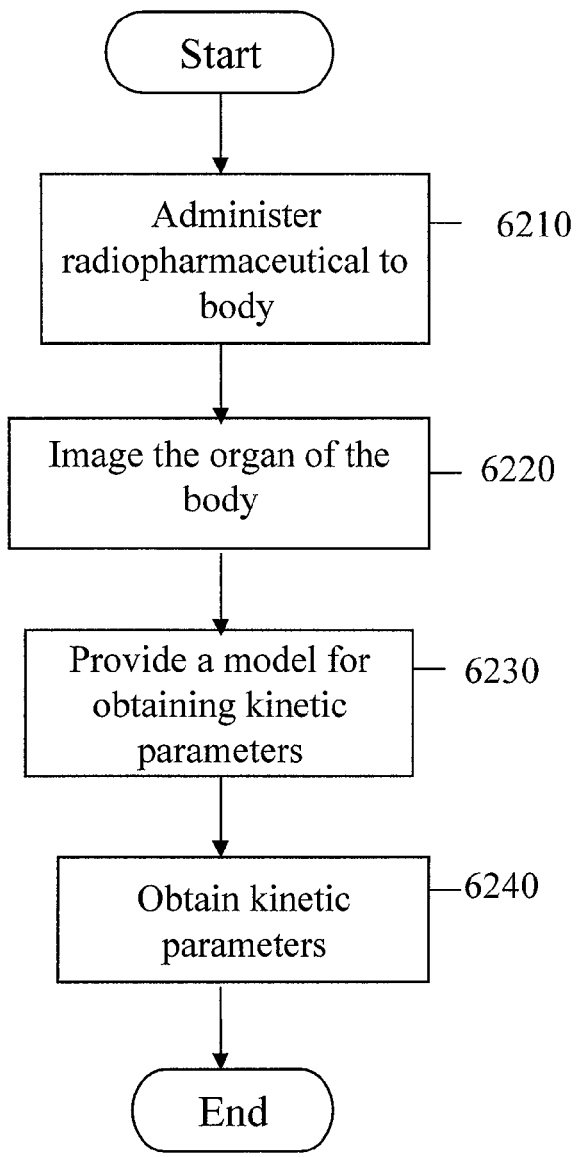
FIG. 96 is a simplified flowchart of a method for measuring kinetic parameters of a radiopharmaceutical in an organ of a body, according to a preferred embodiment of the present invention.

Reference is now made to FIG. 96, which is a simplified flowchart of a method for measuring kinetic parameters of a radiopharmaceutical in an organ of a body, according to a preferred embodiment of the present invention. The present method differs from the method of FIG. 91 in that it images a specific organ of the body. In step 6210, the radiopharmaceutical is administered to the body. In step 6220, the organ is imaged. In step 6230, a model is provided for obtaining kinetic parameters from the imaging is provided. Finally, in step 6240, the kinetic parameters are obtained by applying the measurements to the provided model and extracting the value of the required parameter(s).

Figure 97:
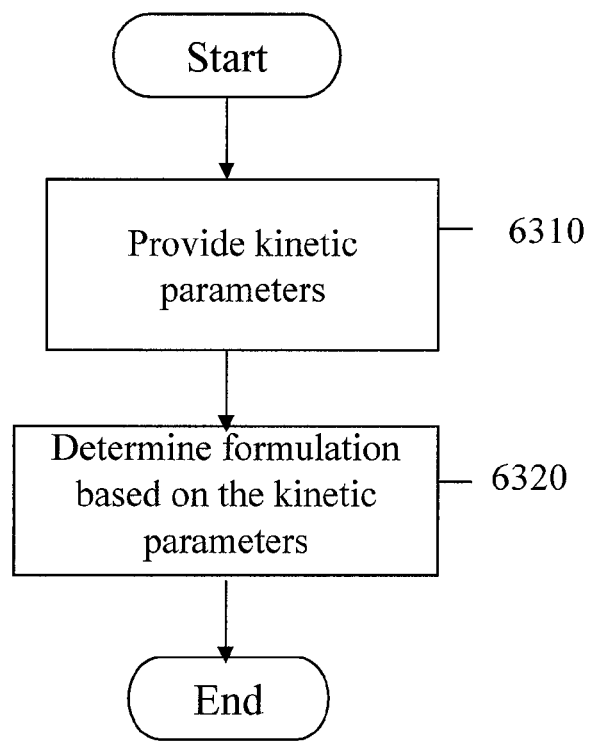
FIG. 97 is a simplified flowchart of a process for obtaining the drug formulation, according to a preferred embodiment of the present invention.

A further preferred embodiment of the present invention is a drug formulation for a radiopharmaceutical. Reference is now made to FIG. 97, which is a simplified flowchart of a process for obtaining the drug formulation, according to a preferred embodiment of the present invention. In step 6310, kinetic parameters for the radiopharmaceutical are provided. In step 6320, the formulation is determined, based on the provided kinetic parameters. The values of the kinetic parameters are preferably obtained by the method of FIG. 91 described above.

In the abovedescribed models C is modeled as a concentration. Alternatively, C may be modeled as a count rate. For each radiopharmaceutical there is a conversion ratio from concentration to count rate which depends on several factors. Factors influencing the conversion may include: mg of matter to number of molecules, the radiopharmaceutical half-life (which determines the average time for a photon to be emitted per molecule), and the rate of isotope decay. If the half-life is short, there is a reduction in available isotopes over the time of acquisition. Modeling the count rate may therefore be easier, and allow later conversion to concentrations.

Commonly, the time for a compound to become widespread in the body is in the time scale of about one minute. Thus the sharp slope in concentration observed immediately following injection lasts only a few seconds before various organs begin uptaking the compound. It is therefore preferable to allow scanning and reconstruction of volumes of interest in a time resolution of about 5-10 seconds. Since the model equations include relatively few parameters, it is assumed that with acquisition of a few minutes long (1, 2, 5, 10 minutes) the number of time points obtained per voxel is in the range of 10-20 (preferably 50 or more), which is expected to enable stable estimation of the kinetic parameters. With radiopharmaceuticals having slower uptake and release activity it may be preferred to have longer acquisition times, such as 20, 30, or 60 minutes.

The analysis and determination of parameter values may be performed in the time domain, the frequency domain, or in any other transform domain. In the time domain, analysis is performed by solving the differential equation, either analytically or numerically, in order to reach a model which best fits the acquired data. Various numerical tools are known to fit equations of this complexity to a given data set. An example of frequency domain analysis is presented below.

The analytical solution may include integration over the input Cg, which may not be available with sufficient accuracy. In such cases, numerical methods for fitting the differential equations may prove more stable and accurate.

It is expected that frequency domain analysis will be particularly effective when the data is acquired in a frequency representation. It is expected that time domain analysis will be particularly effective when the data is obtained over time. Alternative approaches may be tested by converting the data from one form to the other, and the more stable approach may be selected.

In some cases, the model above may further include interstitial volume, so that substances move from capillaries to the interstitial domain and from there to the cells, and vice versa. Transfer to and from the interstitial domain may be added to the equations. In many cases the difference in concentration between the interstitial volume and the capillaries is insignificant, thus they may be modeled as one domain.

It should be noted that the general blood concentration, Cg, may differ from one location to another, for example between veins and arteries. Therefore, it may be preferable to measure the blood concentration by a sample from the arteries or by measuring the concentration inside the left chambers of the heart.

Similarly, in the case of cardiac imaging there might be poor blood flow along one or more of the coronary arteries, and thus uptake of substance by cells in one voxel might reduce the remaining concentration in the artery available for voxels further along the given artery. Thus the value of Cg may actually be lower for the more distal voxels. Changes in the value of Cg may be handled by iterating the parameter estimation while correcting the Cg value once the uptake in the more proximal voxels has been estimated.

Note that if the radiopharmaceutical administration is based on a periodic injection protocol, the concentration in the general blood pool (either arterial or venous) may respond in a periodic pulsatile profile, which has a harmonic spectrum.

Following is a discussion of the application of frequency domain analysis to the abovedescribed voxel dynamic modeling. Frequency domain analysis allows the use of techniques for measuring the frequency response to a periodic injection protocol, similarly to the way frequency response is evaluated in passive electrical circuitries. For example, the frequency response may be measured by injecting the radiopharmaceuticalt several frequencies, and then determining the amplitude of the response at a given frequency, the phase response, or the comparative amplitudes at several frequencies. The results are then compared with the model of the frequency response and parameters of interest are extracted (e.g. resistors and capacitor values in electrical circuitry, or diffusion coefficients and blood flow, F, in the voxel dynamic model).

Taking model 3 as an example, the Fourier transform equivalents of Equations 10-12 are:

$$C = (Ct * Vt + Cb * Vb)/V = Cb * Rb + Ct * (1 - Rb) \tag{18}$$

$$j\omega Ct = Kin \cdot Cb - Kout \cdot Ct \tag{19}$$

$$j\omega Cb = \frac{F}{Vb}(Cg - Cb) - Kin \cdot Cb + Kout \cdot Ct \tag{20}$$

where C, Cb, Ct, Cg are in the frequency domain, w is the angular frequency, and j is the imaginary unit, $\sqrt{-1}$.

Equations 18-20 result in Equation 21, which relates the concentration in the voxel of interest (C) to the concentration in the arterial blood (Cg) in the frequency domain:

$$C = \frac{\frac{F \cdot Cg}{V}\left[\frac{Vt}{Vb} + \frac{jw + Kout}{Kin}\right]}{\left(jw + \frac{F}{Vb} + Kin\right) \cdot \left(\frac{jw + Kout}{Kin}\right) - Kout} \tag{21}$$

The relationship between C and Cg can be measured in several frequencies, enabling the extraction of F, Kin, and Kout.

Equation 21 is useful for analyzing the value of the kinetic parameters. Consider the case of w<<Kout, that is the case in which rate of clearance is much faster than the rates of changes in the blood flow. In practice, it is difficult to obtain w<<Kout for some radiopharmaceuticals, requiring slow and controlled changes in the blood concentration.

For w<<Kout, Equation 21 becomes:

$$\frac{C}{Cg} = \frac{\frac{F}{V}\left[\frac{Vt}{Vb} + \frac{Kout}{Kin}\right]}{\left(jw + \frac{F}{Vb}\right)\cdot\left(\frac{Kout}{Kin}\right)} = \frac{F}{V}\cdot\frac{\frac{Vt\cdot Kin}{Kout} + Vb}{jwVb + F} \quad (22)$$

Equation 22 provides a highly important relationship, as the ratio between two measurements, each with two different low frequencies w1 and w2 (i.e. two slow derivatives of concentration changes), provide a direct measure of flow rate:

$$\frac{(C/Cg)_2}{(C/Cg)_1} = \frac{jw_1\cdot Vb + F}{jw_2\cdot Vb + F} \quad (23)$$

The ability to isolate parameters, so that the values of different parameters do not affect each other, is of high importance. Parameter isolation combined with the high sensitivity and the ability to produce multiple repetitions in different frequencies or slopes may enable extracting some parameters in a quantitative and efficient manner.

Quantification in the case of w<<Kout depends on the prior estimation of the partial volume in each voxel containing the blood compartment. Once F is known, the ratio of Kin/Kout is obtainable from the Equation 22 above.

In a more typical scenario, w>>Kout, and equation 21 becomes:

$$\frac{C}{Cg} \cong \frac{F}{V}\cdot\frac{Kin\cdot Vt + jw\cdot Vb}{jw(jw\cdot Vb + Kin\cdot Vb + F)} \quad (24)$$

For w>>Kout, measuring the ratio of C/Cg in multiple frequencies allows the recovery of the flow F and the wash-in rate Kin (which is associated with the well being of the cells) in a quantitative manner.

It is possible to perform all analyses in terms of the absolute amplitudes of C and Cg by converting the modeling equations (which include complex numbers) to absolute numbers. Alternatively, phase analysis may be used. An additional alternative is to transform time-domain signals into the frequency domain with the Fourier transform, and to perform the remaining analysis in the frequency domain.

Global Zero:

The following relates to a plurality of independently moving detectors, which move independently during data acquisition. Since each detector is associated with one or several motors, the different motors have to be referenced to a single zero point, with an accuracy, which is greater than that of a desired object size for detection. For example, the accuracy may need to be better than about 10% of the object size, and preferably 1%, or even 0.1% of the desired object size for detection.

In accordance with a first global zero embodiment, the various detectors are referenced to a single location, for example, a hot wire, as a radiation reference point of a known position. However, this requires that the position of the radiation reference point be known with a very great accuracy, which is in itself difficult.

In accordance with a second global zero embodiment, relative measurements of at least two and preferably, at least three radiation reference points are performed, by the detectors, moving independently, and a global zero point is determined from the relative measurements, using dedicated algorithms developed for the purpose. This bypasses the need for the exact position of the reference source of the first global zero embodiment and decreases uncertainties.

Pixel Sensitivity Map:

The evenly illuminated board used by present day Anger cameras for obtaining a pixel sensitivity map is inapplicable for the radioimaging cameras of the present invention, as described for example, in Appendix A, due to their curvatures. Yet, producing a sensitivity map for each detector or assembly, individually, is very time consuming. Given a structure of at least 10 assemblies, this may require 10 individual sensitivity maps.

In accordance with embodiments of the present invention, a hot wire of substantially even illumination is used as a radiation reference point, for obtaining a sensitivity map of the all detectors—that all detecting units or detecting pixels, simultaneously—in parallel. This is done by performing measurements of the evenly illuminated wire with the plurality of detectors, each from its respective position and orientation, and comparing the sensitivity of each detector, after correcting for distance and viewing angle of each.

Pixel and Collimator Integrity Check:

The method of performing a pixel sensitivity map is further applicable for ensuring the integrity of the pixels and their collimators, simultaneously, for all pixels. A large discrepancy in the readings will suggest that there may be a structural problem, for example, a broken collimator, a chipped detector, or a broken electrical connector.

Detecting Patient's Motion:

Present day Anger cameras generally view enough of the body to have several reference edges in the image, so that patient's motion is immediately seen. But the radioimaging cameras of the present invention, for example, as described in Appendix A, view a very small region of the patient's body, with little to use as a point of reference, so patient's motion may not be apparent.

In accordance with a first embodiment, the acquisition time for a full image is divided to N periods, where N≥2, and N full images are acquired, each for 1/N of the time. The N images are then compared by various methods, to determine if the two or more images are different, for example, by using a statistical technique. If the images appear to have come from different distributions, new images may be taken.

Additionally or alternatively, panoramic views may be constructed from the N images, which include superposition of about 90% or so. The panorama is a method of display that enables to easily identify objects in the raw data, and the difference between panoramic views of different acquisition slices provides the information on possible patient's movement.

Temporal Resolution:

In accordance with a first embodiment of the present invention, a CZT module contains 256 pixels of a CZT detector, the 256 pixels being associated with 2 ASICS, each ASIC receiving photon count events from 128 pixels.

It will be appreciated that a smaller number of pixels may be associated with a single ASIC, for example, 64, or 32, or another number, as desired.

The solid-state CdZnTe (CZT) detector may be obtained, for example, from eV Products, a division of II-VI Corporation, Saxonburg Pa., 16056, or from IMARAD IMAGING SYSTEMS LTD., of Rehovot, ISRAEL, 76124, www.imarad.com, or from another source.

The ASIC may be, for example, OMS 'XAIM3.4' made by Orbotech Medical Systems, Rehovot, Israel, together with the CZT detector.

In accordance with a first embodiment, the 2 ASICs share a common output and transmit the data to an ADC printed circuit board (PCB) that handles in parallel 4 CZT modules. Thus, a total of 1024 pixels may be channeled through one ADC board, forming an assembly.

In accordance with a second embodiment, the 2 ASICS may be channeled to a single ADC.

In accordance with a third embodiment, a single ASICS may be channeled to a single ADC.

A potential bottle neck in the processing of events is the ASICs of the CZT module and their connection to the ADC PCB.

In accordance with the first embodiment, an ASIC of 128 pixels can process one photon hit within 3.5 µs, or 285,000 events/s over 128 pixels, i.e. over 2200 events/pixel/s—which is an exceedingly high rate.

The 2 ASICS share the same output, and hence coincident event output of the 2 ASICS in a CZT module will cause a collision and information loss. The duration of an event output from the ASIC is 1 µs.

It will be appreciated that the number of events/pixel/s may be increased by associating fewer pixels with each ASIC. For example, given 32 pixels per ASIC, that number may be increased by a factor of 4, to 8800 events/pixel/s.

It will be appreciated that coincident event information loss may be further reduced by associating each ASIC with a single output.

The embodiments thus described provide high temporal resolution since the there is no smearing of the timing of events— no merging of the timing of events in a buffer, and little loss due to coincidence counts.

In accordance with anther embodiment, a buffer may be used, but with a time stamp, for example, as follows: the ASIC has an independent channel of analog pulse processing for each pixel. Each channel is event triggered and contains a low-noise preamplifier, pulse shaper, amplifier, peak-and-hold circuitry. The ASIC also provides selectable gain, threshold, shaping time, hold time and readout delay within the hold window. These parameters are judiciously varied to achieve optimum performance for a given photon energy range and event rate. The ASIC generates energy and position information as well as an event trigger for each gamma event. Common to all pixels served by the ASIC is a control logic block and a buffered multiplexed readout. Such control and readout circuitry provides the means to control the ASIC and to output the photon event data. A time stamp mechanism along with the buffer associates each event with a specific time of arrival, to provide temporal resolution.

Independent Temperature Control for the Plurality of Detectors:

Solid state detectors, such as CdTe and CZT, are susceptible to leakage currents, which are temperature dependent. Often, thermoelectric coolers are employed, based on Pelletier cooling. A single stage thermoelectric cooler can reduce the leakage current by a factor of approximately 100. Natural or forced convection may be further used, to provide a heat sink to the thermoelectric coolers.

Yet, when using a plurality of independently moving detectors, uniform temperature may be required in order to provide uniformity in the drift current, hence the energy window. Since the heat is primarily produced by the electronics, the higher the count rate of a detector, the higher the heat generation, and detectors that experience a high count rate will operate at a higher temperature then those of a low count rate, leading to a shift in the drift current hence energy window of the detector.

Nonetheless, solid state detector systems that are currently employed do not address the issue of uniform temperatures across the plurality of detectors.

In accordance with the present invention, a CZT module containing the solid state detector, such as a CZT detector, is pixilated, to form a detector array or a block, and associated with a dedicated ASIC.

Preferably, each CZT module includes a detector block and the associated ASIC is independently monitored for temperature, by a temperature sensor, which reports to a controller, for providing thermoelectric cooling, responsive to the temperature sensor's input.

Alternatively, each CZT module includes two or more detector blocks, associated with the dedicated ASIC and are monitored as a single unit for temperature, by the temperature sensor, which reports to the controller, for providing thermoelectric cooling, responsive to the temperature sensor's input.

The number of pixels in the CZT Module may be, for example, as low as 10, or as high as 1000, as required.

In accordance with another embodiment, no temperature sensor is required. Rather, the Pelletier cooling is applied to a CZT module, responsive to the count rate from that module.

It will be appreciated that other solid state crystals, for example, CdTe or another may be used.

Spectral Resolution:

In accordance with embodiments of the present invention, the bias and current may be monitored and controlled per 1024 pixels, channeled through an ADC board, and forming a assembly, thus further monitoring and controlling the energy window, and ensuring uniformity of the energy window amongst the different assemblies.

It will be appreciated that the bias and current may be monitored and controlled on the basis of each CZT module or on the basis of each ASIC, where desired. It will be further appreciated that the monitoring and correcting may be dynamically performed, in real time.

Non-Uniform Scanning and Reconstruction:

In accordance with embodiments of the present invention, the radioimaging cameras described in Appendix A and other radioimaging cameras of independently moving detectors, wherein the detectors move independently during data acquisition, may further employ non-uniform scans.

A scanning density may be defined by the angular and translational increment size, or steps, the smaller the increment, the higher the density.

Additionally, the scanning density may be defined by the acquisition time at each position—the longer the time, the higher the density.

The non-uniform scans may relate to non-uniform angular steps of the detector along a sweep, non uniform detector translational steps, or different steps by different detectors. Some detectors may employ dense steps and others may employ sparse steps, for example, based on active vision, as taught in Appendix A, hereinbelow.

A control system may adapt the density of the scan to the distance to the object of interest. Since resolution decreases with distance, the higher density may compensate for increased distance.

Additionally or alternatively, the angular steps may increase in density when scanning the region of interest, and decrease in density, when scanning other regions.

Furthermore, more than one region of interest may be scanned with dense steps, simultaneously. The two regions of interest may be, for example, a tissue region and a blood pool region. This has applicability, for example, to dynamic studies of blood perfusion, by providing even scanning resources both to the blood and to the tissue. Scanning resources include, for example, detector dwell time, number of detectors, angular and translational increments, and the like—features that increase the amount of data collection.

Additionally, convex scans may be employed.

Variable scans, where a same region is scanned first with a first density and then with another density, may be employed. Alternatively, a same region may be scanned by a first group of detectors with a first density and then by a second group of detectors with another density, concurrently, or at different times.

This means that a same region is scanned with at some density by a given detector and at a different density by another detector.

Furthermore, in accordance with embodiments of the present invention, non-uniform reconstructing may be employed, providing non-uniform resolution, so that the resolution increases with the stability, hence reliability, hence reliability of the data.

The non-uniform reconstruction employs a condition number, which is a measure of a stability, hence reliability, hence reliability of a matrix to numerical operations, and is defined as:

$$\kappa(A) = \|A\| \cdot \|A^{-1}\| \quad [1]$$

If a matrix has a large condition number, for example, larger than 1000 then there is a possibility that even a small error in the data will lead to a large error in the solution.

The inaccuracies in the data will always be present because all measurements are finite and because all computers have a finite precision. Hence it is important to be on guard whenever solving ill-conditioned equations. Furthermore, it is ill advised to spend detecting time and other scanning resources in acquiring data that will lead to erroneous results due to instability, hence reliability.

In the present example, count data is processed to reconstruct the intensity distribution within voxels of measured volume. In general, we assume an intensity distribution, I, defined over an input space U, where U comprises a set of basic voxels in a three dimensional space, and I(u) defines the radiation intensity of a basic voxel $u \in U$. A detecting pixel, positioned on the radioimaging camera takes a series of measurements $y = (y_t)_{t=1}^T$ from different positions and orientations around the volume U. The geometrical and physical properties of the detecting pixel, together with its position and orientation for the given measurement, determine the detection probability $\phi_t(u)$ of a photon emitted from the voxel u. Thus the effective intensity of location u as viewed by the detecting unit during measurement t is $\phi_t(u)I(u)$.

The random count $X_t(u)$ of photons that are emitted from location u and detected in measurement t is modeled by a Poisson process with a mean $\phi_t(u)I(u)$. The total count of photons detected in measurement t is:

$$Yt = \text{Poisson } \Sigma_{u \in U} \phi_t(u)I(u) \quad [2]$$

The reconstruction problem is to reconstruct the intensities $(I(u))_{u \in U}$ from the measurements $(y_t)_{t=1}^T$.

Applying equation [1] to the detection probability matrix $\phi_t(u)$, it is possible to evaluate the condition number, hence the measure of stability, hence reliability of the various voxels u.

When the condition number for a particular voxel u is around 1, or no greater than 10, it is advisable to invest scanning resources, and apply dense scanning, and even subdivide the voxel to finer voxels. Thus, non-uniform scanning may be a function of the condition number.

Additionally or alternatively, when the condition number for a particular voxel u is greater than 100, or even greater than 1000, reconstruction is unstable and sensitive to noise. So it may be advisable to do with sparse scanning and even merge several voxels, to a larger voxel. Alternatively, denser scanning may be employed in order to increase the condition number of the voxel.

In accordance with embodiments of the present invention, there are several ways of utilizing the condition number, to direct and employ scanning resources, as follows:

1. add regularization factors (e.g. smoothness constraint, or piecewise smoothness constraints—for edge preservation) or add assumptions to the data (e.g. the range of realistic values per voxel should be, for example, no less than 0 and no greater than a predetermined value, or assume a distribution of counts per voxel, such as gamma distribution, based on typical spatial structures, and the like).

2. define a resolution in each region according to the information provided to that region—for example, if there are 1000 different views independently covering 1 cubic cm and almost not affected by the surrounding, then theoretically that volume can be divided up to about 1000 voxels (e.g. 1 mm square each), if the views create linearly independent set of equations with high condition numbers.

3. if that information is ill-conditioned (less views or views which are practically not independent), then one can decide to divide that volume to fewer voxels. Some approaches can be taken in this case, as follows:

i. use regularization only in regions which are ill-conditioned.

ii. with regard to neighboring voxels with poor reliability, they may be merged into bigger voxels, thus increasing their reliability to the combined one.

iii. point (ii) can be carried out repeatedly on the lowest reliability voxel—merge it with one of the neighboring voxels to form one bigger voxel, to form an aggregate of voxels, until no voxel is left with a reliability below a threshold. It will be appreciated that the aggregate voxels have a lower resolution locally since there is not enough resolution to support splitting, but all other regions with good coverage remain of high resolution, according to their coverage.

iv. the principle of (ii) can be reversed: define the whole volume as a single huge voxel, and split it to form sub-voxels—as long as each voxel maintains enough reliability, then repeatedly divide each voxel as long as the result of such split will maintains reliability high enough for stable results. This process produces a quad-tree, in multi scale of resolutions. The definition of the voxels can be determined in advance, based on the scan pattern, regardless of the count reading from the detectors.

v. same as (iv), but with adaptation of the scanning pattern, when a region is interesting but is still left with coarse resolution, so as to allocate more scanning resources, such as dwell time, number of detectors, angular and translational increments, to cover that region and to form more independent views such as to increase the reliability of the reconstruction of that area. This can still be done before data (detectors counts) is collected.

vi. same as (iv), but with multi-resolution as part of the reconstruction:

starting with reconstructing equations relating to the entire volume as a single voxel, performing iterations where the volume is split, while taking the previous iteration as initial condition, and selecting the stable split. Then repeating the splitting of some of the voxels, for which reconstruction is reliable and perform reconstruction for them, and over again, until reaching a split, which is no longer stable, thereby arriving at the final resolution for that location.

vii. items (v) and (vi) may be combined, by adapting a scanning pattern, not only to enable stability, hence reliability and reliability in reconstruction, but also to improve reconstruction. For example, if the reconstruction from the data, for example, based on item (vi) produced a split of is 1 cm resolution, then additional scanning in that region of interest may allow additional information to reach higher resolution, and further splits, thus improving the resolution in that region of interest.

Two Step Imaging for Dynamic Studies, Based on Anatomic Region of Interest:

In accordance with embodiments of the present invention, two-step protocols are proposed to enable anatomic modeling of small regions of a target.

As a first step, conventional injection and imaging is performed, using standard voxel division, for example, of 5×5×5 mm, to obtain an image of the target, for example, the heart.

An anatomical region of interest is then defined on the image, and a new voxel map is generated, along the anatomical boundary lines. The anatomical region of interest may be a small portion of the overall image.

As a second step, a second injection is made, followed by scanning with detecting recourses aimed at the anatomical region of interest.

In a way, this approach is suggestive of a zooming in approach, for example, as taught in commonly owned PCT/IL2005/001173. But there, voxel reconstruction was rigorous throughout, and here, the first step employs cubical voxels, as known, but these are used to define anatomical voxels for the second step.

Several radioimaging protocols may be employed for this purpose, for example, described as protocol J2 of FIGS. 101D and 101E, as follows:

Step 1: a first injection, for example, a single bolus of a first marker, such as Tl-201, at a low dose of between 0.5 and 2 mCi, and imaging the heart for example, for about 1 minutes, to acquire a high quality image, to be used for constructing the anatomical image, and for defining a finer region of interest; and Step 2: while the patient is immobile, injecting 20-40 mCi, preferably of a second marker, for example, Tc-99m-sestamibi, and performing an up to 10 minute dynamic study, with image reconstruction every several seconds, for example, every 5 or 10 or 20 seconds, the dynamic image being superimposed on the first image.

On the one hand, when the image reconstruction is anatomically defined, the number of variables decrease drastically, for example, by a factor of 10; Additionally, where only a small anatomically defined region is of interest, the scanning sweep is considerably shortened.

Both these factors together reduce the scanning time necessary for obtaining informative images for the anatomically defined region of interest.

In consequence, the two step rigorous-to-anatomic protocol is a highly effective technique for dynamic studies, providing anatomically reconstructed data, at very short time intervals of several seconds, and enabling the acquisition of kinetic parameters of specific tissues and across different tissues.

It will be appreciated that other markers may be used, and for other durations, provided the basic scheme of a first image for defining the anatomical boundaries, and the second image for dynamic reconstruction of anatomical voxels is maintained.

Obtaining Kinetic Parameters:

Dynamic studies, aimed at obtaining kinetic parameters require the acquisition of full reconstructed images at a rate that is no greater than about half the frequency of the sampled kinetic parameter. For example, if blood circulates throughout the body in about 1 minute, than sampling of that process should take place at least twice per minute. Preferably, sampling should be at a much greater frequency, for example, at least 6 times per minute, for example, every 10 seconds.

Furthermore, in order to obtain fully reconstructed images every 10 seconds, detector time slots must be much smaller, for example, a fraction of a second.

FIG. 98 illustrates counts obtained every $\frac{1}{1000}$ of a second, to be used for image reconstruction, for example, every 5 seconds, as seen in FIG. 2A, hereinbelow.

Additionally, based on Garcia et al. (Am. J. Cardiol. $51^{st}$ Annual Scientific Session, 2002), dynamic studies are best performed within about the first 100 seconds after injection, or within the first 60 seconds after injection.

Such studies are possible, when temporal resolution is available, as described hereinabove, and when scanning resources are directed at a specific and small anatomic region, for example, as described in conjunction with the section: Two Step Imaging for Dynamic Studies, Based on Anatomic Region of Interest.

Experimental Results

Experimental results, in accordance with embodiments of the present invention are provided in FIGS. 101A-101H.

Figure 101A:
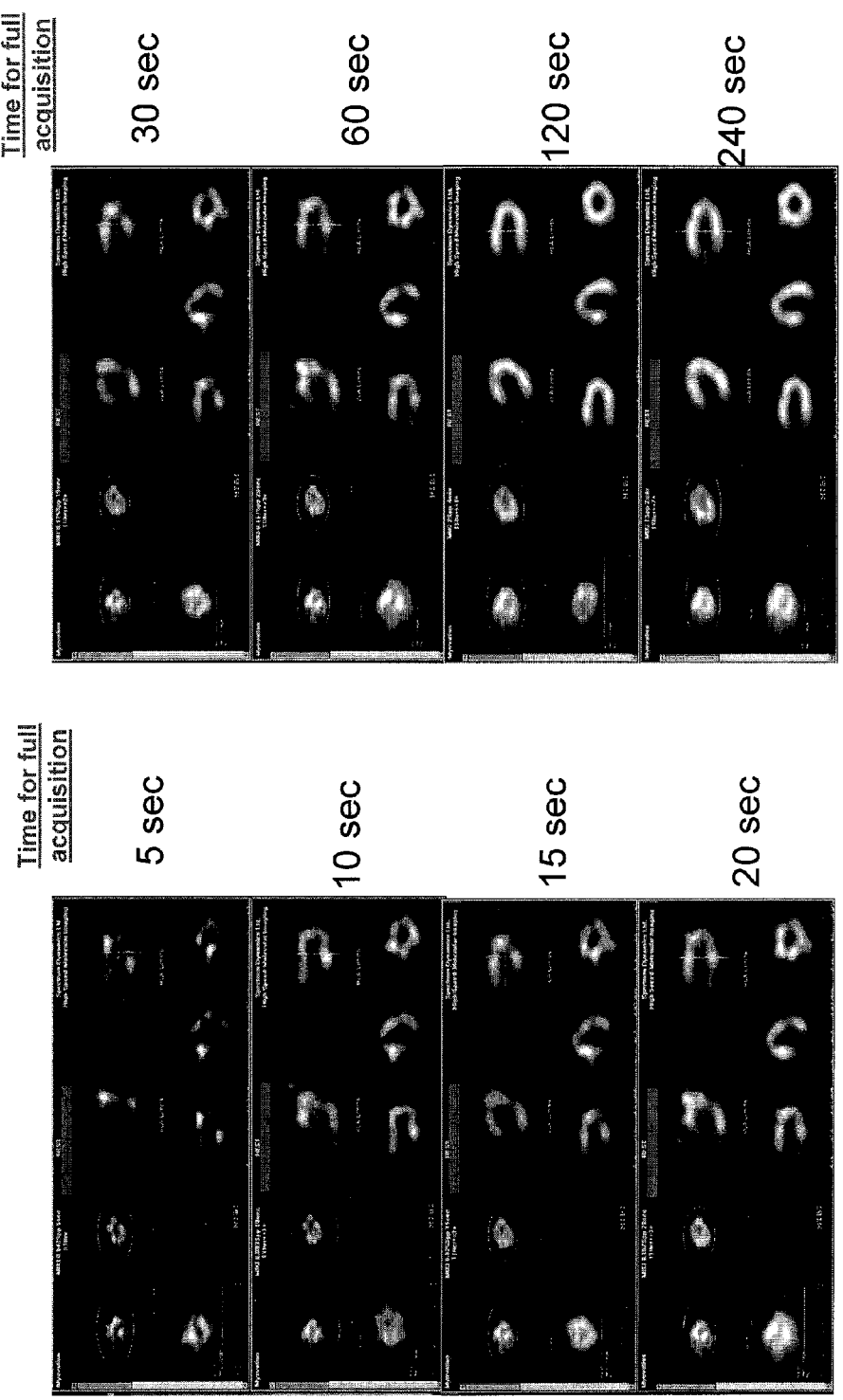
Figure 101F:
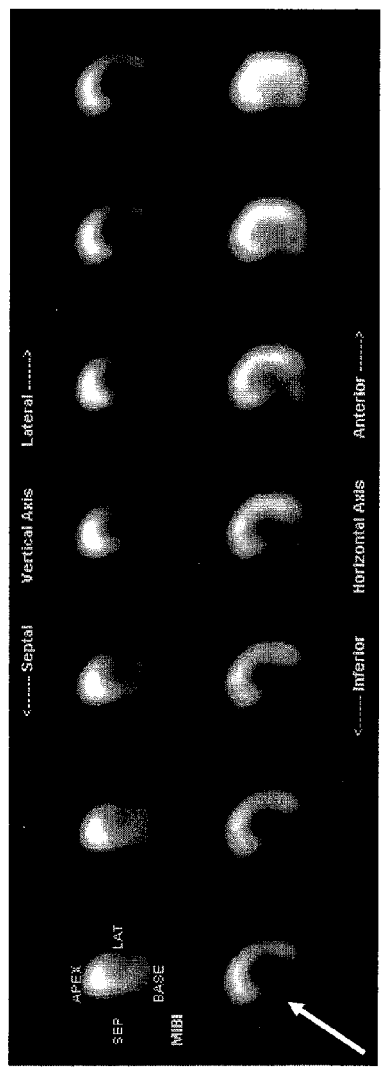

FIG. 101A shows image full cardiac image acquisition in 5 seconds, 10 seconds, 15 seconds, and up to 240 seconds, showing the improvement of the image, with increased imaging time.

Nonetheless, FIG. 101A illustrates that reasonable images, for example, for a two step image acquisition protocol J2 described hereinabove, in conjunction with the section: "Two Step Imaging for Dynamic Studies, Based on Anatomic Region of Interest," can provide meaningful results.

FIG. 101B illustrates contouring, which may be used for defining anatomical boundaries.

FIG. 101C illustrates a dual isotope image, of a 2 cm Tc-99m insert in a Tl-201 window image, wherein it is apparent that the Tc-99m insert is not visible in the Tl-201 window, confirming the spectral resolution of the camera.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of radioimaging a human organ, to obtain a clinically-valuable image having a resolution of at least 7×7×7 cubic mm of a volume of at least 5 cm diameter, comprising:
   administering a radiopharmaceutical to a patient;
   acquiring radiation emission data from an organ of said patient for a period of 5 minutes or less using a SPECT camera, wherein said acquiring comprises blocking radiation from a field of view of said camera using one or more radiation attenuation elements; and
   reconstructing, from said data, a clinically-valuable image of a volume of about at least 5 cm diameter including at least a part of said organ at a resolution of at least 7×7×7 cubic mm.

2. A method according to claim 1, wherein said SPECT camera is a collimated SPECT camera.

3. A method according to claim 1, comprising programming said camera according to a desired protocol.

4. A method according to claim 3, wherein said camera is programmed in response to at least one machine-readable indication provided with a data carrier containing information on one or both of the patient and the radiopharmaceutical.

5. A method according to claim 4, wherein said indication indicates a parameter of a desired protocol.

6. A method according to claim 4, wherein said camera requires said indication in order to operate.

7. A method according to claim 4, wherein said indication includes at least one injection instruction indication.

8. A method according to claim 4, wherein said indication is mechanically coupled to said radiopharmaceutical.

9. A method according to claim 1, wherein said camera includes a user interface which supports said method.

10. A method according to claim 1, wherein said administering is by one or more of oral, transnasal, intravenous, rectal, transmucosal, intestinal, parenteral, intrathecal, intranasal, intraperitoneal, intramuscular and subcutaneous delivery.

11. A method according to claim 1, wherein said acquiring comprises starting acquiring within ten minutes after said administration.

12. A method according to claim 1, wherein said acquiring comprises starting acquiring within one minute or less after said administration.

13. A method according to claim 1, wherein said acquiring comprises starting acquiring simultaneously with or before said administration.

14. A method according to claim 1, wherein said radiopharmaceutical comprises an isotope selected from a group consisting of: Tc-99m at between 20 and 40 mCi, Tl-201 at between 1 and 5 mCi, In-111 at between 2 and 5 mCi and I-123 at between 5 and 15 mCi.

15. A method according to claim 1, comprising:
   early acquiring data for less than two minutes; and
   analyzing the data to determine at least one scanning parameter,
   and wherein said acquiring data comprises acquiring data according to said at least one scanning parameter.

16. A method according to claim 1, wherein said administering comprises:
   administering a low dose of a first amount of a radiopharmaceutical;
   early acquiring data for less than two minutes; and
   analyzing the data; and
   administering a high dose of said radiopharmaceutical, and wherein said acquiring data comprises acquiring data according to said analysis.

17. A method according to claim 16, wherein said low dose is a trace amount.

18. A method according to claim 16, wherein said high amount has a radioactivity dose of at least 10 times said low dose.

19. A method according to claim 16, wherein said high amount has a radioactivity dose of at least 3 times said low dose.

20. A method according to claim 16, wherein said high amount has a radioactivity dose of at least 2.5 times said low dose.

21. A method according to claim 16, wherein said reconstructing comprises reconstructing a dynamic study in which radiopharmaceutical concentration changes dynamically.

22. A method according to claim 16, wherein said patient is not moved out of an imaging system over a period covering both said administering and said acquiring.

23. A method according to claim 1, wherein administering a radiopharmaceutical comprises administering a plurality of radiopharmaceuticals and wherein said acquiring comprises acquiring data from said plurality of radiopharmaceuticals together and wherein said reconstructing comprises reconstructing an image including data from said plurality of radiopharmaceuticals.

24. A method according to claim 23, wherein said plurality of radiopharmaceuticals is greater than two.

25. A method according to claim 23, wherein said plurality of radiopharmaceuticals are delivered substantially simultaneously.

26. A method according to claim 23, wherein a dosage of each said plurality of radiopharmaceuticals is matched to reduce interference therebetween.

27. A method according to claim 16, wherein said reduction is a reduction in interference caused by Compton scatter.

28. A method according to claim 16, wherein said reduction is a reduction in interference caused by spectral interference.

29. A method according to claim 16, wherein said matching comprises using less than half a dosage of tc-99m than a dosage of Tl-201.

30. A method according to claim 23, comprising first administering a first one of said plurality of radiopharmaceuticals, and acquiring interim data from the patient in response thereto, before administering a second one of said plurality of radiopharmaceuticals.

31. A method according to claim 30, comprising using said interim data for one or more of controlling a dosage of said second radio pharmaceutical, controlling an administration of second radiopharmaceutical, controlling said acquiring and controlling image analysis.

32. A method according to claim 30, comprising applying a stressor to said patient in conjunction with at least one of said administering of a radiopharmaceutical.

33. A method according to claim 30, comprising reconstructing a clinically useful image of at least a part of said organ, from said interim data and also completing said reconstructing of an image from said data relating to said second radiopharmaceutical using data acquired within 30 minutes from said first administering.

34. A method according to claim 33, wherein said plurality of radiopharmaceuticals are identical materials at different dosages or administration profiles and wherein a higher dose is provided in association with a stress state.

35. A method according to claim 33, wherein said completing is within 20 minutes.

36. A method according to claim 23, wherein at least one of said plurality of radiopharmaceuticals comprises Tc-99m.

37. A method according to claim 23, wherein at least one of said plurality of radiopharmaceuticals comprises Tl-201.

38. A method according to claim 1, comprising applying a stressor to said patient in conjunction with at least one of said administering of a radiopharmaceutical.

39. A method according to claim 1, wherein said organ is a heart.

40. A method of radioimaging a heart, to obtain a clinically-valuable image having a resolution of at least 7×7×7 mm of a volume of at least 5 cm diameter, comprising:
    administering a radiopharmaceutical to a patient at a low dose having an EDE (effective dose equivalent) of less than 2.5 millirem per Kg weight of said patient;
    acquiring radiation emission data from a heart of said patient using a collimated SPECT camera, said radiation being emitted by said low dose radiopharmaceutical, wherein said acquiring comprises acquiring radiation emission data from said heart for a period of 5 minutes or less using a SPECT camera, wherein said acquiring comprises blocking radiation from a field of view of said camera using one or more radiation attenuation elements; and
    reconstructing, from said data, a clinically-valuable image of a volume of about at least 5 cm diameter including at least a part of said heart at a resolution of at least 7×7×7 cubic mm, from said data.

41. A radiation emission camera, comprising:
    a controller; and
    at least one radiation detector,
    characterized in that, said controller is configured to follow the method of claim 1 for one or both of (a) acquiring and reconstructing data and (b) control timing of imaging relative to said administering.

* * * * *